US006936467B2

(12) United States Patent
Kmiec et al.

(10) Patent No.: US 6,936,467 B2
(45) Date of Patent: Aug. 30, 2005

(54) TARGETED CHROMOSOMAL GENOMIC ALTERATIONS WITH MODIFIED SINGLE STRANDED OLIGONUCLEOTIDES

(75) Inventors: Eric B. Kmiec, Landenberg, PA (US); Howard B. Gamper, Philadelphia, PA (US); Michael C. Rice, Newtown, PA (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 09/818,875

(22) Filed: Mar. 27, 2001

(65) Prior Publication Data

US 2003/0051270 A1 Mar. 13, 2003

Related U.S. Application Data

(60) Provisional application No. 60/244,989, filed on Oct. 30, 2000, provisional application No. 60/208,538, filed on Jun. 1, 2000, provisional application No. 60/192,179, filed on Mar. 27, 2000, and provisional application No. 60/192,176, filed on Mar. 27, 2000.

(51) Int. Cl.[7] .............................................. C12N 15/09
(52) U.S. Cl. ...................... 435/455; 435/440; 435/463; 435/471; 435/6; 536/23.1; 536/24.2; 536/24.3
(58) Field of Search ................................ 435/455, 440, 435/463, 471, 6, 251.11, 320.1, 468; 536/23.1, 24.2, 24.3; 574/44

(56) References Cited

U.S. PATENT DOCUMENTS

| | | | | |
|---|---|---|---|---|
| 5,565,350 | A | 10/1996 | Kmiec ...................... 435/172.3 |
| 5,731,181 | A | 3/1998 | Kmiec ...................... 435/172.3 |
| 5,801,154 | A | * 9/1998 | Baracchini et al. ............ 514/44 |
| 5,912,340 | A | 6/1999 | Kutyavin .................... 536/24.5 |
| 6,004,804 | A | 12/1999 | Kumar ..................... 435/320.1 |
| 6,136,601 | A | * 10/2000 | Meyer, Jr. et al. ........... 435/375 |
| 6,271,360 | B1 | 8/2001 | Metz ......................... 536/23.1 |

FOREIGN PATENT DOCUMENTS

| | | |
|---|---|---|
| WO | WO 99/14226 | 3/1999 |
| WO | WO 00/56748 | 9/2000 |
| WO | WO 00/66604 | 11/2000 |

OTHER PUBLICATIONS

Ronald G. Crystal, SCIENCE, vol. 270, Oct. 20, 1995, pp. 404–410.*
Inder M. Verma et al., NATURE, vol. 389, Sep. 18, 1997, pp. 239–242.*
Howard B Gamper et al., Nucleic Acids Research, 2000, vol. 28, No. 21, pp. 4332–4339.*
Kenneth W. Culver et al., Nature Biotechnology, vol. 17, Oct. 1999, pp. 989–993.*
RJ Yanez et al., Gene Therapy, (1998), 5, pp. 149–159.*
Eugene H. Kaji, et al., JAMA, Feb. 7, 2001, vol. 285, No. 5, pp. 545–550.*
Jon R. Sayers et al., Nucleic Acids Research, vol. 16, No. 3, 1988, pp. 791–801.*
Alexeev & Yoon, "Stable and inheritable changes in genotype and phenotype of albino melanocytes induced by an RNA–DNA oligonucleotide," *Nature Biotech.* 16:1343–1346 (1998).
Campbell et al., "Homologous recombination involving small single–stranded oligonucleotides in human cells," *New Biologist* 1:223–227 (1989).
Chan & Glazer, "Triplex DNA: fundamentals, advances, and potential applications for gene therapy," *J. Mol. Med.* 75:267–282 (1997).
Chan et al., "Targeted correction of an episomal gene in mammalian cells by a short DNA fragment tethered to a triplex–forming oligonucleotide," *J. Biol. Chem.* 274:11541–11548 (1999).
Cole–Strauss et al., "Correction of the mutation responsible for sickle cell anemia by an RNA–DNA oligonucleotide," *Science* 273:1386–1389 (1996).
Culver et al., "Correction of chromosomal point mutations in human cells with bifunctional oligonucleotides," *Nat. Biotechnol.* 17:989–993 (1999).
Gamper et al., "The DNA strand of chimeric RNA/DNA oligonucleotides can direct gene repair/conversion activity in mammalian and plant cell–free extracts," *Nucleic Acids Res.* 28:4332–4339 (2000).
Igoucheva et al., "Targeted gene correction by small single–stranded oligonucleotides in mammalian cells," *Gene Therapy* 8:391–399 (2001).
Kren et al., "Correction of the UDP–glucuronosyltransferase gene defect in the Gunn rat model of Crigler–Najjar syndrome type I with a chimeric oligonucleotide," *Proc. Natl. Acad. Sci. USA* 96:10349–10354 (1999).
Kunzelmann et al., "Gene targeting of CFTR DNA in CF epithelial cells," *Gene Ther.* 3:859–867 (1996).
Moerschell et al., "Transformation of yeast with synthetic oligonucleotides," *Proc. Natl. Acad. Sci. USA* 85:524–528 (1988).
Rando et al., "Rescue of dystrophin expression in *mdx* mouse muscle by RNA/DNA oligonucleotides," *Proc. Natl. Acad. Sci. USA* 97:5363–5368 (2000).
Vasquez et al., "Chromosomal mutations induced by triplex–forming oligonucleotides in mammalian cells," *Nucl. Acids Res.* 27:1176–1181 (1999).
Vasquez et al., "Specific mutations induced by triplex–forming oligonucleotides in mice," *Science* 290:530–532 (2000).

(Continued)

*Primary Examiner*—Dave T. Nguyen
*Assistant Examiner*—Jon Eric Angell
(74) *Attorney, Agent, or Firm*—Heller Ehrman White & McAuliffe LLP; Daniel M. Becker

(57) ABSTRACT

Presented are methods and compositions for targeted chromosomal genomic alterations using modified single-stranded oligonucleotides. The oligonucleotides of the invention have at least one modified nuclease-resistant terminal region comprising phosphorothioate linkages, LNA analogs or 2'-O-Me base analogs.

129 Claims, 12 Drawing Sheets

OTHER PUBLICATIONS

Yamamoto et al., "Strand-specificity in the transformation of yeast with synthetic oligonucleotides," *Genetics* 131:811–819 (1992).

Yanez & Porter, "Therapeutic gene targeting," *Gene Therapy* 5:149–159 (1998).

Xu et al., "Activation of human γ-globin gene expression via triplex-forming oligonucleotide (TFO)- directed mutations in the γ-globin gene 5' flanking region," *Gene* 242:219–228 (2000).

* cited by examiner

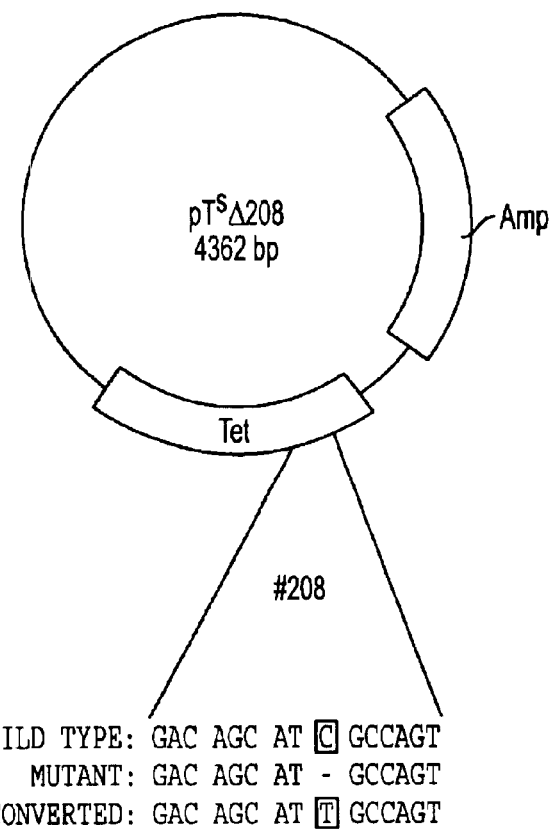
WILD TYPE: GAC AGC AT [C] GCCAGT
MUTANT: GAC AGC AT - GCCAGT
CONVERTED: GAC AGC AT [T] GCCAGT
SEQUENCE ANALYSIS OF Tet$^r$ PLASMID Δ208
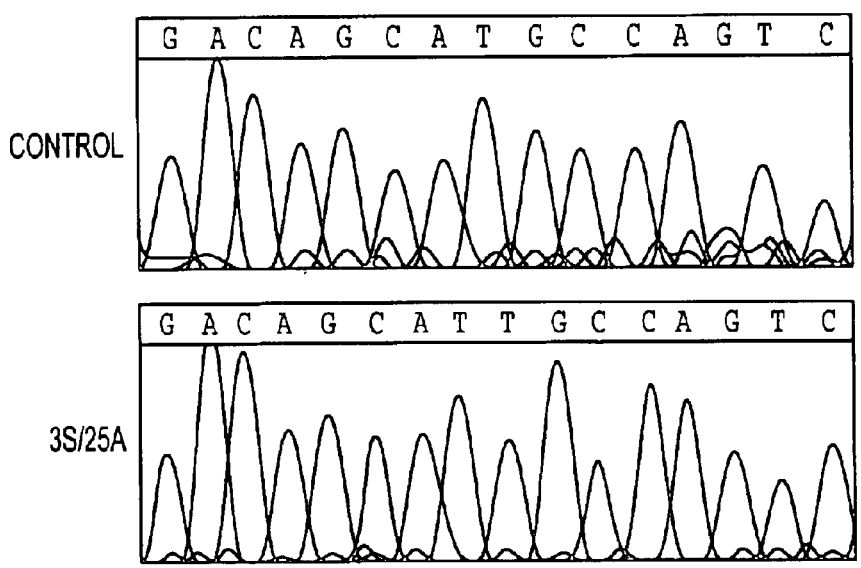
FIG. 3

DNA SEQUENCE ANALYSIS OF Kan[r] PLASMIDS
| TARGET CODON DISTRIBUTION | | | | | |
|---|---|---|---|---|---|
| OLIGOMER | TAG | TAC | TAC/TAG | TGG | TCG |
| 1) 3S/25G (20) | --- | + | --- | --- | --- |
| 2) 6S/25G (20) | --- | + | --- | --- | --- |
| 3) 8S/25G (20) | --- | + | --- | — | — |
| 4) 10S/25G (18) | --- | + | --- | +(2) | +(2) |
| 5) 25S/25G (4) | --- | --- | +(2) | +(2) | --- |
3S/25G
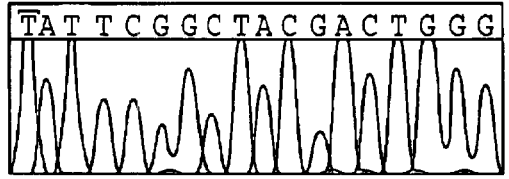
6S/25G
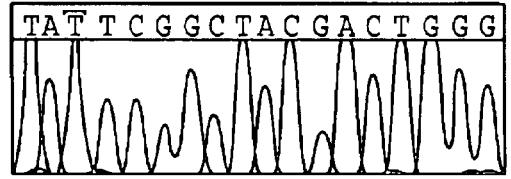
8S/25G
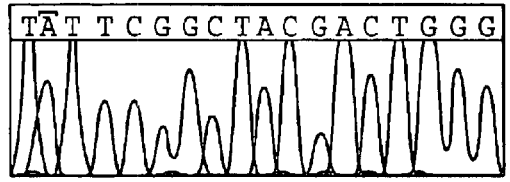
10S/25G
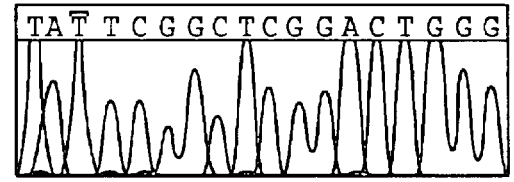
25S/25G
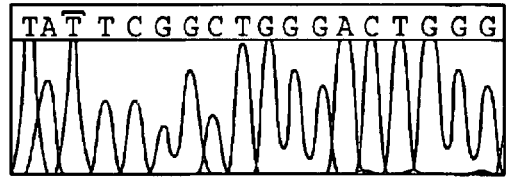
25S/25G
FIG. 4

SEQUENCE OF NORMAL ALLELE:      GTGGATATGTCCT
TARGET/EXISTING MUTANT:         GTGGATAATGTCCT
DESIRED ALTERATION:             GTGGATACGTCCT

SEQUENCE OF NORMAL ALLELE:      GTGGATATGTCCT
TARGET/EXISTING MUTANT:         GTGGATAGGTCCT
DESIRED ALTERATION:             GTGGATACGTCCT

HygE3T/25: 5'-<u>AGG</u> GCG TGG ATA CGT CCT GCG <u>GGT</u> A-3'

HygE3T/74: 5'-<u>CTC</u> GTG CTT TCA GCT TCG ATG TAG GAG GGC
GTG GAT ACG TCC TGC GGG TAA ATA GCT GCG
CCG ATG GTT T<u>CT AC</u>-3'

HygE3T/74α: 5'-<u>GTA</u> GAA ACC ATC GGC GCA GCT ATT TAC CCG
CAG GAC GTA TCC ACG CCC TCC TAC ATC GAA
GCT GAA AGC AC<u>G AG</u>-3'

HygGG/Rev:

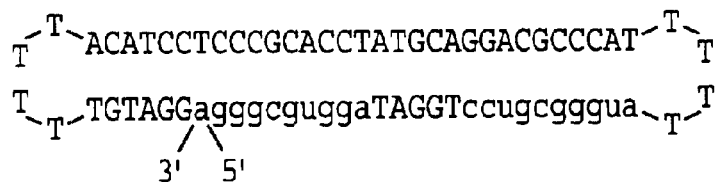

Kan70T: 5'-<u>CAT</u> CAG AGC AGC CAA TTG TCT GTT GTG CCC AGT
CGT AGC CGA ATA GCC TCT CCA CCC AAG CGG CCG <u>GAG</u>
A-3'

FIG. 8

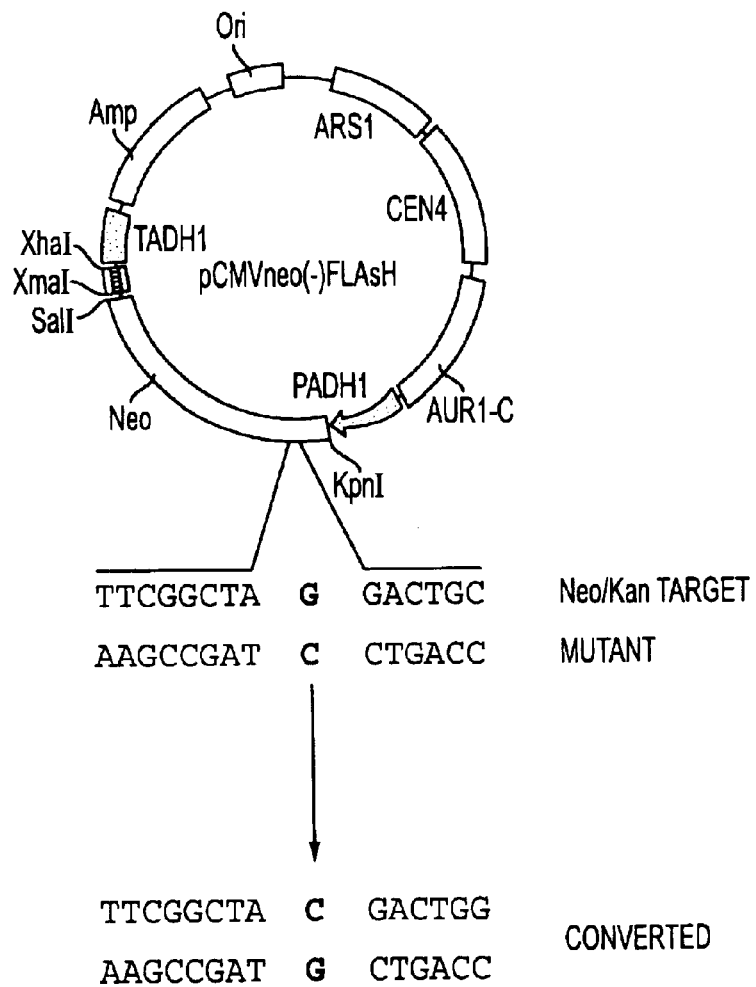
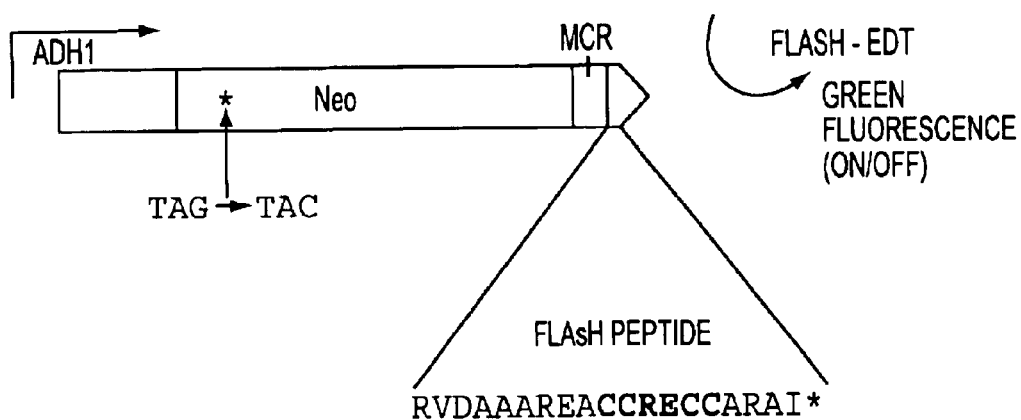
FIG. 9

TARGETED CHROMOSOMAL GENOMIC ALTERATIONS WITH MODIFIED SINGLE STRANDED OLIGONUCLEOTIDES

CROSS REFERENCE TO RELATED APPLICATIONS

This application claims the benefit under 35 U.S.C. §119 (e) of U.S. Provisional Application No. 60/192,176, filed Mar. 27, 2000; U.S. Provisional Application No. 60/192,179, filed Mar. 27, 2000; U.S. Provisional Application No. 60/208,538, filed Jun. 1, 2000; and U.S. Provisional Application No. 60/244,989, filed Oct. 30, 2000.

STATEMENT REGARDING FEDERALLY SPONSORED RESEARCH

This invention was made in the course of research under NIH grants R01 HL58563-05 and R01 DK56134-03. The government has certain rights in this invention.

INCORPORATION-BY-REFERENCE OF MATERIALS FILED ON COMPACT DISC

The present application includes a Sequence Listing filed on a single compact disc (CD-R), filed in duplicate. The Sequence Listing is presented in a single file on each CD-R and is named SequenceListingNapro4. The Sequence Listing was last modified Jul. 23, 2001 at 3:55 PM and comprises 930,816 bytes.

FIELD OF THE INVENTION

The technical field of the invention is oligonucleotide-directed repair or alteration of genetic information using novel chemically modified oligonucleotides. Such genetic information is preferably from a eukaryotic organism, i.e. a plant, animal or fungus.

BACKGROUND OF THE INVENTION

A number of methods have been developed specifically to alter the sequence of an isolated DNA in addition to methods to alter directly the genomic information of various plants, fungi and animals, including humans ("gene therapy"). The latter methods generally include the use of viral or plasmid vectors carrying nucleic acid sequences encoding partial or complete portions of a particular protein which is expressed in a cell or issue to effect the alteration. The expression of the particular protein then results in the desired phenotype. For example, retroviral vectors containing a transgenic DNA sequence allowing for the production of a normal CFTR protein when administered to defective cells are described in U.S. Pat. No. 5,240,846. Others have developed different "gene therapy vectors" which include, for example, portions of adenovirus (Ad) or adeno-associated virus (AAV), or other viruses. The virus portions used are often long terminal repeat sequences which are added to the ends of a transgene of choice along with other necessary control sequences which allow expression of the transgene. See U.S. Pat. Nos. 5,700,470 and 5,139,941. Similar methods have been developed for use in plants. See, for example, U.S. Pat. No. 4,459,355 which describes a method for transforming plants with a DNA vector and U.S. Pat. No. 5,188,642 which describes cloning or expression vectors containing a transgenic DNA sequence which when expressed in plants confers resistance to the herbicide glyphosate. The use of such transgene vectors in any eukaryotic organism adds one or more exogenous copies of a gene, which gene may be foreign to the host, in a usually random fashion at one or more integration sites of the organism's genome at some frequency. The gene which was originally present in the genome, which may be a normal allelic variant, mutated, defective, and/or functional, is retained in the genome of the host.

These methods of gene correction are problematic in that complications which can compromise the health of the recipient, or even lead to death, may result. One such problem is that insertion of exogenous nucleic acid at random location(s) in the genome can have deleterious effects. Another problem with such systems includes the addition of unnecessary and unwanted genetic material to the genome of the recipient, including, for example, viral or other vector remnants, control sequences required to allow production of the transgene protein, and reporter genes or resistance markers. Such remnants and added sequences may have presently unrecognized consequences, for example, involving genetic rearrangements of the recipient genomes. Other problems associated with these types of traditional gene therapy methods include autoimmune suppression of cells expressing an inserted gene due to the presence of foreign antigens. Concerns have also been raised with consumption, especially by humans, of plants containing exogenous genetic material.

More recently, simpler systems involving poly- or oligonucleotides have been described for use in the alteration of genomic DNA. These chimeric RNA-DNA oligonucleotides, requiring contiguous RNA and DNA bases in a double-stranded molecule folded by complementarity into a double hairpin conformation, have been shown to effect single basepair or frameshift alterations, for example, for mutation or repair of plant or animal genomes. See, for example, WO 99/07865 and U.S. Pat. No. 5,565,350. In the chimeric RNA-DNA oligonucleotide, an uninterrupted stretch of DNA bases within the molecule is required for sequence alteration of the targeted genome while the obligate RNA residues are involved in complex stability. Due to the length, backbone composition, and structural configuration of these chimeric RNA-DNA molecules, they are expensive to synthesize and difficult to purify. Moreover, if the RNA-containing strand of the chimeric RNA-DNA oligonucleotide is designed so as to direct gene conversion, a series of mutagenic reactions resulting in nonspecific base alteration can result. Such a result compromises the utility of such a molecule in methods designed to alter the genomes of plants and animals, including in human gene therapy applications.

Alternatively, other oligo- or poly-nucleotides have been used which require a triplex forming, usually polypurine or polypyrimidine, structural domain which binds to a DNA helical duplex through Hoogsteen interactions between the major groove of the DNA duplex and the oligonucleotide. Such oligonucleotides may have an additional DNA reactive moiety, such as psoralen, covalently linked to the oligonucleotide. These reactive moieties function as effective intercalation agents, stabilize the formation of a triplex and can be mutagenic. Such agents may be required in order to stabilize the triplex forming domain of the oligonucleotide with the DNA double helix if the Hoogsteen interactions from the oligonucleotide/target base composition are insufficient. See, e.g., U.S. Pat. No. 5,422,251. The utility of these oligonucleotides for directing gene conversion is compromised by a high frequency of nonspecific base changes.

In more recent work, the domain for altering a genome is linked or tethered to the triplex forming domain of the bi-functional oligonucleotide, adding an additional linking or tethering functional domain to the oligonucleotide. See, e.g., Culver et al., *Nature Biotechnology* 17: 989–93 (1999). Such chimeric or triplex forming molecules have distinct structural requirements for each of the different domains of the complete poly- or oligo-nucleotide in order to effect the desired genomic alteration in either episomal or chromosomal targets.

Other genes, e.g. CFTR, have been targeted by homologous recombination using duplex fragments having several hundred basepairs. See, e.g., Kunzelmann et al., *Gene Ther.* 3:859–867 (1996). Early experiments to mutagenize an antibiotic resistance indicator gene by homologous recombination used an unmodified DNA oligonucleotide with no functional domains other than a region of complementary sequence to the target. See Campbell et al., *New Biologist* 1: 223–227 (1989). These experiments required large concentrations of the oligonucleotide, exhibited a very low frequency of episomal modification of a targeted exogenous plasmid gene not normally found in the cell and have not been reproduced. However, as shown in the examples herein, we have observed that an unmodified DNA oligonucleotide can convert a base at low frequency which is detectable using the assay systems described herein.

Artificial chromosomes can be useful for the screening purposed identified herein. These molecules are man-made linear or circular DNA molecules constructed from essential cis-acting DNA sequence elements that are responsible for the proper replication and partitioning of natural chromosomes (Murray et al., 1983). The essential elements are: (1) Autonomous Replication Sequences (ARS), (2) Centromeres, and (3) Telomeres.

Yeast artificial chromosomes (YACs) allow large genomic DNA to be modified and used for generating transgenic animals [Burke et al., Science 236:806; Peterson et al., Trends Genet. 13:61 (1997); Choi, et al., Nat Genet., 4:117–223 (1993), Davies, et al., Biotechnology 11:911–914 (1993), Matsuura, et al., Hum. Mol. Genet., 5:451–459 (1996), Peterson et al., Proc. Natl. Acad. Sci., 93:6605–6609 (1996); and Schedl, et al., Cell, 86:71–82 (1996)]. Other vectors also have been developed for the cloning of large segments of mammalian DNA, including cosmids, and bacteriophage P1 [Sternberg et al., Proc. Natl. Acad. Sci. U.S.A., 87:103–107 (1990)]. YACs have certain advantages over these alternative large capacity cloning vectors [Burke et al., Science, 236:806–812 (1987)]. The maximum insert size is 35–30 kb for cosmids, and 100 kb for bacteriophage P1, both of which are much smaller than the maximal insert for a YAC.

An alternative to YACs are *E. coli* based cloning systems based on the *E. coli* fertility factor that have been developed to construct large genomic DNA insert libraries. They are bacterial artificial chromosomes (BACs) and P-1 derived artificial chromosomes (PACs) [Mejia et al., Genome Res. 7:179–186 (1997); Shizuya et al., Proc. Natl. Acad. Sci. 89:8794–8797 (1992); Ioannou et al., Nat Genet., 6:84–89 (1994); Hosoda et al., Nucleic Acids Res. 18:3863 (1990)]. BACs are based on the *E. coli* fertility plasmid (F factor); and PACs are based on the bacteriophage P1. These vectors propagate at a very low copy number (1–2 per cell) enabling genomic inserts up to 300 kb in size to be stably maintained in recombination deficient hosts. Furthermore, the PACs and BACs are circular DNA molecules that are readily isolated from the host genomic background by classical alkaline lysis [Birnboim et al., Nucleic Acids Res. 7:1513–1523 (1979].

Oligonucleotides designed for use in the alteration of genetic information are significantly different from oligonucleotides designed for antisense approaches. For example, antisense oligonucleotides are perfectly complementary to and bind an mRNA strand in order to modify expression of a targeted mRNA and are used at high concentration. As a consequence, they are unable to produce a gene conversion event by either mutagenesis or repair of a defect in the chromosomal DNA of a host genome. Furthermore, the backbone chemical composition used in most oligonucleotides designed for use in antisense approaches renders them inactive as substrates for homologous pairing or mismatch repair enzymes and the high concentrations of oligonucleotide required for antisense applications can be toxic with some types of nucleotide modifications. In addition, antisense oligonucleotides must be complementary to the mRNA and therefore, may not be complementary to the other DNA strand or to genomic sequences that span the junction between intron sequence and exon sequence.

A need exists for simple, inexpensive oligonucleotides capable of producing targeted alteration of genetic material such as those described herein as well as methods to identify optimal oligonucleotides that accurately and efficiently alter target DNA.

SUMMARY OF THE INVENTION

Novel, modified single-stranded nucleic acid molecules that direct gene alteration in plants, fungi and animals are identified and the efficiency of alteration is analyzed both in vitro using a cell-free extract assay and in vivo using a yeast cell system. The alteration in an oligonucleotide of the invention may comprise an insertion, deletion, substitution, as well as any combination of these. Site specific alteration of DNA is not only useful for studying function of proteins in vivo, but it is also useful for creating animal models for human disease, and in gene therapy. As described herein, oligonucleotides of the invention target directed specific gene alterations in genomic double-stranded DNA cells. The target DNA can be normal, cellular chromosomal DNA, extrachromosomal DNA present in cells in different forms including, e.g., mammalian artificial chromosomes (MACs), PACs from P-1 vectors, yeast artificial chromosomes (YACs), bacterial artificial chromosomes (BACs), plant artificial chromosomes (PLACs), as well as episomal DNA, including episomal DNA from an exogenous source such as a plasmid or recombinant vector. Many of these artificial chromosome constructs containing human DNA can be obtained from a variety of sources, including, e.g., the Whitehead Institute, and are described, e.g., in Cohen et al., *Nature* 336:698–701 (1993) and Chumakov, et al., *Nature* 377:174–297 (1995). The target DNA may be transcriptionally silent or active. In a preferred embodiment, the target DNA to be altered is the non-transcribed strand of a genomic DNA duplex.

The low efficiency of gene alteration obtained using unmodified DNA oligonucleotides is believed to be largely the result of degradation by nucleases present in the reaction mixture or the target cell. Although different modifications are known to have different effects on the nuclease resistance of oligonucleotides or stability of duplexes formed by such oligonucleotides (see, e.g., Koshkin et al., *J. Am. Chem. Soc.*, 120:13252–3), we have found that it is not possible to predict which of any particular known modification would be most useful for any given alteration event, including for the construction of gene conversion oligonucleotides, because of the interaction of different as yet unidentified proteins during the gene alteration event. Herein, a variety of nucleic acid analogs have been developed that increase the nuclease resistance of oligonucleotides that contain them, including, e.g., nucleotides containing phosphorothioate linkages or 2'-O-methyl analogs. We recently discovered that single-stranded DNA oligonucleotides modified to contain 2'-O-methyl RNA nucleotides or phosphorothioate linkages can enable specific alteration of genetic information at a higher level than either unmodified single-stranded DNA or a chimeric RNA/DNA molecule. See priority applications incorporated herein in their entirety; see also Gamper et al., *Nucleic Acids Research* 28: 4332–4339 (2000). We also found that additional nucleic acid analogs which increase the nuclease resistance of oligonucleotides that contain them, including, e.g., "locked nucleic acids" or "LNAs", xylo-LNAs and L-ribo-LNAs; see, for example, Wengel & Nielsen, WO 99/14226; Wengel, WO 00/56748 and Wengel, WO 00/66604; also allow specific targeted alteration of genetic information.

The assay allows for determining the optimum length of the oligonucleotide, optimum sequence of the oligonucleotide, optimum position of the mismatched base or bases, optimum chemical modification or modifications, optimum strand targeted for identifying and selecting the most efficient oligonucleotide for a particular gene alteration event by comparing to a control oligonucleotide. Control oligonucleotides may include a chimeric RNA-DNA double hairpin oligonucleotide directing the same gene alteration event, an oligonucleotide that matches its target completely, an oligonucleotide in which all linkages are phosphorothiolated, an oligonucleotide fully substituted with 2'-O-methyl analogs or an RNA oligonucleotide. Such control oligonucleotides either fail to direct a targeted alteration or do so at a lower efficiency as compared to the oligonucleotides of the invention. The assay further allows for determining the optimum position of a gene alteration event within an oligonucleotide, optimum concentration of the selected oligonucleotide for maximum alteration efficiency by systematically testing a range of concentrations, as well as optimization of either the source of cell extract by testing different organisms or strains, or testing cells derived from different organisms or strains, or cell lines. Using a series of single-stranded oligonucleotides, comprising all RNA or DNA residues and various mixtures of the two, several new structures are identified as viable molecules in nucleotide conversion to direct or repair a genomic mutagenic event. When extracts from mammalian, plant and fungal cells are used and are analyzed using a genetic readout assay in bacteria, single-stranded oligonucleotides having one of several modifications are found to be more active than a control RNA-DNA double hairpin chimera structure when evaluated using an in vitro gene repair assay. Similar results are also observed in vivo using yeast, mammalian, rodent, monkey, human and embryonic cells, including stem cells. Molecules containing various lengths of modified bases were found to possess greater activity than unmodified single-stranded DNA molecules.

DETAILED DESCRIPTION OF THE INVENTION

The present invention provides oligonucleotides having chemically modified, nuclease resistant residues, preferably at or near the termini of the oligonucleotides, and methods for their identification and use in targeted alteration of genetic material, including gene mutation, targeted gene repair and gene knockout. The oligonucleotides are preferably used for mismatch repair or alteration by changing at least one nucleic acid base, or for frameshift repair or alteration by addition or deletion of at least one nucleic acid base. The oligonucleotides of the invention direct any such alteration, including gene correction, gene repair or gene mutation and can be used, for example, to introduce a polymorphism or haplotype or to eliminate ("knockout") a particular protein activity.

The oligonucleotides of the invention are designed as substrates for homologous pairing and repair enzymes and as such have a unique backbone composition that differs from chimeric RNA-DNA double hairpin oligonucleotides, antisense oligonucleotides, and/or other poly- or oligonucleotides used for altering genomic DNA, such as triplex forming oligonucleotides. The single-stranded oligonucleotides described herein are inexpensive to synthesize and easy to purify. In side-by-side comparisons, an optimized single-stranded oligonucleotide comprising modified residues as described herein is significantly more efficient than a chimeric RNA-DNA double hairpin oligonucleotide in directing a base substitution or frameshift mutation in a cell-free extract assay.

We have discovered that single-stranded oligonucleotides having a DNA domain surrounding the targeted base, with the domain preferably central to the poly- or oligonucleotide, and having at least one modified end, preferably at the 3' terminal region are able to alter a target genetic sequence and with an efficiency that is higher than chimeric RNA-DNA double hairpin oligonucleotides disclosed in U.S. Pat. No. 5,565,350. Oligonucleotides of the invention can efficiently be used to introduce targeted alterations in a genetic sequence of DNA in the presence of human, animal, plant, fungal (including yeast) proteins and in cultured cells of human liver, lung, colon, cervix, kidney, epethelium and cancer cells and in monkey, hamster, rat and mouse cells of different types, as well as embryonic stem cells. Cells for use in the invention include, e.g., fungi including *S. cerevisiae, Ustillago maydis* and *Candida albicans*, mammalian, mouse, hamster, rat, monkey, human and embryonic cells including stem cells. The DNA domain is preferably fully complementary to one strand of the gene target, except for the mismatch base or bases responsible for the gene alteration or conversion events. On either side of the preferably central DNA domain, the contiguous bases may be either RNA bases or, preferably, are primarily DNA bases. The central DNA domain is generally at least 8 nucleotides in length. The base(s) targeted for alteration in the most preferred embodiments are at least about 8, 9 or 10 bases from one end of the oligonucleotide.

According to certain embodiments, the termini of the oligonucleotides of the present invention comprise phosphorothioate modifications, LNA backbone modifications, or 2'-O-methyl base analogs, or any combination of these modifications. Oligonucleotides comprising 2'-O-methyl or LNA analogs are a mixed DNA/RNA polymer. These oligonucleotides are, however, single-stranded and are not designed to form a stable internal duplex structure within the oligonucleotide. The efficiency of gene alteration is surprisingly increased with oligonucleotides having internal complementary sequence comprising phosphorothioate modified bases as compared to 2'-O-methyl modifications. This result indicates that specific chemical interactions are involved between the converting oligonucleotide and the proteins involved in the conversion. The effect of other such chemical interactions to produce nuclease resistant termini using modifications other than LNA, phosphorothioate linkages, or 2'-O-methyl analog incorporation into an oligonucleotide can not yet be predicted because the proteins involved in the alteration process and their particular chemical interaction with the oligonucleotide substituents are not yet known and cannot be predicted.

In the examples, correcting oligonucleotides of defined sequence are provided for correction of genes mutated in human diseases. In the tables of these examples, the oligonucleotides of the invention are not limited to the particular sequences disclosed. The oligonucleotides of the invention include extensions of the appropriate sequence of the longer 120 base oligonucleotides which can be added base by base to the smallest disclosed oligonucleotides of 17 bases. Thus the oligonucleotides of the invention include for each correcting change, oligonucleotides of length 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 with further single-nucleotide additions up to the longest sequence disclosed. Moreover, the oligonucleotides of the invention do not require a symmetrical extension on either side of the central DNA domain. Similarly, the oligonucleotides of the invention as disclosed in the various tables for correction of human diseases contain phosphorothioate linkages, 2'-O-methyl analogs or LNAs or any combination of these modifications just as the assay oligonucleotides do.

The present invention, however, is not limited to oligonucleotides that contain any particular nuclease resistant modification. Oligonucleotides of the invention may be altered with any combination of additional LNAs, phosphorothioate linkages or 2'-O-methyl analogs to maximize conversion efficiency. For oligonucleotides of the invention that are longer than about 17 to about 25 bases in length, internal as well as terminal region segments of the backbone may be altered. Alternatively, simple fold-back structures at each end of a oligonucleotide or appended end groups may be used in addition to a modified backbone for conferring additional nuclease resistance.

The different oligonucleotides of the present invention preferably contain more than one of the aforementioned backbone modifications at each end. In some embodiments, the backbone modifications are adjacent to one another. However, the optimal number and placement of backbone modifications for any individual oligonucleotide will vary with the length of the oligonucleotide and the particular type of backbone modification(s) that are used. If constructs of identical sequence having phosphorothioate linkages are compared, 2, 3, 4, 5, or 6 phosphorothioate linkages at each end are preferred. If constructs of identical sequence having 2'-O-methyl base analogs are compared, 1, 2, 3 or 4 analogs are preferred. The optimal number and type of backbone modifications for any particular oligo-nucleotide useful for altering target DNA may be determined empirically by comparing the alteration efficiency of the oligonucleotide comprising any combination of the modifications to a control molecule of comparable sequence using any of the assays described herein. The optimal position(s) for oligonucleotide modifications for a maximally efficient altering oligonucleotide can be determined by testing the various modifications as compared to control molecule of comparable sequence in one of the assays disclosed herein. In such assays, a control molecule includes, e.g., a completely 2'-O-methyl substituted molecule, a completely complementary oligonucleotide, or a chimeric RNA-DNA double hairpin.

Increasing the number of phosphorothioate linkages, LNAs or 2'-O-methyl bases beyond the preferred number generally decreases the gene repair activity of a 25 nucleotide long oligonucleotide. Based on analysis of the concentration of oligonucleotide present in the extract after different time periods of incubation, it is believed that the terminal modifications impart nuclease resistance to the oligonucleotide thereby allowing it to survive within the cellular environment However, this may not be the only possible mechanism by which such modifications confer greater efficiency of conversion. For example, as disclosed herein, certain modifications to oligonucleotides confer a greater improvement to the efficiency of conversion than other modifications.

Efficiency of conversion is defined herein as the percentage of recovered substate molecules that have undergone a conversion event Depending on the nature of the target genetic material, e.g. the genome of a cell, efficiency could be represented as the proportion of cells or clones containing an extrachromosomal element that exhibit a particular phenotype. Alternatively, representative samples of the target genetic material can be sequenced to determine the percentage that have acquired the desire change. The oligonucleotides of the invention in different embodiments can alter DNA one, two, three, four, five, six, seven, eight, nine, ten, twelve, fifteen, twenty, thirty, and fifty or more fold more than control oligonucleotides. Such control oligonucleotides are oligonucleotides with fully phosphorothiolated linkages, oligonucleotides that are fully substituted with 2'-O-methyl analogs, a perfectly matched oligonucleotide that is fully complementary to a target sequence or a chimeric DNA-RNA double hairpin oligonucleotide such as disclosed in U.S. Pat. No. 5,565,350.

In addition, for a given oligonucleotide length, additional modifications interfere with the ability of the oligonucleotide to act in concert with the cellular recombination or repair enzyme machinery which is necessary and required to mediate a targeted substitution, addition or deletion event in DNA. For example, fully phosphorothiolated or fully 2-O-methylated molecules are inefficient in targeted gene alteration.

The oligonucleotides of the invention as optimized for the purpose of targeted alteration of genetic material, including gene knockout or repair, are different in structure from antisense oligonucleotides that may possess a similar mixed chemical composition backbone. The oligonucleotides of the invention differ from such antisense oligonucleotides in chemical composition, structure, sequence, and in their ability to alter genomic DNA. Significantly, antisense oligonucleotides fail to direct targeted gene alteration. The oligonucleotides of the invention may target either the Watson or the Crick strand of DNA and can include any component of the genome including, for example, intron and exon sequences. The preferred embodiment of the invention is a modified oligonucleotide that binds to the non-transcribed strand of a genomic DNA duplex. In other words, the preferred oligonucleotides of the invention target the sense strand of the DNA, i.e. the oligonucleotides of the invention are complementary to the non-transcribed strand of the target duplex DNA. The sequence of the non-transcribed strand of a DNA duplex is found in the mRNA produced from that duplex, given that mRNA uses uracil-containing nucleotides in place of thymine-containing nucleotides.

Moreover, the initial observation that single-stranded oligonucleotides comprising these modifications and lacking any particular triplex forming domain have reproducibly enhanced gene repair activity in a variety of assay systems as compared to a chimeric RNA-DNA double-stranded hairpin control or single-stranded oligonucleotides comprising other backbone modifications was surprising. The single-stranded molecules of the invention totally lack the complementary RNA binding structure that stabilizes a normal chimeric double-stranded hairpin of the type disclosed in U.S. Pat. No. 5,565,350 yet is more effective in producing targeted base conversion as compared to such a chimeric RNA-DNA double-stranded hairpin. In addition, the molecules of the invention lack any particular triplex forming domain involved in Hoogsteen interactions with the DNA double helix and required by other known oligonucleotides in other oligonucleotide dependant gene conversion systems. Although the lack of these functional domains was expected to decrease the efficiency of an alteration in a sequence, just the opposite occurs: the efficiency of sequence alteration using the modified oligonucleotides of the invention is higher than the efficiency of sequence alteration using a chimeric RNA-DNA hairpin targeting the same sequence alteration. Moreover, the efficiency of sequence alteration or gene conversion directed by an unmodified oligonucleotide is many times lower as compared to a control chimeric RNA-DNA molecule or the modified oligonucleotides of the invention targeting the same sequence alteration. Similarly, molecules containing at least 3 2'-O-methyl base analogs are about four to five fold less efficient as compared to an oligonucleotide having the same number of phosphorothioate linkages.

The oligonucleotides of the present invention for alteration of a single base are about 17 to about 121 nucleotides in length, preferably about 17 to about 74 nucleotides in length. Most preferably, however, the oligonucleotides of the present invention are at least about 25 bases in length, unless there are self-dimerization structures within the oligonucleotide. If the oligonucleotide has such an unfavorable structure, lengths longer than 35 bases are preferred. Oligonucleotides with modified ends both shorter and longer than certain of the exemplified, modified oligonucleotides herein function as gene repair or gene knockout agents and are within the scope of the present invention.

Once an oligomer is chosen, it can be tested for its tendency to self-dimerize, since self-dimerization may result in reduced efficiency of alteration of genetic information. Checking for self-dimerizaton tendency can be accomplished manually or, more preferably, by using a software program. One such program is Oligo Analyzer 2.0, available through Integrated DNA Technologies (Coralville, Iowa 52241); this program is available for use on the world wide web at the Integrated DNA Technologies web site.

For each oligonucleotide sequence input into the program, Oligo Analyzer 2.0 reports possible self-dimerized duplex forms, which are usually only partially duplexed, along with the free energy change associated with such self-dimerization. Delta G-values that are negative and large in magnitude, indicating strong self-dimerization potential, are automatically flagged by the software as "bad". Another software program that analyzes oligomers for pair dimer formation is Primer Select from DNASTAR, Inc., 1228 S. Park St., Madison, Wis. 53715, Phone: (608) 258-7420.

If the sequence is subject to significant self-dimerization, the addition of further sequence flanking the "repair" nucleotide can improve gene correction frequency.

Generally, the oligonucleotides of the present invention are identical in sequence to one strand of the target DNA, which can be either strand of the target DNA, with the exception of one or more targeted bases positioned within the DNA domain of the oligonucleotide, and preferably toward the middle between the modified terminal regions. Preferably, the difference in sequence of the oligonucleotide as compared to the targeted genomic DNA is located at about the middle of the oligonucleotide sequence. In a preferred embodiment, the oligonucleotides of the invention are complementary to the non-transcribed strand of a duplex. In other words, the preferred oligonucleotides target the sense strand of the DNA, i.e. the oligonucleotides of the invention are preferably complementary to the strand of the target DNA the sequence of which is found in the mRNA.

The oligonucleotides of the invention can include more than a single base change. In an oligonucleotide that is about a 70-mer, with at least one modified residue incorporated on the ends, as disclosed herein, multiple bases can be simultaneously targeted for change. The target bases may be up to 27 nucleotides apart and may not be changed together in all resultant plasmids in all cases. There is a frequency distribution such that the closer the target bases are to each other in the central DNA domain within the oligonucleotides of the invention, the higher the frequency of change in a given cell. Target bases only two nucleotides apart are changed together in every case that has been analyzed. The farther apart the two target bases are, the less frequent the simultaneous change. Thus, oligonucleotides of the invention may be used to repair or alter multiple bases rather than just one single base. For example, in a 74-mer oligonucleotide having a central base targeted for change, a base change event up to about 27 nucleotides away can also be effected. The positions of the altering bases within the oligonucleotide can be optimized using any one of the assays described herein. Preferably, the altering bases are at least about 8 nucleotides from one end of the oligonucleotide.

The oligonucleotides of the present invention can be introduced into cells by any suitable means. According to certain preferred embodiments, the modified oligonucleotides may be used alone. Suitable means, however, include the use of polycations, cationic lipids, liposomes, polyethylenimine (PEI), electroporation, biolistics, microinjection and other methods known in the art to facilitate cellular uptake. According to certain preferred embodiments of the present invention, the isolated cells are treated in culture according to the methods of the invention, to mutate or repair a target gene. Modified cells may then be reintroduced into the organism as, for example, in bone marrow having a targeted gene. Alternatively, modified cells may be used to regenerate the whole organism as, for example, in a plant having a desired targeted genomic change. In other instances, targeted genomic alteration, including repair or mutagenesis, may take place in vivo following direct administration of the modified, single-stranded oligonucleotides of the invention to a subject.

The single-stranded, modified oligonucleotides of the present invention have numerous applications as gene repair, gene modification, or gene knockout agents. Such oligonucleotides may be advantageously used, for example, to introduce or correct multiple point mutations. Each mutation leads to the addition, deletion or substitution of at least one base pair. The methods of the present invention offer distinct advantages over other methods of altering the genetic makeup of an organism, in that only the individually targeted bases are altered. No additional foreign DNA sequences are added to the genetic complement of the organism. Such agents may, for example, be used to develop plants or animals with improved traits by rationally changing the sequence of selected genes in cultured cells. Modified cells are then cloned into whole plants or animals having the altered gene. See, e.g., U.S. Pat. Nos. 6,046,380 and 5,905,185 incorporated hererin by reference. Such plants or animals produced using the compositions of the invention lack additional undesirable selectable markers or other foreign DNA sequences. Targeted base pair substitution or frameshift mutations introduced by an oligo-nucleotide in the presence of a cell-free extract also provides a way to modify the sequence of extrachromosomal elements, including, for example, plasmids, cosmids and artificial chromosomes. The oligonucleotides of the invention also simplify the production of transgenic animals having particular modified or inactivated genes. Altered animal or plant model systems such as those produced using the methods and oligonucleotides of the invention are invaluable in determining the function of a gene and in evaluating drugs. The oligonucleotides and methods of the present invention may also be used for gene therapy to correct mutations causative of human diseases.

The purified oligonucleotide compositions may be formulated in accordance with routine procedures as a pharmaceutical composition adapted for bathing cells in culture, for microinjection into cells in culture, and for intravenous administration to human beings or animals. Typically, compositions for cellular administration or for intravenous administration into animals, including humans, are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, for example, as a dry, lyophilized powder or water-free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection" or saline. Where the composition is to be administered by injection, an ampule of sterile water for injection or saline may be provided so that the ingredients may be mixed prior to administration.

Pharmaceutical compositions of this invention comprise the compounds of the present invention and pharmaceutically acceptable salts thereof, with any pharmaceutically acceptable ingredient, excipient, carrier, adjuvant or vehicle.

The oliqonucleotides of the invention are preferably administered to the subject in the form of an injectable composition. The composition is preferably administered parenterally, meaning intravenously, intraarterially, intrathecally, interstitially or intracavitarilly. Pharmaceutical compositions of this invention can be administered to mammals including humans in a manner similar to other diagnostic or therapeutic agents. The dosage to be administered, and the mode of administration will depend on a variety of factors including age, weight, sex, condition of the subject and genetic factors, and will ultimately be decided by medical personnel subsequent to experimental determinations of varying dosage as described herein. In general, dosage required for correction and therapeutic efficacy will range from about 0.001 to 50,000 μg/kg, preferably between 1 to 250 μg/kg of host cell or body mass, and most preferably at a concentration of between 30 and 60 micromolar.

For cell administration, direct injection into the nucleus, biolistic bombardment, electroporation, liposome transfer and calcium phosphate precipitation may be used. In yeast, lithium acetate or spheroplast transformation may also be used. In a preferred method, the administration is performed with a liposomal transfer compound, e.g., DOTAP (Boehringer-Mannheim) or an equivalent such as lipofectin. The amount of the oligonucleotide used is about 500 nanograms in 3 micrograms of DOTAP per 100,000 cells. For electroporation, between 20 and 2000 nanograms of oligonucleotide per million cells to be electroporated is an appropriate range of dosages which can be increased to improve efficiency of genetic alteration upon review of the appropriate sequence according to the methods described herein.

Another aspect of the invention is a kit comprising at least one oligonucleotide of the invention. The kit may comprise an addition reagent or article of manufacture. The additional reagent or article of manufacture may comprise a cell extract, a cell, or a plasmid, such as one of those disclosed in the Figures herein, for use in an assay of the invention.

BRIEF DESCRIPTION OF THE DRAWINGS

In FIG. 1(D), the Kan mutant sequence corresponds to SEQ ID NO: 4343 and SEQ ID NO: 4344; the Kan converted sequence corresponds to SEQ ID NO: 4345 and SEQ ID NO: 4346; the mutant sequence in the sequence trace corresponds to SEQ ID NO: 4347 and the converted sequences in the sequence trace corresponds to SEQ ID NO: 4348.

FIG. 3: Target plasmid and sequence correction of a frameshift mutation by chimeric and single-stranded oligonucleotides. (A) Plasmid pT$^s$Δ208 contains a single base deletion mutation at position 208 rendering it unable to confer tet resistance. The target sequence presented below indicates the insertion of a T directed by the oligonucleotides to re-establish the resistant phenotype. (B) DNA sequence confirming base insertion directed by Tet 3S/25G; the yellow highlight indicates the position of frameshift repair. The wild type sequence corresponds to SEQ ID NO: 4350, the mutant sequence corresponds to SEQ ID NO: 4351 and the converted sequence corresponds to SEQ ID NO: 4352. The control sequence in the sequence trace corresponds to SEQ ID NO: 4353 and the 3S/25A sequence in the sequence trace corresponds to SEQ ID NO: 4354.

FIG. 4. DNA sequences of representative kan[r] colonies. Confirmation of sequence alteration directed by the indicated molecule is presented along with a table outlining codon distribution. Note that 10S/25G and 12S/25G elicit both mixed and unfaithful gene repair. The number of clones sequenced is listed in parentheses next to the designation for the single-stranded oligonucleotide. A plus (+) symbol indicates the codon identified while a figure after the (+) symbol indicates the number of colonies with a particular sequence. TAC/TAG indicates a mixed peak. Representative DNA sequences are presented below the table with yellow highlighting altered residues. The sequences in the sequence traces have been assigned numbers as follows: 3S/25G, 6S/25G and 8S/25G correspond to SEQ ID NO: 4355, 10S/25G correspond to SEQ ID NO: 4356, 25S/25G on the lower left corresponds to SEQ ID NO: 4357 and 25S/25G on the lower right corresponds to SEQ ID NO: 4358.

FIG. 7. Hygromycin-eGFP target plasmids. (A) Plasmid pAURHYG(ins)GFP contains a single base insertion mutation between nucleotides 136 and 137, at codon 46, of the Hygromycin B coding sequence (cds) which is transcribed from the constitutive ADH1 promoter. The target sequence presented below indicates the deletion of an A and the substitution of a C for a T directed by the oligonucleotides to re-establish the resistant phenotype.

FIG. 8. Oligonucleotides for correction of hygromycin resistance gene. The sequence of the oligonucleotides used in experiments to assay correction of a hygromycin resistance gene are shown. DNA residues are shown in capital letters, RNA residues are shown in lowercase and nucleotides with a phosphorothioate backbone are capitalized and underlined. In FIG. 8, the sequence of HygEb 3T/25 corresponds to SEQ ID NO: 4363, the sequence of HygE3T/74 corresponds to SEQ ID NO: 4364, the sequence of HygE3T/74a corresponds to SEQ ID NO: 4365, the sequence of HygGG/Rev corresponds to SEQ ID NO: 4366 and the sequence of Kan70T corresponds to SEQ ID NO: 4367.

FIG. 9. pAURNeo(−)FIAsH plasmid. This figure describes the plasmid structure, target sequence, oligonucleotides, and the basis for detection of the gene alteration event by fluorescence. In FIG. 9, the sequence of the Neo/kan target mutant corresponds to SEQ ID NO: 4343 and SEQ ID NO: 4344, the converted sequence corresponds to SEQ ID NO: 4345 and SEQ ID NO: 4346 and the FIAsH peptide sequence corresponds to SEQ ID NO: 4368.

Figure 1A:
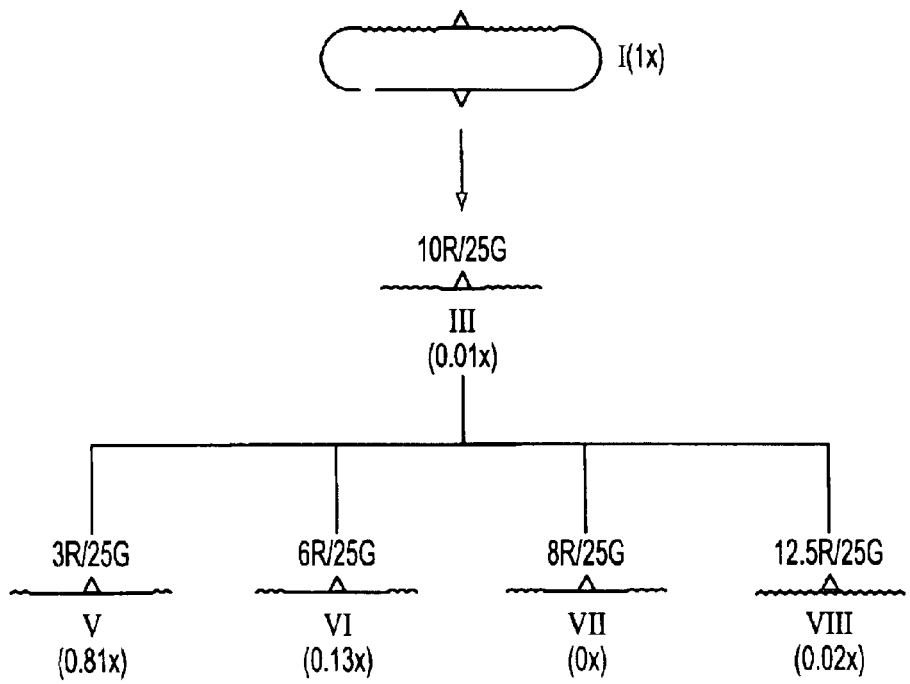
FIG. 1. Flow diagram for the generation of modified single-stranded oligonucleotides. The upper strands of chimeric oligonucleotides I and II are separated into pathways resulting in the generation of single-stranded oligonucleotides that contain (A) 2'-O-methyl RNA nucleotides or (B) phosphorothioate linkages. Fold changes in repair activity for correction of kan$^s$ in the HUH7 cell-free extract are presented in parenthesis. HUH7 cells are described in Nakabayashi et al., Cancer Research 42: 3858–3863 (1982). Each single-stranded oligonucleotide is 25 bases in length and contains a G residue mismatched to the complementary sequence of the kan$^s$ gene. The numbers 3, 6, 8, 10, 12 and 12.5 respectively indicate how many phosphorothioate linkages (S) or 2'-O-methyl RNA nucleotides (R) are at each end of the molecule. Hence oligo 12S/25G contains an all phosphorothioate backbone, displayed as a dotted line. Smooth lines indicate DNA residues, wavy lines indicate 2'-O-methyl RNA residues and the carat indicates the mismatched base site (G).
FIG. 1(C) provides a schematic plasmid indicating the sequence of the kan chimeric double-stranded hairpin oligonucleotide (left; SEQ ID NO: 4341) and the sequence the tet chimeric double-stranded hairpin oligonucleotide used in other experiments (SEQ ID NO: 4342).
FIG. 1(D) provides a flow chart of a kan experiment in which a chimeric double-stranded hairpin oligonucleotide (SEQ ID NO: 4341) is used.

The following examples are provided by way of illustration only, and are not intended to limit the scope of the invention disclosed herein.

EXAMPLE 1

Assay Method for Base Alteration and Preferred Oligonucleotide Selection

In this example, single-stranded and double-hairpin oligonucleotides with chimeric backbones (see FIG. 1 for structures (A and B) and sequences (C and D) of assay oligonucleotides) are used to correct a point mutation in the kanamycin gene of pK$^s$m4021 (FIG. 2) or the tetracycline gene of pT$^s$Δ208 (FIG. 3). All kan oligonucleotides share the same 25 base sequence surrounding the target base identified for change, just as all tet oligonucleotides do. The sequence is given in FIGS. 1C and 1D. Each plasmid contains a functional ampicillin gene. Kanamycin gene function is restored when a G at position 4021 is converted to a C (via a substitution mutation); tetracycline gene function is restored when a deletion at position 208 is replaced by a C (via frameshift mutation). A separate plasmid, pAURNeo(−)FIAsH (FIG. 9), bearing the kan$^s$ gene is used in the cell culture experiments. This plasmid was constructed by inserting a synthetic expression cassette containing a neomycin phosphotransferase (kanamycin resistance) gene and an extended reading frame that encodes a receptor for the FIAsH ligand into the pAUR123 shuttle vector (Panvera Corp., Madison, Wis.). The resulting construct replicates in S. cerevisiae at low copy number, confers resistance to aureobasidinA and constitutively expresses either the Neo+/FIAsH fusion product (after alteration) or the truncated Neo-/FIAsH product (before alteration) from the ADH1 promoter. By extending the reading frame of this gene to code for a unique peptide sequence capable of binding a small ligand to form a fluorescent complex, restoration of expression by correction of the stop codon can be detected in real time using confocal microscopy. Additional constructs can be made to test additional gene alteration events.

We also construct three mammalian expression vectors, pHyg(rep)eGFP, pHyg(Δ)eGFP, pHyg(ins)eGFP, that contain a substitution mutation at nucleotide 137 of the hygromycin-B coding sequence. (rep) indicates a T137→G replacement, (Δ) represents a deletion of the G137 and (ins) represents an A insertion between nucleotides 136 and 137. All point mutations create a nonsense termination codon at residue 46. We use pHygEGFP plasmid (Invitrogen, Calif.) DNA as a template to introduce the mutations into the hygromycin-eGFP fusion gene by a two step site-directed mutagenesis PCR protocol. First, we generate overlapping 5' and a 3' amplicons surrounding the mutation site by PCR for each of the point mutation sites. A 215 bp 5' amplicon for the (rep), (Δ) or (ins) was generated by polymerization from oligonucleotide primer HygEGFPf (5'-AATACGACTCACTATAGG-3'; SEQ ID NO: 4369) to primer Hygrepr (5'GACCTATCCACGCCCTCC-3'; SEQ ID NO: 4370), HygΔr (5'-GACTATCCACGCCCTCC-3'; SEQ ID NO: 4371), or Hyginsr (5'-GACATTATCCACGCCCTCC-3'; SEQ ID NO: 4372), respectively. We generate a 300 bp 3' amplicon for the (rep), (Δ) or (ins) by polymerization from oligonucleotide primers Hygrepf (5'-CTGGGATAGGTCCTGCGG-3'; SEQ ID NO: 4373), HygΔf (5'-CGTGGATAGTCCTGCGG-3'; SEQ ID NO: 4374), Hyginsf (5'-CGTGGATMTGTCCTGCGG-3'; SEQ ID NO: 4375), respectively to primer HygEGFPr (5'-AAATCACGCCATGTAGTG-3'; SEQ ID NO: 4376). We mix 20 ng of each of the resultant 5' and 3' overlapping amplicon mutation sets and use the mixture as a template to amplify a 523 bp fragment of the Hygromycin gene spanning the KpnI and RsrII restriction endonuclease sites. We use the Expand PCR system (Roche) to generate all amplicons with 25 cycles of denaturing at 94° C. for 10 seconds, annealing at 55° C. for 20 seconds and elongation at 68° C. for 1 minute. We digest 10 μg of vector pHygEGFP and 5 μg of the resulting fragments for each mutation with KpnI and RsrII (NEB) and gel purify the fragment for enzymatic ligation. We ligate each mutated insert into pHygEGFP vector at 3:1 molar ration using T4 DNA ligase (Roche). We screen clones by restriction digest, confirm the mutation by Sanger dideoxy chain termination sequencing and purify the plasmid using a Qiagen maxiprep kit.

Oligonucleotide synthesis and cells. Chimeric oligonucleotides and single-stranded oligonucleotides (including those with the indicated modifications) are synthesized using available phosphoramidites on controlled pore glass supports. After deprotection and detachment from the solid support, each oligonucleotide is gel-purified using, for example, procedures such as those described in Gamper et al., Biochem. 39, 5808–5816 (2000) and the concentrations determined spectrophotometrically (33 or 40 μg/ml per $A_{260}$ unit of single-stranded or hairpin oligomer). HUH7 cells are grown in DMEM, 10% FBS, 2 mM glutamine, 0.5% pen/strep. The E. coli strain, DH10B, is obtained from Life Technologies (Gaithersburg, Md.); DH10B cells contain a mutation in the RECA gene (recA).

Cell-free extracts. We prepare cell-free extracts from HUH7 cells or other mammalian cells, as follows. We employ this protocol with essentially any mammalian cell including, for example, H1299 cells (human epithelial carcinoma, non-small cell lung cancer), C127I (immortal murine mammary epithelial cells), MEF (mouse embryonic fibroblasts), HEC-1-A (human uterine carcinoma), HCT15 (human colon cancer), HCT116 (human colon carcinoma), LoVo (human colon adenocarcinoma), and HeLa (human cervical carcinoma). We harvest approximately $2 \times 10^8$ cells. We then wash the cells immediately in cold hypotonic buffer (20 mM HEPES, pH7.5; 5 mM KCl; 1.5 mM $MgCl_2$; 1 mM DTT) with 250 mM sucrose. We then resuspend the cells in cold hypotonic buffer without sucrose and after 15 minutes we lyse the cells with 25 strokes of a Dounce homogenizer using a tight fitting pestle. We incubate the lysed cells for 60 minutes on ice and centrifuge the sample for 15 minutes at 12000×g. The cytoplasmic fraction is enriched with nuclear proteins due to the extended co-incubation of the fractions following cell breakage. We then immediately aliquote and freeze the supernatant at −80° C. We determine the protein concentration in the extract by the Bradford assay.

We also perform these experiments with cell-free extracts obtained from fungal cells, including, for example, S. cerevisiae (yeast), Ustilago maydis, and Candida albicans. For example, we grow yeast cells into log phase in 2L YPD medium for 3 days at 30° C. We then centrifuge the cultures at 5000×g, resuspend the pellets in a 10% sucrose, 50 mM Tris, 1 mM EDTA lysis solution and freeze them on dry ice. After thawing, we add KCl, spermidine and lyticase to final concentrations of 0.25 mM, 5 mM and 0.1 mg/ml, respectively. We incubate the suspension on ice for 60 minutes, add PMSF and Triton X100 to final concentrations of 0.1 mM and 0.1% and continue to incubate on ice for 20 minutes. We centrifuge the lysate at 3000×g for 10 minutes to remove larger debris. We then remove the supernatant and clarify it by centrifuging at 30000×g for 15 minutes. We then add glycerol to the clarified extract to a concentration of 10% (v/v) and freeze aliquots at −80° C. We determine the protein concentration of the extract by the Bradford assay.

Reaction mixtures of 50 μl are used, consisting of 10–30 μg protein of cell-free extract, which can be optionally substituted with purified proteins or enriched fractions, about 1.5 μg chimeric double-hairpin oligonucleotide or 0.55 μg single-stranded molecule (3S/25G or 6S/25G, see FIG. 1), and 1 μg of plasmid DNA (see FIGS. 2 and 3) in a reaction buffer of 20 mM Tris, pH 7.4, 15 mM $MgCl_2$, 0.4 mM DTT, and 1.0 mM ATP. Reactions are initiated with extract and incubated at 30° C. for 45 min. The reaction is stopped by placing the tubes on ice and then immediately deproteinized by two phenol/chloroform (1:1) extractions. Samples are then ethanol precipitated. The nucleic acid is pelleted at 15,000 r.p.m. at 4° C. for 30 min., is washed with 70% ethanol, resuspended in 50 μl $H_2O$, and is stored at −20° C. 5 μl of plasmid from the resuspension (~100 ng) was transfected in 20 μl of DH10B cells by electroporation (400 V, 300 μF, 4 kΩ) in a Cell-Porator apparatus (Life Technologies). After electroporation, cells are transferred to a 14 ml Falcon snap-cap tube with 2 ml SOC and shaken at 37° C. for 1 h. Enhancement of final kan colony counts is achieved by then adding 3 ml SOC with 10 μg/ml kanamycin and the cell suspension is shaken for a further 2 h at 37° C. Cells are then spun down at 3750×g and the pellet is resuspended in 500 μl, SOC. 200 μl is added undiluted to each of two kanamycin (50 μg/ml) agar plates and 200 μl of a $10^5$ dilution is added to an ampicillin (100 μg/ml) plate. After overnight 37° C. incubation, bacterial colonies are counted using an Accucount 1000 (Biologics). Gene conversion effectiveness is measured as the ratio of the average of the kan colonies on both plates per amp colonies multiplied by $10^{-5}$ to correct for the amp dilution.

The following procedure can also be used. 5 μl of resuspended reaction mixtures (total volume 50 μl) are used to transform 20 μl aliquots of electro-competent ΔH10B bacteria using a Cell-Porator apparatus (Life Technologies). The mixtures are allowed to recover in 1 ml SOC at 37° C. for 1 hour at which time 50 μg/ml kanamycin or 12 μg/ml tetracycline is added for an additional 3 hours. Prior to plating, the bacteria are pelleted and resuspended in 200 μl of SOC. 100 μl aliquots are plated onto kan or tet agar plates and 100 μl of a $10^{-4}$ dilution of the cultures are concurrently plated on agar plates containing 100 μg/ml of ampicillin. Plating is performed in triplicate using sterile Pyrex beads. Colony counts are determined by an Accu-count 1000 plate reader (Biologics). Each plate contains 200–500 ampicillin resistant colonies or 0–500 tetracycline or kanamycin resistant colonies. Resistant colonies are selected for plasmid extraction and DNA sequencing using an ABI Prism kit on an ABI 310 capillary sequencer (PE Biosystems).

Chimeric single-stranded oligonucleotides. In FIG. 1 the upper strands of chimeric oligonucleotides I and II are separated into pathways resulting in the generation of single-stranded oligonucleotides that contain (FIG. 1A) 2'-O-methyl RNA nucleotides or (FIG. 1 B) phosphorothioate linkages. Fold changes in repair activity for correction of kan$^s$ in the HUH7 cell-free extract are presented in parenthesis. Each single-stranded oligonucleotide is 25 bases in length and contains a G residue mismatched to the complementary sequence of the kan$^s$ gene.

Figure 1B:
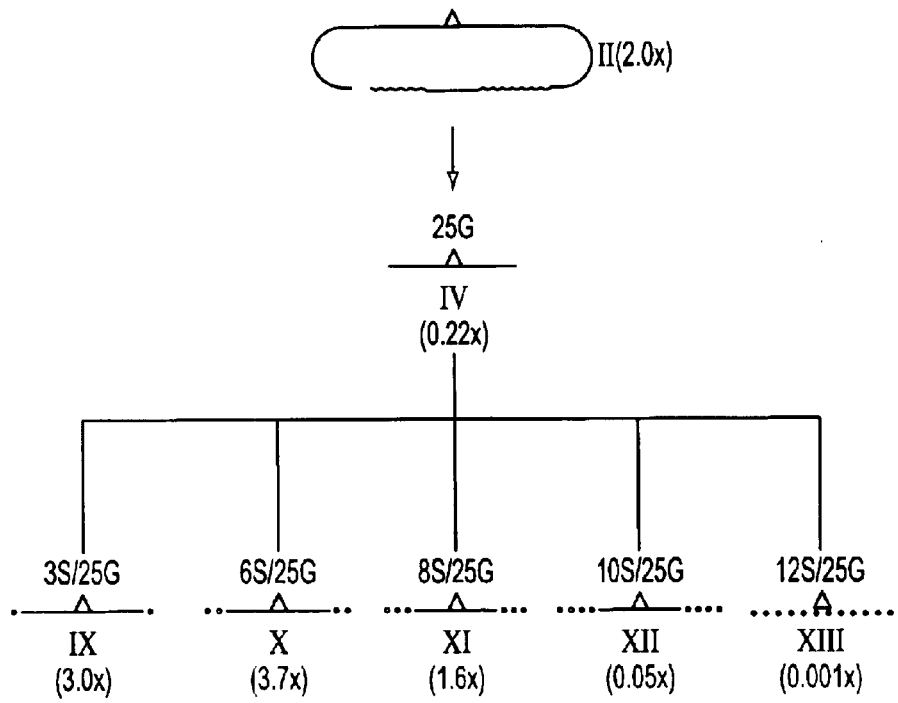
Figure 1C:
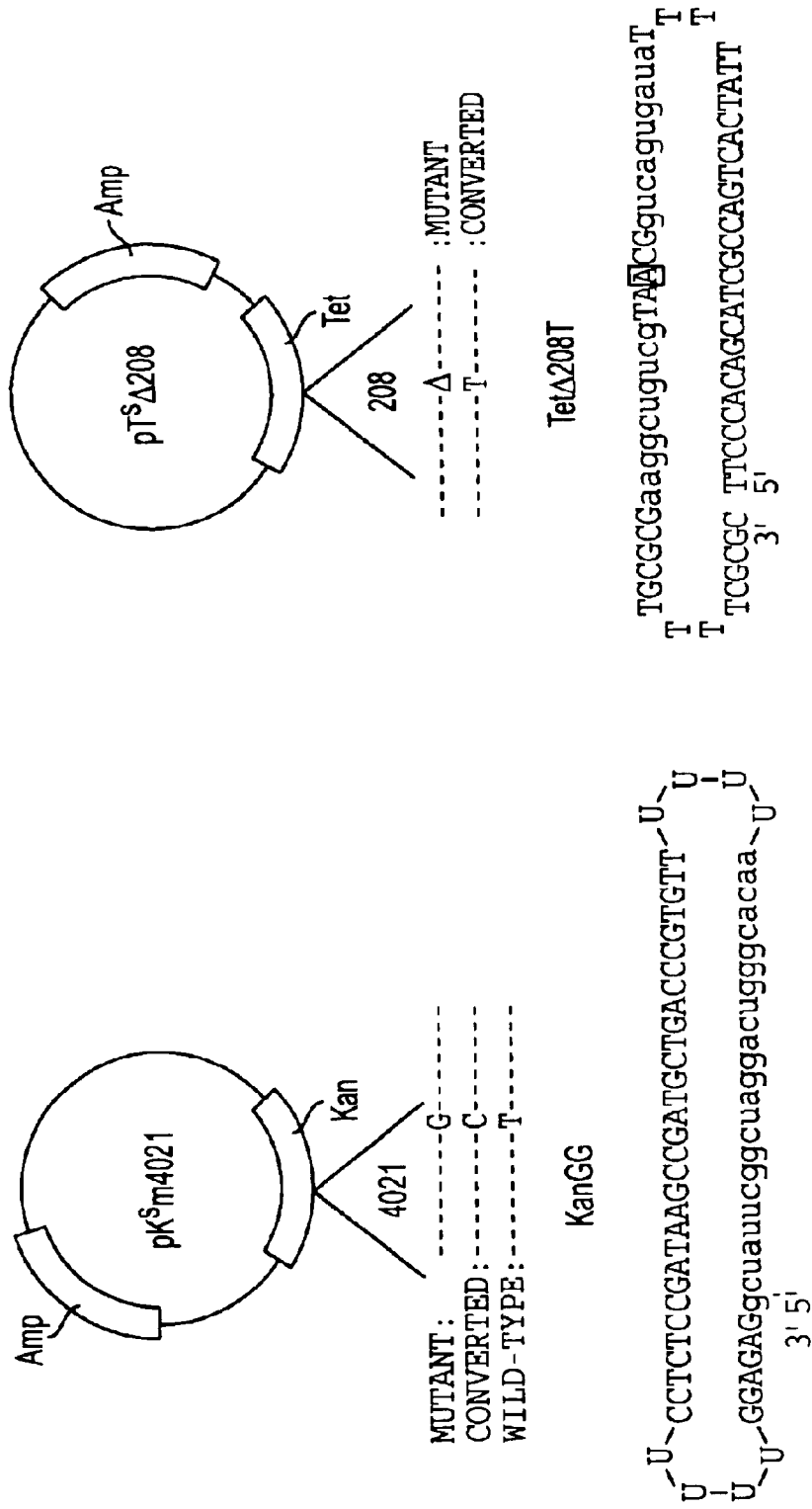
Figure 1D:
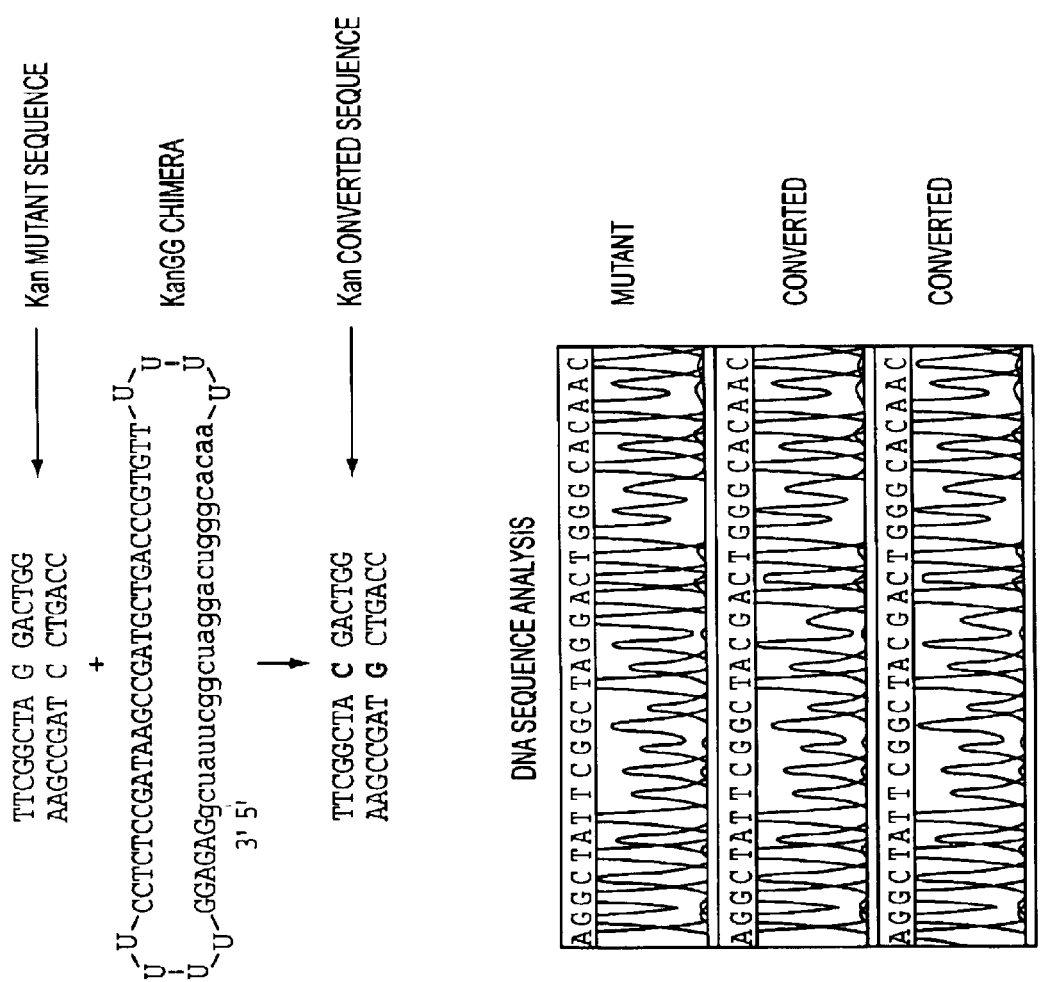
Figure 2:
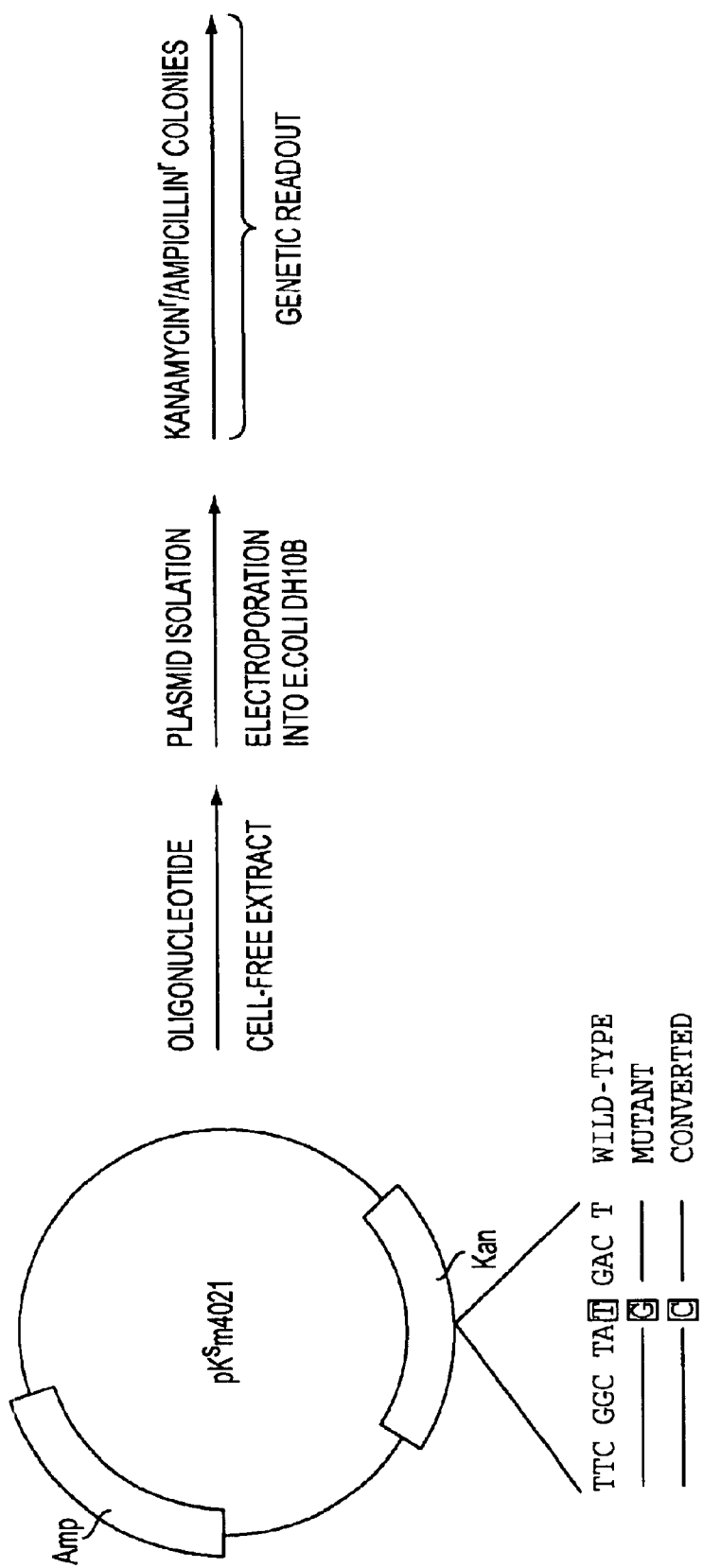
FIG. 2. Genetic readout system for correction of a point mutation in plasmid pK$^s$m4021. A mutant kanamycin gene harbored in plasmid pK$^s$m4021 is the target for correction by oligonucleotides. The mutant G is converted to a C by the action of the oligo. Corrected plasmids confer resistance to kanamycin in E. coli (DH10B) after electroporation leading to the genetic readout and colony counts. The wild type sequence corresponds to SEQ ID NO: 4349.

Molecules bearing 3, 6, 8, 10 and 12 phosphorothioate linkages in the terminal regions at each end of a backbone with a total of 24 linkages (25 bases) are tested in the kan$^s$ system. Alternatively, molecules bearing 2, 4, 5, 7, 9 and 11 in the terminal regions at each end are tested. The results of one such experiment, presented in Table 1 and FIG. 1B, illustrate an enhancement of correction activity directed by some of these modified structures. In this illustrative example, the most efficient molecules contained 3 or 6 phosphorothioate linkages at each end of the 25-mer; the activities are approximately equal (molecules IX and X with results of 3.09 and 3.7 respectively). A reduction in alteration activity may be observed as the number of modified linkages in the molecule is further increased. Interestingly, a single-strand molecule containing 24 phosphorothioate linkages is minimally active suggesting that this backbone modification when used throughout the molecule supports only a low level of targeted gene repair or alteration. Such a non-altering, completely modified molecule can provide a baseline control for determining efficiency of correction for a specific oligonucleotide molecule of known sequence in defining the optimum oligonucleotide for a particular alteration event.

The efficiency of gene repair directed by phosphorothioate-modified, single-stranded molecules, in a length dependent fashion, led us to examine the length of the RNA modification used in the original chimera as it relates to correction. Construct III represents the "RNA-containing" strand of chimera I and, as shown in Table 1 and FIG. 2A, it promotes inefficient gene repair. But, as shown in the same figure, reducing the RNA residues on each end from 10 to 3 increases the frequency of repair. At equal levels of modification, however, 25-mers with 2'-O-methyl ribonucleotides were less effective gene repair agents than the same oligomers with phosphorothioate linkages. These results reinforce the fact that an RNA containing oligonucleotide is not as effective in promoting gene repair or alteration as a modified DNA oligonucleotide.

Repair of the kanamycin mutation requires a G→C exchange. To confirm that the specific desired correction alteration was obtained, colonies selected at random from multiple experiments are processed and the isolated plasmid DNA is sequenced. As seen in FIG. 4, colonies generated through the action of the single-stranded molecules 3S/25G (IX), 6S/25G (X) and 8S/25G (XI) respectively contained plasmid molecules harboring the targeted base correction. While a few colonies appeared on plates derived from reaction mixtures containing 25-mers with 10 or 12 thioate linkages on both ends, the sequences of the plasmid molecules from these colonies contain nonspecific base changes. In these illustrative examples, the second base of the codon is changed (see FIG. 3). These results show that modified single-strands can direct gene repair, but that efficiency and specificity are reduced when the 25-mers contain 10 or more phosphorothioate linkages at each end.

In FIG. 1, the numbers 3, 6, 8, 10, 12 and 12.5 respectively indicate how many phosphorothioate linkages (S) or 2'-O-methyl RNA nucleotides (R) are at each end of the examplified molecule although other molecules with 2, 4, 5, 7, 9 and 11 modifications at each end can also be tested. Hence oligo 12S/25G represents a 25-mer oligonucleotide which contains 12 phosphorothioate linkages on each side of the central G target mismatch base producing a fully phosphorothioate linked backbone, displayed as a dotted line. The dots are merely representative of a linkage in the figure and do not depict the actual number of linkages of the oligonucleotide. Smooth lines indicate DNA residues, wavy lines indicate 2'-O-methyl RNA residues and the carat indicates the mismatched base site (G).

Correction of a mutant kanamycin gene in cultured mammalian cells. The experiments are performed using different mammalian cells, including, for example, 293 cells (transformed human primary kidney cells), HeLa cells (human cervical carcinoma), and H1299 (human epithelial carcinoma, non-small cell lung cancer). HeLa cells are grown at 37° C. and 5% $CO_2$ in a humidified incubator to a density of $2\times10^5$ cells/ml in an 8 chamber slide (Lab-Tek). After replacing the regular DMEM with Optimem, the cells are co-transfected with 10 μg of plasmid pAURNeo(−) FIAsH and 5 μg of modified single-stranded oligonucleotide (3S/25G) that is previously complexed with 10 μg lipofectamine, according to the manufacturer's directions (Life Technologies). The cells are treated with the liposome-DNA-oligo mix for 6 hrs at 37° C. Treated cells are washed with PBS and fresh DMEM is added. After a 16–18 hr recovery period, the culture is assayed for gene repair. The same oligonucleotide used in the cell-free extract experiments is used to target transfected plasmid bearing the kan$^s$ gene. Correction of the point mutation in this gene eliminates a stop codon and restores full expression. This expression can be detected by adding a small non-fluorescent ligand that bound to a C-C-R-E-C-C (SEQ ID NO: 4385) sequence in the genetically modified carboxy terminus of the kan protein, to produce a highly fluorescent complex (FIAsH system, Aurora Biosciences Corporation). Following a 60 min incubation at room temperature with the ligand (FIAsH-EDT2),cells expressing full length kan product acquire an intense green fluorescence detectable by fluorescence microscopy using a fluorescein filter set. Similar experiments are performed using the HygeGFP target as described in Example 2 with a variety of mammalian cells, including, for example, COS-1 and COS-7 cells (African green monkey), and CHO-K1 cells (Chinese hamster ovary). The experiments are also performed with PG12 cells (rat pheochromocytoma) and ES cells (human embryonic stem cells).

Summary of experimental results. Tables 1, 2 and 3 respectively provide data on the efficiency of gene repair directed by single-stranded oligonucleotides. Table 1 presents data using a cell-free extract from human liver cells (HUH7) to catalyze repair of the point mutation in plasmid pkan$^s$m4021 (see FIG. 1). Table 2 illustrates that the oligomers are not dependent on MSH2 or MSH3 for optimal gene repair activity. Table 3 illustrates data from the repair of a frameshift mutation (FIG. 3) in the tet gene contained in plasmid pTetΔ208. Table 4 illustrates data from repair of the pkan$^s$m4021 point mutation catalyzed by plant cell extracts prepared from canola and musa (banana). Colony numbers are presented as kan$^r$ or tet$^r$ and fold increases (single strand versus double hairpin) are presented for kan$^r$ in Table 1.

Figure 5:
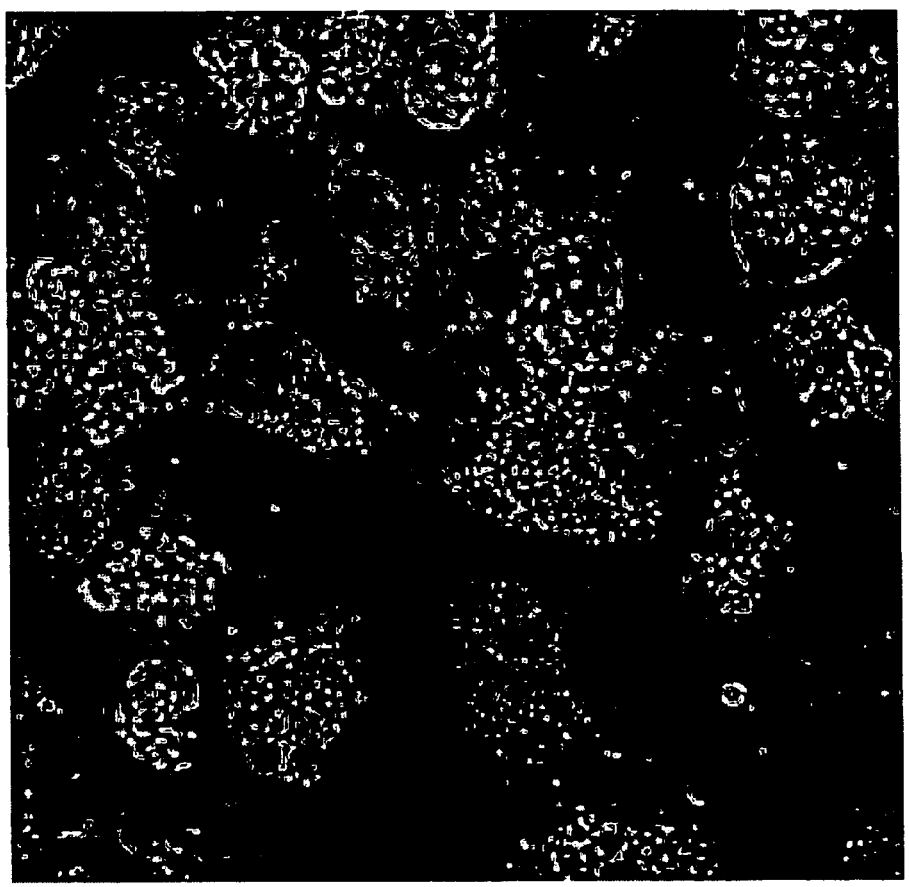
FIG. 5. Gene correction in HeLa cells. Representative oligonucleotides of the invention are co-transfected with the pCMVneo(−)FIAsH plasmid (shown in FIG. 9) into HeLa cells. Ligand is diffused into cells after co-transfection of plasmid and oligonucleotides. Green fluorescence indicates gene correction of the mutation in the antibiotic resistance gene. Correction of the mutation results in the expression of a fusion protein that carries a marker ligand binding site and when the fusion protein binds the ligand, a green fluorescence is emitted. The ligand is produced by Aurora Biosciences and can readily diffuse into cells enabling a measurement of corrected protein function; the protein must bind the ligand directly to induce fluorescence. Hence cells bearing the corrected plasmid gene appear green while "uncorrected" cells remain colorless.
Figure 6:
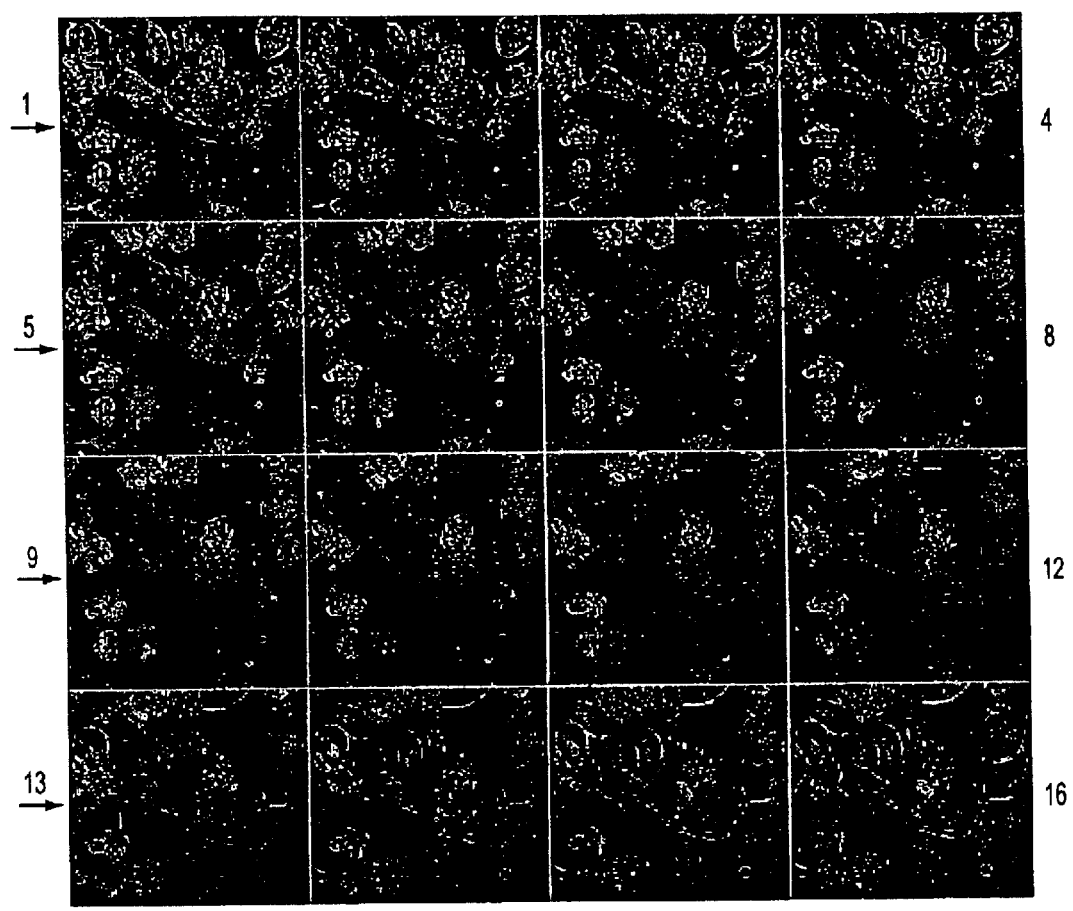
FIG. 6. Z-series imaging of corrected cells. Serial cross-sections of the HeLa cell represented in FIG. 5 are produced by Zeiss 510 LSM confocal microscope revealing that the fusion protein is contained within the cell.

FIG. 5A is a confocal picture of HeLa cells expressing corrected fusion protein from an episomal target. Gene repair is accomplished by the action of a modified single-stranded oligonucleotide containing 3 phosphorothioate linkages at each end (3S/25G). FIG. 5B represents a "Z-series" of HeLa cells bearing the corrected fusion gene. This series sections the cells from bottom to top and illustrates that the fluorescent signal is "inside the cells".

Results. In summary, we have designed a novel class of single-stranded oligonucleotides with backbone modifications at the termini and demonstrate gene repair/conversion activity in mammalian and plant cell-free extracts. We confirm that the all DNA strand of the RNA-DNA double-stranded double hairpin chimera is the active component in the process of gene repair. In some cases, the relative frequency of repair by the novel oligonucleotides of the invention is elevated approximately 3–4-fold when compared to frequencies directed by chimeric RNA-DNA double hairpin oligonucleotides.

This strategy centers around the use of extracts from various sources to correct a mutation in a plasmid using a modified single-stranded or a chimeric RNA-DNA double hairpin oligonucleotide. A mutation is placed inside the coding region of a gene conferring antibiotic resistance in bacteria, here kanamycin or tetracycline. The appearance of resistance is measured by genetic readout in $E.$ $coli$ grown in the presence of the specified antibiotic. The importance of this system is that both phenotypic alteration and genetic inheritance can be measured. Plasmid pK$^s$m4021 contains a mutation (T→G) at residue 4021 rendering it unable to confer antibiotic resistance in $E.$ $coli$. This point mutation is targeted for repair by oligonucleotides designed to restore kanamycin resistance. To avoid concerns of plasmid contamination skewing the colony counts, the directed correction is from G→C rather than G→T (wild-type). After isolation, the plasmid is electroporated into the DH10B strain of $E.$ $coli$, which contains inactive RecA protein. The number of kanamycin colonies is counted and normalized by ascertaining the number of ampicillin colonies, a process that controls for the influence of electroporation. The number of colonies generated from three to five independent reactions was averaged and is presented for each experiment. A fold increase number is recorded to aid in comparison.

The original RNA-DNA double hairpin chimera design, e.g., as disclosed in U.S. Pat. No. 5,565,350, consists of two hybridized regions of a single-stranded oligonucleotide folded into a double hairpin configuration. The double-stranded targeting region is made up of a 5 base pair DNA/DNA segment bracketed by 10 base pair RNA/DNA segments. The central base pair is mismatched to the corresponding base pair in the target gene. When a molecule of this design is used to correct the kan$^s$ mutation, gene repair is observed (I in FIG. 1A). Chimera II (FIG. 1B) differs partly from chimera I in that only the DNA strand of the double hairpin is mismatched to the target sequence. When this chimera was used to correct the kan$^s$ mutation, it was twice as active. In the same study, repair function could be further increased by making the targeting region of the chimera a continuous RNA/DNA hybrid.

Frame shift mutations are repaired. By using plasmid pT$^s$Δ208, described in FIG. 1(C) and FIG. 3, the capacity of the modified single-stranded molecules that showed activity in correcting a point mutation, can be tested for repair of a frameshift. To determine efficiency of correction of the mutation, a chimeric oligonucleotide (Tet I), which is designed to insert a T residue at position 208, is used. A modified single-stranded oligonucleotide (Tet IX) directs the insertion of a T residue at this same site. FIG. 3 illustrates the plasmid and target bases designated for change in the experiments. When all reaction components are present (extract, plasmid, oligomer), tetracycline resistant colonies appear. The colony count increases with the amount of oligonucleotide used up to a point beyond which the count falls off (Table 3). No colonies above background are observed in the absence of either extract or oligonucleotide, nor when a modified single-stranded molecule bearing perfect complementarity is used. FIG. 3 represents the sequence surrounding the target site and shows that a T residue is inserted at the correct site. We have isolated plasmids from fifteen colonies obtained in three independent experiments and each analyzed sequence revealed the same precise nucleotide insertion. These data suggest that the single-stranded molecules used initially for point mutation correction can also repair nucleotide deletions.

Comparison of phosphorothioate oligonucleotides to 2'-O-methyl substituted oligonucleotides. From a comparison of molecules VII and XI, it is apparent that gene repair is more subject to inhibition by RNA residues than by phosphorothioate linkages. Thus, even though both of these oligonucleotides contain an equal number of modifications to impart nuclease resistance, XI (with 16 phosphorothioate linkages) has good gene repair activity while VII (with 16 2'-O-methyl RNA residues) is inactive. Hence, the original chimeric double hairpin oligonucleotide enabled correction directed, in large part, by the strand containing a large region of contiguous DNA residues.

Oligonucleotides can target multiple nucleotide alterations within the same template. The ability of individual single-stranded oligonucleotides to correct multiple mutations in a single target template is tested using the plasmid pK$^s$m4021 and the following single-stranded oligonucleotides modified with 3 phosphorothioate linkages at each end (indicated as underlined nucleotides): Oligo1 is a 25-mer with the sequence TTCGATAAGCCTATGCTGACCCGTG (SEQ ID NO: 4377) corrects the original mutation present in the kanamycin resistance gene of pK$^s$m4021 as well as directing another alteration 2 basepairs away in the target sequence (both indicated in boldface); Oligo2 is a 70-mer with the 5'-end sequence TTCGGCTACGACTGGGCACAACAG-ACAATTGGC (SEQ ID NO: 4378) with the remaining nucleotides being completely complementary to the kanamycin resistance gene and also ending in 3 phosphorothioate linkages at the 3' end. Oligo2 directs correction of the mutation in pK$^s$m4021 as well as directing another alteration 21 basepairs away in the target sequence (both indicated in boldface).

We also use additional oligonucleotides to assay the ability of individual oligonucleotides to correct multiple mutations in the pK$^s$M4021 plasmid. These include, for example, a second 25-mer that alters two nucleotides that are three nucleotides apart with the sequence 5'-TTGTGCCCAGTCGTATCCGAATAGC-3' (SEQ ID NO: 4379); a 70-mer that alters two nucleotides that are 21 nucleotides apart with the sequence 5'-CATCAGAGCAGCCAATTGTCTGTTGTGCCCAGTC-GTAGCCGAATAGCCTCTCCACCCAAGCGGCCGGAG-A-3' (SEQ ID NO: 4380); and another 70-mer that alters two nucleotides that are 21 nucleotides apart with the sequence 5'-GCTGACAGCCGGAACACGGCGGCATCA- GAG-CAGCCAATTGTCTGTTGTGCCCAGTC GTAGCCGAATAGCCT-3' (SEQ ID NO: 4381). The nucleotides in the oligonucleotides that direct alteration of the target sequence are underlined and in boldface. These oligonucleotides are modified in the same way as the other oligonucleotides of the invention.

We assay correction of the original mutation in pK$^s$m4021 by monitoring kanamycin resistance (the second alterations which are directed by Oligo2 and Oligo3 are silent with respect to the kanamycin resistance phenotype). In addition, in experiments with Oligo2, we also monitor cleavage of the resulting plasmids using the restriction enzyme Tsp509I which cuts at a specific site present only when the second alteration has occurred (at ATT in Oligo2). We then sequence these clones to determine whether the additional, silent alteration has also been introduced. The results of an analysis are presented below:

|  | Oligo1 (25-mer) | Oligo2 (70-mer) |
|---|---|---|
| Clones with both sites changed | 9 | 7 |
| Clones with a single site changed | 0 | 2 |
| Clones that were not changed | 4 | 1 |

Nuclease sensitivity of unmodified DNA oligonucleotide. Electrophoretic analysis of nucleic acid recovered from the cell-free extract reactions conducted here confirm that the unmodified single-stranded 25-mer did not survive incubation whereas greater than 90% of the terminally modified oligos did survive (as judged by photo-image analyses of agarose gels).

Plant extracts direct repair. The modified single-stranded constructs can be tested in plant cell extracts. We have observed gene alteration using extracts from multiple plant sources, including, for example, Arabidopsis, tobacco, banana, maize, soybean, canola, wheat, spinach as well as spinach chloroplast extract We prepare the extracts by grinding plant tissue or cultured cells under liquid nitrogen with a mortar and pestle. We extract 3 ml of the ground plant tissue with 1.5 ml of extraction buffer (20 mM HEPES, pH7.5; 5 mM Kcl; 1.5 mM MgCl$_2$; 10 mM DTT; 10% [v/v] glycerol; and 1% [w/v] PVP). We then homogenize the samples with 15 strokes of a Dounce homogenizer. Following homogenization, we incubate the samples on ice for 1 hour and centrifuge at 3000×g for 5 minutes to remove plant cell debris. We then determine the protein concentration in the supernatants (extracts) by Bradford assay. We dispense 100 μg (protein) aliquots of the extracts which we freeze in a dry ice-ethanol bath and store at −80° C.

We describe experiments using two sources here: a dicot (canola) and a monocot (banana, *Musa acuminata* cv. Rasthali). Each vector directs gene repair of the kanamycin mutation (Table 4); however, the level of correction is elevated 2–3 fold relative to the frequency observed with the chimeric oligonucleotide. These results are similar to those observed in the mammalian system wherein a significant improvement in gene repair occurred when modified single-stranded molecules were used.

Tables are attached hereto.

TABLE I

Gene repair activity is directed by single-stranded oligonucleotides.

| Oligonucleotide | Plasmid | Extract (ug) | kan$^r$ colonies | Fold increase |
|---|---|---|---|---|
| I | pK$^s$m4021 | 10 | 300 | |
| I | I | 20 | 418 | 1.0 × |
| II | I | 10 | 537 | |
| II | I | 20 | 748 | 1.78 × |
| III | I | 10 | 3 | |
| III | I | 20 | 5 | 0.01 × |

TABLE I-continued

Gene repair activity is directed by single-stranded oligonucleotides.

| Oligonucleotide | Plasmid | Extract (ug) | kan$^r$ colonies | Fold increase |
|---|---|---|---|---|
| IV | I | 10 | 112 | |
| IV | I | 20 | 96 | 0.22 × |
| V | I | 10 | 217 | |
| V | I | 20 | 342 | 0.81 × |
| VI | I | 10 | 6 | |
| VI | I | 20 | 39 | 0.093 × |
| VII | I | 10 | 0 | |
| VII | I | 20 | 0 | 0 × |
| VIII | I | 10 | 3 | |
| VIII | I | 20 | 5 | 0.01 × |
| IX | I | 10 | 936 | |
| IX | I | 20 | 1295 | 3.09 × |
| X | I | 10 | 1140 | |
| X | I | 20 | 1588 | 3.7 × |
| XI | I | 10 | 480 | |
| XI | I | 20 | 681 | 1.6 × |
| XII | I | 10 | 18 | |
| XII | I | 20 | 25 | 0.059 × |
| XIII | I | 10 | 0 | |
| XIII | I | 20 | 4 | 0.009 × |
| — | I | 20 | 0 | |
| I | I | — | 0 | |

Plasmid pK$^s$m4021 (1 μg), the indicated oligonucleotide (1.5 μg chimeric oligonucleotide or 0.55 μg single-stranded oligonucleotide; molar ratio of oligo to plasmid of 360 to 1) and either 10 or 20 μg of HUH7 cell-free extract were incubated 45 min at 37° C. Isolated plasmid DNA was electroporated into *E. coli* (strain DH10B) and the number of kan$^r$ colonies counted. The data represent the number of kanamycin resistant colonies per 10$^6$ ampicillin resistant colonies generated from the same reaction and is the average of three experiments (standard deviation usually less than +/−15%). Fold increase is defined relative to 418 kan$^r$ colonies (second reaction) and in all reactions was calculated using the 20 μg sample.

TABLE II

Modified single-stranded oligomers are not dependent on MSH2 or MSH3 for optimal gene repair activity.

| A. Oligonucleotide | Plasmid | Extract | kan$^r$ colonies |
|---|---|---|---|
| IX (3S/25G) | I | HUH7 | 637 |
| X (6S/25G) | I | HUH7 | 836 |
| IX | I | MEF2$^{-/-}$ | 781 |
| X | I | MEF2$^{-/-}$ | 676 |
| IX | I | MEF3$^{-/-}$ | 582 |
| X | I | MEF3$^{-/-}$ | 530 |
| IX | I | MEF$^{+/+}$ | 332 |
| X | I | MEF$^{+/+}$ | 497 |
| — | I | MEF2$^{-/-}$ | 10 |
| — | I | MEF3$^{-/-}$ | 5 |
| — | I | MEF$^{+/+}$ | 14 |

Chimeric oligonucleotide (1.5 μg) or modified single-stranded oligonucleotide (0.55 μg) was incubated with 1 μg of plasmid pK$^s$m4021 and 20 μg of the indicated extracts. MEF represents mouse embryonic fibroblasts with either MSH2 (2$^{-/-}$) or MSH3 (3$^{-/-}$) deleted. MEF$^{+/+}$ indicates wild-type mouse embryonic fibroblasts. The other reaction components were then added and processed through the bacterial readout system. The data represent the number of kanamycin resistant colonies per 10$^6$ ampicillin resistant colonies.

TABLE III

Frameshift mutation repair is directed by single-stranded oligonucleotides

| Oligonucleotide | Plasmid | Extract | tet$^r$ colonies |
|---|---|---|---|
| Tet IX (3S/25A; 0.5 μg) | pT$^s$Δ208 (1 μg) | — | 0 |
| — | 1 | 20 μg | 0 |
| Tet IX (0.5 μg) | 1 | 1 | 48 |
| Tet IX (1.5 μg) | 1 | 1 | 130 |
| Tet IX (2.0 μg) | 1 | 1 | 68 |
| Tet I (chimera; 1.5 μg) | 1 | 1 | 48 |

Each reaction mixture contained the indicated amounts of plasmid and oligonucleotide. The extract used for these experiments came from HUH7 cells. The data represent the number of tetracycline resistant colonies per $10^6$ ampicillin resistant colonies generated from the same reaction and is the average of 3 independent experiments. Tet I is a chimeric oligonucleotide and Tet IX is a modified single-stranded oligonucleotide that are designed to insert a T residue at position 208 of pT$^s$Δ208. These oligonucleotides are equivalent to structures I and IX in FIG. 2.

TABLE IV

Plant cell-free extracts support gene repair by single-stranded oligonucleotides

| Oligonucleotide | Plasmid | Extract | kan$^r$ colonies |
|---|---|---|---|
| II (chimera) | pK$^s$m4021 | 30 μg Canola | 337 |
| IX (3S/25G) | 1 | Canola | 763 |
| X (6S/25G) | 1 | Canola | 882 |
| II | 1 | Musa | 203 |
| IX | 1 | Musa | 343 |
| X | 1 | Musa | 746 |
| — | 1 | Canola | 0 |
| — | 1 | Musa | 0 |
| IX | 1 | — Canola | 0 |
| X | 1 | — Musa | 0 |

Canola or Musa cell-free extracts were tested for gene repair activity on the kanamycin-sensitive gene as previously described in (18). Chimeric oligonucleotide II (1.5 μg) and modified single-stranded oligonucleotides IX and X (0.55 μg) were used to correct pK$^s$m4021. Total number of kan$^r$ colonies are present per $10^7$ ampicillin resistant colonies and represent an average of four independent experiments.

TABLE V

Gene repair activity in cell-free extracts prepared from yeast (Saccharomyces cerevisiae)

| Cell-type | Plasmid | Chimeric Oligo | SS Oligo | kan$^r$/amp$^r$ × $10^6$ |
|---|---|---|---|---|
| Wild type | pKan$^s$m4021 | 1 μg | | 0.36 |
| Wild type | 1 | | 1 μg | 0.81 |
| ΔRAD52 | 1 | 1 μg | | 10.72 |
| ΔRAD52 | 1 | | 1 μg | 17.41 |
| ΔPMS1 | 1 | 1 μg | | 2.02 |
| ΔPMS1 | 1 | | 1 μg | 3.23 |

In this experiment, the kan$^r$ gene in pKan$^s$4021 is corrected by either a chimeric double-hairpin oligonucleotide or a single-stranded oligonucleotide containing three thioate linkages at each end (3S/25G).

EXAMPLE 2

Figures 7A, 7B:
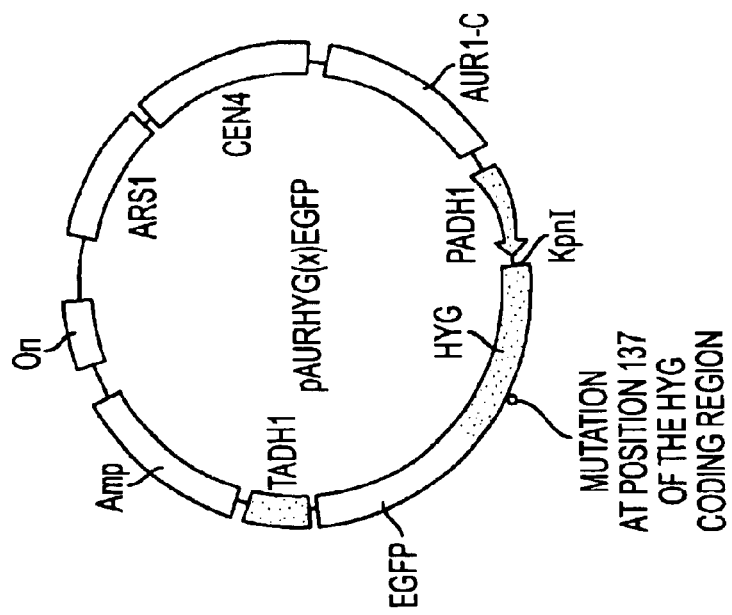
In FIG. 7A, the sequence of the normal allele corresponds to SEQ ID NO: 4359, the sequence of the target/existing mutation corresponds to SEQ ID NO: 4360 and the sequence of the desired alteration corresponds to SEQ ID NO: 4361. (B) Plasmid pAURHYG(rep)GFP contains a base substitution mutation introducing a G at nucleotide 137, at codon 46, of the Hygromycin B coding sequence (cds). The target sequence presented below the diagram indicates the amino acid conservative replacement of G with C, restoring gene function.
In FIG. 7B, the sequence of the normal allele corresponds to SEQ ID NO: 4359, the sequence of the target/existing mutation corresponds to SEQ ID NO: 4362 and the sequence of the desired alteration corresponds to SEQ ID NO: 4361.

Yeast Cell Targeting Assay Method for Base Alteration and Preferred Oligonucleotide Selection In this example, single-stranded oligonucleotides with modified backbones and double-hairpin oligonucleotides with chimeric, RNA-DNA backbones are used to measure gene repair using two episomal targets with a fusion between a hygromycin resistance gene and eGFP as a target for gene repair. These plasmids are pAURHYG(rep)GFP, which contains a point mutation in the hygromycin resistance gene (FIG. 7), pAURHYG(ins)GFP, which contains a single-base insertion in the hygromycin resistance gene (FIG. 7) and pAURHYG(Δ)GFP which has a single base deletion. We also use the plasmid containing a wild-type copy of the hygromycin-eGFP fusion gene, designated pAURHYG(wt) GFP, as a control. These plasmids also contain an aureobasidinA resistance gene. In pAURHYG(rep)GFP, hygromycin resistance gene function and green fluorescence from the eGFP protein are restored when a G at position 137, at codon 46 of the hygromycin B coding sequence, is converted to a C thus removing a premature stop codon in the hygromycin resistance gene coding region. In pAURHYG(ins)GFP, hygromycin resistance gene function and green fluorescence from the eGFP protein are restored when an A inserted between nucleotide positions 136 and 137, at codon 46 of the hygromycin B coding sequence, is deleted and a C is substituted for the T at position 137, thus correcting a frameshift mutation and restoring the reading frame of the hygromycin-eGFP fusion gene.

We synthesize the set of three yeast expression constructs pAURHYG(rep)eGFP, pAURHYG(Δ)eGFP, pAURHYG(ins)eGFP, that contain a point mutation at nucleotide 137 of the hygromycin-B coding sequence as follows. (rep) indicates a T137→G replacement, (Δ) represents a deletion of the G137 and (ins) represents an A insertion between nucleotides 136 and 137. We construct this set of plasmids by excising the respective expression cassettes by restriction digest from pHyg(x)EGFP and ligation into pAUR123 (Panvera, Calif.). We digest 10 μg pAUR123 vector DNA, as well as, 10 μg of each pHyg(x)EGFP construct with Kpnl and SalI (NEB). We gel purify each of the DNA fragments and prepare them for enzymatic ligation. We ligate each mutated insert into pHygEGFP vector at 3:1 molar ration using T4 DNA ligase (Roche). We screen clones by restriction digest, confirm by Sanger dideoxy chain termination sequencing and purify using a Qiagen maxiprep kit.

We use this system to assay the ability of five oligonucleotides (shown in FIG. 8) to support correction under a variety of conditions. The oligonucleotides which direct correction of the mutation in pAURHYG(rep)GFP can also direct correction of the mutation in pAURHYG(ins)GFP. Three of the four oligonucleotides (HygE3T/25, HygE3T/74 and HygGG/Rev) share the same 25-base sequence surrounding the base targeted for alteration. HygGG/Rev is an RNA-DNA chimeric double hairpin oligonucleotide of the type described in the prior art. One of these oligonucleotides, HygE3T/74, is a 74-base oligonucleotide with the 25-base sequence centrally positioned. The fourth oligonucleotide, designated HygE3T/74α, is the reverse complement of HygE3T/74. The fifth oligonucleotide, designated Kan70T, is a non-specific, control oligonucleotide which is not complementary to the target sequence. Alternatively, an oligonucleotide of identical sequence but lacking a mismatch to the target or a completely thioate modified oligonucleotide or a completely 2-O-methylated modified oligonucleotide may be used as a control.

Oligonucleotide synthesis and cells. We synthesized and purified the chimeric, double-hairpin oligonucleotides and single-stranded oligonucleotides (including those with the indicated modifications) as described in Example 1. Plasmids used for assay were maintained stably in yeast (Saccharomyces cerevisiae) strain LSY678 MAT α at low copy number under aureobasidin selection. Plasmids and oligonucleotides are introduced into yeast cells by electroporation as follows: to prepare electrocompetent yeast cells, we inoculate 10 ml of YPD media from a single colony and grow the cultures overnight with shaking at 300 rpm at 30° C. We then add 30 ml of fresh YPD media to the overnight cultures and continue shaking at 30° C. until the OD$_{600}$ was between 0.5 and 1.0 (3–5 hours) then wash the cells by centrifuging at 4° C. at 3000 rpm for 5 minutes and twice resuspending the cells in 25 ml ice-cold distilled water. We then centrifuge at 4° C. at 3000 rpm for 5 minutes and resuspend in 1 ml ice-cold 1M sorbitol and then finally centrifuge the cells at 4° C. at 5000 rpm for 5 minutes and resuspend the cells in 120 µl 1M sorbitol. To transform electrocompetent cells with plasmids or oligonucleotides, we mix 40 µl of cells with 5 µg of nucleic acid, unless otherwise stated, and incubate on ice for 5 minutes. We then transfer the mixture to a 0.2 cm electroporation cuvette and electroporate with a BIO-RAD Gene Pulser apparatus at 1.5 kV, 25 µF, 200Ω for one five-second pulse. We then immediately resuspend the cells in 1 ml YPD supplemented with 1M sorbitol and incubate the cultures at 30° C. with shaking at 300 rpm for 6 hours. We then spread 200 µl of this culture on selective plates containing 300 µg/ml hygromycin and spread 200 µl of a $10^5$ dilution of this culture on selective plates containing 500 ng/ml aureobasidinA and/or and incubate at 30° C. for 3 days to allow individual yeast colonies to grow. We then count the colonies on the plates and calculate the gene conversion efficiency by determining the number of hygromycin resistance colonies per $10^5$ aureobasidinA resistant colonies.

Frameshift mutations are repaired in yeast cells. We test the ability of the oligonucleotides shown in FIG. 8 to correct a frameshift mutation in vivo using LSY678 yeast cells containing the plasmid pAURHYG(ins)GFP. These experiments, presented in Table 6, indicate that these oligonucleotides can support gene correction in yeast cells. These data reinforce the results described in Example 1 indicating that oligonucleotides comprising phosphorothioate linkages facilitate gene correction much more efficiently than control duplex, chimeric RNA-DNA oligonucleotides. This gene correction activity is also specific as transformation of cells with the control oligonucleotide Kan70T produced no hygromycin resistant colonies above background and thus Kan70T did not support gene correction in this system. In addition, we observe that the 74-base oligonucleotide (HygE3T/74) corrects the mutation in pAURHYG(ins)GFP approximately five-fold more efficiently than the 25-base oligonucleotide (HygE3T/25). We also perform control experiments with LSY678 yeast cells containing the plasmid pAURHYG(wt)GFP. With this strain we observed that even without added oligonucleotides, there are too many hygromycin resistant colonies to count.

We also use additional oligonucleotides to assay the ability of individual oligonucleotides to correct multiple mutations in the pAURHYG(x)eGFP plasmid. These include, for example, one that alters two basepairs that are 3 nucleotides apart is a 74-mer with the sequence 5'-CTCGTGCTTTCAGCTTCGATGTAGGAGGGCGTG GGTACGTCCTGCGGGTAAATAGCTGCGCCGATGGT-TTCTAC-3' (SEQ ID NO: 4382); a 74-mer that alters two basepairs that are 15 nucleotides apart with the sequence 5'-CTCGTGCTTTCAGCTTCGATGTAGGAGGGCGTGG-ATACGTCCTGCGGGTAAACAGCTGCGCCGATGGT-TTCTAC-3' (SEQ ID NO: 4383); and a 74-mer that alters two basepairs that are 27 nucleotides apart with the sequence 5'-CTCGTGCTTTCAGCTTCGATGTAGGAGGGCGTG-GATACGTCCTGCGGGTAAATAGCTGCGCCGACGG-TTTCTAC (SEQ ID NO: 4384). The nucleotides in these oligonucleotides that direct alteration of the target sequence are underlined and in boldface. These oligonucleotides are modified in the same ways as the other oligonucleotides of the invention.

Figure 10:
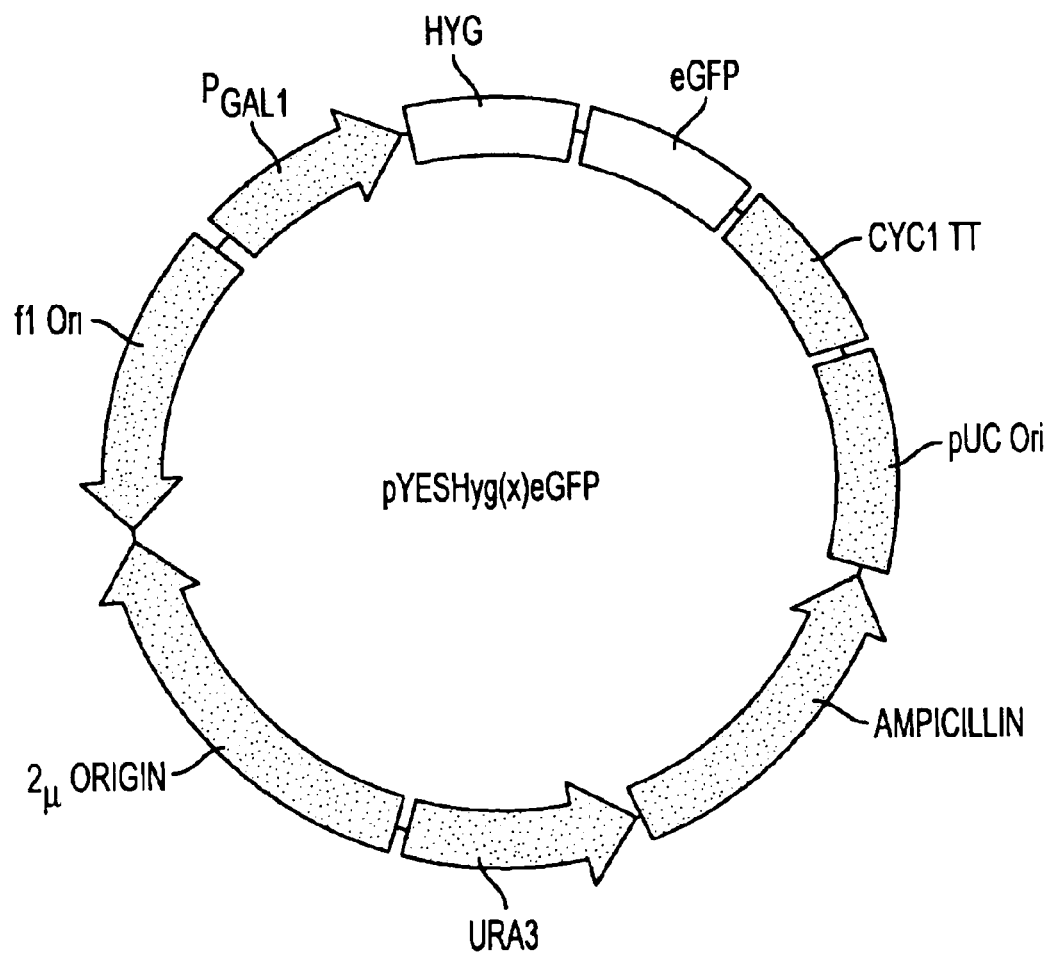
FIG. 10. pYESHyg(x)eGFP plasmid. This plasmid is a construct similar to the pAURHyg(x)eGFP construct shown in FIG. 7, except the promoter is the inducible GAL1 promoter. This promoter is inducible with galactose, leaky in the presence of raffinose, and repressed in the presence of dextrose.

Oligonucleotides targeting the sense strand direct gene correction more efficiently. We compare the ability of single-stranded oligonucleotides to target each of the two strands of the target sequence of both pAURHYG(ins)GFP and pAURHYG(rep)GFP. These experiments, presented in Tables 7 and 8, indicate that an oligonucleotide, HygE3T/74α, with sequence complementary to the sense strand (i.e. the strand of the target sequence that is identical to the mRNA) of the target sequence facilitates gene correction approximately ten-fold more efficiently than an oligonucleotide, HygE3T/74, with sequence complementary to the non-transcribed strand which serves as the template for the synthesis of RNA. As indicated in Table 7, this effect was observed over a range of oligonucleotide concentrations from 0–3.6 µg, although we did observe some variability in the difference between the two oligonucleotides (indicated in Table 7 as a fold difference between HygE3T/74α and HygE3T/74). Furthermore, as shown in Table 8, we observe increased efficiency of correction by HygE3T/74α relative to HygE3T/74 regardless of whether the oligonucleotides were used to correct the base substitution mutation in pAURHYG(rep)GFP or the insertion mutation in pAURHYG(ins)GFP. The data presented in Table 8 further indicate that the single-stranded oligonucleotides correct a base substitution mutation more efficiently than an insertion mutation. However, this last effect was much less pronounced and the oligonucleotides of the invention are clearly able efficiently to correct both types of mutations in yeast cells. In addition, the role of transcription is investigated using plasmids with inducible promoters such as that described in FIG. 10.

Optimization of oligonucleotide concentration. To determine the optimal concentration of oligonucleotide for the purpose of gene alteration, we test the ability of increasing concentrations of Hyg3T/74α to correct the mutation in pAURHYG(rep)GFP contained in yeast LSY678. We chose this assay system because our previous experiments indicated that it supports the highest level of correction. However, this same approach could be used to determine the optimal concentration of any given oligonucleotide. We test the ability of Hyg3T/74α to correct the mutation in pAURHYG(rep)GFP contained in yeast LSY678 over a range of oligonucleotide concentrations from 0–10.0 µg. As shown in Table 9, we observe that the correction efficiency initially increases with increasing oligonucleotide concentration, but then declines at the highest concentration tested.

Tables are attached hereto.

TABLE 6

Correction of an insertion mutation in pAURHYG(ins)GFP by HygGG/Rev, HygE3T/25 and HygE3T/74

| Oligonucleotide Tested | Colonies on Hygromycin | Colonies on Aureobasidin (/$10^5$) | Correction Efficiency |
| --- | --- | --- | --- |
| HygGG/Rev | 3 | 157 | 0.02 |
| HygE3T/25 | 64 | 147 | 0.44 |

TABLE 6-continued

Correction of an insertion mutation in pAURHYG(ins)GFP by HygGG/Rev, HygE3T/25 and HygE3T/74

| Oligonucleotide Tested | Colonies on Hygromycin | Colonies on Aureobasidin (/10⁵) | Correction Efficiency |
|---|---|---|---|
| HygE3T/74 | 280 | 174 | 1.61 |
| Kan70T | 0 | — | — |

TABLE 7

An oligonucleotide targeting the sense strand of the target sequence corrects more efficiently.

| | Colonies per hygromycin plate | |
|---|---|---|
| Amount of Oligonuleotide (μg) | HygE3T/74 | HygE3T/74α |
| 0 | 0 | 0 |
| 0.6 | 24 | 128 (8.4x)* |
| 1.2 | 69 | 140 (7.5x)* |
| 2.4 | 62 | 167 (3.8x)* |
| 3.6 | 29 | 367 (15x)* |

*The numbers in parentheses represent the fold increase in efficiency for targeting the non-transcribed strand as compared to the other strand of a DNA duplex that encodes a protein.

TABLE 8

Correction of a base substitution mutation is more efficient than correction of a frame shift mutation.

| Oligonucleotide | Plasmid tested (contained in LSY678) | |
|---|---|---|
| Tested (5 μg) | pAURHYG(ins)GFP | pAURHYG(rep)GFP |
| HygE3T/74 | 72 | 277 |
| HygE3T/74α | 1464 | 2248 |
| Kan70T | 0 | 0 |

TABLE 9

Optimization of oligonucleotide concentration in electroporated yeast cells.

| Amount (μg) | Colonies on hygromycin | Colonies on aureobasidin (/10⁵) | Correction efficiency |
|---|---|---|---|
| 0 | 0 | 67 | 0 |
| 1.0 | 5 | 64 | 0.08 |
| 2.5 | 47 | 30 | 1.57 |
| 5.0 | 199 | 33 | 6.08 |
| 7.5 | 383 | 39 | 9.79 |
| 10.0 | 191 | 33 | 5.79 |

EXAMPLE 3

Cultured Cell Manipulation

Mononuclear cells are isolated from human umbilical cord blood of normal donors using Ficoll Hypaque (Pharmacia Biotech, Uppsala, Sweden) density centrifugation. CD34+ cells are immunomagnetically purified from mononuclear cells using either the progenitor or Multisort Kits (Miltenyi Biotec, Auburn, Calif.). Lin⁻CD38⁻ cells are purified from the mononuclear cells using negative selection with StemSep system according to the manufacturer's protocol (Stem Cell Technologies, Vancouver, Calif.). Cells used for microinjection are either freshly isolated or cryopreserved and cultured in Stem Medium (S Medium) for 2 to 5 days prior to microinjection. S Medium contains Iscoves' Modified Dulbecco's Medium without phenol red (IMDM) with 100 μg/ml glutamine/penicillin/streptomycin, 50 mg/ml bovine serum albumin, 50 μg/ml bovine pancreatic insulin, 1 mg/ml human transferrin, and IMDM; Stem Cell Technologies), 40 μg/ml low-density lipoprotein (LDL; Sigma, St. Louis, Mo.), 50 mM HEPEs buffer and 50 μM 2-mercaptoethanol, 20 ng/ml each of thrombopoietin, flt-3 ligand, stem cell factor and human IL-6 (Pepro Tech Inc., Rocky Hill, N.J.). After microinjection, cells are detached and transferred in bulk into wells of 48 well plates for culturing.

35 mm dishes are coated overnight at 4° C. with 50 μg/ml Fibronectin (FN) fragment CH-296 (Retronectin; TaKaRa Biomedicals, Panvera, Madison, Wis.) in phosphate buffered saline and washed with IMDM containing glutamine/penicillin/streptomycin. 300 to 2000 cells are added to cloning rings and attached to the plates for 45 minutes at 37° C. prior to microinjection. After incubation, cloning rings are removed and 2 ml of S Medium are added to each dish for microinjection. Pulled injection needles with a range of 0.22μ to 0.3μ outer tip diameter are used. Cells are visualized with a microscope equipped with a temperature controlled stage set at 37° C. and injected using an electronically interfaced Eppendorf Micromanipulator and Transjector. Successfully injected cells are intact, alive and remain attached to the plate post injection. Molecules that are flourescently labeled allow determination of the amount of oligonucleotide delivered to the cells.

For in vitro erythropoiesis from Lin⁻CD38⁻ cells, the procedure of Malik, 1998 can be used. Cells are cultured in ME Medium for 4 days and then cultured in E Medium for 3 weeks. Erythropoiesis is evident by glycophorin A expression as well as the presence of red color representing the presence of hemoglobin in the cultured cells. The injected cells are able to retain their proliferative capacity and the ability to generate myeloid and erythoid progeny. CD34+ cells can convert a normal A ($β^A$) to sickle T ($β^S$) mutation in the β-globin gene or can be altered using any of the oligonucleotides of the invention herein for correction or alteration of a normal gene to a mutant gene. Alternatively, stem cells can be isolated from blood of humans having genetic disease mutations and the oligonucleotides of the invention can be used to correct a defect or to modify genomes within those cells.

Alternatively, non-stem cell populations of cultured cells can be manipulated using any method known to those of skill in the art including, for example, the use of polycatons, cationic lipids, liposomes, polyethylenimine (PEI), electroporation, biolistics, calcium phophate precipitation, or any other method known in the art.

Notes on the Tables Presented Below:

Each of the following tables presents, for the specified human gene, a plurality of mutations that are known to confer a clinically-relevant phenotype and, for each mutation, the oligonucleotides that can be used to correct the respective mutation site-specifically in the human genome according to the present invention.

The left-most column identifies each mutation and the clinical phenotype that the mutation confers.

For most entries, the mutation is identified at both the nucleic acid and protein level. At the amino acid level, mutations are presented according to the following standard nomenclature. The centered number identifies the position of the mutated codon in the protein sequence; to the left of the number is the wild type residue and to the right of the number is the mutant codon. Codon numbering is according to the Human Gene Mutation Database, Cardiff, Wales, UK (http://archive.uwcm.ac.uk/search/mg/allgenes). Terminator codons are shown as "TERM". At the nucleic acid level, the entire triplet of the wild type and mutated codons is shown.

The middle column presents, for each mutation, four oligonucleotides capable of repairing the mutation site-specifically in the human genome or in cloned human DNA including human DNA in artificial chromosomes, episomes, plasmids, or other types of vectors. The oligonucleotides of the invention, however, may include any of the oligonucleotides sharing portions of the sequence of the 121 base sequence. Thus, oligonucleotides of the invention for each of the depicted targets may be 18, 19, 20 up to about 121 nucleotides in length. Sequence may be added non-symmetrically.

All oligonucleotides are presented, per convention, in the 5' to 3' orientation. The nucleotide that effects the change in the genome is underlined and presented in bold.

The first of the four oligonucleotides for each mutation is a 121 nt oligonucleotide centered about the repair nucleotide. The second oligonucleotide, its reverse complement, targets the opposite strand of the DNA duplex for repair. The third oligonucleotide is the minimal 17 nt domain of the first oligonucleotide, also centered about the repair nucleotide. The fourth oligonucleotide is the reverse complement of the third, and thus represents the minimal 17 nt domain of the second.

The third column of each table presents the SEQ ID NO: of the respective repair oligonucleotide.

EXAMPLE 4

Adenosine Deaminase (ADA)

Adenosine deaminase (ADA, EC 3.5.4.4) catalyses the deamination of adenosine and 2'-deoxyadenosine to inosine or 2'-deoxyinosine respectively. ADA deficiency has been identified as the metabolic basis for 20–30% of cases with recessively inherited severe combined immunodeficiency (SCID). Affected infants are subject to recurrent chronic viral, fungal, protozoal, and bacterial infections and frequently present with persistent diarrhea, failure to thrive and candidiasis. In patents homozygous for ADA deficiency, 2'-deoxyadenosine accumulating during the rapid turnover of cells rich in DNA is converted back to dATP, either by adenosine kinase or deoxycytidine kinase. Many hypotheses have been advanced to explain the specific toxicity to the immune system in ADA deficiency. The apparently selective accumulation of dATP in thymocytes and peripheral blood B cells, with resultant inhibition of ribonucleotide reductase and DNA synthesis is probably the principal mechanism.

The structural gene for ADA is encoded as a single 32 kb locus containing 12 exons. Studies of the molecular defect in ADA-deficient patents have shown that mRNA is usually detectable in normal or supranormal amounts. Specific base substitution mutations have been detected in the majority of cases with the complete deficiency. A C-to-T base substitution mutation in exon 11 accounts for a high proportion of these, whilst a few patents are homozygous for large deletions encompassing exon 1. A common point mutation resulting in a heat-labile ADA has been characterised in some patients with partial ADA deficiency, a disorder with an apparently increased prevalence in the Caribbean.

As yet no totally effective therapy for ADA deficiency has been reported, except in those few cases where bone marrow from an HLA/MLR compatible sibling donor was available.

Two therapeutic approaches have provided long-term benefit in specific instances. First, reconstitution using T cell depleted mismatched sibling marrow has been encouraging, particularly in early presenters completely deficient in ADA. Secondly, therapy with polyethylene glycol-modified adenosine deaminase (PEG-ADA) for more than 5 years has produced a sustained increase in lymphocyte numbers and mitogen responses together with evidence of in vivo B cell function. Success has generally been achieved in late presenters with residual ADA activity in mononuclear cells.

ADA deficiency has been chosen as the candidate disease for gene replacement therapy and the first human experiment commenced in 1990. The clinical consequences of overexpression of ADA activity—one of the potential hazards of gene implant—are known and take the form of an hereditary haemolytic anaemia associated with a tissue-specific increase in ADA activity. The genetic basis for the latter autosomal dominant disorder seemingly relates to markedly increased levels of structurally normal ADA mRNA.

TABLE 10

ADA Mutations and Genome-Correcting Oligos

| Clinical Phenotype & Mutation | Correcting Oligos | SEQ ID NO: |
|---|---|---|
| Adenosine deaminase deficiency GLN3TERM CAG to TAG | AGAGACCCACCGAGCGGCGGCGGAGGGAGCAGCGCCGGGG | 1 |
| | CGCACGAGGGCACCATGGCCCAGACGCCCGCCTTCGACAAG | |
| | CCCAAAGTGAGCGCGCGCGGGGGCTCCGGGGACGGGGGTC | |
| | GACCCCCGTCCCCGGAGCCCCCGCGCGCGCTCACTTTGGG | 2 |
| | CTTGTCGAAGGCGGGCGTCTGGGCCATGGTGCCCTCGTGCG | |
| | CCCCGGCGCTGCTCCCTCCGCCGCCGCTCGGTGGGTCTCT | |
| | CCATGGCCCAGACGCCC | 3 |
| | GGGCGTCTGGGCCATGG | 4 |
| Adenosine deaminase deficiency HIS15ASP CAT to GAT | TATTTGTTCTCTCTCTCCCTTTCTCTCTCTCTTCCCCCTGCCC | 5 |
| | CCTTGCAGGTAGAACTGCATGTCCACCTAGACGGATCCATCA | |
| | AGCCTGAAACCATCTTATACTATGGCAGGTAAGTCC | |
| | GGACTTACCTGCCATAGTATAAGATGGTTTCAGGCTTGATGGA | 6 |
| | TCCGTCTAGGTGGACATGCAGTTCTACCTGCAAGGGGCAG | |
| | GGGGAAGAGAGAGAGAAAGGGAGAGAGAGAACAAATA | |
| | TAGAACTGCATGTCCAC | 7 |
| | GTGGACATGCAGTTCTA | 8 |
| Adenosine deaminase deficiency | TCCCTTTCTCTCTCTCTTCCCCCTGCCCCCTTGCAGGTAGAA | 9 |
| | CTGCATGTCCACCTAGACGGATCCATCAAGCCTGAAACCATC | |

TABLE 10-continued

ADA Mutations and Genome-Correcting Oligos

| Clinical Phenotype & Mutation | Correcting Oligos | SEQ ID NO: |
|---|---|---|
| GLY20ARG<br>GGA to AGA | TTATACTATGGCAGGTAAGTCCATACAGAAGAGCCCT<br>AGGGCTCTTCTGTATGGACTTACCTGCCATAGTATAAGATGGT<br>TTCAGGCTTGATGGATCCGTCTAGGTGGACATGCAGTTCTAC<br>CTGCAAGGGGGCAGGGGGAAGAGAGAGAGAAAGGGA | 10 |
| | ACCTAGACGGATCCATC | 11 |
| | GATGGATCCGTCTAGGT | 12 |
| Adenosine deaminase deficiency<br>GLY74CYS<br>GGC to TGC | CCTGGAGCTCCCAAGGGACTTGGGGAAGGTTGTTCCCAACC<br>CCTTTCTTCCCTTCCCAGGGGCTGCCGGGAGGCTATCAAAAG<br>GATCGCCTATGAGTTTGTAGAGATGAAGGCCAAAGAGG<br>CCTCTTTGGCCTTCATCTCTACAAACTCATAGGCGATCCTTTT<br>GATAGCCTCCCGGCAGCCCCTGGGAAGGGAAGAAAGGGGTT<br>GGGAACAACCTTCCCCAAGTCCCTTGGGAGCTCCAGG | 13<br><br>14 |
| | CTATCGCGGGCTGCCGG | 15 |
| | CCGGCAGCCCGCGATAG | 16 |
| Adenosine Deaminase Deficiency<br>ARG76TRP<br>CGG to TGG | GCTCCCAAGGGACTTGGGGAAGGTTGTTCCCAACCCCTTTCT<br>TCCCTTCCCAGGGGCTGCCGGGAGGCTATCAAAAGGATCGC<br>CTATGAGTTTGTAGAGATGAAGGCCAAAGAGGGCGTGG<br>CCACGCCCTCTTTGGCCTTCATCTCTACAAACTCATAGGCGAT<br>CCTTTTGATAGCCTCCCGGCAGCCCCTGGGAAGGGAAGAAA<br>GGGGTTGGGAACAACCTTCCCCAAGTCCCTTGGGAGC | 17<br><br>18 |
| | GGGGCTGCCGGGAGGCT | 19 |
| | AGCCTCCCGGCAGCCCC | 20 |
| Adenosine Deaminase Deficiency<br>LYS80ARG<br>AAA to AGA | TTGGGGAAGGTTGTTCCCAACCCCTTTCTTCCCTTCCCAGGG<br>GCTGCCGGGAGGCTATCAAAAGGATCGCCTATGAGTTTGTAG<br>AGATGAAGGCCAAAGAGGGCGTGGTGTATGTGGAGGT<br>ACCTCCACATACACCACGCCCTCTTTGGCCTTCATCTCTACAA<br>ACTCATAGGCGATCCTTTTGATAGCCTCCCGGCAGCCCCTGG<br>GAAGGGAAGAAAGGGGTTGGGAACAACCTTCCCCAA | 21<br><br>22 |
| | GGCTATCAAAAGGATCG | 23 |
| | CGATCCTTTTGATAGCC | 24 |
| Adenosine deaminase deficiency<br>ALA83ASP<br>GCC to GAC | GTTGTTCCCAACCCCTTTCTTCCCTTCCCAGGGGCTGCCGGG<br>AGGCTATCAAAAGGATCGCCTATGAGTTTGTAGAGATGAAGG<br>CCAAAGAGGGCGTGGTGTATGTGGAGGTGCGGTACAG<br>CTGTACCGCACCTCCACATACACCACGCCCTCTTTGGCCTTC<br>ATCTCTACAAACTCATAGGCGATCCTTTTGATAGCCTCCCGGC<br>AGCCCCTGGGAAGGGAAGAAAGGGGTTGGGAACAAC | 25<br><br>26 |
| | AAGGATCGCCTATGAGT | 27 |
| | ACTCATAGGCGATCCTT | 28 |
| Adenosine deaminase deficiency<br>TYR97CYS<br>TAT to TGT | AGGCTATCAAAAGGATCGCCTATGAGTTTGTAGAGATGAAGG<br>CCAAAGAGGGCGTGGTGTATGTGGAGGTGCGGTACAGTCCG<br>CACCTGCTGGCCAACTCCAAAGTGGAGCCAATCCCCTG<br>CAGGGGATTGGCTCCACTTTGGAGTTGGCCAGCAGGTGCGG<br>ACTGTACCGCACCTCCACATACACCACGCCCTCTTTGGCCTT<br>CATCTCTACAAACTCATAGGCGATCCTTTTGATAGCCT | 29<br><br>30 |
| | CGTGGTGTATGTGGAGG | 31 |
| | CCTCCACATACACCACG | 32 |
| Adenosine deaminase deficiency<br>ARG101GLN<br>CGG to CAG | GGATCGCCTATGAGTTTGTAGAGATGAAGGCCAAAGAGGGCG<br>TGGTGTATGTGGAGGTGCGGTACAGTCCGCACCTGCTGGCC<br>AACTCCAAAGTGGAGCCAATCCCCTGGAACCAGGCTGA<br>TCAGCCTGGTTCCAGGGGATTGGCTCCACTTTGGAGTTGGCC<br>AGCAGGTGCGGACTGTACCGCACCTCCACATACACCACGCC<br>CTCTTTGGCCTTCATCTCTACAAACTCATAGGCGATCC | 33<br><br>34 |
| | GGAGGTGCGGTACAGTC | 35 |
| | GACTGTACCGCACCTCC | 36 |
| Adenosine deaminase deficiency<br>ARG101LEU<br>CGG to CTG | GGATCGCCTATGAGTTTGTAGAGATGAAGGCCAAAGAGGGCG<br>TGGTGTATGTGGAGGTGCGGTACAGTCCGCACCTGCTGGCC<br>AACTCCAAAGTGGAGCCAATCCCCTGGAACCAGGCTGA<br>TCAGCCTGGTTCCAGGGGATTGGCTCCACTTTGGAGTTGGCC<br>AGCAGGTGCGGACTGTACCGCACCTCCACATACACCACGCC<br>CTCTTTGGCCTTCATCTCTACAAACTCATAGGCGATCC | 37<br><br>38 |
| | GGAGGTGCGGTACAGTC | 39 |
| | GACTGTACCGCACCTCC | 40 |
| Adenosine deaminase deficiency<br>ARG101TRP<br>CGG to TGG | AGGATCGCCTATGAGTTTGTAGAGATGAAGGCCAAAGAGGGC<br>GTGGTGTATGTGGAGGTGCGGTACAGTCCGCACCTGCTGGC<br>CAACTCCAAAGTGGAGCCAATCCCCTGGAACCAGGCTG<br>CAGCCTGGTTCCAGGGGATTGGCTCCACTTTGGAGTTGGCCA<br>GCAGGTGCGGACTGTACCGCACCTCCACATACACCACGCCC<br>TCTTTGGCCTTCATCTCTACAAACTCATAGGCGATCCT | 41<br><br>42 |
| | TGGAGGTGCGGTACAGT | 43 |
| | ACTGTACCGCACCTCCA | 44 |
| Adenosine deaminase deficiency<br>PRO104LEU<br>CCG to CTG | ATGAGTTTGTAGAGATGAAGGCCAAAGAGGGCGTGGTGTATG<br>TGGAGGTGCGGTACAGTCCGCACCTGCTGGCCAACTCCAAA<br>GTGGAGCCAATCCCCTGGAACCAGGCTGAGTGAGTGAT<br>ATCACTCACTCAGCCTGGTTCCAGGGGATTGGCTCCACTTTG | 45<br><br>46 |

TABLE 10-continued

ADA Mutations and Genome-Correcting Oligos

| Clinical Phenotype & Mutation | Correcting Oligos | SEQ ID NO: |
|---|---|---|
| | GAGTTGGCCAGCAGGTGCGGACTGTACCGCACCTCCACATA CACCACGCCCTCTTTGGCCTTCATCTCTACAAACTCAT | |
| | GTACAGTCCGCACCTGC | 47 |
| | GCAGGTGCGGACTGTAC | 48 |
| Adenosine deaminase deficiency LEU106VAL CTG to GTG | TTTGTAGAGATGAAGGCCAAAGAGGGCGTGGTGTATGTGGAG GTGCGGTACAGTCCGCACCTGCTGGCCAACTCCAAAGTGGA GCCAATCCCCTGGAACCAGGCTGAGTGAGTGATGGGCC | 49 |
| | GGCCCATCACTCACTCAGCCTGGTTCCAGGGGATTGGCTCCA CTTTGGAGTTGGCCAGCAGGTGCGGACTGTACCGCACCTCC ACATACACCACGCCCTCTTTGGCCTTCATCTCTACAAA | 50 |
| | GTCCGCACCTGCTGGCC | 51 |
| | GGCCAGCAGGTGCGGAC | 52 |
| Adenosine deaminase deficiency LEU107PRO CTG to CCG | TAGAGATGAAGGCCAAAGAGGGCGTGGTGTATGTGGAGGTG CGGTACAGTCCGCACCTGCTGGCCAACTCCAAAGTGGAGCC AATCCCCTGGAACCAGGCTGAGTGATGGGCCTGGA | 53 |
| | TCCAGGCCCATCACTCACTCAGCCTGGTTCCAGGGGATTGGC TCCACTTTGGAGTTGGCCAGCAGGTGCGGACTGTACCGCAC CTCCACATACACCACGCCCTCTTTGGCCTTCATCTCTA | 54 |
| | GCACCTGCTGGCCAACT | 55 |
| | AGTTGGCCAGCAGGTGC | 56 |
| Adenosine deaminase deficiency PRO126GLN CCA to CAA | GCCTTCCTTTTGCCTCAGGCCCATCCCTACTCCTCTCCTCAC ACAGAGGGGACCTCACCCCAGACGAGGTGGTGGCCCTAGTG GGCCAGGGCCTGCAGGAGGGGGAGCGAGACTTCGGGGT | 57 |
| | ACCCCGAAGTCTCGCTCCCCCTCCTGCAGGCCCTGGCCCAC TAGGGCCACCACCTCGTCTGGGGTGAGGTCCCCTCTGTGTG AGGAGAGGAGTAGGGATGGGCCTGAGGCAAAAGGAAGGC | 58 |
| | CCTCACCCCAGACGAGG | 59 |
| | CCTCGTCTGGGGTGAGG | 60 |
| Adenosine deaminase deficiency VAL129MET GTG to ATG | TTTGCCTCAGGCCCATCCCTACTCCTCTCCTCACACAGAGGG GACCTCACCCCAGACGAGGTGGTGGCCCTAGTGGGCCAGGG CCTGCAGGAGGGGAGCGAGACTTCGGGGTCAAGGCCC | 61 |
| | GGGCCTTGACCCCGAAGTCTCGCTCCCCCTCCTGCAGGCCC TGGCCCACTAGGGCCACCACCTCGTCTGGGGTGAGGTCCCC TCTGTGTGAGGAGAGGAGTAGGGATGGGCCTGAGGCAAA | 62 |
| | CAGACGAGGTGGTGGCC | 63 |
| | GGCCACCACCTCGTCTG | 64 |
| Adenosine deaminase deficiency GLY140GLU GGG to GAG | ACAGAGGGGACCTCACCCCAGACGAGGTGGTGGCCCTAGTG GGCCAGGGCCTGCAGGAGGGGGAGCGAGACTTCGGGGTCA AGGCCCGGTCCATCCTGTGCTGCATGCGCCACCAGCCCAG | 65 |
| | CTGGGCTGGTGGCGCATGCAGCACAGGATGGACCGGGCCTT GACCCCGAAGTCTCGCTCCCCCTCCTGCAGGCCCTGGCCCA CTAGGGCCACCACCTCGTCTGGGGTGAGGTCCCCTCTGT | 66 |
| | GCAGGAGGGGGAGCGAG | 67 |
| | CTCGCTCCCCCTCCTGC | 68 |
| Adenosine deaminase deficiency ARG142GLN CGA to CAA | GGGACCTCACCCCAGACGAGGTGGTGGCCCTAGTGGGCCAG GGCCTGCAGGAGGGGAGCGAGACTTCGGGGTCAAGGCCC GGTCCATCCTGTGCTGCATGCGCCACCAGCCCAGTGAGTA | 69 |
| | TACTCACTGGGCTGGTGGCGCATGCAGCACAGGATGGACCG GGCCTTGACCCCGAAGTCTCGCTCCCCCTCCTGCAGGCCCT GGCCCACTAGGGCCACCACCTCGTCTGGGGTGAGGTCCC | 70 |
| | GGGGGAGCGAGACTTCG | 71 |
| | CGAAGTCTCGCTCCCCC | 72 |
| Adenosine deaminase deficiency ARG142TERM CGA to TGA | GGGACCTCACCCCAGACGAGGTGGTGGCCCTAGTGGGCCA GGGCCTGCAGGAGGGGGAGCGAGACTTCGGGGTCAAGGCCC CGGTCCATCCTGTGCTGCATGCGCCACCAGCCCAGTGAGT | 73 |
| | ACTCACTGGGCTGGTGGCGCATGCAGCACAGGATGGACCGG GCCTTGACCCCGAAGTCTCGCTCCCCCTCCTGCAGGCCCTG GCCCACTAGGGCCACCACCTCGTCTGGGGTGAGGTCCCC | 74 |
| | AGGGGGAGCGAGACTTC | 75 |
| | GAAGTCTCGCTCCCCCT | 76 |
| Adenosine deaminase deficiency ARG149GLN CGG to CAG | TGGTGGCCCTAGTGGGCCAGGGCCTGCAGGAGGGGGAGCG AGACTTCGGGGTCAAGGCCCGGTCCATCCTGTGCTGCATGC GCCACCAGCCCAGTGAGTAGGATCACCGCCCTGCCCAGGG | 77 |
| | CCCTGGGCAGGGCGGTGATCCTACTCACTGGGCTGGTGGCG CATGCAGCACAGGATGGACCGGGCCTTGACCCCGAAGTCTC GCTCCCCTCCTGCAGGCCCTGGCCCACTAGGGCCACCA | 78 |
| | CAAGGCCCGGTCCATCC | 79 |
| | GGATGGACCGGGCCTTG | 80 |
| Adenosine deaminase deficiency ARG149TRP CGG to TGG | GTGGTGGCCCTAGTGGGCCAGGGCCTGCAGGAGGGGGAGC GAGACTTCGGGGTCAAGGCCCCGGTCCATCCTGTGCTGCATG CGCCACCAGCCCAGTGAGTAGGATCACCGCCCTGCCCAGG | 81 |
| | CCTGGGCAGGGCGGTGATCCTACTCACTGGGCTGGTGGCGC ATGCAGCACAGGATGGACCGGGCCTTGACCCCGAAGTCTCG CTCCCCCTCCTGCAGGCCCTGGCCCACTAGGGCCACCAC | 82 |

TABLE 10-continued

ADA Mutations and Genome-Correcting Oligos

| Clinical Phenotype & Mutation | Correcting Oligos | SEQ ID NO: |
|---|---|---|
| | TCAAGGCCCGGTCCATC | 83 |
| | GATGGACCGGGCCTTGA | 84 |
| Adenosine deaminase deficiency LEU152MET CTG to ATG | CTAGTGGGCCAGGGCCTGCAGGAGGGGGAGCGAGACTTCG GGGTCAAGGCCCGGTCCATCCTGTGCTGCATGCGCCACCAG CCCAGTGAGTAGGATCACCGCCCTGCCCAGGGCCGCCCGT | 85 |
| | ACGGGCGGCCCTGGGCAGGGCGGTGATCCTACTCACTGGG CTGGTGGCGCATGCAGCACAGGATGGACCGGGCCTTGACCC CGAAGTCTCGCTCCCCCTCCTGCAGGCCCTGGCCCACTAG | 86 |
| | GGTCCATCCTGTGCTGC | 87 |
| | GCAGCACAGGATGGACC | 88 |
| Adenosine deaminase deficiency ARG156CYS CGC to TGC | GGCCTGCAGGAGGGGGAGCGAGACTTCGGGGTCAAGGCCC GGTCCATCCTGTGCTGCATGCGCCACCAGCCCAGTGAGTAG GATCACCGCCCTGCCCAGGGCCGCCCGTCTCACCCTGGCC | 89 |
| | GGCCAGGGTGAGACGGGCGGCCCTGGGCAGGGCGGTGATC CTACTCACTGGGCTGGTGGCGCATGCAGCACAGGATGGACC GGGCCTTGACCCCGAAGTCTCGCTCCCCCTCCTGCAGGCC | 90 |
| | GCTGCATGCGCCACCAG | 91 |
| | CTGGTGGCGCATGCAGC | 92 |
| Adenosine deaminase deficiency ARG156HIS CGC to CAC | GCCTGCAGGAGGGGGAGCGAGACTTCGGGGTCAAGGCCCG GTCCATCCTGTGCTGCATGCGCCACCAGCCCAGTGAGTAGG ATCACCGCCCTGCCCAGGGCCGCCCGTCTCACCCTGGCCC | 93 |
| | GGGCCAGGGTGAGACGGGCGGCCCTGGGCAGGGCGGTGAT CCTACTCACTGGGCTGGTGGCGCATGCAGCACAGGATGGAC CGGGCCTTGACCCCGAAGTCTCGCTCCCCCTCCTGCAGGC | 94 |
| | CTGCATGCGCCACCAGC | 95 |
| | GCTGGTGGCGCATGCAG | 96 |
| Adenosine deaminase deficiency VAL177MET GTG to ATG | CTGCCCACAGACTGGTCCCCCAAGGTGGTGGAGCTGTGTAA GAAGTACCAGCAGCAGACCGTGGTAGCCATTGACCTGGCTG GAGATGAGACCATCCCAGGAAGCAGCCTCTTGCCTGGAC | 97 |
| | GTCCAGGCAAGAGGCTGCTTCCTGGGATGGTCTCATCTCCAG CCAGGTCAATGGCTACCACGGTCTGCTGCTGGTACTTCTTAC ACAGCTCCACCACCTTGGGGGACCAGTCTGTGGGCAG | 98 |
| | AGCAGACCGTGGTAGCC | 99 |
| | GGCTACCACGGTCTGCT | 100 |
| Adenosine deaminase deficiency ALA179ASP GCC to GAC | CAGACTGGTCCCCCAAGGTGGTGGAGCTGTGTAAGAAGTAC CAGCAGCAGACCGTGGTAGCCATTGACCTGGCTGGAGATGA GACCATCCCAGGAAGCAGCCTCTTGCCTGGACATGTCCA | 101 |
| | TGGACATGTCCAGGCAAGAGGCTGCTTCCTGGGATGGTCTCA TCTCCAGCCAGGTCAATGGCTACCACGGTCTGCTGCTGGTAC TTCTTACACAGCTCCACCACCTTGGGGGACCAGTCTG | 102 |
| | CGTGGTAGCCCATTGACC | 103 |
| | GGTCAATGGCTACCACG | 104 |
| Adenosine deaminase deficiency GLN199PRO CAG to CCG | CCATTGACCTGGCTGGAGATGAGACCATCCCAGGAAGCAGC CTCTTGCCTGGACATGTCCAGGCCTACCAGGTGGGTCCTGT GAGAAGGAATGGAGAGGCTGGCCCTGGGTGAGCTTGTCT | 105 |
| | AGACAAGCTCACCCAGGGCCAGCCTCTCCATTCCTTCTCACA GGACCCACCTGGTAGGCCTGGACATGTCCAGGCAAGAGGCT GCTTCCTGGGATGGTCTCATCTCCAGCCAGGTCAATGG | 106 |
| | ACATGTCCAGGCCTACC | 107 |
| | GGTAGGCCTGGACATGT | 108 |
| Adenosine deaminase deficiency ARG211CYS CGT to TGT | GCTAGGGCACCCATGACCTGGCTCTCCCCCTTCCAGGAGGC TGTGAAGAGCGGCATTCACCGTACTGTCCACGCCGGGGAGG TGGGCTCGGCCGAAGTAGTAAAAGAGGTGAGGGCCTGGG | 109 |
| | CCCAGGCCCTCACCTCTTTTACTACTTCGGCCGAGCCCACCT CCCCGGCGTGGACAGTACGGTGAATGCCGCTCTTCACAGCC TCCTGGAAGGGGGAGAGCCAGGTCATGGGTGCCCTAGC | 110 |
| | GCATTCACCGTACTGTC | 111 |
| | GACAGTACGGTGAATGC | 112 |
| Adenosine deaminase deficiency ARG211HIS CGT to CAT | CTAGGGCACCCATGACCTGGCTCTCCCCCTTCCAGGAGGCT GTGAAGAGCGGCATTCACCGTACTGTCCACGCCGGGGAGGT GGGCTCGGCCGAAGTAGTAAAAGAGGTGAGGGCCTGGC | 113 |
| | GCCCAGGCCCTCACCTCTTTTACTACTTCGGCCGAGCCCACC TCCCCGGCGTGGACAGTACGGTGAATGCCGCTCTTCACAGC CTCCTGGAAGGGGGAGAGCCAGGTCATGGGTGCCCTAG | 114 |
| | CATTCACCGTACTGTCC | 115 |
| | GGACAGTACGGTGAATG | 116 |
| Adenosine deaminase deficiency ALA215THR GCC to ACC | ATGACCTGGCTCTCCCCCTTCCAGGAGGCTGTGAAGAGCGG CATTCACCGTACTGTCCACGCCGGGGAGGTGGGCTCGGCCG AAGTAGTAAAAGAGGTGAGGGCTGGCCATGGGG | 117 |
| | CCCCATGGCCAGCCCAGGCCCTCACCTCTTTTACTACTTCGG CCGAGCCCACCTCCCCGGCGTGGACAGTACGGTGAATGCCG CTCTTCACAGCCTCCTGGAAGGGGGAGAGCCAGGTCAT | 118 |
| | CTGTCCACGCCGGGGAG | 119 |
| | CTCCCCGGCGTGGACAG | 120 |

TABLE 10-continued

ADA Mutations and Genome-Correcting Oligos

| Clinical Phenotype & Mutation | Correcting Oligos | SEQ ID NO: |
|---|---|---|
| Adenosine deaminase deficiency GLY216ARG GGG to AGG | ACCTGGCTCTCCCCCTTCCAGGAGGCTGTGAAGAGCGGCAT TCACCGTACTGTCCACGCCGGGGAGGTGGGCTCGGCCGAAG TAGTAAAAGAGGTGAGGGCCTGGGCTGGCCATGGGGTCC | 121 |
| | GGACCCCATGGCCAGCCCAGGCCCTCACCTCTTTTACTACTT CGGCCGAGCCCACCTCCCCGGCGTGGACAGTACGGTGAATG CCGCTCTTCACAGCCTCCTGGAAGGGGGAGAGCCAGGT | 122 |
| | TCCACGCCGGGGAGGTG | 123 |
| | CACCTCCCCGGCGTGGA | 124 |
| Adenosine deaminase deficiency GLU217LYS GAG to AAG | TGGCTCTCCCCCTTCCAGGAGGCTGTGAAGAGCGGCATTCA CCGTACTGTCCACGCCGGGGAGGTGGGCTCGGCCGAAGTAG TAAAAGAGGTGAGGGCCTGGGCTGGCCATGGGGTCCCTC | 125 |
| | GAGGGACCCCATGGCCAGCCCAGGCCCTCACCTCTTTTACTA CTTCGGCCGAGCCCACCTCCCCGGCGTGGACAGTACGGTGA ATGCCGCTCTTCACAGCCTCCTGGAAGGGGGAGAGCCA | 126 |
| | ACGCCGGGGAGGTGGGC | 127 |
| | GCCCACCTCCCCGGCGT | 128 |
| Adenosine deaminase deficiency THR233ILE ACA to ATA | CTGCCTCCTCCCCATACTTGGCTCTATTCTGCTTCTCTACAGGC TGTGGACATACTCAAGACAGAGCGGCTGGGACACGGCTACC ACACCCTGGAAGACCAGGCCCTTTATAACAGGCTGCG | 129 |
| | CGCAGCCTGTTATAAAGGGCCTGGTCTTCCAGGGTGTGGTAG CCGTGTCCCAGCCGCTCTGTCTTGAGTATGTCCACAGCCTGT AGAGAAGCAGAATAGAGCCAAGTATGGGAGGAGGCAG | 130 |
| | ACTCAAGACAGAGCGGC | 131 |
| | GCCGCTCTGTCTTGAGT | 132 |
| Adenosine deaminase deficiency ARG253PRO CGG to CCG | CAGAGCGGCTGGGACACGGCTACCACACCCTGGAAGACCAG GCCCTTTATAACAGGCTGCGGCAGGAAAACATGCACTTCGAG GTAAGCGGGCCAGGGAGTGGGGAGGAACCATCCCCGGC | 133 |
| | GCCGGGGATGGTTCCTCCCCACTCCCTGGCCCGCTTACCTC GAAGTGCATGTTTTCCTGCCGCAGCCTGTTATAAAGGGCCTG GTCTTCCAGGGTGTGGTAGCCGTGTCCCAGCCGCTCTG | 134 |
| | CAGGCTGCGGCAGGAAA | 135 |
| | TTTCCTGCCGCAGCCTG | 136 |
| Adenosine deaminase deficiency GLN254TERM CAG to TAG | GAGCGGCTGGGACACGGCTACCACACCCTGGAAGACCAGGC CCTTTATAACAGGCTGCGGCAGGAAAACATGCACTTCGAGGT AAGCGGGCCAGGGAGTGGGGAGGAACCATCCCCGGCTG | 137 |
| | CAGCCGGGGATGGTTCCTCCCCACTCCCTGGCCCGCTTACC TCGAAGTGCATGTTTTCCTGCCGCAGCCTGTTATAAAGGGCC TGGTCTTCCAGGGTGTGGTAGCCGTGTCCCAGCCGCTC | 138 |
| | GGCTGCGGCAGGAAAAC | 139 |
| | GTTTTCCTGCCGCAGCC | 140 |
| Adenosine deaminase deficiency PRO274LEU CCG to CTG | CCACACACCTGCTCTTCCAGATCTGCCCCTGGTCCAGCTACC TCACTGGTGCCTGGAAGCCGGACACGGAGCATGCAGTCATT CGGTGAGCTCTGTTCCCCTGGGCCTGTTCAATTTTGTT | 141 |
| | AACAAAATTGAACAGGCCCAGGGGAACAGAGCTCACCGAATG ACTGCATGCTCCGTGTCCGGCTTCCAGGCACCAGTGAGGTA GCTGGACCAGGGGCAGATCTGGAAGAGCAGGTGTGTGG | 142 |
| | CTGGAAGCCGGACACGG | 143 |
| | CCGTGTCCGGCTTCCAG | 144 |
| Adenosine deaminase deficiency SER291LEU TCG to TTG | GGAGGCTGATTCTCTCCTCCTCCCTCTTCTGCAGGCTCAAAA ATGACCAGGCTAACTACTCGCTCAACACAGATGACCCGCTCA TCTTCAAGTCCACCCTGGACACTGATTACCAGATGAC | 145 |
| | GTCATCTGGTAATCAGTGTCCAGGGTGGACTTGAAGATGAGC GGGTCATCTGTGTTGAGCGAGTAGTTAGCCTGGTCATTTTTGA GCCTGCAGAAGAGGGAGGAGGAGAGAATCAGCCTCC | 146 |
| | TAACTACTCGCTCAACA | 147 |
| | TGTTGAGCGAGTAGTTA | 148 |
| Adenosine deaminase deficiency PRO297GLN CCG to CAG | CCTCCCTCTTCTGCAGGCTCAAAAATGACCAGGCTAACTACT CGCTCAACACAGATGACCCGCTCATCTTCAAGTCCACCCTGG ACACTGATTACCAGATGACCAAACGGGACATGGGCTT | 149 |
| | AAGCCCATGTCCCGTTTGGTCATCTGGTAATCAGTGTCCAGG GTGGACTTGAAGATGAGCGGGTCATCTGTGTTGAGCGAGTAG TTAGCCTGGTCATTTTTGAGCCTGCAGAAGAGGGAGG | 150 |
| | AGATGACCCGCTCATCT | 151 |
| | AGATGAGCGGGTCATCT | 152 |
| Adenosine deaminase deficiency LEU304ARG CTG to CGG | AAAATGACCAGGCTAACTACTCGCTCAACACAGATGACCCGC TCATCTTCAAGTCCACCCTGGACACTGATTACCAGATGACCAA ACGGGACATGGGCTTTACTGAAGAGGAGTTTAAAAG | 153 |
| | CTTTTAAACTCCTCTTCAGTAAAGCCCATGTCCCGTTTGGTCA TCTGGTAATCAGTGTCCAGGGTGGACTTGAAGATGAGCGGGT CATCTGTGTTGAGCGAGTAGTTAGCCTGGTCATTTT | 154 |
| | GTCCACCCTGGACACTG | 155 |
| | CAGTGTCCAGGGTGGAC | 156 |
| Adenosine deaminase deficiency | GCCTTCTTTGTTCTCTGGTTCCATGTTGTCTGCCATTCTGGCC TTTCCAGAACATCAATGCGGCCAAATCTAGTTTCCTCCCAGAA | 157 |

TABLE 10-continued

ADA Mutations and Genome-Correcting Oligos

| Clinical Phenotype & Mutation | Correcting Oligos | SEQ ID NO: |
|---|---|---|
| ALA329VAL C-to-T at base 1081 | GATGAAAAGAGGGAGCTTCTCGACCTGCTCTATAA TTATAGAGCAGGTCGAGAAGCTCCCTCTTTTCATCTTCTGGGA GGAAACTAGATTTGGCCCCATTGATGTTCTGGAAAGGCCAGA ATGGCAGACAACATGGAACCAGAGAACAAAGAAGGC | 158 |
| | CATCAATGCGGCCAAAT | 159 |
| | ATTTGGCCGCATTGATG | 160 |

EXAMPLE 5

P53 Mutations

The p53 gene codes for a protein that acts as a transcription factor and serves as a key regulator of the cell cycle. Mutation in this gene is probably the most significant genetic change characterizing the transformation of cells from normalcy to malignancy.

Inactivation of p53 by mutation disrupts the cell cycle which, in turn, sets the stage for tumor formation. Mutations in the p53 gene are among the most commonly diagnosed genetic disorders, occuring in as many as 50% of cancer patients. For some types of cancer, most notably of the breast, lung and colon, p53 mutations are the predominant genetic alternations found thus far. These mutations are associated with genomic instability and thus an increased susceptibility to cancer. Some p53 lesions result in malignancies that are resistant to the most widely used therapeutic regimens and therefore demand more aggressive treatment.

That p53 is associated with different malignant tumors is illustrated in the Li-Fraumeni autosomal dominant hereditary disorder characterized by familial multiple tumors due to mutation in the p53 gene. Affected individuals can develop one or more tumors, including: brain (12%); soft-tissue sarcoma (12%); breast cancer (25%); adrenal tumors (1%); bone cancer (osteosarcoma) (6%); cancer of the lung, prostate, pancreas, and colon as well as lymphoma and melanoma can also occur.

Certain of the most frequently mutated codons are codons 175, 248 and 273, however a variety of oligonucleotides are described below in the attached table.

TABLE 11 p53 Mutations and Genome-Correcting Oligos

| Clinical Phenotype & Mutation | Correcting Oligos | SEQ ID NO: |
|---|---|---|
| In 2 families with Li-Fraumeni syndrome, there was a C-to-T mutation at the first nucleotide of codon 248 which changed arginine to tryptophan. | GACTGTACCACCATCCACTACAACTACATGTGTAACAGTTCCT GCATGGGCGGCATGAACCGGAGGCCCATCCTCACCATCATC ACACTGGAAGACTCCAGGTCAGGAGCCACTTGCCACC | 161 |
| | GGTGGCAAGTGGCTCCTGACCTGGAGTCTTCCAGTGTGATGA TGGTGAGGATGGGCCTCCGGTTCATGCCGCCCATGCAGGAA CTGTTACACATGTAGTTGTAGTGGATGGTGGTACAGTC | 162 |
| | GCATGAACCGGAGGCCC | 163 |
| | GGGCCTCCGGTTCATGC | 164 |
| In a family with the Li-Fraumeni syndrome, a G-to-A mutation at the first nucleotide of codon 258 resulting in the substitution of lysine for glutamic acid. | TGTAACAGTTCCTGCATGGGCGGCATGAACCGGAGGCCCAT CCTCACCATCATCACACTGGAAGACTCCAGGTCAGGAGCCAC TTGCCACCCTGCACACTGGCCTGCTGTGCCCCAGCCTC | 165 |
| | GAGGCTGGGGCACAGCAGGCCAGTGTGCAGGGTGGCAAGT GGCTCCTGACCTGGAGTCTTCCAGTGTGATGATGGTGAGGAT GGGCCTCCGGTTCATGCCGCCCATGCAGGAACTGTTACA | 166 |
| | TCACACTGGAAGACTCC | 167 |
| | GGAGTCTTCCAGTGTGA | 168 |
| In a family with the Li-Fraumeni syndrome, a G-to-T mutation at the first nucleotide of codon 245 resulting in the substitution of cysteine for glycine. | GTTGGCTCTGACTGTACCACCATCCACTACAACTACATGTGTA ACAGTTCCTGCATGGGCGGCATGAACCGGAGGCCCATCCTC ACCATCATCACACTGGAAGACTCCAGGTCAGGAGCCA | 169 |
| A gly245-to-ser, GGC-to-AGC, mutation was found in a patient in whom osteosarcoma was diagnosed at the age of 18 years. | TGGCTCCTGACCTGGAGTCTTCCAGTGTGATGATGGTGAGGA TGGGCCTCCGGTTCATGCCGCCCATGCAGGAACTGTTACACA TGTAGTTGTAGTGGATGGTGGTACAGTCAGAGCCAAC | 170 |
| | GCATGGGCGGCATGAAC | 171 |
| | GTTCATGCCGCCCATGC | 172 |
| In a family with the Li-Fraumeni syndrome, a germline mutation at codon 252: | TCCACTACAACTACATGTGTAACAGTTCCTGCATGGGCGGCA TGAACCGGAGGCCCATCCTCACCATCATCACACTGGAAGACT CCAGGTCAGGAGCCACTTGCCACCCTGCACACTGGCC | 173 |
| | GGCCAGTGTGCAGGGTGGCAAGTGGCTCCTGACCTGGAGTC | 174 |

TABLE 11-continued p53 Mutations and Genome-Correcting Oligos

| Clinical Phenotype & Mutation | Correcting Oligos | SEQ ID NO: |
|---|---|---|
| a T-to-C change at the second position resulted in substitution of proline for leucine. Researchers analyzed for mutations in p53 hepatocellular carcinomas from patients in Qidong, an area of high incidence in China, in which both hepatitis B virus and aflatoxin B1 are risk factors. Eight of 16 tumors had a point mutation at the third base position of codon 249. The G-to-T mutation at codon 249 led to a change from arginine to serine (AGG to AGT). | TTCCAGTGTGATGATGGTGAGGATGGGCCTCCGGTTCATGCC GCCCATGCAGGAACTGTTACACATGTAGTTGTAGTGGA GCCCATCCTCACCATCA TGATGGTGAGGATGGGC TACCACCATCCACTACAACTACATGTGTAACAGTTCCTGCATG GGCGGCATGAACCGGAGGCCCATCCTCACCATCATCACACT GGAAGACTCCAGGTCAGGAGCCACTTGCCACCCTGCA TGCAGGGTGGCAAGTGGCTCCTGACCTGGAGTCTTCCAGTG TGATGATGGTGAGGATGGGCCTCCGGTTCATGCCGCCCATG CAGGAACTGTTACACATGTAGTTGTAGTGGATGGTGGTA AACCGGAGGCCCATCCT AGGATGGGCCTCCGGTT | 175 176 177 178 179 180 |
| In cases of hepatocellular carcinoma in southern Africa, a G-to-T substitution in codon 157 resulting in a change from valine to phenylalanine. | CTGGCCAAGACCTGCCCTGTGCAGCTGTGGGTTGATTCCACA CCCCCGCCCGGCACCCGCGTCCGCGCCATGGCCATCTACAA GCAGTCACAGCACATGACGGAGGTTGTGAGGCGCTGCC GGCAGCGCCTCACAACCTCCGTCATGTGCTGTGACTGCTTGT AGATGGCCATGGCGCGGACGCGGGTGCCGGGCGGGGTGT GGAATCAACCCACAGCTGCACAGGGCAGGTCTTGGCCAG GCACCCGCGTCCGCGCC GGCGCGGACGCGGGTGC | 181 182 183 184 |
| In a family with Li-Fraumeni in which noncancerous skin fibroblasts from affected individuals showed an unusual radiation-resistant phenotype, a point mutation in codon 245 of the P53 gene. A change from GGC to GAC predicted substitution of aspartic acid for glycine. | TTGGCTCTGACTGTACCACCATCCACTACAACTACATGTGTAA CAGTTCCTGCATGGGCGGCATGAACCGGAGGCCCATCCTCA CCATCATCACACTGGAAGACTCCAGGTCAGGAGCCAC GTGGCTCCTGACCTGGAGTCTTCCAGTGTGATGATGGTGAGG ATGGGCCTCCGGTTCATGCCGCCCATGCAGGAACTGTTACAC ATGTAGTTGTAGTGGTGGTACAGTCAGAGCCAA CATGGGCGGCATGAACC GGTTCATGCCGCCCATG | 185 186 187 188 |
| In 2 of 8 families with Li-Fraumeni syndrome, a mutation in codon 248: a CGG-to-CAG change resulting in substitution of glutamine for arginine. | ACTGTACCACCATCCACTACAACTACATGTGTAACAGTTCCTG CATGGGCGGCATGAACCGGAGGCCCATCCTCACCATCATCA CACTGGAAGACTCCAGGTCAGGAGCCACTTGCCACCC GGGTGGCAAGTGGCTCCTGACCTGGAGTCTTCCAGTGTGAT GATGGTGAGGATGGGCCTCCGGTTCATGCCGCCCATGCAGG AACTGTTACACATGTAGTTGTAGTGGATGGTGGTACAGT CATGAACCGGAGGCCCA TGGGCCTCCGGTTCATG | 189 190 191 192 |
| In 9 members of an extended family with Li-Fraumeni syndrome, a germline mutation at codon 133 (ATG-to-ACG), resulted in the substitution of threonine for methionine (M133T), and completely cosegregated with the cancer syndrome. | CCCTGACTTTCAACTCTGTCTCCTTCCTCTTCCTACAGTACTC CCCTGCCCTCAACAAGATGTTTTGCCAACTGGCCAAGACCTG CCCTGTGCAGCTGTGGGTTGATTCCACACCCCCGCC GGCGGGGTGTGGAATCAACCCACAGCTGCACAGGGCAGGT CTTGGCCAGTTGGCAAAACATCTTGTTGAGGGCAGGGAGTA CTGTAGGAAGAGGAAGGAGACAGAGTTGAAAGTCAGGG CAACAAGATGTTTTGCC GGCAAAACATCTTGTTG | 193 194 195 196 |
| In 1 pedigree consistent with the Li-Fraumeni syndrome, a germline G-to-T transversion at codon 272 (valine to leucine) was found. | TCTTGCTTCTCTTTTCCTATCCTGAGTAGTGGTAATCTACTGG GACGGAACAGCTTTGAGGTGCGTGTTTGTGCCTGTCCTGGGA GAGACCGGCGCACAGAGGAAGAGAATCTCCGCAAGA TCTTGCGGAGATTCTCTTCCTCTGCGCCGGTCTCTCCCAG GACAGGCACAAACACGCACCTCAAAGCTGTTCCGTCCCAGTA GATTACCACTACTCAGGATAGGAAAAGAGAAGCAAGA GCTTTGAGGTGCGTGTT AACACGCACCTCAAAGC | 197 198 199 200 |
| A ser241-to-phe | TTATCTCCTAGGTTGGCTCTGACTGTACCACCATCCACTACAA | 201 |

TABLE 11-continued p53 Mutations and Genome-Correcting Oligos

| Clinical Phenotype & Mutation | Correcting Oligos | SEQ ID NO: |
|---|---|---|
| mutation due to a TCC-to-TTC change was found in a patient with hepatoblastoma and multiple foci of osteosarcoma | CTACATGTGTAACAGTTCCTGCATGGGCGGCATGAACCGGAG GCCCATCCTCACCATCATCACACTGGAAGACTCCAG | |
| | CTGGAGTCTTCCAGTGTGATGATGGTGAGGATGGGCCTCCG GTTCATGCCGCCCATGCAGGAACTGTTACACATGTAGTTGTA GTGGATGGTGGTACAGTCAGAGCCAACCTAGGAGATAA | 202 |
| | TAACAGTTCCTGCATGG | 203 |
| | CCATGCAGGAACTGTTA | 204 |
| An AAG-to-TAG change of codon 120, resulting in conversion from lysine to a stop codon, was found in a patient with osteosarcoma and adenocarcinoma of the lung at age 18 and brain tumor (glioma) at the age of 27. | CAGAAAACCTACCAGGGCAGCTACGGTTTCCGTCTGGGCTTC TTGCATTCTGGGACAGCCAAGTCTGTGACTTGCACGGTCAGT TGCCCTGAGGGGCTGGCTTCCATGAGACTTCAATGCC | 205 |
| | GGCATTGAAGTCTCATGGAAGCCAGCCCCTCAGGGCAACTG ACCGTGCAAGTCACAGACTTGGCTGTCCCAGAATGCAAGAAG CCCAGACGGAAACCGTAGCTGCCCTGGTAGGTTTTCTG | 206 |
| | GGACAGCCAAGTCTGTG | 207 |
| | CACAGACTTGGCTGTCC | 208 |
| A CGG-to-TGG change at codon 282, resulting in the substitution of tryptophan for arginine, was found in a patient who developed osteosarcoma at the age of 10 years. | GGTAATCTACTGGGACGGAACAGCTTTGAGGTGCGTGTTTGT GCCTGTCCTGGGAGAGACCGGCGCACAGAGGAAGAGAATCT CCGCAAGAAAGGGGAGCCTCACCACGAGCTGCCCCCAG | 209 |
| | CTGGGGGCAGCTCGTGGTGAGGCTCCCCTTTCTTGCGGAGA TTCTCTTCCTCTGTGCGCCGGTCTCTCCCAGGACAGGCACAA ACACGCACCTCAAAGCTGTTCCGTCCCAGTAGATTACC | 210 |
| | GGAGAGACCGGCGCACA | 211 |
| | TGTGCGCCGGTCTCTCC | 212 |
| In 5 of 6 anaplastic carcinomas of the thyroid and in an anaplastic carcinoma thyroid cell line ARO, a CGT-to-CAT mutation converted arginine-273 to histidine. | GCTTCTCTTTTCCTATCCTGAGTAGTGGTAATCTACTGGGACG GAACAGCTTTGAGGTGCGTGTTTGTGCCTGTCCTGGGAGAGA CCGGCGCACAGAGGAAGAGAATCTCCGCAAGAAAGG | 213 |
| | CCTTTCTTGCGGAGATTCTCTTCCTCTGTGCGCCGGTCTCTC CCAGGACAGGCACAAACACACACCTCAAAGCTGTTCCGTCCC AGTAGATTACCACTACTCAGGATAGGAAAAGAGAAGC | 214 |
| | TGAGGTGCGTGTTTGTG | 215 |
| | CACAAACACGCACCTCA | 216 |
| A germline GGA-to-GTA mutation resulting in a change of glycine-325 to valine was found in a patient who had non-Hodgkin lymphoma diagnosed at age 17 and colon carcinoma at age 26. | TCCTAGCACTGCCCAACAACACCAGCTCCTCTCCCCAGCCAA AGAAGAAACCACTGGATGGAGAATATTTCACCCTTCAGGTACT AAGTCTTGGGACCTCTTATCAAGTGGAAAGTTTCCA | 217 |
| | TGGAAACTTTCCACTTGATAAGAGGTCCCAAGACTTAGTACCT GAAGGGTGAAATATTCTCCATCCAGTGGTTTCTTCTTTGGCTG GGGAGAGGAGCTGGTGTTGTTGGGCAGTGCTAGGA | 218 |
| | ACTGGATGGAGAATATT | 219 |
| | AATATTCTCCATCCAGT | 220 |
| CGC-CCC Arg-72 to Pro association with Lung cancer | AATGGTTCACTGAAGACCCAGGTCCAGATGAAGCTCCCAGAA TGCCAGAGGCTGCTCCCCGCGTGGCCCCTGCACCAGCAGCT CCTACACCGGCGGCCCCTGCACCAGCCCCTCCTGGCC | 221 |
| | GGCCAGGAGGGGGCTGGTGCAGGGGCCGCCGGTGTAGGAG CTGCTGGTGCAGGGGCCACGCGGGGAGCAGCCTCTGGCATT CTGGGAGCTTCATCTGGACCTGGGTCTTCAGTGAACCATT | 222 |
| | TGCTCCCCGCGTGGCCC | 223 |
| | GGGCCACGCGGGGAGCA | 224 |
| CCG-CTG Pro-82 to Leu Breast cancer | AAGCTCCCAGAATGCCAGAGGCTGCTCCCCGCGTGGCCCCT GCACCAGCAGCTCCTACACCGGCGGCCCCTGCACCAGCCCC CTCCTGGCCCCTGTCATCTTCTGTCCCTTCCCAGAAAAC | 225 |
| | GTTTTCTGGGAAGGGACAGAAGATGACAGGGGCCAGGAGGG GGCTGGTGCAGGGGCCGCCGGTGTAGGAGCTGCTGGTGCA GGGGCCACGCGGGGAGCAGCCTCTGGCATTCTGGGAGCTT | 226 |
| | TCCTACACCGGCGGCCC | 227 |
| | GGGCCGCCGGTGTAGGA | 228 |
| cCAA-TAA Gln-136 to Term Li-Fraumeni syndrome | TTCAACTCTGTCTCCTTCCTCTTCCTACAGTACTCCCCTGCCC TCAACAAGATGTTTTGCCAACTGGCCAAGACCTGCCCTGTGC AGCTGTGGGTTGATTCCACACCCCCGCCCGGCACCC | 229 |
| | GGGTGCCGGGCGGGGTGTGGAATCAACCCACAGCTGCACA GGGCAGGTCTTGGCCAGTTGGCAAAACATCTTGTTGAGGGCA GGGGAGTACTGTAGGAAGAGGAAGGAGACAGAGTTGAA | 230 |
| | TGTTTTGCCAACTGGCC | 231 |
| | GGCCAGTTGGCAAAACA | 232 |
| TGC-TAC Cys-141 to Tyr Li-Fraumeni syndrome | TCCTCTTCCTACAGTACTCCCCTGCCCTCAACAAGATGTTTTG CCAACTGGCCAAGACCTGCCCTGTGCAGCTGTGGGTTGATTC CACACCCCCGCCCGGCACCCGCGTCCGCGCCATGGC | 233 |
| | GCCATGGCGCGGACGCGGGTGCCGGGCGGGGTGTGGAAT | 234 |

TABLE 11-continued p53 Mutations and Genome-Correcting Oligos

| Clinical Phenotype & Mutation | Correcting Oligos | SEQ ID NO: |
|---|---|---|
| | CAACCCACAGCTGCACAGGGCAGGTCTTGGCCAGTTGGCAA AACATCTTGTTGAGGGCAGGGGAGTACTGTAGGAAGAGGA | |
| | CAAGACCTGCCCTGTGC | 235 |
| | GCACAGGGCAGGTCTTG | 236 |
| aCCC-TCC Pro-151 to Ser Li-Fraumeni syndrome | AACAAGATGTTTTGCCAACTGGCCAAGACCTGCCCTGTGCAG CTGTGGGTTGATTCCACACCCCCGCCCGGCACCCGCGTCCG CGCCATGGCCATCTACAAGCAGTCACAGCACATGACGG | 237 |
| | CCGTCATGTGCTGTGACTGCTTGTAGATGGCCATGGCGCGG ACGCGGGTGCCGGGCGGGGGTGTGGAATCAACCCACAGCT GCACAGGGCAGGTCTTGGCCAGTTGGCAAAACATCTTGTT | 238 |
| | ATTCCACACCCCCGCCC | 239 |
| | GGGCGGGGGTGTGGAAT | 240 |
| CCG-CTG Pro-152 to Leu Adrenocortical carcinoma | AGATGTTTTGCCAACTGGCCAAGACCTGCCCTGTGCAGCTGT GGGTTGATTCCACACCCCCGCCCGGCACCCGCGTCCGCGCC ATGGCCATCTACAAGCAGTCACAGCACATGACGGAGGT | 241 |
| | ACCTCCGTCATGTGCTGTGACTGCTTGTAGATGGCCATGGCG CGGACGCGGGTGCCGGGCGGGGTGTGGAATCAACCCACA GCTGCACAGGGCAGGTCTTGGCCAGTTGGCAAAACATCT | 242 |
| | CACACCCCCGCCCGGCA | 243 |
| | TGCCGGGCGGGGGTGTG | 244 |
| GGC-GTC Gly-154 to Val Glioblastoma | TTTGCCAACTGGCCAAGACCTGCCCTGTGCAGCTGTGGGTTG ATTCCACACCCCCGCCCGGCACCCGCGTCCGCGCCATGGCC ATCTACAAGCAGTCACAGCACATGACGGAGGTTGTGAG | 245 |
| | CTCACAACCTCCGTCATGTGCTGTGACTGCTTGTAGATGGCC ATGGCGCGGACGCGGGTGCCGGGCGGGGTGTGGAATCAA CCCACAGCTGCACAGGGCAGGTCTTGGCCAGTTGGCAAA | 246 |
| | CCCGCCCGGCACCCGCG | 247 |
| | CGCGGGTGCCGGGCGGG | 248 |
| CGC-CAC Arg-175 to His Li-Fraumeni syndrome | CCCGCGTCCGCGCCATGGCCATCTACAAGCAGTCACAGCAC ATGACGGAGGTTGTGAGGCGCTGCCCCACCATGAGCGCTG CTCAGATAGCGATGGTGAGCAGCTGGGGCTGGAGAGACG | 249 |
| | CGTCTCTCCAGCCCCAGCTGCTCACCATCGCTATCTGAGCAG CGCTCATGGTGGGGGCAGCGCCTCACAACCTCCGTCATGTG CTGTGACTGCTTGTAGATGGCCATGGCGCGGACGCGGG | 250 |
| | TGTGAGGCGCTGCCCCC | 251 |
| | GGGGGCAGCGCCTCACA | 252 |
| tGAG-AAG Glu-180 to Lys Li-Fraumeni syndrome | ATGGCCATCTACAAGCAGTCACAGCACATGACGGAGGTTGTG AGGCGCTGCCCCCACCATGAGCGCTGCTCAGATAGCGATGG TGAGCAGCTGGGGCTGGAGAGACGACAGGGCTGGTTGC | 253 |
| | GCAACCAGCCCTGTCGTCTCTCCAGCCCCAGCTGCTCACCAT CGCTATCTGAGCAGCGCTCATGGTGGGGGCAGCGCCTCACA ACCTCCGTCATGTGCTGTGACTGCTTGTAGATGGCCAT | 254 |
| | CCCACCATGAGCGCTGC | 255 |
| | GCAGCGCTCATGGTGGG | 256 |
| gCGC-TGC Arg-181 to Cys Breast cancer | GCCATCTACAAGCAGTCACAGCACATGACGGAGGTTGTGAGG CGCTGCCCCCACCATGAGCGCTGCTCAGATAGCGATGGTGA GCAGCTGGGGCTGGAGAGACGACAGGGCTGGTTGCCCA | 257 |
| | TGGGCAACCAGCCCTGTCGTCTCTCCAGCCCCAGCTGCTCA CCATCGCTATCTGAGCAGCGCTCATGGTGGGGCAGCGCCT CACAACCTCCGTCATGTGCTGTGACTGCTTGTAGATGGC | 258 |
| | ACCATGAGCGCTGCTCA | 259 |
| | TGAGCAGCGCTCATGGT | 260 |
| CGC-CAC Arg-81 to His Breast cancer | CCATCTACAAGCAGTCACAGCACATGACGGAGGTTGTGAGGC GCTGCCCCCACCATGAGCGCTGCTCAGATAGCGATGGTGAG CAGCTGGGGCTGGAGAGACGACAGGGCTGGTTGCCCAG | 261 |
| | CTGGGCAACCAGCCCTGTCGTCTCTCCAGCCCCAGCTGCTC ACCATCGCTATCTGAGCAGCGCTCATGGTGGGGCAGCGCC TCACAACCTCCGTCATGTGCTGTGACTGCTTGTAGATGG | 262 |
| | CCATGAGCGCTGCTCAG | 263 |
| | CTGAGCAGCGCTCATGG | 264 |
| CAT-CGT His-193 to Arg Li-Fraumeni syndrome | CCAGGGTCCCCAGGCCTCTGATTCCTCACTGATTGCTCTTAG GTCTGGCCCCTCCTCAGCATCTTATCCGAGTGGAAGGAAATT TGCGTGTGGAGTATTTGGATGACAGAAACACTTTTCG | 265 |
| | CGAAAAGTGTTTCTGTCATCCAAATACTCCACACGCAAATTTC CTTCCACTCGGATAAGATGCTGAGGAGGGGCCAGACCTAAGA GCAATCAGTGAGGAATCAGAGGCCTGGGGACCCTGG | 266 |
| | TCCTCAGCATCTTATCC | 267 |
| | GGATAAGATGCTGAGGA | 268 |
| cCGA-TGA Arg-196 to Term Adrenocortical carcinoma | CCCAGGCCTCTGATTCCTCACTGATTGCTCTTAGGTCTGGCC CCTCCTCAGCATCTTATCCGAGTGGAAGGAAATTTGCGTGTG GAGTATTTGGATGACAGAAACACTTTTCGACATAGTG | 269 |
| | CACTATGTCGAAAAGTGTTTCTGTCATCCAAATACTCCACACG CAAATTTCCTTCCACTCGGATAAGATGCTGAGGAGGGGCCAG ACCTAAGAGCAATCAGTGAGGAATCAGAGGCCTGGG | 270 |

TABLE 11-continued p53 Mutations and Genome-Correcting Oligos

| Clinical Phenotype & Mutation | Correcting Oligos | SEQ ID NO: |
|---|---|---|
| | ATCTTATCCGAGTGGAA | 271 |
| | TTCCACTCGGATAAGAT | 272 |
| cAGA-TGA Arg-209 to Term Li-Fraumeni syndrome | GCCCCTCCTCAGCATCTTATCCGAGTGGAAGGAAATTTGCGT GTGGAGTATTTGGATGACAGAAACACTTTTCGACATAGTGTG GTGGTGCCCTATGAGCCGCCTGAGGTCTGGTTTGCAA | 273 |
| | TTGCAAACCAGACCTCAGGCGGCTCATAGGGCACCACCACA CTATGTCGAAAAGTGTTTCTGTCATCCAAATACTCCACACGCA AATTTCCTTCCACTCGGATAAGATGCTGAGGAGGGGC | 274 |
| | TGGATGACAGAAACACT | 275 |
| | AGTGTTTCTGTCATCCA | 276 |
| tCGA-TGA Arg-213 to Term Li-Fraumeni syndrome | CATCTTATCCGAGTGGAAGGAAATTTGCGTGTGGAGTATTTG GATGACAGAAACACTTTTCGACATAGTGTGGTGGTGCCCTAT GAGCCGCCTGAGGTCTGGTTTGCAACTGGGGTCTCTG | 277 |
| | CAGAGACCCCAGTTGCAAACCAGACCTCAGGCGGCTCATAG GGCACCACCACACTATGTCGAAAAGTGTTTCTGTCATCCAAAT ACTCCACACGCAAATTTCCTTCCACTCGGATAAGATG | 278 |
| | ACACTTTTCGACATAGT | 279 |
| | ACTATGTCGAAAAGTGT | 280 |
| gCCC-TCC Pro-219 to Ser Adrenocortical carcinoma | GGAAATTTGCGTGTGGAGTATTTGGATGACAGAAACACTTTTC GACATAGTGTGGTGGTGCCCTATGAGCCGCCTGAGGTCTGG TTTGCAACTGGGGTCTCTGGGAGGAGGGGTTAAGGGT | 281 |
| | ACCCTTAACCCCTCCTCCCAGAGACCCCAGTTGCAAACCAGA CCTCAGGCGGCTCATAGGGCACCACCACACTATGTCGAAAAG TGTTTCTGTCATCCAAATACTCCACACGCAAATTTCC | 282 |
| | TGGTGGTGCCCTATGAG | 283 |
| | CTCATAGGGCACCACCA | 284 |
| TAT-TGT Tyr-220 to Cys Li-Fraumeni syndrome | ATTTGCGTGTGGAGTATTTGGATGACAGAAACACTTTTCGACA TAGTGTGGTGGTGCCCTATGAGCCGCCTGAGGTCTGGTTTG CAACTGGGGTCTCTGGGAGGAGGGGTTAAGGGTGGTT | 285 |
| | AACCACCCTTAACCCCTCCTCCCAGAGACCCCAGTTGCAAAC CAGACCTCAGGCGGCTCATAGGGCACCACCACACTATGTCG AAAAGTGTTTCTGTCATCCAAATACTCCACACGCAAAT | 286 |
| | GGTGCCCTATGAGCCGC | 287 |
| | GCGGCTCATAGGGCACC | 288 |
| cTCT-ACT Ser-227 to Thr Rhabdomyosarcoma | CACAGGTCTCCCCAAGGCGCACTGGCCTCATCTTGGGCCTG TGTTATCTCCTAGGTTGGCTCTGACTGTACCACCATCCACTAC AACTACATGTGTAACAGTTCCTGCATGGGCGGCATGA | 289 |
| | TCATGCCGCCCATGCAGGAACTGTTACACATGTAGTTGTAGT GGATGGTGGTACAGTCAGAGCCAACCTAGGAGATAACACAG GCCCAAGATGAGGCCAGTGCGCCTTGGGGAGACCTGTG | 290 |
| | AGGTTGGCTCTGACTGT | 291 |
| | ACAGTCAGAGCCAACCT | 292 |
| cCAC-AAC His-233 to Asn Glioma | GCACTGGCCTCATCTTGGGCCTGTGTTATCTCCTAGGTTGGC TCTGACTGTACCACCATCCACTACAACTACATGTGTAACAGTT CCTGCATGGGCGGCATGAACCGGAGGCCCATCCTCA | 293 |
| | TGAGGATGGGCCTCCGGTTCATGCCGCCCATGCAGGAACTG TTACACATGTAGTTGTAGTGGATGGTGGTACAGTCAGAGCCA ACCTAGGAGATAACACAGGCCCAAGATGAGGCCAGTGC | 294 |
| | CCACCATCCACTACAAC | 295 |
| | GTTGTAGTGGATGGTGG | 296 |
| cAAC-GAC Asn-235 to Asp Adrenocortical carcinoma | GCCTCATCTTGGGCCTGTGTTATCTCCTAGGTTGGCTCTGAC TGTACCACCATCCACTACAACTACATGTGTAACAGTTCCTGCA TGGGCGGCATGAACCGGAGGCCCATCCTCACCATCA | 297 |
| | TGATGGTGAGGATGGGCCTCCGGTTCATGCCGCCCATGCAG GAACTGTTACACATGTAGTTGTAGTGGATGGTGGTACAGTCA GAGCCAACCTAGGAGATAACACAGGCCCAAGATGAGGC | 298 |
| | TCCACTACAACTACATG | 299 |
| | CATGTAGTTGTAGTGGA | 300 |
| AAC-AGC Asn-235 to Ser Rhabdomyosarcoma | CCTCATCTTGGGCCTGTGTTATCTCCTAGGTTGGCTCTGACT GTACCACCATCCACTACAACTACATGTGTAACAGTTCCTGCAT GGGCGGCATGAACCGGAGGCCCATCCTCACCATCAT | 301 |
| | ATGATGGTGAGGATGGGCCTCCGGTTCATGCCGCCCATGCA GGAACTGTTACACATGTAGTTGTAGTGGATGGTGGTACAGTC AGAGCCAACCTAGGAGATAACACAGGCCCAAGATGAGG | 302 |
| | CCACTACAACTACATGT | 303 |
| | ACATGTAGTTGTAGTGG | 304 |
| ATCc-ATG Ile-251 to Met Glioma | CATCCACTACAACTACATGTGTAACAGTTCCTGCATGGGCGG CATGAACCGGAGGCCCATCCTCACCATCATCACACTGGAAGA CTCCAGGTCAGGAGCCACTTGCCACCCTGCACACTGG | 305 |
| | CCAGTGTGCAGGGTGGCAAGTGGCTCCTGACCTGGAGTCTT CCAGTGTGATGATGGTGAGGATGGGCCTCCGGTTCATGCCG CCCATGCAGGAACTGTTACACATGTAGTTGTAGTGGATG | 306 |
| | AGGCCCATCCTCACCAT | 307 |
| | ATGGTGAGGATGGGCCT | 308 |

TABLE 11-continued p53 Mutations and Genome-Correcting Oligos

| Clinical Phenotype & Mutation | Correcting Oligos | SEQ ID NO: |
|---|---|---|
| ACA-ATA<br>Thr-256 to Ile<br>Glioblastoma | ACATGTGTAACAGTTCCTGCATGGGCGGCATGAACCGGAGG<br>CCCATCCTCACCATCATCACACTGGAAGACTCCAGGTCAGGA<br>GCCACTTGCCACCCTGCACACTGGCCTGCTGTGCCCCA | 309 |
| | TGGGGCACAGCAGGCCAGTGTGCAGGGTGGCAAGTGGCTCC<br>TGACCTGGAGTCTTCCAGTGTGATGATGGTGAGGATGGGCCT<br>CCGGTTCATGCCGCCCATGCAGGAACTGTTACACATGT | 310 |
| | CATCATCACACTGGAAG | 311 |
| | CTTCCAGTGTGATGATG | 312 |
| CTG-CAG<br>Leu-257 to Gln<br>Li-Fraumeni syndrome | TGTGTAACAGTTCCTGCATGGGCGGCATGAACCGGAGGCCC<br>ATCCTCACCATCATCACACTGGAAGACTCCAGGTCAGGAGCC<br>ACTTGCCACCCTGCACACTGGCCTGCTGTGCCCCAGCC | 313 |
| | GGCTGGGGCACAGCAGGCCAGTGTGCAGGGTGGCAAGTGG<br>CTCCTGACCTGGAGTCTTCCAGTGTGATGATGGTGAGGATGG<br>GCCTCCGGTTCATGCCGCCCATGCAGGAACTGTTACACA | 314 |
| | CATCACACTGGAAGACT | 315 |
| | AGTCTTCCAGTGTGATG | 316 |
| CTG-CCG<br>Leu-265 to Pro<br>Li-Fraumeni syndrome | GACCTGATTTCCTTACTGCCTCTTGCTTCTCTTTTCCTATCCT<br>GAGTAGTGGTAATCTACTGGGACGGAACAGCTTTGAGGTGCG<br>TGTTTGTGCCTGTCCTGGGAGAGACCGGCGCACAGA | 317 |
| | TCTGTGCGCCGGTCTCTCCCAGGACAGGCACAAACACGCAC<br>CTCAAAGCTGTTCCGTCCCAGTAGATTACCACTACTCAGGAT<br>AGGAAAAGAGAAGCAAGAGGCAGTAAGGAAATCAGGTC | 318 |
| | TAATCTACTGGGACGGA | 319 |
| | TCCGTCCCAGTAGATTA | 320 |
| gCGT-TGT<br>Arg-273 to Cys<br>Li-Fraumeni syndrome | TGCTTCTCTTTTCCTATCCTGAGTAGTGGTAATCTACTGGGAC<br>GGAACAGCTTTGAGGTGCGTGTTTGTGCCTGTCCTGGGAGA<br>GACCGGCGCACAGAGGAAGAGAATCTCCGCAAGAAAG | 321 |
| | CTTTCTTGCGGAGATTCTCTTCCTCTGTGCGCCGGTCTCTCC<br>CAGGACAGGCACAAACACGCACCTCAAAGCTGTTCCGTCCCA<br>GTAGATTACCACTACTCAGGATAGGAAAGAGAAGCA | 322 |
| | TTGAGGTGCGTGTTTGT | 323 |
| | ACAAACACGCACCTCAA | 324 |
| TGT-TAT<br>Cys-275 to Tyr<br>Li-Fraumeni syndrome | CTTTTCCTATCCTGAGTAGTGGTAATCTACTGGGACGGAACA<br>GCTTTGAGGTGCGTGTTTGTGCCTGTCCTGGGAGAGACCGG<br>CGCACAGAGGAAGAGAATCTCCGCAAGAAAGGGGAGCC | 325 |
| | GGCTCCCCTTTCTTGCGGAGATTCTCTTCCTCTGTGCGCCGG<br>TCTCTCCCAGGACAGGCACAAACACGCACCTCAAAGCTGTTC<br>CGTCCCAGTAGATTACCACTACTCAGGATAGGAAAAG | 326 |
| | GCGTGTTTGTGCCTGTC | 327 |
| | GACAGGCACAAACACGC | 328 |
| CCT-CTT<br>Pro-278 to Leu<br>Breast cancer | TCCTGAGTAGTGGTAATCTACTGGGACGGAACAGCTTTGAGG<br>TGCGTGTTTGTGCCTGTCCTGGGAGAGACCGGCGCACAGAG<br>GAAGAGAATCTCCGCAAGAAAGGGGAGCCTCACCACGA | 329 |
| | TCGTGGTGAGGCTCCCCTTTCTTGCGGAGATTCTCTTCCTCT<br>GTGCGCCGGTCTCTCCCAGGACAGGCACAAACACGCACCTC<br>AAAGCTGTTCCGTCCCAGTAGATTACCACTACTCAGGA | 330 |
| | TGCCTGTCCTGGGAGAG | 331 |
| | CTCTCCCAGGACAGGCA | 332 |
| AGA-AAA<br>Arg-280 to Lys<br>Glioma | GTAGTGGTAATCTACTGGGACGGAACAGCTTTGAGGTGCGTG<br>TTTGTGCCTGTCCTGGGAGAGACCGGCGCACAGAGGAAGAG<br>AATCTCCGCAAGAAAGGGGAGCCTCACCACGAGCTGCC | 333 |
| | GGCAGCTCGTGGTGAGGCTCCCCTTTCTTGCGGAGATTCTCT<br>TCCTCTGTGCGCCGGTCTCTCCCAGGACAGGCACAAACACG<br>CACCTCAAAGCTGTTCCGTCCCAGTAGATTACCACTAC | 334 |
| | TCCTGGGAGAGACCGGC | 335 |
| | GCCGGTCTCTCCCAGGA | 336 |
| GAA-GCA<br>Glu-286 to Ala<br>Adrenocortical<br>carcinoma | GGAACAGCTTTGAGGTGCGTGTTTGTGCCTGTCCTGGGAGA<br>GACCGGCGCACAGAGGAAGAGAATCTCCGCAAGAAAGGGGA<br>GCCTCACCACGAGCTGCCCCCAGGGAGCACTAAGCGAGG | 337 |
| | CCTCGCTTAGTGCTCCCTGGGGGCAGCTCGTGGTGAGGCTC<br>CCCTTTCTTGCGGAGATTCTTCTTCCTCTGTGCGCCGGTCTCT<br>CCCAGGACAGGCACAAACACGCACCTCAAAGCTGTTCC | 338 |
| | AGAGGAAGAGAATCTCC | 339 |
| | GGAGATTCTTCTTCCTCT | 340 |
| CGA-CCA<br>Arg-306 to Pro<br>Rhabdomyosarcoma | AAGAGAATCTCCGCAAGAAAGGGGAGCCTCACCACGAGCTG<br>CCCCCAGGGAGCACTAAGCGAGGTAAGCAAGCAGGACAAGA<br>AGCGGTGGAGGAGACCAAGGGTGCAGTTATGCCTCAGAT | 341 |
| | ATCTGAGGCATAACTGCACCCTTGGTCTCCTCCACCGCTTCT<br>TGTCCTGCTTGCTTACCTCGCTTAGTGCTCCCTGGGGGCAGC<br>TCGTGGTGAGGCTCCCCTTTCTTGCGGAGATTCTCTT | 342 |
| | CACTAAGCGAGGTAAGC | 343 |
| | GCTTACCTCGCTTAGTG | 344 |
| gCGA-TGA<br>Arg-306 to Term | GAAGAGAATCTCCGCAAGAAAGGGGAGCCTCACCACGAGCT<br>GCCCCCAGGGAGCACTAAGCCGAGGTAAGCAAGCAGGACAAG | 345 |

TABLE 11-continued p53 Mutations and Genome-Correcting Oligos

| Clinical Phenotype & Mutation | Correcting Oligos | SEQ ID NO: |
|---|---|---|
| Li-Fraumeni syndrome | AAGCGGTGGAGGAGACCAAGGGTGCAGTTATGCCTCAGA | |
| | TCTGAGGCATAACTGCACCCTTGGTCTCCTCCACCGCTTCTT | 346 |
| | GTCCTGCTTGCTTACCTCGCTTAGTGCTCCCTGGGGGCAGCT | |
| | CGTGGTGAGGCTCCCCTTTCTTGCGGAGATTCTCTTC | |
| | GCACTAAGCGAGGTAAG | 347 |
| | CTTACCTCGCTTAGTGC | 348 |
| gCGC-TGC | GGTACTGTGAATATACTTACTTCTCCCCCTCCTCTGTTGCTGC | 349 |
| Arg-337 to Cys | AGATCCGTGGGCGTGAGCGCTTCGAGATGTTCCGAGAGCTG | |
| Osteosarcoma | AATGAGGCCTTGGAACTCAAGGATGCCCAGGCTGGGA | |
| | TCCCAGCCTGGGCATCCTTGAGTTCCAAGGCCTCATTCAGCT | 350 |
| | CTCGGAACATCTCGAAGCGCTCACGCCCACGGATCTGCAGC | |
| | AACAGAGGAGGGGGAGAAGTAAGTATATTCACAGTACC | |
| | GGCGTGAGCGCTTCGAG | 351 |
| | CTCGAAGCGCTCACGCC | 352 |
| CTG-CCG | CTCCCCCTCCTCTGTTGCTGCAGATCCGTGGGCGTGAGCGC | 353 |
| Leu-344 to Pro | TTCGAGATGTTCCGAGAGCTGAATGAGGCCTTGGAACTCAAG | |
| Li-Fraumeni syndrome | GATGCCCAGGCTGGGAAGGAGCCAGGGGGGAGCAGGGC | |
| | GCCCTGCTCCCCCCTGGCTCCTTCCCAGCCTGGGCATCCTT | 354 |
| | GAGTTCCAAGGCCTCATTCAGCTCTCGGAACATCTCGAAGCG | |
| | CTCACGCCCACGGATCTGCAGCAACAGAGGAGGGGGAG | |
| | CCGAGAGCTGAATGAGG | 355 |
| | CCTCATTCAGCTCTCGG | 356 |

EXAMPLE 6

Beta Globin

Hemoglobin, the major protein in the red blood cell, binds oxygen reversibly and is responsible for the cells' capacity to transport oxygen to the tissues. In adults, the major hemoglobin is hemoglobin A, a tetrameric protein consisting of two identical alpha globin chains and two beta globin chains. Disorders involving hemoglobin are among the most common genetic disorders worldwide, with approximately 5% of the world's population being carriers for clinically important hemoglobin mutations. Approximately 300,000 severely affected homozygotes or compound heterozygotes are born each year.

Mutation of the glutamic acid at position 7 in beta globin to valine causes sickle cell anemia, the clinical manifestations of which are well known. Mutations that cause absence of beta chain cause beta-zero-thalassemia. Reduced amounts of detectable beta globin causes beta-plus-thalassemia. For clinical purposes, beta-thalassemia is divided into thalassemia major (transfusion dependent), thalassemia intermedia (of intermediate severity), and thalassemia minor (asymptomatic). Patients with thalassemia major present in the first year of life with severe anemia; they are unable to maintain a hemoglobin level about 5 gm/dl.

The beta-thalassemias were among the first human genetic diseases to be examined by means of recombinant DNA analysis. Baysal et al., *Hemoglobin* 19(3–4):213–36 (1995) and others provide a compendium of mutations that result in beta-thalassemia.

Hemoglobin disorders were among the first to be considered for gene therapy. Transcriptional silencing of genes transferred into hematopoietic stem cells, however, poses one of the most significant challenges to its success. If the transferred gene is not completely silenced, a progressive decline in gene expression is often observed. Position effect variegation (PEV) and silencing mechanisms may act on a transferred globin gene residing in chromatin outside of the normal globin locus during the important terminal phases of erythroblast development when globin transcripts normally accumulate rapidly despite heterochromatization and shutdown of the rest of the genome. The attached table discloses the correcting oligonucleotide base sequences for the beta globin oligonucleotides of the invention.

TABLE 12

Beta Globin Mutations and Genome-Correcting Oligos

| Clinical Phenotype & Mutation | Correcting Oligos | SEQ ID NO: |
|---|---|---|
| Sickle Cell Anemia | TCTGACACAACTGTGTTCACTAGCAACCTCAAACAGACACCA | 357 |
| GLU-7-VAL | TGGTGCACCTGACTCCTGAGGAGAAGTCTGCCGTTACTGCC | |
| GAG to GTG | CTGTGGGGCAAGGTGAACGTGGATGAAGTTGGTGGTGA | |
| | TCACCACCAACTTCATCCACGTTCACCTTGCCCCACAGGGCA | 358 |
| | GTAACGGCAGACTTCTCCTCAGGAGTCAGGTGCACCATGGT | |
| | GTCTGTTTGAGGTTGCTAGTGAACACAGTTGTGTCAGA | |
| | GACTCCTGAGGAGAAGT | 359 |
| | ACTTCTCCTCAGGAGTC | 360 |
| Thalassaemia Beta | CTATTGCTTACATTTGCTTCTGACACAACTGTGTTCACTAGCA | 361 |
| MET-0-ARG | ACCTCAAACAGACACCATGGTGCACCTGACTCCTGAGGAGA | |
| ATG to AGG | AGTCTGCCGTTACTGCCCTGTGGGGCAAGGTGAACGT | |

TABLE 12-continued

Beta Globin Mutations and Genome-Correcting Oligos

| Clinical Phenotype & Mutation | Correcting Oligos | SEQ ID NO: |
|---|---|---|
| | ACGTTCACCTTGCCCCACAGGGCAGTAACGGCAGACTTCTC CTCAGGAGTCAGGTGCACCATGGTGTCTGTTTGAGGTTGCT AGTGAACACAGTTGTGTCAGAAGCAAATGTAAGCAATAG | 362 |
| | AGACACCATGGTGCACC | 363 |
| | GGTGCACCATGGTGTCT | 364 |
| Thalassaemia Beta MET-0-ILE ATG to ATA | TATTGCTTACATTTGCTTCTGACACAACTGTGTTCACTAGCAA CCTCAAACAGACACCATGGTGCACCTGACTCCTGAGGAGAA GTCTGCCGTTACTGCCCTGTGGGGCAAGGTGAACGTG | 365 |
| | CACGTTCACCTTGCCCCACAGGGCAGTAACGGCAGACTTCT CCTCAGGAGTCAGGTGCACCCATGGTGTCTGTTTGAGGTTGC TAGTGAACACAGTTGTGTCAGAAGCAAATGTAAGCAATA | 366 |
| | GACACCATGGTGCACCT | 367 |
| | AGGTGCACCCATGGTGTC | 368 |
| Thalassaemia Beta MET-0-ILE ATG to ATT | TATTGCTTACATTTGCTTCTGACACAACTGTGTTCACTAGCAA CCTCAAACAGACACCATGGTGCACCTGACTCCTGAGGACAA GTCTGCCGTTACTGCCCTGTGGGGCAAGGTGAACGTG | 369 |
| | CACGTTCACCTTGCCCCACAGGGCAGTAACGGCAGACTTCT CCTCAGGAGTCAGGTGCACCCATGGTGTCTGTTTGAGGTTGC TAGTGAACACAGTTGTGTCAGAAGCAAATGTAAGCAATA | 370 |
| | GACACCATGGTGCACCT | 371 |
| | AGGTGCACCCATGGTGTC | 372 |
| Thalassaemia Beta MET-0-LYS ATG to AAG | CTATTGCTTACATTTGCTTCTGACACAACTGTGTTCACTAGCA ACCTCAAACAGACACCATGGTGCACCTGACTCCTGAGGAGA AGTCTGCCGTTACTGCCCTGTGGGGCAAGGTGAACGT | 373 |
| | ACGTTCACCTTGCCCCACAGGGCAGTAACGGCAGACTTCTC CTCAGGAGTCAGGTGCACCATGGTGTCTGTTTGAGGTTGCT AGTGAACACAGTTGTGTCAGAAGCAAATGTAAGCAATAG | 374 |
| | AGACACCATGGTGCACC | 375 |
| | GGTGCACCATGGTGTCT | 376 |
| Thalassaemia Beta MET-0-THR ATG to ACG | CTATTGCTTACATTTGCTTCTGACACAACTGTGTTCACTAGCA ACCTCAAACAGACACCATGGTGCACCTGACTCCTGAGGAGA AGTCTGCCGTTACTGCCCTGTGGGGCAAGGTGAACGT | 377 |
| | ACGTTCACCTTGCCCCACAGGGCAGTAACGGCAGACTTCTC CTCAGGAGTCAGGTGCACCATGGTGTCTGTTTGAGGTTGCT AGTGAACACAGTTGTGTCAGAAGCAAATGTAAGCAATAG | 378 |
| | AGACACCATGGTGCACC | 379 |
| | GGTGCACCATGGTGTCT | 380 |
| Thalassaemia Beta MET-0-VAL ATG to GTG | TCTATTGCTTACATTTGCTTCTGACACAACTGTGTTCACTAGC AACCTCAAACAGACACCATGGTGCACCTGACTCCTGAGGAG AAGTCTGCCGTTACTGCCCTGTGGGGCAAGGTGAACG | 381 |
| | CGTTCACCTTGCCCCACAGGGCAGTAACGGCAGACTTCTCC TCAGGAGTCAGGTGCACCATGGTGTCTGTTTGAGGTTGCTAG TGAACACAGTTGTGTCAGAAGCAAATGTAAGCAATAGA | 382 |
| | CAGACACCATGGTGCAC | 383 |
| | GTGCACCATGGTGTCTG | 384 |
| Thalassaemia Beta TRP-16-Term TGG to TGA | TCAAACAGACACCATGGTGCACCTGACTCCTGAGGAGAAGT CTGCCGTTACTGCCCTGTGGGGCAAGGTGAACGTGGATGAA GTTGGTGGTGAGGCCCTGGGCAGGTTGGTATCAAGGTTA | 385 |
| | TAACCTTGATACCAACCTGCCCAGGGCCTCACCACCAACTTC ATCCACGTTCACCTTGCCCCACAGGGCAGTAACGGCAGACT TCTCCTCAGGAGTCAGGTGCACCATGGTGTCTGTTTGA | 386 |
| | GCCCTGTGGGGCAAGGT | 387 |
| | ACCTTGCCCCACAGGGC | 388 |
| Thalassaemia Beta TRP-16-Term TGG to TAG | CTCAAACAGACACCATGGTGCACCTGACTCCTGAGGAGAAG TCTGCCGTTACTGCCCTGTGGGGCAAGGTGAACGTGGATGA AGTTGGTGGTGAGGCCCTGGGCAGGTTGGTATCAAGGTT | 389 |
| | AACCTTGATACCAACCTGCCCAGGGCCTCACCACCAACTTCA TCCACGTTCACCTTGCCCCACAGGGCAGTAACGGCAGACTT CTCCTCAGGAGTCAGGTGCACCATGGTGTCTGTTTGAG | 390 |
| | TGCCCTGTGGGGCAAGG | 391 |
| | CCTTGCCCCACAGGGCA | 392 |
| Thalassaemia Beta LYS-18-Term AAG to TAG | ACAGACACCATGGTGCACCTGACTCCTGAGGAGAAGTCTGC CGTTACTGCCCTGTGGGGCAAGGTGAACGTGGATGAAGTTG GTGGTGAGGCCCTGGGCAGGTTGGTATCAAGGTTACAAG | 393 |
| | CTTGTAACCTTGATACCAACCTGCCCAGGGCCTCACCACCAA CTTCATCCACGTTCACCTTGCCCCACAGGGCAGTAACGGCA GACTTCTCCTCAGGAGTCAGGTGCACCATGGTGTCTGT | 394 |
| | TGTGGGGCAAGGTGAAC | 395 |
| | GTTCACCTTGCCCCACA | 396 |
| Thalassaemia Beta ASN-20-SER AAC to AGC | CCATGGTGCACCTGACTCCTGAGGAGAAGTCTGCCGTTACT GCCCTGTGGGGCAAGGTGAACGTGGATGAAGTTGGTGGTGA GGCCCTGGGCAGGTTGGTATCAAGGTTACAAGACAGGTT | 397 |
| | AACCTGTCTTGTAACCTTGATACCAACCTGCCCAGGGCCTCA CCACCAACTTCATCCACGTTCACCTTGCCCCACAGGGCAGTA | 398 |

TABLE 12-continued

Beta Globin Mutations and Genome-Correcting Oligos

| Clinical Phenotype & Mutation | Correcting Oligos | SEQ ID NO: |
|---|---|---|
| | ACGGCAGACTTCTCCTCAGGAGTCAGGTGCACCATGG CAAGGTGAACGTGGATG | 399 |
| | CATCCACGTTCACCTTG | 400 |
| Thalassaemia Beta GLU-23-ALA GAA to GCA | ACCTGACTCCTGAGGAGAAGTCTGCCGTTACTGCCCTGTGG GGCAAGGTGAACGTGGATGAAGTTGGTGGTGAGGCCCTGG GCAGGTTGGTATCAAGGTTACAAGACAGGTTTAAGGAGAC | 401 |
| | GTCTCCTTAAACCTGTCTTGTAACCTTGATACCAACCTGCCC AGGGCCTCACCACCAACTTCATCCACGTTCACCTTGCCCCAC | 402 |
| | AGGGCAGTAACGGCAGACTTCTCCTCAGGAGTCAGGT CGTGGATGAAGTTGGTG | 403 |
| | CACCAACTTCATCCACG | 404 |
| Thalassaemia Beta GLU-23-term GAA to TAA | CACCTGACTCCTGAGGAGAAGTCTGCCGTTACTGCCCTGTG GGGCAAGGTGAACGTGGATGAAGTTGGTGGTGAGGCCCTG GGCAGGTTGGTATCAAGGTTACAAGACAGGTTTAAGGAGA | 405 |
| | TCTCCTTAAACCTGTCTTGTAACCTTGATACCAACCTGCCCA GGGCCTCACCACCAACTTCATCCACGTTCACCTTGCCCCACA | 406 |
| | GGGCAGTAACGGCAGACTTCTCCTCAGGAGTCAGGTG ACGTGGATGAAGTTGGT | 407 |
| | ACCAACTTCATCCACGT | 408 |
| Thalassaemia Beta GLU-27-LYS GAG to AAG | GAGGAGAAGACTGCTGTCAATGCCCTGTGGGGCAAAGTGAA CGTGGATGCAGTTGGTGGTGAGGCCCTGGGCAGGTTGGTAT CAAGGTTATAAGAGAGGCTCAAGGAGGCAAATGGAAACT | 409 |
| | AGTTTCCATTTGCCTCCTTGAGCCTCTCTTATAACCTTGATAC CAACCTGCCCAGGGCCTCACCACCAACTGCATCCACGTTCA CTTTGCCCCACAGGGCATTGACAGCAGTCTTCTCCTC | 410 |
| | TTGGTGGTGAGGCCCTG | 411 |
| | CAGGGCCTCACCACCAA | 412 |
| Thalassaemia Beta GLU-27-Term GAG to TAG | GAGGAGAAGACTGCTGTCAATGCCCTGTGGGGCAAAGTGAA CGTGGATGCAGTTGGTGGTGAGGCCCTGGGCAGGTTGGTAT CAAGGTTATAAGAGAGGCTCAAGGAGGCAAATGGAAACT | 413 |
| | AGTTTCCATTTGCCTCCTTGAGCCTCTCTTATAACCTTGATAC CAACCTGCCCAGGGCCTCACCACCAACTGCATCCACGTTCA CTTTGCCCCACAGGGCATTGACAGCAGTCTTCTCCTC | 414 |
| | TTGGTGGTGAGGCCCTG | 415 |
| | CAGGGCCTCACCACCAA | 416 |
| Thalassaemia Beta ALA-28-SER GCC to TCC | GAGAAGACTGCTGTCAATGCCCTGTGGGGCAAAGTGAACGT GGATGCAGTTGGTGGTGAGGCCCTGGGCAGGTTGGTATCAA GGTTATAAGAGAGGCTCAAGGAGGCAAATGGAAACTGGG | 417 |
| | CCCAGTTTCCATTTGCCTCCTTGAGCCTCTCTTATAACCTTGA TACCAACCTGCCCAGGGCCTCACCACCAACTGCATCCACGT TCACTTTGCCCCACAGGGCATTGACAGCAGTCTTCTC | 418 |
| | GTGGTGAGGCCCTGGGC | 419 |
| | GCCCAGGGCCTCACCAC | 420 |
| Thalassaemia Beta ARG-31-THR AGG to ACG | CTGTCAATGCCCTGTGGGGCAAAGTGAACGTGGATGCAGTT GGTGGTGAGGCCCTGGGCAGGTTGGTATCAAGGTTATAAGA GAGGCTCAAGGAGGCAAATGGAAACTGGGCATGTGTAGA | 421 |
| | TCTACACATGCCCAGTTTCCATTTGCCTCCTTGAGCCTCTCTT ATAACCTTGATACCAACCTGCCCAGGGCCTCACCACCAACTG CATCCACGTTCACTTTGCCCCACAGGGCATTGACAG | 422 |
| | CCTGGGCAGGTTGGTAT | 423 |
| | ATACCAACCTGCCCAGG | 424 |
| Thalassaemia Beta Leu-33-GLN CTG to CAG | TGGGTTTCTGATAGGCACTGACTCTCTGTCCCTTGGGCTGTT TTCCTACCCTCAGATTACTGGTGGTCTACCCTTGGACCCAGA GGTTCTTTGAGTCCTTTGGGGATCTGTCCTCTCCTGA | 425 |
| | TCAGGAGAGGACAGATCCCCAAAGGACTCAAAGAACCTCTG GGTCCAAGGGTAGACCACCAGTAATCTGAGGGTAGGAAAAC AGCCCAAGGGACAGAGAGTCAGTGCCTATCAGAAACCCA | 426 |
| | CAGATTACTGGTGGTCT | 427 |
| | AGACCACCAGTAATCTG | 428 |
| Thalassaemia Beta TYR-36-Term TAC to TAA | ATAGGCACTGACTCTCTGTCCCTTGGGCTGTTTTCCTACCCT CAGATTACTGGTGGTCTACCCTTGGACCCAGAGGTTCTTTGA GTCCTTTGGGGATCTGTCCTCTCCTGATGCTGTTATG | 429 |
| | CATAACAGCATCAGGAGAGGACAGATCCCCAAAGGACTCAAA GAACCTCTGGGTCCAAGGGTAGACCACCAGTAATCTGAGGG TAGGAAAACAGCCCAAGGGACAGAGAGTCAGTGCCTAT | 430 |
| | GTGGTCTACCCTTGGAC | 431 |
| | GTCCAAGGGTAGACCAC | 432 |
| Thalassaemia Beta TRP-38-Term TGG to TGA | ACTGACTCTCTGTCCCTTGGGCTGTTTTCCTACCCTCAGATT ACTGGTGGTCTACCCTTGGACCCAGAGGTTCTTTGAGTCCTT TGGGGATCTGTCCTCTCCTGATGCTGTTATGGGCAAC | 433 |
| | GTTGCCCATAACAGCATCAGGAGAGGACAGATCCCCAAAGG ACTCAAAGAACCTCTGGGTCCAAGGGTAGACCACCAGTAATC | 434 |

TABLE 12-continued

Beta Globin Mutations and Genome-Correcting Oligos

| Clinical Phenotype & Mutation | Correcting Oligos | SEQ ID NO: |
|---|---|---|
| | TGAGGGTAGGAAAACAGCCCAAGGGACAGAGAGTCAGT TACCCTTGGACCCAGAG | 435 |
| | CTCTGGGTCCAAGGGTA | 436 |
| Thalassaemia Beta TRP-38-Term TGG to TAG | CACTGACTCTCTGTCCCTTGGGCTGTTTTCCTACCCTCAGAT TACTGGTGGTCTACCCTTGGACCCAGAGGTTCTTTGAGTCCT TTGGGGATCTGTCCTCTCCTGATGCTGTTATGGGCAA | 437 |
| | TTGCCCATAACAGCATCAGGAGAGGACAGATCCCCAAAGGA CTCAAAGAACCTCTGGGTCCAAGGGTAGACCACCAGTAATCT GAGGGTAGGAAAACAGCCCAAGGGACAGAGAGTCAGTG | 438 |
| | CTACCCTTGGACCCAGA | 439 |
| | TCTGGGTCCAAGGGTAG | 440 |
| Thalassaemia Beta GLN-40-Term CAG-TAG | ACTCTCTGTCCCTTGGGCTGTTTTCCTACCCTCAGATTACTG GTGGTCTACCCTTGGACCCAGAGGTTCTTTGAGTCCTTTGGG GATCTGTCCTCTCCTGATGCTGTTATGGGCAACCCTA | 441 |
| | TAGGGTTGCCCATAACAGCATCAGGAGAGGACAGATCCCCA AAGGACTCAAAGAACCTCTGGGTCCAAGGGTAGACCACCAG TAATCTGAGGGTAGGAAAACAGCCCAAGGGACAGAGAGT | 442 |
| | CTTGGACCCAGAGGTTC | 443 |
| | GAACCTCTGGGTCCAAG | 444 |
| Thalassaemia Beta GLU-44-Term GAG to TAG | TTGGGCTGTTTTCCTACCCTCAGATTACTGGTGGTCTACCCT TGGACCCAGAGGTTCTTTGAGTCCTTTGGGGATCTGTCCTCT CCTGATGCTGTTATGGGCAACCCTAAGGTGAAGGCTC | 445 |
| | GAGCCTTCACCTTAGGGTTGCCCATAACAGCATCAGGAGAG GACAGATCCCCAAAGGACTCAAAGAACCTCTGGGTCCAAGG GTAGACCACCAGTAATCTGAGGGTAGGAAAACAGCCCAA | 446 |
| | GGTTCTTTGAGTCCTTT | 447 |
| | AAAGGACTCAAAGAACC | 448 |
| Thalassaemia Beta LYS-62-Term AAG to TAG | TTCTTTGAGTCCTTTGGGGATCTGTCCTCTCCTGATGCTGTTA TGGGCAACCCTAAGGTGAAGGCTCATGGCAAGAAGGTGCTA GGTGCCTTTAGTGATGGCCTGGCTCACCTGGACAACC | 449 |
| | GGTTGTCCAGGTGAGCCAGGCCATCACTAAAGGCACCTAGC ACCTTCTTGCCATGAGCCTTCACCTTAGGGTTGCCCATAACA GCATCAGGAGAGGACAGATCCCCAAAGGACTCAAAGAA | 450 |
| | CTAAGGTGAAGGCTCAT | 451 |
| | ATGAGCCTTCACCTTAG | 452 |
| Thalassaemia Beta SER-73-ARG AGT to AGA | TGCTGTTATGGGCAACCCTAAGGTGAAGGCTCATGGCAAGA AGGTGCTAGGTGCCTTTAGTGATGGCCTGGCTCACCTGGAC AACCTCAAGGGCACTTTTTCTCAGCTGAGTGAGCTGCAC | 453 |
| | GTGCAGCTCACTCAGCTGAGAAAAAGTGCCCTTGAGGTTGTC CAGGTGAGCCAGGCCATCACTAAAGGCACCTAGCACCTTCT TGCCATGAGCCTTCACCTTAGGGTTGCCCATAACAGCA | 454 |
| | GCCTTTAGTGATGGCCT | 455 |
| | AGGCCATCACTAAAGGC | 456 |
| Haemolytic Anaemia GLY-75-VAL GGC to GTC | TTATGGGCAACCCTAAGGTGAAGGCTCATGGCAAGAAGGTG CTAGGTGCCTTTAGTGATGGCCTGGCTCACCTGGACAACCT CAAGGGCACTTTTTCTCAGCTGAGTGAGCTGCACTGTGA | 457 |
| | TCACAGTGCAGCTCACTCAGCTGAGAAAAAGTGCCCTTGAG GTTGTCCAGGTGAGCCAGGCCATCACTAAAGGCACCTAGCA CCTTCTTGCCATGAGCCTTCACCTTAGGGTTGCCCATAA | 458 |
| | TAGTGATGGCCTGGCTC | 459 |
| | GAGCCAGGCCATCACTA | 460 |
| Thalassaemia Beta GLU-91-Term GAG to TAG | GCCTTTAGTGATGGCCTGGCTCACCTGGACAACCTCAAGGG CACCTTTGCCACACTGAGTGAGCTGCACTGTGACAAGCTGC ACGTGGATCCTGAGAACTTCAGGGTGAGTCTATGGGACC | 461 |
| | GGTCCCATAGACTCACCCTGAAGTTCTCAGGATCCACGTGCA GCTTGTCACAGTGCAGCTCACTCAGTGTGGCAAAGGTGCCC TTGAGGTTGTCCAGGTGAGCCAGGCCATCACTAAAGGC | 462 |
| | CACTGAGTGAGCTGCAC | 463 |
| | GTGCAGCTCACTCAGTG | 464 |
| Thalassaemia Beta VAL-99-MET GTG to ATG | CTGGACAACCTCAAGGGCACTTTTTCTCAGCTGAGTGAGCTG CACTGTGACAAGCTGCACGTGGATCCTGAGAACTTCAGGGT GAGTCCAGGAGATGCTTCACTTTTCTCTTTTTACTTTC | 465 |
| | GAAAGTAAAAAGAGAAAAGTGAAGCATCTCCTGGACTCACCC TGAAGTTCTCAGGATCCACGTGCAGCTTGTCACAGTGCAGCT CACTCAGCTGAGAAAAAGTGCCCTTGAGGTTGTCCAG | 466 |
| | AGCTGCACGTGGATCCT | 467 |
| | AGGATCCACGTGCAGCT | 468 |
| Thalassaemia Beta LEU-111-PRO CTG-CCG | CCCTTTTGCTAATCATGTTCATACCTCTTATCTTCCTCCCACA GCTCCTGGGCAACGTGCTGGTCTGTGTGCTGGCCCATCACT TTGGCAAAGAATTCACCCCACCAGTGCAGGCTGCCTA | 469 |
| | TAGGCAGCCTGCACTGGTGGGGTGAATTCTTTGCCAAAGTG ATGGGCCAGCACACAGACCAGCACGTTGCCCAGGAGCTGTG GGAGGAAGATAAGAGGTATGAACATGATTAGCAAAAGGG | 470 |

TABLE 12-continued

Beta Globin Mutations and Genome-Correcting Oligos

| Clinical Phenotype & Mutation | Correcting Oligos | SEQ ID NO: |
|---|---|---|
| | CAACGTGCTGGTCTGTG | 471 |
| | CACAGACCAGCACGTTG | 472 |
| Thalassaemia Beta CYS-113-Term TGT to TGA | GCTAATCATGTTCATACCTCTTATCTTCCTCCCACAGCTCCTG GGCAACGTGCTGGTCTGTGTGCTGGCCCATCACTTTGGCAA AGAATTCACCCCACCAGTGCAGGCTGCCTATCAGAAA | 473 |
| | TTTCTGATAGGCAGCCTGCACTGGTGGGGTGAATTCTTTGCC AAAGTGATGGGCCAGCACACAGACCAGCACGTTGCCCAGGA GCTGTGGGAGGAAGATAAGAGGTATGAACATGATTAGC | 474 |
| | CTGGTCTGTGTGCTGGC | 475 |
| | GCCAGCACACAGACCAG | 476 |
| Thalassaemia Beta LEU-115-PRO CTG to CCG | TCATGTTCATACCTCTTATCTTCCTCCCACAGCTCCTGGGCA ACGTGCTGGTCTGTGTGCTGGCCCATCACTTTGGCAAAGAAT TCACCCCACCAGTGCAGGCTGCCTATCAGAAAGTGGT | 477 |
| | ACCACTTTCTGATAGGCAGCCTGCACTGGTGGGGTGAATTCT TGCCAAAGTGATGGGCCAGCACACAGACCAGCACGTTGCC CAGGAGCTGTGGGAGGAAGATAAGAGGTATGAACATGA | 478 |
| | CTGTGTGCTGGCCCATC | 479 |
| | GATGGGCCAGCACACAG | 480 |
| Thalassaemia Beta ALA-116-ASP GCC to GAC | TGTTCATACCTCTTATCTTCCTCCCACAGCTCCTGGGCAACG TGCTGGTCTGTGTGCTGGCCCATCACTTTGGCAAAGAATTCA CCCCACCAGTGCAGGCTGCCTATCAGAAAGTGGTGGC | 481 |
| | GCCACCACTTTCTGATAGGCAGCCTGCACTGGTGGGGTGAA TTCTTTGCCAAAGTGATGGGCCAGCACACAGACCAGCACGTT GCCCAGGAGCTGTGGGAGGAAGATAAGAGGTATGAACA | 482 |
| | TGTGCTGGCCCATCACT | 483 |
| | AGTGATGGGCCAGCACA | 484 |
| Thalassaemia Beta GLU-122-Term GAA to TAA | TTCCTCCCACAGCTCCTGGGCAACGTGCTGGTCTGTGTGCT GGCCCATCACTTTGGCAAAGAATTCACCCCACCAGTGCAGG CTGCCTATCAGAAAGTGGTGGCTGGTGTGGCTAATGCCC | 485 |
| | GGGCATTAGCCACACCAGCCACCACTTTCTGATAGGCAGCC TGCACTGGTGGGGTGAATTCTTTGCCAAAGTGATGGGCCAG CACACAGACCAGCACGTTGCCCAGGAGCTGTGGGAGGAA | 486 |
| | TTGGCAAAGAATTCACC | 487 |
| | GGTGAATTCTTTGCCAA | 488 |
| Thalassaemia Beta GLN-128-PRO CAG to CCG | GCAACGTGCTGGTCTGTGTGCTGGCCCATCACTTTGGCAAA GAATTCACCCCACCAGTGCAGGCTGCCTATCAGAAAGTGGT GGCTGGTGTGGCTAATGCCCTGGCCCACAAGTATCACTA | 489 |
| | TAGTGATACTTGTGGGCCAGGGCATTAGCCACACCAGCCAC CACTTTCTGATAGGCAGCCTGCACTGGTGGGGTGAATTCTTT GCCAAAGTGATGGGCCAGCACACAGACCAGCACGTTGCC | 490 |
| | ACCAGTGCAGGCTGCCT | 491 |
| | AGGCAGCCTGCACTGGT | 492 |
| Thalassaemia Beta GLN-128-Term CAG to TAG | GGCAACGTGCTGGTCTGTGTGCTGGCCCATCACTTTGGCAAA AGAATTCACCCCACCAGTGCAGGCTGCCTATCAGAAAGTGGT GGCTGGTGTGGCTAATGCCCTGGCCCACAAGTATCACT | 493 |
| | AGTGATACTTGTGGGCCAGGGCATTAGCCACACCAGCCACC ACTTTCTGATAGGCAGCCTGCACTGGTGGGGTGAATTCTTTG CCAAAGTGATGGGCCAGCACACAGACCAGCACGTTGCC | 494 |
| | CACCAGTGCAGGCTGCC | 495 |
| | GGCAGCCTGCACTGGTG | 496 |
| Thalassaemia Beta GLN-132-LYS CAG to AAG | GTCTGTGTGCTGGCCCATCACTTTGGCAAAGAATTCACCCCA CCAGTGCAGGCTGCCTATCAGAAAGTGGTGGCTGGTGTGGC TAATGCCCTGGCCCACAAGTATCACTAAGCTCGCTTTC | 497 |
| | GAAAGCGAGCTTAGTGATACTTGTGGGCCAGGGCATTAGCC ACACCAGCCACCACTTTCTGATAGGCAGCCTGCACTGGTGG GGTGAATTCTTTGCCAAAGTGATGGGCCAGCACACAGAC | 498 |
| | CTGCCTATCAGAAAGTG | 499 |
| | CACTTTCTGATAGGCAG | 500 |

EXAMPLE 7

Retinoblastoma

Retinoblastoma (RB) is an embryonic neoplasm of retinal origin. It almost always presents in early childhood and is often bilateral. The risk of osteogenic sarcoma is increased 500-fold in bilateral retinoblastoma patents, the bone malignancy being at sites removed from those exposed to radiation treatment of the eye tumor.

The retinoblastoma susceptibility gene (pRB; pRb) plays a pivotal role in the regulation of the cell cycle. pRB restrains cell cycle progression by maintaining a checkpoint in late $G_1$ that controls commitment of cells to enter S phase. The critical role that pRB plays in cell cycle regulation explains its status as archetypal tumor suppressor: loss of pRB function results in an inability to maintain control of the $G_1$ checkpoint; unchecked progression through the cell cycle is, in turn, a hallmark of neoplasia.

Blanquet et al., *Hum. Molec. Genet.* 4: 383–388 (1995) performed a mutation survey of the RB1 gene in 232 patents with hereditary or nonhereditary retinoblastoma. They systematically explored all 27 exons and flanking sequences, as well as the promoter. All types of point mutations were represented and found to be unequally distributed along the RB1 gene sequence. In the population studied, exons 3, 8, 18, and 19 were preferentially altered. The attached table discloses the correcting oligonucleotide base sequences for the retinoblastoma oligonucleotides of the invention.

TABLE 13 pRB Mutations and Genome-Correcting Oligos

| Clinical Phenotype & Mutation | Correcting Oligos | SEQ ID NO: |
|---|---|---|
| Retinoblastoma Trp99Term TGG-TAG | AATATTTGATCTTTATTTTTGTTCCCAGGGAGGTTATATTCAA AAGAAAAAGGAACTGTGGGGAATCTGTATCTTTATTGCAGCA GTTGACCTAGATGAGATGTCGTTCACTTTTACTGA | 501 |
| | TCAGTAAAAGTGAACGACATCTCATCTAGGTCAACTGCTGCA ATAAAGATACAGATTCCCCACAGTTCCTTTTTCTTTTGAATATA ACCTCCCTGGGAACAAAAAATAAAGATCAAATATT | 502 |
| | GGAACTGTGGGGAATCT | 503 |
| | AGATTCCCCACAGTTCC | 504 |
| Retinoblastoma Glu137Asp GAA-GAT | ATTTACTTTTTTCTATTCTTTCCTTTGTAGTGTCCATAAATTCTT TAACTTACTAAAAGAAATTGATACCAGTACCAAAGTTGATAAT GCTATGTCAAGACTGTTGAAGAAGTATGATGTA | 505 |
| | TACATCATACTTCTTCAACAGTCTTGACATAGCATTATCAACTT TGGTACTGGTATCAATTTCTTTTAGTAAGTTAAAGAATTTATGG ACACTACAAAGGAAAGAATAGAAAAAAGTAAAT | 506 |
| | CTAAAAGAAATTGATAC | 507 |
| | GTATCAATTTCTTTTAG | 508 |
| Retinoblastoma Glu137Term GAA-TAA | TGATTTACTTTTTTCTATTCTTTCCTTTGTAGTGTCCATAAATT CTTTAACTTACTAAAAGAAAATTGATACCAGTACCAAAGTTGAT AATGCTATGTCAAGACTGTTGAAGAAGTATGATG | 509 |
| | CATCATACTTCTTCAACAGTCTTGACATAGCATTATCAACTTT GGTACTGGTATCAATTTCTTTTAGTAAGTTAAAGAATTTATGG ACACTACAAAGGAAAGAATAGAAAAAAGTAAATCA | 510 |
| | TACTAAAAGAAAATTGAT | 511 |
| | ATCAATTTCTTTTAGTA | 512 |
| Retinoblastoma Gln176Term CAA-TAA | AAAATGTTAAAAAGTCATAATGTTTTTCTTTTCAGGACATGTGA ACTTATATATTTGACACAACCCAGCAGTTCGTAAGTAGTTCAC AGAATGTTATTTTTCACTTAAAAAAAAAGATTTT | 513 |
| | AAAATCTTTTTTTTAAGTGAAAAATAACATTCTGTGAACTACT TACGAACTGCTGGGTTGTGTCAAATATATAAGTTCACATGTCC TGAAAAGAAAAACATTATGACTTTTTAACATTTT | 514 |
| | ATTTGACACAACCCAGC | 515 |
| | GCTGGGTTGTGTCAAAT | 516 |
| Retinoblastoma Ile185Thr ATA-ACA | TGATACATTTTTCCTGTTTTTTTTCTGCTTTCTATTTGTTTAATA GGATATCTACTGAAATAAATTCTGCATTGGTGCTAAAAGTTTC TTGGATCACATTTTTATTAGCTAAAGGTAAGTT | 517 |
| | AACTTACCTTTAGCTAATAAAAATGTGATCCAAGAAACTTTTA GCACCAATGCAGAATTTATTTCAGTAGATATCCTATTAAACAA ATAGAAAGCAGAAAAAAAACAGGAAAAATGTATCA | 518 |
| | TACTGAAATAAATTCTG | 519 |
| | CAGAATTTATTTCAGTA | 520 |
| Retinoblastoma Gln207Term CAA-TAA | AAAGATCTGAATCTCTAACTTTCTTTAAAAATGTACATTTTTTT TTCAGGGGAAGTATTACAAATGGAAGATGATCTGGTGATTTC ATTTCAGTTAATGCTATGTGTCCTTGACTATTTTA | 521 |
| | TAAAATAGTCAAGGACACATAGCATTAACTGAAATGAAATCAC CAGATCATCTTCCATTTGTAATACTTCCCCTGAAAAAAAAATG TACATTTTTAAAGAAAGTTAGAGATTCAGATCTTT | 522 |
| | AAGTATTACAAATGGAA | 523 |
| | TTCCATTTGTAATACTT | 524 |
| Retinoblastoma Arg251Term CGA to TGA | GTTCTTATCTAATTTACCACTTTTACAGAAACAGCTGTTATACC CATTAATGGTTCACCTCGAACACCCAGGCGAGGTCAGAACA GGAGTGCACGGATAGCAAAACAACTAGAAAATGATA | 525 |
| | TATCATTTTCTAGTTGTTTTGCTATCCGTGCACTCCTGTTCTG ACCTCGCCTGGGTGTTCGAGGTGAACCATTAATGGGTATAAC AGCTGTTTCTGTAAAAGTGGTAAATTAGATAAGAAC | 526 |
| | GTTCACCTCGAACACCC | 527 |
| | GGGTGTTCGAGGTGAAC | 528 |
| Retinoblastoma Arg255Term CGA to TGA | TTTACCACTTTTACAGAAACAGCTGTTATACCCATTAATGGTT CACCTCGAACACCCAGGCGAGGTCAGAACAGGAGTGCACG GATAGCAAAACAACTAGAAAATGATACAAGAATTATTG | 529 |
| | CAATAATTCTTGTATCATTTTCTAGTTGTTTTGCTATCCGTGCA CTCCTGTTCTGACCTCGCCTGGGTGTTCGAGGTGAACCATTA ATGGGTATAACAGCTGTTTCTGTAAAAGTGGTAAA | 530 |
| | CACCCAGGCGAGGTCAG | 531 |
| | CTGACCTCGCCTGGGTG | 532 |
| Retinoblastoma Gln266Term CAA to TAA | ATTAATGGTTCACCTCGAACACCCAGGCGAGGTCAGAACAG GAGTGCACGGATAGCAAAACAACTAGAAAATGATACAAGAAT TATTGAAGTTCTCTGTAAAGAACATGAATGTAATATAG | 533 |
| | CTATATTACATTCATGTTCTTTACAGAGAACTTCAATAATTCTT GTATCATTTTCTAGTTGTTTTGCTATCCGTGCACTCCTGTTCT | 534 |

TABLE 13-continued pRB Mutations and Genome-Correcting Oligos

| Clinical Phenotype & Mutation | Correcting Oligos | SEQ ID NO: |
|---|---|---|
| | GACCTCGCCTGGGTGTTCGAGGTGAACCATTAAT TAGCAAAACAACTAGAA | 535 |
| | TTCTAGTTGTTTTGCTA | 536 |
| Retinoblastoma Arg320Term CGA to TGA | TGACATGTAAAGGATAATTGTCAGTGACTTTTTTCTTTCAAGG TTGAAAATCTTTCTAAACGATACGAAGAAATTTATCTTAAAAAT AAAGATCTAGATGCAAGATTATTTTTGGATCATG | 537 |
| | CATGATCCAAAAATAATCTTGCATCTAGATCTTTATTTTTAAGA TAAATTTCTTCGTATCGTTTAGAAAGATTTTCAACCTTGAAAGA AAAAAGTCACTGACAATTATCCTTTACATGTCA | 538 |
| | TTTCTAAACGATACGAA | 539 |
| | TTCGTATCGTTTAGAAA | 540 |
| Retinoblastoma Gln354Term CAG to TAG | ACAAATTGTAAATTTTCAGTATGTGAATGACTTCACTTATTGTT ATTTAGTTTTGAAACACAGAGAACACCACGAAAAAGTAACCTT GATGAAGAGGTGAATGTAATTCCTCCACACACTC | 541 |
| | GAGTGTGTGGAGGAATTACATTCACCTCTTCATCAAGGTTAC TTTTTCGTGGTGTTCTCTGTGTTTCAAAACTAAATAACAATAA GTGAAGTCATTCACATACTGAAAATTTACAATTTGT | 542 |
| | TTGAAACACAGAGAACA | 543 |
| | TGTTCTCTGTGTTTCAA | 544 |
| Retinoblastoma Arg358Gly CGA to GGA | TTTTCAGTATGTGAATGACTTCACTTATTGTTATTTAGTTTTGA AACACAGAGAACACCACGAAAAAGTAACCTTGATGAAGAGGT GAATGTAATTCCTCCACACACTCCAGTTAGGTATG | 545 |
| | CATACCTAACTGGAGTGTGTGGAGGAATTACATTCACCTCTT CATCAAGGTTACTTTTTCGTGGTGTTCTCTGTGTTTCAAAACT AAATAACAATAAGTGAAGTCATTCACATACTGAAAA | 546 |
| | GAACACCACGAAAAAGT | 547 |
| | ACTTTTTCGTGGTGTTC | 548 |
| Retinoblastoma Arg358Term CGA to TGA | TTTTCAGTATGTGAATGACTTCACTTATTGTTATTTAGTTTTGA AACACAGAGAACACCACGAAAAAGTAACCTTGATGAAGAGGT GAATGTAATTCCTCCACACACTCCAGTTAGGTATG | 549 |
| | CATACCTAACTGGAGTGTGTGGAGGAATTACATTCACCTCTT CATCAAGGTTACTTTTTCGTGGTGTTCTCTGTGTTTCAAAACT AAATAACAATAAGTGAAGTCATTCACATACTGAAAA | 550 |
| | GAACACCACGAAAAAGT | 551 |
| | ACTTTTTCGTGGTGTTC | 552 |
| Retinoblastoma Ser397Term TCA to TAA | CTGTTATGAACACTATCCAACAATTAATGATGATTTTAAATTCA GCAAGTGATCAACCTTCAGAAAATCTGATTTCCTATTTTAACG TAAGCCATATATGAAACATTATTTATTGTAATAT | 553 |
| | ATATTACAATAAATAATGTTTCATATATGGCTTACGTTAAAATA GGAAATCAGATTTTCTGAAGGTTGATCACTTGCTGAATTTAAA ATCATCATTAATTGTTGGATAGTGTTCATAACAG | 554 |
| | TCAACCTTCAGAAAATC | 555 |
| | GATTTTCTGAAGGTTGA | 556 |
| Retinoblastoma Arg445Term CGA to TGA | TTTCATAATTGTGATTTTCTAAAATAGCAGGCTCTTATTTTTCT TTTTGTTTGTTTGTAGCGATACAAACTTGGAGTTCGCTTGTAT TACCGAGTAATGGAATCCATGCTTAAATCAGTAA | 557 |
| | TTACTGATTTAAGCATGGATTCCATTACTCGGTAATACAAGCG AACTCCAAGTTTGTATCGCTACAAACAAACAAAAAGAAAAATA AGAGCCTGCTATTTTAGAAAATCACAATTATGAAA | 558 |
| | GTTTGTAGCGATACAAA | 559 |
| | TTTGTATCGCTACAAAC | 560 |
| Retinoblastoma Arg455Term CGA to TGA | GCTCTTATTTTTCTTTTTGTTGTTTGTAGCGATACAAACTTGG AGTTCGCTTGTATTACCGAGTAATGGAATCCATGCTTAAATCA GTAAGTTAAAAACAATATAAAAAAATTTCAGCCG | 561 |
| | CGGCTGAAATTTTTTTATATTGTTTTTAACTTACTGATTTAAGC ATGGATTCCATTACTCGGTAATACAAGCGAACTCCAAGTTTGT ATCGCTACAAACAAACAAAAAGAAAAATAAGAGC | 562 |
| | TGTATTACCGAGTAATG | 563 |
| | CATTACTCGGTAATACA | 564 |
| Retinoblastoma Arg552Term CGA to TGA | ATCGAAAGTTTTATCAAAGCAGAAGGCAACTTGACAAGAGAA ATGATAAAACATTTAGAACGATGTGAACATCGAATCATGGAAT CCCTTGCATGGCTCTCAGTAAGTAGCTAAATAATTG | 565 |
| | CAATTATTTAGCTACTTACTGAGAGCCATGCAAGGGATTCCAT GATTCGATGTTCACATCGTTCTAAATGTTTTATCATTTCTCTTG TCAAGTTGCCTTCTGCTTTGATAAAACTTTCGAT | 566 |
| | ATTTAGAACGATGTGAA | 567 |
| | TTCACATCGTTCTAAAT | 568 |
| Retinoblastoma Cys553Term TGT to TGA | AAGTTTTATCAAAGCAGAAGGCAACTTGACAAGAGAAATGATA AAACATTTAGAACGATGTGAACATCGAATCATGGAATCCCTTG CATGGCTCTCAGTAAGTAGCTAAATAATTGAAGAA | 569 |
| | TTCTTCAATTATTTAGCTACTTACTGAGAGCCATGCAAGGGAT TCCATGATTCGATGTTCACATCGTTCTAAATGTTTTATCATTTC TCTTGTCAAGTTGCCTTCTGCTTTGATAAAACTT | 570 |

TABLE 13-continued pRB Mutations and Genome-Correcting Oligos

| Clinical Phenotype & Mutation | Correcting Oligos | SEQ ID NO: |
|---|---|---|
| | GAACGATGTGAACATCG | 571 |
| | CGATGTTCACATCGTTC | 572 |
| Retinoblastoma Glu554Term GAA to TAA | AGTTTTATCAAAGCAGAAGGCAACTTGACAAGAGAAATGATAA AACATTTAGAACGATGTGAACATCGAATCATGGAATCCCTTG CATGGCTCTCAGTAAGTAGCTAAATAATTGAAGAAA | 573 |
| | TTTCTTCAATTATTTAGCTACTTACTGAGAGCCATGCAAGGGA TTCCATGATTCGATGTTCACATCGTTCTAAATGTTTTATCATTT CTCTTGTCAAGTTGCCTTCTGCTTTGATAAAACT | 574 |
| | AACGATGTGAACATCGA | 575 |
| | TCGATGTTCACATCGTT | 576 |
| Retinoblastoma Ser567Leu TCA to TTA | TACCTGGGAAAATTATGCTTACTAATGTGGTTTTAATTTCATC ATGTTTCATATAGGATTCACCTTTATTTGATCTTATTAAACAAT CAAAGGACCGAGAAGGACCAACTGATCACCTTGA | 577 |
| | TCAAGGTGATCAGTTGGTCCTTCTCGGTCCTTTGATTGTTTAA TAAGATCAAATAAAGGTGAATCCTATATGAAACATGATGAAAT TAAAACCACATTAGTAAGCATAATTTTCCCAGGTA | 578 |
| | ATAGGATTCACCTTTAT | 579 |
| | ATAAAGGTGAATCCTAT | 580 |
| Retinoblastoma Gln575Term CAA to TAA | AATGTGGTTTTAATTTCATCATGTTTCATATAGGATTCACCTTT ATTTGATCTTATTAAACAATCAAAGGACCGAGAAGGACCAACT GATCACCTTGAATCTGCTTGTCCTCTTAATCTTC | 581 |
| | GAAGATTAAGAGGACAAGCAGATTCAAGGTGATCAGTTGGTC CTTCTCGGTCCTTTGATTGTTTAATAAGATCAAATAAAGGTGA ATCCTATATGAAACATGATGAAATTAAAACCACATT | 582 |
| | TTATTAAACAATCAAAG | 583 |
| | CTTTGATTGTTTAATAA | 584 |
| Retinoblastoma Arg579Term CGA to TGA | ATTTCATCATGTTTCATATAGGATTCACCTTTATTTGATCTTAT TAAACAATCAAAGGACCGAGAAGGACCAACTGATCACCTTGA ATCTGCTTGTCCTCTTAATCTTCCTCTCCAGAATA | 585 |
| | TATTCTGGAGAGGAAGATTAAGAGGACAAGCAGATTCAAGGT GATCAGTTGGTCCTTCTCGGTCCTTTGATTGTTTAATAAGATC AAATAAAGGTGAATCCTATATGAAACATGATGAAAT | 586 |
| | CAAAGGACCGAGAAGGA | 587 |
| | TCCTTCTCGGTCCTTTG | 588 |
| Retinoblastoma Glu580Term GAA to TAA | TCATCATGTTTCATATAGGATTCACCTTTATTTGATCTTATTAA ACAATCAAAGGACCGAGAAGGACCAACTGATCACCTTGAATC TGCTTGTCCTCTTAATCTTCCTCTCCAGAATAATC | 589 |
| | GATTATTCTGGAGAGGAAGATTAAGAGGACAAGCAGATTCAA GGTGATCAGTTGGTCCTTCTCGGTCCTTTGATTGTTTAATAAG ATCAAATAAAGGTGAATCCTATATGAAACATGATGA | 590 |
| | AGGACCGAGAAGGACCA | 591 |
| | TGGTCCTTCTCGGTCCT | 592 |
| Retinoblastoma Ser634Term TCA to TGA | AGAAAAAAGGTTCAACTACGCGTGTAAATTCTACTGCAAATG CAGAGACACAAGCAACCTCAGCCTTCCAGACCCAGAAGCCA TTGAAATCTACCTCTCTTTCACTGTTTTATAAAAAAGG | 593 |
| | CCTTTTTTATAAAACAGTGAAAGAGAGGTAGATTTCAATGGCT TCTGGGTCTGGAAGGCTGAGGTTGCTTGTGTCTCTGCATTTG CAGTAGAATTTACACGCGTAGTTGAACCTTTTTTCT | 594 |
| | AGCAACCTCAGCCTTCC | 595 |
| | GGAAGGCTGAGGTTGCT | 596 |
| Retinoblastoma Ala635Pro GCC to CCC | AAAAAAGGTTCAACTACGCGTGTAAATTCTACTGCAAATGCA GAGACACAAGCAACCTCAGCCTTCCAGACCCAGAAGCCATT GAAATCTACCTCTCTTTCACTGTTTTATAAAAAAGGTT | 597 |
| | AACCTTTTTTATAAAACAGTGAAAGAGAGGTAGATTTCAATGG CTTCTGGGTCTGGAAGGCTGAGGTTGCTTGTGTCTCTGCATT TGCAGTAGAATTTACACGCGTAGTTGAACCTTTTT | 598 |
| | CAACCTCAGCCTTCCAG | 599 |
| | CTGGAAGGCTGAGGTTG | 600 |
| Retinoblastoma Gln639Term CAG to TAG | ACTACGCGTGTAAATTCTACTGCAAATGCAGAGACACAAGCA ACCTCAGCCTTCCAGACCCAGAAGCCATTGAAATCTACCTCT CTTTCACTGTTTTATAAAAAGGTTAGTAGATGATTA | 601 |
| | TAATCATCTACTAACCTTTTTTATAAAACAGTGAAAGAGAGGT AGATTTCAATGGCTTCTGGGTCTGGAAGGCTGAGGTTGCTTG TGTCTCTGCATTTGCAGTAGAATTTACACGCGTAGT | 602 |
| | TCCAGACCCAGAAGCCA | 603 |
| | TGGCTTCTGGGTCTGGA | 604 |
| Retinoblastoma Leu657Pro CTA to CCA | TTGTAATTCAAAATGAACAGTAAAAATGACTAATTTTTCTTATT CCCACAGTGTATCGGCTAGCCTATCTCCGGCTAAATACACTT TGTGAACGCCTTCTGTCTGAGCACCCAGAATTAGA | 605 |
| | TCTAATTCTGGGTGCTCAGACAGAAGGCGTTCACAAAGTGTA TTTAGCCGGAGATAGGCTAGCCGATACACTGTGGGAATAAG AAAAATTAGTCATTTTTACTGTTCATTTGAATTACAA | 606 |
| | GTATCGGCTAGCCTATC | 607 |
| | GATAGGCTAGCCGATAC | 608 |

TABLE 13-continued pRB Mutations and Genome-Correcting Oligos

| Clinical Phenotype & Mutation | Correcting Oligos | SEQ ID NO: |
|---|---|---|
| Retinoblastoma Arg661Trp CGG to TGG | AATGAACAGTAAAAATGACTAATTTTTCTTATTCCCACAGTGTA TCGGCTAGCCTATCTCCGGCTAAATACACTTTGTGAACGCCT TCTGTCTGAGCACCCAGAATTAGAACATATCATCT | 609 |
| | AGATGATATGTTCTAATTCTGGGTGCTCAGACAGAAGGCGTT CACAAAGTGTATTTAGCCGGAGATAGGCTAGCCGATACACTG TGGGAATAAGAAAAATTAGTCATTTTTACTGTTCATT | 610 |
| | CCTATCTCCGGCTAAAT | 611 |
| | ATTTAGCCGGAGATAGG | 612 |
| Retinoblastoma Leu662Pro CTA to CCA | AACAGTAAAAATGACTAATTTTTCTTATTCCCACAGTGTATCG GCTAGCCTATCTCCGGCTAAATACACTTTGTGAACGCCTTCT GTCTGAGCACCCAGAATTAGAACATATCATCTGGAC | 613 |
| | GTCCAGATGATATGTTCTAATTCTGGGTGCTCAGACAGAAGG CGTTCACAAAGTGTATTTAGCCGGAGATAGGCTAGCCGATAC ACTGTGGGAATAAGAAAAATTAGTCATTTTTACTGTT | 614 |
| | TCTCCGGCTAAATACAC | 615 |
| | GTGTATTTAGCCGGAGA | 616 |
| Retinoblastoma Glu675Term GAA to TAA | TATCGGCTAGCCTATCTCCGGCTAAATACACTTTGTGAACGC CTTCTGTCTGAGCACCCAGAATTAGAACATATCATCTGGACC CTTTTCCAGCACACCCTGCAGAATGAGTATGAACTCA | 617 |
| | TGAGTTCATACTCATTCTGCAGGGTGTGCTGGAAAAGGGTCC AGATGATATGTTCTAATTCTGGGTGCTCAGACAGAAGGCGTT CACAAAGTGTATTTAGCCGGAGATAGGCTAGCCGATA | 618 |
| | AGCACCCAGAATTAGAA | 619 |
| | TTCTAATTCTGGGTGCT | 620 |
| Retinoblastoma Gln685Pro CAG to CCG | TTTGTGAACGCCTTCTGTCTGAGCACCCAGAATTAGAACATA TCATCTGGACCCTTTTCCAGCACACCCTGCAGAATGAGTATG AACTCATGAGAGACAGGCATTTGGACCAAGTAAGAAA | 621 |
| | TTTCTTACTTGGTCCAAATGCCTGTCTCTCATGAGTTCATACT CATTCTGCAGGGTGTGCTGGAAAAGGGTCCAGATGATATGTT CTAATTCTGGGTGCTCAGACAGAAGGCGTTCACAAA | 622 |
| | CCTTTTCCAGCACACCC | 623 |
| | GGGTGTGCTGGAAAAGG | 624 |
| Retinoblastoma Cys706Tyr TGT to TAT | AAAACCATGTAATAAAATTCTGACTACTTTTACATCAATTTATT TACTAGATTATGATGTGTTCCATGTATGGCATATGCAAAGTGA AGAATATAGACCTTAAATTCAAAATCATTGTAAC | 625 |
| | GTTACAATGATTTTGAATTTAAGGTCTATATTCTTCACTTTGCA TATGCCATACATGGAACACATCATAATCTAGTAAATAAATTGA TGTAAAAGTAGTCAGAATTTTATTACATGGTTTT | 626 |
| | TATGATGTGTTCCATGT | 627 |
| | ACATGGAACACATCATA | 628 |
| Retinoblastoma Cys712Arg TGC to CGC | TTCTGACTACTTTTACATCAATTTATTTACTAGATTATGATGTG TTCCATGTATGGCATATGCAAAGTGAAGAATATAGACCTTAAA TTCAAAATCATTGTAACAGCATACAAGGATCTTC | 629 |
| | GAAGATCCTTGTATGCTGTTACAATGATTTTGAATTTAAGGTC TATATTCTTCACTTTGCATATGCCATACATGGAACACATCATA ATCTAGTAAATAAATTGATGTAAAAGTAGTCAGAA | 630 |
| | ATGGCATATGCAAAGTG | 631 |
| | CACTTTGCATATGCCAT | 632 |
| Retinoblastoma Tyr728Term TAC to TAA | GTATGGCATATGCAAAGTGAAGAATATAGACCTTAAATTCAAA ATCATTGTAACAGCATACAAGGATCTTCCTCATGCTGTTCAG GAGGTAGGTAATTTTCCATAGTAAGTTTTTTTGATA | 633 |
| | TATCAAAAAAACTTACTATGGAAAATTACCTACCTCCTGAACA GCATGAGGAAGATCCTTGTATGCTGTTACAATGATTTTGAATT TAAGGTCTATATTCTTCACTTTGCATATGCCATAC | 634 |
| | ACAGCATACAAGGATCT | 635 |
| | AGATCCTTGTATGCTGT | 636 |
| Retinoblastoma Glu748Term GAG to TAG | TTTTTTTTTTTTTTTACTGTTCTTCCTCAGACATTCAAACGTGT TTTGATCAAAGAAGAGGAGTATGATTCTATTATAGTATTCTATA ACTCGGTCTTCATGCAGAGACTGAAAACAAATA | 637 |
| | TATTTGTTTTCAGTCTCTGCATGAAGACCGAGTTATAGAATAC TATAATAGAATCATACTCCTCTTCTTTGATCAAAACACGTTTGA ATGTCTGAGGAAGAACAGTAAAAAAAAAAAAAAA | 638 |
| | AAGAAGAGGAGTATGAT | 639 |
| | ATCATACTCCTCTTCTT | 640 |
| Retinoblastoma Gln762Term CAG to TAG | GTTTTGATCAAAGAAGAGGAGTATGATTCTATTATAGTATTCT ATAACTCGGTCTTCATGCAGAGACTGAAAACAAATATTTTGCA GTATGCTTCCACCAGGGTAGGTCAAAAGTATCCTT | 641 |
| | AAGGATACTTTTGACCTACCCTGGTGGAAGCATACTGCAAAA TATTTGTTTTCAGTCTCTGCATGAAGACCGAGTTATAGAATAC TATAATAGAATCATACTCCTCTTCTTTGATCAAAAC | 642 |
| | TCTTCATGCAGAGACTG | 643 |
| | CAGTCTCTGCATGAAGA | 644 |
| Retinoblastoma Arg787Term | TAATCTACTTTTTTGTTTTGCTCTAGCCCCCTACCTTGTCAC CAATACCCTCACATTCCTCGAAGCCCTTACAAGTTTCCTAGTTC | 645 |

TABLE 13-continued pRB Mutations and Genome-Correcting Oligos

| Clinical Phenotype & Mutation | Correcting Oligos | SEQ ID NO: |
|---|---|---|
| CGA-TGA | ACCCTTACGGATTCCTGGAGGGAACATCTATATTT AAATATAGATGTTCCCTCCAGGAATCCGTAAGGGTGAACTAG GAAACTTGTAAGGGCTTCGAGGAATGTGAGGTATTGGTGACA AGGTAGGGGGCTAGAGCAAAAACAAAAAAGTAGATTA | 646 |
| | ACATTCCTCGAAGCCCT | 647 |
| | AGGGCTTCGAGGAATGT | 648 |
| Retinoblastoma Ser816Term TCA to TGA | CCTTACGGATTCCTGGAGGGAACATCTATATTTCACCCCTGA AGAGTCCATATAAAATTTCAGAAGGTCTGCCAACACCAACAA AAATGACTCCAAGATCAAGGTGTGTGTTTTCTCTTTA | 649 |
| | TAAAGAGAAAACACACACCTTGATCTTGGAGTCATTTTTGTTG GTGTTGGCAGACCTTCTGAAATTTTATATGGACTCTTCAGGG GTGAAATATAGATGTTCCCTCCAGGAATCCGTAAGG | 650 |
| | TAAAATTTCAGAAGGTC | 651 |
| | GACCTTCTGAAATTTTA | 652 |

EXAMPLE 8

BRCA1 and BRCA2

Breast cancer is the second major cause of cancer death in American women, with an estimated 44,190 lives lost (290 men and 43,900 women) in the US in 1997. While ovarian cancer accounts for fewer deaths than breast cancer, it still represents 4% of all female cancers. In 1994, two breast cancer susceptibility genes were identified: BRCA1 on chromosome 17 and BRCA2 on chromosome 13. When a woman carries a mutation in either BRCA1 or BRCA2, she is at increased risk of being diagnosed with breast or ovarian cancer at some point in her life.

Ford et al., Am. J. Hum. Genet. 62: 676–689 (1998) assessed the contribution of BRCA1 and BRCA2 to inherited breast cancer by linkage and mutation analysis in 237 families, each with at least 4 cases of breast cancer. Families were included without regard to the occurrence of ovarian or other cancers. Overall, disease was linked to BRCA1 in an estimated 52% of families, to BRCA2 in 32% of families, and to neither gene in 16%, suggesting other predisposition genes. The majority (81%) of the breast-ovarian cancer families were due to BRCA1, with most others (14%) due to BRCA2. Conversely, the majority (76%) of families with both male and female breast cancer were due to BRCA2. The largest proportion (67%) of families due to other genes were families with 4 or 5 cases of female breast cancer only.

More than 75% of the reported mutations in the BRCA1 gene result in truncated proteins. Couch et al., Hum. Mutat. 8: 8–18, 1996. (1996) reported a total of 254 BRCA1 mutations, 132 (52%) of which were unique. A total of 221 (87%) of all mutations or 107 (81%) of the unique mutations are small deletions, insertions, nonsense point mutations, splice variants, and regulatory mutations that result in truncation or absence of the BRCA1 protein. A total of 11 disease-associated missense mutations (5 unique) and 21 variants (19 unique) as yet unclassified as missense mutations or polymorphisms had been detected. Thirty-five independent benign polymorphisms had been described. The most common mutations were 185delAG and 5382insC, which accounted for 30 (11.7%) and 26 (10.1%), respectively, of all the mutations.

Most BRCA2 mutations are predicted to result in a truncated protein product The smallest known cancer-associated deletion removes from the C terminus only 224 of the 3,418 residues constituting BRCA2, suggesting that these terminal amino acids are critical for BRCA2 function. Studies (Spain et al., Proc. Natl. Acad. Sci. 96:13920–13925 (1999)) suggest that such truncations eliminate or interfere with 2 nuclear localizaton signals that reside within the final 156 residues of BRCA2, suggesting that the vast majority of BRCA2 mutants are nonfunctional because they are not translocated into the nucleus.

The attached table discloses the correcting oligonucleotide base sequences for the BRACA1 and BRACA2 oligonucleotides of the invention.

TABLE 14

BRCA1 Mutations and Genome-Correcting Oligos

| Clinical Phenotype & Mutation | Correcting Oligos | SEQ ID NO: |
|---|---|---|
| Breast Cancer Met-1-Ile ATG to ATT | CTGCGCTCAGGAGGCCTTCACCCTCTGCTCTGGGTAAAGTT CATTGGAACAGAAAGAAATGGATTTATCTGCTCTTCGCGTTG AAGAAGTACAAAATGTCATTAATGCTATGCAGAAAATC | 653 |
| | GATTTTCTGCATAGCATTAATGACATTTTGTACTTCTTCAACG CGAAGAGCAGATAAATCCATTTCTTTCTGTTCCAATGAACTTT ACCCAGAGCAGAGGGTGAAGGCCTCCTGAGCGCAG | 654 |
| | AAAGAAATGGATTTATC | 655 |
| | GATAAATCCATTTCTTT | 656 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Val-11-Ala GTA to GCA | CTGGGTAAAGTTCATTGGAACAGAAAGAAATGGATTTATCTG CTCTTCGCGTTGAAGAAGTACAAAATGTCATTAATGCTATGCA GAAAATCTTAGAGTGTCCCATCTGTCTGGAGTTGAT | 657 |
| | ATCAACTCCAGACAGATGGGACACTCTAAGATTTTCTGCATA GCATTAATGACATTTTGTACTTCTTCAACGCGAAGAGCAGATA AATCCATTTCTTTCTGTTCCAATGAACTTTACCCAG | 658 |
| | TGAAGAAGTACAAAATG | 659 |
| | CATTTTGTACTTCTTCA | 660 |
| Breast Cancer Ile-21-Val ATC to GTC | ATGGATTTATCTGCTCTTCGCGTTGAAGAAGTACAAAATGTCA TTAATGCTATGCAGAAAATCTTAGAGTGTCCCATCTGTCTGG AGTTGATCAAGGAACCTGTCTCCACAAAGTGTGACC | 661 |
| | GGTCACACTTTGTGGAGACAGGTTCCTTGATCAACTCCAGAC AGATGGGACACTCTAAGATTTTCTGCATAGCATTAATGACATT TTGTACTTCTTCAACGCGAAGAGCAGATAAATCCAT | 662 |
| | TGCAGAAAATCTTAGAG | 663 |
| | CTCTAAGATTTTCTGCA | 664 |
| Breast Cancer Leu-22-Ser TTA to TCA | ATTTATCTGCTCTTCGCGTTGAAGAAGTACAAAATGTCATTAA TGCTATGCAGAAAATCTTAGAGTGTCCCATCTGTCTGGAGTT GATCAAGGAACCTGTCTCCACAAAGTGTGACCACAT | 665 |
| | ATGTGGTCACACTTTGTGGAGACAGGTTCCTTGATCAACTCC AGACAGATGGGACACTCTAAGATTTTCTGCATAGCATTAATG ACATTTTGTACTTCTTCAACGCGAAGAGCAGATAAAT | 666 |
| | GAAAATCTTAGAGTGTC | 667 |
| | GACACTCTAAGATTTTC | 668 |
| Breast Cancer Cys-39-Tyr TGT to TAT | AGAAAATCTTAGAGTGTCCCATCTGTCTGGAGTTGATCAAGG AACCTGTCTCCACAAAGTGTGACCACATATTTTGCAAATTTTG CATGCTGAAACTTCTCAACCAGAAGAAAGGGCCTTC | 669 |
| | GAAGGCCCTTTCTTCTGGTTGAGAAGTTTCAGCATGCAAAAT TTGCAAAATATGTGGTCACACTTTGTGGAGACAGGTTCCTTG ATCAACTCCAGACAGATGGGACACTCTAAGATTTTCT | 670 |
| | CACAAAGTGTGACCACA | 671 |
| | TGTGGTCACACTTTGTG | 672 |
| Breast Cancer Cys-61-Gly TGT to GGT | CACATATTTTGCAAATTTTGCATGCTGAAACTTCTCAACCAGA AGAAAGGGCCTTCACAGTGTCCTTTATGTAAGAATGATATAAC CAAAAGGAGCCTACAAGAAAGTACGAGATTTAGTC | 673 |
| | GACTAAATCTCGTACTTTCTTGTAGGCTCCTTTTGGTTATATC ATTCTTACATAAAGGACACTGTGAAGGCCCTTTCTTCTGGTT GAGAAGTTTCAGCATGCAAAATTTGCAAAATATGTG | 674 |
| | CTTCACAGTGTCCTTTA | 675 |
| | TAAAGGACACTGTGAAG | 676 |
| Breast Cancer Leu-63-Stop TTA to TAA | TTTGCAAATTTTGCATGCTGAAACTTCTCAACCAGAAGAAAGG GCCTTCACAGTGTCCTTTATGTAAGAATGATATAACCAAAAGG AGCCTACAAGAAAGTACGAGATTTAGTCAACTTGT | 677 |
| | ACAAGTTGACTAAATCTCGTACTTTCTTGTAGGCTCCTTTTGG TTATATCATTCTTACATAAAGGACACTGTGAAGGCCCTTTCTT CTGGTTGAGAAGTTTCAGCATGCAAAATTTGCAAA | 678 |
| | GTGTCCTTTATGTAAGA | 679 |
| | TCTTACATAAAGGACAC | 680 |
| Breast Cancer Cys-64-Arg TGT to CGT | TGCAAATTTTGCATGCTGAAACTTCTCAACCAGAAGAAAGGG CCTTCACAGTGTCCTTTATGTAAGAATGATATAACCAAAAGGA GCCTACAAGAAAGTACGAGATTTAGTCAACTTGTTG | 681 |
| Breast Cancer Cys-64-Gly TGT to GGT | CAACAAGTTGACTAAATCTCGTACTTTCTTGTAGGCTCCTTTT GGTTATATCATTCTTACATAAAGGACACTGTGAAGGCCCTTTC TTCTGGTTGAGAAGTTTCAGCATGCAAAATTTGCA | 682 |
| | GTCCTTTATGTAAGAAT | 683 |
| | ATTCTTACATAAAGGAC | 684 |
| Breast Cancer Cys-64-Tyr TGT to TAT | GCAAATTTTGCATGCTGAAACTTCTCAACCAGAAGAAAGGGC CTTCACAGTGTCCTTTATGTAAGAATGATATAACCAAAAGGAG CCTACAAGAAAGTACGAGATTTAGTCAACTTGTTGA | 685 |
| | TCAACAAGTTGACTAAATCTCGTACTTTCTTGTAGGCTCCTTT TGGTTATATCATTCTTACATAAAGGACACTGTGAAGGCCCTTT CTTCTGGTTGAGAAGTTTCAGCATGCAAAATTTGC | 686 |
| | TCCTTTATGTAAGAATG | 687 |
| | CATTCTTACATAAAGGA | 688 |
| Breast Cancer Gln-74-Stop CAA to TAA | CAGAAGAAAGGCCTTCACAGTGTCCTTTATGTAAGAATGAT ATAACCAAAAGGAGCCTACAAGAAAGTACGAGATTTAGTCAA CTTGTTGAAGAGCTATTGAAAATCATTTGTGCTTTTC | 689 |
| | GAAAAGCACAAATGATTTTCAATAGCTCTTCAACAAGTTGACT AAATCTCGTACTTTCTTGTAGGCTCCTTTTGGTTATATCATTCT TACATAAAGGACACTGTGAAGGCCCTTTCTTCTG | 690 |
| | GGAGCCTACAAGAAAGT | 691 |
| | ACTTTCTTGTAGGCTCC | 692 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Tyr-105-Cys TAT to TGT | AGCTATTGAAAATCATTTGTGCTTTTCAGCTTGACACAGGTTT GGAGTATGCAAACAGCTATAATTTTGCAAAAAAGGAAAATAAC TCTCCTGAACATCTAAAAGATGAAGTTTCTATCAT | 693 |
| | ATGATAGAAACTTCATCTTTTAGATGTTCAGGAGAGTTATTTT CCTTTTTTGCAAAATTATAGCTGTTTGCATACTCCAAACCTGT GTCAAGCTGAAAAGCACAAATGATTTTCAATAGCT | 694 |
| | AAACAGCTATAATTTTG | 695 |
| | CAAAATTATAGCTGTTT | 696 |
| Breast Cancer Asn-158-Tyr AAC to TAC | CTACAGAGTGAACCCGAAAATCCTTCCTTGCAGGAAACCAGT CTCAGTGTCCAACTCTCTAACCTTGGAACTGTGAGAACTCTG AGGACAAAGCAGCGGATACAACCTCAAAAGACGTCTG | 697 |
| | CAGACGTCTTTTGAGGTTGTATCCGCTGCTTTGTCCTCAGAG TTCTCACAGTTCCAAGGTTAGAGAGTTGGACACTGAGACTGG TTTCCTGCAAGGAAGGATTTTCGGGTTCACTCTGTAG | 698 |
| | AACTCTCTAACCTTGGA | 699 |
| | TCCAAGGTTAGAGAGTT | 700 |
| Breast Cancer Gln-169-Stop CAG to TAG | GAAACCAGTCTCAGTGTCCAACTCTCTAACCTTGGAACTGTG AGAACTCTGAGGACAAAGCAGCGGATACAACCTCAAAAGAC GTCTGTCTACATTGAATTGGGATCTGATTCTTCTGAAG | 701 |
| | CTTCAGAAGAATCAGATCCCAATTCAATGTAGACAGACGTCTT TTGAGGTTGTATCCGCTGCTTTGTCCTCAGAGTTCTCACAGT TCCAAGGTTAGAGAGTTGGACACTGAGACTGGTTTC | 702 |
| | GGACAAAGCAGCGGATA | 703 |
| | TATCCGCTGCTTTGTCC | 704 |
| Breast Cancer Trp-353-Stop TGG to TAG | CTCCCAGCACAGAAAAAAAGGTAGATCTGAATGCTGATCCCC TGTGTGAGAGAAAAGAATGGAATAAGCAGAAACTGCCATGCT CAGAGAATCCTAGAGATACTGAAGATGTTCCTTGGAT | 705 |
| | ATCCAAGGAACATCTTCAGTATCTCTAGGATTCTCTGAGCAT GGCAGTTTCTGCTTATTCCATTCTTTTCTCTCACACAGGGGAT CAGCATTCAGATCTACCTTTTTTTCTGTGCTGGGAG | 706 |
| | AAAAGAATGGAATAAGC | 707 |
| | GCTTATTCCATTCTTTT | 708 |
| Breast Cancer Ile-379-Met ATT to ATG | ATGCTCAGAGAATCCTAGAGATACTGAAGATGTTCCTTGGAT AACACTAAATAGCAGCATTCAGAAAGTTAATGAGTGGTTTTCC AGAAGTGATGAACTGTTAGGTTCTGATGACTCACAT | 709 |
| | ATGTGAGTCATCAGAACCTAACAGTTCATCACTTCTGGAAAAC CACTCATTAACTTTCTGAATGCTGCTATTTAGTGTTATCCAAG GAACATCTTCAGTATCTCTAGGATTCTCTGAGCAT | 710 |
| | AGCAGCATTCAGAAAGT | 711 |
| | ACTTTCTGAATGCTGCT | 712 |
| Breast Cancer Glu-421-Gly GAA to GGA | GGGAGTCTGAATCAAATGCCAAAGTAGCTGATGTATTGGACG TTCTAAATGAGGTAGATGAATATTCTGGTTCTTCAGAGAAAAT AGACTTACTGGCCAGTGATCCTCATGAGGCTTTAAT | 713 |
| | ATTAAAGCCTCATGAGGATCACTGGCCAGTAAGTCTATTTTCT CTGAAGAACCAGAATATTCATCTACCTCATTTAGAACGTCCAA TACATCAGCTACTTTGGCATTTGATTCAGACTCCC | 714 |
| | GGTAGATGAATATTCTG | 715 |
| | CAGAATATTCATCTACC | 716 |
| Breast Cancer Phe-461-Leu TTT to CTT | ATATGTAAAAGTGAAAGAGTTCACTCCAAATCAGTAGAGAGTA ATATTGAAGACAAAATATTTGGGAAAACCTATCGGAAGAAGG CAAGCCTCCCCAACTTAAGCCATGTAACTGAAAATC | 717 |
| | GATTTTCAGTTACATGGCTTAAGTTGGGGAGGCTTGCCTTCT TCCGATAGGTTTTCCCAAATATTTTGTCTTCAATATTACTCTCT ACTGATTTGGAGTGAACTCTTTCACTTTTACATAT | 718 |
| | ACAAAATATTTGGGAAA | 719 |
| | TTTCCCAAATATTTTGT | 720 |
| Breast Cancer Tyr-465-Leu TAT to GAT | GAAAGAGTTCACTCCAAATCAGTAGAGAGTAATATTGAAGAC AAAATATTTGGGAAAACCTATCGGAAGAAGGCAAGCCTCCCC AACTTAAGCCATGTAACTGAAAATCTAATTATAGGAG | 721 |
| | CTCCTATAATTAGATTTTCAGTTACATGGCTTAAGTTGGGGAG GCTTGCCTTCTTCCGATAGGTTTTCCCAAATATTTTGTCTTCA ATATTACTCTCTACTGATTTGGAGTGAACTCTTTC | 722 |
| | GGAAAACCTATCGGAAG | 723 |
| | CTTCCGATAGGTTTTCC | 724 |
| Breast Cancer Gly-484-Stop GGA to TGA | ACCTATCGGAAGAAGGCAAGCCTCCCCAACTTAAGCCATGTA ACTGAAAATCTAATTATAGGAGCATTTGTTACTGAGCCACAGA TAATACAAGAGCGTCCCCTCACAAATAAATTAAAGC | 725 |
| | GCTTTAATTTATTTGTGAGGGGACGCTCTTGTATTATCTGTGG CTCAGTAACAAATGCTCCTATAATTAGATTTTCAGTTACATGG CTTAAGTTGGGGAGGCTTGCCTTCTTCCGATAGGT | 726 |
| | TAATTATAGGAGCATTT | 727 |
| | AAATGCTCCTATAATTA | 728 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Arg-507-Ile AGA to ATA | TTACTGAGCCACAGATAATACAAGAGCGTCCCCTCACAAATA AATTAAAGCGTAAAAGGAGACCTACATCAGGCCTTCATCCTG AGGATTTTATCAAGAAAGCAGATTTGGCAGTTCAAAA | 729 |
| | TTTTGAACTGCCAAATCTGCTTTCTTGATAAAATCCTCAGGAT GAAGGCCTGATGTAGGTCTCCTTTTACGCTTTAATTTATTTGT GAGGGGACGCTCTTGTATTATCTGTGGCTCAGTAA | 730 |
| | TAAAAGGAGACCTACAT | 731 |
| | ATGTAGGTCTCCTTTTA | 732 |
| Breast Cancer Ser-510-Stop TCA to TGA | CACAGATAATACAAGAGCGTCCCCTCACAAATAAATTAAAGC GTAAAAGGAGACCTACATCAGGCCTTCATCCTGAGGATTTTA TCAAGAAAGCAGATTTGGCAGTTCAAAAGACTCCTGA | 733 |
| | TCAGGAGTCTTTTTGAACTGCCAAATCTGCTTTCTTGATAAAAT CCTCAGGATGAAGGCCTGATGTAGGTCTCCTTTTACGCTTTA ATTTATTTGTGAGGGGACGCTCTTGTATTATCTGTG | 734 |
| | ACCTACATCAGGCCTTC | 735 |
| | GAAGGCCTGATGTAGGT | 736 |
| Breast Cancer Gln-526-Stop CAA to TAA | AGGAGACCTACATCAGGCCTTCATCCTGAGGATTTTATCAAG AAAGCAGATTTGGCAGTTCAAAAGACTCCTGAAATGATAAATC AGGGAACTAACCAAACGGAGCAGAATGGTCAAGTGA | 737 |
| | TCACTTGACCATTCTGCTCCGTTTGGTTAGTTCCCTGATTTAT CATTTCAGGAGTCTTTTGAACTGCCAAATCTGCTTTCTTGATA AAATCCTCAGGATGAAGGCCTGATGTAGGTCTCCT | 738 |
| | TGGCAGTTCAAAAGACT | 739 |
| | AGTCTTTTGAACTGCCA | 740 |
| Breast Cancer Gln-541-Stop CAG to TAG | AGGAGACCTACATCAGGCCTTCATCCTGAGGATTTTATCAAG AAAGCAGATTTGGCAGTTCAAAAGACTCCTGAAATGATAAATC AGGGAACTAACCAAACGGAGCAGAATGGTCAAGTGA | 741 |
| | TCACTTGACCATTCTGCTCCGTTTGGTTAGTTCCCTGATTTAT CATTTCAGGAGTCTTTTGAACTGCCAAATCTGCTTTCTTGATA AAATCCTCAGGATGAAGGCCTGATGTAGGTCTCCT | 742 |
| | AAACGGAGCAGAATGGT | 743 |
| | ACCATTCTGCTCCGTTT | 744 |
| Breast Cancer Gly-552-Val GGT to GTT | TAAATCAGGGAACTAACCAAACGGAGCAGAATGGTCAAGTGA TGAATATTACTAATAGTGGTCATGAGAATAAAACAAAAGGTGA TTCTATTCAGAATGAGAAAAATCCTAACCCAATAGA | 745 |
| | TCTATTGGGTTAGGATTTTTCTCATTCTGAATAGAATCACCTTT TGTTTTATTCTCATGACCACTATTAGTAATATTCATCACTTGAC CATTCTGCTCCGTTTGGTTAGTTCCCTGATTTA | 746 |
| | TAATAGTGGTCATGAGA | 747 |
| | TCTCATGACCACTATTA | 748 |
| Breast Cancer Gln-563-Stop CAG to TAG | GGTCAAGTGATGAATATTACTAATAGTGGTCATGAGAATAAAA CAAAAGGTGATTCTATTCAGAATGAGAAAAATCCTAACCCAAT AGAATCACTCGAAAAAGAATCTGCTTTCAAAACGA | 749 |
| | TCGTTTTGAAAGCAGATTCTTTTTCGAGTGATTCTATTGGGTT AGGATTTTTCTCATTCTGAATAGAATCACCTTTTGTTTTATTCT CATGACCACTATTAGTAATATTCATCACTTGACC | 750 |
| | ATTCTATTCAGAATGAG | 751 |
| | CTCATTCTGAATAGAAT | 752 |
| Ovarian Cancer Lys-607-Stop AAA to TAA | ATAAGCAGCAGTATAAGCAATATGGAACTCGAATTAAATATCC ACAATTCAAAAGCACCTAAAAAGAATAGGCTGAGGAGGAAGT CTTCTACCAGGCATATTCATGCGCTTGAACTAGTAG | 753 |
| | CTACTAGTTCAAGCGCATGAATATGCCTGGTAGAAGACTTCC TCCTCAGCCTATTCTTTTTAGGTGCTTTTGAATTGTGGATATT TAATTCGAGTTCCATATTGCTTATACTGCTGCTTAT | 754 |
| | AAGCACCTAAAAAGAAT | 755 |
| | ATTCTTTTTAGGTGCTT | 756 |
| Breast Cancer Leu-639-Stop TTG to TAG | ATATTCATGCGCTTGAACTAGTAGTCAGTAGAAATCTAAGCCC ACCTAATTGTACTGAATTGCAAATTGATAGTTGTTCTAGCAGT GAAGAGATAAAGAAAAAAAAGTACAACCAAATGCC | 757 |
| | GGCATTTGGTTGTACTTTTTTTTCTTTATCTCTTCACTGCTAGA ACAACTATCAATTTGCAATTCAGTACAATTAGGTGGGCTTAGA TTTCTACTGACTACTAGTTCAAGCGCATGAATAT | 758 |
| | TACTGAATTGCAAATTG | 759 |
| | CAATTTGCAATTCAGTA | 760 |
| Breast Cancer Asp-693-Asn GAC to AAC | GAACCTGCAACTGGAGCCAAGAAGAGTAACAAGCCAAATGAA CAGACAAGTAAAAGACATGACAGCGATACTTTCCCAGAGCTG AAGTTAACAAATGCACCTGGTTCTTTTACTAAGTGTT | 761 |
| | AACACTTAGTAAAAGAACCAGGTGCATTTGTTAACTTCAGCTC TGGGAAAGTATCGCTGTCATGTCTTTTACTTGTCTGTTCATTT GGCTTGTTACTCTTCTTGGCTCCAGTTGCAGGTTC | 762 |
| | AAAGACATGACAGCGAT | 763 |
| | ATCGCTGTCATGTCTTT | 764 |

TABLE 14-continued

BRCA1 Mutations and Genome-Correcting Oligos

| Clinical Phenotype & Mutation | Correcting Oligos | SEQ ID NO: |
|---|---|---|
| Ovarian Cancer Glu-720-Stop GAA to TAA | CTGAAGTTAACAAATGCACCTGGTTCTTTTACTAAGTGTTCAA ATACCAGTGAACTTAAAGAATTTGTCAATCCTAGCCTTCCAAG AGAAGAAAAAGAAGAGAAACTAGAAACAGTTAAAG | 765 |
| | CTTTAACTGTTTCTAGTTTCTCTTCTTTTTCTTCTCTTGGAAGG CTAGGATTGACAAATTCTTTAAGTTCACTGGTATTTGAACACT TAGTAAAAGAACCAGGTGCATTTGTTAACTTCAG | 766 |
| | AACTTAAAGAATTTGTC | 767 |
| | GACAAATTCTTTAAGTT | 768 |
| Breast Cancer Glu-755-Stop GAA to TAA | CTAGAAACAGTTAAAGTGTCTAATAATGCTGAAGACCCCAAA GATCTCATGTTAAGTGGAGAAAGGGTTTTGCAAACTGAAAGA TCTGTAGAGAGTAGCAGTATTTCATTGGTACCTGGTA | 769 |
| | TACCAGGTACCAATGAAATACTGCTACTCTCTACAGATCTTTC AGTTTGCAAAACCCTTTCTCCACTTAACATGAGATCTTTGGGG TCTTCAGCATTATTAGACACTTTAACTGTTTCTAG | 770 |
| | TAAGTGGAGAAAGGGTT | 771 |
| | AACCCTTTCTCCACTTA | 772 |
| Breast Cancer Ser-770-Stop TCA to TAA | TCATGTTAAGTGGAGAAAGGGTTTTGCAAACTGAAAGATCTG TAGAGAGTAGCAGTATTTCATTGGTACCTGGTACTGATTATG GCACTCAGGAAAGTATCTCGTTACTGGAAGTTAGCAC | 773 |
| | GTGCTAACTTCCAGTAACGAGATACTTTCCTGAGTGCCATAA TCAGTACCAGGTACCAATGAAATACTGCTACTCTCTACAGAT CTTTCAGTTTGCAAAACCCTTTCTCCACTTAACATGA | 774 |
| | CAGTATTTCATTGGTAC | 775 |
| | GTACCAATGAAATACTG | 776 |
| Breast Cancer Val-772-Ala GTA to GCA | TAAGTGGAGAAAGGGTTTTGCAAACTGAAAGATCTGTAGAGA GTAGCAGTATTTCATTGGTACCTGGTACTGATTATGGCACTC AGGAAAGTATCTCGTTACTGGAAGTTAGCACTCTAGG | 777 |
| | CCTAGAGTGCTAACTTCCAGTAACGAGATACTTTCCTGAGTG CCATAATCAGTACCAGGTACCAATGAAATACTGCTACTCTCTA CAGATCTTTCAGTTTGCAAAACCCTTTCTCCACTTA | 778 |
| | TTCATTGGTACCTGGTA | 779 |
| | TACCAGGTACCAATGAA | 780 |
| Breast Cancer Gln-780-Stop CAG to TAG | ACTGAAAGATCTGTAGAGAGTAGCAGTATTTCATTGGTACCT GGTACTGATTATGGCACTCAGGAAAGTATCTCGTTACTGGAA GTTAGCACTCTAGGGAAGGCAAAAACAGAACCAAATA | 781 |
| | TATTTGGTTCTGTTTTTGCCTTCCCTAGAGTGCTAACTTCCAG TAACGAGATACTTTCCTGAGTGCCATAATCAGTACCAGGTAC CAATGAAATACTGCTACTCTCTACAGATCTTTCAGT | 782 |
| | ATGGCACTCAGGAAAGT | 783 |
| | ACTTTCCTGAGTGCCAT | 784 |
| Breast Cancer Glu-797-Stop GAA to TAA | TATGGCACTCAGGAAAGTATCTCGTTACTGGAAGTTAGCACT CTAGGGAAGGCAAAAACAGAACCAAATAAATGTGTGAGTCAG TGTGCAGCATTTGAAAACCCCAAGGGACTAATTCATG | 785 |
| | CATGAATTAGTCCCTTGGGGTTTTCAAATGCTGCACACTGAC TCACACATTTATTTGGTTCTGTTTTTGCCTTCCCTAGAGTGCT AACTTCCAGTAACGAGATACTTTCCTGAGTGCCATA | 786 |
| | CAAAAACAGAACCAAAT | 787 |
| | ATTTGGTTCTGTTTTTG | 788 |
| Breast Cancer Lys-820-Glu AAA to GAA | AAATGTGTGAGTCAGTGTGCAGCATTTGAAAACCCCAAGGGA CTAATTCATGGTTGTTCCAAAGATAATAGAAATGACACAGAAG GCTTTAAGTATCCATTGGGACATGAAGTTAACCACA | 789 |
| | TGTGGTTAACTTCATGTCCCAATGGATACTTAAAGCCTTCTGT GTCATTTCTATTATCTTTGGAACAACCATGAATTAGTCCCTTG GGGTTTTCAAATGCTGCACACTGACTCACACATTT | 790 |
| | GTTGTTCCAAAGATAAT | 791 |
| | ATTATCTTTGGAACAAC | 792 |
| Breast Cancer Thr-826-Lys ACA to AAA | CAGCATTTGAAAACCCCAAGGGACTAATTCATGGTTGTTCCA AAGATAATAGAAATGACACAGAAGGCTTTAAGTATCCATTGG GACATGAAGTTAACCACAGTCGGGAAACAAGCATAGA | 793 |
| | TCTATGCTTGTTTCCCGACTGTGGTTAACTTCATGTCCCAATG GATACTTAAAGCCTTCTGTGTCATTTCTATTATCTTTGGAACA ACCATGAATTAGTCCCTTGGGGTTTTCAAATGCTG | 794 |
| | AAATGACACAGAAGGCT | 795 |
| | AGCCTTCTGTGTCATTT | 796 |
| Breast Cancer Arg-841-Trp CGG to TGG | GATAATAGAAATGACACAGAAGGCTTTAAGTATCCATTGGGA CATGAAGTTAACCACAGTCGGGAAACAAGCATAGAAATGGAA GAAAGTGAACTTGATCGTCAGTATTTGCAGAATACAT | 797 |
| | ATGTATTCTGCAAATACTGAGCATCAAGTTCACTTTCTTCCAT TTCTATGCTTGTTTCCCGACTGTGGTTAACTTCATGTCCCAAT GGATACTTAAAGCCTTCTGTGTCATTTCTATTATC | 798 |
| | ACCACAGTCGGGAAACA | 799 |
| | TGTTTCCCGACTGTGGT | 800 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Pro-871-Leu CCG to CTG | AACTTGATGCTCAGTATTTGCAGAATACATTCAAGGTTTCAAA GCGCCAGTCATTTGCTCCGTTTTCAAATCCAGGAAATGCAGA AGAGGAATGTGCAACATTCTCTGCCCACTCTGGGTC | 801 |
| | GACCCAGAGTGGGCAGAGAATGTTGCACATTCCTCTTCTGCA TTTCCTGGATTTGAAAACGGAGCAAATGACTGGCGCTTTGAA ACCTTGAATGTATTCTGCAAATACTGAGCATCAAGTT | 802 |
| | ATTTGCTCCGTTTTCAA | 803 |
| | TTGAAAACGGAGCAAAT | 804 |
| Breast Cancer Leu-892-Ser TTA to TCA | TTTCAAATCCAGGAAATGCAGAAGAGGAATGTGCAACATTCT CTGCCCACTCTGGGTCCTTAAAGAAACAAAGTCCAAAAGTCA CTTTTGAATGTGAACAAAAGGAAGAAAATCAAGGAAA | 805 |
| | TTTCCTTGATTTTCTTCCTTTTGTTCACATTCAAAAGTGACTTT TGGACTTTGTTTCTTTAAGGACCCAGAGTGGGCAGAGAATGT TGCACATTCCTCTTCTGCATTTCCTGGATTTGAAA | 806 |
| | TGGGTCCTTAAAGAAAC | 807 |
| | GTTTCTTTAAGGACCCA | 808 |
| Breast Cancer Glu-908-Stop GAA to TAA | CACTCTGGGTCCTTAAAGAAACAAAGTCCAAAAGTCACTTTTG AATGTGAACAAAAGGAAGAAAATCAAGGAAAGAATGAGTCTA ATATCAAGCCTGTACAGACAGTTAATATCACTGCAG | 809 |
| | CTGCAGTGATATTAACTGTCTGTACAGGCTTGATATTAGACTC ATTCTTTCCTTGATTTTCTTCCTTTTGTTCACATTCAAAAGTGA CTTTTGGACTTTGTTTCTTTAAGGACCCAGAGTG | 810 |
| | AAAAGGAAGAAAATCAA | 811 |
| | TTGATTTTCTTCCTTTT | 812 |
| Breast Cancer Gly-960-Asp GGC to GAC | ATAATGCCAAATGTAGTATCAAAGGAGGCTCTAGGTTTTGTCT ATCATCTCAGTTCAGAGGCAACGAAACTGGACTCATTACTCC AAATAAACATGGACTTTTACAAAACCCATATCGTAT | 813 |
| | ATACGATATGGGTTTTGTAAAAGTCCATGTTTATTTGGAGTAA TGAGTCCAGTTTCGTTGCCTCTGAACTGAGATGATAGACAAA ACCTAGAGCCTCCTTTGATACTACATTTGGCATTAT | 814 |
| | GTTCAGAGGCAACGAAA | 815 |
| | TTTCGTTGCCTCTGAAC | 816 |
| Breast Cancer Met-1008-Ile ATG to ATA | ATTTGTTAAAACTAAATGTAAGAAAAATCTGCTAGAGGAAAAC TTTGAGGAACATTCAATGTCACCTGAAAGAGAAATGGGAAAT GAGAACATTCCAAGTACAGTGAGCACAATTAGCCGT | 817 |
| | ACGGCTAATTGTGCTCACTGTACTTGGAATGTTCTCATTTCCC ATTTCTCTTTCAGGTGACATTGAATGTTCCTCAAAGTTTTCCT CTAGCAGATTTTTCTTACATTTAGTTTTAACAAAT | 818 |
| | CATTCAATGTCACCTGA | 819 |
| | TCAGGTGACATTGAATG | 820 |
| Breast Cancer Thr-1025-Ile ACA to ATA | ACTTTGAGGAACATTCAATGTCACCTGAAAGAGAAATGGGAA ATGAGAACATTCCAAGTACAGTGAGCACAATTAGCCGTAATA ACATTAGAGAAATGTTTTTAAAGAAGCCAGCTCAAG | 821 |
| | CTTGAGCTGGCTTCTTTAAAAACATTTTCTCTAATGTTATTACG GCTAATTGTGCTCACTGTACTTGGAATGTTCTCATTTCCCATT TCTCTTTCAGGTGACATTGAATGTTCCTCAAAGT | 822 |
| | TCCAAGTACAGTGAGCA | 823 |
| | TGCTCACTGTACTTGGA | 824 |
| Breast Cancer Glu-1038-Gly GAA to GGA | ACATTCCAAGTACAGTGAGCACAATTAGCCGTAATAACATTAG AGAAAATGTTTTTAAAGAAGCCAGCTCAAGCAATATTAATGAA GTAGGTTCCAGTACTAATGAAGTGGGCTCCAGTAT | 825 |
| | ATACTGGAGCCCACTTCATTAGTACTGGAACCTACTTCATTAA TATTGCTTGAGCTGGCTTCTTTAAAAACATTTTCTCTAATGTTA TTACGGCTAATTGTGCTCACTGTACTTGGAATGT | 826 |
| | TTTTAAAGAAGCCAGCT | 827 |
| | AGCTGGCTTCTTTAAAA | 828 |
| Breast Cancer Ser-1040-Asn AGC to AAC | CAAGTACAGTGAGCACAATTAGCCGTAATAACATTAGAGAAA ATGTTTTTAAAGAAGCCAGCTCAAGCAATATTAATGAAGTAGG TTCCAGTACTAATGAAGTGGGCTCCAGTATTAATGA | 829 |
| | TCATTAATACTGGAGCCCACTTCATTAGTACTGGAACCTACTT CATTAATATTGCTTGAGCTGGCTTCTTTAAAAACATTTTCTCTA ATGTTATTACGGCTAATTGTGCTCACTGTACTTG | 830 |
| | AGAAGCCAGCTCAAGCA | 831 |
| | TGCTTGAGCTGGCTTCT | 832 |
| Breast Cancer Val-1047-Ala GTA to GCA | GCCGTAATAACATTAGAGAAAATGTTTTTAAAGAAGCCAGCTC AAGCAATATTAATGAAGTAGGTTCCAGTACTAATGAAGTGGG CTCCAGTATTAATGAAATAGGTTCCAGTGATGAAAA | 833 |
| | TTTTCATCACTGGAACCTATTTCATTAATACTGGAGCCCACTT CATTAGTACTGGAACCTACTTCATTAATATTGCTTGAGCTGGC TTCTTTAAAAACATTTTCTCTAATGTTATTACGGC | 834 |
| | TAATGAAGTAGGTTCCA | 835 |
| | TGGAACCTACTTCATTA | 836 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Leu-1080-Stop TTG to TAG | AAATAGGTTCCAGTGATGAAAACATTCAAGCAGAACTAGGTA GAAACAGAGGGCCAAAATTGAATGCTATGCTTAGATTAGGGG TTTTGCAACCTGAGGTCTATAAACAAAGTCTTCCTGG | 837 |
| | CCAGGAAGACTTTGTTTATAGACCTCAGGTTGCAAAACCCCT AATCTAAGCATAGCATTCAATTTTGGCCCTCTGTTTCTACCTA GTTCTGCTTGAATGTTTTCATCACTGGAACCTATTT | 838 |
| | GCCAAAATTGAATGCTA | 839 |
| | TAGCATTCAATTTTGGC | 840 |
| Breast Cancer Leu-1086-Stop TTA to TGA | AAAACATTCAAGCAGAACTAGGTAGAAACAGAGGGCCAAAAT TGAATGCTATGCTTAGATTAGGGGTTTTGCAACCTGAGGTCT ATAAACAAAGTCTTCCTGGAAGTAATTGTAAGCATCC | 841 |
| | GGATGCTTACAATTACTTCCAGGAAGACTTTGTTTATAGACCT CAGGTTGCAAAACCCCTAATCTAAGCATAGCATTCAATTTTG GCCCTCTGTTTCTACCTAGTTCTGCTTGAATGTTTT | 842 |
| | GCTTAGATTAGGGGTTT | 843 |
| | AAACCCCTAATCTAAGC | 844 |
| Breast Cancer Ser-1130-Stop TCA to TGA | AGCAAGAATATGAAGAAGTAGTTCAGACTGTTAATACAGATTT CTCTCCATATCTGATTTCAGATAACTTAGAACAGCCTATGGGA AGTAGTCATGCATCTCAGGTTTGTTCTGAGACACC | 845 |
| | GGTGTCTCAGAACAAACCTGAGATGCATGACTACTTCCCATA GGCTGTTCTAAGTTATCTGAAATCAGATATGGAGAGAAATCT GTATTAACAGTCTGAACTACTTCTTCATATTCTTGCT | 846 |
| | TCTGATTTCAGATAACT | 847 |
| | AGTTATCTGAAATCAGA | 848 |
| Breast Cancer Lys-1183-Arg AAA to AGA | CTAGTTTTGCTGAAAATGACATTAAGGAAAGTTCTGCTGTTTT TAGCAAAAGCGTCCAGAAAGGAGAGCTTAGCAGGAGTCCTA GCCCTTTCACCCATACACATTTGGCTCAGGGTTACCG | 849 |
| | CGGTAACCCTGAGCCAAATGTGTATGGGTGAAAGGGCTAGG ACTCCTGCTAAGCTCTCCTTTCTGGACGCTTTTGCTAAAAACA GCAGAACTTTCCTTAATGTCATTTTCAGCAAAACTAG | 850 |
| | CGTCCAGAAAGGAGAGC | 851 |
| | GCTCTCCTTTCTGGACG | 852 |
| Breast Cancer Gln-1200-Stop CAG to TAG | AGCGTCCAGAAAGGAGAGCTTAGCAGGAGTCCTAGCCCTTT CACCCATACACATTTGGCTCAGGGTTACCGAAGAGGGGCCA AGAAATTAGAGTCCTCAGAAGAGAACTTATCTAGTGAGG | 853 |
| | CCTCACTAGATAAGTTCTCTTCTGAGGACTCTAAATTTCTTGGC CCCTCTTCGGTAACCCTGAGCCAAATGTGTATGGGTGAAAGG GCTAGGACTCCTGCTAAGCTCTCCTTTCTGGACGCT | 854 |
| | ATTTGGCTCAGGGTTAC | 855 |
| | GTAACCCTGAGCCAAAT | 856 |
| Breast Cancer Arg-1203-Stop CGA to TGA | AAAGGAGAGCTTAGCAGGAGTCCTAGCCCTTTCACCCATACA CATTTGGCTCAGGGTTACCGAAGAGGGGCCAAGAAATTAGA GTCCTCAGAAGAGAACTTATCTAGTGAGGATGAAGAGC | 857 |
| | GCTCTTCATCCTCACTAGATAAGTTCTCTTCTGAGGACTCTAA TTTCTTGGCCCCTCTTCGGTAACCCTGAGCCAAATGTGTATG GGTGAAAGGGCTAGGACTCCTGCTAAGCTCTCCTTT | 858 |
| | AGGGTTACCGAAGAGGG | 859 |
| | CCCTCTTCGGTAACCCT | 860 |
| Breast Cancer Glu-1214-Stop GAG to TAG | ACCCATACACATTTGGCTCAGGGTTACCGAAGAGGGGCCAA GAAATTAGAGTCCTCAGAAGAGAACTTATCTAGTGAGGATGA AGAGCTTCCCTGCTTCCAACACTTGTTATTTGGTAAAG | 861 |
| | CTTTACCAAATAACAAGTGTTGGAAGCAGGGAAGCTCTTCAT CCTCACTAGATAAGTTCTCTTCTGAGGACTCTAATTTCTTGGC CCCTCTTCGGTAACCCTGAGCCAAATGTGTATGGGT | 862 |
| | CCTCAGAAGAGAACTTA | 863 |
| | TAAGTTCTCTTCTGAGG | 864 |
| Breast Cancer Glu-1219-Asp GAG to GAC | TCAGGGTTACCGAAGAGGGGCCAAGAAATTAGAGTCCTCAG AAGAGAACTTATCTAGTGAGGATGAAGAGCTTCCCTGCTTCC AACACTTGTTATTTGGTAAAGTAAACAATATACCTTCT | 865 |
| | AGAAGGTATATTGTTTACTTTACCAAATAACAAGTGTTGGAAG CAGGGAAGCTCTTCATCCTCACTAGATAAGTTCTCTTCTGAG GACTCTAATTTCTTGGCCCCTCTTCGGTAACCCTGA | 866 |
| | TCTAGTGAGGATGAAGA | 867 |
| | TCTTCATCCTCACTAGA | 868 |
| Breast Cancer Glu-1221-Stop GAA to TAA | GGTTACCGAAGAGGGGCCAAGAAATTAGAGTCCTCAGAAGA GAACTTATCTAGTGAGGATGAAGAGCTTCCCTGCTTCCAACA CTTGTTATTTGGTAAAGTAAACAATATACCTTCTCAGT | 869 |
| | ACTGAGAAGGTATATTGTTTACTTTACCAAATAACAAGTGTTG GAAGCAGGGAAGCTCTTCATCCTCACTAGATAAGTTCTCTTC TGAGGACTCTAATTTCTTGGCCCCTCTTCGGTAACC | 870 |
| | GTGAGGATGAAGAGCTT | 871 |
| | AAGCTCTTCATCCTCAC | 872 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Glu-1250-Stop GAG to TAG | TTATTTGGTAAAGTAAACAATATACCTTCTCAGTCTACTAGGC ATAGCACCGTTGCTACCGAGTGTCTGTCTAAGAACACAGAGG AGAATTTATTATCATTGAAGAATAGCTTAAATGACT | 873 |
|  | AGTCATTTAAGCTATTCTTCAATGATAATAAATTCTCCTCTGTG TTCTTAGACAGACACTCGGTAGCAACGGTGCTATGCCTAGTA GACTGAGAAGGTATATTGTTTACTTTACCAAATAA | 874 |
|  | TTGCTACCGAGTGTCTG | 875 |
|  | CAGACACTCGGTAGCAA | 876 |
| Breast Cancer Ser-1262-Stop TCA to TAA | CTAGGCATAGCACCGTTGCTACCGAGTGTCTGTCTAAGAACA CAGAGGAGAATTTATTATCATTGAAGAATAGCTTAAATGACTG CAGTAACCAGGTAATATTGGCAAAGGCATCTCAGGA | 877 |
|  | TCCTGAGATGCCTTTGCCAATATTACCTGGTTACTGCAGTCAT TTAAGCTATTCTTCAATGATAATAAATTCTCCTCTGTGTTCTTA GACAGACACTCGGTAGCAACGGTGCTATGCCTAG | 878 |
|  | TTTATTATCATTGAAGA | 879 |
|  | TCTTCAATGATAATAAA | 880 |
| Breast Cancer Gln-1281-Stop CAG to TAG | TTATCATTGAAGAATAGCTTAAATGACTGCAGTAACCAGGTAA TATTGGCAAAGGCATCTCAGGAACATCACCTTAGTGAGGAAA CAAAATGTTCTGCTAGCTTGTTTTCTTCACAGTGCA | 881 |
|  | TGCACTGTGAAGAAAACAAGCTAGCAGAACATTTTGTTTCCTC ACTAAGGTGATGTTCCTGAGATGCCTTTGCCAATATTACCTG GTTACTGCAGTCATTTAAGCTATTCTTCAATGATAA | 882 |
|  | AGGCATCTCAGGAACAT | 883 |
|  | ATGTTCCTGAGATGCCT | 884 |
| Breast Cancer Gln-1313-Stop CAG to TAG | GCTAGCTTGTTTTCTTCACAGTGCAGTGAATTGGAAGACTTG ACTGCAAATACAAACACCCAGGATCCTTTCTTGATTGGTTCTT CCAAACAAATGAGGCATCAGTCTGAAAGCCAGGGAG | 885 |
|  | CTCCCTGGCTTTCAGACTGATGCCTCATTGTTTGGAAGAAC CAATCAAGAAAGGATCCTGGGTGTTTGTATTTGCAGTCAAGT CTTCCAATTCACTGCACTGTGAAGAAAACAAGCTAGC | 886 |
|  | CAAACACCCAGGATCCT | 887 |
|  | AGGATCCTGGGTGTTTG | 888 |
| Breast Cancer Ile-1318-Val ATT to GTT | TCACAGTGCAGTGAATTGGAAGACTTGACTGCAAATACAAAC ACCCAGGATCCTTTCTTGATTGGTTCTTCCAAACAAATGAGG CATCAGTCTGAAAGCCAGGGAGTTGGTCTGAGTGACA | 889 |
|  | TGTCACTCAGACCAACTCCCTGGCTTTCAGACTGATGCCTCA TTTGTTTGGAAGAACCAATCAAGAAAGGATCCTGGGTGTTTG TATTTGCAGTCAAGTCTTCCAATTCACTGCACTGTGA | 890 |
|  | CTTTCTTGATTGGTTCT | 891 |
|  | AGAACCAATCAAGAAAG | 892 |
| Breast Cancer Gln-1323-Stop CAA to TAA | TTGGAAGACTTGACTGCAAATACAAACACCCAGGATCCTTTC TTGATTGGTTCTTCCAAACAAATGAGGCATCAGTCTGAAAGC CAGGGAGTTGGTCTGAGTGACAAGGAATTGGTTTCAG | 893 |
|  | CTGAAACCAATTCCTTGTCACTCAGACCAACTCCCTGGCTTT CAGACTGATGCCTCATTTGTTTGGAAGAACCAATCAAGAAAG GATCCTGGGTGTTTGTATTTGCAGTCAAGTCTTCCAA | 894 |
|  | CTTCCAAACAAATGAGG | 895 |
|  | CCTCATTTGTTTGGAAG | 896 |
| Breast Cancer Arg-1347-Gly AGA to GGA | CAGTCTGAAAGCCAGGGAGTTGGTCTGAGTGACAAGGAATT GGTTTCAGATGATGAAGAAAGAGGAACGGGCTTGGAAGAAA ATAATCAAGAAGAGCAAAGCATGGATTCAAACTTAGGTA | 897 |
|  | TACCTAAGTTTGAATCCATGCTTTGCTCTTCTTGATTATTTTCT TCCAAGCCCGTTCCTCTTTCTTCATCATCTGAAACCAATTCCT TGTCACTCAGACCAACTCCCTGGCTTTCAGACTG | 898 |
|  | ATGAAGAAAGAGGAACG | 899 |
|  | CGTTCCTCTTTCTTCAT | 900 |
| Breast Cancer Gln-1395-Stop CAG to TAG | GAAACAAGCGTCTCTGAAGACTGCTCAGGGCTATCCTCTCAG AGTGACATTTTAACCACTCAGGTAAAAAGCGTGTGTGTGTGT GCACATGCGTGTGTGGTGTCCTTTGCATTCAGTAG | 901 |
|  | CTACTGAATGCAAAGGACACCACACACACGCATGTGCACACA CACACACGCTTTTTACCTGAGTGGTTAAAATGTCACTCTGAG AGGATAGCCCTGAGCAGTCTTCAGAGACGCTTGTTTC | 902 |
|  | TAACCACTCAGGTAAAA | 903 |
|  | TTTTACCTGAGTGGTTA | 904 |
| Breast Cancer Gln-1408-Stop CAG to TAG | TGGTGCCATTTATCGTTTTTGAAGCAGAGGGATACCATGCAA CATAACCTGATAAAGCTCCAGCAGGAAATGGCTGAACTAGAA GCTGTGTTAGAACAGCATGGGAGCCAGCCTTCTAACA | 905 |
|  | TGTTAGAAGGCTGGCTCCCATGCTGTTCTAACACAGCTTCTA GTTCAGCCATTTCCTGCTGGAGCTTTATCAGGTTATGTTGCAT GGTATCCCTCTGCTTCAAAAACGATAAATGGCACCA | 906 |
|  | TAAAGCTCCAGCAGGAA | 907 |
|  | TTCCTGCTGGAGCTTTA | 908 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Arg-1443-Gly CGA to GGA | AGCCAGCCTTCTAACAGCTACCCTTCCATCATAAGTGACTCT TCTGCCCTTGAGGACCTGCGAAATCCAGAACAAAGCACATCA GAAAAAGGTGTGTATTGTTGGCCAAACACTGATATCT | 909 |
| Arg-1443-Stop CGA to TGA | AGATATCAGTGTTTGGCCAACAATACACACCTTTTTCTGATGT GCTTTGTTCTGGATTTCGCAGGTCCTCAAGGGCAGAAGAGTC ACTTATGATGGAAGGGTAGCTGTTAGAAGGCTGGCT | 910 |
| | AGGACCTGCGAAATCCA | 911 |
| | TGGATTTCGCAGGTCCT | 912 |
| Breast Cancer Ser-1512-Ile AGT to ATT | CAGAATAGAAACTACCCATCTCAAGAGGAGCTCATTAAGGTT GTTGATGTGGAGGAGCAACAGCTGGAAGAGTCTGGGCCACA CGATTTGACGGAAACATCTTACTTGCCAAGGCAAGATC | 913 |
| | GATCTTGCCTTGGCAAGTAAGATGTTTCCGTCAAATCGTGTG GCCCAGACTCTTCCAGCTGTTGCTCCTCCACATCAACAACCT TAATGAGCTCCTCTTGAGATGGGTAGTTTCTATTCTG | 914 |
| | AGGAGCAACAGCTGGAA | 915 |
| | TTCCAGCTGTTGCTCCT | 916 |
| Breast Cancer Gln-1538-Stop CAG to TAG | ATCTTTCTAGGTCATCCCCTTCTAAATGCCCATCATTAGATGA TAGGTGGTACATGCACAGTTGCTCTGGGAGTCTTCAGAATAG AAACTACCCATCTCAAGAGGAGCTCATTAAGGTTGT | 917 |
| | ACAACCTTAATGAGCTCCTCTTGAGATGGGTAGTTTCTATTCT GAAGACTCCCAGAGCAACTGTGCATGTACCACCTATCATCTA ATGATGGGCATTTAGAAGGGGATGACCTAGAAAGAT | 918 |
| | CATGCACAGTTGCTCTG | 919 |
| | CAGAGCAACTGTGCATG | 920 |
| Breast Cancer Glu-1541-Stop GAG to TAG | CAGAATAGAAACTACCCATCTCAAGAGGAGCTCATTAAGGTT GTTGATGTGGAGGAGCAACAGCTGGAAGAGTCTGGGCCACA CGATTTGACGGAAACATCTTACTTGCCAAGGCAAGATC | 921 |
| | GATCTTGCCTTGGCAAGTAAGATGTTTCCGTCAAATCGTGTG GCCCAGACTCTTCCAGCTGTTGCTCCTCCACATCAACAACCT TAATGAGCTCCTCTTGAGATGGGTAGTTTCTATTCTG | 922 |
| | AGGAGCAACAGCTGGAA | 923 |
| | TTCCAGCTGTTGCTCCT | 924 |
| Breast Cancer Thr-1561-Ile ACC to ATC | AACTACCCATCTCAAGAGGAGCTCATTAAGGTTGTTGATGTG GAGGAGCAACAGCTGGAAGAGTCTGGGCCACACGATTTGAC GGAAACATCTTACTTGCCAAGGCAAGATCTAGGTAATA | 925 |
| | TATTACCTAGATCTTGCCTTGGCAAGTAAGATGTTTCCGTCAA ATCGTGTGGCCCAGACTCTTCCAGCTGTTGCTCCTCCACATC AACAACCTTAATGAGCTCCTCTTGAGATGGGTAGTT | 926 |
| | AGCTGGAAGAGTCTGGG | 927 |
| | CCCAGACTCTTCCAGCT | 928 |
| Breast Cancer Tyr-1563-Stop TAC to TAG | TTTGTAATTCAACATTCATCGTTGTGTAAATTAAACTTCTCCCA TTCCTTTCAGAGGGAACCCCTTACCTGGAATCTGGAATCAGC CTCTTCTCTGATGACCCTGAATCTGATCCTTCTGA | 929 |
| | TCAGAAGGATCAGATTCAGGGTCATCAGAGAAGAGGCTGATT CCAGATTCCAGGTAAGGGGTTCCCTCTGAAAGGAATGGGAG AAGTTTAATTTACACAACGATGAATGTTGAATTACAAA | 930 |
| | AGAGGGAACCCCTTACC | 931 |
| | GGTAAGGGGTTCCCTCT | 932 |
| Breast Cancer Leu-1564-Pro CTG to CCG | CAACATTCATCGTTGTGTAAATTAAACTTCTCCCATTCCTTTC AGAGGGAACCCCTTACCTGGAATCTGGAATCAGCCTCTTCTC TGATGACCCTGAATCTGATCCTTCTGAAGACAGAGC | 933 |
| | GCTCTGTCTTCAGAAGGATCAGATTCAGGGTCATCAGAGAAG AGGCTGATTCCAGATTCCAGGTAAGGGGTTCCCTCTGAAAG GAATGGGAGAAGTTTAATTTACACAACGATGAATGTT | 934 |
| | CCCTTACCTGGAATCTG | 935 |
| | CAGATTCCAGGTAAGGG | 936 |
| Breast Cancer Gln-1604-Stop CAA to TAA | GCCCCAGAGTCAGCTCGTGTTGGCAACATACCATCTTCAACC TCTGCATTGAAAGTTCCCCAATTGAAAGTTGCAGAATCTGCC CAGAGTCCAGCTGCTGCTCATACTACTGATACTGCTG | 937 |
| | CAGCAGTATCAGTAGTATGAGCAGCAGCTGGACTCTGGGCA GATTCTGCAACTTTCAATTGGGGAACTTTCAATGCGAGAGGTT GAAGATGGTATGTTGCCAACACGAGCTGACTCTGGGC | 938 |
| | AAGTTCCCCAATTGAAA | 939 |
| | TTTCAATTGGGGAACTT | 940 |
| Breast Cancer Lys-1606-Glu AAA to GAA | GAGTCAGCTCGTGTTGGCAACATACCATCTTCAACCTCTGCA TTGAAAGTTCCCCAATTGAAAGTTGCAGAATCTGCCCAGAGT CCAGCTGCTGCTCATACTACTGATACTGCTGGGTATA | 941 |
| | TATACCCAGCAGTATCAGTAGTATGAGCAGCAGCTGGACTCT GGGCAGATTCTGCAACTTTCAATTGGGGAACTTTCAATGCAG AGGTTGAAGATGGTATGTTGCCAACACGAGCTGACTC | 942 |
| | CCCAATTGAAAGTTGCA | 943 |
| | TGCAACTTTCAATTGGG | 944 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Met-1628-Thr ATG to ACG | CAGAATCTGCCCAGAGTCCAGCTGCTGCTCATACTACTGATA CTGCTGGGTATAATGCAATGGAAGAAAGTGTGAGCAGGGAG AAGCCAGAATTGACAGCTTCAACAGAAAGGGTCAACAA | 945 |
| | TTGTTGACCCTTTCTGTTGAAGCTGTCAATTCTGGCTTCTCCC TGCTCACACTTTCTTCCATTGCATTATACCCAGCAGTATCAGT AGTATGAGCAGCAGCTGGACTCTGGGCAGATTCTG | 946 |
| | TAATGCAATGGAAGAAA | 947 |
| | TTTCTTCCATTGCATTA | 948 |
| Breast Cancer Met-1628-Val ATG to GTG | GCAGAATCTGCCCAGAGTCCAGCTGCTGCTCATACTACTGAT ACTGCTGGGTATAATGCAATGGAAGAAAGTGTGAGCAGGGA GAAGCCAGAATTGACAGCTTCAACAGAAAGGGTCAACA | 949 |
| | TGTTGACCCTTTCTGTTGAAGCTGTCAATTCTGGCTTCTCCT GCTCACACTTTCTTCCATTGCATTATACCCAGCAGTATCAGTA GTATGAGCAGCAGCTGGACTCTGGGCAGATTCTGC | 950 |
| | ATAATGCAATGGAAGAA | 951 |
| | TTCTTCCATTGCATTAT | 952 |
| Breast Cancer Pro-1637-Leu CCA to CTA | CTCATACTACTGATACTGCTGGGTATAATGCAATGGAAGAAA GTGTGAGCAGGGAGAAGCCAGAATTGACAGCTTCAACAGAA AGGGTCAACAAAAGAATGTCCATGGTGGTGTCTGGCCT | 953 |
| | AGGCCAGACACCACCATGGACATTCTTTTGTTGACCCTTTCT GTTGAAGCTGTCAATTCTGGCTTCTCCCTGCTCACACTTTCTT CCATTGCATTATACCCAGCAGTATCAGTAGTATGAG | 954 |
| | GGAGAAGCCAGAATTGA | 955 |
| | TCAATTCTGGCTTCTCC | 956 |
| Breast Cancer Met-1652-Ile ATG to ATA | GAGCAGGGAGAAGCCAGAATTGACAGCTTCAACAGAAAGGG TCAACAAAAGAATGTCCATGGTGGTGTCTGGCCTGACCCCAG AAGAATTTGTGAGTGTATCCATATGTATCTCCCTAATG | 957 |
| | CATTAGGGAGATACATATGGATACACTCACAAATTCTTCTGG GGTCAGGCCAGACACCACCATGGACATTCTTTTGTTGACCCT TTCTGTTGAAGCTGTCAATTCTGGCTTCTCCCTGCTC | 958 |
| | ATGTCCATGGTGGTGTC | 959 |
| | GACACCACCATGGACAT | 960 |
| Breast Cancer Glu-1694-Stop GAG to TAG | CACTTCCTGATTTTGTTTTCAACTTCTAATCCTTTGAGTGTTTT TCATTCTGCAGATGCTGAGTTTGTGTGTGAACGGACACTGAA ATATTTTCTAGGAATTGCGGGAGGAAAATGGGTAG | 961 |
| | CTACCCCATTTTCCTCCCGCAATTCCTAGAAAATATTTCAGTGT CCGTTCACACACAAACTCAGCATCTGCAGAATGAAAAACACT CAAAGGATTAGAAGTTGAAAACAAAATCAGGAAGTG | 962 |
| | CAGATGCTGAGTTTGTG | 963 |
| | CACAAACTCAGCATCTG | 964 |
| Breast Cancer Gly-1706-Glu GGA to GAA | GTGTTTTTCATTCTGCAGATGCTGAGTTTGTGTGTGAACGGA CACTGAAATATTTTCTAGGAATTGCGGGAGGAAAATGGGTAG TTAGCTATTTCTGTAAGTATAATACTATTTCTCCCCT | 965 |
| | AGGGGAGAAATAGTATTATACTTACAGAAATAGCTAACTACCC ATTTTCCTCCCGCAATTCCTAGAAAATATTTCAGTGTCCGTTC ACACACAAACTCAGCATCTGCAGAATGAAAAACAC | 966 |
| | TTTTCTAGGAATTGCGG | 967 |
| | CCGCAATTCCTAGAAAA | 968 |
| Breast Cancer Ala-1708-Glu GCG to GAG | TTCATTCTGCAGATGCTGAGTTTGTGTGTGAACGGACACTGA AATATTTTCTAGGAATTGCGGGAGGAAAATGGGTAGTTAGCT ATTTCTGTAAGTATAATACTATTTCTCCCCTCCTCCC | 969 |
| | GGGAGGAGGGGAGAAATAGTATTATACTTACAGAAATAGCTA ACTACCCATTTTCCTCCCGCAATTCCTAGAAAATATTTCAGTG TCCGTTCACACACAAACTCAGCATCTGCAGAATGAA | 970 |
| | AGGAATTGCGGGAGGAA | 971 |
| | TTCCTCCCGCAATTCCT | 972 |
| Breast Cancer Val-1713-Ala GTA to GCA | CTGAGTTTGTGTGTGAACGGACACTGAAATATTTTCTAGGAAT TGCGGGAGGAAAATGGGTAGTTAGCTATTTCTGTAAGTATAA TACTATTTCTCCCCTCCTCCCTTTAACACCTCAGAA | 973 |
| | TTCTGAGGTGTTAAAGGGAGGAGGGGAGAAATAGTATTATAC TTACAGAAATAGCTAACTACCCATTTTCCTCCCGCAATTCCTA GAAAATATTTCAGTGTCCGTTCACACACAAACTCAG | 974 |
| | AAAATGGGTAGTTAGCT | 975 |
| | AGCTAACTACCCATTTT | 976 |
| Breast Cancer Trp-1718-Stop TGG to TAG | AACGGACACTGAAATATTTTCTAGGAATTGCGGGAGGAAAAT GGGTAGTTAGCTATTTCTGTAAGTATAATACTATTTCTCCCCT CCTCCCTTTAACACCTCAGAATTGCATTTTTACACC | 977 |
| | GGTGTAAAAATGCAATTCTGAGGTGTTAAAGGGAGGAGGG AGAAATAGTATTATACTTACAGAAATAGCTAACTACCCATTTTC CTCCCGCAATTCCTAGAAAATATTTCAGTGTCCGTT | 978 |
| | CTATTTCTGTAAGTATA | 979 |
| | TATACTTACAGAAATAG | 980 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Glu-1725-Stop GAA to TAA | TTCTGCTGTATGTAACCTGTCTTTTCTATGATCTCTTTAGGGG TGACCCAGTCTATTAAAGAAAGAAAAATGCTGAATGAGGTAA GTACTTGATGTTACAAACTAACCAGAGATATTCATT | 981 |
| | AATGAATATCTCTGGTTAGTTTGTAACATCAAGTACTTACCTC ATTCAGCATTTTTCTTTCTTTAATAGACTGGGTCACCCCTAAA GAGATCATAGAAAAGACAGGTTACATACAGCAGAA | 982 |
| | CTATTAAAGAAAGAAAA | 983 |
| | TTTTCTTTCTTTAATAG | 984 |
| Breast Cancer Lys-1727-Stop AAA to TAA | TGTATGTAACCTGTCTTTTCTATGATCTCTTTAGGGGTGACCC AGTCTATTAAAGAAAGAAAAATGCTGAATGAGGTAAGTACTTG ATGTTACAAACTAACCAGAGATATTCATTCAGTCA | 985 |
| | TGACTGAATGAATATCTCTGGTTAGTTTGTAACATCAAGTACT TACCTCATTCAGCATTTTTCTTTCTTTAATAGACTGGGTCACC CCTAAAGAGATCATAGAAAAGACAGGTTACATACA | 986 |
| | AAGAAAGAAAAATGCTG | 987 |
| | CAGCATTTTTCTTTCTT | 988 |
| Breast Cancer Pro-1749-Arg CCA to CGA | TCTTTCAGCATGATTTTGAAGTCAGAGGAGATGTGGTCAATG GAAGAAACCACCAAGGTCCAAAGCGAGCAAGAGAATCCCAG GACAGAAAGGTAAAGCTCCCTCCCTCAAGTTGACAAAA | 989 |
| | TTTTGTCAACTTGAGGGAGGGAGCTTTACCTTTCTGTCCTGG GATTCTCTTGCTCGCTTTGGACCTTGGTGGTTTCTTCCATTGA CCACATCTCCTCTGACTTCAAAATCATGCTGAAAGA | 990 |
| | CCAAGGTCCAAAGCGAG | 991 |
| | CTCGCTTTGGACCTTGG | 992 |
| Breast Cancer Arg-1751-Stop CGA to TGA | CAGCATGATTTTGAAGTCAGAGGAGATGTGGTCAATGGAAGA AACCACCAAGGTCCAAAGCGAGCAAGAGAATCCCAGGACAG AAAGGTAAAGCTCCCTCCCTCAAGTTGACAAAAATCTC | 993 |
| | GAGATTTTTGTCAACTTGAGGGAGGGAGCTTTACCTTTCTGT CCTGGGATTCTCTTGCTCGCTTTGGACCTTGGTGGTTTCTTC CATTGACCACATCTCCTCTGACTTCAAAATCATGCTG | 994 |
| | GTCCAAAGCGAGCAAGA | 995 |
| | TCTTGCTCGCTTTGGAC | 996 |
| Breast Cancer Gln-1756-Stop CAG to TAG | GTCAGAGGAGATGTGGTCAATGGAAGAAACCACCAAGGTCC AAAGCGAGCAAGAGAATCCCAGGACAGAAAGGTAAAGCTCC CTCCCTCAAGTTGACAAAAATCTCACCCCACCACTCTGT | 997 |
| | ACAGAGTGGTGGGGTGAGATTTTTGTCAACTTGAGGGAGGG AGCTTTACCTTTCTGTCCTGGGATTCTCTTGCTCGCTTTGGA CCTTGGTGTTTCTTCCATTGACCACATCTCCTCTGAC | 998 |
| | GAGAATCCCAGGACAGA | 999 |
| | TCTGTCCTGGGATTCTC | 1000 |
| Breast Cancer Met-1775-Arg ATG to AGG | CTCTCTTCTTCCAGATCTTCAGGGGGCTAGAAATCTGTTGCT ATGGGCCCTTCACCAACATGCCCACAGGTAAGAGCCTGGGA GAACCCCAGAGTTCCAGCACCAGCCTTTGTCTTACATA | 1001 |
| | TATGTAAGACAAAGGCTGGTGCTGGAACTCTGGGGTTCTCCC AGGCTCTTACCTGTGGGCATGTTGGTGAAGGGCCCATAGCA ACAGATTTCTAGCCCCCTGAAGATCTGGAAGAAGAGAG | 1002 |
| | CACCAACATGCCCACAG | 1003 |
| | CTGTGGGCATGTTGGTG | 1004 |
| Breast Cancer Trp-1782-Stop TGG to TGA | AGTATGCAGATTACTGCAGTGATTTTACATCTAAATGTCCATT TTAGATCAACTGGAATGGATGGTACAGCTGTGTGGTGCTTCT GTGGTGAAGGAGCTTTCATCATTCACCCTTGGCACA | 1005 |
| | TGTGCCAAGGGTGAATGATGAAAGCTCCTTCACCACAGAAGC ACCACACAGCTGTACCATCCATTCCAGTTGATCTAAAATGGA CATTTAGATGTAAAATCACTGCAGTAATCTGCATACT | 1006 |
| | CTGGAATGGATGGTACA | 1007 |
| | TGTACCATCCATTCCAG | 1008 |
| Breast Cancer Gln-1785-His CAG to CAT | ATTACTGCAGTGATTTTACATCTAAATGTCCATTTTAGATCAAC TGGAATGGATGGTACAGCTGTGTGGTGCTTCTGTGGTGAAG GAGCTTTCATCATTCACCCTTGGCACAGTAAGTATT | 1009 |
| | AATACTTACTGTGCCAAGGGTGAATGATGAAAGCTCCTTCAC CACAGAAGCACCACACAGCTGTACCATCCATTCCAGTTGATC TAAAATGGACATTTAGATGTAAAATCACTGCAGTAAT | 1010 |
| | ATGGTACAGCTGTGTGG | 1011 |
| | CCACACAGCTGTACCAT | 1012 |
| Breast Cancer Glu-1794-Asp GAG to GAT | GTCCATTTTAGATCAACTGGAATGGATGGTACAGCTGTGTGG TGCTTCTGTGGTGAAGGAGCTTTCATCATTCACCCTTGGCAC AGTAAGTATTGGGTGCCCTGTCAGAGAGGGAGGACAC | 1013 |
| | GTGTCCTCCCTCTCTGACAGGGCACCCAATACTTACTGTGCC AAGGGTGAATGATGAAAGCTCCTTCACCACAGAAGCACCACA CAGCTGTACCATCCATTCCAGTTGATCTAAAATGGAC | 1014 |
| | GTGAAGGAGCTTTCATC | 1015 |
| | GATGAAAGCTCCTTCAC | 1016 |

TABLE 14-continued

BRCA1 Mutations and Genome-Correcting Oligos

| Clinical Phenotype & Mutation | Correcting Oligos | SEQ ID NO: |
|---|---|---|
| Breast Cancer Arg-1835-Stop CGA to TGA | CTCTGCTTGTGTTCTCTGTCTCCAGCAATTGGGCAGATGTGT GAGGCACCTGTGGTGACCCGAGAGTGGGTGTTGGACAGTGT AGCACTCTACCAGTGCCAGGAGCTGGACACCTACCTGA | 1017 |
|  | TCAGGTAGGTGTCCAGCTCCTGGCACTGGTAGAGTGCTACA CTGTCCAACACCCACTCTCGGGTCACCACAGGTGCCTCACA CATCTGCCCAATTGCTGGAGACAGAGAACACAAGCAGAG | 1018 |
|  | TGGTGACCCGAGAGTGG | 1019 |
|  | CCACTCTCGGGTCACCA | 1020 |
| Breast Cancer Trp-1837-Arg TGG to CGG | TTGTGTTCTCTGTCTCCAGCAATTGGGCAGATGTGTGAGGCA CCTGTGGTGACCCGAGAGTGGGTGTTGGACAGTGTAGCACT CTACCAGTGCCAGGAGCTGGACACCTACCTGATACCCC | 1021 |
|  | GGGGTATCAGGTAGGTGTCCAGCTCCTGGCACTGGTAGAGT GCTACACTGTCCAACACCCACTCTCGGGTCACCACAGGTGC CTCACACATCTGCCCAATTGCTGGAGACAGAGAACACAA | 1022 |
|  | CCCGAGAGTGGGTGTTG | 1023 |
|  | CAACACCCACTCTCGGG | 1024 |
| Breast Cancer Trp-1837-Stop TGG to TAG | TGTGTTCTCTGTCTCCAGCAATTGGGCAGATGTGTGAGGCAC CTGTGGTGACCCGAGAGTGGGTGTTGGACAGTGTAGCACTC TACCAGTGCCAGGAGCTGGACACCTACCTGATACCCCA | 1025 |
|  | TGGGGTATCAGGTAGGTGTCCAGCTCCTGGCACTGGTAGAG TGCTACACTGTCCAACACCCACTCTCGGGTCACCACAGGTG CCTCACACATCTGCCCAATTGCTGGAGACAGAGAACACA | 1026 |
|  | CCGAGAGTGGGTGTTGG | 1027 |
|  | CCAACACCCACTCTCGG | 1028 |

TABLE 15

BRCA2 Mutations and Genome-Correcting Oligos

| Clinical Phenotype & Mutation | Correcting Oligos | SEQ ID NO: |
|---|---|---|
| Breast cancer PHE32LEU TTT to CTT | GTTAAAACTAAGGTGGGATTTTTTTTTTAAATAGATTTAGGAC CAATAAGTCTTAATTGGTTTGAAGAACTTTCTTCAGAAGCTCC ACCCTATAATTCTGAACCTGCAGAAGAATCTGAAC | 1029 |
|  | GTTCAGATTCTTCTGCAGGTTCAGAATTATAGGGTGGAGCTT CTGAAGAAAGTTCTTCAAACCAATTAAGACTTATTGGTCCTAA ATCTATTTAAAAAAAAAATCCCACCTTAGTTTTAAC | 1030 |
|  | TTAATTGGTTTGAAGAA | 1031 |
|  | TTCTTCAAACCAATTAA | 1032 |
| Breast cancer TYR42CYS TAT to TGT | TAGATTTAGGACCAATAAGTCTTAATTGGTTTGAAGAACTTTC TTCAGAAGCTCCACCCTATAATTCTGAACCTGCAGAAGAATC TGAACATAAAAACAACAATTACGAACCAAACCTATT | 1033 |
|  | AATAGGTTTGGTTCGTAATTGTTGTTTTTATGTTCAGATTCTTC TGCAGGTTCAGAATTATAGGGTGGAGCTTCTGAAGAAAGTTC TTCAAACCAATTAAGACTTATTGGTCCTAAATCTA | 1034 |
|  | TCCACCCTATAATTCTG | 1035 |
|  | CAGAATTATAGGGTGGA | 1036 |
| Breast cancer LYS53ARG AAA to AGA | AAGAACTTTCTTCAGAAGCTCCACCCTATAATTCTGAACCTGC AGAAGAATCTGAACATAAAAACAACAATTACGAACCAAACCTA TTTAAAACTCCACAAAGGAAACCATCTTATAATCA | 1037 |
|  | TGATTATAAGATGGTTTCCTTTGTGGAGTTTTAAATAGGTTTG GTTCGTAATTGTTGTTTTTATGTTCAGATTCTTCTGCAGGTTC AGAATTATAGGGTGGAGCTTCTGAAGAAAGTTCTT | 1038 |
|  | TGAACATAAAAACAACA | 1039 |
|  | TGTTGTTTTTATGTTCA | 1040 |
| Breast cancer Phe81Leu TTC to CTC | CTATTTAAAACTCCACAAAGGAAACCATCTTATAATCAGCTGG CTTCAACTCCAATAATATTCAAAGAGCAAGGGCTGACTCTGC CGCTGTACCAATCTCCTGTAAAAGAATTAGATAAAT | 1041 |
|  | ATTTATCTAATTCTTTTACAGGAGATTGGTACAGCGGCAGAGT CAGCCCTTGCTCTTTGAATATTATTGGAGTTGAAGCCAGCTG ATTATAAGATGGTTTCCTTTGTGGAGTTTTAAATAG | 1042 |
|  | CAATAATATTCAAAGAG | 1043 |
|  | CTCTTTGAATATTATTG | 1044 |
| Breast cancer TRP194TERM TGG to TAG | GTCAGACACCAAAACATATTTCTGAAAGTCTAGGAGCTGAGG TGGATCCTGATATGTCTTGGTCAAGTTCTTTAGCTACACCACC CACCCTTAGTTCTACTGTGCTCATAGGTAATAATAG | 1045 |
|  | CTATTATTACCTATGAGCACAGTAGAACTAAGGGTGGGTGGT GTAGCTAAAGAACTTGACCAAGACATATCAGGATCCACCTCA GCTCCTAGACTTTCAGAAATATGTTTTGGTGTCTGAC | 1046 |

TABLE 15-continued

BRCA2 Mutations and Genome-Correcting Oligos

| Clinical Phenotype & Mutation | Correcting Oligos | SEQ ID NO: |
|---|---|---|
| | TATGTCTTGGTCAAGTT | 1047 |
| | AACTTGACCAAGACATA | 1048 |
| Breast cancer PRO201ARG CCA to CGA | CTGAAAGTCTAGGAGCTGAGGTGGATCCTGATATGTCTTGGT CAAGTTCTTTAGCTACACCACCCACCCTTAGTTCTACTGTGCT CATAGGTAATAATAGCAAATGTGTATTTACAAGAAA | 1049 |
| | TTTCTTGTAAATACACATTTGCTATTATTACCTATGAGCACAGT AGAACTAAGGGTGGGTGGTGTAGCTAAAGAACTTGACCAAGA CATATCAGGATCCACCTCAGCTCCTAGACTTTCAG | 1050 |
| | AGCTACACCACCCACCC | 1051 |
| | GGGTGGGTGGTGTAGCT | 1052 |
| Breast cancer Pro222Ser CCT to TCT | ACAATACACATAAATTTTTATCTTACAGTCAGAAATGAAGAAG CATCTGAAACTGTATTTCCTCATGATACTACTGCTGTAAGTAA ATATGACATTGATTAGACTGTTGAAATTGCTAACA | 1053 |
| | TGTTAGCAATTTCAACAGTCTAATCAATGTCATATTTACTTACA GCAGTAGTATCATGAGGAAATACAGTTTCAGATGCTTCTTCAT TTCTGACTGTAAGATAAAAATTTATGTGTATTGT | 1054 |
| | CTGTATTTCCTCATGAT | 1055 |
| | ATCATGAGGAAATACAG | 1056 |
| Breast cancer Leu-414-Term TTG to TAG | AATGGTCTCAACTAACCCTTTCAGGTCTAAATGGAGCCCAGA TGGAGAAAATACCCCTATTGCATATTTCTTCATGTGACCAAAA TATTTCAGAAAAAGACCTATTAGACACAGAGAACAA | 1057 |
| | TTGTTCTCTGTGTCTAATAGGTCTTTTTCTGAAATATTTTGGTC ACATGAAGAAATATGCAATAGGGGTATTTTCTCCATCTGGGC TCCATTTAGACCTGAAAGGGTTAGTTGAGACCATT | 1058 |
| | ACCCCTATTGCATATTT | 1059 |
| | AAATATGCAATAGGGGT | 1060 |
| Breast cancer, male Cys554Trp TGT to TGG | AGCCTCTGAAAGTGGACTGGAAATACATACTGTTTGCTCACA GAAGGAGGACTCCTTATGTCCAAATTTAATTGATAATGGAAG CTGGCCAGCCACCACCACACAGAATTCTGTAGCTTTG | 1061 |
| | CAAAGCTACAGAATTCTGTGTGGTGGTGGCTGGCCAGCTTC CATTATCAATTAAATTTGGACATAAGGAGTCCTCCTTCTGTGA GCAAACAGTATGTATTTCCAGTCCACTTTCAGAGGCT | 1062 |
| | TCCTTATGTCCAAATTT | 1063 |
| | AAATTTGGACATAAGGA | 1064 |
| Breast cancer Lys944Term AAA to TAA | AACTCTACCATGGTTTTATATGGAGACACAGGTGATAAACAA GCAACCCAAGTGTCAATTAAAAAAAGATTTGGTTTATGTTCTTG CAGAGGAGAACAAAAATAGTGTAAAGCAGCATATAA | 1065 |
| | TTATATGCTGCTTTACACTATTTTTGTTCTCCTCTGCAAGAAC ATAAACCAAATCTTTTTTAATTGACACTTGGGTTGCTTGTTTAT CACCTGTGTCTCCATATAAAACCATGGTAGAGTT | 1066 |
| | TGTCAATTAAAAAAGAT | 1067 |
| | ATCTTTTTTAATTGACA | 1068 |
| Breast cancer, male Glu1320Term GAA to TAA | ATGACTACTGGCACTTTTGTTGAAGAAATTACTGAAAATTACA AGAGAAATACTGAAAATGAAGATAACAAATATACTGCTGCCAG TAGAAATTCTCATAACTTAGAATTTGATGGCAGTG | 1069 |
| | CACTGCCATCAAATTCTAAGTTATGAGAATTTCTACTGGCAGC AGTATATTTGTTATCTTCATTTTCAGTATTTCTCTTGTAATTTTC AGTAATTTCTTCAACAAAAGTGCCAGTAGTCAT | 1070 |
| | CTGAAAATGAAGATAAC | 1071 |
| | GTTATCTTCATTTTCAG | 1072 |
| Breast cancer Glu1876Term GAA to TAA | CATGAAACAATTAAAAAAGTGAAAGACATATTTACAGACAGTT TCAGTAAAGTAATTAAGGAAAACAACGAGAATAAATCAAAAAT TTGCCAAACGAAAATTATGGCAGGTTGTTACGAGG | 1073 |
| | CCTCGTAACAACCTGCCATAATTTTCGTTTGGCAAATTTTTGA TTTATTCTCGTTGTTTTCCTTAATTACTTTACTGAAACTGTCTG TAAATATGTCTTTCACTTTTTTAATTGTTTCATG | 1074 |
| | TAATTAAGGAAAACAAC | 1075 |
| | GTTGTTTTCCTTAATTA | 1076 |
| Breast cancer Ser1882Term TCA to TAA | TGAAAGACATATTTACAGACAGTTTCAGTAAAGTAATTAAGGA AAACAACGAGAATAAATCAAAAATTTGCCAAACGAAAATTATG GCAGGTTGTTACGAGGCATTGGATGATTCAGAGGA | 1077 |
| | TCCTCTGAATCATCCAATGCCTCGTAACAACCTGCCATAATTT TCGTTTGGCAAATTTTTGATTTATTCTCGTTGTTTTCCTTAATT ACTTTACTGAAACTGTCTGTAAATATGTCTTTCA | 1078 |
| | GAATAAATCAAAAATTT | 1079 |
| | AAATTTTTGATTTATTC | 1080 |
| Breast cancer Glu1953Term GAA to TAA | AACCAAAATATGTCTGGATTGGAGAAAGTTTCTAAAATATCAC CTTGTGATGTTAGTTTGGAAACTTCAGATATATGTAAATGTAG TATAGGGAAGCTTCATAAGTCAGTCTCATCTGCAA | 1081 |
| | TTGCAGATGAGACTGACTTATGAAGCTTCCCTATACTACATTT ACATATATCTGAAGTTTCCAAACTAACATCACAAGGTGATATT TTAGAAACTTTCTCCAATCCAGACATATTTTGGTT | 1082 |
| | TTAGTTTGGAAACTTCA | 1083 |
| | TGAAGTTTCCAAACTAA | 1084 |

TABLE 15-continued

BRCA2 Mutations and Genome-Correcting Oligos

| Clinical Phenotype & Mutation | Correcting Oligos | SEQ ID NO: |
|---|---|---|
| Breast cancer Ser1970Term TCA to TAA | TTAGTTTGGAAACTTCAGATATATGTAAATGTAGTATAGGGAA GCTTCATAAGTCAGTCTCATCTGCAAATACTTGTGGGATTTTT AGCACAGCAAGTGGAAAATCTGTCCAGGTATCAGA | 1085 |
| | TCTGATACCTGGACAGATTTTCCACTTGCTGTGCTAAAAATCC CACAAGTATTTGCAGATGAGACTGACTTATGAAGCTTCCCTAT ACTACATTTACATATATCTGAAGTTTCCAAACTAA | 1086 |
| | GTCAGTCTCATCTGCAA | 1087 |
| | TTGCAGATGAGACTGAC | 1088 |
| Breast cancer Gln1987Term CAG to TAG | AAGTCAGTCTCATCTGCAAATACTTGTGGGATTTTTAGCACAG CAAGTGGAAAATCTGTCCAGGTATCAGATGCTTCATTACAAAA CGCAAGACAAGTGTTTTCTGAAATAGAAGATAGTA | 1089 |
| | TACTATCTTCTATTTCAGAAAACACTTGTCTTGCGTTTTGTAAT GAAGCATCTGATACCTGGACAGATTTTCCACTTGCTGTGCTA AAAATCCCACAAGTATTTGCAGATGAGACTGACTT | 1090 |
| | AATCTGTCCAGGTATCA | 1091 |
| | TGATACCTGGACAGATT | 1092 |
| Breast cancer Ala2466Val GCA to GTA | AAAATAAGATTAATGACAATGAGATTCATCAGTTTAACAAAAA CAACTCCAATCAAGCAGCAGCTGTAACTTTCACAAAGTGTGA AGAAGAACCTTTAGGTATTGTATGACAATTTGTGTG | 1093 |
| | CACACAAATTGTCATACAATACCTAAAGGTTCTTCTTCACACT TTGTGAAAGTTACAGCTGCTGCTTGATTGGAGTTGTTTTTGTT AAACTGATGAATCTCATTGTCATTAATCTTATTTT | 1094 |
| | TCAAGCAGCAGCTGTAA | 1095 |
| | TTACAGCTGCTGCTTGA | 1096 |
| Breast cancer Arg2520Term CGA to TGA | AGGCAACGCGTCTTTCCACAGCCAGGCAGTCTGTATCTTGCA AAAACATCCACTCTGCCTCGAATCTCTCTGAAAGCAGCAGTA GGAGGCCAAGTCCCCTCTGCGTGTCCTCATAAACAGG | 1097 |
| | CCTGTTTATGAGGACACGCAGAGGGGACTTGGCCTCCTACT GCTGCTTTCAGAGAGATTCGAGGCAGAGTGGATGTTTTTGCA AGATACAGACTGCCTGGCTGTGGAAAGACGCGTTGCCT | 1098 |
| | CTCTGCCTCGAATCTCT | 1099 |
| | AGAGATTCGAGGCAGAG | 1100 |
| Breast cancer Gln2714Term CAA to TAA | ATTTCATTGAGCGCAAATATATCTGAAACTTCTAGCAATAAAA CTAGTAGTGCAGATACCCAAAAAGTGGCCATTATTGAACTTA CAGATGGGTGGTATGCTGTTAAGGCCCAGTTAGATC | 1101 |
| | GATCTAACTGGGCCTTAACAGCATACCACCCATCTGTAAGTT CAATAATGGCCACTTTTTGGGTATCTGCACTACTAGTTTTATT GCTAGAAGTTTCAGATATATTTGCGCTCAATGAAAT | 1102 |
| | CAGATACCCAAAAAGTG | 1103 |
| | CACTTTTTGGGTATCTG | 1104 |
| Breast cancer Leu2776Term TTA to TGA | CAGAACTGGTGGGCTCTCCTGATGCCTGTACACCTCTTGAAG CCCCAGAATCTCTTATGTTAAAGGTAAATTAATTTGCACTCTT GGTAAAAATCAGTCATTGATTCAGTTAAATTCTAGA | 1105 |
| | TCTAGAATTTAACTGAATCAATGACTGATTTTTACCAAGAGTG CAAATTAATTTACCTTTAACATAAGAGATTCTGGGGCTTCAAG AGGTGTACAGGCATCAGGAGAGCCCACCAGTTCTG | 1106 |
| | TCTTATGTTAAAGATTT | 1107 |
| | AAATCTTTAACATAAGA | 1108 |
| Breast cancer Gln2893Term CAG to TAG | CCTTTTGTTTTCTTAGAAAAACACAACAAAACCATATTTACCATC ACGTGCACTAACAAGACAGCAAGTTCGTGCTTTGCAAGATGG TGCAGAGCTTTATGAAGCAGTGAAGAATGCAGCAG | 1109 |
| | CTGCTGCATTCTTCACTGCTTCATAAAGCTCTGCACCATCTTG CAAAGCACGAACTTGCTGTCTTGTTAGTGCACGTGATGGTAA ATATGGTTTTGTTGTGTTTTCTAAGAAAACAAAAGG | 1110 |
| | TAACAAGACAGCAAGTT | 1111 |
| | AACTTGCTGTCTTGTTA | 1112 |
| Breast cancer Ala2951Thr GCC to ACC | AATCACAGGCAAATGTTGAATGATAAGAAACAAGCTCAGATC CAGTTGGAAATTAGGAAGGCCATGGAATCTGCTGAACAAAAG GAACAAGGTTTATCAAGGGATGTCACAACCGTGTGGA | 1113 |
| | TCCACACGGTTGTGACATCCCTTGATAAACCTTGTTCCTTTTG TTCAGCAGATTCCATGGCCTTCCTAATTTCCAACTGGATCTGA GCTTGTTTCTTATCATTCAACATTTGCCTGTGATT | 1114 |
| | TTAGGAAGGCCATGGAA | 1115 |
| | TTCCATGGCCTTCCTAA | 1116 |
| Breast cancer Met3118Thr ATG to ACG | ACAATTTACTGGCAATAAAGTTTTGGATAGACCTTAATGAGGA CATTATTAAGCCTCATATGTTAATTGCTGCAAGCAACCTCCAG TGGCGACCAGAATCCAAATCAGGCCTTCTTACTTT | 1117 |
| | AAAGTAAGAAGGCCTGATTTGGATTCTGGTCGCCACTGGAG GTTGCTTGCAGCAATTAACATATGAGGCTTAATAATGTCCTCA TTAAGGTCTATCCAAAACTTTATTGCCAGTAAATTGT | 1118 |
| | GCCTCATATGTTAATTG | 1119 |
| | CAATTAACATATGAGGC | 1120 |

TABLE 15-continued

BRCA2 Mutations and Genome-Correcting Oligos

| Clinical Phenotype & Mutation | Correcting Oligos | SEQ ID NO: |
|---|---|---|
| Breast cancer Thr3401Met ACG to ATG | GACTGAAACGACGTTGTACTACATCTCTGATCAAAGAACAGG AGAGTTCCCAGGCCAGTACGGAAGAATGTGAGAAAAATAAGC AGGACACAATTACAACTAAAAAATATATCTAAGCATT | 1121 |
| | AATGCTTAGATATATTTTTTAGTTGTAATTGTGTCCTGCTTATT TTTCTCACATTCTTCCGTACTGGCCTGGGAACTCTCCTGTTCT TTGATCAGAGATGTAGTACAACGTCGTTTCAGTC | 1122 |
| | GGCCAGTACGGAAGAAT | 1123 |
| | ATTCTTCCGTACTGGCC | 1124 |
| Breast cancer Ile3412Val ATT to GTT | AAAGAACAGGAGAGTTCCCAGGCCAGTACGGAAGAATGTGA GAAAAATAAGCAGGACACAATTACAACTAAAAAATATATCTAA GCATTTGCAAAGGCGACAATAAATTATTGACGCTTAA | 1125 |
| | TTAAGCGTCAATAATTTATTGTCGCCTTTGCAAATGCTTAGAT ATATTTTTTAGTTGTAATTGTGTCCTGCTTATTTTTCTCACATT CTTCCGTACTGGCCTGGGAACTCTCCTGTTCTTT | 1126 |
| | AGGACACAATTACAACT | 1127 |
| | AGTTGTAATTGTGTCCT | 1128 |

EXAMPLE 9

Cystic Fibrosis—CFTR

Cystic fibrosis is a lethal disease affecting approximately one in 2,500 live Caucasian births and is the most common autosomal recessive disease in Caucasians. Patients with this disease have reduced chloride ion permeability in the secretory and absorptive cells of organs with epithelial cell linings, including the airways, pancreas, intestine, sweat glands and male genital tract. This, in turn, reduces the transport of water across the epithelia. The lungs and the GI tract are the predominant organ systems affected in this disease and the pathology is characterized by blocking of the respiratory and GI tracts with viscous mucus. The chloride impermeability in affected tissues is due to mutations in a specific chloride channel, the cystic fibrosis transmembrane conductance regulator protein (CFTR), which prevents normal passage of chloride ions through the cell membrane (Welsh et al., Neuron, 8:821–829 (1992)). Damage to the lungs due to mucus blockage, frequent bacterial infections and inflammation is the primary cause of morbidity and mortality in CF patients and, although maintenance therapy has improved the quality of patients' lives, the median age at death is still only around 30 years. There is no effective treatment for the disease, and therapeutic research is focused on gene therapy using exogenous transgenes in viral vectors and/or activating the defective or other chloride channels in the cell membrane to normalize chloride permeability (Tizzano et al., J. Pediat., 120:337–349 (1992)). However, the death of a teenage patent treated with an adenovirus vector carrying an exogenous CFTR gene in clinical trials in the late 1990's has impacted this area of research.

The oligonucleotides of the invention for correction of the CFTR gene are attached as a table.

TABLE 16

CFTR Mutations and Genome-Correcting Oligos

| Clinical Phenotype & Mutation | Correcting Oligos | SEQ ID NO: |
|---|---|---|
| Cystic fibrosis Ala46Asp GCT to GAT | AAGGATACAGACAGCGCCTGGAATTGTCAGACATATACCAAA TCCCTTCTGTTGATTCTGCTGACAATCTATCTGAAAAATTGGA AAGGTATGTTCATGTACATTGTTTAGTTGAAGAGAG | 1129 |
| | CTCTCTTCAACTAAACAATGTACATGAACATACCTTTCCAATTT TTCAGATAGATTGTCAGCAGAATCAACAGAAGGGATTTGGTA TATGTCTGACAATTCCAGGCGCTGTCTGTATCCTT | 1130 |
| | TGATTCTGCTGACAATC | 1131 |
| | GATTGTCAGCAGAATCA | 1132 |
| Cystic fibrosis Ser50Tyr TCT to TAT | AGCGCCTGGAATTGTCAGACATATACCAAATCCCTTCTGTTG ATTCTGCTGACAATCTATCTGAAAAATAGGAAAGGTATGTTCA TGTACATTGTTTAGTTGAAGAGAGAAATTCATATTA | 1133 |
| | TAATATGAATTTCTCTCTTCAACTAAACAATGTACATGAACATA CCTTTCCAATTTTTCAGATAGATTGTCAGCAGAATCAACAGAA GGGATTTGGTATATGTCTGACAATTCCAGGCGCT | 1134 |
| | CAATCTATCTGAAAAT | 1135 |
| | ATTTTTCAGATAGATTG | 1136 |
| Congenital absence of vas deferens Glu56Lys GAA-AAA | AGGACAACTAAAATATTTGCACATGCAACTTATTGGTCCCACT TTTTATTCTTTTGCAGAGAATGGGATAGAGAGCTGGCTTCAAA GAAAAATCCTAAACTCATTAATGCCCTTCGGCGAT | 1137 |
| | ATCGCCGAAGGGCATTAATGAGTTTAGGATTTTTCTTTGAAGC CAGCTCTCTATCCCATTCTCTGCAAAAGAATAAAAAGTGGGA CCAATAAGTTGCATGTGCAAATATTTTAGTTGTCCT | 1138 |
| | TTTGCAGAGAATGGGAT | 1139 |
| | ATCCCATTCTCTGCAAA | 1140 |

TABLE 16-continued

CFTR Mutations and Genome-Correcting Oligos

| Clinical Phenotype & Mutation | Correcting Oligos | SEQ ID NO: |
|---|---|---|
| Cystic fibrosis Trp57Gly TGG to GGG | AGGACAACTAAAATATTTGCACATGCAACTTATTGGTCCCACT TTTTATTCTTTTGCAGAGAATGGGATAGAGAGCTGGCTTCAAA GAAAAATCCTAAACTCATTAATGCCCTTCGGCGAT | 1141 |
| | ATCGCCGAAGGGCATTAATGAGTTTAGGATTTTTCTTTGAAGC CAGCTCTCTATCCCATTCTCTGCAAAAGAATAAAAAGTGGGA CCAATAAGTTGCATGTGCAAATATTTTAGTTGTCCT | 1142 |
| | TTTGCAGAGAATGGGAT | 1143 |
| | ATCCCATTCTCTGCAAA | 1144 |
| Cystic fibrosis Trp57Term TGG to TGA | AACTAAAATATTTGCACATGCAACTTATTGGTCCCACTTTTTAT TCTTTTGCAGAGAATGGGATAGAGAGCTGGCTTCAAAGAAAA ATCCTAAACTCATTAATGCCCTTCGGCGATGTTTT | 1145 |
| | AAAACATCGCCGAAGGGCATTAATGAGTTTAGGATTTTTCTTT GAAGCCAGCTCTCTATCCCATTCTCTGCAAAAGAATAAAAAGT GGGACCAATAAGTTGCATGTGCAAATATTTTAGTT | 1146 |
| | AGAGAATGGGATAGAGA | 1147 |
| | TCTCTATCCCATTCTCT | 1148 |
| Congenital absence of vas deferens Asp58Asn GAT to AAT | ACTAAAATATTTGCACATGCAACTTATTGGTCCCACTTTTTATT CTTTTGCAGAGAATGGATAGAGAGCTGGCTTCAAAGAAAAA TCCTAAACTCATTAATGCCCTTCGGCGATGTTTTT | 1149 |
| | AAAAACATCGCCGAAGGGCATTAATGAGTTTAGGATTTTTCTT TGAAGCCAGCTCTCTATCCCATTCTCTGCAAAAGAATAAAAAG TGGGACCAATAAGTTGCATGTGCAAATATTTTAGT | 1150 |
| | GAGAATGGATAGAGAG | 1151 |
| | CTCTCTATCCCATTCTC | 1152 |
| Cystic fibrosis Glu60Term GAG to TAG | ATATTTGCACATGCAACTTATTGGTCCCACTTTTTATTCTTTTG CAGAGAATGGGATAGAGAGCTGGCTTCAAAGAAAAATCCTAA ACTCATTAATGCCCTTCGGCGATGTTTTTTCTGGA | 1153 |
| | TCCAGAAAAAACATCGCCGAAGGGCATTAATGAGTTTAGGAT TTTTCTTTGAAGCCAGCTCTCTATCCCATTCTCTGCAAAAGAA TAAAAAGTGGGACCAATAAGTTGCATGTGCAAATAT | 1154 |
| | GGGATAGAGAGCTGGCT | 1155 |
| | AGCCAGCTCTCTATCCC | 1156 |
| Cystic fibrosis Pro67Leu CCT to CTT | GGTCCCACTTTTTATTCTTTTGCAGAGAATGGGATAGAGAGC TGGCTTCAAAGAAAAATCCTAAACTCATTAATGCCCTTCGGC GATGTTTTTTCTGGAGATTTATGTTCTATGGAATCTT | 1157 |
| | AAGATTCCATAGAACATAAATCTCCAGAAAAAACATCGCCGAA GGGCATTAATGAGTTTAGGATTTTTCTTTGAAGCCAGCTCTCT ATCCCATTCTCTGCAAAAGAATAAAAAGTGGGACC | 1158 |
| | GAAAAATCCTAAACTCA | 1159 |
| | TGAGTTTAGGATTTTTC | 1160 |
| Cystic fibrosis Arg74Trp CGG to TGG | TGCAGAGAATGGGATAGAGAGCTGGCTTCAAAGAAAAATCCT AAACTCATTAATGCCCTTCGGCGATGTTTTTTCTGGAGATTTA TGTTCTATGGAATCTTTTTATATTTAGGGGTAAGGA | 1161 |
| | TCCTTACCCCTAAATATAAAAAGATTCCATAGAACATAAATCT CCAGAAAAAACATCGCCGAAGGGCATTAATGAGTTTAGGATT TTTCTTTGAAGCCAGCTCTCTATCCCATTCTCTGCA | 1162 |
| | ATGCCCTTCGGCGATGT | 1163 |
| | ACATCGCCGAAGGGCAT | 1164 |
| Congenital absence of vas deferens ARG75GLN CGA to CAA | GAGAATGGGATAGAGAGCTGGCTTCAAAGAAAAATCCTAAAC TCATTAATGCCCTTCGGCGATGTTTTTTCTGGAGATTTATGTT CTATGGAATCTTTTTATATTTAGGGGTAAGGATCTC | 1165 |
| | GAGATCCTTACCCCTAAATATAAAAAGATTCCATAGAACATAA ATCTCCAGAAAAAACATCGCCGAAGGGCATTAATGAGTTTAG GATTTTTCTTTGAAGCCAGCTCTCTATCCCATTCTC | 1166 |
| | CCTTCGGCGATGTTTTT | 1167 |
| | AAAAACATCGCCGAAGG | 1168 |
| Cystic fibrosis Arg75Leu CGA to CTA | GAGAATGGGATAGAGAGCTGGCTTCAAAGAAAAATCCTAAAC TCATTAATGCCCTTCGGCGATGTTTTTTCTGGAGATTTATGTT CTATGGAATCTTTTTATATTTAGGGGTAAGGATCTC | 1169 |
| | GAGATCCTTACCCCTAAATATAAAAAGATTCCATAGAACATAA ATCTCCAGAAAAAACATCGCCGAAGGGCATTAATGAGTTTAG GATTTTTCTTTGAAGCCAGCTCTCTATCCCATTCTC | 1170 |
| | CCTTCGGCGATGTTTTT | 1171 |
| | AAAAACATCGCCGAAGG | 1172 |
| Cystic fibrosis Arg75Term CGA to TGA | AGAGAATGGGATAGAGAGCTGGCTTCAAAGAAAAATCCTAAA CTCATTAATGCCCTTCGGCGATGTTTTTTCTGGAGATTTATGT TCTATGGAATCTTTTTATATTTAGGGGTAAGGATCT | 1173 |
| | AGATCCTTACCCCTAAATATAAAAAGATTCCATAGAACATAAA TCTCCAGAAAAAACATCGCCGAAGGGCATTAATGAGTTTAGG ATTTTTCTTTGAAGCCAGCTCTCTATCCCATTCTCT | 1174 |
| | CCCTTCGGCGATGTTTT | 1175 |
| | AAAACATCGCCGAAGGG | 1176 |

TABLE 16-continued

CFTR Mutations and Genome-Correcting Oligos

| Clinical Phenotype & Mutation | Correcting Oligos | SEQ ID NO: |
|---|---|---|
| Cystic fibrosis Gly85Glu GGA to GAA | AAAATCCTAAACTCATTAATGCCCTTCGGCGATGTTTTTTCTG GAGATTTATGTTCTATGGAATCTTTTTATATTTAGGGGTAAGG ATCTCATTTGTACATTCATTATGTATCACATAACT | 1177 |
| | AGTTATGTGATACATAATGAATGTACAAATGAGATCCTTACCC CTAAATATAAAAAGATTCCATAGAACATAAATCTCCAGAAAAA ACATCGCCGAAGGGCATTAATGAGTTTAGGATTTT | 1178 |
| | GTTCTATGGAATCTTTT | 1179 |
| | AAAAGATTCCATAGAAC | 1180 |
| Cystic fibrosis Gly85Val GGA to GTA | AAAATCCTAAACTCATTAATGCCCTTCGGCGATGTTTTTTCTG GAGATTTATGTTCTATGGAATCTTTTTATATTTAGGGGTAAGG ATCTCATTTGTACATTCATTATGTATCACATAACT | 1181 |
| | AGTTATGTGATACATAATGAATGTACAAATGAGATCCTTACCC CTAAATATAAAAAGATTCCATAGAACATAAATCTCCAGAAAAA ACATCGCCGAAGGGCATTAATGAGTTTAGGATTTT | 1182 |
| | GTTCTATGGAATCTTTT | 1183 |
| | AAAAGATTCCATAGAAC | 1184 |
| Cystic fibrosis Leu88Ser TTA to TCA | AACTCATTAATGCCCTTCGGCGATGTTTTTTCTGGAGATTTAT GTTCTATGGAATCTTTTTTATATTTAGGGGTAAGGATCTCATTT GTACATTCATTATGTATCACATAACTATATGCATT | 1185 |
| | AATGCATATAGTTATGTGATACATAATGAATGTACAAATGAGA TCCTTACCCCTAAATATAAAAAGATTCCATAGAACATAAATCT CCAGAAAAAACATCGCCGAAGGGCATTAATGAGTT | 1186 |
| | AATCTTTTTATATTTAG | 1187 |
| | CTAAATATAAAAAGATT | 1188 |
| Cystic fibrosis Phe87Leu TTT to CTT | CCTAAACTCATTAATGCCCTTCGGCGATGTTTTTTCTGGAGAT TTATGTTCTATGGAATCTTTTTATATTTAGGGGTAAGGATCTC ATTTGTACATTCATTATGTATCACATAACTATATG | 1189 |
| | CATATAGTTATGTGATACATAATGAATGTACAAATGAGATCCT TACCCCTAAATATAAAAAGATTCCATAGAACATAAATCTCCAG AAAAAACATCGCCGAAGGGCATTAATGAGTTTAGG | 1190 |
| | ATGGAATCTTTTTATAT | 1191 |
| | ATATAAAAAGATTCCAT | 1192 |
| Cystic fibrosis Leu88Term TTA to TGA | AACTCATTAATGCCCTTCGGCGATGTTTTTTCTGGAGATTTAT GTTCTATGGAATCTTTTTTATATTTAGGGGTAAGGATCTCATTT GTACATTCATTATGTATCACATAACTATATGCATT | 1193 |
| | AATGCATATAGTTATGTGATACATAATGAATGTACAAATGAGA TCCTTACCCCTAAATATAAAAAGATTCCATAGAACATAAATCT CCAGAAAAAACATCGCCGAAGGGCATTAATGAGTT | 1194 |
| | AATCTTTTTATATTTAG | 1195 |
| | CTAAATATAAAAAGATT | 1196 |
| Cystic fibrosis Leu88Term TTA to TAA | AACTCATTAATGCCCTTCGGCGATGTTTTTTCTGGAGATTTAT GTTCTATGGAATCTTTTTTATATTTAGGGGTAAGGATCTCATTT GTACATTCATTATGTATCACATAACTATATGCATT | 1197 |
| | AATGCATATAGTTATGTGATACATAATGAATGTACAAATGAGA TCCTTACCCCTAAATATAAAAAGATTCCATAGAACATAAATCT CCAGAAAAAACATCGCCGAAGGGCATTAATGAGTT | 1198 |
| | AATCTTTTTATATTTAG | 1199 |
| | CTAAATATAAAAAGATT | 1200 |
| Cystic fibrosis Gly91Arg GGG to AGG | AATGCCCTTCGGCGATGTTTTTTCTGGAGATTTATGTTCTATG GAATCTTTTTATATTTAGGGGTAAGGATCTCATTTGTACATTC ATTATGTATCACATAACTATATGCATTTTTGTGAT | 1201 |
| | ATCACAAAAATGCATATAGTTATGTGATACATAATGAATGTAC AAATGAGATCCTTACCCCTAAATATAAAAAGATTCCATAGAAC ATAAATCTCCAGAAAAAACATCGCCGAAGGGCATT | 1202 |
| | TATATTTAGGGGTAAGG | 1203 |
| | CCTTACCCCTAAATATA | 1204 |
| Cystic fibrosis Gln98Arg CAG to CGG | AATAAATGAAATTTAATTTCTCTGTTTTTCCCCTTTTGTAGGAA GTCACCAAAGCAGTACAGCCTCTCTTACTGGGAAGAATCATA GCTTCCTATGACCCGGATAACAAGGAGGAACGCTC | 1205 |
| | GAGCGTTCCTCCTTGTTATCCGGGTCATAGGAAGCTATGATT CTTCCCAGTAAGAGAGGCTGTACTGCTTTGGTGACTTCCTAC AAAAGGGAAAAACAGAGAAATTAAATTTCATTTATT | 1206 |
| | AGCAGTACAGCCTCTCT | 1207 |
| | AGAGAGGCTGTACTGCT | 1208 |
| Cystic fibrosis Gln98Term CAG-TAG | AAATAAATGAAATTTAATTTCTCTGTTTTTCCCCTTTTGTAGGA AGTCACCAAAGCAGTACAGCCTCTCTTACTGGGAAGAATCAT AGCTTCCTATGACCCGGATAACAAGGAGGAACGCT | 1209 |
| | AGCGTTCCTCCTTGTTATCCGGGTCATAGGAAGCTATGATTC TTCCCAGTAAGAGAGGCTGTACTGCTTTGGTGACTTCCTACA AAAGGGAAAAACAGAGAAATTAAATTTCATTTATTT | 1210 |
| | AAGCAGTACAGCCTCTC | 1211 |
| | GAGAGGCTGTACTGCTT | 1212 |

TABLE 16-continued

CFTR Mutations and Genome-Correcting Oligos

| Clinical Phenotype & Mutation | Correcting Oligos | SEQ ID NO: |
|---|---|---|
| Cystic fibrosis Ser108Phe TCC to TTC | CCCTTTTGTAGGAAGTCACCAAAGCAGTACAGCCTCTCTTAC TGGGAAGAATCATAGCTTCCTATGACCCGGATAACAAGGAGG AACGCTCTATCGCGATTTATCTAGGCATAGGCTTATG | 1213 |
| | CATAAGCCTATGCCTAGATAAATCGCGATAGAGCGTTCCTCC TTGTTATCCGGGTCATAGGAAGCTATGATTCTTCCCAGTAAG AGAGGCTGTACTGCTTTGGTGACTTCCTACAAAAGGG | 1214 |
| | CATAGCTTCCTATGACC | 1215 |
| | GGTCATAGGAAGCTATG | 1216 |
| Cystic fibrosis Tyr109Cys TAT to TGT | TTTTGTAGGAAGTCACCAAAGCAGTACAGCCTCTCTTACTGG GAAGAATCATAGCTTCCTATGACCCGGATAACAAGGAGGAAC GCTCTATCGCGATTTATCTAGGCATAGGCTTATGCCT | 1217 |
| | AGGCATAAGCCTATGCCTAGATAAATCGCGATAGAGCGTTCC TCCTTGTTATCCGGGTCATAGGAAGCTATGATTCTTCCCAGT AAGAGAGGCTGTACTGCTTTGGTGACTTCCTACAAAA | 1218 |
| | AGCTTCCTATGACCCGG | 1219 |
| | CCGGGTCATAGGAAGCT | 1220 |
| Cystic fibrosis Asp110His GAC to CAC | TTGTAGGAAGTCACCAAAGCAGTACAGCCTCTCTTACTGGGA AGAATCATAGCTTCCTATGACCCGGATAACAAGGAGGAACGC TCTATCGCGATTTATCTAGGCATAGGCTTATGCCTTC | 1221 |
| | GAAGGCATAAGCCTATGCCTAGATAAATCGCGATAGAGCGTT CCTCCTTGTTATCCGGGTCATAGGAAGCTATGATTCTTCCCA GTAAGAGAGGCTGTACTGCTTTGGTGACTTCCTACAA | 1222 |
| | CTTCCTATGACCCGGAT | 1223 |
| | ATCCGGGTCATAGGAAG | 1224 |
| Congenital absence of vas deferens Pro111Leu CCG to CTG | AGGAAGTCACCAAAGCAGTACAGCCTCTCTTACTGGGAAGAA TCATAGCTTCCTATGACCCGGATAACAAGGAGGAACGCTCTA TCGCGATTTATCTAGGCATAGGCTTATGCCTTCTCTT | 1225 |
| | AAGAGAAGGCATAAGCCTATGCCTAGATAAATCGCGATAGAG CGTTCCTCCTTGTTATCCGGGTCATAGGAAGCTATGATTCTT CCCAGTAAGAGAGGCTGTACTGCTTTGGTGACTTCCT | 1226 |
| | CTATGACCCGGATAACA | 1227 |
| | TGTTATCCGGGTCATAG | 1228 |
| Cystic fibrosis Arg117Cys CGC to TGC | GTACAGCCTCTCTTACTGGGAAGAATCATAGCTTCCTATGAC CCGGATAACAAGGAGGAACGCTCTATCGCGATTTATCTAGGC ATAGGCTTATGCCTTCTCTTTATTGTGAGGACACTGC | 1229 |
| | GCAGTGTCCTCACAATAAAGAGAAGGCATAAGCCTATGCCTA GATAAATCGCGATAGAGCGTTCCTCCTTGTTATCCGGGTCAT AGGAAGCTATGATTCTTCCCAGTAAGAGAGGCTGTAC | 1230 |
| | AGGAGGAACGCTCTATC | 1231 |
| | GATAGAGCGTTCCTCCT | 1232 |
| Cystic fibrosis Arg117His CGC to CAC | TACAGCCTCTCTTACTGGGAAGAATCATAGCTTCCTATGACC CGGATAACAAGGAGGAACGCTCTATCGCGATTTATCTAGGCA TAGGCTTATGCCTTCTCTTTATTGTGAGGACACTGCT | 1233 |
| | AGCAGTGTCCTCACAATAAAGAGAAGGCATAAGCCTATGCCT AGATAAATCGCGATAGAGCGTTCCTCCTTGTTATCCGGGTCA TAGGAAGCTATGATTCTTCCCAGTAAGAGAGGCTGTA | 1234 |
| | GGAGGAACGCTCTATCG | 1235 |
| | CGATAGAGCGTTCCTCC | 1236 |
| Cystic fibrosis Arg117Leu CGC to CTC | TACAGCCTCTCTTACTGGGAAGAATCATAGCTTCCTATGACC CGGATAACAAGGAGGAACGCTCTATCGCGATTTATCTAGGCA TAGGCTTATGCCTTCTCTTTATTGTGAGGACACTGCT | 1237 |
| | AGCAGTGTCCTCACAATAAAGAGAAGGCATAAGCCTATGCCT AGATAAATCGCGATAGAGCGTTCCTCCTTGTTATCCGGGTCA TAGGAAGCTATGATTCTTCCCAGTAAGAGAGGCTGTA | 1238 |
| | GGAGGAACGCTCTATCG | 1239 |
| | CGATAGAGCGTTCCTCC | 1240 |
| Cystic fibrosis Arg117Pro CGC to CCC | TACAGCCTCTCTTACTGGGAAGAATCATAGCTTCCTATGACC CGGATAACAAGGAGGAACGCTCTATCGCGATTTATCTAGGCA TAGGCTTATGCCTTCTCTTTATTGTGAGGACACTGCT | 1241 |
| | AGCAGTGTCCTCACAATAAAGAGAAGGCATAAGCCTATGCCT AGATAAATCGCGATAGAGCGTTCCTCCTTGTTATCCGGGTCA TAGGAAGCTATGATTCTTCCCAGTAAGAGAGGCTGTA | 1242 |
| | GGAGGAACGCTCTATCG | 1243 |
| | CGATAGAGCGTTCCTCC | 1244 |
| Cystic fibrosis Ala120Thr GCG-ACG | CTCTTACTGGGAAGAATCATAGCTTCCTATGACCCGGATAAC AAGGAGGAACGCTCTATCGCGATTTATCTAGGCATAGGCTTA TGCCTTCTCTTTATTGTGAGGACACTGCTCCTACACC | 1245 |
| | GGTGTAGGAGCAGTGTCCTCACAATAAAGAGAAGGCATAAG CCTATGCCTAGATAAATCGCGATAGAGCGTTCCTCCTTGTTA TCCGGGTCATAGGAAGCTATGATTCTTCCCAGTAAGAG | 1246 |
| | GCTCTATCGCGATTTAT | 1247 |
| | ATAAATCGCGATAGAGC | 1248 |

TABLE 16-continued

CFTR Mutations and Genome-Correcting Oligos

| Clinical Phenotype & Mutation | Correcting Oligos | SEQ ID NO: |
|---|---|---|
| Cystic fibrosis Tyr122Term TAT to TAA | GGGAAGAATCATAGCTTCCTATGACCCGGATAACAAGGAGGA ACGCTCTATCGCGATTTATCTAGGCATAGGCTTATGCCTTCT CTTTATTGTGAGGACACTGCTCCTACACCCAGCCATT | 1249 |
| | AATGGCTGGGTGTAGGAGCAGTGTCCTCACAATAAAGAGAA GGCATAAGCCTATGCCTAGATAAATCGCGATAGAGCGTTCCT CCTTGTTATCCGGGTCATAGGAAGCTATGATTCTTCCC | 1250 |
| | GCGATTTATCTAGGCAT | 1251 |
| | ATGCCTAGATAAATCGC | 1252 |
| Cystic fibrosis Gly126Asp GGC-GAC | TAGCTTCCTATGACCCGGATAACAAGGAGGAACGCTCTATCG CGATTTATCTAGGCATAGGCTTATGCCTTCTCTTTATTGTGAG GACACTGCTCCTACACCCAGCCATTTTTGGCCTTCA | 1253 |
| | TGAAGGCCAAAAATGGCTGGGTGTAGGAGCAGTGTCCTCAC AATAAAGAGAAGGCATAAGCCTATGCCTAGATAAATCGCGAT AGAGCGTTCCTCCTTGTTATCCGGGTCATAGGAAGCTA | 1254 |
| | AGGCATAGGCTTATGCC | 1255 |
| | GGCATAAGCCTATGCCT | 1256 |
| Cystic fibrosis His139Arg CAC to CGC | TCGCGATTTATCTAGGCATAGGCTTATGCCTTCTCTTTATTGT GAGGACACTGCTCCTACACCCAGCCATTTTTGGCCTTCATCA CATTGGAATGCAGATGAGAATAGCTATGTTTAGTTT | 1257 |
| | AAACTAAACATAGCTATTCTCATCTGCATTCCAATGTGATGAA GGCCAAAAATGGCTGGGTGTAGGAGCAGTGTCCTCACAATA AAGAGAAGGCATAAGCCTATGCCTAGATAAATCGCGA | 1258 |
| | GCTCCTACACCCAGCCA | 1259 |
| | TGGCTGGGTGTAGGAGC | 1260 |
| Cystic fibrosis Ala141Asp GCC to GAC | TTTATCTAGGCATAGGCTTATGCCTTCTCTTTATTGTGAGGAC ACTGCTCCTACACCCAGCCATTTTTGGCCTTCATCACATTGG AATGCAGATGAGAATAGCTATGTTTAGTTTGATTTA | 1261 |
| | TAAATCAAACTAAACATAGCTATTCTCATCTGCATTCCAATGT GATGAAGGCCAAAAATGGCTGGGTGTAGGAGCAGTGTCCTC ACAATAAAGAGAAGGCATAAGCCTATGCCTAGATAAA | 1262 |
| | ACACCCAGCCATTTTTG | 1263 |
| | CAAAAATGGCTGGGTGT | 1264 |
| Cystic fibrosis Ile148Thr ATT to ACT | GCCTTCTCTTTATTGTGAGGACACTGCTCCTACACCCAGCCA TTTTTGGCCTTCATCACATTGGAATGCAGATGAGAATAGCTAT GTTTAGTTTGATTTATAAGAAGGTAATACTTCCTTG | 1265 |
| | CAAGGAAGTATTACCTTCTTATAAATCAAACTAAACATAGCTA TTCTCATCTGCATTCCAATGTGATGAAGGCCAAAAATGGCTG GGTGTAGGAGCAGTGTCCTCACAATAAAGAGAAGGC | 1266 |
| | TCATCACATTGGAATGC | 1267 |
| | GCATTCCAATGTGATGA | 1268 |
| Cystic fibrosis Gly149Arg GGA to AGA | CTTCTCTTTATTGTGAGGACACTGCTCCTACACCCAGCCATTT TTGGCCTTCATCACATTGGAATGCAGATGAGAATAGCTATGTT TAGTTTGATTTATAAGAAGGTAATACTTCCTTGCA | 1269 |
| | TGCAAGGAAGTATTACCTTCTTATAAATCAAACTAAACATAGC TATTCTCATCTGCATTCCAATGTGATGAAGGCCAAAAATGGCT GGGTGTAGGAGCAGTGTCCTCACAATAAAGAGAAG | 1270 |
| | ATCACATTGGAATGCAG | 1271 |
| | CTGCATTCCAATGTGAT | 1272 |
| Cystic fibrosis Gln151Term CAG to TAG | TTTATTGTGAGGACACTGCTCCTACACCCAGCCATTTTTGGC CTTCATCACATTGGAATGCAGATGAGAATAGCTATGTTTAGTT TGATTTATAAGAAGGTAATACTTCCTTGCACAGGCC | 1273 |
| | GGCCTGTGCAAGGAAGTATTACCTTCTTATAAATCAAACTAAA CATAGCTATTCTCATCTGCATTCCAATGTGATGAAGGCCAAAA ATGGCTGGGTGTAGGAGCAGTGTCCTCACAATAAA | 1274 |
| | TTGGAATGCAGATGAGA | 1275 |
| | TCTCATCTGCATTCCAA | 1276 |
| Cystic fibrosis Lys166Glu AAG-GAG | AATATATTTGTATTTTGTTTGTTGAAATTATCTAACTTTCCATTTT TTCTTTTTAGACTTTAAAGCTGTCAAGCCGTGTTCTAGATAAAA TAAGTATTGGACAACTTGTTAGTCTCCTTTCCA | 1277 |
| | TGGAAAGGAGACTAACAAGTTGTCCAATACTTATTTTATCTAG AACACGGCTTGACAGCTTTAAAGTCTAAAAGAAAAATGGAAA GTTAGATAATTTCAACAAACAAAATACAAATATATT | 1278 |
| | AGACTTTAAAGCTGTCA | 1279 |
| | TGACAGCTTTAAAGTCT | 1280 |
| Cystic fibrosis Ile175Val ATA-GTA | TTATCTAACTTTCCATTTTTCTTTTAGACTTTAAAGCTGTCAAG CCGTGTTCTAGATAAAATAAGTATTGGACAACTTGTTAGTCTC CTTTCCAACAACCTGAACAAATTTGATGAAGTAT | 1281 |
| | ATACTTCATCAAATTTGTTCAGGTTGTTGGAAAGGAGACTAAC AAGTTGTCCAATACTTATTTTATCTAGAACACGGCTTGACAGC TTTAAAGTCTAAAAGAAAAATGGAAAGTTAGATAA | 1282 |
| | TAGATAAAATAAGTATT | 1283 |
| | AATACTTATTTTATCTA | 1284 |

TABLE 16-continued

CFTR Mutations and Genome-Correcting Oligos

| Clinical Phenotype & Mutation | Correcting Oligos | SEQ ID NO: |
|---|---|---|
| Cystic fibrosis Gly178Arg GGA to AGA | TTTCCATTTTTCTTTTAGACTTTAAAGCTGTCAAGCCGTGTTCT AGATAAAATAAGTATTGGACAACTTGTTAGTCTCCTTTCCAAC AACCTGAACAAATTTGATGAAGTATGTACCTATT | 1285 |
| | AATAGGTACATACTTCATCAAATTTGTTCAGGTTGTTGGAAAG GAGACTAACAAGTTGTCCAATACTTATTTTATCTAGAACACGG CTTGACAGCTTTAAAGTCTAAAAGAAAAATGGAAA | 1286 |
| | TAAGTATTGGACAACTT | 1287 |
| | AAGTTGTCCAATACTTA | 1288 |
| Cystic fibrosis His199Gln CAT to CAG | AAGATACAATGACACCTGTTTTTGCTGTGCTTTTATTTTCCAG GGACTTGCATTGGCACATTTCGTGTGGATCGCTCCTTTGCAA GTGGCACTCCTCATGGGGCTAATCTGGGAGTTGTTA | 1289 |
| | TAACAACTCCCAGATTAGCCCCATGAGGAGTGCCACTTGCAA AGGAGCGATCCACACGAAAATGTGCCAATGCAAGTCCCTGGA AAATAAAAGCACAGCAAAAACAGGTGTCATTGTATCTT | 1290 |
| | TTGGCACATTTCGTGTG | 1291 |
| | CACACGAAATGCCAA | 1292 |
| Cystic fibrosis His199Tyr CAT to TAT | GGAAGATACAATGACACCTGTTTTTGCTGTGCTTTTATTTTCC AGGGACTTGCATTGGCACATTTCGTGTGGATCGCTCCTTTGC AAGTGGCACTCCTCATGGGGCTAATCTGGGAGTTGT | 1293 |
| | ACAACTCCCAGATTAGCCCCATGAGGAGTGCCACTTGCAAAG GAGCGATCCACACGAAATGTGCCAATGCAAGTCCCTGGAAA ATAAAAGCACAGCAAAAACAGGTGTCATTGTATCTTCC | 1294 |
| | CATTGGCACATTTCGTG | 1295 |
| | CACGAAATGTGCCAATG | 1296 |
| Cystic fibrosis Pro205Ser CCT to TCT | TGTTTTTGCTGTGCTTTTATTTTCCAGGGACTTGCATTGGCAC ATTTCGTGTGGATCGCTCCTTTGCAAGTGGCACTCCTCATGG GGCTAATCTGGGAGTTGTTACAGGCGTCTGCCTTCT | 1297 |
| | AGAAGGCAGACGCCTGTAACAACTCCCAGATTAGCCCCATG AGGAGTGCCACTTGCAAAGGAGCGATCCACACGAAATGTGC CAATGCAAGTCCCTGGAAAATAAAAGCACAGCAAAAACA | 1298 |
| | GGATCGCTCCTTTGCAA | 1299 |
| | TTGCAAAGGAGCGATCC | 1300 |
| Cystic fibrosis Leu206Trp TTG to TGG | TTTGCTGTGCTTTTATTTTCCAGGGACTTGCATTGGCACATTT CGTGTGGATCGCTCCTTTTGCAAGTGGCACTCCTCATGGGGC TAATCTGGGAGTTGTTACAGGCGTCTGCCTTCTGTGG | 1301 |
| | CCACAGAAGGCAGACGCCTGTAACAACTCCCAGATTAGCCC CATGAGGAGTGCCACTTGCAAAGGAGCGATCCACACGAAAT GTGCCAATGCAAGTCCCTGGAAAATAAAAGCACAGCAAA | 1302 |
| | CGCTCCTTTGCAAGTGG | 1303 |
| | CCACTTGCAAAGGAGCG | 1304 |
| Cystic fibrosis Gln220Term CAG to TAG | TTCGTGTGGATCGCTCCTTTGCAAGTGGCACTCCTCATGGG GCTAATCTGGGAGTTGTTACAGGCGTCTGCCTTCTGTGGACT TGGTTTCCTGATAGTCCTTGCCCTTTTTCAGGCTGGGC | 1305 |
| | GCCCAGCCTGAAAAAGGGCAAGGACTATCAGGAAACCAAGT CCACAGAAGGCAGACGCCTGTAACAACTCCCAGATTAGCCC CATGAGGAGTGCCACTTGCAAAGGAGCGATCCACACGAA | 1306 |
| | AGTTGTTACAGGCGTCT | 1307 |
| | AGACGCCTGTAACAACT | 1308 |
| Cystic fibrosis Cys225Arg TGT-CGT | CCTTTGCAAGTGGCACTCCTCATGGGGCTAATCTGGGAGTT GTTACAGGCGTCTGCCTTCTGTGGACTTGGTTTCCTGATAGT CCTTGCCCTTTTTCAGGCTGGGCTAGGGAGAATGATGA | 1309 |
| | TCATCATTCTCCCTAGCCCAGCCTGAAAAAGGGCAAGGACTA TCAGGAAACCAAGTCCACAGAAGGCAGACGCCTGTAACAAC TCCCAGATTAGCCCCATGAGGAGTGCCACTTGCAAAGG | 1310 |
| | CTGCCTTCTGTGGACTT | 1311 |
| | AAGTCCACAGAAGGCAG | 1312 |
| Cystic fibrosis Val232Asp GTC to GAC | TGGGGCTAATCTGGGAGTTGTTACAGGCGTCTGCCTTCTGT GGACTTGGTTTCCTGATAGTCCTTGCCCTTTTTCAGGCTGGG CTAGGGAGAATGATGATGAAGTACAGGTAGCAACCTAT | 1313 |
| | ATAGGTTGCTACCTGTACTTCATCATCATTCTCCCTAGCCCA GCCTGAAAAAGGGCAAGGACTATCAGGAAACCAAGTCCACA GAAGGCAGACGCCTGTAACAACTCCCAGATTAGCCCCA | 1314 |
| | CCTGATAGTCCTTGCCC | 1315 |
| | GGGCAAGGACTATCAGG | 1316 |
| Cystic fibrosis Gly239Arg GGG to AGG | GTTACAGGCGTCTGCCTTCTGTGGACTTGGTTTCCTGATAGT CCTTGCCCTTTTTCAGGCTGGGCTAGGGAGAATGATGATGAA GTACAGGTAGCAACCTATTTTCATAACTTGAAAGTTT | 1317 |
| | AAACTTTCAAGTTATGAAAATAGGTTGCTACCTGTACTTCATC ATCATTCTCCCTAGCCCAGCCTGAAAAAGGGCAAGGACTATC AGGAAACCAAGTCCACAGAAGGCAGACGCCTGTAAC | 1318 |
| | TTTCAGGCTGGGCTAGG | 1319 |
| | CCTAGCCCAGCCTGAAA | 1320 |

EXAMPLE 10

Cyclin-dependent Kinase Inhibitor 2A—CDKN2A

The human CDKN2A gene was also designated MTS-1 for multiple tumor suppressor-1 and has been implicated in multiple cancers including, for example, malignant melanoma. Malignant melanoma is a cutaneous neoplasm of melanocytes. Melanomas generally have features of asymmetry, irregular border, variegated color, and diameter greater than 6 mm. The precise cause of melanoma is unknown, but sunlight and heredity are risk factors. Melanoma has been increasing during the past few decades.

The CDKN2A gene has been found to be homozygously deleted at high frequency in cell lines derived from tumors of lung, breast, brain, bone, skin, bladder, kidney, ovary, and lymphocyte. Melanoma cell lines carried at least one copy of CDKN2A in combination with a deleted allele. Melanoma cell lines that carried at least 1 copy of CDKN2A frequently showed nonsense, missense, or frameshift mutations in the gene. Thus, CDKN2A may rival p53 (see Example 5) in the universality of its involvement in tumorigenesis. The attached table discloses the correcting oligonucleotide base sequences for the CDKN2A oligonucleotides of the invention.

TABLE 17

CDKN2A Mutations and Genome-Correcting Oligos

| Clinical Phenotype & Mutation | Correcting Oligos | SEQ ID NO: |
|---|---|---|
| Melanoma Trp15Term TGG-TAG | GGGCGGCGGGGAGCAGCATGGAGCCGGCGGCGGGGAGCAG | 1321 |
| | CATGGAGCCTTCGGCTGACTGGCTGGCCACGGCCGCGGCCC | |
| | GGGGTCGGGTAGAGGAGGTGCGGGCGCTGCTGGAGGCGGG | |
| | CCCGCCTCCAGCAGCGCCCGCACCTCCTCTACCCGACCCCG | 1322 |
| | GGCCGCGGCCGTGGCCAGCCAGTCAGCCGAAGGCTCCATGC | |
| | TGCTCCCCGCCGCCGGCTCCATGCTGCTCCCCGCCGCCC | |
| | GGCTGACTGGCTGGCCA | 1323 |
| | TGGCCAGCCAGTCAGCC | 1324 |
| Melanoma Leu16Pro CTG-CCG | CGGCGGCGGGGAGCAGCATGGAGCCGGCGGCGGGGAGCAGCAT | 1325 |
| | GGAGCCTTCGGCTGACTGGCTGGCCACGGCCGCGGCCCGG | |
| | GGTCGGGTAGAGGAGGTGCGGGCGCTGCTGGAGGCGGGGC | |
| | GCCCCCGCCTCCAGCAGCGCCCGCACCTCCTCTACCCGACC | 1326 |
| | CCGGGCCGCGGCCGTGGCCAGCCAGTCAGCCGAAGGCTCC | |
| | ATGCTGCTCCCCGCCGCCGGCTCCATGCTGCTCCCCGCCG | |
| | TGACTGGCTGGCCACGG | 1327 |
| | CCGTGGCCAGCCAGTCA | 1328 |
| Melanoma Gly23Asp GGT-GAT | CGGCGGCGGGGAGCAGCATGGAGCCTTCGGCTGACTGGCTG | 1329 |
| | GCCACGGCCGCGGCCCGGGGTCGGGTAGAGGAGGTGCGGG | |
| | CGCTGCTGGAGGCGGGGGCGCTGCCCAACGCACCGAATAG | |
| | CTATTCGGTGCGTTGGGCAGCGCCCCCGCCTCCAGCAGCGC | 1330 |
| | CCGCACCTCCTCTACCCGACCCCGGGCCGCGGCCGTGGCCA | |
| | GCCAGTCAGCCGAAGGCTCCATGCTGCTCCCCGCCGCCG | |
| | GGCCCGGGGTCGGGTAG | 1331 |
| | CTACCCGACCCCGGGCC | 1332 |
| Melanoma Arg24Pro CGG-CCG | CGGCGGGGAGCAGCATGGAGCCTTCGGCTGACTGGCTGGCC | 1333 |
| | ACGGCCGCGGCCCGGGGTCGGGTAGAGGAGGTGCGGGCGC | |
| | TGCTGGAGGCGGGGGCGCTGCCCAACGCACCGAATAGTTA | |
| | TAACTATTCGGTGCGTTGGGCAGCGCCCCCGCCTCCAGCAGC | 1334 |
| | GCCCGCACCTCCTCTACCCGACCCCGGGCCGCGGCCGTGGC | |
| | CAGCCAGTCAGCCGAAGGCTCCATGCTGCTCCCCGCCG | |
| | CCGGGGTCGGGTAGAGG | 1335 |
| | CCTCTACCCGACCCCGG | 1336 |
| Melanoma Leu32Pro CTG-CCG | CGGCTGACTGGCTGGCCACGGCCGCGGCCCGGGGTCGGGT | 1337 |
| | AGAGGAGGTGCGGGCGCTGCTGGAGGCGGGGCGCTGCCC | |
| | AACGCACCGAATAGTTACGGTCGGAGGCCGATCCAGGTGGG | |
| | CCCACCTGGATCGGCCTCCGACCGTAACTATTCGGTGCGTTG | 1338 |
| | GGCAGCGCCCCCGCCTCCAGCAGCGCCCGCACCTCCTCTAC | |
| | CCGACCCCGGGCCGCGGCCGTGGCCAGCCAGTCAGCCG | |
| | GGCGCTGCTGGAGGCGG | 1339 |
| | CCGCCTCCAGCAGCGCC | 1340 |
| Melanoma Gly35Ala GGG-GCG | GGCTGGCCACGGCCGCGGCCCGGGGTCGGGTAGAGGAGGT | 1341 |
| | GCGGGCGCTGCTGGAGGCGGGGGCGCTGCCCAACGCACCG | |
| | AATAGTTACGGTCGGAGGCCGATCCAGGTGGGTAGAGGGTC | |
| | GACCCTCTACCCACCTGGATCGGCCTCCGACCGTAACTATTC | 1342 |
| | GGTGCGTTGGGCAGCGCCCCCGCCTCCAGCAGCGCCCGCAC | |
| | CTCCTCTACCCGACCCCGGGCCGCGGCCGTGGCCAGCC | |
| | GGAGGCGGGGGCGCTGC | 1343 |
| | GCAGCGCCCCCGCCTCC | 1344 |
| Melanoma Tyr44Term TACg-TAA | GGTAGAGGAGGTGCGGGCGCTGCTGGAGGCGGGGCGCTG | 1345 |
| | CCCAACGCACCGAATAGTTACGGTCGGAGGCCGATCCAGGTG | |
| | GGTAGAGGGTCTGCAGCGGGAGGGGATGGCGGGCGA | |
| | TCGCCCGCCATCCCCTGCTCCCGCTGCAGACCCTCTACCCAC | 1346 |
| | CTGGATCGGCCTCCGACCGTAACTATTCGGTGCGTTGGGCAG | |
| | CGCCCCCGCCTCCAGCAGCGCCCGCACCTCCTCTACC | |
| | AATAGTTACGGTCGGAG | 1347 |
| | CTCCGACCGTAACTATT | 1348 |

TABLE 17-continued

CDKN2A Mutations and Genome-Correcting Oligos

| Clinical Phenotype & Mutation | Correcting Oligos | SEQ ID NO: |
|---|---|---|
| Melanoma Met53Ile ATGa-ATC | TCTCCCATACCTGCCCCCACCCTGGCTCTGACCACTCTGCTC TCTCTGGCAGGTCATGATGATGGGCAGCGCCCGCGTGGCGG AGCTGCTGCTGCTCCACGGCGCGGAGCCCAACTGCGCA | 1349 |
| | TGCGCAGTTGGGCTCCGCGCCGTGGAGCAGCAGCAGCTCCG CCACGCGGGCGCTGCCCATCATCATGACCTGCCAGAGAGAG CAGAGTGGTCAGAGCCAGGGTGGGGGCAGGTATGGGAGA | 1350 |
| | GTCATGATGATGGGCAG | 1351 |
| | CTGCCCATCATCATGAC | 1352 |
| Melanoma Met54Ile ATGg-ATT | CCCATACCTGCCCCCACCCTGGCTCTGACCACTCTGCTCTCT CTGGCAGGTCATGATGATGGGCAGCGCCCGCGTGGCGGAGC TGCTGCTGCTCCACGGCGCGGAGCCCAACTGCGCAGAC | 1353 |
| | GTCTGCGCAGTTGGGCTCCGCGCCGTGGAGCAGCAGCAGCT CCGCCACGCGGGCGCTGCCCATCATCATGACCTGCCAGAGA GAGCAGAGTGGTCAGAGCCAGGGTGGGGGCAGGTATGGG | 1354 |
| | ATGATGATGGGCAGCGC | 1355 |
| | GCGCTGCCCATCATCAT | 1356 |
| Melanoma Ser56Ile AGC-ATC | GCCGGCCCCCACCCTGGCTCTGACCATTCTGTTCTCTCTGGC AGGTCATGATGATGGGCAGCGCCCGAGTGGCGGAGCTGCTG CTGCTCCACGGCGCGGAGCCCAACTGCGCCGACCCCGC | 1357 |
| | GCGGGGTCGGCGCAGTTGGGCTCCGCGCCGTGGAGCAGCA GCAGCTCCGCCACTCGGGCGCTGCCCATCATCATGACCTGCC AGAGAGAACAGAATGGTCAGAGCCAGGGTGGGGGCCGGC | 1358 |
| | GATGGGCAGCGCCCGAG | 1359 |
| | CTCGGGCGCTGCCCATC | 1360 |
| Melanoma Ala57Val GCC-GTC | GGCCCCCACCCTGGCTCTGACCATTCTGTTCTCTCTGGCAGG TCATGATGATGGGCAGCGCCCGAGTGGCGGAGCTGCTGCTG CTCCACGGCGCGGAGCCCAACTGCGCCGACCCCGCCAC | 1361 |
| | GTGGCGGGGTCGGCGCAGTTGGGCTCCGCGCCGTGGAGCA GCAGCAGCTCCGCCACTCGGGCGCTGCCCATCATCATGACCT GCCAGAGAGAACAGAATGGTCAGAGCCAGGGTGGGGGCC | 1362 |
| | GGGCAGCGCCCGAGTGG | 1363 |
| | CCACTCGGGCGCTGCCC | 1364 |
| Melanoma Arg58Term cCGA-TGA | CCCCCACCCTGGCTCTGACCATTCTGTTCTCTCTGGCAGGTC ATGATGATGGGCAGCGCCCGAGTGGCGGAGCTGCTGCTGCT CCACGGCGCGGAGCCCAACTGCGCCGACCCCGCCACTC | 1365 |
| | GAGTGGCGGGGTCGGCGCAGTTGGGCTCCGCGCCGTGGAG CAGCAGCAGCTCCGCCACTCGGGCGCTGCCCATCATCATGAC CTGCCAGAGAGAACAGAATGGTCAGAGCCAGGGTGGGGG | 1366 |
| | GCAGCGCCCGAGTGGCG | 1367 |
| | CGCCACTCGGGCGCTGC | 1368 |
| Melanoma Val59Gly GTG-GGG | CACCCTGGCTCTGACCATTCTGTTCTCTCTGGCAGGTCATGAT GATGGGCAGCGCCCGAGTGGCGGAGCTGCTGCTGCTCCACG GCGCGGAGCCCAACTGCGCCGACCCCGCCACTCTCAC | 1369 |
| | GTGAGAGTGGCGGGGTCGGCGCAGTTGGGCTCCGCGCCGTG GAGCAGCAGCAGCTCCGCCACTCGGGCGCTGCCCATCATCA TGACCTGCCAGAGAGAACAGAATGGTCAGAGCCAGGGTG | 1370 |
| | CGCCCGAGTGGCGGAGC | 1371 |
| | GCTCCGCCACTCGGGCG | 1372 |
| Melanoma Leu62Pro CTG-CCG | TCTGACCACTCTGCTCTCTCTGGCAGGTCATGATGATGGGCA GCGCCCGCGTGGCGGAGCTGCTGCTGCTCCACGGCGCGGA GCCCAACTGCGCAGACCCTGCCACTCTCACCCGACCGGT | 1373 |
| | ACCGGTCGGGTGAGAGTGGCAGGGTCTGCGCAGTTGGGCTC CGCGCCGTGGAGCAGCAGCAGCTCCGCCACGCGGGCGCTG CCCATCATCATGACCTGCCAGAGAGAGCAGAGTGGTCAGA | 1374 |
| | GGCGGAGCTGCTGCTGC | 1375 |
| | GCAGCAGCAGCTCCGCC | 1376 |
| Melanoma Ala68Val GCG-GTG | TCTGGCAGGTCATGATGATGGGCAGCGCCCGCGTGGCGGAG CTGCTGCTGCTCCACGGCGCGGAGCCCAACTGCGCAGACCC TGCCACTCTCACCCGACCGGTGCATGATGCTGCCCGGA | 1377 |
| | TCCCGGGCAGCATCATGCACCGGTCGGGTGAGAGTGGCAGG GTCTGCGCAGTTGGGCTCCGCGCCGTGGAGCAGCAGCAGCT CCGCCACGCGGGCGCTGCCCATCATCATGACCTGCCAGA | 1378 |
| | CCACGGCGCGGAGCCCA | 1379 |
| | TGGGCTCCGCGCCGTGG | 1380 |
| Melanoma Asn71Lys AACt-AAA | CATGATGATGGGCAGCGCCCGAGTGGCGGAGCTGCTGCTGC TCCACGGCGCGGAGCCCAACTGCGCCGACCCCGCCACTCTC ACCCGACCCGTGCACGACGCTGCCCGGGAGGGCTTCCTG | 1381 |
| | CAGGAAGCCCTCCCGGGCAGCGTCGTGCACGGGTCGGGTGA GAGTGGCGGGGTCGGCGCAGTTGGGCTCCGCGCCGTGGAG CAGCAGCAGCTCCGCCACTCGGGCGCTGCCCATCATCATG | 1382 |
| | GAGCCCAACTGCGCCGA | 1383 |
| | TCGGCGCAGTTGGGCTC | 1384 |

TABLE 17-continued

CDKN2A Mutations and Genome-Correcting Oligos

| Clinical Phenotype & Mutation | Correcting Oligos | SEQ ID NO: |
|---|---|---|
| Melanoma Asn71Ser AAC-AGC | TCATGATGATGGGCAGCGCCCGAGTGGCGGAGCTGCTGCTG CTCCACGGCGCGGAGCCCAACTGCGCCGACCCCGCCACTCT CACCCGACCCGTGCACGACGCTGCCCGGGAGGGCTTCCT | 1385 |
| | AGGAAGCCCTCCCGGGCAGCGTCGTGCACGGGTCGGGTGAG AGTGGCGGGTCGGCGCAGTTGGGCTCCGCGCCGTGGAGCA GCAGCAGCTCCGCCACTCGGGCGCTGCCCATCATCATGA | 1386 |
| | GGAGCCCAACTGCGCCG | 1387 |
| | CGGCGCAGTTGGGCTCC | 1388 |
| Melanoma Pro81Leu CCC-CTC | AGCTGCTGCTGCTCCACGGCGCGGAGCCCAACTGCGCCGAC CCCGCCACTCTCACCCGACCCGTGCACGACGCTGCCCGGGA GGGCTTCCTGGACACGCTGGTGGTGCTGCACCGGGCCGG | 1389 |
| | CCGGCCCGGTGCAGCACCACCAGCGTGTCCAGGAAGCCCTC CCGCGCAGCGTCGTGCACGGGTCGGGTGAGAGTGGCGGGG TCGGCGCAGTTGGGCTCCGCGCCGTGGAGCAGCAGCAGCT | 1390 |
| | CACCCGACCCGTGCACG | 1391 |
| | CGTGCACGGGTCGGGTG | 1392 |
| Melanoma Asp84Tyr cGAC-TAC | CTGCTCCACGGCGCGGAGCCCAACTGCGCCGACCCCGCCAC TCTCACCCGACCCGTGCACGACGCTGCCCGGGAGGGCTTCC TGGACACGCTGGTGGTGCTGCACCGGGCCGGGGCGCGGC | 1393 |
| | GCCGCGCCCCGGCCCGGTGCAGCACCACCAGCGTGTCCAGG AAGCCCTCCCGGGCAGCGTCGTGCACGGGTCGGGTGAGAGT GGCGGGGTCGGCGCAGTTGGGCTCCGCGCCGTGGAGCAG | 1394 |
| | CCGTGCACGACGCTGCC | 1395 |
| | GGCAGCGTCGTGCACGG | 1396 |
| Melanoma Ala85Thr cGCT-ACT | CTCCACGGCGCGGAGCCCAACTGCGCCGACCCCGCCACTCT CACCCGACCCGTGCACGACGCTGCCCGGGAGGGCTTCCTGG ACACGCTGGTGGTGCTGCACCGGGCCGGGGCGCGGCTGG | 1397 |
| | CCAGCCGCGCCCCGGCCCGGTGCAGCACCACCAGCGTGTCC AGGAAGCCCTCCCGGGCAGCGTCGTGCACGGGTCGGGTGAG AGTGGCGGGTCGGCGCAGTTGGGCTCCGCGCCGTGGAG | 1398 |
| | TGCACGACGCTGCCCGG | 1399 |
| | CCGGGCAGCGTCGTGCA | 1400 |
| Melanoma Arg87Pro CGG-CCG | GCGCGGAGCCCAACTGCGCCGACCCCGCCACTCTCACCCGA CCCGTGCACGACGCTGCCCGGGAGGGCTTCCTGGACACGCT GGTGGTGCTGCACCGGGCCGGGGCGCGGCTGGACGTGCG | 1401 |
| | CGCACGTCCAGCCGCGCCCCGGCCCGGTGCAGCACCACCAG CGTGTCCAGGAAGCCCTCCCGGGCAGCGTCGTGCACGGGTC GGGTGAGAGTGGCGGGTCGGCGCAGTTGGGCTCCGCGC | 1402 |
| | CGCTGCCCGGGAGGGCT | 1403 |
| | AGCCCTCCCGGGCAGCG | 1404 |
| Melanoma Arg87Trp cCGG-TGG | GGCGCGGAGCCCAACTGCGCCGACCCCGCCACTCTCACCCG ACCCGTGCACGACGCTGCCCGGGAGGGCTTCCTGGACACGC TGGTGGTGCTGCACCGGGCCGGGGCGCGGCTGGACGTGC | 1405 |
| | GCACGTCCAGCCGCGCCCCGGCCCGGTGCAGCACCACCAGC GTGTCCAGGAAGCCCTCCCGGGCAGCGTCGTGCACGGGTCG GGTGAGAGTGGCGGGTCGGCGCAGTTGGGCTCCGCGCC | 1406 |
| | ACGCTGCCCGGGAGGGC | 1407 |
| | GCCCTCCCGGGCAGCGT | 1408 |
| Melanoma Leu97Arg CTG-CGG | CTCTCACCCGACCGGTGCATGATGCTGCCCGGGAGGGCTTC CTGGACACGCTGGTGGTGCTGCACCGGGCCGGGGCGCGGCT GGACGTGCGCGATGCCTGGGGTCGTCTGCCCGTGGACTT | 1409 |
| | AAGTCCACGGGCAGACGACCCCAGGCATCGCGCACGTCCAG CCGCGCCCCGGCCCGGTCCAGCACCACCAGCGTGTCCAGGA AGCCCTCCCGGGCAGCATCATGCACCGGTCGGGTGAGAG | 1410 |
| | GGTGGTGCTGCACCGGG | 1411 |
| | CCCGGTGCAGCACCACC | 1412 |
| Melanoma Arg99Pro CGG-CCG | CCCGACCGGTGCATGATGCTGCCCGGGAGGGCTTCCTGGAC ACGCTGGTGGTGCTGCACCGGGCCGGGGCGCGGCTGGACG TGCGCGATGCCTGGGGTCGTCTGCCCGTGGACTTGGCCGA | 1413 |
| | TCGGCCAAGTCCACGGGCAGACGACCCCAGGCATCGCGCAC GTCCAGCCGCGCCCCGGCCCGGTGCAGCACCACCAGCGTGT CCAGGAAGCCCTCCCGGGCAGCATCATGCACCGGTCGG | 1414 |
| | GCTGCACCGGGCCGGGG | 1415 |
| | CCCCGGCCCGGTGCAGC | 1416 |
| Melanoma Gly101Trp cGGG-TGG | CCGGTGCATGATGCTGCCCGGGAGGGCTTCCTGGACACGCT GGTGGTGCTGCACCGGGCCGGGGCGCGGCTGGACGTGCGC GATGCCTGGGGTCGTCTGCCCGTGGACTTGGCCGAGGAGC | 1417 |
| | GCTCCTCGGCCAAGTCCACGGGCAGACGACCCCAGGCATCG CGCACGTCCAGCCGCGCCCCGGCCCGGTGCAGCACCACCAG CGTGTCCAGGAAGCCCTCCCGGGCAGCATCATGCACCGG | 1418 |
| | ACCGGGCCGGGGCGCGG | 1419 |
| | CCGCGCCCCGGCCCGGT | 1420 |

TABLE 17-continued

CDKN2A Mutations and Genome-Correcting Oligos

| Clinical Phenotype & Mutation | Correcting Oligos | SEQ ID NO: |
|---|---|---|
| Melanoma Arg107Cys gCGC-TGC | CGGGAGGGCTTCCTGGACACGCTGGTGGTGCTGCACCGGGC | 1421 |
| | CGGGGCGCGGCTGGACGTGCGCGATGCCTGGGGTCGTCTGC | |
| | CCGTGGACTTGGCCGAGGAGCGGGGCCACCGCGACGTTG | |
| | CAACGTCGCGGTGGCCCCGCTCCTCGGCCAAGTCCACGGGC | 1422 |
| | AGACGACCCCAGGCATCGCGCACGTCCAGCCGCGCCCCGGC | |
| | CCGGTGCAGCACCACCAGCGTGTCCAGGAAGCCCTCCCG | |
| | TGGACGTGCGCGATGCC | 1423 |
| | GGCATCGCGCACGTCCA | 1424 |
| Melanoma Ala118Thr gGCT-ACT | CACCGGGCCGGGGCGCGGCTGGACGTGCGCGATGCCTGGG | 1425 |
| | GCCGTCTGCCCGTGGACCTGGCTGAGGAGCTGGGCCATCGC | |
| | GATGTCGCACGGTACCTGCGCGCGGCTGCGGGGGGCACCA | |
| | TGGTGCCCCCCGCAGCCGCGCGCAGGTACCGTGCGACATCG | 1426 |
| | CGATGGCCCAGCTCCTCAGCCAGGTCCACGGGCAGACGGCC | |
| | CCAGGCATCGCGCACGTCCAGCCGCGCCCCGGCCCGGTG | |
| | TGGACCTGGCTGAGGAG | 1427 |
| | CTCCTCAGCCAGGTCCA | 1428 |
| Melanoma Val126Asp GTC-GAC | TGCGCGATGCCTGGGGCCGTCTGCCCGTGGACCTGGCTGAG | 1429 |
| | GAGCTGGGCCATCGCGATGTCGCACGGTACCTGCGCGCGGC | |
| | TGCGGGGGGCACCAGAGGCAGTAACCATGCCCGCATAGA | |
| | TCTATGCGGGCATGGTTACTGCCTCTGGTGCCCCCCGCAGCC | 1430 |
| | GCGCGCAGGTACCGTGCGACATCGCGATGGCCCACCTCCTC | |
| | AGCCAGGTCCACGGGCAGACGGCCCCAGGCATCGCGCA | |
| | TCGCGATGTCGCACGGT | 1431 |
| | ACCGTGCGACATCGCGA | 1432 |

EXAMPLE 11

Adenomatous Polyposis of the Colon—APC

Adenomatous polyposis of the colon is characterized by adenomatous polyps of the colon and rectum; in extreme cases the bowel is carpeted with a myriad of polyps. This is a viciously premalignant disease with one or more polyps progressing through dysplasia to malignancy in untreated gene carriers with a median age at diagnosis of 40 years.

Mutations in the APC gene are an initiating event for both familial and sporadic colorectal tumorigenesis and many alleles of the APC gene have been identified. Carcinoma may arise at any age from late childhood through the seventh decade with presenting features including, for example, weight loss and inanition, bowel obstruction, or bloody diarrhea. Cases of new mutation still present in these ways but in areas with well organized registers most other gene carriers are detected. The attached table discloses the correcting oligonucleotide base sequences for the APC oligonucleotides of the invention.

TABLE 18

APC Mutations and Genome-Correcting Oligos

| Clinical Phenotype & Mutation | Correcting Oligos | SEQ ID NO: |
|---|---|---|
| Adenomatous polyposis coli Arg121Term AGA-TGA | GGATCTGTATCAAGCCGTTCTGGAGAGTGCAGTCCTGTTCCT | 1433 |
| | ATGGGTTCATTTCCAAGAAGAGGGTTTGTAAATGGAAGCAGA | |
| | GAAAGTACTGGATATTTAGAAGAACTTGAGAAAGAGA | |
| | TCTCTTTCTCAAGTTCTTCTAAATATCCAGTACTTTCTCTGCTT | 1434 |
| | CCATTTACAAACCCTCTTCTTGGAAATGAACCCATAGGAACAG | |
| | GACTGCACTCTCCAGAACGGCTTGATACAGATCC | |
| | TTCCAAGAAGAGGGTTT | 1435 |
| | AAACCCTCTTCTTGGAA | 1436 |
| Adenomatous polyposis coli Trp157Term TGG-TAG | AAAAAAAAAATAGGTCATTGCTTCTTGCTGATCTTGACAAAGAA | 1437 |
| | GAAAAGGAAAAAGACTGGTATTACGCTCAACTTCAGAATCTCA | |
| | CTAAAAGAATAGATAGTCTTCCTTTAACTGAAAA | |
| | TTTTCAGTTAAAGGAAGACTATCTATTCTTTTAGTGAGATTCTG | 1438 |
| | AAGTTGAGCGTAATACCAGTCTTTTTCCTTTTCTTCTTTGTCAA | |
| | GATCAGCAAGAAGCAATGACCTATTTTTTTTTT | |
| | AAAAGACTGGTATTACG | 1439 |
| | CGTAATACCAGTCTTTT | 1440 |
| Adenomatous polyposis coli Tyr159Term TAC-TAG | AAATAGGTCATTGCTTCTTGCTGATCTTGACAAAGAAGAAAAG | 1441 |
| | GAAAAAGACTGGTATTACGCTCAACTTCAGAATCTCACTAAAA | |
| | GAATAGATAGTCTTCCTTTAACTGAAAATGTAAGT | |
| | ACTTACATTTTCAGTTAAAGGAAGACTATCTATTCTTTTAGTGA | 1442 |
| | GATTCTGAAGTTGAGCGTAATACCAGTCTTTTTCCTTTTCTTCT | |
| | TTGTCAAGATCAGCAAGAAGCAATGACCTATTT | |
| | TGGTATTACGCTCAACT | 1443 |
| | AGTTGAGCGTAATACCA | 1444 |

TABLE 18-continued

APC Mutations and Genome-Correcting Oligos

| Clinical Phenotype & Mutation | Correcting Oligos | SEQ ID NO: |
|---|---|---|
| Adenomatous polyposis coli Gln163Term CAG-TAG | TTGCTTCTTGCTGATCTTGACAAAGAAGAAAAGGAAAAAGACT GGTATTACGCTCAACTTCAGAATCTCACTAAAAGAATAGATAG TCTTCCTTTAACTGAAAATGTAAGTAACTGGCAGT | 1445 |
| | ACTGCCAGTTACTTACATTTTCAGTTAAAGGAAGACTATCTATT CTTTTAGTGAGATTCTGAAGTTGAGCGTAATACCAGTCTTTTTC CTTTTCTTCTTTGTCAAGATCAGCAAGAAGCAA | 1446 |
| | CTCAACTTCAGAATCTC | 1447 |
| | GAGATTCTGAAGTTGAG | 1448 |
| Adenomatous polyposis coli Arg168Term AGA-TGA | CTTGACAAAGAAGAAAAGGAAAAAGACTGGTATTACGCTCAAC TTCAGAATCTCACTAAAAGAATAGATAGTCTTCCTTTAACTGAA AATGTAAGTAACTGGCAGTACAACTTATTTGAAA | 1449 |
| | TTTCAAATAAGTTGTACTGCCAGTTACTTACATTTTCAGTTAAA GGAAGACTATCTATTCTTTTAGTGAGATTCTGAAGTTGAGCGT AATACCAGTCTTTTTCCTTTTCTTCTTTGTCAAG | 1450 |
| | TCACTAAAAGAATAGAT | 1451 |
| | ATCTATTCTTTTAGTGA | 1452 |
| Adenomatous polyposis coli Ser171Ile AGT-ATT | AAGAAAAGGAAAAAGACTGGTATTACGCTCAACTTCAGAATCT CACTAAAAGAATAGATAGTCTTCCTTTAACTGAAAATGTAAGTA ACTGGCAGTACAACTTATTTGAAACTTTAATAAC | 1453 |
| | GTTATTAAAGTTTCAAATAAGTTGTACTGCCAGTTACTTACATT TTCAGTTAAAGGAAGACTATCTATTCTTTTAGTGAGATTCTGAA GTTGAGCGTAATACCAGTCTTTTTCCTTTTCTT | 1454 |
| | AATAGATAGTCTTCCTT | 1455 |
| | AAGGAAGACTATCTATT | 1456 |
| Adenomatous polyposis coli Gln181Term CAA-TAA | GATTAACGTAAATACAAGATATTGATACTTTTTTATTATTTGTGG TTTAGTTTTCCTTACAAACAGATATGACCAGAAGGCAATTGG TAATATGAAGCAAGGCAAATCAGAGTTGCGATGG | 1457 |
| | CCATCGCAACTCTGATTTGCCTTGCTTCATATTCCAATTGCCT TCTGGTCATATCTGTTTGTAAGGAAAACTAAAACCACAAATAAT AAAAAAGTATCAATATCTTGTATTTACGTTAATC | 1458 |
| | TTTCCTTACAAACAGAT | 1459 |
| | ATCTGTTTGTAAGGAAA | 1460 |
| Adenomatous polyposis coli Glu190Term GAA-TAA | CTTTTTTATTATTTGTGGTTTTAGTTTTCCTTACAAACAGATATG ACCAGAAGGCAATTGGAATATGAAGCAAGGCAAATCAGAGTT GCGATGGAAGAACAACTAGGTACCTGCCAGGATA | 1461 |
| | TATCCTGGCAGGTACCTAGTTGTTCTTCCATCGCAACTCTGAT TTGCCTTGCTTCATATTCCAATTGCCTTCTGGTCATATCTGTTT GTAAGGAAAACTAAAACCACAAATAATAAAAAAG | 1462 |
| | GGCAATTGGAATATGAA | 1463 |
| | TTCATATTCCAATTGCC | 1464 |
| Adenomatous polyposis coli Gln208Term CAG-TAG | CAATTGGAATATGAAGCAAGGCAAATCAGAGTTGCGATGGAA GAACAACTAGGTACCTGCCCAGGATATGGAAAAACGAGCACAG GTAAGTTACTTGTTTCTAAGTGATAAAACAGCGAAGA | 1465 |
| | TCTTCGCTGTTTTATCACTTAGAAACAAGTAACTTACCTGTGCT CGTTTTTCCATATCCTGGCAGGTACCTAGTTGTTCTTCCATCG CAACTCTGATTTGCCTTGCTTCATATTCCAATTG | 1466 |
| | GTACCTGCCCAGGATATG | 1467 |
| | CATATCCTGGCAGGTAC | 1468 |
| Adenomatous polyposis coli Arg213Term CGA-TGA | GCAAGGCAAATCAGAGTTGCGATGGAAGAACAACTAGGTACC TGCCAGGATATGGAAAAACGAGCACAGGTAAGTTACTTGTTTC TAAGTGATAAAACAGCGAAGAGCTATTAGGAATAAA | 1469 |
| | TTTATTCCTAATAGCTCTTCGCTGTTTTATCACTTAGAAACAAG TAACTTACCTGTGCTCGTTTTTCCATATCCTGGCAGGTACCTA GTTGTTCTTCCATCGCAACTCTGATTTGCCTTGC | 1470 |
| | TGGAAAAACGAGCACAG | 1471 |
| | CTGTGCTCGTTTTTCCA | 1472 |
| Adenomatous polyposis coli Arg232Term CGA-TGA | GTTTTATTTTAGCGAAGAATAGCCAGAATTCAGCAAATCGAAA AGGACATACTTCGTATACGACAGCTTTTACAGTCCCAAGCAAC AGAAGCAGAGGTTAGTAAATTGCCTTTCTTGTTTG | 1473 |
| | CAAACAAGAAAGGCAATTTACTAACCTCTGCTTCTGTTGCTTG GGACTGTAAAAGCTGTCGTATACGAAGTATGTCCTTTTCGATT TGCTGAATTCTGGCTATTCTTCGCTAAAATAAAAC | 1474 |
| | TTCGTATACGACAGCTT | 1475 |
| | AAGCTGTCGTATACGAA | 1476 |
| Adenomatous polyposis coli Gln233Term CAG-TAG | TTATTTTAGCGAAGAATAGCCAGAATTCAGCAAATCGAAAGG ACATACTTCGTATACGACAGCTTTTACAGTCCCAAGCAACAGA AGCAGAGGTTAGTAAATTGCCTTTCTTGTTTGTGG | 1477 |
| | CCACAAACAAGAAAGGCAATTTACTAACCTCTGCTTCTGTTGC TTGGGACTGTAAAAGCTGTCGTATACGAAGTATGTCCTTTTCG ATTTGCTGAATTCTGGCTATTCTTCGCTAAAATAA | 1478 |
| | GTATACGACAGCTTTTA | 1479 |
| | TAAAAGCTGTCGTATAC | 1480 |
| Adenomatous polyposis coli | AGAAAGCCTACACCATTTTTGCATGTACTGATGTTAACTCCAT CTTAACAGAGGTCATCTCAGAACAAGCATGAAACCGGCTCAC | 1481 |

TABLE 18-continued

APC Mutations and Genome-Correcting Oligos

| Clinical Phenotype & Mutation | Correcting Oligos | SEQ ID NO: |
|---|---|---|
| Gln247Term<br>CAG-TAG | ATGATGCTGAGCGGCAGAATGAAGGTCAAGGAGTGG<br>CCACTCCTTGACCTTCATTCTGCCGCTCAGCATCATGTGAGC<br>CGGTTTCATGCTTGTTCTGAGATGACCTCTGTTAAGATGGAGT<br>TAACATCAGTACATGCAAAAATGGTGTAGGCTTTCT | 1482 |
| | GGTCATCTCAGAACAAG | 1483 |
| | CTTGTTCTGAGATGACC | 1484 |
| Adenomatous polyposis coli<br>Gly267Term<br>GGA-TGA | CAGAACAAGCATGAAACCGGCTCACATGATGCTGAGCGGCAG<br>AATGAAGGTCAAGGAGTGGGAGAAATCAACATGGCAACTTCT<br>GGTAATGGTCAGGTAAATAAATTATTTTATCATATTT | 1485 |
| | AAAATGATAAAATAATTTATTTACCTGACCATTACCAGAAGTT<br>GCCATGTTGATTTCTCCCACTCCTTGACCTTCATTCTGCCGCT<br>CAGCATCATGTGAGCCGGTTTCATGCTTGTTCTG | 1486 |
| | AAGGAGTGGGAGAAATC | 1487 |
| | GATTTCTCCCACTCCTT | 1488 |
| Adenomatous polyposis coli<br>Glu443Term<br>GAA-TAA | CTTCAAATAACAAAGCATTATGGTTTATGTTGATTTTATTTTTCA<br>GTGCCAGCTCCTGTTGAACATCAGATCTGTCCTGCTGTGTGT<br>GTTCTAATGAAACTTTCATTTGATGAAGAGCATA | 1489 |
| | TATGCTCTTCATCAAATGAAAGTTTCATTAGAACACACACAGCA<br>GGACAGATCTGATGTTCAACAGGAGCTGGCACTGAAAAATAA<br>AATCAACATAAACCATAATGCTTTGTTATTTGAAG | 1490 |
| | CTCCTGTTGAACATCAG | 1491 |
| | CTGATGTTCAACAGGAG | 1492 |
| Adenomatous polyposis coli<br>SER457TER<br>TCA-TAA | CAGTGCCAGCTCCTGTTGAACATCAGATCTGTCCTGCTGTGT<br>GTGTTCTAATGAAACTTTCATTTGATGAAGAGCATAGACATGC<br>AATGAATGAACTAGGTAAGACAAAAATGTTTTTTAA | 1493 |
| | TTAAAAAACATTTTTGTCTTACCTAGTTCATTCATTGCATGTCTA<br>TGCTCTTCATCAAATGAAAGTTTCATTAGAACACACACAGCAG<br>GACAGATCTGATGTTCAACAGGAGCTGGCACTG | 1494 |
| | GAAACTTTCATTTGATG | 1495 |
| | CATCAAATGAAAGTTTC | 1496 |
| Adenomatous polyposis coli<br>Gln473Term<br>CAG-TAG | AGTTGTTTTATTTTAGATGATTGTCTTTTTCCTCTTGCCCTTTTT<br>AAATTAGGGGGACTACAGGCCATTGCAGAATTATTGCAAGTG<br>GACTGTGAAATGTACGGGCTTACTAATGACCACT | 1497 |
| | AGTGGTCATTAGTAAGCCCGTACATTTCACAGTCCACTTGCAA<br>TAATTCTGCAATGGCCTGTAGTCCCCCTAATTTAAAAAGGGCA<br>AGAGGAAAAGACAATCATCTAAAATAAAACAACT | 1498 |
| | GGGGACTACAGGCCATT | 1499 |
| | AATGGCCTGTAGTCCCC | 1500 |
| Adenomatous polyposis coli<br>Tyr486Term<br>TAC-TAG | TTTTAAATTAGGGGGACTACAGGCCATTGCAGAATTATTGCAA<br>GTGGACTGTGAAATGTACGGGCTTACTAATGACCACTACAGTA<br>TTACACTAAGACGATATGCTGGAATGGCTTTGACA | 1501 |
| | TGTCAAAGCCATTCCAGCATATCGTCTTAGTGTAATACTGTAG<br>TGGTCATTAGTAAGCCCGTACATTTCACAGTCCACTTGCAATA<br>ATTCTGCAATGGCCTGTAGTCCCCCTAATTTAAAA | 1502 |
| | GAAATGTACGGGCTTAC | 1503 |
| | GTAAGCCCGTACATTTC | 1504 |
| Adenomatous polyposis coli<br>Arg499Term<br>CGA-TGA | TTGCAAGTGGACTGTGAAATGTATGGGCTTACTAATGACCACT<br>ACAGTATTACACTAAGACGATATGCTGGAATGGCTTTGACAAA<br>CTTGACTTTTGGAGATGTAGCCAACAAGGTATGTT | 1505 |
| | AACATACCTTGTTGGCTACATCTCCAAAAGTCAAGTTTGTCAA<br>AGCCATTCCAGCATATCGTCTTAGTGTAATACTGTAGTGGTCA<br>TTAGTAAGCCCATACATTTCACAGTCCACTTGCAA | 1506 |
| | CACTAAGACGATATGCT | 1507 |
| | AGCATATCGTCTTAGTG | 1508 |
| Adenomatous polyposis coli<br>Tyr500Term<br>TAT-TAG | AGTGGACTGTGAAATGTATGGGCTTACTAATGACCACTACAGT<br>ATTACACTAAGACGATATGCTGGAATGGCTTTGACAAACTTGA<br>CTTTTGGAGATGTAGCCAACAAGGTATGTTTTTAT | 1509 |
| | ATAAAAACATACCTTGTTGGCTACATCTCCAAAAGTCAAGTTTG<br>TCAAAGCCATTCCAGCATATCGTCTTAGTGTAATACTGTAGTG<br>GTCATTAGTAAGCCCATACATTTCACAGTCCACT | 1510 |
| | AGACGATATGCTGGAAT | 1511 |
| | ATTCCAGCATATCGTCT | 1512 |
| Adenomatous polyposis coli<br>Lys586Term<br>AAA-TAA | GACAAATTCCAACTCTAATTAGATGACCCATATTCTGTTTCTTA<br>CTAGGAATCAACCCTCAAAAGCGTATTGAGTGCCTTATGGAAT<br>TTGTCAGCACATTGCACTGAGAATAAAGCTGATA | 1513 |
| | TATCAGCTTTATTCTCAGTGCAATGTGCTGACAAATTCCATAA<br>GGCACTCAATACGCTTTTGAGGGTTGATTCCTAGTAAGAAACA<br>GAATATGGGTCATCTAATTAGAGTTGGAATTTGTC | 1514 |
| | CAACCCTCAAAAGCGTA | 1515 |
| | TACGCTTTTGAGGGTTG | 1516 |
| Adenomatous polyposis coli<br>Leu592Term<br>TTA-TGA | TAGATGACCCATATTCTGTTTCTTACTAGGAATCAACCCTCAAA<br>AGCGTATTGAGTGCCTTATGGAATTTGTCAGCACATTGCACTG<br>AGAATAAAGCTGATATATGTGCTGTAGATGGTGC | 1517 |
| | GCACCATCTACAGCACATATATCAGCTTTATTCTCAGTGCAAT | 1518 |

TABLE 18-continued

APC Mutations and Genome-Correcting Oligos

| Clinical Phenotype & Mutation | Correcting Oligos | SEQ ID NO: |
|---|---|---|
| | GTGCTGACAAATTCCATAAGGCACTCAATACGCTTTTGAGGGT TGATTCCTAGTAAGAAACAGAATATGGGTCATCTA | |
| | GAGTGCCTTATGGAATT | 1519 |
| | AATTCCATAAGGCACTC | 1520 |
| Adenomatous polyposis coli Trp593Term TGG-TAG | ATGACCCATATTCTGTTTCTTACTAGGAATCAACCCTCAAAAG CGTATTGAGTGCCTTATGGAATTTGTCAGCACATTGCACTGAG AATAAAGCTGATATATGTGCTGTAGATGGTGCACT | 1521 |
| | AGTGCACCATCTACAGCACATATATCAGCTTTATTCTCAGTGC AATGTGCTGACAAATTCCATAAGGCACTCAATACGCTTTTGAG GGTTGATTCCTAGTAAGAAACAGAATATGGGTCAT | 1522 |
| | TGCCTTATGGAATTTGT | 1523 |
| | ACAAATTCCATAAGGCA | 1524 |
| Adenomatous polyposis coli Trp593Term TGG-TGA | TGACCCATATTCTGTTTCTTACTAGGAATCAACCCTCAAAAGC GTATTGAGTGCCTTATGGAATTTGTCAGCACATTGCACTGAGA ATAAAGCTGATATATGTGCTGTAGATGGTGCACTT | 1525 |
| | AAGTGCACCATCTACAGCACATATATCAGCTTTATTCTCAGTG CAATGTGCTGACAAATTCCATAAGGCACTCAATACGCTTTTGA GGGTTGATTCCTAGTAAGAAACAGAATATGGGTCA | 1526 |
| | GCCTTATGGAATTTGTC | 1527 |
| | GACAAATTCCATAAGGC | 1528 |
| Adenomatous polyposis coli Tyr622Term TAC-TAA | TAAAGCTGATATATGTGCTGTAGATGGTGCACTTGCATTTTTG GTTGGCACTCTTACTTACCGGAGCCAGACAAACACTTTAGCC ATTATTGAAAGTGGAGGTGGGATATTACGGAATGTG | 1529 |
| | CACATTCCGTAATATCCCACCTCCACTTTCAATAATGGCTAAA GTGTTTGTCTGGCTCCGGTAAGTAAGAGTGCCAACCAAAAAT GCAAGTGCACCATCTACAGCACATATATCAGCTTTA | 1530 |
| | CTTACTTACCGGAGCCA | 1531 |
| | TGGCTCCGGTAAGTAAG | 1532 |
| Adenomatous polyposis coli Gln625Term CAG-TAG | GATATATGTGCTGTAGATGGTGCACTTGCATTTTTGGTTGGCA CTCTTACTTACCGGAGCCAGACAAACACTTTAGCCATTATTGA AAGTGGAGGTGGGATATTACGGAATGTGTCCAGCT | 1533 |
| | AGCTGGACACATTCCGTAATATCCCACCTCCACTTTCAATAAT GGCTAAAGTGTTTGTCTGGCTCCGGTAAGTAAGAGTGCCAAC CAAAAATGCAAGTGCACCATCTACAGCACATATATC | 1534 |
| | ACCGGAGCCAGACAAAC | 1535 |
| | GTTTGTCTGGCTCCGGT | 1536 |
| Adenomatous polyposis coli Leu629Term TTA-TAA | TAGATGGTGCACTTGCATTTTTGGTTGGCACTCTTACTTACCG GAGCCAGACAAACACTTTAGCCATTATTGAAAGTGGAGGTGG GATATTACGGAATGTGTCCAGCTTGATAGCTACAAA | 1537 |
| | TTTGTAGCTATCAAGCTGGACACATTCCGTAATATCCCACCTC CACTTTCAATAATGCTAAAGTGTTTGTCTGGCTCCGGTAAGT AAGAGTGCCAACCAAAAATGCAAGTGCACCATCTA | 1538 |
| | AAACACTTTTAGCCATTA | 1539 |
| | TAATGGCTAAAGTGTTT | 1540 |
| Adenomatous polyposis coli Glu650Term GAG-TAG | GCCATTATTGAAAGTGGAGGTGGGATATTACGGAATGTGTCC AGCTTGATAGCTACAAATGAGGACCACAGGTATATATAGAGTT TTATATTACTTTTAAAGTACAGAATTCATACTCTCA | 1541 |
| | TGAGAGTATGAATTCTGTACTTTAAAAGTAATATAAAACTCTAT ATATACCTGTGGTCCTCATTTGTAGCTATCAAGCTGGACACAT TCCGTAATATCCCACCTCCACTTTCAATAATGGCT | 1542 |
| | CTACAAATGAGGACCAC | 1543 |
| | GTGGTCCTCATTTGTAG | 1544 |
| Adenomatous polyposis coli Trp699Term TGG-TGA | TGCATGTGGAACTTTGTGGAATCTCTCAGCAAGAAATCCTAAA GACCAGGAAGCATTATGGGACATGGGGCAGTTAGCATGCTC AAGAACCTCATTCATTCAAAGCACAAAATGATTGCT | 1545 |
| | AGCAATCATTTTGTGCTTTGAATGAATGAGGTTCTTGAGCATG CTAACTGCCCCCATGTCCCATAATGCTTCCTGGTCTTTAGGAT TTCTTGCTGAGAGATTCCACAAAGTTCCACATGCA | 1546 |
| | GCATTATGGGACATGGG | 1547 |
| | CCCATGTCCCATAATGC | 1548 |
| Adenomatous polyposis coli Ser713Term TCA-TGA | AAGACCAGGAAGCATTATGGGACATGGGGCAGTTAGCATGC TCAAGAACCTCATTCATTCAAAGCACAAAATGATTGCTATGGG AAGTGCTGCAGCTTTAAGGAATCTCATGGCAAATAG | 1549 |
| | CTATTTGCCATGAGATTCCTTAAAGCTGCAGCACTTCCCATAG CAATCATTTTGTGCTTTGAATGAATGAGGTTCTTGAGCATGCT AACTGCCCCCATGTCCCATAATGCTTCCTGGTCTT | 1550 |
| | CATTCATTCAAAGCACA | 1551 |
| | TGTGCTTTGAATGAATG | 1552 |
| Adenomatous polyposis coli Ser722Gly AGT-GGT | GGGGCAGTTAGCATGCTCAAGAACCTCATTCATTCAAAGCAC AAAATGATTGCTATGGGAAGTGCTGCAGCTTTAAGGAATCTCA TGGCAAATAGGCCTGCGAAGTACAAGGATGCCAATA | 1553 |
| | TATTGGCATCCTTGTACTTCGCAGGCCTATTTGCCATGAGATT CCTTAAAGCTGCAGCACTTCCCATAGCAATCATTTTGTGCTTT GAATGAATGAGGTTCTTGAGCATGCTAACTGCCCC | 1554 |

TABLE 18-continued

APC Mutations and Genome-Correcting Oligos

| Clinical Phenotype & Mutation | Correcting Oligos | SEQ ID NO: |
|---|---|---|
| | CTATGGGAAGTGCTGCA | 1555 |
| | TGCAGCACTTCCCATAG | 1556 |
| Adenomatous polyposis coli Leu764Term TTA-TAA | TCTCCTGGCTCAGCTTGCCATCTCTTCATGTTAGGAAACAAAA AGCCCTAGAAGCAGAATTAGATGCTCAGCACTTATCAGAAACT TTTGACAATATAGACAATTTAAGTCCCAAGGCATC | 1557 |
| | GATGCCTTGGGACTTAAATTGTCTATATTGTCAAAAGTTTCTGA TAAGTGCTGAGCATCTAATTCTGCTTCTAGGGCTTTTTGTTTC CTAACATGAAGAGATGGCAAGCTGAGCCAGGAGA | 1558 |
| | AGCAGAATTAGATGCTC | 1559 |
| | GAGCATCTAATTCTGCT | 1560 |
| Adenomatous polyposis coli Ser784Thr TCT-ACT | TTAGATGCTCAGCACTTATCAGAAACTTTTGACAATATAGACAA TTTAAGTCCCAAGGCATCTCATCGTAGTAAGCAGAGACACAG CAAGTCTCTATGGTGATTATGTTTTGACACCATC | 1561 |
| | GATGGTGTCAAAAACATAATCACCATAGAGACTTGCTGTGTCT CTGCTTACTACGATGAGATGCCTTGGGACTTAAATTGTCTATA TTGTCAAAAGTTTCTGATAAGTGCTGAGCATCTAA | 1562 |
| | CCAAGGCATCTCATCGT | 1563 |
| | ACGATGAGATGCCTTGG | 1564 |
| Adenomatous polyposis coli Arg805Term CGA-TGA | CTCATCGTAGTAAGCAGAGACACAGCAAGTCTCTATGGTGATT ATGTTTTTGACACCAATCGACATGATGATAATAGGTCAGACAT TTTAATACTGGCACATGACTGTCCTTTCACCATAT | 1565 |
| | ATATGGTGAAAGGACAGTCATGTGCCAGTATTAAAATGTCTGA CCTATTATCATCATGTCGATTGGTGTCAAAAACATAATCACCAT AGAGACTTGCTGTGTCTCTGCTTACTACGATGAG | 1566 |
| | ACACCAATCGACATGAT | 1567 |
| | ATCATGTCGATTGGTGT | 1568 |
| Adenomatous polyposis coli Gln879Term CAG-TAG | GGTCTAGGCAACTACCATCCAGCAACAGAAAATCCAGGAACT TCTTCAAAGCGAGGTTTGCAGATCTCCACCACTGCAGCCCAG ATTGCCAAAGTCATGGAAGAAGTGTCAGCCATTCATA | 1569 |
| | TATGAATGGCTGACACTTCTTCCATGACTTTGGCAATCTGGGC TGCAGTGGTGGAGATCTGCAAACCTCGCTTTGAAGAAGTTCC TGGATTTTCTGTTGCTGGATGGTAGTTGCCTAGACC | 1570 |
| | GAGGTTTGCAGATCTCC | 1571 |
| | GGAGATCTGCAAACCTC | 1572 |
| Adenomatous polyposis coli Ser932Term TCA-TAA | TACATTGTGTGACAGATGAGAGAAATGCACTTAGAAGAAGCTC TGCTGCCCATACACATTCAAACACTTACAATTTCACTAAGTCG GAAAATTCAAATAGGACATGTTCTATGCCTTATGC | 1573 |
| | GCATAAGGCATAGAACATGTCCTATTTGAATTTTCCGACTTAG TGAAATTGTAAGTGTTTGAATGTGTATGGGCAGCAGAGCTTCT TCTAAGTGCATTTCTCTCATCTGTCACACAATGTA | 1574 |
| | TACACATTCAAACACTT | 1575 |
| | AAGTGTTTGAATGTGTA | 1576 |
| Adenomatous polyposis coli Ser932Term TCA-TGA | TACATTGTGTGACAGATGAGAGAAATGCACTTAGAAGAAGCTC TGCTGCCCATACACATTCAAACACTTACAATTTCACTAAGTCG GAAAATTCAAATAGGACATGTTCTATGCCTTATGC | 1577 |
| | GCATAAGGCATAGAACATGTCCTATTTGAATTTTCCGACTTAG TGAAATTGTAAGTGTTTGAATGTGTATGGGCAGCAGAGCTTCT TCTAAGTGCATTTCTCTCATCTGTCACACAATGTA | 1578 |
| | TACACATTCAAACACTT | 1579 |
| | AAGTGTTTGAATGTGTA | 1580 |
| Adenomatous polyposis coli Tyr935Term TAC-TAG | GACAGATGAGAGAAATGCACTTAGAAGAAGCTCTGCTGCCCA TACACATTCAAACACTTACAATTTCACTAAGTCGGAAAATTCAA ATAGGACATGTTCTATGCCTTATGCCAAATTAGAA | 1581 |
| | TTCTAATTTGGCATAAGGCATAGAACATGTCCTATTTGAATTTT CCGACTTAGTGAAATTGTAAGTGTTTGAATGTGTATGGGCAGC AGAGCTTCTTCTAAGTGCATTTCTCTCATCTGTC | 1582 |
| | AACACTTACAATTTCAC | 1583 |
| | GTGAAATTGTAAGTGTT | 1584 |
| Adenomatous polyposis coli Tyr935Term TAC-TAA | GACAGATGAGAGAAATGCACTTAGAAGAAGCTCTGCTGCCCA TACACATTCAAACACTTACAATTTCACTAAGTCGGAAAATTCAA ATAGGACATGTTCTATGCCTTATGCCAAATTAGAA | 1585 |
| | TTCTAATTTGGCATAAGGCATAGAACATGTCCTATTTGAATTTT CCGACTTAGTGAAATTGTAAGTGTTTGAATGTGTATGGGCAGC AGAGCTTCTTCTAAGTGCATTTCTCTCATCTGTC | 1586 |
| | AACACTTACAATTTCAC | 1587 |
| | GTGAAATTGTAAGTGTT | 1588 |
| Adenomatous polyposis coli Tyr1000Term TAC-TAA | ACCCTCGATTGAATCCTATTCTGAAGATGATGAAAGTAAGTTTT GCAGTTATGGTCAATACCCAGCCGACCTAGCCCATAAAATACA TAGTGCAAATCATATGGATGATAATGATGGAGAA | 1589 |
| | TTCTCCATCATTATCATCCATATGATTTGCACTATGTATTTTAT GGGCTAGGTCGGCTGGGTATTGACCATAACTGCAAAACTTAC TTTCATCATCTTCAGAATAGGATTCAATCGAGGGT | 1590 |
| | GGTCAATACCCAGCCGA | 1591 |
| | TCGGCTGGGTATTGACC | 1592 |

TABLE 18-continued

APC Mutations and Genome-Correcting Oligos

| Clinical Phenotype & Mutation | Correcting Oligos | SEQ ID NO: |
|---|---|---|
| Adenomatous polyposis coli Glu1020Term GAA-TAA | TACCCAGCCGACCTAGCCCATAAAATACATAGTGCAAATCATA | 1593 |
| | TGGATGATAATGATGGAGAACTAGATACACCAATAAATTATAG | |
| | TCTTAAATATTCAGATGAGCAGTTGAACTCTGGAA | |
| | TTCCAGAGTTCAACTGCTCATCTGAATATTTAAGACTATAATTT | 1594 |
| | ATTGGTGTATCTAGTTCTCCATCATTATCATCCATATGATTTGC | |
| | ACTATGTATTTTATGGGCTAGGTCGGCTGGGTA | |
| | ATGATGGAGAACTAGAT | 1595 |
| | ATCTAGTTCTCCATCAT | 1596 |
| Adenomatous polyposis coli Ser1032Term TCA-TAA | ATGAAACCCTCGATTGAATCCTATTCTGAAGATGATGAAAGTA | 1597 |
| | AGTTTTGCAGTTATGGTCAATACCCAGCCGACCTAGCCCATAA | |
| | AATACATAGTGCAAATCATATGGATGATAATGATG | |
| | CATCATTATCATCCATATGATTTGCACTATGTATTTTATGGGCT | 1598 |
| | AGGTCGGCTGGGTATTGACCATAACTGCAAAACTTACTTTCAT | |
| | CATCTTCAGAATAGGATTCAATCGAGGGTTTCAT | |
| | GTTATGGTCAATACCCA | 1599 |
| | TGGGTATTGACCATAAC | 1600 |
| Adenomatous polyposis coli Gln1041Term CAA-TAA | TGAAGATGATGAAAGTAAGTTTTGCAGTTATGGTCAATACCCA | 1601 |
| | GCCGACCTAGCCCATAAAATACATAGTGCAAATCATATGGATG | |
| | ATAATGATGGAGAACTAGATACACCAATAAATTAT | |
| | ATAATTTATTGGTGTATCTAGTTCTCCATCATTATCATCCATAT | 1602 |
| | GATTTGCACTATGTATTTTATGGGCTAGGTCGGCTGGGTATTG | |
| | ACCATAACTGCAAAACTTACTTTCATCATCTTCA | |
| | GCCCATAAAATACATAG | 1603 |
| | CTATGTATTTTATGGGC | 1604 |
| Adenomatous polyposis coli Gln1045Term CAG-TAG | ATAAATTATAGTCTTAAATATTCAGATGAGCAGTTGAACTCTGG | 1605 |
| | AAGGCAAAGTCCTTCACAGAATGAAAGATGGGCAAGACCCAA | |
| | ACACATAATAGAAGATGAAATAAAACAAAGTGAGC | |
| | GCTCACTTTGTTTTATTTCATCTTCTATTATGTGTTTGGGTCTT | 1606 |
| | GCCCATCTTTCATTCTGTGAAGGACTTTGCCTTCCAGAGTTCA | |
| | ACTGCTCATCTGAATATTTAAGACTATAATTTAT | |
| | GTCCTTCACAGAATGAA | 1607 |
| | TTCATTCTGTGAAGGAC | 1608 |
| Adenomatous polyposis coli Gln1067Term CAA-TAA | GAAAGATGGGCAAGACCCAAACACATAATAGAAGATGAAATAA | 1609 |
| | AACAAAGTGAGCAAAGACAATCAAGGAATCAAAGTACAACTTA | |
| | TCCTGTTTATACTGAGAGCACTGATGATAAACACC | |
| | GGTGTTTATCATCAGTGCTCTCAGTATAAACAGGATAAGTTGT | 1610 |
| | ACTTTGATTCCTTGATTGTCTTTGCTCACTTTGTTTTATTTCATC | |
| | TTCTATTATGTGTTTGGGTCTTGCCCATCTTTC | |
| | AGCAAAGACAATCAAGG | 1611 |
| | CCTTGATTGTCTTTGCT | 1612 |
| Adenomatous polyposis coli Tyr1075Term TAT-TAG | AATAGAAGATGAAATAAAACAAAGTGAGCAAAGACAATCAAGG | 1613 |
| | AATCAAAGTACAACTTATCCTGTTTATACTGAGAGCACTGATG | |
| | ATAAACACCTCAAGTTCCAACCACATTTTGGACAG | |
| | CTGTCCAAAATGTGGTTGGAACTTGAGGTGTTTATCATCAGTG | 1614 |
| | CTCTCAGTATAAACAGGATAAGTTGTACTTTGATTCCTTGATTG | |
| | TCTTTGCTCACTTTGTTTTATTTCATCTTCTATT | |
| | ACAACTTATCCTGTTTA | 1615 |
| | TAAACAGGATAAGTTGT | 1616 |
| Adenomatous polyposis coli Tyr1102Term TAC-TAG | TGATGATAAACACCTCAAGTTCCAACCACATTTTGGACAGCAG | 1617 |
| | GAATGTGTTTCTCCATACAGGTCACGGGGAGCCAATGGTTCA | |
| | GAAACAAATCGAGTGGGTTCTAATCATGGAATTAAT | |
| | ATTAATTCCATGATTAGAACCCACTCGATTTGTTTCTGAACCAT | 1618 |
| | TGGCTCCCCGTGACCTGTATGGAGAAACACATTCCTGCTGTC | |
| | CAAAATGTGGTTGGAACTTGAGGTGTTTATCATCA | |
| | TCTCCATACAGGTCACG | 1619 |
| | CGTGACCTGTATGGAGA | 1620 |
| Adenomatous polyposis coli Ser1110Term TCA-TGA | AACCACATTTTGGACAGCAGGAATGTGTTTCTCCATACAGGTC | 1621 |
| | ACGGGGAGCCAATGGTTCAGAAACAAATCGAGTGGGTTCTAA | |
| | TCATGGAATTAATCAAAATGTAAGCCAGTCTTTGTG | |
| | CACAAAGACTGGCTTACATTTTGATTAATTCCATGATTAGAACC | 1622 |
| | CACTCGATTTGTTTCTGAACCATTGGCTCCCCGTGACCTGTAT | |
| | GGAGAAACACATTCCTGCTGTCCAAAATGTGGTT | |
| | CAATGGTTCAGAAACAA | 1623 |
| | TTGTTTCTGAACCATTG | 1624 |
| Adenomatous polyposis coli Arg1114Term CGA-TGA | GGACAGCAGGAATGTGTTTCTCCATACAGGTCACGGGGAGCC | 1625 |
| | AATGGTTCAGAAACAAATCGAGTGGGTTCTAATCATGGAATTA | |
| | ATCAAAATGTAAGCCAGTCTTTGTGTCAAGAAGATG | |
| | CATCTTCTTGACACAAAGACTGGCTTACATTTTGATTAATTCCA | 1626 |
| | TGATTAGAACCCACTCGATTTGTTTCTGAACCATTGGCTCCCC | |
| | GTGACCTGTATGGAGAAACACATTCCTGCTGTCC | |
| | AAACAAATCGAGTGGGT | 1627 |
| | ACCCACTCGATTTGTTT | 1628 |
| Adenomatous polyposis coli | GGGTTCTAATCATGGAATTAATCAAAATGTAAGCCAGTCTTTG | 1629 |
| | TGTCAAGAAGATGACTATGAAGATGATAAGCCTACCAATTATA | |

TABLE 18-continued

APC Mutations and Genome-Correcting Oligos

| Clinical Phenotype & Mutation | Correcting Oligos | SEQ ID NO: |
|---|---|---|
| Tyr1135Term TAT-TAG | GTGAACGTTACTCTGAAGAAGAACAGCATGAAGAA TTCTTCATGCTGTTCTTCTTCAGAGTAACGTTCACTATAATTGG TAGGCTTATCATCTTCATAGTCATCTTCTTGACACAAAGACTG GCTTACATTTTGATTAATTCCATGATTAGAACCC | 1630 |
| | GATGACTATGAAGATGA | 1631 |
| | TCATCTTCATAGTCATC | 1632 |
| Adenomatous polyposis coli Gln1152Term CAG-TAG | GAAGATGACTATGAAGATGATAAGCCTACCAATTATAGTGAAC GTTACTCTGAAGAAGAACAGCATGAAGAAGAAGAGAGACCAA CAAATTATAGCATAAAATATAATGAAGAGAAACGTC | 1633 |
| | GACGTTTCTCTTCATTATATTTTATGCTATAATTTGTTGGTCTCT CTTCTTCTTCATGCTGTTCTTCTTCAGAGTAACGTTCACTATAA TTGGTAGGCTTATCATCTTCATAGTCATCTTC | 1634 |
| | AAGAAGAACAGCATGAA | 1635 |
| | TTCATGCTGTTCTTCTT | 1636 |
| Adenomatous polyposis coli Gln1175Term CAG-TAG | GAAGAAGAGAGACCAACAAATTATAGCATAAAATATAATGAAG AGAAACGTCATGTGGATCAGCCTATTGATTATAGTTTAAAATAT GCCACAGATATTCCTTCATCACAGAAACAGTCAT | 1637 |
| | ATGACTGTTTCTGTGATGAAGGAATATCTGTGGCATATTTTAAA CTATAATCAATAGGCTGATCCACATGACGTTTCTCTTCATTATA TTTTATGCTATAATTTGTTGGTCTCTCTTCTTC | 1638 |
| | ATGTGGATCAGCCTATT | 1639 |
| | AATAGGCTGATCCACAT | 1640 |
| Adenomatous polyposis coli Pro1176Leu CCT-CTT | AAGAGAGACCAACAAATTATAGCATAAAATATAATGAAGAGAA ACGTCATGTGGATCAGCCTATTGATTATAGTTTAAAATATGCCA CAGATATTCCTTCATCACAGAAACAGTCATTTTC | 1641 |
| | GAAAATGACTGTTTCTGTGATGAAGGAATATCTGTGGCATATT TTAAACTATAATCAATAGGCTGATCCACATGACGTTTCTCTTCA TTATATTTTATGCTATAATTTGTTGGTCTCTCTT | 1642 |
| | GGATCAGCCTATTGATT | 1643 |
| | AATCAATAGGCTGATCC | 1644 |
| Adenomatous polyposis coli Ala1184Pro GCC-CCC | ATAAAATATAATGAAGAGAAACGTCATGTGGATCAGCCTATTG ATTATAGTTTAAAATATGCCACAGATATTCCTTCATCACAGAAA CAGTCATTTTCATTCTCAAAGAGTTCATCTGGAC | 1645 |
| | GTCCAGATGAACTCTTTGAGAATGAAAATGACTGTTTCTGTGA TGAAGGAATATCTGTGGCATATTTTAAACTATAATCAATAGGCT GATCCACATGACGTTTCTCTTCATTATATTTTAT | 1646 |
| | TAAAATATGCCACAGAT | 1647 |
| | ATCTGTGGCATATTTTA | 1648 |
| Adenomatous polyposis coli Ser1194Term TCA-TGA | ATCAGCCTATTGATTATAGTTTAAAATATGCCACAGATATTCCT TCATCACAGAAACAGTCATTTTCATTCTCAAAGAGTTCATCTG GACAAAGCAGTAAAACCGAACATATGTCTTCAAG | 1649 |
| | CTTGAAGACATATGTTCGGTTTTACTGCTTTGTCCAGATGAAC TCTTTGAGAATGAAAATGACTGTTTCTGTGATGAAGGAATATCT GTGGCATATTTTAAACTATAATCAATAGGCTGAT | 1650 |
| | GAAACAGTCATTTTCAT | 1651 |
| | ATGAAAATGACTGTTTC | 1652 |
| Adenomatous polyposis coli Ser1198Term TCA-TGA | ATTATAGTTTAAAATATGCCACAGATATTCCTTCATCACAGAAA CAGTCATTTTCATTCTCAAAGAGTTCATCTGGACAAAGCAGTA AAACCGAACATATGTCTTCAAGCAGTGAGAATAC | 1653 |
| | GTATTCTCACTGCTTGAAGACATATGTTCGGTTTTACTGCTTTG TCCAGATGAACTCTTTGAGAATGAAAATGACTGTTTCTGTGAT GAAGGAATATCTGTGGCATATTTTAAACTATAAT | 1654 |
| | TTCATTCTCAAAGAGTT | 1655 |
| | AACTCTTTGAGAATGAA | 1656 |
| Adenomatous polyposis coli Gln1228Term CAG-TAG | ACCGAACATATGTCTTCAAGCAGTGAGAATACGTCCACACCTT CATCTAATGCCAAGAGGCAGAATCAGCTCCATCCAGTTCTGC ACAGAGTAGAAGTGGTCAGCCTCAAAGGCTGCCACT | 1657 |
| | AGTGGCAGCCTTTGAGGCTGACCACTTCTACTCTGTGCAGAA CTGGATGGAGCTGATTCTGCCTCTTGGCATTAGATGAAGGTG TGGACGTATTCTCACTGCTTGAAGACATATGTTCGGT | 1658 |
| | CCAAGAGGCAGAATCAG | 1659 |
| | CTGATTCTGCCTCTTGG | 1660 |
| Adenomatous polyposis coli Gln1230Term CAG-TAG | CATATGTCTTCAAGCAGTGAGAATACGTCCACACCTTCATCTA ATGCCAAGAGGCAGAATCAGCTCCATCCAGTTCTGCACAGAG TAGAAGTGGTCAGCCTCAAAGGCTGCCACTTGCAAG | 1661 |
| | CTTGCAAGTGGCAGCCTTTGAGGCTGACCACTTCTACTCTGT GCAGAACTGGATGGAGCTGATTCTGCCTCTTGGCATTAGATG AAGGTGTGGACGTATTCTCACTGCTTGAAGACATATG | 1662 |
| | GGCAGAATCAGCTCCAT | 1663 |
| | ATGGAGCTGATTCTGCC | 1664 |
| Adenomatous polyposis coli Cys1249Term TGC-TGA | TCAGCTCCATCCAAGTTCTGCACAGAGTAGAAGTGGTCAGCC TCAAAAGGCTGCCACTTGCAAAGTTTCTTCTATTAACCAAGAA ACAATACAGACTTATTGTGTAGAAGATACTCCAATA | 1665 |
| | TATTGGAGTATCTTCTACACAATAAGTCTGTATTGTTTCTTGGT | 1666 |

TABLE 18-continued

APC Mutations and Genome-Correcting Oligos

| Clinical Phenotype & Mutation | Correcting Oligos | SEQ ID NO: |
|---|---|---|
| | TAATAGAAGAAACTTTGCAAGTGGCAGCCTTTTGAGGCTGACC ACTTCTACTCTGTGCAGAACTTGGATGGAGCTGA | |
| | GCCACTTGCAAAGTTTC | 1667 |
| | GAAACTTTGCAAGTGGC | 1668 |
| Adenomatous polyposis coli Cys1270Term TGT-TGA | AGTTTCTTCTATTAACCAAGAAACAATACAGACTTATTGTGTAG AAGATACTCCAATATGTTTTTCAAGATGTAGTTCATTATCATCT TTGTCATCAGCTGAAGATGAAATAGGATGTAAT | 1669 |
| | ATTACATCCTATTTCATCTTCAGCTGATGACAAAGATGATAATG AACTACATCTTGAAAAACATATTGGAGTATCTTCTACACAATAA GTCTGTATTGTTTCTTGGTTAATAGAAGAAACT | 1670 |
| | CCAATATGTTTTTCAAG | 1671 |
| | CTTGAAAAACATATTGG | 1672 |
| Adenomatous polyposis coli Ser1276Term TCA-TGA | AAGAAACAATACAGACTTATTGTGTAGAAGATACTCCAATATGT TTTTCAAGATGTAGTTCATTATCATCTTTGTCATCAGCTGAAGA TGAAATAGGATGTAATCAGACGACACAGGAAGC | 1673 |
| | GCTTCCTGTGTCGTCTGATTACATCCTATTTCATCTTCAGCTG ATGACAAAGATGATAATGAACTACATCTTGAAAAACATATTGGA GTATCTTCTACACAATAAGTCTGTATTGTTTCTT | 1674 |
| | ATGTAGTTCATTATCAT | 1675 |
| | ATGATAATGAACTACAT | 1676 |
| Adenomatous polyposis coli Glu1286Term GAA-TAA | GATACTCCAATATGTTTTTCAAGATGTAGTTCATTATCATCTTT GTCATCAGCTGAAGATGAAATAGGATGTAATCAGACGACACA GGAAGCAGATTCTGCTAATACCCTGCAAATAGCAG | 1677 |
| | CTGCTATTTGCAGGGTATTAGCAGAATCTGCTTCCTGTGTCGT CTGATTACATCCTATTTCATCTTCAGCTGATGACAAAGATGATA ATGAACTACATCTTGAAAAACATATTGGAGTATC | 1678 |
| | CTGAAGATGAAATAGGA | 1679 |
| | TCCTATTTCATCTTCAG | 1680 |
| Adenomatous polyposis coli Gln1294Term CAG-TAG | TGTAGTTCATTATCATCTTTGTCATCAGCTGAAGATGAAATAGG ATGTAATCAGACGACACAGGAAGCAGATTCTGCTAATACCCTG CAAATAGCAGAAATAAAAGAAAAGATTGGAACTA | 1681 |
| | TAGTTCCAATCTTTTCTTTTATTTCTGCTATTTGCAGGGTATTA GCAGAATCTGCTTCCTGTGTCGTCTGATTACATCCTATTTCAT CTTCAGCTGATGACAAAGATGATAATGAACTACA | 1682 |
| | AGACGACACAGGAAGCA | 1683 |
| | TGCTTCCTGTGTCGTCT | 1684 |
| Predisposition to, association with, colorectal cancer Ile1307Lys ATA-AAA | TAGGATGTAATCAGACGACACAGGAAGCAGATTCTGCTAATAC CCTGCAAATAGCAGAAATAAAAGAAAAGATTGGAACTAGGTCA GCTGAAGATCCTGTGAGCGAAGTTCCAGCAGTGTC | 1685 |
| | GACACTGCTGGAACTTCGCTCACAGGATCTTCAGCTGACCTA GTTCCAATCTTTTCTTTTATTTCTGCTATTTGCAGGGTATTAGC AGAATCTGCTTCCTGTGTCGTCTGATTACATCCTA | 1686 |
| | AGCAGAAATAAAAGAAA | 1687 |
| | TTTCTTTTATTTCTGCT | 1688 |
| Adenomatous polyposis coli Glu1309Term GAA-TAA | CCAAGAAACAATACAGACTTATTGTGTAGAAGATACTCCAATA TGTTTTTCAAGATGTAGTTCATTATCATCTTTGTCATCAGCTGA AGATGAAATAGGATGTAATCAGACGACACAGGAA | 1689 |
| | TTCCTGTGTCGTCTGATTACATCCTATTTCATCTTCAGCTGATG ACAAAGATGATAATGAACTACATCTTGAAAAACATATTGGAGTA TCTTCTACACAATAAGTCTGTATTGTTTCTTGG | 1690 |
| | AGATGTAGTTCATTATC | 1691 |
| | GATAATGAACTACATCT | 1692 |
| Predisposition to Colorectal Cancer Glu1317Gln GAA-CAA | GATTCTGCTAATACCCTGCAAATAGCAGAAATAAAAGAAAAGA TTGGAACTAGGTCAGCTGAAGATCCTGTGAGCGAAGTTCCAG CAGTGTCACAGCACCCTAGAACCAAATCCAGCAGAC | 1693 |
| | GTCTGCTGGATTTGGTTCTAGGGTGCTGTGACACTGCTGGAA CTTCGCTCACAGGATCTTCAGCTGACCTAGTTCCAATCTTTTC TTTTATTTCTGCTATTTGCAGGGTATTAGCAGAATC | 1694 |
| | GGTCAGCTGAAGATCCT | 1695 |
| | AGGATCTTCAGCTGACC | 1696 |
| Adenomatous polyposis coli Gln1328Term CAG-TAG | AAAGAAAAGATTGGAACTAGGTCAGCTGAAGATCCTGTGAGC GAAGTTCCAGCAGTGTCACAGCACCCTAGAACCAAATCCAGC AGACTGCAGGGTTCTAGTTTATCTTCAGAATCAGCCA | 1697 |
| | TGGCTGATTCTGAAGATAAACTAGAACCCTGCAGTCTGCTGG ATTTGGTTCTAGGGTGCTGTGACACTGCTGGAACTTCGCTCA CAGGATCTTCAGCTGACCTAGTTCCAATCTTTTCTTT | 1698 |
| | CAGTGTCACAGCACCCT | 1699 |
| | AGGGTGCTGTGACACTG | 1700 |
| Adenomatous polyposis coli Gln1338Term CAG-TAG | GATCCTGTGAGCGAAGTTCCAGCAGTGTCACAGCACCCTAGA ACCAAATCCAGCAGACTGCAGGGTTCTAGTTTATCTTCAGAAT CAGCCAGGCACAAAGCTGTTGAATTTTCTTCAGGAG | 1701 |
| | CTCCTGAAGAAAATTCAACAGCTTTGTGCCTGGCTGATTCTGA AGATAAACTAGAACCCTGCAGTCTGCTGGATTTGGTTCTAGG GTGCTGTGACACTGCTGGAACTTCGCTCACAGGATC | 1702 |

TABLE 18-continued

APC Mutations and Genome-Correcting Oligos

| Clinical Phenotype & Mutation | Correcting Oligos | SEQ ID NO: |
|---|---|---|
| | GCAGACTGCAGGGTTCT | 1703 |
| | AGAACCCTGCAGTCTGC | 1704 |
| Adenomatous polyposis coli Leu1342Term TTA-TAA | AAGTTCCAGCAGTGTCACAGCACCCTAGAACCAAATCCAGCA GACTGCAGGGTTCTAGTTTATCTTCAGAATCAGCCAGGCACAA AGCTGTTGAATTTTCTTCAGGAGCGAAATCTCCCTC | 1705 |
| | GAGGGAGATTTCGCTCCTGAAGAAAATTCAACAGCTTTGTGC CTGGCTGATTCTGAAGATAAACTAGAACCCTGCAGTCTGCTG GATTTGGTTCTAGGGTGCTGTGACACTGCTGGAACTT | 1706 |
| | TTCTAGTTTATCTTCAG | 1707 |
| | CTGAAGATAAACTAGAA | 1708 |
| Adenomatous polyposis coli Arg1348Trp AGG-TGG | CAGCACCCTAGAACCAAATCCAGCAGACTGCAGGGTTCTAGT TTATCTTCAGAATCAGCCAGGCACAAAGCTGTTGAATTTTCTT CAGGAGCGAAATCTCCCTCCCGAAAGTGGTGCTCAG | 1709 |
| | CTGAGCACCACTTTCGGGAGGGAGATTTCGCTCCTGAAGAAA ATTCAACAGCTTTGTGCCTGGCTGATTCTGAAGATAAACTAGA ACCCTGCAGTCTGCTGGATTTGGTTCTAGGGTGCTG | 1710 |
| | AATCAGCCAGGCACAAA | 1711 |
| | TTTGTGCCTGGCTGATT | 1712 |
| Adenomatous polyposis coli Gly1357Term GGA-TGA | CTGCAGGGTTCTAGTTTATCTTCAGAATCAGCCAGGCACAAAG CTGTTGAATTTTCTTCAGGAGCGAAATCTCCCTCCCGAAAGTG GTGCTCAGACACCCCAAAGTCCACCTGAACACTAT | 1713 |
| | ATAGTGTTCAGGTGGACTTTGGGGTGTCTGAGCACCACTTTC GGGAGGGAGATTTCGCTCCTGAAGAAAATTCAACAGCTTTGT GCCTGGCTGATTCTGAAGATAAACTAGAACCCTGCAG | 1714 |
| | TTTCTTCAGGAGCGAAA | 1715 |
| | TTTCGCTCCTGAAGAAA | 1716 |
| Adenomatous polyposis coli Gln1367Term CAG-TAG | CCAGGCACAAAGCTGTTGAATTTTCTTCAGGAGCGAAATCTCC CTCCCGAAAGTGGTGCTCAGACACCCCAAAGTCCACCTGAAC ACTATGTTCAGGAGACCCCACTCATGTTTAGCAGAT | 1717 |
| | ATCTGCTAAACATGAGTGGGGTCTCCTGAACATAGTGTTCAG GTGGACTTTGGGGTGTCTGAGCACCACTTTCGGGAGGGAGAT TTCGCTCCTGAAGAAAATTCAACAGCTTTGTGCCTGG | 1718 |
| | GTGGTGCTCAGACACCC | 1719 |
| | GGGTGTCTGAGCACCAC | 1720 |
| Adenomatous polyposis coli Lys1370Term AAA-TAA | AAAGCTGTTGAATTTTCTTCAGGAGCGAAATCTCCCTCCAAAA GTGGTGCTCAGACACCCAAAAGTCCACCTGAACACTATGTTC AGGAGACCCCACTCATGTTTAGCAGATGTACTTCTG | 1721 |
| | CAGAAGTACATCTGCTAAACATGAGTGGGGTCTCCTGAACATA GTGTTCAGGTGGACTTTTGGGTGTCTGAGCACCACTTTTGGA GGGAGATTTCGCTCCTGAAGAAAATTCAACAGCTTT | 1722 |
| | AGACACCCAAAAGTCCA | 1723 |
| | TGGACTTTTGGGTGTCT | 1724 |
| Adenomatous polyposis coli Ser1392Term TCA-TAA | CACCTGAACACTATGTTCAGGAGACCCCACTCATGTTTAGCA GATGTACTTCTGTCAGTTCACTTGATAGTTTTGAGAGTCGTTC GATTGCCAGCTCCGTTCAGAGTGAACCATGCAGTGG | 1725 |
| | CCACTGCATGGTTCACTCTGAACGGAGCTGGCAATCGAACGA CTCTCAAAACTATCAAGTGAACTGACGAAGTACATCTGCTAA ACATGAGTGGGGTCTCCTGAACATAGTGTTCAGGTGG | 1726 |
| | TGTCAGTTCACTTGATA | 1727 |
| | TATCAAGTGAACTGACA | 1728 |
| Adenomatous polyposis coli Ser1392Term TCA-TGA | CACCTGAACACTATGTTCAGGAGACCCCACTCATGTTTAGCA GATGTACTTCTGTCAGTTCACTTGATAGTTTTGAGAGTCGTTC GATTGCCAGCTCCGTTCAGAGTGAACCATGCAGTGG | 1729 |
| | CCACTGCATGGTTCACTCTGAACGGAGCTGGCAATCGAACGA CTCTCAAAACTATCAAGTGAACTGACGAAGTACATCTGCTAA ACATGAGTGGGGTCTCCTGAACATAGTGTTCAGGTG | 1730 |
| | TGTCAGTTCACTTGATA | 1731 |
| | TATCAAGTGAACTGACA | 1732 |
| Adenomatous polyposis coli Glu1397Term GAG-TAG | GTTCAGGAGACCCCACTCATGTTTAGCAGATGTACTTCTGTCA GTTCACTTGATAGTTTTGAGAGTCGTTCGATTGCCAGCTCCGT TCAGAGTGAACCATGCAGTGGAATGGTAGGTGGCA | 1733 |
| | TGCCACCTACCATTCCACTGCATGGTTCACTCTGAACGGAGC TGGCAATCGAACGACTCTCAAAACTATCAAGTGAACTGACAGA AGTACATCTGCTAAACATGAGTGGGGTCTCCTGAAC | 1734 |
| | ATAGTTTTGAGAGTCGT | 1735 |
| | ACGACTCTCAAAACTAT | 1736 |
| Adenomatous polyposis coli | CAAACCATGCCACCAAGCAGAAGTAAAACACCTCCACCACCT CCTCAAACAGCTCAAACCAAGCGAGAAGTACCTAAAAATAAAG | 1737 |

TABLE 18-continued

APC Mutations and Genome-Correcting Oligos

| Clinical Phenotype & Mutation | Correcting Oligos | SEQ ID NO: |
|---|---|---|
| Lys1449Term<br>AAG-TAG | CACCTACTGCTGAAAAGAGAGAGAGTGGACCTAAGC | |
| | GCTTAGGTCCACTCTCTCTCTTTTCAGCAGTAGGTGCTTTATT<br>TTTAGGTACTTCTCGCTTGGTTTGAGCTGTTTGAGGAGGTGGT<br>GGAGGTGTTTTACTTCTGCTTGGTGGCATGGTTTG | 1738 |
| | CTCAAACCAAGCGAGAA | 1739 |
| | TTCTCGCTTGGTTTGAG | 1740 |
| Adenomatous polyposis coli<br>Arg1450Term<br>CGA-TGA | ACCATGCCACCAAGCAGAAGTAAAACACCTCCACCACCTCCT<br>CAAACAGCTCAAACCAAGCGAGAAGTACCTAAAAATAAAGCAC<br>CTACTGCTGAAAAGAGAGAGTGGACCTAAGCAAG | 1741 |
| | CTTGCTTAGGTCCACTCTCTCTCTTTTCAGCAGTAGGTGCTTT<br>ATTTTTAGGTACTTCTCGCTTGGTTTGAGCTGTTTGAGGAGGT<br>GGTGGAGGTGTTTTACTTCTGCTTGGTGGCATGGT | 1742 |
| | AAACCAAGCGAGAAGTA | 1743 |
| | TACTTCTCGCTTGGTTT | 1744 |
| Adenomatous polyposis coli<br>Ser1503Term<br>TCA-TAA | CAGATGCTGATACTTTATTACATTTTGCCACGGAAAGTACTCC<br>AGATGGATTTTCTTGTTCATCCAGCCTGAGTGCTCTGAGCCTC<br>GATGAGCCATTTATACAGAAAGATGTGGAATTAAG | 1745 |
| | CTTAATTCCACATCTTTCTGTATAAATGGCTCATCGAGGCTCA<br>GAGCACTCAGGCTGGATGAACAAGAAAATCCATCTGGAGTAC<br>TTTCCGTGGCAAAATGTAATAAAGTATCAGCATCTG | 1746 |
| | TTCTTGTTCATCCAGCC | 1747 |
| | GGCTGGATGAACAAGAA | 1748 |
| Adenomatous polyposis coli<br>Gln1529Term<br>CAG-TAG | CTGAGCCTCGATGAGCCATTTATACAGAAAGATGTGGAATTAA<br>GAATAATGCCTCCAGTTCAGGAAAATGACAATGGGAATGAAAC<br>AGAATCAGAGCAGCCTAAAGAATCAAATGAAAACC | 1749 |
| | GGTTTTCATTTGATTCTTTAGGCTGCTCTGATTCTGTTTCATTC<br>CCATTGTCATTTTCCTGAACTGGAGGCATTATTCTTAATTCCAC<br>ATCTTTCTGTATAAATGGCTCATCGAGGCTCAG | 1750 |
| | CTCCAGTTCAGGAAAAT | 1751 |
| | ATTTTCCTGAACTGGAG | 1752 |
| Adenomatous polyposis coli<br>Ser1539Term<br>TCA-TAA | ATGTGGAATTAAGAATAATGCCTCCAGTTCAGGAAAATGACAA<br>TGGGAATGAAACAGAATCAGAGCAGCCTAAAGAATCAAATGAA<br>AACCAAGAGAAAGAGGCAGAAAAAACTATTGATTC | 1753 |
| | GAATCAATAGTTTTTTCTGCCTCTTTCTCTTGGTTTTCATTTGA<br>TTCTTTAGGCTGCTCTGATTCTGTTTCATTCCCATTGTCATTTT<br>CCTGAACTGGAGGCATTATTCTTAATTCCACAT | 1754 |
| | AACAGAATCAGAGCAGC | 1755 |
| | GCTGCTCTGATTCTGTT | 1756 |
| Adenomatous polyposis coli<br>Ser1567Term<br>TCA-TGA | AAAACCAAGAGAAAGAGGCAGAAAAAACTATTGATTCTGAAAA<br>GGACCTATTAGATGATTCAGATGATGATGATATTGAAATACTA<br>GAAGAATGTATTATTTCTGCCATGCCAACAAAGTC | 1757 |
| | GACTTTGTTGGCATGGCAGAAATAATACATTCTTCTAGTATTTC<br>AATATCATCATCATCTGAATCATCTAATAGGTCCTTTTCAGAAT<br>CAATAGTTTTTTCTGCCTCTTTCTCTTGGTTTT | 1758 |
| | AGATGATTCAGATGATG | 1759 |
| | CATCATCTGAATCATCT | 1760 |
| Adenomatous polyposis coli<br>Asp1822Val<br>GAC-GTC | AGAGAGTTTTCTCAGACAACAAAGATTCAAAGAAACAGAATTT<br>GAAAAATAATTCCAAGGACTTCAATGATAAGCTCCCAAATAAT<br>GAAGATAGAGTCAGAGGAAGTTTTGCTTTTGATTC | 1761 |
| | GAATCAAAAGCAAAACTTCCTCTGACTCTATCTTCATTATTTGG<br>GAGCTTATCATTGAAGTCCTTGGAATTATTTTTCAAATTCTGTT<br>TCTTTGAATCTTTGTTGTCTGAGAAAACTCTCT | 1762 |
| | TTCCAAGGACTTCAATG | 1763 |
| | CATTGAAGTCCTTGGAA | 1764 |
| Adenomatous polyposis coli<br>Leu2839Phe<br>CTT-TTT | AAAACTGACAGCACAGAATCCAGTGGAACCCAAAGTCCTAAG<br>CGCCATTCTGGGTCTTACCTTGTGACATCTGTTTAAAAGAGAG<br>GAAGAATGAAACTAAGAAAATTCTATGTTAATTACA | 1765 |
| | TGTAATTAACATAGAATTTTCTTAGTTTCATTCTTCCTCTCTTTT<br>AAACAGATGTCACAAGGTAAGACCCAGAATGGCGCTTAGGAC<br>TTTGGGTTCCACTGGATTCTGTGCTGTCAGTTTT | 1766 |
| | GGTCTTACCTTGTGACA | 1767 |
| | TGTCACAAGGTAAGACC | 1768 |

EXAMPLE 12

Parahemophilia—Factor V Deficiency

Deficiency in clotting Factor V is associated with a lifelong predisposition to thrombosis. The disease typically manifests itself with usually mild bleeding, although bleeding times and clotting times are consistently prolonged. Individuals that are heterozygous for a mulation in Factor V have lowered levels of factor V but probably never have abnormal bleeding. A large number of alleles with a range of presenting symptoms have been identified. The attached table disclosed the correcting oligonucleotide base sequences for the Factor V oligonucleotides of the invention.

TABLE 19

Factor V Mutations and Genome-Correcting Oligos

| Clinical Phenotype & Mutation | Correcting Oligos | SEQ ID NO: |
|---|---|---|
| Factor V deficiency Ala221Val GCC-GTC | TTGACTGAATGCTTATTTTGGCCTGTGTCTCTCCCTCTTTCTCA GATATAACAGTTTGTGCCCATGACCACATCAGCTGGCATCTGC TGGGAATGAGCTCGGGGCCAGAATTATTCTCCAT | 4340 |
| | ATGGAGAATAATTCTGGCCCCGAGCTCATTCCCAGCAGATGC CAGCTGATGTGGTCATGGGCACAAACTGTTATATCTGAGAAAG AGGGAGAGACACAGGCCAAAATAAGCATTCAGTCAA | 1769 |
| | AGTTTGTGCCCATGACC | 1770 |
| | GGTCATGGGCACAAACT | 1771 |
| Thrombosis Arg306Gly AGG-GGG | TGTCCTAACTCAGCTGGGATGCAGGCTTACATTGACATTAAAA ACTGCCCAAAGAAAACCAGGAATCTTAAGAAAATAACTCGTGA GCAGAGGCGGCACATGAAGAGGTGGGAATACTTCA | 1772 |
| | TGAAGTATTCCCACCTCTTCATGTGCCGCCTCTGCTCACGAGT TATTTTCTTAAGATTCCTGGTTTTCTTTGGGCAGTTTTTAATGT CAATGTAAGCCTGCATCCCAGCTGAGTTAGGACA | 1773 |
| | AGAAAACCAGGAATCTT | 1774 |
| | AAGATTCCTGGTTTTCT | 1775 |
| Thrombosis Arg306Thr AGG-ACG | GTCCTAACTCAGCTGGGATGCAGGCTTACATTGACATTAAAAA CTGCCCAAAGAAAACCAGGAATCTTAAGAAAATAACTCGTGAG CAGAGGCGGCACATGAAGAGGTGGGAATACTTCAT | 1776 |
| | ATGAAGTATTCCCACCTCTTCATGTGCCGCCTCTGCTCACGA GTTATTTTCTTAAGATTCCCTGGTTTTCTTTGGGCAGTTTTTAAT GTCAATGTAAGCCTGCATCCCAGCTGAGTTAGGAC | 1777 |
| | GAAAACCAGGAATCTTA | 1778 |
| | TAAGATTCCCTGGTTTTC | 1779 |
| Increased Risk Thrombosis Arg485Lys AGA-AAA | CCACAGAAAATGATGCCCAGTGCTTAACAAGACCATACTACAG TGACGTGGACATCATGAAGAGACATCGCCTCTGGGCTAATAGG ACTACTTCTAATCTGTAAGAGCAGATCCCTGGACAG | 1780 |
| | CTGTCCAGGGATCTGCTCTTACAGATTAGAAGTAGTCCTATTA GCCCAGAGGCGATGTCTTCATGATGTCCACGTCACTGTAGT ATGGTCTTGTTAAGCACTGGGCATCATTTTCTGTGG | 1781 |
| | CATCATGAAGAGACATCG | 1782 |
| | CGATGTCTTCATGATG | 1783 |
| Increased Risk Thrombosis Arg506Gln CGA-CAA | ACATCGCCTCTGGGCTAATAGGACTACTTCTAATCTGTAAGAG CAGATCCCTGGACAGGCGAGGAATACAGGTATTTTGTCCTTG AAGTAACCTTTCAGAAATTCTGAGAATTTCTTCTGG | 1784 |
| | CCAGAAGAAATTCTCAGAATTTCTGAAAGGTTACTTCAAGGAC AAAATACCTGTATTCCTCGCCTGTCCAGGGATCTGCTCTTACA GATTAGAAGTAGTCCTATTAGCCCAGAGGCGATGT | 1785 |
| | GGACAGGCGAGGAATAC | 1786 |
| | GTATTCCTCGCCTGTCC | 1787 |
| Factor V Deficiency Arg506Term CGA-TGA | GACATCGCCTCTGGGCTAATAGGACTACTTCTAATCTGTAAGA GCAGATCCCTGGACAGGCGAGGAATACAGGTATTTTGTCCTT GAAGTAACCTTTCAGAAATTCTGAGAATTTCTTCTG | 1788 |
| | CAGAAGAAATTCTCAGAATTTCTGAAAGGTTACTTCAAGGACA AAATACCTGTATTCCTCGCCTGTCCAGGGATCTGCTCTTACAG ATTAGAAGTAGTCCTATTAGCCCAGAGGCGATGTC | 1789 |
| | TGGACAGGCGAGGAATA | 1790 |
| | TATTCCTCGCCTGTCCA | 1791 |
| Thrombosis Arg712Term CGA-TGA | AGTGATGCTGACTATGATTACCAGAACAGACTGGCTGCAGCA TTAGGAATCAGGTCATTCCGAAACTCATCATTGAATCAGGAAG AAGAAGAGTTCAATCTTACTGCCCTAGCTCTGGAGA | 1792 |
| | TCTCCAGAGCTAGGGCAGTAAGATTGAACTCTTCTTCCTG ATTCAATGATGAGTTTCGGAATGACCTGATTCCTAATGCTGCA GCCAGTCTGTTCTGGTAATCATAGTCAGCATCACT | 1793 |
| | GGTCATTCCGAAACTCA | 1794 |
| | TGAGTTTCGGAATGACC | 1795 |
| Thrombosis His1299Arg CAT-CGT | TCAGTCAGACAAACCTTTCCCCAGCCCTCGGTCAGATGCCCA TTTCTCCAGACCTCAGCCATACAACCCTTTCTCTAGACTTCAG CCAGACAAACCTCTCTCCAGAACTCAGTCAAACAAA | 1796 |
| | TTTGTTTGACTGAGTTCTGGAGAGAGGTTTGTCTGGCTGAAGT CTAGAGAAAGGGTTGTATGGCTGAGGTCTGGAGAAATGGGCA TCTGACCGAGGGCTGGGGAAAGGTTTGTCTGACTGA | 1797 |
| | CCTCAGCCATACAACCC | 1798 |
| | GGGTTGTATGGCTGAGG | 1799 |

EXAMPLE 13

Hemophilia—Factor VIII Deficiency

The attached table discloses the correcting oligonucleotide base sequences for the Factor VIII oligonucleotides of the invention.

TABLE 20

Factor VIII Mutations and Genome-Correcting Oligos

| Clinical Phenotype & Mutation | Correcting Oligos | SEQ ID NO: |
|---|---|---|
| Haemophilia A Tyr5Cys TAC-TGC | AGCTCTCCACCTGCTTCTTTCTGTGCCTTTTGCGATTCTGCTT TAGTGCCACCAGAAGATACTACCTGGGTGCAGTGGAACTGTC ATGGGACTATATGCAAAGTGATCTCGGTGAGCTGCC | 1800 |
| | GGCAGCTCACCGAGATCACTTTGCATATAGTCCCATGACAGT TCCACTGCACCCAGGTAGTATCTTCTGGTGGCACTAAAGCAG AATCGCAAAAGGCACAGAAAGAAGCAGGTGGAGAGCT | 1801 |
| | CAGAAGATACTACCTGG | 1802 |
| | CCAGGTAGTATCTTCTG | 1803 |
| Haemophilia A Leu7Arg CTG-CGG | CCACCTGCTTCTTTCTGTGCCTTTTGCGATTCTGCTTTAGTGC CACCAGAAGATACTACCTGGGTGCAGTGGAACTGTCATGGGA CTATATGCAAAGTGATCTCGGTGAGCTGCCTGTGGA | 1804 |
| | TCCACAGGCAGCTCACCGAGATCACTTTGCATATAGTCCCAT GACAGTTCCACTGCACCCAGGTAGTATCTTCTGGTGGCACTA AAGCAGAATCGCAAAAGGCACAGAAAGAAGCAGGTGG | 1805 |
| | ATACTACCTGGGTGCAG | 1806 |
| | CTGCACCCAGGTAGTAT | 1807 |
| Haemophilia A Ser(-1)Arg AGTg-AGG | AGTCATGCAAATAGAGCTCTCCACCTGCTTCTTTCTGTGCCTT TTGCGATTCTGCTTTAGTGCCACCAGAAGATACTACCTGGGT GCAGTGGAACTGTCATGGGACTATATGCAAAGTGAT | 1808 |
| | ATCACTTTGCATATAGTCCCATGACAGTTCCACTGCACCCAG GTAGTATCTTCTGGTGGCACTAAAGCAGAATCGCAAAAGGCA CAGAAAGAAGCAGGTGGAGAGCTCTATTTGCATGACT | 1809 |
| | TGCTTTAGTGCCACCAG | 1810 |
| | CTGGTGGCACTAAAGCA | 1811 |
| Haemophilia A Arg(-5)Term gCGA-TGA | CATTTGTAGCAATAAGTCATGCAAATAGAGCTCTCCACCTGCT TCTTTCTGTGCCTTTTGCGATTCTGCTTTAGTGCCACCAGAAG ATACTACCTGGGTGCAGTGGAACTGTCATGGGACT | 1812 |
| | AGTCCCATGACAGTTCCACTGCACCCAGGTAGTATCTTCTGG TGGCACTAAAGCAGAATCGCAAAAGGCACAGAAAGAAGCAGG TGGAGAGCTCTATTTGCATGACTTATTGCTACAAATG | 1813 |
| | GCCTTTTGCGATTCTGC | 1814 |
| | GCAGAATCGCAAAAGGC | 1815 |
| Haemophilia A Glu11Val GAA-GTA | TTCTGTGCCTTTTGCGATTCTGCTTTAGTGCCACCAGAAGATA CTACCTGGGTGCAGTGGAACTGTCATGGGACTATATGCAAAG TGATCTCGGTGAGCTGCCTGTGGACGCAAGGTAAAG | 1816 |
| | CTTTACCTTGCGTCCACAGGCAGCTCACCGAGATCACTTTGC ATATAGTCCCATGACAGTTCCACTGCACCCAGGTAGTATCTTC TGGTGGCACTAAAGCAGAATCGCAAAAGGCACAGAA | 1817 |
| | TGCAGTGGAACTGTCAT | 1818 |
| | ATGACAGTTCCACTGCA | 1819 |
| Haemophilia A Trp14Gly aTGG-GGG | CTTTTGCGATTCTGCTTTAGTGCCACCAGAAGATACTACCTGG GTGCAGTGGAACTGTCATGGGACTATATGCAAAGTGATCTCG GTGAGCTGCCTGTGGACGCAAGGTAAAGGCATGTCC | 1820 |
| | GGACATGCCTTTACCTTGCGTCCACAGGCAGCTCACCGAGAT CACTTTGCATATAGTCCCATGACAGTTCCACTGCACCCAGGT AGTATCTTCTGGTGGCACTAAAGCAGAATCGCAAAAG | 1821 |
| | AACTGTCATGGGACTAT | 1822 |
| | ATAGTCCCATGACAGTT | 1823 |
| Haemophilia A Tyr46Term TACa-TAA | TTCACGCAGATTTCCTCCTAGAGTGCCAAAATCTTTTCCATTC AACACCTCAGTCGTGTACAAAAAGACTCTGTTTGTAGAATTCA CGGATCACCTTTTCAACATCGCTAAGCCAAGGCCA | 1824 |
| | TGGCCTTGGCTTAGCGATGTTGAAAAGGTGATCCGTGAATTC TACAAACAGAGTCTTTTTGTACACGACTGAGGTGTTGAATGGA AAAGATTTTGGCACTCTAGGAGGAAATCTGCGTGAA | 1825 |
| | GTCGTGTACAAAAAGAC | 1826 |
| | GTCTTTTTGTACACGAC | 1827 |
| Haemophilia A Asp56Glu GATc-GAA | ATCTTTTCCATTCAACACCTCAGTCGTGTACAAAAAGACTCTG TTTGTAGAATTCACGGATCACCTTTTCAACATCGCTAAGCCAA GGCCACCCTGGATGGGTAATGAAAACAATGTTGAA | 1828 |
| | TTCAACATTGTTTTCATTACCCATCCAGGGTGGCCTTGGCTTA GCGATGTTGAAAAGGTGATCCGTGAATTCTACAAACAGAGTC TTTTTGTACACGACTGAGGTGTTGAATGGAAAAGAT | 1829 |
| | TTCACGGATCACCTTTT | 1830 |
| | AAAAGGTGATCCGTGAA | 1831 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Gly73Val GGT-GTT | TTCTGGAGTACTATCCCCAAGTAACCTTTGGCGGACATCTCAT TCTTACAGGTCTGCTAGGTCCTACCATCCAGGCTGAGGTTTA TGATACAGTGGTCATTACACTTAAGAACATGGCTTC | 1832 |
| | GAAGCCATGTTCTTAAGTGTAATGACCACTGTATCATAAACCT CAGCCTGGATGGTAGGACCTAGCAGACCTGTAAGAATGAGAT GTCCGCCAAAGGTTACTTGGGGATAGTACTCCAGAA | 1833 |
| | TCTGCTAGGTCCTACCA | 1834 |
| | TGGTAGGACCTAGCAGA | 1835 |
| Haemophilia A Glu79Lys tGAG-AAG | CAAGTAACCTTTGGCGGACATCTCATTCTTACAGGTCTGCTAG GTCCTACCATCCAGGCTGAGGTTTATGATACAGTGGTCATTAC ACTTAAGAACATGGCTTCCCATCCTGTCAGTCTTC | 1836 |
| | GAAGACTGACAGGATGGGAAGCCATGTTCTTAAGTGTAATGA CCACTGTATCATAAACCTCAGCCTGGATGGTAGGACCTAGCA GACCTGTAAGAATGAGATGTCCGCCAAAGGTTACTTG | 1837 |
| | TCCAGGCTGAGGTTTAT | 1838 |
| | ATAAACCTCAGCCTGGA | 1839 |
| Haemophilia A Val80Asp GTT-GAT | TAACCTTTGGCGGACATCTCATTCTTACAGGTCTGCTAGGTCC TACCATCCAGGCTGAGGTTTATGATACAGTGGTCATTACACTT AAGAACATGGCTTCCCATCCTGTCAGTCTTCATGC | 1840 |
| | GCATGAAGACTGACAGGATGGGAAGCCATGTTCTTAAGTGTA ATGACCACTGTATCATAAACCTCAGCCTGGATGGTAGGACCT AGCAGACCTGTAAGAATGAGATGTCCGCCAAAGGTTA | 1841 |
| | GGCTGAGGTTTATGATA | 1842 |
| | TATCATAAACCTCAGCC | 1843 |
| Haemophilia A Asp82Val GAT-GTT | TTGGCGGACATCTCATTCTTACAGGTCTGCTAGGTCCTACCAT CCAGGCTGAGGTTTATGATACAGTGGTCATTACACTTAAGAAC ATGGCTTCCCATCCTGTCAGTCTTCATGCTGTTGG | 1844 |
| | CCAACAGCATGAAGACTGACAGGATGGGAAGCCATGTTCTTA AGTGTAATGACCACTGTATCATAAACCTCAGCCTGGATGGTA GGACCTAGCAGACCTGTAAGAATGAGATGTCCGCCAA | 1845 |
| | GGTTTATGATACAGTGG | 1846 |
| | CCACTGTATCATAAACC | 1847 |
| Haemophilia A Asp82Gly GAT-GGT | TTGGCGGACATCTCATTCTTACAGGTCTGCTAGGTCCTACCAT CCAGGCTGAGGTTTATGATACAGTGGTCATTACACTTAAGAAC ATGGCTTCCCATCCTGTCAGTCTTCATGCTGTTGG | 1848 |
| | CCAACAGCATGAAGACTGACAGGATGGGAAGCCATGTTCTTA AGTGTAATGACCACTGTATCATAAACCTCAGCCTGGATGGTA GGACCTAGCAGACCTGTAAGAATGAGATGTCCGCCAA | 1849 |
| | GGTTTATGATACAGTGG | 1850 |
| | CCACTGTATCATAAACC | 1851 |
| Haemophilia A Val85Asp GTC-GAC | ATCTCATTCTTACAGGTCTGCTAGGTCCTACCATCCAGGCTGA GGTTTATGATACAGTGGTCATTACACTTAAGAACATGGCTTCC CATCCTGTCAGTCTTCATGCTGTTGGTGTATCCTA | 1852 |
| | TAGGATACACCAACAGCATGAAGACTGACAGGATGGGAAGCC ATGTTCTTAAGTGTAATGACCACTGTATCATAAACCTCAGCCT GGATGGTAGGACCTAGCAGACCTGTAAGAATGAGAT | 1853 |
| | TACAGTGGTCATTACAC | 1854 |
| | GTGTAATGACCACTGTA | 1855 |
| Haemophilia A Lys89Thr AAG-ACG | CAGGTCTGCTAGGTCCTACCATCCAGGCTGAGGTTTATGATA CAGTGGTCATTACACTTAAGAACATGGCTTCCCATCCTGTCA GTCTTCATGCTGTTGGTGTATCCTACTGGAAAGCTTC | 1856 |
| | GAAGCTTTCCAGTAGGATACACCAACAGCATGAAGACTGACA GGATGGGAAGCCATGTTCTTAAGTGTAATGACCACTGTATCAT AAACCTCAGCCTGGATGGTAGGACCTAGCAGACCTG | 1857 |
| | TACACTTAAGAACATGG | 1858 |
| | CCATGTTCTTAAGTGTA | 1859 |
| Haemophilia A Met91Val cATG-GTG | CTGCTAGGTCCTACCATCCAGGCTGAGGTTTATGATACAGTG GTCATTACACTTAAGAACATGGCTTCCCATCCTGTCAGTCTTC ATGCTGTTGGTGTATCCTACTGGAAAGCTTCTGAGG | 1860 |
| | CCTCAGAAGCTTTCCAGTAGGATACACCAACAGCATGAAGAC TGACAGGATGGGAAGCCATGTTCTTAAGTGTAATGACCACTG TATCATAAACCTCAGCCTGGATGGTAGGACCTAGCAG | 1861 |
| | TTAAGAACATGGCTTCC | 1862 |
| | GGAAGCCATGTTCTTAA | 1863 |
| Haemophilia A His94Arg CAT-CGT | CTACCATCCAGGCTGAGGTTTATGATACAGTGGTCATTACACT TAAGAACATGGCTTCCCATCCTGTCAGTCTTCATGCTGTTGGT GTATCCTACTGGAAAGCTTCTGAGGGTGAGTAAAA | 1864 |
| | TTTTACTCACCCTCAGAAGCTTTCCAGTAGGATACACCAACAG CATGAAGACTGACAGGATGGGAAGCCATGTTCTTAAGTGTAA TGACCACTGTATCATAAACCTCAGCCTGGATGGTAG | 1865 |
| | GGCTTCCCATCCTGTCA | 1866 |
| | TGACAGGATGGGAAGCC | 1867 |

TABLE 20-continued

Factor VIII Mutations and Genome-Correcting Oligos

| Clinical Phenotype & Mutation | Correcting Oligos | SEQ ID NO: |
|---|---|---|
| Haemophilia A His94Tyr cCAT-TAT | CCTACCATCCAGGCTGAGGTTTATGATACAGTGGTCATTACAC TTAAGAACATGGCTTCCCATCCTGTCAGTCTTCATGCTGTTGG TGTATCCTACTGGAAAGCTTCTGAGGGTGAGTAAA | 1868 |
| | TTTACTCACCCTCAGAAGCTTTCCAGTAGGATACACCAACAGC ATGAAGACTGACAGGATGGGAAGCCATGTTCTTAAGTGTAAT GACCACTGTATCATAAACCTCAGCCTGGATGGTAGG | 1869 |
| | TGGCTTCCCATCCTGTC | 1870 |
| | GACAGGATGGGAAGCCA | 1871 |
| Haemophilia A Leu98Arg CTT-CGT | CTGAGGTTTATGATACAGTGGTCATTACACTTAAGAACATGGC TTCCCATCCTGTCAGTCTTCATGCTGTTGGTGTATCCTACTGG AAAGCTTCTGAGGGTGAGTAAAATACCCTCCTATT | 1872 |
| | AATAGGAGGGTATTTTACTCACCCTCAGAAGCTTTCCAGTAGG ATACACCAACAGCATGAAGACTGACAGGATGGGAAGCCATGT TCTTAAGTGTAATGACCACTGTATCATAAACCTCAG | 1873 |
| | TGTCAGTCTTCATGCTG | 1874 |
| | CAGCATGAAGACTGACA | 1875 |
| Haemophilia A Gly102Ser tGGT-AGT | GATACAGTGGTCATTACACTTAAGAACATGGCTTCCCATCCTG TCAGTCTTCATGCTGTTGGTGTATCCTACTGGAAAGCTTCTGA GGGTGAGTAAAATACCCTCCTATTGTCCTGTCATT | 1876 |
| | AATGACAGGACAATAGGAGGGTATTTTACTCACCCTCAGAAG CTTTCCAGTAGGATACACCAACAGCATGAAGACTGACAGGAT GGGAAGCCATGTTCTTAAGTGTAATGACCACTGTATC | 1877 |
| | ATGCTGTTGGTGTATCC | 1878 |
| | GGATACACCAACAGCAT | 1879 |
| Haemophilia A Glu113Asp GAAt-GAC | CTTTGAGTGTACAGTGGATATAGAAAGGACAATTTTATTTCTTC CTGCTATAGGAGCTGAATATGATGATCAGACCAGTCAAAGGG AGAAAGAAGATGATAAAGTCTTCCCTGGTGGAAGC | 1880 |
| | GCTTCCACCAGGGAAGACTTTATCATCTTCTTTCTCCCTTTGA CTGGTCTGATCATCATATTCAGCTCCTATAGCAGGAAGAAATA AAATTGTCCTTTCTATATCCACTGTACACTCAAAG | 1881 |
| | GGAGCTGAATATGATGA | 1882 |
| | TCATCATATTCAGCTCC | 1883 |
| Haemophilia A Tyr114Cys TAT-TGT | TTGAGTGTACAGTGGATATAGAAAGGACAATTTTATTTCTTCCT GCTATAGGAGCTGAATATGATGATCAGACCAGTCAAAGGGAG AAAGAAGATGATAAAGTCTTCCCTGGTGGAAGCCA | 1884 |
| | TGGCTTCCACCAGGGAAGACTTTATCATCTTCTTTCTCCCTTT GACTGGTCTGATCATCATATTCAGCTCCTATAGCAGGAAGAAA TAAAATTGTCCTTTCTATATCCACTGTACACTCAA | 1885 |
| | AGCTGAATATGATGATC | 1886 |
| | GATCATCATATTCAGCT | 1887 |
| Haemophilia A Asp116Gly GAT-GGT | GTACAGTGGATATAGAAAGGACAATTTTATTTCTTCCTGCTATA GGAGCTGAATATGATGATCAGACCAGTCAAAGGGAGAAAGAA GATGATAAAGTCTTCCCTGGTGGAAGCCATACATA | 1888 |
| | TATGTATGGCTTCCACCAGGGAAGACTTTATCATCTTCTTTCT CCCTTTGACTGGTCTGATCATCATATTCAGCTCCTATAGCAGG AAGAAATAAAATTGTCCTTTCTATATCCACTGTAC | 1889 |
| | ATATGATGATCAGACCA | 1890 |
| | TGGTCTGATCATCATAT | 1891 |
| Haemophilia A Gln117Term tCAG-TAG | ACAGTGGATATAGAAAGGACAATTTTATTTCTTCCTGCTATAG GAGCTGAATATGATGATCAGACCAGTCAAAGGGAGAAAGAAG ATGATAAAGTCTTCCCTGGTGGAAGCCATACATATG | 1892 |
| | CATATGTATGGCTTCCACCAGGGAAGACTTTATCATCTTCTTT CTCCCTTTGACTGGTCTGATCATCATATTCAGCTCCTATAGCA GGAAGAAATAAAATTGTCCTTTCTATATCCACTGT | 1893 |
| | ATGATGATCAGACCAGT | 1894 |
| | ACTGGTCTGATCATCAT | 1895 |
| Haemophilia A Thr118Ile ACC-ATC | TGGATATAGAAAGGACAATTTTATTTCTTCCTGCTATAGGAGC TGAATATGATGATCAGACCAGTCAAAGGGAGAAAGAAGATGA TAAAGTCTTCCCTGGTGGAAGCCATACATATGTCTG | 1896 |
| | CAGACATATGTATGGCTTCCACCAGGGAAGACTTTATCATCTT CTTTCTCCCTTTGACTGGTCTGATCATCATATTCAGCTCCTAT AGCAGGAAGAAATAAAATTGTCCTTTCTATATCCA | 1897 |
| | TGATCAGACCAGTCAAA | 1898 |
| | TTTGACTGGTCTGATCA | 1899 |
| Haemophilia A Glu122Term gGAG-TAG | AGGACAATTTTATTTCTTCCTGCTATAGGAGCTGAATATGATG ATCAGACCAGTCAAAGGGAGAAAGAAGATGATAAAGTCTTCC CTGGTGGAAGCCATACATATGTCTGGCAGGTCCTGA | 1900 |
| | TCAGGACCTGCCAGACATATGTATGGCTTCCACCAGGGAAGA CTTTATCATCTTCTTTCTCCCTTTGACTGGTCTGATCATCATAT TCAGCTCCTATAGCAGGAAGAAATAAAATTGTCCT | 1901 |
| | GTCAAAGGGAGAAAGAA | 1902 |
| | TTCTTTCTCCCTTTGAC | 1903 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Asp126His tGAT-CAT | TTTCTTCCTGCTATAGGAGCTGAATATGATGATCAGACCAGTC | 1904 |
| | AAAGGGAGAAAGAAGATGATAAAGTCTTCCCTGGTGGAAGCC | |
| | ATACATATGTCTGGCAGGTCCTGAAAGAGAATGGTC | |
| | GACCATTCTCTTTCAGGACCTGCCAGACATATGTATGGCTTCC | 1905 |
| | ACCAGGGAAGACTTTATCATCTTCTTTCTCCCTTTGACTGGTC | |
| | TGATCATCATATTCAGCTCCTATAGCAGGAAGAAA | |
| | AAGAAGATGATAAAGTC | 1906 |
| | GACTTTATCATCTTCTT | 1907 |
| Haemophilia A Gln139Term gCAG-TAG | AGTCAAAGGGAGAAAGAAGATGATAAAGTCTTCCCTGGTGGA | 1908 |
| | AGCCATACATATGTCTGGCAGGTCCTGAAAGAGAATGGTCCA | |
| | ATGGCCTCTGACCCACTGTGCCTTACCTACTCATATC | |
| | GATATGAGTAGGTAAGGCACAGTGGGTCAGAGGCCATTGGA | 1909 |
| | CCATTCTCTTTCAGGACCTGCCAGACATATGTATGGCTTCCAC | |
| | CAGGGAAGACTTTATCATCTTCTTTCTCCCTTTGACT | |
| | ATGTCTGGCAGGTCCTG | 1910 |
| | CAGGACCTGCCAGACAT | 1911 |
| Haemophilia A Val140Ala GTC-GCC | AAAGGGAGAAAGAAGATGATAAAGTCTTCCCTGGTGGAAGCC | 1912 |
| | ATACATATGTCTGGCAGGTCCTGAAAGAGAATGGTCCAATGG | |
| | CCTCTGACCCACTGTGCCTTACCTACTCATATCTTTC | |
| | GAAAGATATGAGTAGGTAAGGCACAGTGGGTCAGAGGCCATT | 1913 |
| | GGACCATTCTCTTTCAGGACCTGCCAGACATATGTATGGCTT | |
| | CCACCAGGGAAGACTTTATCATCTTCTTTCTCCCTTT | |
| | CTGGCAGGTCCTGAAAG | 1914 |
| | CTTTCAGGACCTGCCAG | 1915 |
| Haemophilia A Asn144Lys AATg-AAA | AGATGATAAAGTCTTCCCTGGTGGAAGCCATACATATGTCTG | 1916 |
| | GCAGGTCCTGAAAGAGAATGGTCCAATGGCCTCTGACCCACT | |
| | GTGCCTTACCTACTCATATCTTTCTCATGTGGACCTG | |
| | CAGGTCCACATGAGAAAGATATGAGTAGGTAAGGCACAGTGG | 1917 |
| | GTCAGAGGCCATTGGACCATTCTCTTTCAGGACCTGCCAGAC | |
| | ATATGTATGGCTTCCACCAGGGAAGACTTTATCATCT | |
| | AAAGAGAATGGTCCAAT | 1918 |
| | ATTGGACCATTCTCTTT | 1919 |
| Haemophilia AG Gly145Asp GGT-GAT | ATGATAAAGTCTTCCCTGGTGGAAGCCATACATATGTCTGGCA | 1920 |
| | GGTCCTGAAAGAGAATGGTCCAATGGCCTCTGACCCACTGTG | |
| | CCTTACCTACTCATATCTTTCTCATGTGGACCTGGT | |
| | ACCAGGTCCACATGAGAAAGATATGAGTAGGTAAGGCACAGT | 1921 |
| | GGGTCAGAGGCCATTGGACCATTCTCTTTCAGGACCTGCCAG | |
| | ACATATGTATGGCTTCCACCAGGGAAGACTTTATCAT | |
| | AGAGAATGGTCCAATGG | 1922 |
| | CCATTGGACCATTCTCT | 1923 |
| Haemophilia A Gly145Val GGT-GTT | ATGATAAAGTCTTCCCTGGTGGAAGCCATACATATGTCTGGCA | 1924 |
| | GGTCCTGAAAGAGAATGGTCCAATGGCCTCTGACCCACTGTG | |
| | CCTTACCTACTCATATCTTTCTCATGTGGACCTGGT | |
| | ACCAGGTCCACATGAGAAAGATATGAGTAGGTAAGGCACAGT | 1925 |
| | GGGTCAGAGGCCATTGGACCATTCTCTTTCAGGACCTGCCAG | |
| | ACATATGTATGGCTTCCACCAGGGAAGACTTTATCAT | |
| | AGAGAATGGTCCAATGG | 1926 |
| | CCATTGGACCATTCTCT | 1927 |
| Haemophilia A Pro146Ser tCCA-TCA | GATAAAGTCTTCCCTGGTGGAAGCCATACATATGTCTGGCAG | 1928 |
| | GTCCTGAAAGAGAATGGTCCAATGGCCTCTGACCCACTGTGC | |
| | CTTACCTACTCATATCTTTCTCATGTGGACCTGGTAA | |
| | TTACCAGGTCCACATGAGAAAGATATGAGTAGGTAAGGCACA | 1929 |
| | GTGGGTCAGAGGCCATTGGACCATTCTCTTTCAGGACCTGCC | |
| | AGACATATGTATGGCTTCCACCAGGGAAGACTTTATC | |
| | AGAATGGTCCAATGGCC | 1930 |
| | GGCCATTGGACCATTCT | 1931 |
| Haemophilia A Cys153Trp TGCc-TGG | CCATACATATGTCTGGCAGGTCCTGAAAGAGAATGGTCCAAT | 1932 |
| | GGCCTCTGACCCACTGTGCCTTACCTACTCATATCTTTCTCAT | |
| | GTGGACCTGGTAAAAGACTTGAATTCAGGCCTCATT | |
| | AATGAGGCCTGAATTCAAGTCTTTTACCAGGTCCACATGAGAA | 1933 |
| | AGATATGAGTAGGTAAGGCACAGTGGGTCAGAGGCCATTGGA | |
| | CCATTCTCTTTCAGGACCTGCCAGACATATGTATGG | |
| | CCACTGTGCCTTACCTA | 1934 |
| | TAGGTAAGGCACAGTGG | 1935 |
| Haemophilia A Tyr156Term TACt-TAA | TGTCTGGCAGGTCCTGAAAGAGAATGGTCCAATGGCCTCTGA | 1936 |
| | CCCACTGTGCCTTACCTACTCATATCTTTCTCATGTGGACCTG | |
| | GTAAAAGACTTGAATTCAGGCCTCATTGGAGCCCTA | |
| | TAGGGCTCCAATGAGGCCTGAATTCAAGTCTTTTACCAGGTC | 1937 |
| | CACATGAGAAAGATATGAGTAGGTAAGGCACAGTGGGTCAGA | |
| | GGCCATTGGACCATTCTCTTTCAGGACCTGCCAGACA | |
| | CTTACCTACTCATATCT | 1938 |
| | AGATATGAGTAGGTAAG | 1939 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Ser157Pro cTCA-CCA | GTCTGGCAGGTCCTGAAAGAGAATGGTCCAATGGCCTCTGAC CCACTGTGCCTTACCTACTCATATCTTTCTCATGTGGACCTGG TAAAAGACTTGAATTCAGGCCTCATTGGAGCCCTAC | 1940 |
| | GTAGGGCTCCAATGAGGCCTGAATTCAAGTCTTTTACCAGGT CCACATGAGAAAGATATGAGTAGGTAAGGCACAGTGGGTCAG AGGCCATTGGACCATTCTCTTTCAGGACCTGCCAGAC | 1941 |
| | TTACCTACTCATATCTT | 1942 |
| | AAGATATGAGTAGGTAA | 1943 |
| Haemophilia A Ser160Pro tTCT-CCT | GTCCTGAAAGAGAATGGTCCAATGGCCTCTGACCCACTGTGC CTTACCTACTCATATCTTTCTCATGTGGACCTGGTAAAAGACT TGAATTCAGGCCTCATTGGAGCCCTACTAGTATGTA | 1944 |
| | TACATACTAGTAGGGCTCCAATGAGGCCTGAATTCAAGTCTTT TACCAGGTCCACATGAGAAAGATATGAGTAGGTAAGGCACAG TGGGTCAGAGGCCATTGGACCATTCTCTTTCAGGAC | 1945 |
| | CATATCTTTCTCATGTG | 1946 |
| | CACATGAGAAAGATATG | 1947 |
| Haemophilia A Val162Met tGTG-ATG | AAAGAGAATGGTCCAATGGCCTCTGACCCACTGTGCCTTACC TACTCATATCTTTCTCATGTGGACCTGGTAAAAGACTTGAATT CAGGCCTCATTGGAGCCCTACTAGTATGTAGAGAAG | 1948 |
| | CTTCTCTACATACTAGTAGGGCTCCAATGAGGCCTGAATTCAA GTCTTTTACCAGGTCCACATGAGAAAGATATGAGTAGGTAAG GCACAGTGGGTCAGAGGCCATTGGACCATTCTCTTT | 1949 |
| | TTTCTCATGTGGACCTG | 1950 |
| | CAGGTCCACATGAGAAA | 1951 |
| Haemophilia A Lys166Thr AAA-ACA | CAATGGCCTCTGACCCACTGTGCCTTACCTACTCATATCTTTC TCATGTGGACCTGGTAAAAGACTTGAATTCAGGCCTCATTGG AGCCCTACTAGTATGTAGAGAAGGTAAGTGTATGAA | 1952 |
| | TTCATACACTTACCTTCTCTACATACTAGTAGGGCTCCAATGA GGCCTGAATTCAAGTCTTTTACCAGGTCCACATGAGAAAGATA TGAGTAGGTAAGGCACAGTGGGTCAGAGGCCATTG | 1953 |
| | CCTGGTAAAAGACTTGA | 1954 |
| | TCAAGTCTTTTACCAGG | 1955 |
| Haemophilia A Ser170Leu TCA-TTA | ACCCACTGTGCCTTACCTACTCATATCTTTCTCATGTGGACCT GGTAAAAGACTTGAATTCAGGCCTCATTGGAGCCCTACTAGT ATGTAGAGAAGGTAAGTGTATGAAAGCGTAGGATTG | 1956 |
| | CAATCCTACGCTTTCATACACTTACCTTCTCTACATACTAGTAG GGCTCCAATGAGGCCTGAATTCAAGTCTTTTACCAGGTCCAC ATGAGAAAGATATGAGTAGGTAAGGCACAGTGGGT | 1957 |
| | CTTGAATTCAGGCCTCA | 1958 |
| | TGAGGCCTGAATTCAAG | 1959 |
| Haemophilia A Phe195Val aTTT-GTT | AATGTTCTCACTTCTTTTTCAGGGAGTCTGGCCAAGGAAAAGA CACAGACCTTGCACAAATTTATACTACTTTTTGCTGTATTTGAT GAAGGTTAGTGAGTCTTAATCTGAATTTTGGATT | 1960 |
| | AATCCAAAATTCAGATTAAGACTCACTAACCTTCATCAAATACA GCAAAAAGTAGTATAAATTTGTGCAAGGTCTGTGTCTTTTCCT TGGCCAGACTCCCTGAAAAAGAAGTGAGAACATT | 1961 |
| | TGCACAAATTTATACTA | 1962 |
| | TAGTATAAATTTGTGCA | 1963 |
| Haemophilia A Leu198His CTT-CAT | CTTCTTTTTCAGGGAGTCTGGCCAAGGAAAAGACACAGACCT TGCACAAATTTATACTACTTTTTGCTGTATTTGATGAAGGTTAG TGAGTCTTAATCTGAATTTTGGATTCCTGAAAGAA | 1964 |
| | TTCTTTCAGGAATCCAAAATTCAGATTAAGACTCACTAACCTTC ATCAAATACAGCAAAAAGTAGTATAAATTTGTGCAAGGTCTGT GTCTTTTCCTTGGCCAGACTCCCTGAAAAAGAAG | 1965 |
| | TATACTACTTTTTGCTG | 1966 |
| | CAGCAAAAAGTAGTATA | 1967 |
| Haemophilia A Ala200Asp GCT-GAT | TTTCAGGGAGTCTGGCCAAGGAAAAGACACAGACCTTGCACA AATTTATACTACTTTTTGCTGTATTTGATGAAGGTTAGTGAGTC TTAATCTGAATTTTGGATTCCTGAAAGAAATCCT | 1968 |
| | GAGGATTTCTTTCAGGAATCCAAAATTCAGATTAAGACTCACT AACCTTCATCAAATACAGCAAAAAGTAGTATAAATTTGTGCAA GGTCTGTGTCTTTTCCTTGGCCAGACTCCCTGAAA | 1969 |
| | ACTTTTTGCTGTATTTG | 1970 |
| | CAAATACAGCAAAAAGT | 1971 |
| Haemophilia A Ala200Thr tGCT-ACT | TTTTCAGGGAGTCTGGCCAAGGAAAAGACACAGACCTTGCAC AAATTTATACTACTTTTTGCTGTATTTGATGAAGGTTAGTGAGT CTTAATCTGAATTTTGGATTCCTGAAAGAAATCCT | 1972 |
| | AGGATTTCTTTCAGGAATCCAAAATTCAGATTAAGACTCACTA ACCTTCATCAAATACAGCAAAAAGTAGTATAAATTTGTGCAAG GTCTGTGTCTTTTCCTTGGCCAGACTCCCTGAAAA | 1973 |
| | TACTTTTTGCTGTATTT | 1974 |
| | AAATACAGCAAAAAGTA | 1975 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Val234Phe aGTC-TTC | AACTCCTTGATGCAGGATAGGGATGCTGCATCTGCTCGGGCC TGGCCTAAAATGCACACAGTCAATGGTTATGTAAACAGGTCTC TGCCAGGTATGTACACACCTGCTCAACAATCCTCAG | 1976 |
| | CTGAGGATTGTTGAGCAGGTGTGTACATACCTGGCAGAGACC TGTTTACATAACCATTGACTGTGTGCATTTTAGGCCAGGCCCG AGCAGATGCAGCATCCCTATCCTGCATCAAGGAGTT | 1977 |
| | TGCACACAGTCAATGGT | 1978 |
| | ACCATTGACTGTGTGCA | 1979 |
| Haemophilia A Gly247Glu GGA-GAA | ATTTCAGATTCTCTACTTCATAGCCATAGGTGTCTTATTCCTAC TTTACAGGTCTGATTGGATGCCACAGGAAATCAGTCTATTGGC ATGTGATTGGAATGGGCACCACTCCTGAAGTGCA | 1980 |
| | TGCACTTCAGGAGTGGTGCCCATTCCAATCACATGCCAATAG ACTGATTTCCTGTGGCATCCAATCAGACCTGTAAAGTAGGAAT AAGACACCTATGGCTATGAAGTAGAGAATCTGAAAT | 1981 |
| | TCTGATTGGATGCCACA | 1982 |
| | TGTGGCATCCAATCAGA | 1983 |
| Haemophilia A Trp255Cys TGGc-TGT | ATAGGTGTCTTATTCCTACTTTACAGGTCTGATTGGATGCCAC AGGAAATCAGTCTATTGGCATGTGATTGGAATGGGCACCACT CCTGAAGTGCACTCAATATTCCTCGAAGGTCACACA | 1984 |
| | TGTGTGACCTTCGAGGAATATTGAGTGCACTTCAGGAGTGGT GCCCATTCCAATCACATGCCAATAGACTGATTTCCTGTGGCAT CCAATCAGACCTGTAAAGTAGGAATAAGACACCTAT | 1985 |
| | GTCTATTGGCATGTGAT | 1986 |
| | ATCACATGCCAATAGAC | 1987 |
| Haemophilia A Trp255Term TGGc-TGA | ATAGGTGTCTTATTCCTACTTTACAGGTCTGATTGGATGCCAC AGGAAATCAGTCTATTGGCATGTGATTGGAATGGGCACCACT CCTGAAGTGCACTCAATATTCCTCGAAGGTCACACA | 1988 |
| | TGTGTGACCTTCGAGGAATATTGAGTGCACTTCAGGAGTGGT GCCCATTCCAATCACATGCCAATAGACTGATTTCCTGTGGCAT CCAATCAGACCTGTAAAGTAGGAATAAGACACCTAT | 1989 |
| | GTCTATTGGCATGTGAT | 1990 |
| | ATCACATGCCAATAGAC | 1991 |
| Haemophilia A His256Leu CAT-CTT | AGGTGTCTTATTCCTACTTTACAGGTCTGATTGGATGCCACAG GAAATCAGTCTATTGGCATGTGATTGGAATGGGCACCACTCC TGAAGTGCACTCAATATTCCTCGAAGGTCACACATT | 1992 |
| | AATGTGTGACCTTCGAGGAATATTGAGTGCACTTCAGGAGTG GTGCCCATTCCAATCACATGCCAATAGACTGATTTCCTGTGG CATCCAATCAGACCTGTAAAGTAGGAATAAGACACCT | 1993 |
| | CTATTGGCATGTGATTG | 1994 |
| | CAATCACATGCCAATAG | 1995 |
| Haemophilia A Gly259Arg tGGA-AGA | TATTCCTACTTTACAGGTCTGATTGGATGCCACAGGAAATCAG TCTATTGGCATGTGATTGGAATGGGCACCACTCCTGAAGTGC ACTCAATATTCCTCGAAGGTCACACATTTCTTGTGA | 1996 |
| | TCACAAGAAATGTGTGACCTTCGAGGAATATTGAGTGCACTTC AGGAGTGGTGCCCATTCCAATCACATGCCAATAGACTGATTT CCTGTGGCATCCAATCAGACCTGTAAAGTAGGAATA | 1997 |
| | ATGTGATTGGAATGGGC | 1998 |
| | GCCCATTCCAATCACAT | 1999 |
| Haemophilia A Val266Gly GTG-GGG | TTGGATGCCACAGGAAATCAGTCTATTGGCATGTGATTGGAAT GGGCACCACTCCTGAAGTGCACTCAATATTCCTCGAAGGTCA CACATTTCTTGTGAGGAACCATCGCCAGGCGTCCTT | 2000 |
| | AAGGACGCCTGGCGATGGTTCCTCACAAGAAATGTGTGACCT TCGAGGAATATTGAGTGCACTTCAGGAGTGGTGCCCATTCCA ATCACATGCCAATAGACTGATTTCCTGTGGCATCCAA | 2001 |
| | TCCTGAAGTGCACTCAA | 2002 |
| | TTGAGTGCACTTCAGGA | 2003 |
| Haemophilia A Glu272Gly GAA-GGA | CAGTCTATTGGCATGTGATTGGAATGGGCACCACTCCTGAAG TGCACTCAATATTCCTCGAAGGTCACACATTTCTTGTGAGGAA CCATCGCCAGGCGTCCTTGGAAATCTCGCCAATAAC | 2004 |
| | GTTATTGGCGAGATTTCCAAGGACGCCTGGCGATGGTTCCTC ACAAGAAATGTGTGACCTTCGAGGAATATTGAGTGCACTTCAG GAGTGGTGCCCATTCCAATCACATGCCAATAGACTG | 2005 |
| | ATTCCTCGAAGGTCACA | 2006 |
| | TGTGACCTTCGAGGAAT | 2007 |
| Haemophilia A Glu272Lys cGAA-AAA | TCAGTCTATTGGCATGTGATTGGAATGGGCACCACTCCTGAA GTGCACTCAATATTCCTCGAAGGTCACACATTTCTTGTGAGGA ACCATCGCCAGGCGTCCTTGGAAATCTCGCCAATAA | 2008 |
| | TTATTGGCGAGATTTCCAAGGACGCCTGGCGATGGTTCCTCA CAAGAAATGTGTGACCTTCGAGGAATATTGAGTGCACTTCAG GAGTGGTGCCCATTCCAATCACATGCCAATAGACTGA | 2009 |
| | TATTCCTCGAAGGTCAC | 2010 |
| | GTGACCTTCGAGGAATA | 2011 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Thr275Ile ACA-ATA | GGCATGTGATTGGAATGGGCACCACTCCTGAAGTGCACTCAA TATTCCTCGAAGGTCACACATTTCTTGTGAGGAACCATCGCCA GGCGTCCTTGGAAATCTCGCCAATAACTTTCCTTAC | 2012 |
| | GTAAGGAAAGTTATTGGCGAGATTTCCAAGGACGCCTGGCGA TGGTTCCTCACAAGAAATGTGTGACCTTCGAGGAATATTGAGT GCACTTCAGGAGTGGTGCCCATTCCAATCACATGCC | 2013 |
| | AGGTCACACATTTCTTG | 2014 |
| | CAAGAAATGTGTGACCT | 2015 |
| Haemophilia A Val278Ala GTG-GCG | TTGGAATGGGCACCACTCCTGAAGTGCACTCAATATTCCTCG AAGGTCACACATTTCTTGTGAGGAACCATCGCCAGGCGTCCT TGGAAATCTCGCCAATAACTTTCCTTACTGCTCAAAC | 2016 |
| | GTTTGAGCAGTAAGGAAAGTTATTGGCGAGATTTCCAAGGAC GCCTGGCGATGGTTCCTCACAAGAAATGTGTGACCTTCGAGG AATATTGAGTGCACTTCAGGAGTGGTGCCCATTCCAA | 2017 |
| | ATTTCTTGTGAGGAACC | 2018 |
| | GGTTCCTCACAAGAAAT | 2019 |
| Haemophilia A Asn280Ile AAC-ATC | TGGGCACCACTCCTGAAGTGCACTCAATATTCCTCGAAGGTC ACACATTTCTTGTGAGGAACCATCGCCAGGCGTCCTTGGAAA TCTCGCCAATAACTTTCCTTACTGCTCAAACACTCTT | 2020 |
| | AAGAGTGTTTGAGCAGTAAGGAAAGTTATTGGCGAGATTTCCA AGGACGCCTGGCGATGGTTCCTCACAAGAAATGTGTGACCTT CGAGGAATATTGAGTGCACTTCAGGAGTGGTGCCCA | 2021 |
| | TGTGAGGAACCATCGCC | 2022 |
| | GGCGATGGTTCCTCACA | 2023 |
| Haemophilia A Arg282Cys tCGC-TGC | ACCACTCCTGAAGTGCACTCAATATTCCTCGAAGGTCACACAT TTCTTGTGAGGAACCATCGCCAGGCGTCCTTGGAAATCTCGC CAATAACTTTCCTTACTGCTCAAACACTCTTGATGG | 2024 |
| | CCATCAAGAGTGTTTGAGCAGTAAGGAAAGTTATTGGCGAGA TTTCCAAGGACGCCTGGGATGGTTCCTCACAAGAAATGTGT GACCTTCGAGGAATATTGAGTGCACTTCAGGAGTGGT | 2025 |
| | GGAACCATCGCCAGGCG | 2026 |
| | CGCCTGGGATGGTTCC | 2027 |
| Haemophilia A Arg282His CGC-CAC | CCACTCCTGAAGTGCACTCAATATTCCTCGAAGGTCACACATT TCTTGTGAGGAACCATCGCCAGGCGTCCTTGGAAATCTCGCC AATAACTTTCCTTACTGCTCAAACACTCTTGATGGA | 2028 |
| | TCCATCAAGAGTGTTTGAGCAGTAAGGAAAGTTATTGGCGAG ATTTCCAAGGACGCCTGGCCGATGGTTCCTCACAAGAAATGTG TGACCTTCGAGGAATATTGAGTGCACTTCAGGAGTGG | 2029 |
| | GAACCATCGCCAGGCGT | 2030 |
| | ACGCCTGGCCGATGGTTC | 2031 |
| Haemophilia A Arg282Leu CGC-CTC | CCACTCCTGAAGTGCACTCAATATTCCTCGAAGGTCACACATT TCTTGTGAGGAACCATCGCCAGGCGTCCTTGGAAATCTCGCC AATAACTTTCCTTACTGCTCAAACACTCTTGATGGA | 2032 |
| | TCCATCAAGAGTGTTTGAGCAGTAAGGAAAGTTATTGGCGAG ATTTCCAAGGACGCCTGGCGATGGTTCCTCACAAGAAATGTG TGACCTTCGAGGAATATTGAGTGCACTTCAGGAGTGG | 2033 |
| | GAACCATCGCCAGGCGT | 2034 |
| | ACGCCTGGCGATGGTTC | 2035 |
| Haemophilia A Ala284Glu GCG-GAG | CTGAAGTGCACTCAATATTCCTCGAAGGTCACACATTTCTTGT GAGGAACCATCGCCAGGCGTCCTTGGAAATCTCGCCAATAAC TTTCCTTACTGCTCAAACACTCTTGATGGACCTTGG | 2036 |
| | CCAAGGTCCATCAAGAGTGTTTGAGCAGTAAGGAAAGTTATT GGCGAGATTTCCAAGGACGCCTGGCGATGGTTCCTCACAAG AAATGTGTGACCTTCGAGGAATATTGAGTGCACTTCAG | 2037 |
| | TCGCCAGGCGTCCTTGG | 2038 |
| | CCAAGGACGCCTGGCGA | 2039 |
| Haemophilia A Ala284Pro gGCG-CCG | CCTGAAGTGCACTCAATATTCCTCGAAGGTCACACATTTCTTG TGAGGAACCATCGCCAGGGCGTCCTTGGAAATCTCGCCAATAA CTTTCCTTACTGCTCAAACACTCTTGATGGACCTTG | 2040 |
| | CAAGGTCCATCAAGAGTGTTTGAGCAGTAAGGAAAGTTATTG GCGAGATTTCCAAGGACGCCTGGCGATGGTTCCTCACAAGAA ATGTGTGACCTTCGAGGAATATTGAGTGCACTTCAGG | 2041 |
| | ATCGCCAGGGCGTCCTTG | 2042 |
| | CAAGGACGCCTGGCGAT | 2043 |
| Haemophilia A Ser289Leu TCG-TTG | TATTCCTCGAAGGTCACACATTTCTTGTGAGGAACCATCGCCA GGCGTCCTTGGAAATCTCGCCAATAACTTTCCTTACTGCTCAA ACACTCTTGATGGACCTTGGACAGTTTCTACTGTT | 2044 |
| | AACAGTAGAAACTGTCCAAGGTCCATCAAGAGTGTTTGAGCA GTAAGGAAAGTTATTGGCGAGATTTCCAAGGACGCCTGGCGA TGGTTCCTCACAAGAAATGTGTGACCTTCGAGGAATA | 2045 |
| | GGAAATCTCGCCAATAA | 2046 |
| | TTATTGGCGAGATTTCC | 2047 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Phe293Ser TTC-TCC | GTCACACATTTCTTGTGAGGAACCATCGCCAGGCGTCCTTGG AAATCTCGCCAATAACTTTCCTTACTGCTCAAACACTCTTGAT GGACCTTGGACAGTTTCTACTGTTTTGTCATATCTC | 2048 |
| | GAGATATGACAAAACAGTAGAAACTGTCCAAGGTCCATCAAG AGTGTTTGAGCAGTAAGGAAAGTTATTGGCGAGATTTCCAAG GACGCCTGGCGATGGTTCCTCACAAGAAATGTGTGAC | 2049 |
| | AATAACTTTCCTTACTG | 2050 |
| | CAGTAAGGAAAGTTATT | 2051 |
| Haemophilia A Thr295Ala tACT-GCT | ACATTTCTTGTGAGGAACCATCGCCAGGCGTCCTTGGAAATC TCGCCAATAACTTTCCTTACTGCTCAAACACTCTTGATGGACC TTGGACAGTTTCTACTGTTTTGTCATATCTCTTCCC | 2052 |
| | GGGAAGAGATATGACAAAACAGTAGAAACTGTCCAAGGTCCA TCAAGAGTGTTTGAGCAGTAAGGAAAGTTATTGGCGAGATTTC CAAGGACGCCTGGCGATGGTTCCTCACAAGAAATGT | 2053 |
| | CTTTCCTTACTGCTCAA | 2054 |
| | TTGAGCAGTAAGGAAAG | 2055 |
| Haemophilia A Thr295Ile ACT-ATT | CATTTCTTGTGAGGAACCATCGCCAGGCGTCCTTGGAAATCT CGCCAATAACTTTCCTTACTGCTCAAACACTCTTGATGGACCT TGGACAGTTTCTACTGTTTTGTCATATCTCTTCCCA | 2056 |
| | TGGGAAGAGATATGACAAAACAGTAGAAACTGTCCAAGGTCC ATCAAGAGTGTTTGAGCAGTAAGGAAAGTTATTGGCGAGATTT CCAAGGACGCCTGGCGATGGTTCCTCACAAGAAATG | 2057 |
| | TTTCCTTACTGCTCAAA | 2058 |
| | TTTGAGCAGTAAGGAAA | 2059 |
| Haemophilia A Ala296Val GCT-GTT | TTCTTGTGAGGAACCATCGCCAGGCGTCCTTGGAAATCTCGC CAATAACTTTCCTTACTGCTCAAACACTCTTGATGGACCTTGG ACAGTTTCTACTGTTTTGTCATATCTCTTCCCACCA | 2060 |
| | TGGTGGGAAGAGATATGACAAAACAGTAGAAACTGTCCAAGG TCCATCAAGAGTGTTTGAGCAGTAAGGAAAGTTATTGGCGAG ATTTCCAAGGACGCCTGGCGATGGTTCCTCACAAGAA | 2061 |
| | CCTTACTGCTCAAACAC | 2062 |
| | GTGTTTGAGCAGTAAGG | 2063 |
| Haemophilia A Leu308Pro CTG-CCG | TCTCGCCAATAACTTTCCTTACTGCTCAAACACTCTTGATGGA CCTTGGACAGTTTCTACTGTTTTGTCATATCTCTTCCCACCAA CATGGTAATATCTTGGATCTTTAAAATGAATATTA | 2064 |
| | TAATATTCATTTTAAAGATCCAAGATATTACCATGTTGGTGGGA AGAGATATGACAAAACAGTAGAAACTGTCCAAGGTCCATCAA GAGTGTTTGAGCAGTAAGGAAAGTTATTGGCGAGA | 2065 |
| | GTTTCTACTGTTTTGTC | 2066 |
| | GACAAAACAGTAGAAAC | 2067 |
| Haemophilia A Glu321Lys gGAA-AAA | ACAGCCTAATATAGCAAGACACTCTGACATTGTTTGGTTTGTC TGACTCCAGATGGCATGGAAGCTTATGTCAAAGTAGACAGCT GTCCAGAGGAACCCCAACTACGAATGAAAAATAATG | 2068 |
| | CATTATTTTTCATTCGTAGTTGGGGTTCCTCTGGACAGCTGTC TACTTTGACATAAGCTTCCATGCCATCTGGAGTCAGACAAACC AAACAATGTCAGAGTGTCTTGCTATATTAGGCTGT | 2069 |
| | ATGGCATGGAAGCTTAT | 2070 |
| | ATAAGCTTCCATGCCAT | 2071 |
| Haemophilia A Tyr323Term TATg-TAA | ATATAGCAAGACACTCTGACATTGTTTGGTTTGTCTGACTCCA GATGGCATGGAAGCTTATGTCAAAGTAGACAGCTGTCCAGAG GAACCCCAACTACGAATGAAAAATAATGAAGAAGCG | 2072 |
| | CGCTTCTTCATTATTTTTCATTCGTAGTTGGGGTTCCTCTGGA CAGCTGTCTACTTTGACATAAGCTTCCATGCCATCTGGAGTCA GACAAACCAAACAATGTCAGAGTGTCTTGCTATAT | 2073 |
| | GAAGCTTATGTCAAAGT | 2074 |
| | ACTTTGACATAAGCTTC | 2075 |
| Haemophilia A Val326Leu aGTA-CTA | AAGACACTCTGACATTGTTTGGTTTGTCTGACTCCAGATGGCA TGGAAGCTTATGTCAAAGTAGACAGCTGTCCAGAGGAACCCC AACTACGAATGAAAAATAATGAAGAAGCGGAAGACT | 2076 |
| | AGTCTTCCGCTTCTTCATTATTTTTCATTCGTAGTTGGGGTTC CTCTGGACAGCTGTCTACTTTGACATAAGCTTCCATGCCATCT GGAGTCAGACAAACCAAACAATGTCAGAGTGTCTT | 2077 |
| | ATGTCAAAGTAGACAGC | 2078 |
| | GCTGTCTACTTTGACAT | 2079 |
| Haemophilia A Cys329Arg cTGT-CGT | TGACATTGTTTGGTTTGTCTGACTCCAGATGGCATGGAAGCTT ATGTCAAAGTAGACAGCTGTCCAGAGGAACCCCAACTACGAA TGAAAAATAATGAAGAAGCGGAAGACTATGATGATG | 2080 |
| | CATCATCATAGTCTTCCGCTTCTTCATTATTTTTCATTCGTAGT TGGGGTTCCTCTGGACAGCTGTCTACTTTGACATAAGCTTCC ATGCCATCTGGAGTCAGACAAACCAAACAATGTCA | 2081 |
| | TAGACAGCTGTCCAGAG | 2082 |
| | CTCTGGACAGCTGTCTA | 2083 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Cys329Tyr TGT-TAT | GACATTGTTTGGTTTGTCTGACTCCAGATGGCATGGAAGCTTA TGTCAAAGTAGACAGCTGTCCAGAGGAACCCCAACTACGAAT GAAAAATAATGAAGAAGCGGAAGACTATGATGATGA | 2084 |
| | TCATCATCATAGTCTTCCGCTTCTTCATTATTTTTCATTCGTAG TTGGGGTTCCTCTGGACAGCTGTCTACTTTGACATAAGCTTCC ATGCCATCTGGAGTCAGACAAACCAAACAATGTC | 2085 |
| | AGACAGCTGTCCAGAGG | 2086 |
| | CCTCTGGACAGCTGTCT | 2087 |
| Haemophilia A Arg336Term aCGA-TGA | ACTCCAGATGGCATGGAAGCTTATGTCAAAGTAGACAGCTGT CCAGAGGAACCCCAACTACGAATGAAAAATAATGAAGAAGCG GAAGACTATGATGATGACTTACTGATTCTGAAATGG | 2088 |
| | CCATTTCAGAATCAGTAAGATCATCATCATAGTCTTCCGCTTC TTCATTATTTTTCATTCGTAGTTGGGGTTCCTCTGGACAGCTG TCTACTTTGACATAAGCTTCCATGCCATCTGGAGT | 2089 |
| | CCCAACTACGAATGAAA | 2090 |
| | TTTCATTCGTAGTTGGA | 2091 |
| Haemophilia A Arg372Cys tCGC-TGC | GATTCTGAAATGGATGTGGTCAGGTTTGATGATGACAACTCTC CTTCCTTTATCCAAATTCGCTCAGTTGCCAAGAAGCATCCTAA AACTTGGGTACATTACATTGCTGCTGAAGAGGAGG | 2092 |
| | CCTCCTCTTCAGCAGCAATGTAATGTACCCAAGTTTTAGGATG CTTCTTGGCAACTGAGCGAATTTGGATAAAGGAAGGAGAGTT GTCATCATCAAACCTGACCACATCCATTTCAGAATC | 2093 |
| | TCCAAATTCGCTCAGTT | 2094 |
| | AACTGAGCGAATTTGGA | 2095 |
| Haemophilia A Arg372His CGC-CAC | ATTCTGAAATGGATGTGGTCAGGTTTGATGATGACAACTCTCC TTCCTTTATCCAAATTCGCTCAGTTGCCAAGAAGCATCCTAAA ACTTGGGTACATTACATTGCTGCTGAAGAGGAGGA | 2096 |
| | TCCTCCTCTTCAGCAGCAATGTAATGTACCCAAGTTTTAGGAT GCTTCTTGGCAACTGAGCGAATTTGGATAAAGGAAGGAGAGT TGTCATCATCAAACCTGACCACATCCATTTCAGAAT | 2097 |
| | CCAAATTCGCTCAGTTG | 2098 |
| | CAACTGAGCCGAATTTGG | 2099 |
| Haemophilia A Ser373Leu TCA-TTA | CTGAAATGGATGTGGTCAGGTTTGATGATGACAACTCTCCTTC CTTTATCCAAATTCGCTCAGTTGCCAAGAAGCATCCTAAAACT TGGGTACATTACATTGCTGCTGAAGAGGAGGACTG | 2100 |
| | CAGTCCTCCTCTTCAGCAGCAATGTAATGTACCCAAGTTTTAG GATGCTTCTTGGCAACTGAGCGAATTTGGATAAAGGAAGGAG AGTTGTCATCATCAAACCTGACCACATCCATTTCAG | 2101 |
| | AATTCGCTCAGTTGCCA | 2102 |
| | TGGCAACTGAGCGAATT | 2103 |
| Haemophilia A Ser373Pro cTCA-CCA | TCTGAAATGGATGTGGTCAGGTTTGATGATGACAACTCTCCTT CCTTTATCCAAATTCGCTCAGTTGCCAAGAAGCATCCTAAAAC TTGGGTACATTACATTGCTGCTGAAGAGGAGGACT | 2104 |
| | AGTCCTCCTCTTCAGCAGCAATGTAATGTACCCAAGTTTTAGG ATGCTTCTTGGCAACTGAGCGAATTTGGATAAAGGAAGGAGA GTTGTCATCATCAAACCTGACCACATCCATTTCAGA | 2105 |
| | AAATTCGCTCAGTTGCC | 2106 |
| | GGCAACTGAGCGAATTT | 2107 |
| Haemophilia A Ser373Term TCA-TAA | CTGAAATGGATGTGGTCAGGTTTGATGATGACAACTCTCCTTC CTTTATCCAAATTCGCTCAGTTGCCAAGAAGCATCCTAAAACT TGGGTACATTACATTGCTGCTGAAGAGGAGGACTG | 2108 |
| | CAGTCCTCCTCTTCAGCAGCAATGTAATGTACCCAAGTTTTAG GATGCTTCTTGGCAACTGAGCGAATTTGGATAAAGGAAGGAG AGTTGTCATCATCAAACCTGACCACATCCATTTCAG | 2109 |
| | AATTCGCTCAGTTGCCA | 2110 |
| | TGGCAACTGAGCGAATT | 2111 |
| Haemophilia A Ile386Phe cATT-TTT | CCTTCCTTTATCCAAATTCGCTCAGTTGCCAAGAAGCATCCTA AAACTTGGGTACATTACATTGCTGCTGAAGAGGAGGACTGGG ACTATGCTCCCTTAGTCCTCGCCCCGATGACAGGT | 2112 |
| | ACCTGTCATCGGGGCGAGGACTAAGGGAGCATAGTCCCAG TCCTCCTCTTCAGCAGCAATGTAATGTACCCAAGTTTTAGGAT GCTTCTTGGCAACTGAGCGAATTTGGATAAAGGAAGG | 2113 |
| | TACATTACATTGCTGCT | 2114 |
| | AGCAGCAATGTAATGTA | 2115 |
| Haemophilia A Ile386Ser ATT-AGT | CTTCCTTTATCCAAATTCGCTCAGTTGCCAAGAAGCATCCTAA AACTTGGGTACATTACATTGCTGCTGAAGAGGAGGACTGGGA CTATGCTCCCTTAGTCCTCGCCCCGATGACAGGTA | 2116 |
| | TACCTGTCATCGGGGCGAGGACTAAGGGAGCATAGTCCCA GTCCTCCTCTTCAGCAGCAATGTAATGTACCCAAGTTTTAGGA TGCTTCTTGGCAACTGAGCGAATTTGGATAAAGGAAG | 2117 |
| | ACATTACATTGCTGCTG | 2118 |
| | CAGCAGCAATGTAATGT | 2119 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Glu390Gly GAG-GGG | AAAATTCGCTCAGTTGCCAAGAAGCATCCTAAAACTTGGGTACA TTACATTGCTGCTGAAGAGGAGGACTGGGACTATGCTCCCTT AGTCCTCGCCCCCGATGACAGGTAAGCACTTTTTGA | 2120 |
| | TCAAAAAGTGCTTACCTGTCATCGGGGGCGAGGACTAAGGGA GCATAGTCCCAGTCCTCCTCTTCAGCAGCAATGTAATGTACC CAAGTTTTAGGATGCTTCTTGGCAACTGAGCGAATTT | 2121 |
| | TGCTGAAGAGGAGGACT | 2122 |
| | AGTCCTCCTCTTCAGCA | 2123 |
| Haemophilia A Trp393Gly cTGG-GGG | TCAGTTGCCAAGAAGCATCCTAAAACTTGGGTACATTACATTG CTGCTGAAGAGGAGGACTGGGACTATGCTCCCTTAGTCCTCG CCCCCGATGACAGGTAAGCACTTTTTGACTATTGGT | 2124 |
| | ACCAATAGTCAAAAAGTGCTTACCTGTCATCGGGGGCGAGGA CTAAGGGAGCATAGTCCCAGTCCTCCTCTTCAGCAGCAATGT AATGTACCCAAGTTTTAGGATGCTTCTTGGCAACTGA | 2125 |
| | AGGAGGACTGGGACTAT | 2126 |
| | ATAGTCCCAGTCCTCCT | 2127 |
| Haemophilia A Lys408Ile AAA-ATA | GCCTACCTAGAATTTTTCTTCCCAACCTCTCATCTTTTTTTCTC TTATACAGAAGTTATAAAAGTCAATATTTGAACAATGGCCCTC AGCGGATTGGTAGGAAGTACAAAAAAGTCCGATT | 2128 |
| | AATCGGACTTTTTTGTACTTCCTACCAATCCGCTGAGGGCCAT TGTTCAAATATTGACTTTTATAACTTCTGTATAAGAGAAAAAAA GATGAGAGGTTGGGAAGAAAAATTCTAGGTAGGC | 2129 |
| | AAGTTATAAAAGTCAAT | 2130 |
| | ATTGACTTTTATAACTT | 2131 |
| Haemophilia A Leu412Phe TTGa-TTT | TTTTCTTCCCAACCTCTCATCTTTTTTTCTCTTATACAGAAGTT ATAAAAGTCAATATTTGAACAATGGCCCTCAGCGGATTGGTAG GAAGTACAAAAAAGTCCGATTTATGGCATACACA | 2132 |
| | TGTGTATGCCATAAATCGGACTTTTTTGTACTTCCTACCAATC CGCTGAGGGCCATTGTTCAAATATTGACTTTTATAACTTCTGT ATAAGAGAAAAAAGATGAGAGGTTGGGAAGAAAA | 2133 |
| | CAATATTTGAACAATGG | 2134 |
| | CCATTGTTCAAATATTG | 2135 |
| Haemophilia A Arg418Trp gCGG-TGG | TCATCTTTTTTTCTCTTATACAGAAGTTATAAAAGTCAATATTTG AACAATGCCCCTCAGCGGGATTGGTAGGAAGTACAAAAAAGTC CGATTTATGGCATACACAGATGAAACCTTTAAGA | 2136 |
| | TCTTAAAGGTTTCATCTGTGTATGCCATAAATCGGACTTTTTTG TACTTCCTACCAATCCGCTGAGGGCCATTGTTCAAATATTGAC TTTTATAACTTCTGTATAAGAGAAAAAAAGATGA | 2137 |
| | GCCCTCAGCGGGATTGGT | 2138 |
| | ACCAATCCGCTGAGGGC | 2139 |
| Haemophilia A Gly420Val GGT-GTT | TTTTTCTCTTATACAGAAGTTATAAAAGTCAATATTTGAACAAT GGCCCTCAGCGGATTGGTAGGAAGTACAAAAAAGTCCGATTT ATGGCATACACAGATGAAACCTTTAAGACTCGTGA | 2140 |
| | TCACGAGTCTTAAAGGTTTCATCTGTGTATGCCATAAATCGGA CTTTTTTGTACTTCCTACCAATCCGCTGAGGGCCATTGTTCAA ATATTGACTTTTATAACTTCTGTATAAGAGAAAAA | 2141 |
| | GCGGATTGGTAGGAAGT | 2142 |
| | ACTTCCTACCAATCCGC | 2143 |
| Haemophilia A Lys425Arg AAA-AGA | GAAGTTATAAAAGTCAATATTTGAACAATGGCCCTCAGCGGAT TGGTAGGAAGTACAAAAAAGTCCGATTTATGGCATACACAGAT GAAACCTTTAAGACTCGTGAAGCTATTCAGCATGA | 2144 |
| | TCATGCTGAATAGCTTCACGAGTCTTAAAGGTTTCATCTGTGT ATGCCATAAATCGGACTTTTTTGTACTTCCTACCAATCCGCTG AGGGCCATTGTTCAAATATTGACTTTTATAACTTC | 2145 |
| | GTACAAAAAAGTCCGAT | 2146 |
| | ATCGGACTTTTTTGTAC | 2147 |
| Haemophilia A Arg427Term cCGA-TGA | TATAAAAGTCAATATTTGAACAATGGCCCTCAGCGGATTGGTA GGAAGTACAAAAAAGTCCGATTTATGGCATACACAGATGAAAC CTTTAAGACTCGTGAAGCTATTCAGCATGAATCAG | 2148 |
| | CTGATTCATGCTGAATAGCTTCACGAGTCTTAAAGGTTTCATC TGTGTATGCCATAAATCGGACTTTTTTGTACTTCCTACCAATC CGCTGAGGGCCATTGTTCAAATATTGACTTTTATA | 2149 |
| | AAAAAGTCCGATTTATG | 2150 |
| | CATAAATCGGACTTTTT | 2151 |
| Haemophilia A Tyr431Asn aTAC-AAC | TATTTGAACAATGGCCCTCAGCGGATTGGTAGGAAGTACAAA AAAGTCCGATTTATGGCATACACAGATGAAACCTTTAAGACTC GTGAAGCTATTCAGCATGAATCAGGAATCTGGGAC | 2152 |
| | GTCCCAAGATTCCTGATTCATGCTGAATAGCTTCACGAGTCTT AAAGGTTTCATCTGTGTATGCCATAAATCGGACTTTTTTGTAC TTCCTACCAATCCGCTGAGGGCCATTGTTCAAATA | 2153 |
| | TTATGGCATACACAGAT | 2154 |
| | ATCTGTGTATGCCATAA | 2155 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Thr435Ile ACC-ATC | GCCCTCAGCGGATTGGTAGGAAGTACAAAAAAGTCCGATTTA TGGCATACACAGATGAAACCTTTAAGACTCGTGAAGCTATTCA GCATGAATCAGGAATCTTGGGACCTTTACTTTATGG | 2156 |
| | CCATAAAGTAAAGGTCCCAAGATTCCTGATTCATGCTGAATAG CTTCACGAGTCTTAAAGGTTTCATCTGTGTATGCCATAAATCG GACTTTTTTGTACTTCCTACCAATCCGCTGAGGGC | 2157 |
| | AGATGAAACCTTTAAGA | 2158 |
| | TCTTAAAGGTTTCATCT | 2159 |
| Haemophilia A Pro451Leu CCT-CTT | ACACAGATGAAACCTTTAAGACTCGTGAAGCTATTCAGCATGA ATCAGGAATCTTGGGACCTTTACTTTATGGGGAAGTTGGAGA CACACTGTTGGTAAGTTGAAGAAAAGATTTAAGGTC | 2160 |
| | GACCTTAAATCTTTTCTTCAACTTACCAACAGTGTGTCTCCAA CTTCCCCATAAAGTAAAGGTCCCAAGATTCCTGATTCATGCTG AATAGCTTCACGAGTCTTAAAGGTTTCATCTGTGT | 2161 |
| | CTTGGGACCTTTACTTT | 2162 |
| | AAAGTAAAGGTCCCAAG | 2163 |
| Haemophilia A Pro451Thr aCCT-ACT | TACACAGATGAAACCTTTAAGACTCGTGAAGCTATTCAGCATG AATCAGGAATCTTGGGACCTTTACTTTATGGGGAAGTTGGAGA CACACTGTTGGTAAGTTGAAGAAAAGATTTAAGGT | 2164 |
| | ACCTTAAATCTTTTCTTCAACTTACCAACAGTGTGTCTCCAACT TCCCCATAAAGTAAAGGTCCCAAGATTCCTGATTCATGCTGAA TAGCTTCACGAGTCTTAAAGGTTTCATCTGTGTA | 2165 |
| | TCTTGGGACCTTTACTT | 2166 |
| | AAGTAAAGGTCCCAAGA | 2167 |
| Haemophilia A Gly455Arg tGGG-AGG | ACCTTTAAGACTCGTGAAGCTATTCAGCATGAATCAGGAATCT TGGGACCTTTACTTTATGGGGAAGTTGGAGACACACTGTTGG TAAGTTGAAGAAAAGATTTAAGGTCAGGTAAGAAGA | 2168 |
| | TCTTCTTACCTGACCTTAAATCTTTTCTTCAACTTACCAACAGT GTGTCTCCAACTTCCCCATAAAGTAAAGGTCCCAAGATTCCTG ATTCATGCTGAATAGCTTCACGAGTCTTAAAGGT | 2169 |
| | TACTTTATGGGGAAGTT | 2170 |
| | AACTTCCCCATAAAGTA | 2171 |
| Haemophilia A Gly455Glu GGG-GAG | CCTTTAAGACTCGTGAAGCTATTCAGCATGAATCAGGAATCTT GGGACCTTTACTTTATGGGGAAGTTGGAGACACACTGTTGGT AAGTTGAAGAAAAGATTTAAGGTCAGGTAAGAAGAA | 2172 |
| | TTCTTCTTACCTGACCTTAAATCTTTTCTTCAACTTACCAACAG TGTGTCTCCAACTTCCCCATAAAGTAAAGGTCCCAAGATTCCT GATTCATGCTGAATAGCTTCACGAGTCTTAAAGG | 2173 |
| | ACTTTATGGGGAAGTTG | 2174 |
| | CAACTTCCCCATAAAGT | 2175 |
| Haemophilia A Asp459Asn aGAC-AAC | CGTGAAGCTATTCAGCATGAATCAGGAATCTTGGGACCTTTAC TTTATGGGGAAGTTGGAGACACACTGTTGGTAAGTTGAAGAA AAGATTTAAGGTCAGGTAAGAAGAAAAGTCTGGAG | 2176 |
| | CTCCAGACTTTTTCTTCTTACCTGACCTTAAATCTTTTCTTCAA CTTACCAACAGTGTGTCTCCAACTTCCCCATAAAGTAAAGGTC CCAAGATTCCTGATTCATGCTGAATAGCTTCACG | 2177 |
| | AAGTTGGAGACACACTG | 2178 |
| | CAGTGTGTCTCCAACTT | 2179 |
| Haemophilia A Phe465Cys TTT-TGT | TGTTGATCCTAGTCGTTTTAGGATTTGATCTTAGATCTCGCTTA TACTTTCAGATTATATTTAAGAATCAAGCAAGCAGACCATATAA CATCTACCCTCACGGAATCACTGATGTCCGTCC | 2180 |
| | GGACGGACATCAGTGATTCCGTGAGGGTAGATGTTATATGGT CTGCTTGCTTGATTCTTAAATATAATCTGAAAGTATAAGCGAG ATCTAAGATCAAATCCTAAAACGACTAGGATCAACA | 2181 |
| | GATTATATTTAAGAATC | 2182 |
| | GATTCTTAAATATAATC | 2183 |
| Haemophilia A Ala469Gly GCA-GGA | TCGTTTTAGGATTTGATCTTAGATCTCGCTTATACTTTCAGATT ATATTTAAGAATCAAGCAAGCAGACCATATAACATCTACCCTC ACGGAATCACTGATGTCCGTCCTTTGTATTCAAG | 2184 |
| | CTTGAATACAAAGGACGGACATCAGTGATTCCGTGAGGGTAG ATGTTATATGGTCTGCTTGCTTGATTCTTAAATATAATCTGAAA GTATAAGCGAGATCTAAGATCAAATCCTAAAACGA | 2185 |
| | GAATCAAGCAAGCAGAC | 2186 |
| | GTCTGCTTGCTTGATTC | 2187 |
| Haemophilia A Arg471Gly cAGA-GGA | TTAGGATTTGATCTTAGATCTCGCTTATACTTTCAGATTATATT TAAGAATCAAGCAAGCAGACCATATAACATCTACCCTCACGG AATCACTGATGTCCGTCCTTTGTATTCAAGGAGAT | 2188 |
| | ATCTCCTTGAATACAAAGGACGGACATCAGTGATTCCGTGAG GGTAGATGTTATATGGTCTGCTTGCTTGATTCTTAAATATAATC TGAAAGTATAAGCGAGATCTAAGATCAAATCCTAA | 2189 |
| | AAGCAAGCAGACCATAT | 2190 |
| | ATATGGTCTGCTTGCTT | 2191 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Tyr473Cys TAT-TGT | TTGATCTTAGATCTCGCTTATACTTTCAGATTATATTTAAGAAT CAAGCAAGCAGACCATATAACATCTACCCTCACGGAATCACT GATGTCCGTCCTTTGTATTCAAGGAGATTACCAAA | 2192 |
| | TTTGGTAATCTCCTTGAATACAAAGGACGGACATCAGTGATTC CGTGAGGGTAGATGTTATATGGTCTGCTTGCTTGATTCTTAAA TATAATCTGAAAGTATAAGCGAGATCTAAGATCAA | 2193 |
| | CAGACCATATAACATCT | 2194 |
| | AGATGTTATATGGTCTG | 2195 |
| Haemophilia A Tyr473His aTAT-CAT | TTTGATCTTAGATCTCGCTTATACTTTCAGATTATATTTAAGAA TCAAGCAAGCAGACCATATAACATCTACCCTCACGGAATCACT GATGTCCGTCCTTTGTATTCAAGGAGATTACCAA | 2196 |
| | TTGGTAATCTCCTTGAATACAAAGGACGGACATCAGTGATTCC GTGAGGGTAGATGTTATATGGTCTGCTTGCTTGATTCTTAAAT ATAATCTGAAAGTATAAGCGAGATCTAAGATCAAA | 2197 |
| | GCAGACCATATAACATC | 2198 |
| | GATGTTATATGGTCTGC | 2199 |
| Haemophilia A Ile475Thr ATC-ACC | TTAGATCTCGCTTATACTTTCAGATTATATTTAAGAATCAAGCA AGCAGACCATATAACACTCTACCCTCACGGAATCACTGATGTCC GTCCTTTGTATTCAAGGAGATTACCAAAAGGTAA | 2200 |
| | TTACCTTTTGGTAATCTCCTTGAATACAAAGGACGGACATCAG TGATTCCGTGAGGGTAGATGTTATATGGTCTGCTTGCTTGATT CTTAAATATAATCTGAAAGTATAAGCGAGATCTAA | 2201 |
| | ATATAACATCTACCCTC | 2202 |
| | GAGGGTAGATGTTATAT | 2203 |
| Haemophilia A Gly479Arg cGGA-AGA | TTATACTTTCAGATTATATTTAAGAATCAAGCAAGCAGACCATA TAACATCTACCCTCACGGAATCACTGATGTCCGTCCTTTGTAT TCAAGGAGATTACCAAAAGGTAAATATTCCCTCG | 2204 |
| | CGAGGGAATATTTACCTTTTGGTAATCTCCTTGAATACAAAGG ACGGACATCAGTGATTCCGTGAGGGTAGATGTTATATGGTCT GCTTGCTTGATTCTTAAATATAATCTGAAAGTATAA | 2205 |
| | ACCCTCACGGAATCACT | 2206 |
| | AGTGATTCCGTGAGGGT | 2207 |
| Haemophilia A Thr522Ser aACT-TCT | CCAATTCTGCCAGGAGAAATATTCAAATATAAATGGACAGTGA CTGTAGAAGATGGGCCAACTAAATCAGATCCTCGGTGCCTGA CCCGCTATTACTCTAGTTTCGTTAATATGGAGAGAG | 2208 |
| | CTCTCTCCATATTAACGAAACTAGAGTAATAGCGGGTCAGGC ACCGAGGATCTGATTTAGTTGGCCCATCTTCTACAGTCACTGT CCATTTATATTTGAATATTTCTCCTGGCAGAATTGG | 2209 |
| | ATGGGCCAACTAAATCA | 2210 |
| | TGATTTAGTTGGCCCAT | 2211 |
| Haemophilia A Asp525Asn aGAT-AAT | CCAGGAGAAATATTCAAATATAAATGGACAGTGACTGTAGAAG ATGGGCCAACTAAATCAGATCCTCGGTGCCTGACCCGCTATT ACTCTAGTTTCGTTAATATGGAGAGAGATCTAGCTT | 2212 |
| | AAGCTAGATCTCTCTCCATATTAACGAAACTAGAGTAATAGCG GGTCAGGCACCGAGGATCTGATTTAGTTGGCCCATCTTCTAC AGTCACTGTCCATTTATATTTGAATATTTCTCCTGG | 2213 |
| | CTAAATCAGATCCTCGG | 2214 |
| | CCGAGGATCTGATTTAG | 2215 |
| Haemophilia A Arg527Trp tCGG-TGG | GAAATATTCAAATATAAATGGACAGTGACTGTAGAAGATGGGC CAACTAAATCAGATCCTCGGTGCCTGACCCGCTATTACTCTA GTTTCGTTAATATGGAGAGAGATCTAGCTTCAGGAC | 2216 |
| | GTCCTGAAGCTAGATCTCTCTCCATATTAACGAAACTAGAGTA ATAGCGGGTCAGGCACCGAGGATCTGATTTAGTTGGCCCATC TTCTACAGTCACTGTCCATTTATATTTGAATATTTC | 2217 |
| | CAGATCCTCGGTGCCTG | 2218 |
| | CAGGCACCGAGGATCTG | 2219 |
| Haemophilia A Arg531Cys cCGC-TGC | TATAAATGGACAGTGACTGTAGAAGATGGGCCAACTAAATCA GATCCTCGGTGCCTGACCCGCTATTACTCTAGTTTCGTTAATA TGGAGAGAGATCTAGCTTCAGGACTCATTGGCCCTC | 2220 |
| | GAGGGCCAATGAGTCCTGAAGCTAGATCTCTCTCCATATTAA CGAAACTAGAGTAATAGCGGGTCAGGCACCGAGGATCTGATT TAGTTGGCCCATCTTCTACAGTCACTGTCCATTTATA | 2221 |
| | GCCTGACCCGCTATTAC | 2222 |
| | GTAATAGCGGGTCAGGC | 2223 |
| Haemophilia A Arg531Gly cCGC-GGC | TATAAATGGACAGTGACTGTAGAAGATGGGCCAACTAAATCA GATCCTCGGTGCCTGACCCGCTATTACTCTAGTTTCGTTAATA TGGAGAGAGATCTAGCTTCAGGACTCATTGGCCCTC | 2224 |
| | GAGGGCCAATGAGTCCTGAAGCTAGATCTCTCTCCATATTAA CGAAACTAGAGTAATAGCGGGTCAGGCACCGAGGATCTGATT TAGTTGGCCCATCTTCTACAGTCACTGTCCATTTATA | 2225 |
| | GCCTGACCCGCTATTAC | 2226 |
| | GTAATAGCGGGTCAGGC | 2227 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Arg531His CGC-CAC | ATAAATGGACAGTGACTGTAGAAGATGGGCCAACTAAATCAG ATCCTCGGTGCCTGACCCGCTATTACTCTAGTTTCGTTAATAT GGAGAGAGATCTAGCTTCAGGACTCATTGGCCCTCT | 2228 |
| | AGAGGGCCAATGAGTCCTGAAGCTAGATCTCTCTCCATATTAA CGAAACTAGAGTAATAGCGGGTCAGGCACCGAGGATCTGATT TAGTTGGCCCATCTTCTACAGTCACTGTCCATTTAT | 2229 |
| | CCTGACCCGCTATTACT | 2230 |
| | AGTAATAGCGGGTCAGG | 2231 |
| Haemophilia A Ser534Pro cTCT-CCT | ACAGTGACTGTAGAAGATGGGCCAACTAAATCAGATCCTCGG TGCCTGACCCGCTATTACTCTAGTTTCGTTAATATGGAGAGAG ATCTAGCTTCAGGACTCATTGGCCCTCTCCTCATCT | 2232 |
| | AGATGAGGAGAGGGCCAATGAGTCCTGAAGCTAGATCTCTCT CCATATTAACGAAACTAGAGTAATAGCGGGTCAGGCACCGAG GATCTGATTTAGTTGGCCCATCTTCTACAGTCACTGT | 2233 |
| | GCTATTACTCTAGTTTC | 2234 |
| | GAAACTAGAGTAATAGC | 2235 |
| Haemophilia A Ser535Gly tAGT-GGT | GTGACTGTAGAAGATGGGCCAACTAAATCAGATCCTCGGTGC CTGACCCGCTATTACTCTAGTTTCGTTAATATGGAGAGAGATC TAGCTTCAGGACTCATTGGCCCTCTCCTCATCTGCT | 2236 |
| | AGCAGATGAGGAGAGGGCCAATGAGTCCTGAAGCTAGATCTC TCTCCATATTAACGAAACTAGAGTAATAGCGGGTCAGGCACC GAGGATCTGATTTAGTTGGCCCATCTTCTACAGTCAC | 2237 |
| | ATTACTCTAGTTTCGTT | 2238 |
| | AACGAAACTAGAGTAAT | 2239 |
| Haemophilia A Val537Asp GTT-GAT | TAGAAGATGGGCCAACTAAATCAGATCCTCGGTGCCTGACCC GCTATTACTCTAGTTTCGTTAATATGGAGAGAGATCTAGCTTC AGGACTCATTGGCCCTCTCCTCATCTGCTACAAAGA | 2240 |
| | TCTTTGTAGCAGATGAGGAGAGGGCCAATGAGTCCTGAAGCT AGATCTCTCTCCATATTAACGAAACTAGAGTAATAGCGGGTCA GGCACCGAGGATCTGATTTAGTTGGCCCATCTTCTA | 2241 |
| | TAGTTTCGTTAATATGG | 2242 |
| | CCATATTAACGAAACTA | 2243 |
| Haemophilia A Arg541Thr AGA-ACA | CAACTAAATCAGATCCTCGGTGCCTGACCCGCTATTACTCTA GTTTCGTTAATATGGAGAGAGATCTAGCTTCAGGACTCATTGG CCCTCTCCTCATCTGCTACAAAGAATCTGTAGATCA | 2244 |
| | TGATCTACAGATTCTTTGTAGCAGATGAGGAGAGGGCCAATG AGTCCTGAAGCTAGATCTCTCTCCATATTAACGAAACTAGAGT AATAGCGGGTCAGGCACCGAGGATCTGATTTAGTTG | 2245 |
| | TATGGAGAGAGATCTAG | 2246 |
| | CTAGATCTCTCTCCATA | 2247 |
| Haemophilia A Asp542Gly GAT-GGT | CTAAATCAGATCCTCGGTGCCTGACCCGCTATTACTCTAGTTT CGTTAATATGGAGAGAGATCTAGCTTCAGGACTCATTGGCCC TCTCCTCATCTGCTACAAAGAATCTGTAGATCAAAG | 2248 |
| | CTTTGATCTACAGATTCTTTGTAGCAGATGAGGAGAGGGCCA ATGAGTCCTGAAGCTAGATCTCTCTCCATATTAACGAAACTAG AGTAATAGCGGGTCAGGCACCGAGGATCTGATTTAG | 2249 |
| | GGAGAGAGATCTAGCTT | 2250 |
| | AAGCTAGATCTCTCTCC | 2251 |
| Haemophilia A Asp542His aGAT-CAT | ACTAAATCAGATCCTCGGTGCCTGACCCGCTATTACTCTAGTT TCGTTAATATGGAGAGAGATCTAGCTTCAGGACTCATTGGCC CTCTCCTCATCTGCTACAAAGAATCTGTAGATCAAA | 2252 |
| | TTTGATCTACAGATTCTTTGTAGCAGATGAGGAGAGGGCCAAT GAGTCCTGAAGCTAGATCTCTCTCCATATTAACGAAACTAGAG TAATAGCGGGTCAGGCACCGAGGATCTGATTTAGT | 2253 |
| | TGGAGAGAGATCTAGCT | 2254 |
| | AGCTAGATCTCTCTCCA | 2255 |
| Haemophilia A Asp542Tyr aGAT-TAT | ACTAAATCAGATCCTCGGTGCCTGACCCGCTATTACTCTAGTT TCGTTAATATGGAGAGAGATCTAGCTTCAGGACTCATTGGCC CTCTCCTCATCTGCTACAAAGAATCTGTAGATCAAA | 2256 |
| | TTTGATCTACAGATTCTTTGTAGCAGATGAGGAGAGGGCCAAT GAGTCCTGAAGCTAGATCTCTCTCCATATTAACGAAACTAGAG TAATAGCGGGTCAGGCACCGAGGATCTGATTTAGT | 2257 |
| | TGGAGAGAGATCTAGCT | 2258 |
| | AGCTAGATCTCTCTCCA | 2259 |
| Haemophilia A Glu557Term aGAA-TAA | GTTAATATGGAGAGAGATCTAGCTTCAGGACTCATTGGCCCT CTCCTCATCTGCTACAAAGAATCTGTAGATCAAAGAGGAAACC AGGTGAGTTCTTGCCTTTCCAAGTGCTGGGTTTCAT | 2260 |
| | ATGAAACCCAGCACTTGGAAAGGCAAGAACTCACCTGGTTTC CTCTTTGATCTACAGATTCTTTGTAGCAGATGAGGAGAGGGC CAATGAGTCCTGAAGCTAGATCTCTCTCCATATTAAC | 2261 |
| | GCTACAAAGAATCTGTA | 2262 |
| | TACAGATTCTTTGTAGC | 2263 |

TABLE 20-continued

Factor VIII Mutations and Genome-Correcting Oligos

| Clinical Phenotype & Mutation | Correcting Oligos | SEQ ID NO: |
|---|---|---|
| Haemophilia A Ser558Phe TCT-TTT | ATATGGAGAGAGATCTAGCTTCAGGACTCATTGGCCCTCTCC TCATCTGCTACAAAGAATCTGTAGATCAAAGAGGAAACCAGGT GAGTTCTTGCCTTTCCAAGTGCTGGGTTTCATTCTC | 2264 |
| | GAGAATGAAACCCAGCACTTGGAAAGGCAAGAACTCACCTGG TTTCCTCTTTGATCTACAGATTCTTTGTAGCAGATGAGGAGAG GGCCAATGAGTCCTGAAGCTAGATCTCTCTCCATAT | 2265 |
| | CAAAGAATCTGTAGATC | 2266 |
| | GATCTACAGATTCTTTG | 2267 |
| Haemophilia A Val559Ala GTA-GCA | TGGAGAGAGATCTAGCTTCAGGACTCATTGGCCCTCTCCTCA TCTGCTACAAAGAATCTGTAGATCAAAGAGGAAACCAGGTGA GTTCTTGCCTTTCCAAGTGCTGGGTTTCATTCTCAGT | 2268 |
| | ACTGAGAATGAAACCCAGCACTTGGAAAGGCAAGAACTCACC TGGTTTCCTCTTTGATCTACAGATTCTTTGTAGCAGATGAGGA GAGGGCCAATGAGTCCTGAAGCTAGATCTCTCTCCA | 2269 |
| | AGAATCTGTAGATCAAA | 2270 |
| | TTTGATCTACAGATTCT | 2271 |

EXAMPLE 14

Hemophilia—Factor IX Deficiency

The attached table discloses the correcting oligonucleotide base sequences for the Factor IX oligonucleotides of the invention.

TABLE 21

Factor IX Mutations and Genome-Correcting Oligos

| Clinical Phenotype & Mutation | Correcting Oligos | SEQ ID NO: |
|---|---|---|
| Haemophilia B Asn2Asp tAAT-GAT | ATTTCAGTTTTTCTTGATCATGAAAACGCCAACAAAATTCTGAA TCGGCCAAAGAGGTATAATTCAGGTAAATTGGAAGAGTTTGTT CAAGGGAACCTTGAGAGAGAATGTATGGAAGAAA | 2272 |
| | TTTCTTCCATACATTCTCTCTCAAGGTTCCCTTGAACAAACTCT TCCAATTTACCTGAATTATACCTCTTTGGCCGATTCAGAATTTT GTTGGCGTTTTCATGATCAAGAAAAACTGAAAT | 2273 |
| | AGAGGTATAATTCAGGT | 2274 |
| | ACCTGAATTATACCTCT | 2275 |
| Haemophilia B Asn2Ile AAT-ATT | TTTCAGTTTTTCTTGATCATGAAAACGCCAACAAAATTCTGAAT CGGCCAAAGAGGTATAATTCAGGTAAATTGGAAGAGTTTGTT CAAGGGAACCTTGAGAGAGAATGTATGGAAGAAA | 2276 |
| | TTTTCTTCCATACATTCTCTCTCAAGGTTCCCTTGAACAAACTC TTCCAATTTACCTGAATTATACCTCTTTGGCCGATTCAGAATTT TGTTGGCGTTTTCATGATCAAGAAAAACTGAAA | 2277 |
| | GAGGTATAATTCAGGTA | 2278 |
| | TACCTGAATTATACCTC | 2279 |
| Haemophilia B Asn2Tyr tAAT-TAT | ATTTCAGTTTTTCTTGATCATGAAAACGCCAACAAAATTCTGAA TCGGCCAAAGAGGTATAATTCAGGTAAATTGGAAGAGTTTGTT CAAGGGAACCTTGAGAGAGAATGTATGGAAGAAA | 2280 |
| | TTTCTTCCATACATTCTCTCTCAAGGTTCCCTTGAACAAACTCT TCCAATTTACCTGAATTATACCTCTTTGGCCGATTCAGAATTTT GTTGGCGTTTTCATGATCAAGAAAAACTGAAAT | 2281 |
| | AGAGGTATAATTCAGGT | 2282 |
| | ACCTGAATTATACCTCT | 2283 |
| Haemophilia B Ser3Pro tTCA-CCA | TCAGTTTTTCTTGATCATGAAAACGCCAACAAAATTCTGAATC GGCCAAAGAGGTATAATTCAGGTAAATTGGAAGAGTTTGTTCA AGGGAACCTTGAGAGAGAATGTATGGAAGAAAGT | 2284 |
| | ACTTTTCTTCCATACATTCTCTCTCAAGGTTCCCTTGAACAAAC TCTTCCAATTTACCTGAATTATACCTCTTTGGCCGATTCAGAA TTTTGTTGGCGTTTTCATGATCAAGAAAAACTGA | 2285 |
| | GGTATAATTCAGGTAAA | 2286 |
| | TTTACCTGAATTATACC | 2287 |
| Haemophilia B Gly4Asp GGT-GAT | TTTTTCTTGATCATGAAAACGCCAACAAAATTCTGAATCGGCC AAAGAGGTATAATTCAGGTAAATTGGAAGAGTTTGTTCAAGGG AACCTTGAGAGAGAATGTATGGAAGAAAGTGTAG | 2288 |
| | CTACACTTTTCTTCCATACATTCTCTCTCAAGGTTCCCTTGAAC AAACTCTTCCAATTTACCTGAATTATACCTCTTTGGCCGATTCA | 2289 |

TABLE 21-continued

Factor IX Mutations and Genome-Correcting Oligos

| Clinical Phenotype & Mutation | Correcting Oligos | SEQ ID NO: |
|---|---|---|
| | GAATTTTGTTGGCGTTTTCATGATCAAGAAAAA | |
| | TAATTCAGGTAAATTGG | 2290 |
| | CCAATTTACCTGAATTA | 2291 |
| Haemophilia B Gly4Ser aGGT-AGT | GTTTTTCTTGATCATGAAAACGCCAACAAAATTCTGAATCGGC CAAAGAGGTATAATTCAGGTAAATTGGAAGAGTTTGTTCAAGG GAACCTTGAGAGAGAATGTATGGAAGAAAAGTGTA | 2292 |
| | TACACTTTTCTTCCATACATTCTCTCTCAAGGTTCCCTTGAACA AACTCTTCCAATTTACCTGAATTATACCTCTTTGGCCGATTCA GAATTTTGTTGGCGTTTTCATGATCAAGAAAAAC | 2293 |
| | ATAATTCAGGTAAATTG | 2294 |
| | CAATTTACCTGAATTAT | 2295 |
| Haemophilia B Lys5Glu tAAA-GAA | TTTCTTGATCATGAAAACGCCAACAAAATTCTGAATCGGCCAA AGAGGTATAATTCAGGTAAATTGGAAGAGTTTGTTCAAGGGAA CCTTGAGAGAGAATGTATGGAAGAAAAGTGTAGTT | 2296 |
| | AACTACACTTTTCTTCCATACATTCTCTCTCAAGGTTCCCTTGA ACAAACTCTTCCAATTTACCTGAATTATACCTCTTTGGCCGATT CAGAATTTTGTTGGCGTTTTCATGATCAAGAAA | 2297 |
| | ATTCAGGTAAATTGGAA | 2298 |
| | TTCCAATTTACCTGAAT | 2299 |
| Haemophilia B Glu7Ala GAA-GCA | ATCATGAAAACGCCAACAAAATTCTGAATCGGCCAAAGAGGTA TAATTCAGGTAAATTGGAAGAGTTTGTTCAAGGGAACCTTGAG AGAGAATGTATGGAAGAAAAGTGTAGTTTTGAAGA | 2300 |
| | TCTTCAAAACTACACTTTTCTTCCATACATTCTCTCTCAAGGTT CCCTTGAACAAACTCTTCCAATTTACCTGAATTATACCTCTTTG GCCGATTCAGAATTTTGTTGGCGTTTTCATGAT | 2301 |
| | TAAATTGGAAGAGTTTG | 2302 |
| | CAAACTCTTCCAATTTA | 2303 |
| Haemophilia B Glu7Lys gGAA-AAA | GATCATGAAAACGCCAACAAAATTCTGAATCGGCCAAAGAGG TATAATTCAGGTAAATTGGAAGAGTTTGTTCAAGGGAACCTTG AGAGAGAATGTATGGAAGAAAAGTGTAGTTTTGAAG | 2304 |
| | CTTCAAAACTACACTTTTCTTCCATACATTCTCTCTCAAGGTTC CCTTGAACAAACTCTTCCAATTTACCTGAATTATACCTCTTTGG CCGATTCAGAATTTTGTTGGCGTTTTCATGATC | 2305 |
| | GTAAATTGGAAGAGTTT | 2306 |
| | AAACTCTTCCAATTTAC | 2307 |
| Haemophilia B Glu7Val GAA-GTA | ATCATGAAAACGCCAACAAAATTCTGAATCGGCCAAAGAGGTA TAATTCAGGTAAATTGGAAGAGTTTGTTCAAGGGAACCTTGAG AGAGAATGTATGGAAGAAAAGTGTAGTTTTGAAGA | 2308 |
| | TCTTCAAAACTACACTTTTCTTCCATACATTCTCTCTCAAGGTT CCCTTGAACAAACTCTTCCAATTTACCTGAATTATACCTCTTTG GCCGATTCAGAATTTTGTTGGCGTTTTCATGAT | 2309 |
| | TAAATTGGAAGAGTTTG | 2310 |
| | CAAACTCTTCCAATTTA | 2311 |
| Haemophilia B Glu8Ala GAG-GCG | ATGAAAACGCCAACAAAATTCTGAATCGGCCAAAGAGGTATAA TTCAGGTAAATTGGAAGAGTTTGTTCAAGGGAACCTTGAGAG AGAATGTATGGAAGAAAAGTGTAGTTTTGAAGAAGC | 2312 |
| | GCTTCTTCAAAACTACACTTTTCTTCCATACATTCTCTCTCAAG GTTCCCTTGAACAAACTCTTCCAATTTACCTGAATTATACCTCT TTGGCCGATTCAGAATTTTGTTGGCGTTTTCAT | 2313 |
| | ATTGGAAGAGTTTGTTC | 2314 |
| | GAACAAACTCTTCCAAT | 2315 |
| Haemophilia B Glu8Gly GAG-GGG | ATGAAAACGCCAACAAAATTCTGAATCGGCCAAAGAGGTATAA TTCAGGTAAATTGGAAGAGTTTGTTCAAGGGAACCTTGAGAG AGAATGTATGGAAGAAAAGTGTAGTTTTGAAGAAGC | 2316 |
| | GCTTCTTCAAAACTACACTTTTCTTCCATACATTCTCTCTCAAG GTTCCCTTGAACAAACTCTTCCAATTTACCTGAATTATACCTCT TTGGCCGATTCAGAATTTTGTTGGCGTTTTCAT | 2317 |
| | ATTGGAAGAGTTTGTTC | 2318 |
| | GAACAAACTCTTCCAAT | 2319 |
| Haemophilia B Phe9Cys TTT-TGT | AAAACGCCAACAAAATTCTGAATCGGCCAAAGAGGTATAATTC AGGTAAATTGGAAGAGTTTGTTCAAGGGAACCTTGAGAGAGA ATGTATGGAAGAAAAGTGTAGTTTTGAAGAAGCACG | 2320 |
| | CGTGCTTCTTCAAAACTACACTTTTCTTCCATACATTCTCTCTC AAGGTTCCCTTGAACAAACTCTTCCAATTTACCTGAATTATAC CTCTTTGGCCGATTCAGAATTTTGTTGGCGTTTT | 2321 |
| | GGAAGAGTTTGTTCAAG | 2322 |
| | CTTGAACAAACTCTTCC | 2323 |
| Haemophilia B Phe9Ile gTTT-ATT | GAAAACGCCAACAAAATTCTGAATCGGCCAAAGAGGTATAATT CAGGTAAATTGGAAGAGTTTGTTCAAGGGAACCTTGAGAGAG AATGTATGGAAGAAAAGTGTAGTTTTGAAGAAGCAC | 2324 |
| | GTGCTTCTTCAAAACTACACTTTTCTTCCATACATTCTCTCTCA AGGTTCCCTTGAACAAACTCTTCCAATTTACCTGAATTATACC | 2325 |

TABLE 21-continued

Factor IX Mutations and Genome-Correcting Oligos

| Clinical Phenotype & Mutation | Correcting Oligos | SEQ ID NO: |
|---|---|---|
| | TCTTTGGCCGATTCAGAATTTTGTTGGCGTTTTC TGGAAGAGTTTGTTCAA | 2326 |
| | TTGAACAAACTCTTCCA | 2327 |
| Haemophilia B Arg(-1)Ser AGGt-AGC | TTACATTTCAGTTTTTCTTGATCATGAAAACGCCAACAAAATTC TGAATCGGCCAAAGAGGTATAATTCAGGTAAATTGGAAGAGTT TGTTCAAGGGAACCTTGAGAGAGAATGTATGGAA | 2328 |
| | TTCCATACATTCTCTCTCAAGGTTCCCTTGAACAAACTCTTCC AATTTACCTGAATTATACCTCTTTGGCCGATTCAGAATTTTGTT GGCGTTTTCATGATCAAGAAAAACTGAAATGTAA | 2329 |
| | CCAAAGAGGTATAATTC | 2330 |
| | GAATTATACCTCTTTGG | 2331 |
| Haemophilia B Arg(-1)Thr AGG-ACG | TTTACATTTCAGTTTTTCTTGATCATGAAAACGCCAACAAAATT CTGAATCGGCCAAAGAGGTATAATTCAGGTAAATTGGAAGAG TTTGTTCAAGGGAACCTTGAGAGAGAATGTATGGA | 2332 |
| | TCCATACATTCTCTCTCAAGGTTCCCTTGAACAAACTCTTCCA ATTTACCTGAATTATACCTCTTTGGCCGATTCAGAATTTTGTTG GCGTTTTCATGATCAAGAAAAACTGAAATGTAAA | 2333 |
| | GCCAAAGAGGTATAATT | 2334 |
| | AATTATACCTCTTTGGC | 2335 |
| Haemophilia B Lys(-2)Asn AAGa-AAT | CTTTTACATTTCAGTTTTTCTTGATCATGAAAACGCCAACAAAA TTCTGAATCGGCCAAAGAGGTATAATTCAGGTAAATTGGAAGA GTTTGTTCAAGGGAACCTTGAGAGAGAATGTATG | 2336 |
| | CATACATTCTCTCTCAAGGTTCCCTTGAACAAACTCTTCCAAT TTACCTGAATTATACCTCTTTGGCCGATTCAGAATTTTGTTGG CGTTTTCATGATCAAGAAAAACTGAAATGTAAAAG | 2337 |
| | CGGCCAAAGAGGTATAA | 2338 |
| | TTATACCTCTTTGGCCG | 2339 |
| Haemophilia B Arg(-4)Gln CGG-CAG | AATTATTCTTTTACATTTCAGTTTTTCTTGATCATGAAAACGCC AACAAAATTCTGAATCGGCCAAAGAGGTATAATTCAGGTAAAT TGGAAGAGTTTGTTCAAGGGAACCTTGAGAGAGA | 2340 |
| | TCTCTCTCAAGGTTCCCTTGAACAAACTCTTCCAATTTACCTG AATTATACCTCTTTGGCCGATTCAGAATTTTGTTGGCGTTTTCA TGATCAAGAAAAACTGAAATGTAAAGAATAATT | 2341 |
| | TCTGAATCGGCCAAAGA | 2342 |
| | TCTTTGGCCGATTCAGA | 2343 |
| Haemophilia B Arg(-4)Leu CGG-CTG | AATTATTCTTTTACATTTCAGTTTTTCTTGATCATGAAAACGCC AACAAAATTCTGAATCGGCCAAAGAGGTATAATTCAGGTAAAT TGGAAGAGTTTGTTCAAGGGAACCTTGAGAGAGA | 2344 |
| | TCTCTCTCAAGGTTCCCTTGAACAAACTCTTCCAATTTACCTG AATTATACCTCTTTGGCCGATTCAGAATTTTGTTGGCGTTTTCA TGATCAAGAAAAACTGAAATGTAAAGAATAATT | 2345 |
| | TCTGAATCGGCCAAAGA | 2346 |
| | TCTTTGGCCGATTCAGA | 2347 |
| Haemophilia B Arg(-4)Trp tCGG-TGG | GAATTATTCTTTTACATTTCAGTTTTTCTTGATCATGAAAACGC CAACAAAATTCTGAATCGGCCAAAGAGGTATAATTCAGGTAAA TTGGAAGAGTTTGTTCAAGGGAACCTTGAGAGAG | 2348 |
| | CTCTCTCAAGGTTCCCTTGAACAAACTCTTCCAATTTACCTGA ATTATACCTCTTTGGCCGATTCAGAATTTTGTTGGCGTTTTCAT GATCAAGAAAAACTGAAATGTAAAGAATAATTC | 2349 |
| | TTCTGAATCGGCCAAAG | 2350 |
| | CTTTGGCCGATTCAGAA | 2351 |
| Haemophilia B Gln11Term tCAA-TAA | GCCAACAAAATTCTGAATCGGCCAAAGAGGTATAATTCAGGTA AATTGGAAGAGTTTGTTCAAGGGAACCTTGAGAGAGAATGTAT GGAAGAAAGTGTAGTTTTGAAGAAGCACGAGAAG | 2352 |
| | CTTCTCGTGCTTCTTCAAAACTACACTTTTCTTCCATACATTCT CTCTCAAGGTTCCCTTGAACAAACTCTTCCAATTTACCTGAAT TATACCTCTTTGGCCGATTCAGAATTTTGTTGGC | 2353 |
| | AGTTTGTTCAAGGGAAC | 2354 |
| | GTTCCCTTGAACAAACT | 2355 |
| Haemophilia B Gly12Ala GGG-GCG | ACAAAATTCTGAATCGGCCAAAGAGGTATAATTCAGGTAAATT GGAAGAGTTTGTTCAAGGGAACCTTGAGAGAGAATGTATGGA AGAAAAGTGTAGTTTTGAAGAAGCACGAGAAGTTTT | 2356 |
| | AAAACTTCTCGTGCTTCTTCAAAACTACACTTTTCTTCCATACA TTCTCTCTCAAGGTTCCCTTGAACAAACTCTTCCAATTTACCT GAATTATACCTCTTTGGCCGATTCAGAATTTTGT | 2357 |
| | TGTTCAAGGGAACCTTG | 2358 |
| | CAAGGTTCCCTTGAACA | 2359 |
| Haemophilia B Gly12Arg aGGG-AGG | AACAAAATTCTGAATCGGCCAAAGAGGTATAATTCAGGTAAAT TGGAAGAGTTTGTTCAAGGGAACCTTGAGAGAGAATGTATGG AAGAAAAGTGTAGTTTTGAAGAAGCACGAGAAGTTT | 2360 |
| | AAACTTCTCGTGCTTCTTCAAAACTACACTTTTCTTCCATACAT TCTCTCTCAAGGTTCCCTTGAACAAACTCTTCCAATTTACCTG AATTATACCTCTTTGGCCGATTCAGAATTTTGTT | 2361 |

TABLE 21-continued

Factor IX Mutations and Genome-Correcting Oligos

| Clinical Phenotype & Mutation | Correcting Oligos | SEQ ID NO: |
|---|---|---|
| | TTGTTCAAGGGAACCTT | 2362 |
| | AAGGTTCCCTTGAACAA | 2363 |
| Haemophilia B Gly12Glu GGG-GAG | ACAAAATTCTGAATCGGCCAAAGAGGTATAATTCAGGTAAATT GGAAGAGTTTGTTCAAGGGAACCTTGAGAGAGAATGTATGGA AGAAAAGTGTAGTTTTGAAGAAGCACGAGAAGTTTT | 2364 |
| | AAAACTTCTCGTGCTTCTTCAAAACTACACTTTTCTTCCATACA TTCTCTCTCAAGGTTCCCTTGAACAAACTCTTCCAATTTACCT GAATTATACCTCTTTGGCCGATTCAGAATTTTGT | 2365 |
| | TGTTCAAGGGAACCTTG | 2366 |
| | CAAGGTTCCCTTGAACA | 2367 |
| Haemophilia B Glu17Gln aGAA-CAA | CGGCCAAAGAGGTATAATTCAGGTAAATTGGAAGAGTTTGTTC AAGGGAACCTTGAGAGAGAATGTATGGAAGAAAAGTGTAGTT TTGAAGAAGCACGAGAAGTTTTTGAAAACACTGAAA | 2368 |
| | TTTCAGTGTTTTCAAAAACTTCTCGTGCTTCTTCAAAACTACAC TTTTCTTCCATACATTCTCTCTCAAGGTTCCCTTGAACAAACTC TTCCAATTTACCTGAATTATACCTCTTTGGCCG | 2369 |
| | TTGAGAGAGAATGTATG | 2370 |
| | CATACATTCTCTCTCAA | 2371 |
| Haemophilia B Glu17Lys aGAA-AAA | CGGCCAAAGAGGTATAATTCAGGTAAATTGGAAGAGTTTGTTC AAGGGAACCTTGAGAGAAAATGTATGGAAGAAAAGTGTAGTT TTGAAGAAGCACGAGAAGTTTTTGAAAACACTGAAA | 2372 |
| | TTTCAGTGTTTTCAAAAACTTCTCGTGCTTCTTCAAAACTACAC TTTTCTTCCATACATTTTCTCTCAAGGTTCCCTTGAACAAACTC TTCCAATTTACCTGAATTATACCTCTTTGGCCG | 2373 |
| | TTGAGAGAAAATGTATG | 2374 |
| | CATACATTTTCTCTCAA | 2375 |
| Haemophilia B Cys18Arg aTGT-CGT | CCAAAGAGGTATAATTCAGGTAAATTGGAAGAGTTTGTTCAAG GGAACCTTGAGAGAGAATGTATGGAAGAAAAGTGTAGTTTTG AAGAAGCACGAGAAGTTTTTGAAAACACTGAAAGAA | 2376 |
| | TTCTTTCAGTGTTTTCAAAAACTTCTCGTGCTTCTTCAAAACTA CACTTTTCTTCCATACATTCTCTCTCAAGGTTCCCTTGAACAA ACTCTTCCAATTTACCTGAATTATACCTCTTTGG | 2377 |
| | AGAGAGAATGTATGGAA | 2378 |
| | TTCCATACATTCTCTCT | 2379 |
| Haemophilia B Cys18Tyr TGT-TAT | CAAAGAGGTATAATTCAGGTAAATTGGAAGAGTTTGTTCAAGG GAACCTTGAGAGAGAATGTATGGAAGAAAAGTGTAGTTTTGAA GAAGCACGAGAAGTTTTTGAAAACACTGAAAGAAC | 2380 |
| | GTTCTTTCAGTGTTTTCAAAAACTTCTCGTGCTTCTTCAAAACT ACACTTTTCTTCCATACATTCTCTCTCAAGGTTCCCTTGAACAA ACTCTTCCAATTTACCTGAATTATACCTCTTTG | 2381 |
| | GAGAGAATGTATGGAAG | 2382 |
| | CTTCCATACATTCTCTC | 2383 |
| Haemophilia B Glu20Val GAA-GTA | GGTATAATTCAGGTAAATTGGAAGAGTTTGTTCAAGGGAACCT TGAGAGAGAATGTATGGAAGAAAAGTGTAGTTTTGAAGAAGC ACGAGAAGTTTTTGAAAACACTGAAAGAACAGTGAG | 2384 |
| | CTCACTGTTCTTTCAGTGTTTTCAAAAACTTCTCGTGCTTCTTC AAAACTACACTTTTCTTCCATACATTCTCTCTCAAGGTTCCCTT GAACAAACTCTTCCAATTTACCTGAATTATACC | 2385 |
| | ATGTATGGAAGAAAAGT | 2386 |
| | ACTTTTCTTCCATACAT | 2387 |
| Haemophilia B Glu21Lys aGAA-AAA | TATAATTCAGGTAAATTGGAAGAGTTTGTTCAAGGGAACCTTG AGAGAGAATGTATGGAAGAAAAGTGTAGTTTTGAAGAAGCAC GAGAAGTTTTTGAAAACACTGAAAGAACAGTGAGTA | 2388 |
| | TACTCACTGTTCTTTCAGTGTTTTCAAAAACTTCTCGTGCTTCT TCAAAACTACACTTTTCTTCCATACATTCTCTCTCAAGGTTCCC TTGAACAAACTCTTCCAATTTACCTGAATTATA | 2389 |
| | GTATGGAAGAAAAGTGT | 2390 |
| | ACACTTTTCTTCCATAC | 2391 |
| Haemophilia B Cys23Arg gTGT-CGT | TCAGGTAAATTGGAAGAGTTTGTTCAAGGGAACCTTGAGAGA GAATGTATGGAAGAAAAGTGTAGTTTTGAAGAAGCACGAGAA GTTTTTGAAAACACTGAAAGAACAGTGAGTATTTCCA | 2392 |
| | TGGAAATACTCACTGTTCTTTCAGTGTTTTCAAAAACTTCTCGT GCTTCTTCAAAACTACACTTTTCTTCCATACATTCTCTCTCAAG GTTCCCTTGAACAAACTCTTCCAATTTACCTGA | 2393 |
| | AAGAAAAGTGTAGTTTT | 2394 |
| | AAAACTACACTTTTCTT | 2395 |
| Haemophilia B Cys23Tyr TGT-TAT | CAGGTAAATTGGAAGAGTTTGTTCAAGGGAACCTTGAGAGAG AATGTATGGAAGAAAAGTGTAGTTTTGAAGAAGCACGAGAAGT TTTTGAAAACACTGAAAGAACAGTGAGTATTTCCAC | 2396 |
| | GTGGAAATACTCACTGTTCTTTCAGTGTTTTCAAAAACTTCTC GTGCTTCTTCAAAACTACACTTTTCTTCCATACATTCTCTCTCA AGGTTCCCTTGAACAAACTCTTCCAATTTACCTG | 2397 |
| | AGAAAAGTGTAGTTTTG | 2398 |
| | CAAAACTACACTTTTCT | 2399 |

TABLE 21-continued

Factor IX Mutations and Genome-Correcting Oligos

| Clinical Phenotype & Mutation | Correcting Oligos | SEQ ID NO: |
|---|---|---|
| Haemophilia B Phe25Ser TTT-TCT | AATTGGAAGAGTTTGTTCAAGGGAACCTTGAGAGAGAATGTAT GGAAGAAAAGTGTAGTTTTGAAGAAGCACGAGAAGTTTTTGAA AACACTGAAAGAACAGTGAGTATTTCCACATAATA | 2400 |
| | TATTATGTGGAAATACTCACTGTTCTTTCAGTGTTTTCAAAAAC TTCTCGTGCTTCTTCAAACTACACTTTTCTTCCATACATTCTC TCTCAAGGTTCCCTTGAACAAACTCTTCCAATT | 2401 |
| | GTGTAGTTTTGAAGAAG | 2402 |
| | CTTCTTCAAACTACAC | 2403 |
| Haemophilia B Glu26Gln tGAA-CAA | TTGGAAGAGTTTGTTCAAGGGAACCTTGAGAGAGAATGTATG GAAGAAAAGTGTAGTTTTGAAGAAGCACGAGAAGTTTTTGAAA ACACTGAAAGAACAGTGAGTATTTCCACATAATACC | 2404 |
| | GGTATTATGTGGAAATACTCACTGTTCTTTCAGTGTTTTCAAAA ACTTCTCGTGCTTCTTCAAACTACACTTTTCTTCCATACATTC TCTCTCAAGGTTCCCTTGAACAAACTCTTCCAA | 2405 |
| | GTAGTTTTGAAGAAGCA | 2406 |
| | TGCTTCTTCAAAACTAC | 2407 |
| Haemophilia B Glu27Ala GAA-GCA | AAGAGTTTGTTCAAGGGAACCTTGAGAGAGAATGTATGGAAG AAAAGTGTAGTTTTGAAGAAGCACGAGAAGTTTTTGAAAACAC TGAAAGAACAGTGAGTATTTCCACATAATACCCTTC | 2408 |
| | GAAGGGTATTATGTGGAAATACTCACTGTTCTTTCAGTGTTTT CAAAAACTTCTCGTGCTTCTTCAAAACTACACTTTTCTTCCATA CATTCTCTCTCAAGGTTCCCTTGAACAAACTCTT | 2409 |
| | TTTTGAAGAAGCACGAG | 2410 |
| | CTCGTGCTTCTTCAAAA | 2411 |
| Haemophilia B Glu27Asp GAAg-GAC | AGAGTTTGTTCAAGGGAACCTTGAGAGAGAATGTATGGAAGA AAAGTGTAGTTTTGAAGAAGCACGAGAAGTTTTTGAAAACACT GAAAGAACAGTGAGTATTTCCACATAATACCCTTCA | 2412 |
| | TGAAGGGTATTATGTGGAAATACTCACTGTTCTTTCAGTGTTTT TCAAAAACTTCTCGTGCTTCTTCAAAACTACACTTTTCTTCCAT ACATTCTCTCAAGGTTCCCTTGAACAAACTCT | 2413 |
| | TTTGAAGAAGCACGAGA | 2414 |
| | TCTCGTGCTTCTTCAAA | 2415 |
| Haemophilia B Glu27Lys aGAA-AAA | GAAGAGTTTGTTCAAGGGAACCTTGAGAGAGAATGTATGGAA GAAAAGTGTAGTTTTGAAGAAGCACGAGAAGTTTTTGAAAACA CTGAAAGAACAGTGAGTATTCCACATAATACCCTT | 2416 |
| | AAGGGTATTATGTGGAAATACTCACTGTTCTTTCAGTGTTTTC AAAAACTTCTCGTGCTTCTTCAAAACTACACTTTTCTTCCATAC ATTCTCTCAAGGTTCCCTTGAACAAACTCTTC | 2417 |
| | GTTTTGAAGAAGCACGA | 2418 |
| | TCGTGCTTCTTCAAAAC | 2419 |
| Haemophilia B Glu27Val GAA-GTA | AAGAGTTTGTTCAAGGGAACCTTGAGAGAGAATGTATGGAAG AAAAGTGTAGTTTTGAAGAAGCACGAGAAGTTTTTGAAAACAC TGAAAGAACAGTGAGTATTTCCACATAATACCCTTC | 2420 |
| | GAAGGGTATTATGTGGAAATACTCACTGTTCTTTCAGTGTTTT CAAAAACTTCTCGTGCTTCTTCAAAACTACACTTTTCTTCCATA CATTCTCTCAAGGTTCCCTTGAACAAACTCTT | 2421 |
| | TTTTGAAGAAGCACGAG | 2422 |
| | CTCGTGCTTCTTCAAAA | 2423 |
| Haemophilia B Arg29Gln CGA-CAA | TTGTTCAAGGGAACCTTGAGAGAGAATGTATGGAAGAAAAGT GTAGTTTTGAAGAAGCACGAGAAGTTTTTGAAAACACTGAAAG AACAGTGAGTATTTCCACATAATACCCTTCAGATGC | 2424 |
| | GCATCTGAAGGGTATTATGTGGAAATACTCACTGTTCTTTCAG TGTTTTCAAAAACTTCTCGTGCTTCTTCAAAACTACACTTTTCT TCCATACATTCTCTCAAGGTTCCCTTGAACAA | 2425 |
| | AGAAGCACGAGAAGTTT | 2426 |
| | AAACTTCTCGTGCTTCT | 2427 |
| Haemophilia B Arg29Pro CGA-CCA | TTGTTCAAGGGAACCTTGAGAGAGAATGTATGGAAGAAAAGT GTAGTTTTGAAGAAGCACGAGAAGTTTTTGAAAACACTGAAAG AACAGTGAGTATTTCCACATAATACCCTTCAGATGC | 2428 |
| | GCATCTGAAGGGTATTATGTGGAAATACTCACTGTTCTTTCAG TGTTTTCAAAAACTTCTCGTGCTTCTTCAAAACTACACTTTTCT TCCATACATTCTCTCAAGGTTCCCTTGAACAA | 2429 |
| | AGAAGCACGAGAAGTTT | 2430 |
| | AAACTTCTCGTGCTTCT | 2431 |
| Haemophilia B Arg29Term aCGA-TGA | TTTGTTCAAGGGAACCTTGAGAGAGAATGTATGGAAGAAAAGT GTAGTTTTGAAGAAGCACGAGAAGTTTTTGAAAACACTGAAAG AACAGTGAGTATTTCCACATAATACCCTTCAGATG | 2432 |
| | CATCTGAAGGGTATTATGTGGAAATACTCACTGTTCTTTCAGT GTTTTCAAAAACTTCTCGTGCTTCTTCAAAACTACACTTTTCTT CCATACATTCTCTCAAGGTTCCCTTGAACAAA | 2433 |
| | AAGAAGCACGAGAAGTT | 2434 |
| | AACTTCTCGTGCTTCTT | 2435 |

TABLE 21-continued

Factor IX Mutations and Genome-Correcting Oligos

| Clinical Phenotype & Mutation | Correcting Oligos | SEQ ID NO: |
|---|---|---|
| Haemophilia B Glu30Lys aGAA-AAA | GTTCAAGGGAACCTTGAGAGAGAATGTATGGAAGAAAAGTGT AGTTTTGAAGAAGCACGAGAAGTTTTTGAAAACACTGAAAGAA CAGTGAGTATTTCCACATAATACCCTTCAGATGCAG | 2436 |
| | CTGCATCTGAAGGGTATTATGTGGAAATACTCACTGTTCTTTC AGTGTTTTCAAAAACTTCTCGTGCTTCTTCAAAACTACACTTTT CTTCCATACATTCTCTCTCAAGGTTCCCTTGAAC | 2437 |
| | AAGCACGAGAAGTTTTT | 2438 |
| | AAAAACTTCTCGTGCTT | 2439 |
| Haemophilia B Glu30Term aGAA-TAA | GTTCAAGGGAACCTTGAGAGAGAATGTATGGAAGAAAAGTGT AGTTTTGAAGAAGCACGAGAAGTTTTTGAAAACACTGAAAGAA CAGTGAGTATTTCCACATAATACCCTTCAGATGCAG | 2440 |
| | CTGCATCTGAAGGGTATTATGTGGAAATACTCACTGTTCTTTC AGTGTTTTCAAAAACTTCTCGTGCTTCTTCAAAACTACACTTTT CTTCCATACATTCTCTCTCAAGGTTCCCTTGAAC | 2441 |
| | AAGCACGAGAAGTTTTT | 2442 |
| | AAAAACTTCTCGTGCTT | 2443 |
| Haemophilia B Glu33Asp GAAa-GAC | CCTTGAGAGAGAATGTATGGAAGAAAAGTGTAGTTTTGAAGAA GCACGAGAAGTTTTTGAAAACACTGAAAGAACAGTGAGTATTT CCACATAATACCCTTCAGATGCAGAGCATAGAATA | 2444 |
| | TATTCTATGCTCTGCATCTGAAGGGTATTATGTGGAAATACTC ACTGTTCTTTCAGTGTTTTCAAAAACTTCTCGTGCTTCTTCAAA ACTACACTTTTCTTCCATACATTCTCTCTCAAGG | 2445 |
| | GTTTTTGAAAACACTGA | 2446 |
| | TCAGTGTTTTCAAAAAC | 2447 |
| Haemophilia B Glu33Term tGAA-TAA | AACCTTGAGAGAGAATGTATGGAAGAAAAGTGTAGTTTTGAAG AAGCACGAGAAGTTTTTGAAAACACTGAAAGAACAGTGAGTAT TTCCACATAATACCCTTCAGATGCAGAGCATAGAA | 2448 |
| | TTCTATGCTCTGCATCTGAAGGGTATTATGTGGAAATACTCAC TGTTCTTTCAGTGTTTTCAAAAACTTCTCGTGCTTCTTCAAAAC TACACTTTTCTTCCATACATTCTCTCTCAAGGTT | 2449 |
| | AAGTTTTTGAAAACACT | 2450 |
| | AGTGTTTTCAAAAACTT | 2451 |
| Haemophilia B Trp42Term TGG-TAG | CAAAAACACTTTAGATATTACCGTTAATTTGTCTTCTTTTATTCTT TATAGACTGAATTTTGGAAGCAGTATGTTGGTAAGCAATTCAT TTTATCCTCTAGCTAATATATGAAACATATGAG | 2452 |
| | CTCATATGTTTCATATATTAGCTAGAGGATAAAATGAATTGCTT ACCAACATACTGCTTCCAAAATTCAGTCTATAAAGAATAAAAG AAGACAAATTAACGGTAATATCTAAAGTGTTTTG | 2453 |
| | TGAATTTTGGAAGCAGT | 2454 |
| | ACTGCTTCCAAAATTCA | 2455 |
| Haemophilia B Lys43Glu gAAG-GAG | AAACACTTTAGATATTACCGTTAATTTGTCTTCTTTTATTCTTTA TAGACTGAATTTTGGAAGCAGTATGTTGGTAAGCAATTCATTT TATCCTCTAGCTAATATATGAAACATATGAGAA | 2456 |
| | TTCTCATATGTTTCATATATTAGCTAGAGGATAAAATGAATTGC TTACCAACATACTGCTTCCAAAATTCAGTCTATAAAGAATAAAA GAAGACAAATTAACGGTAATATCTAAAGTGTTT | 2457 |
| | AATTTTGGAAGCAGTAT | 2458 |
| | ATACTGCTTCCAAAATT | 2459 |
| Haemophilia B Gln44Term gCAG-TAG | CACTTTAGATATTACCGTTAATTTGTCTTCTTTTATTCTTTATAG ACTGAATTTTGGAAGCAGTATGTTGGTAAGCAATTCATTTTATC CTCTAGCTAATATATGAAACATATGAGAATTA | 2460 |
| | TAATTCTCATATGTTTCATATATTAGCTAGAGGATAAAATGAAT TGCTTACCAACATACTGCTTCCAAAATTCAGTCTATAAAGAATA AAGAAGACAAATTAACGGTAATATCTAAAGTG | 2461 |
| | TTTGGAAGCAGTATGTT | 2462 |
| | AACATACTGCTTCCAAA | 2463 |
| Haemophilia B Asp49Gly GAT-GGT | CCGGGCATTCTAAGCAGTTTACGTGCCAATTCAATTTCTTAAC CTATCTCAAAGATGGAGATCAGTGTGAGTCCAATCCATGTTTA AATGGCGGCAGTTGCAAGGATGACATTAATTCCTA | 2464 |
| | TAGGAATTAATGTCATCCTTGCAACTGCCGCCATTTAAACATG GATTGGACTCACACTGATCTCCATCTTTGAGATAGGTTAAGAA ATTGAATTGGCACGTAAACTGCTTAGAATGCCCGG | 2465 |
| | AGATGGAGATCAGTGTG | 2466 |
| | CACACTGATCTCCATCT | 2467 |
| Haemophilia B Gln50His CAGt-CAC | GCATTCTAAGCAGTTTACGTGCCAATTCAATTTCTTAACCTATC TCAAAGATGGAGATCAGTGTGAGTCCAATCCATGTTTAAATGG CGGCAGTTGCAAGGATGACATTAATTCCTATGAA | 2468 |
| | TTCATAGGAATTAATGTCATCCTTGCAACTGCCGCCATTTAAA CATGGATTGGACTCACACTGATCTCCATCTTTGAGATAGGTTA AGAAATTGAATTGGCACGTAAACTGCTTAGAATGC | 2469 |
| | GGAGATCAGTGTGAGTC | 2470 |
| | GACTCACACTGATCTCC | 2471 |

TABLE 21-continued

Factor IX Mutations and Genome-Correcting Oligos

| Clinical Phenotype & Mutation | Correcting Oligos | SEQ ID NO: |
|---|---|---|
| Haemophilia B Gln50Pro CAG-CCG | GGCATTCTAAGCAGTTTACGTGCCAATTCAATTTCTTAACCTA TCTCAAAGATGGAGATCAGTGTGAGTCCAATCCATGTTTAAAT GGCGGCAGTTGCAAGGATGACATTAATTCCTATGA | 2472 |
| | TCATAGGAATTAATGTCATCCTTGCAACTGCCGCCATTTAAAC ATGGATTGGACTCACACTGATCTCCATCTTTGAGATAGGTTAA GAAATTGAATTGGCACGTAAACTGCTTAGAATGCC | 2473 |
| | TGGAGATCAGTGTGAGT | 2474 |
| | ACTCACACTGATCTCCA | 2475 |
| Haemophilia B Gln50Term tCAG-TAG | GGGCATTCTAAGCAGTTTACGTGCCAATTCAATTTCTTAACCT ATCTCAAAGATGGAGATCAGTGTGAGTCCAATCCATGTTTAAA TGGCGGCAGTTGCAAGGATGACATTAATTCCTATG | 2476 |
| | CATAGGAATTAATGTCATCCTTGCAACTGCCGCCATTTAAACA TGGATTGGACTCACACTGATCTCCATCTTTGAGATAGGTTAAG AAATTGAATTGGCACGTAAACTGCTTAGAATGCCC | 2477 |
| | ATGGAGATCAGTGTGAG | 2478 |
| | CTCACACTGATCTCCAT | 2479 |
| Haemophilia B Cys51Arg gTGT-CGT | CATTCTAAGCAGTTTACGTGCCAATTCAATTTCTTAACCTATCT CAAAGATGGAGATCAGTGTGAGTCCAATCCATGTTTAAATGG CGGCAGTTGCAAGGATGACATTAATTCCTATGAAT | 2480 |
| | ATTCATAGGAATTAATGTCATCCTTGCAACTGCCGCCATTTAA ACATGGATTGGACTCACACTGATCTCCATCTTTGAGATAGGTT AAGAAATTGAATTGGCACGTAAACTGCTTAGAATG | 2481 |
| | GAGATCAGTGTGAGTCC | 2482 |
| | GGACTCACACTGATCTC | 2483 |
| Haemophilia B Cys51Ser gTGT-AGT | CATTCTAAGCAGTTTACGTGCCAATTCAATTTCTTAACCTATCT CAAAGATGGAGATCAGTGTGAGTCCAATCCATGTTTAAATGG CGGCAGTTGCAAGGATGACATTAATTCCTATGAAT | 2484 |
| | ATTCATAGGAATTAATGTCATCCTTGCAACTGCCGCCATTTAA ACATGGATTGGACTCACACTGATCTCCATCTTTGAGATAGGTT AAGAAATTGAATTGGCACGTAAACTGCTTAGAATG | 2485 |
| | GAGATCAGTGTGAGTCC | 2486 |
| | GGACTCACACTGATCTC | 2487 |
| Haemophilia B Cys51Trp TGTg-TGG | TTCTAAGCAGTTTACGTGCCAATTCAATTTCTTAACCTATCTCA AAGATGGAGATCAGTGTGAGTCCAATCCATGTTTAAATGGCG CAGTTGCAAGGATGACATTAATTCCTATGAATGT | 2488 |
| | ACATTCATAGGAATTAATGTCATCCTTGCAACTGCCGCCATTT AAACATGGATTGGACTCACACTGATCTCCATCTTTGAGATAGG TTAAGAAATTGAATTGGCACGTAAACTGCTTAGAA | 2489 |
| | GATCAGTGTGAGTCCAA | 2490 |
| | TTGGACTCACACTGATC | 2491 |
| Haemophilia B Glu52Term tGAG-TAG | TCTAAGCAGTTTACGTGCCAATTCAATTTCTTAACCTATCTCAA AGATGGAGATCAGTGTGAGTCCAATCCATGTTTAAATGGCGG CAGTTGCAAGGATGACATTAATTCCTATGAATGTT | 2492 |
| | AACATTCATAGGAATTAATGTCATCCTTGCAACTGCCGCCATT TAAACATGGATTGGACTCACACTGATCTCCATCTTTGAGATAG GTTAAGAAATTGAATTGGCACGTAAACTGCTTAGA | 2493 |
| | ATCAGTGTGAGTCCAAT | 2494 |
| | ATTGGACTCACACTGAT | 2495 |
| Haemophilia B Pro55Ala tCCA-GCA | TTTACGTGCCAATTCAATTTCTTAACCTATCTCAAAGATGGAG ATCAGTGTGAGTCCAATCCATGTTTAAATGGCGGCAGTTGCA AGGATGACATTAATTCCTATGAATGTTGGTGTCCCT | 2496 |
| | AGGGACACCAACATTCATAGGAATTAATGTCATCCTTGCAACT GCCGCCATTTAAACATGGATTGGACTCACACTGATCTCCATCT TTGAGATAGGTTAAGAAATTGAATTGGCACGTAAA | 2497 |
| | AGTCCAATCCATGTTTA | 2498 |
| | TAAACATGGATTGGACT | 2499 |
| Haemophilia B Pro55Arg CCA-CGA | TTACGTGCCAATTCAATTTCTTAACCTATCTCAAAGATGGAGA TCAGTGTGAGTCCAATCCATGTTTAAATGGCGGCAGTTGCAA GGATGACATTAATTCCTATGAATGTTGGTGTCCCTT | 2500 |
| | AAGGGACACCAACATTCATAGGAATTAATGTCATCCTTGCAAC TGCCGCCATTTAAACATGGATTGGACTCACACTGATCTCCATC TTTGAGATAGGTTAAGAAATTGAATTGGCACGTAA | 2501 |
| | GTCCAATCCATGTTTAA | 2502 |
| | TTAAACATGGATTGGAC | 2503 |
| Haemophilia B Pro55Gln CCA-CAA | TTACGTGCCAATTCAATTTCTTAACCTATCTCAAAGATGGAGA TCAGTGTGAGTCCAATCCATGTTTAAATGGCGGCAGTTGCAA GGATGACATTAATTCCTATGAATGTTGGTGTCCCTT | 2504 |
| | AAGGGACACCAACATTCATAGGAATTAATGTCATCCTTGCAAC TGCCGCCATTTAAACATGGATTGGACTCACACTGATCTCCATC TTTGAGATAGGTTAAGAAATTGAATTGGCACGTAA | 2505 |
| | GTCCAATCCATGTTTAA | 2506 |
| | TTAAACATGGATTGGAC | 2507 |

TABLE 21-continued

Factor IX Mutations and Genome-Correcting Oligos

| Clinical Phenotype & Mutation | Correcting Oligos | SEQ ID NO: |
|---|---|---|
| Haemophilia B Pro55Leu CCA-CTA | TTACGTGCCAATTCAATTTCTTAACCTATCTCAAAGATGGAGA TCAGTGTGAGTCCAATC<u>C</u>ATGTTTAAATGGCGGCAGTTGCAA GGATGACATTAATTCCTATGAATGTTGGTGTCCCTT | 2508 |
| | AAGGGACACCAACATTCATAGGAATTAATGTCATCCTTGCAAC TGCCGCCATTTAAACAT<u>G</u>GATTGGACTCACACTGATCTCCATC TTTGAGATAGGTTAAGAAATTGAATTGGCACGTAA | 2509 |
| | GTCCAATC<u>C</u>ATGTTTAA | 2510 |
| | TTAAACAT<u>G</u>GATTGGAC | 2511 |
| Haemophilia B Pro55Ser tCCA-TCA | TTTACGTGCCAATTCAATTTCTTAACCTATCTCAAAGATGGAG ATCAGTGTGAGTCCAAT<u>C</u>CATGTTTAAATGGCGGCAGTTGCA AGGATGACATTAATTCCTATGAATGTTGGTGTCCCT | 2512 |
| | AGGGACACCAACATTCATAGGAATTAATGTCATCCTTGCAACT GCCGCCATTTAAACATG<u>G</u>ATTGGACTCACACTGATCTCCATCT TTGAGATAGGTTAAGAAATTGAATTGGCACGTAAA | 2513 |
| | AGTCCAAT<u>C</u>CATGTTTA | 2514 |
| | TAAACATG<u>G</u>ATTGGACT | 2515 |
| Haemophilia B Cys56Arg aTGT-CGT | ACGTGCCAATTCAATTTCTTAACCTATCTCAAAGATGGAGATC AGTGTGAGTCCAATCCA<u>T</u>GTTTAAATGGCGGCAGTTGCAAGG ATGACATTAATTCCTATGAATGTTGGTGTCCCTTTG | 2516 |
| | CAAAGGGACACCAACATTCATAGGAATTAATGTCATCCTTGCA ACTGCCGCCATTTAAAC<u>A</u>TGGATTGGACTCACACTGATCTCC ATCTTTGAGATAGGTTAAGAAATTGAATTGGCACGT | 2517 |
| | CCAATCCA<u>T</u>GTTTAAAT | 2518 |
| | ATTTAAAC<u>A</u>TGGATTGG | 2519 |
| Haemophilia B Cys56Ser aTGT-AGT | ACGTGCCAATTCAATTTCTTAACCTATCTCAAAGATGGAGATC AGTGTGAGTCCAATCCA<u>T</u>GTTTAAATGGCGGCAGTTGCAAGG ATGACATTAATTCCTATGAATGTTGGTGTCCCTTTG | 2520 |
| | CAAAGGGACACCAACATTCATAGGAATTAATGTCATCCTTGCA ACTGCCGCCATTTAAAC<u>A</u>TGGATTGGACTCACACTGATCTCC ATCTTTGAGATAGGTTAAGAAATTGAATTGGCACGT | 2521 |
| | CCAATCCA<u>T</u>GTTTAAAT | 2522 |
| | ATTTAAAC<u>A</u>TGGATTGG | 2523 |
| Haemophilia B Cys56Ser TGT-TCT | CGTGCCAATTCAATTTCTTAACCTATCTCAAAGATGGAGATCA GTGTGAGTCCAATCCAT<u>G</u>TTTAAATGGCGGCAGTTGCAAGGA TGACATTAATTCCTATGAATGTTGGTGTCCCTTTGG | 2524 |
| | CCAAAGGGACACCAACATTCATAGGAATTAATGTCATCCTTGC AACTGCCGCCATTTAAA<u>C</u>ATGGATTGGACTCACACTGATCTCC ATCTTTGAGATAGGTTAAGAAATTGAATTGGCACG | 2525 |
| | CAATCCAT<u>G</u>TTTAAATG | 2526 |
| | CATTTAAA<u>C</u>ATGGATTG | 2527 |
| Haemophilia B Cys56Tyr TGT-TAT | CGTGCCAATTCAATTTCTTAACCTATCTCAAAGATGGAGATCA GTGTGAGTCCAATCCAT<u>G</u>TTTAAATGGCGGCAGTTGCAAGGA TGACATTAATTCCTATGAATGTTGGTGTCCCTTTGG | 2528 |
| | CCAAAGGGACACCAACATTCATAGGAATTAATGTCATCCTTGC AACTGCCGCCATTTAAA<u>C</u>ATGGATTGGACTCACACTGATCTCC ATCTTTGAGATAGGTTAAGAAATTGAATTGGCACG | 2529 |
| | CAATCCAT<u>G</u>TTTAAATG | 2530 |
| | CATTTAAA<u>C</u>ATGGATTG | 2531 |
| Haemophilia B Asn58Lys AATg-AAG | ATTCAATTTCTTAACCTATCTCAAAGATGGAGATCAGTGTGAG TCCAATCCATGTTTAAA<u>T</u>GGCGGCAGTTGCAAGGATGACATTA ATTCCTATGAATGTTGGTGTCCCTTTGGATTTGAA | 2532 |
| | TTCAAATCCAAAGGGACACCAACATTCATAGGAATTAATGTCA TCCTTGCAACTGCCGCC<u>A</u>TTTAAACATGGATTGGACTCACACT GATCTCCATCTTTGAGATAGGTTAAGAAATTGAAT | 2533 |
| | TGTTTAAA<u>T</u>GGCGGCAG | 2534 |
| | CTGCCGCC<u>A</u>TTTAAACA | 2535 |
| Haemophilia B Gly59Asp GGC-GAC | TCAATTTCTTAACCTATCTCAAAGATGGAGATCAGTGTGAGTC CAATCCATGTTTAAATG<u>G</u>CGGCAGTTGCAAGGATGACATTAAT TCCTATGAATGTTGGTGTCCCTTTGGATTTGAAGG | 2536 |
| | CCTTCAAATCCAAAGGGACACCAACATTCATAGGAATTAATGT CATCCTTGCAACTGCCG<u>C</u>CATTTAAACATGGATTGGACTCACA CTGATCTCCATCTTTGAGATAGGTTAAGAAATTGA | 2537 |
| | TTTAAATG<u>G</u>CGGCAGTT | 2538 |
| | AACTGCCG<u>C</u>CATTTAAA | 2539 |
| Haemophilia B Gly59Val GGC-GTC | TCAATTTCTTAACCTATCTCAAAGATGGAGATCAGTGTGAGTC CAATCCATGTTTAAATG<u>G</u>CGGCAGTTGCAAGGATGACATTAAT TCCTATGAATGTTGGTGTCCCTTTGGATTTGAAGG | 2540 |
| | CCTTCAAATCCAAAGGGACACCAACATTCATAGGAATTAATGT CATCCTTGCAACTGCCG<u>C</u>CATTTAAACATGGATTGGACTCACA CTGATCTCCATCTTTGAGATAGGTTAAGAAATTGA | 2541 |
| | TTTAAATG<u>G</u>CGGCAGTT | 2542 |
| | AACTGCCG<u>C</u>CATTTAAA | 2543 |

TABLE 21-continued

Factor IX Mutations and Genome-Correcting Oligos

| Clinical Phenotype & Mutation | Correcting Oligos | SEQ ID NO: |
|---|---|---|
| Haemophilia B Gly59Ser tGGC-AGC | TTCAATTTCTTAACCTATCTCAAAGATGGAGATCAGTGTGAGT CCAATCCATGTTTAAATGGCGGCAGTTGCAAGGATGACATTAA TTCCTATGAATGTTGGTGTCCCTTTGGATTTGAAG | 2544 |
| | CTTCAAATCCAAAGGGACACCAACATTCATAGGAATTAATGTC ATCCTTGCAACTGCCGCCATTTAAACATGGATTGGACTCACAC TGATCTCCATCTTTGAGATAGGTTAAGAAATTGAA | 2545 |
| | GTTTAAATGGCGGCAGT | 2546 |
| | ACTGCCGCCATTTAAAC | 2547 |
| Haemophilia B Gly60Ser cGGC-AGC | AATTTCTTAACCTATCTCAAAGATGGAGATCAGTGTGAGTCCA ATCCATGTTTAAATGGCGGCAGTTGCAAGGATGACATTAATTC CTATGAATGTTGGTGTCCCTTTGGATTTGAAGGAA | 2548 |
| | TTCCTTCAAATCCAAAGGGACACCAACATTCATAGGAATTAAT GTCATCCTTGCAACTGCCGCCATTTAAACATGGATTGGACTCA CACTGATCTCCATCTTTGAGATAGGTTAAGAAATT | 2549 |
| | TAAATGGCGGCAGTTGC | 2550 |
| | GCAACTGCCGCCATTTA | 2551 |
| Haemophilia B Gly60Cys cGGC-TGC | AATTTCTTAACCTATCTCAAAGATGGAGATCAGTGTGAGTCCA ATCCATGTTTAAATGGCGGCAGTTGCAAGGATGACATTAATTC CTATGAATGTTGGTGTCCCTTTGGATTTGAAGGAA | 2552 |
| | TTCCTTCAAATCCAAAGGGACACCAACATTCATAGGAATTAAT GTCATCCTTGCAACTGCCGCCATTTAAACATGGATTGGACTCA CACTGATCTCCATCTTTGAGATAGGTTAAGAAATT | 2553 |
| | TAAATGGCGGCAGTTGC | 2554 |
| | GCAACTGCCGCCATTTA | 2555 |
| Haemophilia B Gly60Asp GGC-GAC | ATTTCTTAACCTATCTCAAAGATGGAGATCAGTGTGAGTCCAA TCCATGTTTAAATGGCGGCAGTTGCAAGGATGACATTAATTCC TATGAATGTTGGTGTCCCTTTGGATTTGAAGGAAA | 2556 |
| | TTTCCTTCAAATCCAAAGGGACACCAACATTCATAGGAATTAA TGTCATCCTTGCAACTGCCGCCATTTAAACATGGATTGGACTC ACACTGATCTCCATCTTTGAGATAGGTTAAGAAAT | 2557 |
| | AAATGGCGGCAGTTGCA | 2558 |
| | TGCAACTGCCGCCATTT | 2559 |
| Haemophilia B Gly60Arg cGGC-CGC | AATTTCTTAACCTATCTCAAAGATGGAGATCAGTGTGAGTCCA ATCCATGTTTAAATGGCGGCAGTTGCAAGGATGACATTAATTC CTATGAATGTTGGTGTCCCTTTGGATTTGAAGGAA | 2560 |
| | TTCCTTCAAATCCAAAGGGACACCAACATTCATAGGAATTAAT GTCATCCTTGCAACTGCCGCCATTTAAACATGGATTGGACTCA CACTGATCTCCATCTTTGAGATAGGTTAAGAAATT | 2561 |
| | TAAATGGCGGCAGTTGC | 2562 |
| | GCAACTGCCGCCATTTA | 2563 |
| Haemophilia B Cys62Tyr TGC-TAC | TAACCTATCTCAAAGATGGAGATCAGTGTGAGTCCAATCCATG TTTAAATGGCGGCAGTTGCAAGGATGACATTAATTCCTATGAA TGTTGGTGTCCCTTTGGATTTGAAGGAAAGAACTG | 2564 |
| | CAGTTCTTTCCTTCAAATCCAAAGGGACACCAACATTCATAGG AATTAATGTCATCCTTGCAACTGCCGCCATTTAAACATGGATT GGACTCACACTGATCTCCATCTTTGAGATAGGTTA | 2565 |
| | CGGCAGTTGCAAGGATG | 2566 |
| | CATCCTTGCAACTGCCG | 2567 |
| Haemophilia B Cys62Ser TGC-TCC | TAACCTATCTCAAAGATGGAGATCAGTGTGAGTCCAATCCATG TTTAAATGGCGGCAGTTGCAAGGATGACATTAATTCCTATGAA TGTTGGTGTCCCTTTGGATTTGAAGGAAAGAACTG | 2568 |
| | CAGTTCTTTCCTTCAAATCCAAAGGGACACCAACATTCATAGG AATTAATGTCATCCTTGCAACTGCCGCCATTTAAACATGGATT GGACTCACACTGATCTCCATCTTTGAGATAGGTTA | 2569 |
| | CGGCAGTTGCAAGGATG | 2570 |
| | CATCCTTGCAACTGCCG | 2571 |
| Haemophilia B Cys62Term TGCa-TGA | AACCTATCTCAAAGATGGAGATCAGTGTGAGTCCAATCCATGT TTAAATGGCGGCAGTTGCAAGGATGACATTAATTCCTATGAAT GTTGGTGTCCCTTTGGATTTGAAGGAAAGAACTGT | 2572 |
| | ACAGTTCTTTCCTTCAAATCCAAAGGGACACCAACATTCATAG GAATTAATGTCATCCTTGCAACTGCCGCCATTTAAACATGGAT TGGACTCACACTGATCTCCATCTTTGAGATAGGTT | 2573 |
| | GGCAGTTGCAAGGATGA | 2574 |
| | TCATCCTTGCAACTGCC | 2575 |
| Haemophilia B Asp64Glu GATg-GAG | TCTCAAAGATGGAGATCAGTGTGAGTCCAATCCATGTTTAAAT GGCGGCAGTTGCAAGGATGACATTAATTCCTATGAATGTTGG TGTCCCTTTGGATTTGAAGGAAAGAACTGAATTA | 2576 |
| | TAATTCACAGTTCTTTCCTTCAAATCCAAAGGGACACCAACAT TCATAGGAATTAATGTCATCCTTGCAACTGCCGCCATTTAAAC ATGGATTGGACTCACACTGATCTCCATCTTTGAGA | 2577 |
| | TGCAAGGATGACATTAA | 2578 |
| | TTAATGTCATCCTTGCA | 2579 |

TABLE 21-continued

Factor IX Mutations and Genome-Correcting Oligos

| Clinical Phenotype & Mutation | Correcting Oligos | SEQ ID NO: |
|---|---|---|
| Haemophilia B Asp64Gly GAT-GGT | ATCTCAAAGATGGAGATCAGTGTGAGTCCAATCCATGTTTAAA TGGCGGCAGTTGCAAGGATGACATTAATTCCTATGAATGTTG GTGTCCCTTTGGATTTGAAGGAAAGAACTGTGAATT | 2580 |
| | AATTCACAGTTCTTTCCTTCAAATCCAAAGGGACACCAACATT CATAGGAATTAATGTCATCCTTGCAACTGCCGCCATTTAAACA TGGATTGGACTCACACTGATCTCCATCTTTGAGAT | 2581 |
| | TTGCAAGGATGACATTA | 2582 |
| | TAATGTCATCCTTGCAA | 2583 |
| Haemophilia B Asp64Asn gGAT-AAT | TATCTCAAAGATGGAGATCAGTGTGAGTCCAATCCATGTTTAA ATGGCGGCAGTTGCAAGGATGACATTAATTCCTATGAATGTTG GTGTCCCTTTGGATTTGAAGGAAAGAACTGTGAAT | 2584 |
| | ATTCACAGTTCTTTCCTTCAAATCCAAAGGGACACCAACATTC ATAGGAATTAATGTCATCCTTGCAACTGCCGCCATTTAAACAT GGATTGGACTCACACTGATCTCCATCTTTGAGATA | 2585 |
| | GTTGCAAGGATGACATT | 2586 |
| | AATGTCATCCTTGCAAC | 2587 |
| Haemophilia B Ile66Ser ATT-AGT | AAGATGGAGATCAGTGTGAGTCCAATCCATGTTTAAATGGCG GCAGTTGCAAGGATGACATTAATTCCTATGAATGTTGGTGTCC CTTTGGATTTGAAGGAAAGAACTGTGAATTAGGTAA | 2588 |
| | TTACCTAATTCACAGTTCTTTCCTTCAAATCCAAAGGGACACC AACATTCATAGGAATTAATGTCATCCTTGCAACTGCCGCCATT TAAACATGGATTGGACTCACACTGATCTCCATCTT | 2589 |
| | GGATGACATTAATTCCT | 2590 |
| | AGGAATTAATGTCATCC | 2591 |
| Haemophilia B Ile66Thr ATT-ACT | AAGATGGAGATCAGTGTGAGTCCAATCCATGTTTAAATGGCG GCAGTTGCAAGGATGACATTAATTCCTATGAATGTTGGTGTCC CTTTGGATTTGAAGGAAAGAACTGTGAATTAGGTAA | 2592 |
| | TTACCTAATTCACAGTTCTTTCCTTCAAATCCAAAGGGACACC AACATTCATAGGAATTAATGTCATCCTTGCAACTGCCGCCATT TAAACATGGATTGGACTCACACTGATCTCCATCTT | 2593 |
| | GGATGACATTAATTCCT | 2594 |
| | AGGAATTAATGTCATCC | 2595 |
| Haemophilia B Asn67Lys AATt-AAA | TGGAGATCAGTGTGAGTCCAATCCATGTTTAAATGGCGGCAG TTGCAAGGATGACATTAATTCCTATGAATGTTGGTGTCCCTTT GGATTTGAAGGAAAGAACTGTGAATTAGGTAAGTAA | 2596 |
| | TTACTTACCTAATTCACAGTTCTTTCCTTCAAATCCAAAGGGAC ACCAACATTCATAGGAATTAATGTCATCCTTGCAACTGCCGCC ATTTAAACATGGATTGGACTCACACTGATCTCCA | 2597 |
| | GACATTAATTCCTATGA | 2598 |
| | TCATAGGAATTAATGTC | 2599 |
| Haemophilia B Tyr69Cys TAT-TGT | ATCAGTGTGAGTCCAATCCATGTTTAAATGGCGGCAGTTGCA AGGATGACATTAATTCCTATGAATGTTGGTGTCCCTTTGGATT TGAAGGAAAGAACTGTGAATTAGGTAAGTAACTATT | 2600 |
| | AATAGTTACTTACCTAATTCACAGTTCTTTCCTTCAAATCCAAA GGGACACCAACATTCATAGGAATTAATGTCATCCTTGCAACTG CCGCCATTTAAACATGGACTCACACTGAT | 2601 |
| | TAATTCCTATGAATGTT | 2602 |
| | AACATTCATAGGAATTA | 2603 |
| Haemophilia B Cys71Term TGTt-TGA | TGAGTCCAATCCATGTTTAAATGGCGGCAGTTGCAAGGATGA CATTAATTCCTATGAATGTTGGTGTCCCTTTGGATTTGAAGGA AAGAACTGTGAATTAGGTAAGTAACTATTTTTTGAA | 2604 |
| | TTCAAAAAATAGTTACTTACCTAATTCACAGTTCTTTCCTTCAA ATCCAAAGGGACACCAACATTCATAGGAATTAATGTCATCCTT GCAACTGCCGCCATTTAAACATGGATTGGACTCA | 2605 |
| | TATGAATGTTGGTGTCC | 2606 |
| | GGACACCAACATTCATA | 2607 |
| Haemophilia B Cys71Ser TGT-TCT | GTGAGTCCAATCCATGTTTAAATGGCGGCAGTTGCAAGGATG ACATTAATTCCTATGAATGTTGGTGTCCCTTTGGATTTGAAGG AAAGAACTGTGAATTAGGTAAGTAACTATTTTTTGA | 2608 |
| | TCAAAAAATAGTTACTTACCTAATTCACAGTTCTTTCCTTCAAA TCCAAAGGGACACCAACATTCATAGGAATTAATGTCATCCTTG CAACTGCCGCCATTTAAACATGGATTGGACTCAC | 2609 |
| | CTATGAATGTTGGTGTC | 2610 |
| | GACACCAACATTCATAG | 2611 |
| Haemophilia B Cys71Tyr TGT-TAT | GTGAGTCCAATCCATGTTTAAATGGCGGCAGTTGCAAGGATG ACATTAATTCCTATGAATGTTGGTGTCCCTTTGGATTTGAAGG AAAGAACTGTGAATTAGGTAAGTAACTATTTTTTGA | 2612 |
| | TCAAAAAATAGTTACTTACCTAATTCACAGTTCTTTCCTTCAAA TCCAAAGGGACACCAACATTCATAGGAATTAATGTCATCCTTG CAACTGCCGCCATTTAAACATGGATTGGACTCAC | 2613 |
| | CTATGAATGTTGGTGTC | 2614 |
| | GACACCAACATTCATAG | 2615 |

TABLE 21-continued

Factor IX Mutations and Genome-Correcting Oligos

| Clinical Phenotype & Mutation | Correcting Oligos | SEQ ID NO: |
|---|---|---|
| Haemophilia B Cys71Ser aTGT-AGT | TGTGAGTCCAATCCATGTTTAAATGGCGGCAGTTGCAAGGAT GACATTAATTCCTATGAATGTTGGTGTCCCTTTGGATTTGAAG GAAAGAACTGTGAATTAGGTAAGTAACTATTTTTTG | 2616 |
| | CAAAAAATAGTTACTTACCTAATTCACAGTTCTTTCCTTCAAAT CCAAAGGGACACCAACATTCATAGGAATTAATGTCATCCTTGC AACTGCCGCCATTTAAACATGGATTGGACTCACA | 2617 |
| | CCTATGAATGTTGGTGT | 2618 |
| | ACACCAACATTCATAGG | 2619 |
| Haemophilia B Trp72Arg tTGG-AGG | GAGTCCAATCCATGTTTAAATGGCGGCAGTTGCAAGGATGAC ATTAATTCCTATGAATGTTGGTGTCCCTTTGGATTTGAAGGAA AGAACTGTGAATTAGGTAAGTAACTATTTTTTGAAT | 2620 |
| | ATTCAAAAAATAGTTACTTACCTAATTCACAGTTCTTTCCTTCA AATCCAAAGGGACACCAACATTCATAGGAATTAATGTCATCCT TGCAACTGCCGCCATTTAAACATGGATTGGACTC | 2621 |
| | ATGAATGTTGGTGTCCC | 2622 |
| | GGGACACCAACATTCAT | 2623 |
| Haemophilia B Trp72Term TGGt-TGA | GTCCAATCCATGTTTAAATGGCGGCAGTTGCAAGGATGACAT TAATTCCTATGAATGTTGGTGTCCCTTTGGATTTGAAGGAAAG AACTGTGAATTAGGTAAGTAACTATTTTTTGAATAC | 2624 |
| | GTATTCAAAAAATAGTTACTTACCTAATTCACAGTTCTTTCCTT CAAATCCAAAGGGACACCAACATTCATAGGAATTAATGTCATC CTTGCAACTGCCGCCATTTAAACATGGATTGGAC | 2625 |
| | GAATGTTGGTGTCCCTT | 2626 |
| | AAGGGACACCAACATTC | 2627 |
| Haemophilia B Cys73Tyr TGT-TAT | CCAATCCATGTTTAAATGGCGGCAGTTGCAAGGATGACATTAA TTCCTATGAATGTTGGTGTCCCTTTGGATTTGAAGGAAAGAAC TGTGAATTAGGTAAGTAACTATTTTTTGAATACTC | 2628 |
| | GAGTATTCAAAAAATAGTTACTTACCTAATTCACAGTTCTTTCC TTCAAATCCAAAGGGACACCAACATTCATAGGAATTAATGTCA TCCTTGCAACTGCCGCCATTTAAACATGGATTGG | 2629 |
| | ATGTTGGTGTCCCTTTG | 2630 |
| | CAAAGGGACACCAACAT | 2631 |
| Haemophilia B Cys73Arg gTGT-CGT | TCCAATCCATGTTTAAATGGCGGCAGTTGCAAGGATGACATTA ATTCCTATGAATGTTGGTGTCCCTTTGGATTTGAAGGAAAGAA CTGTGAATTAGGTAAGTAACTATTTTTTGAATACT | 2632 |
| | AGTATTCAAAAAATAGTTACTTACCTAATTCACAGTTCTTTCCT TCAAATCCAAAGGGACACCAACATTCATAGGAATTAATGTCAT CCTTGCAACTGCCGCCATTTAAACATGGATTGGA | 2633 |
| | AATGTTGGTGTCCCTTT | 2634 |
| | AAAGGGACACCAACATT | 2635 |
| Haemophilia B Cys73Phe TGT-TTT | CCAATCCATGTTTAAATGGCGGCAGTTGCAAGGATGACATTAA TTCCTATGAATGTTGGTGTCCCTTTGGATTTGAAGGAAAGAAC TGTGAATTAGGTAAGTAACTATTTTTTGAATACTC | 2636 |
| | GAGTATTCAAAAAATAGTTACTTACCTAATTCACAGTTCTTTCC TTCAAATCCAAAGGGACACCAACATTCATAGGAATTAATGTCA TCCTTGCAACTGCCGCCATTTAAACATGGATTGG | 2637 |
| | ATGTTGGTGTCCCTTTG | 2638 |
| | CAAAGGGACACCAACAT | 2639 |
| Haemophilia B Cys73Term TGTc-TGA | CAATCCATGTTTAAATGGCGGCAGTTGCAAGGATGACATTAAT TCCTATGAATGTTGGTGTCCCTTTGGATTTGAAGGAAAGAACT GTGAATTAGGTAAGTAACTATTTTTTGAATACTCA | 2640 |
| | TGAGTATTCAAAAAATAGTTACTTACCTAATTCACAGTTCTTTC CTTCAAATCCAAAGGGACACCAACATTCATAGGAATTAATGTC ATCCTTGCAACTGCCGCCATTTAAACATGGATTG | 2641 |
| | TGTTGGTGTCCCTTTGG | 2642 |
| | CCAAAGGGACACCAACA | 2643 |
| Haemophilia B Gly76Val GGA-GTA | GTTTAAATGGCGGCAGTTGCAAGGATGACATTAATTCCTATGA ATGTTGGTGTCCCTTTGGATTTGAAGGAAAGAACTGTGAATTA GGTAAGTAACTATTTTTTGAATACTCATGGTTCAA | 2644 |
| | TTGAACCATGAGTATTCAAAAAATAGTTACTTACCTAATTCACA GTTCTTTCCTTCAAATCCAAAGGGACACCAACATTCATAGGAA TTAATGTCATCCTTGCAACTGCCGCCATTTAAAC | 2645 |
| | TCCCTTTGGATTTGAAG | 2646 |
| | CTTCAAATCCAAAGGGA | 2647 |
| Haemophilia B Gly76Arg tGGA-AGA | TGTTTAAATGGCGGCAGTTGCAAGGATGACATTAATTCCTATG AATGTTGGTGTCCCTTTGGATTTGAAGGAAAGAACTGTGAATT AGGTAAGTAACTATTTTTTGAATACTCATGGTTCA | 2648 |
| | TGAACCATGAGTATTCAAAAAATAGTTACTTACCTAATTCACAG TTCTTTCCTTCAAATCCAAAGGGACACCAACATTCATAGGAAT TAATGTCATCCTTGCAACTGCCGCCATTTAAACA | 2649 |
| | GTCCCTTTGGATTTGAA | 2650 |
| | TTCAAATCCAAAGGGAC | 2651 |

TABLE 21-continued

Factor IX Mutations and Genome-Correcting Oligos

| Clinical Phenotype & Mutation | Correcting Oligos | SEQ ID NO: |
|---|---|---|
| Haemophilia B Phe77Cys TTT-TGT | TAAATGGCGGCAGTTGCAAGGATGACATTAATTCCTATGAATG TTGGTGTCCCTTTGGATTTGAAGGAAAGAACTGTGAATTAGGT AAGTAACTATTTTTTGAATACTCATGGTTCAAAGT | 2652 |
| | ACTTTGAACCATGAGTATTCAAAAAATAGTTACTTACCTAATTC ACAGTTCTTTCCTTCAAATCCAAAGGGACACCAACATTCATAG GAATTAATGTCATCCTTGCAACTGCCGCCATTTA | 2653 |
| | CTTTGGATTTGAAGGAA | 2654 |
| | TTCCTTCAAATCCAAAG | 2655 |
| Haemophilia B Phe77Ser TTT-TCT | TAAATGGCGGCAGTTGCAAGGATGACATTAATTCCTATGAATG TTGGTGTCCCTTTGGATTTGAAGGAAAGAACTGTGAATTAGGT AAGTAACTATTTTTTGAATACTCATGGTTCAAAGT | 2656 |
| | ACTTTGAACCATGAGTATTCAAAAAATAGTTACTTACCTAATTC ACAGTTCTTTCCTTCAAATCCAAAGGGACACCAACATTCATAG GAATTAATGTCATCCTTGCAACTGCCGCCATTTA | 2657 |
| | CTTTGGATTTGAAGGAA | 2658 |
| | TTCCTTCAAATCCAAAG | 2659 |
| Haemophilia B Phe77Tyr TTT-TAT | TAAATGGCGGCAGTTGCAAGGATGACATTAATTCCTATGAATG TTGGTGTCCCTTTGGATTTGAAGGAAAGAACTGTGAATTAGGT AAGTAACTATTTTTTGAATACTCATGGTTCAAAGT | 2660 |
| | ACTTTGAACCATGAGTATTCAAAAAATAGTTACTTACCTAATTC ACAGTTCTTTCCTTCAAATCCAAAGGGACACCAACATTCATAG GAATTAATGTCATCCTTGCAACTGCCGCCATTTA | 2661 |
| | CTTTGGATTTGAAGGAA | 2662 |
| | TTCCTTCAAATCCAAAG | 2663 |
| Haemophilia B Glu78Lys tGAA-AAA | AATGGCGGCAGTTGCAAGGATGACATTAATTCCTATGAATGTT GGTGTCCCTTTGGATTTGAAGGAAAGAACTGTGAATTAGGTAA GTAACTATTTTTTGAATACTCATGGTTCAAAGTTT | 2664 |
| | AAACTTTGAACCATGAGTATTCAAAAAATAGTTACTTACCTAAT TCACAGTTCTTTCCTTCAAATCCAAAGGGACACCAACATTCAT AGGAATTAATGTCATCCTTGCAACTGCCGCCATT | 2665 |
| | TTGGATTTGAAGGAAAG | 2666 |
| | CTTTCCTTCAAATCCAA | 2667 |
| Haemophilia B Gly79Val GGA-GTA | GCGGCAGTTGCAAGGATGACATTAATTCCTATGAATGTTGGT GTCCCTTTGGATTTGAAGGAAAGAACTGTGAATTAGGTAAGTA ACTATTTTTTGAATACTCATGGTTCAAAGTTTCCCT | 2668 |
| | AGGGAAACTTTGAACCATGAGTATTCAAAAAATAGTTACTTAC CTAATTCACAGTTCTTTCCTTCAAATCCAAAGGGACACCAACA TTCATAGGAATTAATGTCATCCTTGCAACTGCCG | 2669 |
| | ATTTGAAGGAAAGAACT | 2670 |
| | AGTTCTTTCCTTCAAAT | 2671 |
| Haemophilia B Gly79Arg aGGA-AGA | GGCGGCAGTTGCAAGGATGACATTAATTCCTATGAATGTTGG TGTCCCTTTGGATTTGAAGGAAAGAACTGTGAATTAGGTAAGT AACTATTTTTTGAATACTCATGGTTCAAAGTTTCCC | 2672 |
| | GGGAAACTTTGAACCATGAGTATTCAAAAAATAGTTACTTACC TAATTCACAGTTCTTTCCTTCAAATCCAAAGGGACACCAACAT TCATAGGAATTAATGTCATCCTTGCAACTGCCGCC | 2673 |
| | GATTTGAAGGAAAGAAC | 2674 |
| | GTTCTTTCCTTCAAATC | 2675 |
| Haemophilia B Gly79Glu GGA-GAA | GCGGCAGTTGCAAGGATGACATTAATTCCTATGAATGTTGGT GTCCCTTTGGATTTGAAGGAAAGAACTGTGAATTAGGTAAGTA ACTATTTTTTGAATACTCATGGTTCAAAGTTTCCCT | 2676 |
| | AGGGAAACTTTGAACCATGAGTATTCAAAAAATAGTTACTTAC CTAATTCACAGTTCTTTCCTTCAAATCCAAAGGGACACCAACA TTCATAGGAATTAATGTCATCCTTGCAACTGCCG | 2677 |
| | ATTTGAAGGAAAGAACT | 2678 |
| | AGTTCTTTCCTTCAAAT | 2679 |
| Haemophilia B Cys88Ser TGT-TCT | TTAGAAATGCATGTTAAATGATGCTGTTACTGTCTATTTTGCTT CTTTTAGATGTAACATGTAACATTAAGAATGGCAGATGCGAGC AGTTTTGTAAAAATAGTGCTGATAACAAGGTGGT | 2680 |
| | ACCACCTTGTTATCAGCACTATTTTTACAAAACTGCTCGCATC TGCCATTCTTAATGTTACATGTTACATCTAAAAGAAGCAAATA GACAGTAACAGCATCATTTAACATGCATTTCTAA | 2681 |
| | TGTAACATGTAACATTA | 2682 |
| | TAATGTTACATGTTACA | 2683 |
| Haemophilia B Cys88Phe TGT-TTT | TTAGAAATGCATGTTAAATGATGCTGTTACTGTCTATTTTGCTT CTTTTAGATGTAACATGTAACATTAAGAATGGCAGATGCGAGC AGTTTTGTAAAAATAGTGCTGATAACAAGGTGGT | 2684 |
| | ACCACCTTGTTATCAGCACTATTTTTACAAAACTGCTCGCATC TGCCATTCTTAATGTTACATGTTACATCTAAAAGAAGCAAATA GACAGTAACAGCATCATTTAACATGCATTTCTAA | 2685 |
| | TGTAACATGTAACATTA | 2686 |
| | TAATGTTACATGTTACA | 2687 |

TABLE 21-continued

Factor IX Mutations and Genome-Correcting Oligos

| Clinical Phenotype & Mutation | Correcting Oligos | SEQ ID NO: |
|---|---|---|
| Haemophilia B Cys88Arg aTGT-CGT | TTTAGAAATGCATGTTAAATGATGCTGTTACTGTCTATTTTGCT TCTTTTAGATGTAACATGTAACATTAAGAATGGCAGATGCGAG CAGTTTTGTAAAAATAGTGCTGATAACAAGGTGG | 2688 |
| | CCACCTTGTTATCAGCACTATTTTTACAAAACTGCTCGCATCT GCCATTCTTAATGTTACATGTTACATCTAAAAGAAGCAAAATA GACAGTAACAGCATCATTTAACATGCATTTCTAAA | 2689 |
| | ATGTAACATGTAACATT | 2690 |
| | AATGTTACATGTTACAT | 2691 |
| Haemophilia B Cys88Tyr TGT-TAT | TTAGAAATGCATGTTAAATGATGCTGTTACTGTCTATTTTGCTT CTTTTAGATGTAACATGTAACATTAAGAATGGCAGATGCGAGC AGTTTTGTAAAAATAGTGCTGATAACAAGGTGGT | 2692 |
| | ACCACCTTGTTATCAGCACTATTTTTACAAAACTGCTCGCATC TGCCATTCTTAATGTTACATGTTACATCTAAAAGAAGCAAAATA GACAGTAACAGCATCATTTAACATGCATTTCTAA | 2693 |
| | TGTAACATGTAACATTA | 2694 |
| | TAATGTTACATGTTACA | 2695 |
| Haemophilia B Ile90Thr ATT-ACT | ATGCATGTTAAATGATGCTGTTACTGTCTATTTTGCTTCTTTTA GATGTAACATGTAACATTAAGAATGGCAGATGCGAGCAGTTTT GTAAAAATAGTGCTGATAACAAGGTGGTTTGCTC | 2696 |
| | GAGCAAACCACCTTGTTATCAGCACTATTTTTACAAAACTGCT CGCATCTGCCATTCTTAATGTTACATGTTACATCTAAAAGAAG CAAAATAGACAGTAACAGCATCATTTAACATGCAT | 2697 |
| | ATGTAACATTAAGAATG | 2698 |
| | CATTCTTAATGTTACAT | 2699 |
| Haemophilia B Asn92His gAAT-CAT | TGTTAAATGATGCTGTTACTGTCTATTTTGCTTCTTTTAGATGT AACATGTAACATTAAGAATGGCAGATGCGAGCAGTTTTGTAAA AATAGTGCTGATAACAAGGTGGTTTGCTCCTGTA | 2700 |
| | TACAGGAGCAAACCACCTTGTTATCAGCACTATTTTTACAAAA CTGCTCGCATCTGCCATTCTTAATGTTACATGTTACATCTAAAA GAAGCAAAATAGACAGTAACAGCATCATTTAACA | 2701 |
| | ACATTAAGAATGGCAGA | 2702 |
| | TCTGCCATTCTTAATGT | 2703 |
| Haemophilia B Asn92Lys AATg-AAA | TTAAATGATGCTGTTACTGTCTATTTTGCTTCTTTTAGATGTAA CATGTAACATTAAGAATGGCAGATGCGAGCAGTTTTGTAAAAA TAGTGCTGATAACAAGGTGGTTTGCTCCTGTACT | 2704 |
| | AGTACAGGAGCAAACCACCTTGTTATCAGCACTATTTTTACAA AACTGCTCGCATCTGCCATTCTTAATGTTACATGTTACATCTA AAAGAAGCAAAATAGACAGTAACAGCATCATTTAA | 2705 |
| | ATTAAGAATGGCAGATG | 2706 |
| | CATCTGCCATTCTTAAT | 2707 |
| Haemophilia B Gly93Asp GGC-GAC | AAATGATGCTGTTACTGTCTATTTTGCTTCTTTTAGATGTAACA TGTAACATTAAGAATGGCAGATGCGAGCAGTTTTGTAAAAATA GTGCTGATAACAAGGTGGTTTGCTCCTGTACTGA | 2708 |
| | TCAGTACAGGAGCAAACCACCTTGTTATCAGCACTATTTTTAC AAAACTGCTCGCATCTGCCATTCTTAATGTTACATGTTACATCT AAAAGAAGCAAAATAGACAGTAACAGCATCATTT | 2709 |
| | TAAGAATGGCAGATGCG | 2710 |
| | CGCATCTGCCATTCTTA | 2711 |
| Haemophilia B Gly93Ser tGGC-AGC | TAAATGATGCTGTTACTGTCTATTTTGCTTCTTTTAGATGTAAC ATGTAACATTAAGAATGGCAGATGCGAGCAGTTTTGTAAAAAT AGTGCTGATAACAAGGTGGTTTGCTCCTGTACTG | 2712 |
| | CAGTACAGGAGCAAACCACCTTGTTATCAGCACTATTTTTACA AAACTGCTCGCATCTGCCATTCTTAATGTTACATGTTACATCTA AAAGAAGCAAAATAGACAGTAACAGCATCATTTA | 2713 |
| | TTAAGAATGGCAGATGC | 2714 |
| | GCATCTGCCATTCTTAA | 2715 |
| Haemophilia B Arg94Ser AGAt-AGT | GATGCTGTTACTGTCTATTTTGCTTCTTTTAGATGTAACATGTA ACATTAAGAATGGCAGATGCGAGCAGTTTTGTAAAAATAGTGC TGATAACAAGGTGGTTTGCTCCTGTACTGAGGGA | 2716 |
| | TCCCTCAGTACAGGAGCAAACCACCTTGTTATCAGCACTATTT TTACAAAACTGCTCGCATCTGCCATTCTTAATGTTACATGTTAC ATCTAAAAGAAGCAAAATAGACAGTAACAGCATC | 2717 |
| | AATGGCAGATGCGAGCA | 2718 |
| | TGCTCGCATCTGCCATT | 2719 |
| Haemophilia B Cys95Tyr TGC-TAC | TGCTGTTACTGTCTATTTTGCTTCTTTTAGATGTAACATGTAAC ATTAAGAATGGCAGATGCGAGCAGTTTTGTAAAAATAGTGCTG ATAACAAGGTGGTTTGCTCCTGTACTGAGGGATA | 2720 |
| | TATCCCTCAGTACAGGAGCAAACCACCTTGTTATCAGCACTAT TTTTACAAAACTGCTCGCATCTGCCATTCTTAATGTTACATGTT ACATCTAAAAGAAGCAAAATAGACAGTAACAGCA | 2721 |
| | TGGCAGATGCGAGCAGT | 2722 |
| | ACTGCTCGCATCTGCCA | 2723 |

TABLE 21-continued

Factor IX Mutations and Genome-Correcting Oligos

| Clinical Phenotype & Mutation | Correcting Oligos | SEQ ID NO: |
|---|---|---|
| Haemophilia B Cys95Trp TGCg-TGG | GCTGTTACTGTCTATTTTGCTTCTTTTAGATGTAACATGTAACA TTAAGAATGGCAGATGCGAGCAGTTTTGTAAAAATAGTGCTGA TAACAAGGTGGTTTGCTCCTGTACTGAGGGATAT | 2724 |
| | ATATCCCTCAGTACAGGAGCAAACCACCTTGTTATCAGCACTA TTTTTACAAAACTGCTCGCATCTGCCATTCTTAATGTTACATGT TACATCTAAAAGAAGCAAAATAGACAGTAACAGC | 2725 |
| | GGCAGATGCGAGCAGTT | 2726 |
| | AACTGCTCGCATCTGCC | 2727 |
| Haemophilia B Cys95Term TGCg-TGA | GCTGTTACTGTCTATTTTGCTTCTTTTAGATGTAACATGTAACA TTAAGAATGGCAGATGCGAGCAGTTTTGTAAAAATAGTGCTGA TAACAAGGTGGTTTGCTCCTGTACTGAGGGATAT | 2728 |
| | ATATCCCTCAGTACAGGAGCAAACCACCTTGTTATCAGCACTA TTTTTACAAAACTGCTCGCATCTGCCATTCTTAATGTTACATGT TACATCTAAAAGAAGCAAAATAGACAGTAACAGC | 2729 |
| | GGCAGATGCGAGCAGTT | 2730 |
| | AACTGCTCGCATCTGCC | 2731 |
| Haemophilia B Gln97Pro CAG-CCG | TACTGTCTATTTTGCTTCTTTTAGATGTAACATGTAACATTAAG AATGGCAGATGCGAGCAGTTTTGTAAAAATAGTGCTGATAACA AGGTGGTTTGCTCCTGTACTGAGGGATATCGACT | 2732 |
| | AGTCGATATCCCTCAGTACAGGAGCAAACCACCTTGTTATCA GCACTATTTTTACAAAACTGCTCGCATCTGCCATTCTTAATGTT ACATGTTACATCTAAAAGAAGCAAAATAGACAGTA | 2733 |
| | ATGCGAGCAGTTTTGTA | 2734 |
| | TACAAAACTGCTCGCAT | 2735 |
| Haemophilia B Gln97Glu gCAG-GAG | TTACTGTCTATTTTGCTTCTTTTAGATGTAACATGTAACATTAA GAATGGCAGATGCGAGCAGTTTTGTAAAAATAGTGCTGATAAC AAGGTGGTTTGCTCCTGTACTGAGGGATATCGAC | 2736 |
| | GTCGATATCCCTCAGTACAGGAGCAAACCACCTTGTTATCAG CACTATTTTTACAAAACTGCTCGCATCTGCCATTCTTAATGTTA CATGTTACATCTAAAAGAAGCAAAATAGACAGTAA | 2737 |
| | GATGCGAGCAGTTTTGT | 2738 |
| | ACAAAACTGCTCGCATC | 2739 |
| Haemophilia B Cys99Arg tTGT-CGT | TCTATTTTGCTTCTTTTAGATGTAACATGTAACATTAAGAATGG CAGATGCGAGCAGTTTTTGTAAAAATAGTGCTGATAACAAGGTG GTTTGCTCCTGTACTGAGGGATATCGACTTGCAG | 2740 |
| | CTGCAAGTCGATATCCCTCAGTACAGGAGCAAACCACCTTGT TATCAGCACTATTTTTACAAAACTGCTCGCATCTGCCATTCTT AATGTTACATGTTACATCTAAAAGAAGCAAAATAGA | 2741 |
| | AGCAGTTTTGTAAAAAT | 2742 |
| | ATTTTTACAAAACTGCT | 2743 |
| Haemophilia B Cys99Tyr TGT-TAT | CTATTTTGCTTCTTTTAGATGTAACATGTAACATTAAGAATGGC AGATGCGAGCAGTTTTGTAAAAATAGTGCTGATAACAAGGTG GTTTGCTCCTGTACTGAGGGATATCGACTTGCAGA | 2744 |
| | TCTGCAAGTCGATATCCCTCAGTACAGGAGCAAACCACCTTG TTATCAGCACTATTTTTACAAAACTGCTCGCATCTGCCATTCTT AATGTTACATGTTACATCTAAAAGAAGCAAAATAG | 2745 |
| | GCAGTTTTGTAAAAATA | 2746 |
| | TATTTTTACAAAACTGC | 2747 |
| Warfarin sensitivity Ala(-10)Thr cGCC-ACC | TTTTTTGCTAAAACTAAAGAATTATTCTTTTACATTTCAGTTTTT CTTGATCATGAAAACGCCAACAAAATTCTGAATCGGCCAAAGA GGTATAATTCAGGTAAATTGGAAGAGTTTGTTC | 2748 |
| | GAACAAACTCTTCCAATTTACCTGAATTATACCTCTTTGGCCG ATTCAGAATTTTGTTGGCGTTTTCATGATCAAGAAAAACTGAAA TGTAAAAGAATAATTCTTTAGTTTTAGCAAAAAA | 2749 |
| | ATGAAAACGCCAACAAA | 2750 |
| | TTTGTTGGCGTTTTCAT | 2751 |
| Warfarin sensitivity Ala(-10)Val GCC-GTC | TTTTTGCTAAAACTAAAGAATTATTCTTTTACATTTCAGTTTTTC TTGATCATGAAAACGCCAACAAAATTCTGAATCGGCCAAAGAG GTATAATTCAGGTAAATTGGAAGAGTTTGTTCA | 2752 |
| | TGAACAAACTCTTCCAATTTACCTGAATTATACCTCTTTGGCC GATTCAGAATTTTGTTGGCGTTTTCATGATCAAGAAAAACTGA AATGTAAAAGAATAATTCTTTAGTTTTAGCAAAAA | 2753 |
| | TGAAAACGCCAACAAAA | 2754 |
| | TTTTGTTGGCGTTTTCA | 2755 |
| Haemophilia B Gly(-26)Val GGA-GTA | TGCAGCGCGTGAACATGATCATGGCAGAATCACCAGGCCTCA TCACCATCTGCCTTTTAGGATATCTACTCAGTGCTGAATGTAC AGGTTTGTTTCCTTTTTTAAAATACATTGAGTATGC | 2756 |
| | GCATACTCAATGTATTTTAAAAAAGGAAACAAACCTGTACATTC AGCACTGAGTAGATATCCTAAAAGGCAGATGGTGATGAGGCC TGGTGATTCTGCCATGATCATGTTCACGCGCTGCA | 2757 |
| | CCTTTTAGGATATCTAC | 2758 |
| | GTAGATATCCTAAAAGG | 2759 |

TABLE 21-continued

Factor IX Mutations and Genome-Correcting Oligos

| Clinical Phenotype & Mutation | Correcting Oligos | SEQ ID NO: |
|---|---|---|
| Haemophilia B Leu(-27)Term TTA-TAA | TTATGCAGCGCGTGAACATGATCATGGCAGAATCACCAGGCC TCATCACCATCTGCCTTTTAGGATATCTACTCAGTGCTGAATG TACAGGTTTGTTTCCTTTTTTAAAATACATTGAGTA | 2760 |
| | TACTCAATGTATTTTAAAAAAGGAAACAAACCTGTACATTCAGC ACTGAGTAGATATCCTAAAAGGCAGATGGTGATGAGGCCTGG TGATTCTGCCATGATCATGTTCACGCGCTGCATAA | 2761 |
| | CTGCCTTTTAGGATATC | 2762 |
| | GATATCCTAAAAGGCAG | 2763 |
| Haemophilia B Ile(-30)Asn ATC-AAC | TAGCAAAGGTTATGCAGCGCGTGAACATGATCATGGCAGAAT CACCAGGCCTCATCACCATCTGCCTTTTAGGATATCTACTCAG TGCTGAATGTACAGGTTTGTTTCCTTTTTTAAAATA | 2764 |
| | TATTTTAAAAAAGGAAACAAACCTGTACATTCAGCACTGAGTA GATATCCTAAAAGGCAGATGGTGATGAGGCCTGGTGATTCTG CCATGATCATGTTCACGCGCTGCATAACCTTTGCTA | 2765 |
| | CATCACCATCTGCCTTT | 2766 |
| | AAAGGCAGATGGTGATG | 2767 |
| Haemophilia B Ile(-40)Phe gATC-TTC | ACTAATCGACCTTACCACTTTCACAATCTGCTAGCAAAGGTTA TGCAGCGCGTGAACATGATCATGGCAGAATCACCAGGCCTCA TCACCATCTGCCTTTTAGGATATCTACTCAGTGCTG | 2768 |
| | CAGCACTGAGTAGATATCCTAAAAGGCAGATGGTGATGAGGC CTGGTGATTCTGCCATGATCATGTTCACGCGCTGCATAACCTT TGCTAGCAGATTGTGAAAGTGGTAAGGTCGATTAGT | 2769 |
| | TGAACATGATCATGGCA | 2770 |
| | TGCCATGATCATGTTCA | 2771 |
| Haemophilia B Arg(-44)His CGC-CAC | ACTTTGGTACAACTAATCGACCTTACCACTTTCACAATCTGCT AGCAAAGGTTATGCAGCGCGTGAACATGATCATGGCAGAATC ACCAGGCCTCATCACCATCTGCCTTTTAGGATATCT | 2772 |
| | AGATATCCTAAAAGGCAGATGGTGATGAGGCCTGGTGATTCT GCCATGATCATGTTCACGCGCTGCATAACCTTTGCTAGCAGA TTGTGAAAGTGGTAAGGTCGATTAGTTGTACCAAAGT | 2773 |
| | TATGCAGCGCGTGAACA | 2774 |
| | TGTTCACGCGCTGCATA | 2775 |

EXAMPLE 15

Alpha Thalassemia—Hemoglobin Alpha Locus 1

The thalassemia syndromes are a heterogeneous group of inherited anemias characterized by defects in th synthesis of one or more globin chain subunits. For example, beta-thalassemia discussed in Example 6, is caused by a decrease in beta-chain production relative to alpha-chain production; the converse is the case for alpha-thalassemia. The attached table disclosed the correcting oligonucleotide base sequences for the hemoglobin alpha locus 1 oligonucleotides of the invention.

TABLE 22

HBA1 Mutations and Genome-Correcting Oligos

| Clinical Phenotype & Mutation | Correcting Oligos | SEQ ID NO: |
|---|---|---|
| Thalassaemia alpha Met(-1)Val cATG-GTG | CCCTGGCGCGCTCGCGGCCCGGCACTCTTCTGGTCCCCACA GACTCAGAGAGAACCCACCATGGTGCTGTCTCCTGCCGACA AGACCAACGTCAAGGCCGCCTGGGGTAAGGTCGGCGCGC | 2776 |
| | GCGCGCCGACCTTACCCCAGGCGGCCTTGACGTTGGTCTTG TCGGCAGGAGACAGCACCATGGTGGGTTCTCTCTGAGTCTGT GGGGACCAGAAGAGTGCCGGGCCGCGAGCGCGCCAGGG | 2777 |
| | AACCCACCATGGTGCTG | 2778 |
| | CAGCACCATGGTGGGTT | 2779 |
| Haemoglobin variant Ala12Asp GCC-GAC | CACAGACTCAGAGAGAACCCACCATGGTGCTGTCTCCTGCC GACAAGACCAACGTCAAGGCCGCCTGGGGTAAGGTCGGCGC GCACGCTGGCGAGTATGGTGCGGAGGCCCTGGAGAGGTG | 2780 |
| | CACCTCTCCAGGGCCTCCGCACCATACTCGCCAGCGTGCGC GCCGACCTTACCCCAGGCGGCCTTGACGTTGGTCTTGTCGG CAGGAGACAGCACCATGGTGGGTTCTCTCTGAGTCTGTG | 2781 |
| | CGTCAAGGCCGCCTGGG | 2782 |
| | CCCAGGCGGCCTTGACG | 2783 |
| Haemoglobin variant Gly15Asp GGT-GAT | AGAGAGAACCCACCATGGTGCTGTCTCCTGCCGACAAGACCA ACGTCAAGGCCGCCTGGGGTAAGGTCGGCGCGCACGCTGG CGAGTATGGTGCGGAGGCCCTGGAGAGGTGAGGCTCCCT | 2784 |
| | AGGGAGCCTCACCTCTCCAGGGCCTCCGCACCATACTCGCC AGCGTGCGCGCCGACCTTACCCCAGGCGGCCTTGACGTTGG | 2785 |

TABLE 22-continued

HBA1 Mutations and Genome-Correcting Oligos

| Clinical Phenotype & Mutation | Correcting Oligos | SEQ ID NO: |
|---|---|---|
| | TCTTGTCGGCAGGAGACAGCACCATGGTGGGTTCTCTCT CGCCTGGGGTAAGGTCG | 2786 |
| | CGACCTTACCCCAGGCG | 2787 |
| Haemoglobin variant Tyr24Cys TAT-TGT | CTGCCGACAAGACCAACGTCAAGGCCGCCTGGGGTAAGGTC GGCGCGCACGCTGGCGAGTATGGTGCGGAGGCCCTGGAGA | 2788 |
| | GGTGAGGCTCCCTCCCCTGCTCCGACCCGGGCTCCTCGCC GGCGAGGAGCCCGGGTCGGAGCAGGGGAGGGAGCCTCACC TCTCCAGGGCCTCCGCACCATACTCGCCAGCGTGCGCGCCG ACCTTACCCCAGGCGGCCTTGACGTTGGTCTTGTCGGCAG | 2789 |
| | TGGCGAGTATGGTGCGG | 2790 |
| | CCGCACCATACTCGCCA | 2791 |
| Haemoglobin variant Glu27Asp GAGg-GAT | GACCAACGTCAAGGCCGCCTGGGGTAAGGTCGGCGCGCAC GCTGGCGAGTATGGTGCGGAGGCCCTGGAGAGGTGAGGCT CCCTCCCCTGCTCCGACCCGGGCTCCTCGCCCGCCCGGAC C | 2792 |
| | GGTCCGGGCGGGCGAGGAGCCCGGGTCGGAGCAGGGGAG GGAGCCTCACCTCTCCAGGGCCTCCGCACCATACTCGCCAG CGTGCGCGCCGACCTTACCCCAGGCGGCCTTGACGTTGGTC | 2793 |
| | GGTGCGGAGGCCCTGGA | 2794 |
| | TCCAGGGCCTCCGCACC | 2795 |
| Haemoglobin variant Asn68Lys AACg-AAG | GAGCCACGGCTCTGCCCAGGTTAAGGGCCACGGCAAGAAGG TGGCCGACGCGCTGACCAACGCCGTGGCGCACGTGGACGA CATGCCCAACGCGCTGTCCGCCCTGAGCGACCTGCACGCG | 2796 |
| | CGCGTGCAGGTCGCTCAGGGCGGACAGCGCGTTGGGCATG TCGTCCACGTGCGCCACGGCGTTGGTCAGCGCGTCGGCCAC CTTCTTGCCGTGGCCCTTAACCTGGGCAGAGCCGTGGCTC | 2797 |
| | CTGACCAACGCCGTGGC | 2798 |
| | GCCACGGCGTTGGTCAG | 2799 |
| Haemoglobin variant Asp74Gly GAC-GGC | AGGTTAAGGGCCACGGCAAGAAGGTGGCCGACGCGCTGACC AACGCCGTGGCGCACGTGGACGACATGCCCAACGCGCTGTC CGCCCTGAGCGACCTGCACGCGCACAAGCTTGGGTGGA | 2800 |
| | TCCACCCGAAGCTTGTGCGCGTGCAGGTCGCTCAGGGCGGA CAGCGCGTTGGGCATGTCGTCCACGTGCGCCACGGCGTTGG TCAGCGCGTCGGCCACCTTCTTGCCGTGGCCCTTAACCT | 2801 |
| | GCACGTGGACGACATGC | 2802 |
| | GCATGTCGTCCACGTGC | 2803 |
| Haemoglobin variant Asp74His gGAC-CAC | CAGGTTAAGGGCCACGGCAAGAAGGTGGCCGACGCGCTGAC CAACGCCGTGGCGCACGTGGACGACATGCCCAACGCGCTGT CCGCCCTGAGCGACCTGCACGCGCACAAGCTTCGGGTGG | 2804 |
| | CCACCCGAAGCTTGTGCGCGTGCAGGTCGCTCAGGGCGGAC AGCGCGTTGGGCATGTCGTCCACGTGCGCCACGGCGTTGGT CAGCGCGTCGGCCACCTTCTTGCCGTGGCCCTTAACCTG | 2805 |
| | CGCACGTGGACGACATG | 2806 |
| | CATGTCGTCCACGTGCG | 2807 |
| Haemoglobin variant Asn78His cAAC-CAC | CACGGCAAGAAGGTGGCCGACGCGCTGACCAACGCCGTGG CGCACGTGGACGACATGCCCAACGCGCTGTCCGCCCTGAGC GACCTGCACGCGCACAAGCTTCGGGTGGACCCGGTCAACT | 2808 |
| | AGTTGACCGGGTCCACCCGAAGCTTGTGCGCGTGCAGGTCG CTCAGGGCGGACAGCGCGTTGGGCATGTCGTCCACGTGCGC CACGGCGTTGGTCAGCGCGTCGGCCACCTTCTTGCCGTG | 2809 |
| | ACATGCCCAACGCGCTG | 2810 |
| | CAGCGCGTTGGGCATGT | 2811 |
| Haemoglobin variant His87Tyr gCAC-TAC | ACCAACGCCGTGGCGCACGTGGACGACATGCCCAACGCGCT GTCCGCCCTGAGCGACCTGCACGCGCACAAGCTTCGGGTGG ACCCGGTCAACTTCAAGGTGAGCGGCGGGCCGGGAGCGA | 2812 |
| | TCGCTCCCGGCCCGCCGCTCACCTTGAAGTTGACCGGGTCC ACCCGAAGCTTGTGCGCGTGCAGGTCGCTCAGGGCGGACAG CGCGTTGGGCATGTCGTCCACGTGCGCCACGGCGTTGGT | 2813 |
| | GCGACCTGCACGCGCAC | 2814 |
| | GTGCGCGTGCAGGTCGC | 2815 |
| Haemoglobin variant Lys90Asn AAGc-AAC | GGCGCACGTGGACGACATGCCCAACGCGCTGTCCGCCCTGA GCGACCTGCACGCGCACAAGCTTCGGGTGGACCCGGTCAAC TTCAAGGTGAGCGGCGGGCCGGGAGCGATCTGGGTCGAG | 2816 |
| | CTCGACCCAGATCGCTCCCGGCCCGCCGCTCACCTTGAAGT TGACCGGGTCCACCCGAAGCTTGTGCGCGTGCAGGTCGCTC AGGGCGGACAGCGCGTTGGGCATGTCGTCCACGTGCGCC | 2817 |
| | GCGCACAAGCTTCGGGT | 2818 |
| | ACCCGAAGCTTGTGCGC | 2819 |
| Haemoglobin variant Lys90Thr AAG-ACG | TGGCGCACGTGGACGACATGCCCAACGCGCTGTCCGCCCTG AGCGACCTGCACGCGCACAAAGCTTCGGGTGGACCCGGTCAA CTTCAAGGTGAGCGGCGGGCCGGGAGCGATCTGGGTCGA | 2820 |
| | TCGACCCAGATCGCTCCCGGCCCGCCGCTCACCTTGAAGTT GACCGGGTCCACCCGAAGCTTGTGCGCGTGCAGGTCGCTCA GGGCGGACAGCGCGTTGGGCATGTCGTCCACGTGCGCCA | 2821 |

TABLE 22-continued

HBA1 Mutations and Genome-Correcting Oligos

| Clinical Phenotype & Mutation | Correcting Oligos | SEQ ID NO: |
|---|---|---|
| | CGCGCACAAGCTTCGGG | 2822 |
| | CCCGAAGCTTGTGCGCG | 2823 |
| Haemoglobin variant Arg92Gln CGG-CAG | ACGTGGACGACATGCCCAACGCGCTGTCCGCCCTGAGCGAC CTGCACGCGCACAAGCTTCGGGTGGACCCGGTCAACTTCAA GGTGAGCGGCGGGCCGGGAGCGATCTGGGTCGAGGGGCG | 2824 |
| | CGCCCCTCGACCCAGATCGCTCCCGGCCCGCCGCTCACCTT GAAGTTGACCGGGTCCACCCGAAGCTTGTGCGCGTGCAGGT CGCTCAGGGCGGACAGCGCGTTGGGCATGTCGTCCACGT | 2825 |
| | CAAGCTTCGGGTGGACC | 2826 |
| | GGTCCACCCGAAGCTTG | 2827 |
| Haemoglobin variant Asp94Gly GAC-GGC | ACGACATGCCCAACGCGCTGTCCGCCCTGAGCGACCTGCAC GCGCACAAGCTTCGGGTGGACCCGGTCAACTTCAAGGTGAG CGGCGGGCCGGGAGCGATCTGGGTCGAGGGGCGAGATGG | 2828 |
| | CCATCTCGCCCCTCGACCCAGATCGCTCCCGGCCCGCCGCT CACCTTGAAGTTGACCGGGTCCACCCGAAGCTTGTGCGCGT GCAGGTCGCTCAGGGCGGACAGCGCGTTGGGCATGTCGT | 2829 |
| | TCGGGTGGACCCGGTCA | 2830 |
| | TGACCGGGTCCACCCGA | 2831 |
| Haemoglobin variant Pro95Arg CCG-CGG | ACATGCCCAACGCGCTGTCCGCCCTGAGCGACCTGCACGCG CACAAGCTTCGGGTGGACCCGGTCAACTTCAAGGTGAGCGG CGGGCCGGGAGCGATCTGGGTCGAGGGGCGAGATGGCGC | 2832 |
| | GCGCCATCTCGCCCCTCGACCCAGATCGCTCCCGGCCCGCC GCTCACCTTGAAGTTGACCGGGTCCACCCGAAGCTTGTGCG CGTGCAGGTCGCTCAGGGCGGACAGCGCGTTGGGCATGT | 2833 |
| | GGTGGACCCGGTCAACT | 2834 |
| | AGTTGACCGGGTCCACC | 2835 |
| Haemoglobin variant Ser102Arg AGCc-AGA | CGGCGGCTGCGGGCCTGGGCCCTCGGCCCCACTGACCCTC TTCTCTGCACAGCTCCTAAGCCACTGCCTGCTGGTGACCCTG GCCGCCCACCTCCCCGCCGAGTTCACCCCTGCGGTGCAC | 2836 |
| | GTGCACCGCAGGGGTGAACTCGGCGGGGAGGTGGGCGCC AGGGTCACCAGCAGGCAGTGGCTTAGGAGCTGTGCAGAGAA GAGGGTCAGTGGGGCCGAGGGCCCAGGCCCGCAGCCGCCG | 2837 |
| | CTCCTAAGCCACTGCCT | 2838 |
| | AGGCAGTGGCTTAGGAG | 2839 |
| Haemoglobin variant Glu116Lys cGAG-AAG | TTCTCTGCACAGCTCCTAAGCCACTGCCTGCTGGTGACCCTG GCCGCCCACCTCCCCGCCGAGTTCACCCCTGCGGTGCACGC CTCCCTGGACAAGTTCCTGGCTTCTGTGAGCACCGTGC | 2840 |
| | GCACGGTGCTCACAGAAGCCAGGAACTTGTCCAGGGAGGCG TGCACCGCAGGGGTGAACTCGGCGGGGAGGTGGGCGGCCA GGGTCACCAGCAGGCAGTGGCTTAGGAGCTGTGCAGAGAA | 2841 |
| | TCCCCGCCGAGTTCACC | 2842 |
| | GGTGAACTCGGCGGGGA | 2843 |
| Haemoglobin variant Ala120Glu GCG-GAG | TCCTAAGCCACTGCCTGCTGGTGACCCTGGCCGCCCACCTC CCCGCCGAGTTCACCCCTGCGGTGCACGCCTCCCTGGACAA GTTCCTGGCTTCTGTGAGCACCGTGCTGACCTCCAAATA | 2844 |
| | TATTTGGAGGTCAGCACGGTGCTCACAGAAGCCAGGAACTTG TCCAGGGAGGCGTGCACCGCAGGGGTGAACTCGGCGGGGA GGTGGGCGGCCAGGGTCACCAGCAGGCAGTGGCTTAGGA | 2845 |
| | CACCCCTGCGGTGCACG | 2846 |
| | CGTGCACCGCAGGGGTG | 2847 |
| Thalassaemia alpha Leu129Pro CTG-CCG | TGGCCGCCCACCTCCCCGCCGAGTTCACCCCTGCGGTGCAC GCCTCCCTGGACAAGTTCCTGGCTTCTGTGAGCACCGTGCTG ACCTCCAAATACCGTTAAGCTGGAGCCTCGGTGGCCAT | 2848 |
| | ATGGCCACCGAGGCTCCAGCTTAACGGTATTTGGAGGTCAGC ACGGTGCTCACAGAAGCCAGGAACTTGTCCAGGGAGGCGTG CACCGCAGGGGTGAACTCGGCGGGGAGGTGGGCGGCCA | 2849 |
| | CAAGTTCCTGGCTTCTG | 2850 |
| | CAGAAGCCAGGAACTTG | 2851 |
| Haemoglobin variant Arg141Leu CGT-CTT | TGCACGCCTCCCTGGACAAGTTCCTGGCTTCTGTGAGCACCG TGCTGACCTCCAAATACCGTTAAGCTGGAGCCTCGGTGGCCA TGCTTCTTGCCCCTTGGGCCTCCCCCCAGCCCCTCCT | 2852 |
| | AGGAGGGGCTGGGGGAGGCCCAAGGGCAAGAAGCATGG CCACCGAGGCTCCAGCTTAACGGTATTTGGAGGTCAGCACG GTGCTCACAGAAGCCAGGAACTTGTCCAGGGAGGCGTGCA | 2853 |
| | CAAATACCGTTAAGCTG | 2854 |
| | CAGCTTAACGGTATTTG | 2855 |

EXAMPLE 16

Alpha-thalassemia—Hemoglobin Alpha Locus 2

The attached table discloses the correcting oligonucleotide base sequences for the hemoglobin alpha locus 2 oligonucleotides of the invention.

TABLE 23

HBA2 Mutations and Genome-Correcting Oligos

| Clinical Phenotype & Mutation | Correcting Oligos | SEQ ID NO: |
|---|---|---|
| Thalassaemia alpha Met(-1)Thr ATG-ACG | CCTGGCGCGCTCGCGGGCCGGCACTCTTCTGGTCCCCACAG | 2856 |
| | ACTCAGAGAGAACCCACCATGGTGCTGTCTCCTGCCGACAAG | |
| | ACCAACGTCAAGGCCGCCTGGGGTAAGGTCGGCGCGCA | |
| | TGCGCGCCGACCTTACCCCAGGCGGCCTTGACGTTGGTCTT | 2857 |
| | GTCGGCAGGAGACAGCACCATGGTGGGTTCTCTCTGAGTCT | |
| | GTGGGGACCAGAAGAGTGCCGGCCCGCGAGCGCGCCAGG | |
| | ACCCACCATGGTGCTGT | 2858 |
| | ACAGCACCATGGTGGGT | 2859 |
| Haemoglobin variant Ala12Asp GCC-GAC | CACAGACTCAGAGAGAACCCACCATGGTGCTGTCTCCTGCC | 2860 |
| | GACAAGACCAACGTCAAGGCCGCCTGGGGTAAGGTCGGCGC | |
| | GCACGCTGGCGAGTATGGTGCGGAGGCCCTGGAGAGGTG | |
| | CACCTCTCCAGGGCCTCCGCACCATACTCGCCAGCGTGCGC | 2861 |
| | GCCGACCTTACCCCAGGCGGCCTTGACGTTGGTCTTGTCGG | |
| | CAGGAGACAGCACCATGGTGGGTTCTCTCTGAGTCTGTG | |
| | CGTCAAGGCCGCCTGGG | 2862 |
| | CCCAGGCGGCCTTGACG | 2863 |
| Haemoglobin variant Lys16Glu tAAG-GAG | AGAGAACCCACCATGGTGCTGTCTCCTGCCGACAAGACCAAC | 2864 |
| | GTCAAGGCCGCCTGGGGTAAGGTCGGCGCGCACGCTGGG | |
| | AGTATGGTGCGGAGGCCCTGGAGAGGTGAGGCTCCCTCC | |
| | GGAGGGAGCCTCACCTCTCCAGGGCCTCCGCACCATACTCG | 2865 |
| | CCAGCGTGCGCGCCGACCTTACCCCAGGCGGCCTTGACGTT | |
| | GGTCTTGTCGGCAGGAGACAGCACCATGGTGGGTTCTCT | |
| | CCTGGGGTAAGGTCGGC | 2866 |
| | GCCGACCTTACCCCAGG | 2867 |
| Haemoglobin variant His20Gln CACg-CAA | GGTGCTGTCTCCTGCCGACAAGACCAACGTCAAGGCCGCCT | 2868 |
| | GGGGTAAGGTCGGCGCGCACGCTGGCGAGTATGGTGCGGA | |
| | GGCCCTGGAGAGGTGAGGCTCCCTCCCCTGCTCCGACCCG | |
| | CGGGTCGGAGCAGGGGAGGGAGCCTCACCTCTCCAGGGCC | 2869 |
| | TCCGCACCATACTCGCCAGCGTGCGCGCCGACCTTACCCCA | |
| | GGCGGCCTTGACGTTGGTCTTGTCGGCAGGAGACAGCACC | |
| | GGCGCGCACGCTGGCGA | 2870 |
| | TCGCCAGCGTGCGCGCC | 2871 |
| Haemoglobin variant Glu27Asp GAGg-GAC | GACCAACGTCAAGGCCGCCTGGGGTAAGGTCGGCGCGCAC | 2872 |
| | GCTGGCGAGTATGGTGCGGAGGCCCTGGAGAGGTGAGGCT | |
| | CCCTCCCCTGCTCCGACCCGGGCTCCTCGCCCGCCCGGAC C | |
| | GGTCCGGGCGGGCGAGGAGCCCGGGTCGGAGCAGGGGAG | 2873 |
| | GGAGCCTCACCTCTCCAGGGCCTCCGCACCATACTCGCCAG | |
| | CGTGCGCGCCGACCTTACCCCAGGCGGCCTTGACGTTGGTC | |
| | GGTGCGGAGGCCCTGGA | 2874 |
| | TCCAGGGCCTCCGCACC | 2875 |
| Thalassaemia alpha Leu29Pro CTG-CCG | ACGTCAAGGCCGCCTGGGGTAAGGTCGGCGCGCACGCTGG | 2876 |
| | CGAGTATGGTGCGGAGGCCCTGGAGAGGTGAGGCTCCCTCC | |
| | CCTGCTCCGACCCGGGCTCCTCGCCCGCCCGGACCCACAG | |
| | CTGTGGGTCCGGGCGGGCGAGGAGCCCGGGTCGGAGCAGG | 2877 |
| | GGAGGGAGCCTCACCTCTCCAGGGCCTCCGCACCATACTCG | |
| | CCAGCGTGCGCGCCGACCTTACCCCAGGCGGCCTTGACGT | |
| | GGAGGCCCTGGAGAGGT | 2878 |
| | ACCTCTCCAGGGCCTCC | 2879 |
| Haemoglobin variant Asp47His cGAC-CAC | GCTTCTCCCCGCAGGATGTTCCTGTCCTTCCCCACCACCAAG | 2880 |
| | ACCTACTTCCCGCACTTCGACCTGAGCCACGGCTCTGCCCA | |
| | GGTTAAGGGCCACGGCAAGAAGGTGGCCGACGCGCTGA | |
| | TCAGCGCGTCGGCCACCTTCTTGCCGTGGCCCTTAACCTGG | 2881 |
| | GCAGAGCCGTGGCTCAGGTCGAAGTGCGGGAAGTAGGTCTT | |
| | GGTGGTGGGGAAGGACAGGAACATCCTGCGGGGAGAAGC | |
| | CGCACTTCGACCTGAGC | 2882 |
| | GCTCAGGTCGAAGTGCG | 2883 |
| Haemoglobin variant Leu48Arg CTG-CGG | CTCCCCGCAGGATGTTCCTGTCCTTCCCCACCACCAAGACCT | 2884 |
| | ACTTCCCGCACTTCGACCTGAGCCACGGCTCTGCCCAGGTTA | |
| | AGGGCCACGGCAAGAAGGTGGCCGACGCGCTGACCAA | |
| | TTGGTCAGCGCGTCGGCCACCTTCTTGCCGTGGCCCTTAAC | 2885 |
| | CTGGGCAGAGCCGTGGCTCAGGTCGAAGTGCGGGAAGTAG | |
| | GTCTTGGTGGTGGGGAAGGACAGGAACATCCTGCGGGGAG | |
| | CTTCGACCTGAGCCACG | 2886 |
| | CGTGGCTCAGGTCGAAG | 2887 |

TABLE 23-continued

HBA2 Mutations and Genome-Correcting Oligos

| Clinical Phenotype & Mutation | Correcting Oligos | SEQ ID NO: |
|---|---|---|
| Haemoglobin variant Gln54Glu cCAG-GAG | CTGTCCTTCCCCACCACCAAGACCTACTTCCCGCACTTCGAC CTGAGCCACGGCTCTGCCCAGGTTAAGGGCCACGGCAAGAA GGTGGCCGACGCGCTGACCAACGCCGTGGCGCACGTGG | 2888 |
| | CCACGTGCGCCACGGCGTTGGTCAGCGCGTCGGCCACCTTC TTGCCGTGGCCCTTAACCTGGGCAGAGCCGTGGCTCAGGTC GAAGTGCGGGAAGTAGGTCTTGGTGGTGGGGAAGGACAG | 2889 |
| | GCTCTGCCCAGGTTAAG | 2890 |
| | CTTAACCTGGGCAGAGC | 2891 |
| Haemoglobin variant Gly59Asp GGC-GAC | CCAAGACCTACTTCCCGCACTTCGACCTGAGCCACGGCTCTG CCCAGGTTAAGGGCCACGGCAAGAAGGTGGCCGACGCGCT GACCAACGCCGTGGCGCACGTGGACGACATGCCCAACGC | 2892 |
| | GCGTTGGGCATGTCGTCCACGTGCGCCACGGCGTTGGTCAG CGCGTCGGCCACCTTCTTGCCGTGGCCCTTAACCTGGGCAG AGCCGTGGCTCAGGTCGAAGTGCGGGAAGTAGGTCTTGG | 2893 |
| | GGGCCACGGCAAGAAGG | 2894 |
| | CCTTCTTGCCGTGGCCC | 2895 |
| Haemoglobin variant Asn68Lys AACg-AAG | GAGCCACGGCTCTGCCCAGGTTAAGGGCCACGGCAAGAAGG TGGCCGACGCGCTGACCAACGCCGTGGCGCACGTGGACGA CATGCCCAACGCGCTGTCCGCCCTGAGCGACCTGCACGCG | 2896 |
| | CGCGTGCAGGTCGCTCAGGGCGGACAGCGCGTTGGGCATG TCGTCCACGTGCGCCACGGCGTTGGTCAGCGCGTCGGCCAC CTTCTTGCCGTGGCCCTTAACCTGGGCAGAGCCGTGGCTC | 2897 |
| | CTGACCAACGCCGTGGC | 2898 |
| | GCCACGGCGTTGGTCAG | 2899 |
| Haemoglobin variant Asn68Lys AACg-AAA | GAGCCACGGCTCTGCCCAGGTTAAGGGCCACGGCAAGAAGG TGGCCGACGCGCTGACCAACGCCGTGGCGCACGTGGACGA CATGCCCAACGCGCTGTCCGCCCTGAGCGACCTGCACGCG | 2900 |
| | CGCGTGCAGGTCGCTCAGGGCGGACAGCGCGTTGGGCATG TCGTCCACGTGCGCCACGGCGTTGGTCAGCGCGTCGGCCAC CTTCTTGCCGTGGCCCTTAACCTGGGCAGAGCCGTGGCTC | 2901 |
| | CTGACCAACGCCGTGGC | 2902 |
| | GCCACGGCGTTGGTCAG | 2903 |
| Haemoglobin variant Asn78Lys AACg-AAA | CGGCAAGAAGGTGGCCGACGCGCTGACCAACGCCGTGGCG CACGTGGACGACATGCCCAACGCGCTGTCCGCCCTGAGCGA CCTGCACGCGCACAAGCTTCGGGTGGACCCGGTCAACTTC | 2904 |
| | GAAGTTGACCGGGTCCACCCGAAGCTTGTGCGCGTGCAGGT CGCTCAGGGCGGACAGCGCGTTGGGCATGTCGTCCACGTGC GCCACGGCGTTGGTCAGCGCGTCGGCCACCTTCTTGCCG | 2905 |
| | ATGCCCAACGCGCTGTC | 2906 |
| | GACAGCGCGTTGGGCAT | 2907 |
| Haemoglobin variant Asp85Val GAC-GTC | CGCTGACCAACGCCGTGGCGCACGTGGACGACATGCCCAAC GCGCTGTCCGCCCTGAGCGACCTGCACGCGCACAAGCTTCG GGTGGACCCGGTCAACTTCAAGGTGAGCGGCGGGCCGGG | 2908 |
| | CCCGGCCCGCCGCTCACCTTGAAGTTGACCGGGTCCACCCG AAGCTTGTGCGCGTGCAGGTCGCTCAGGGCGGACAGCGCGT TGGGCATGTCGTCCACGTGCGCCACGGCGTTGGTCAGCG | 2909 |
| | CCTGAGCGACCTGCACG | 2910 |
| | CGTGCAGGTCGCTCAGG | 2911 |
| Haemoglobin variant Lys90Asn AAGc-AAT | GGCGCACGTGGACGACATGCCCAACGCGCTGTCCGCCCTGA GCGACCTGCACGCGCACAAGCTTCGGGTGGACCCGGTCAAC TTCAAGGTGAGCGGCGGGCCGGGAGCGATCTGGGTCGAG | 2912 |
| | CTCGACCCAGATCGCTCCCGGCCCGCCGCTCACCTTGAAGT TGACCGGGTCCACCCGAAGCTTGTGCGCGTGCAGGTCGCTC AGGGCGGACAGCGCGTTGGGCATGTCGTCCACGTGCGCC | 2913 |
| | GCGCACAAGCTTCGGGT | 2914 |
| | ACCCGAAGCTTGTGCGC | 2915 |
| Haemoglobin variant Asp94His gGAC-CAC | GACGACATGCCCAACGCGCTGTCCGCCCTGAGCGACCTGCA CGCGCACAAGCTTCGGGTGGACCCGGTCAACTTCAAGGTGA GCGGCGGGCCGGGAGCGATCTGGGTCGAGGGGCGAGATG | 2916 |
| | CATCTCGCCCCTCGACCCAGATCGCTCCCGGCCCGCCGCTC ACCTTGAAGTTGACCGGGTCCACCCGAAGCTTGTGCGCGTG CAGGTCGCTCAGGGCGGACAGCGCGTTGGGCATGTCGTC | 2917 |
| | TTCGGGTGGACCCGGTC | 2918 |
| | GACCGGGTCCACCCGAA | 2919 |
| Haemoglobin variant Pro95Leu CCG-CTG | ACATGCCCAACGCGCTGTCCGCCCTGAGCGACCTGCACGCG CACAAGCTTCGGGTGGACCCGTCAACTTCAAGGTGAGCGG CGGGCCGGGAGCGATCTGGGTCGAGGGGCGAGATGGCGC | 2920 |
| | GCGCCATCTCGCCCCTCGACCCAGATCGCTCCCGGCCCGCC GCTCACCTTGAAGTTGACCGGGTCCACCCGAAGCTTGTGCG CGTGCAGGTCGCTCAGGGCGGACAGCGCGTTGGGCATGT | 2921 |
| | GGTGGACCCGGTCAACT | 2922 |
| | AGTTGACCGGGTCCACC | 2923 |

TABLE 23-continued

HBA2 Mutations and Genome-Correcting Oligos

| Clinical Phenotype & Mutation | Correcting Oligos | SEQ ID NO: |
|---|---|---|
| Haemoglobin variant Ser102Arg aAGC-CGC | TAGCGCAGGCGGCGGCTGCGGGCCTGGGCCGCACTGACCC TCTTCTCTGCACAGCTCCTAAGCCACTGCCTGCTGGTGACCC | 2924 |
| | TGGCCCGCCCACCTCCCCGCCGAGTTCACCCCTGCGGTGC GCACCGCAGGGGTGAACTCGGCGGGGAGGTGGGCGGCCAG GGTCACCAGCAGGCAGTGGCTTAGGAGCTGTGCAGAGAAGA GGGTCAGTGCGGCCCAGGCCCGCAGCCGCCGCCTGCGCTA | 2925 |
| | AGCTCCTAAGCCACTGC | 2926 |
| | GCAGTGGCTTAGGAGCT | 2927 |
| Haemoglobin H disease Cys104Tyr TGC-TAC | GGCGGCGGCTGCGGGCCTGGGCCGCACTGACCCTCTTCTCT GCACAGCTCCTAAGCCACTGCCTGCTGGTGACCCTGGCCGC CCACCTCCCCGCCGAGTTCACCCCTGCGGTGCACGCCCTC | 2928 |
| | GAGGCGTGCACCGCAGGGGTGAACTCGGCGGGGAGGTGGG CGGCCAGGGTCACCAGCAGGCAGTGGCTTAGGAGCTGTGCA GAGAAGAGGGTCAGTGCGGCCCAGGCCCGCAGCCGCCGCC | 2929 |
| | AAGCCACTGCCTGCTGG | 2930 |
| | CCAGCAGGCAGTGGCTT | 2931 |
| Haemoglobin variant Ala111Val GCC-GTC | CCGCACTGACCCTCTTCTCTGCACAGCTCCTAAGCCACTGCC TGCTGGTGACCCTGGCCGCCCACCTCCCCGCCGAGTTCACC CCTGCGGTGCACGCCTCCCTGGACAAGTTCCTGGCTTC | 2932 |
| | GAAGCCAGGAACTTGTCCAGGGAGGCGTGCACCGCAGGGGT GAACTCGGCGGGGAGGTGGGCGGCCAGGGTCACCAGCAGG CAGTGGCTTAGGAGCTGTGCAGAGAAGAGGGTCAGTGCGG | 2933 |
| | CCTGGCCGCCCACCTCC | 2934 |
| | GGAGGTGGGCGGCCAGG | 2935 |
| Haemoglobin variant Ala120Glu GCG-GAG | TCCTAAGCCACTGCCTGCTGGTGACCCTGGCCGCCCACCTC CCCGCCGAGTTCACCCCTGCGGTGCACGCCTCCCTGGACAA GTTCCTGGCTTCTGTGAGCACCGTGCTGACCTCCAAATA | 2936 |
| | TATTTGGAGGTCAGCACGGTGCTCACAGAAGCCAGGAACTTG TCCAGGGAGGCGTGCACCGCAGGGGTGAACTCGGCGGGGA GGTGGGCGGCCAGGGTCACCAGCAGGCAGTGGCTTAGGA | 2937 |
| | CACCCCTGCGGTGCACG | 2938 |
| | CGTGCACCGCAGGGGTG | 2939 |
| Haemoglobin variant His122Gln CACg-CAG | CCACTGCCTGCTGGTGACCCTGGCCGCCCACCTCCCCGCCG AGTTCACCCCTGCGGTGCACGCCTCCCTGGACAAGTTCCTG GCTTCTGTGAGCACCGTGCTGACCTCCAAATACCGTTAA | 2940 |
| | TTAACGGTATTTGGAGGTCAGCACGGTGCTCACAGAAGCCAG GAACTTGTCCAGGGAGGCGTGCACCGCAGGGGTGAACTCGG CGGGGAGGTGGGCGGCCAGGGTCACCAGCAGGCAGTGG | 2941 |
| | GCGGTGCACGCCTCCCT | 2942 |
| | AGGGAGGCGTGCACCGC | 2943 |
| Haemoglobin variant Ala123Ser cGCC-TCC | CACTGCCTGCTGGTGACCCTGGCCGCCCACCTCCCCGCCGA GTTCACCCCTGCGGTGCACGCCTCCCTGGACAAGTTCCTGG CTTCTGTGAGCACCGTGCTGACCTCCAAATACCGTTAAG | 2944 |
| | CTTAACGGTATTTGGAGGTCAGCACGGTGCTCACAGAAGCCA GGAACTTGTCCAGGGAGGCGTGCACCGCAGGGGTGAACTCG GCGGGGAGGTGGGCGGCCAGGGTCACCAGCAGGCAGTG | 2945 |
| | CGGTGCACGCCTCCCTG | 2946 |
| | CAGGGAGGCGTGCACCG | 2947 |
| Thalassaemia alpha Leu125Pro CTG-CCG | TGCTGGTGACCCTGGCCGCCCACCTCCCCGCCGAGTTCACC CCTGCGGTGCACGCCTCCCTGGACAAGTTCCTGGCTTCTGT GAGCACCGTGCTGACCTCCAAATACCGTTAAGCTGGAGC | 2948 |
| | GCTCCAGCTTAACGGTATTTGGAGGTCAGCACGGTGCTCACA GAAGCCAGGAACTTGTCCAGGGAGGCGTGCACCGCAGGGG TGAACTCGGCGGGGAGGTGGGCGGCCAGGGTCACCAGCA | 2949 |
| | CGCCTCCCTGGACAAGT | 2950 |
| | ACTTGTCCAGGGAGGCG | 2951 |
| Haemoglobin variant Ser131Pro tTCT-CCT | GCCCACCTCCCCGCCGAGTTCACCCCTGCGGTGCACGCCTC CCTGGACAAGTTCCTGGCTTCTGTGAGCACCGTGCTGACCTC CAAATACCGTTAAGCTGGAGCCTCGGTAGCCGTTCCTC | 2952 |
| | GAGGAACGGCTACCGAGGCTCCAGCTTAACGGTATTTGGAG GTCAGCACGGTGCTCACAGAAGCCAGGAACTTGTCCAGGGA GGCGTGCACCGCAGGGGTGAACTCGGCGGGGAGGTGGGC | 2953 |
| | TCCTGGCTTCTGTGAGC | 2954 |
| | GCTCACAGAAGCCAGGA | 2955 |
| Haemoglobin variant Leu136Met gCTG-ATG | GAGTTCACCCCTGCGGTGCACGCCTCCCTGGACAAGTTCCT GGCTTCTGTGAGCACCGTGCTGACCTCCAAATACCGTTAAGC TGGAGCCTCGGTAGCCGTTCCTCCTGCCCGCTGGGCCT | 2956 |
| | AGGCCCAGCGGGCAGGAGGAACGGCTACCGAGGCTCCAGC TTAACGGTATTTGGAGGTCAGCACGGTGCTCACAGAAGCCAG GAACTTGTCCAGGGAGGCGTGCACCGCAGGGGTGAACTC | 2957 |
| | GCACCGTGCTGACCTCC | 2958 |
| | GGAGGTCAGCACGGTGC | 2959 |

TABLE 23-continued

HBA2 Mutations and Genome-Correcting Oligos

| Clinical Phenotype & Mutation | Correcting Oligos | SEQ ID NO: |
|---|---|---|
| Haemoglobin variant Leu136Pro CTG-CCG | AGTTCACCCCTGCGGTGCACGCCTCCCTGGACAAGTTCCTG | 2960 |
| | GCTTCTGTGAGCACCGTGCTGACCTCCAAATACCGTTAAGCT | |
| | GGAGCCTCGGTAGCCGTTCCTCCTGCCCGCTGGGCCTC | |
| | GAGGCCCAGCGGGCAGGAGGAACGGCTACCGAGGCTCCAG | 2961 |
| | CTTAACGGTATTTGGAGGTCAGCACGGTGCTCACAGAAGCCA | |
| | GGAACTTGTCCAGGGAGGCGTGCACCGCAGGGGTGAACT | |
| | CACCGTGCTGACCTCCA | 2962 |
| | TGGAGGTCAGCACGGTG | 2963 |
| Haemoglobin variant Arg141Cys cCGT-TGT | GTGCACGCCTCCCTGGACAAGTTCCTGGCTTCTGTGAGCACC | 2964 |
| | GTGCTGACCTCCAAATACCGTTAAGCTGGAGCCTCGGTAGCC | |
| | GTTCCTCCTGCCCGCTGGGCCTCCCAACGGGCCCTCC | |
| | GGAGGGCCCGTTGGGAGGCCCAGCGGGCAGGAGGAACGGC | 2965 |
| | TACCGAGGCTCCAGCTTAACGGTATTTGGAGGTCAGCACGGT | |
| | GCTCACAGAAGCCAGGAACTTGTCCAGGGAGGCGTGCAC | |
| | CCAAATACCGTTAAGCT | 2966 |
| | AGCTTAACGGTATTTGG | 2967 |
| Haemoglobin variant Term142Gln tTAA-CAA | CACGCCTCCCTGGACAAGTTCCTGGCTTCTGTGAGCACCGTG | 2968 |
| | CTGACCTCCAAATACCGTTAAGCTGGAGCCTCGGTAGCCGTT | |
| | CCTCCTGCCCGCTGGGCCTCCCAACGGGCCCTCCTCC | |
| | GGAGGAGGGCCCGTTGGGAGGCCCAGCGGGCAGGAGGAAC | 2969 |
| | GGCTACCGAGGCTCCAGCTTAACGGTATTTGGAGGTCAGCA | |
| | CGGTGCTCACAGAAGCCAGGAACTTGTCCAGGGAGGCGTG | |
| | AATACCGTTAAGCTGGA | 2970 |
| | TCCAGCTTAACGGTATT | 2971 |
| Haemoglobin variant Term142Lys tTAA-AAA | CACGCCTCCCTGGACAAGTTCCTGGCTTCTGTGAGCACCGTG | 2972 |
| | CTGACCTCCAAATACCGTTAAGCTGGAGCCTCGGTAGCCGTT | |
| | CCTCCTGCCCGCTGGGCCTCCCAACGGGCCCTCCTCC | |
| | GGAGGAGGGCCCGTTGGGAGGCCCAGCGGGCAGGAGGAAC | 2973 |
| | GGCTACCGAGGCTCCAGCTTAACGGTATTTGGAGGTCAGCA | |
| | CGGTGCTCACAGAAGCCAGGAACTTGTCCAGGGAGGCGTG | |
| | AATACCGTTAAGCTGGA | 2974 |
| | TCCAGCTTAACGGTATT | 2975 |
| Haemoglobin variant Term142Tyr TAAg-TAT | CGCCTCCCTGGACAAGTTCCTGGCTTCTGTGAGCACCGTGCT | 2976 |
| | GACCTCCAAATACCGTTAAGCTGGAGCCTCGGTAGCCGTTCC | |
| | TCCTGCCCGCTGGGCCTCCCAACGGGCCCTCCTCCC | |
| | GGGGAGGAGGGCCCGTTGGGAGGCCCAGCGGGCAGGAGG | 2977 |
| | AACGGCTACCGAGGCTCCAGCTTAACGGTATTTGGAGGTCAG | |
| | CACGGTGCTCACAGAAGCCAGGAACTTGTCCAGGGAGGCG | |
| | TACCGTTAAGCTGGAGC | 2978 |
| | GCTCCAGCTTAACGGTA | 2979 |

EXAMPLE 17

Human Mismatch Repair—MLH1

The human MLH1 gene is homologous to the bacterial mutL gene, which is involved in mismatch repair. Mutations in the MLH1 gene have been identified in many individuals with hereditary nonpolyposis colorectal cancer (HNPCC). Mutations in the MLH1 gene are also implicated in predisposition to a variety of cancers associated with, for example, Muir-Torre syndrome and Turcot syndrome. The attached table discloses the correcting oligonucleotide base sequences for the MLH1 oligonucleotides of the invention.

TABLE 24

MLH1 Mutations and Genome-Correcting Oligos

| Clinical Phenotype & Mutation | Correcting Oligos | SEQ ID NO: |
|---|---|---|
| Non-polyposis colorectal cancer Met1Arg ATG-AGG | TTGGCTGAAGGCACTTCCGTTGAGCATCTAGACGTTTCCTTG | 2980 |
| | GCTCTTCTGGCGCCAAAATGTCGTTCGTGGCAGGGGTTATTC | |
| | GGCGGCTGGACGAGACAGTGGTGAACCGCATCGCGGC | |
| | GCCGCGATGCGGTTCACCACTGTCTCGTCCAGCCGCCGAAT | 2981 |
| | AACCCCTGCCACGAACGACATTTTGGCGCCAGAAGAGCCAA | |
| | GGAAACGTCTAGATGCTCAACGGAAGTGCCTTCAGCCAA | |
| | CGCCAAAATGTCGTTCG | 2982 |
| | CGAACGACATTTTGGCG | 2983 |
| Non-polyposis colorectal cancer Met1Lys ATG-AAG | TTGGCTGAAGGCACTTCCGTTGAGCATCTAGACGTTTCCTTG | 2984 |
| | GCTCTTCTGGCGCCAAAATGTCGTTCGTGGCAGGGGTTATTC | |
| | GGCGGCTGGACGAGACAGTGGTGAACCGCATCGCGGC | |
| | GCCGCGATGCGGTTCACCACTGTCTCGTCCAGCCGCCGAAT | 2985 |
| | AACCCCTGCCACGAACGACATTTTGGCGCCAGAAGAGCCAA | |

TABLE 24-continued

MLH1 Mutations and Genome-Correcting Oligos

| Clinical Phenotype & Mutation | Correcting Oligos | SEQ ID NO: |
|---|---|---|
| | GGAAACGTCTAGATGCTCAACGGAAGTGCCTTCAGCCAA | |
| | CGCCAAAATGTCGTTCG | 2986 |
| | CGAACGACATTTTGGCG | 2987 |
| Non-polyposis colorectal cancer Met35Arg ATG-AGG | TGGTGAACCGCATCGCGGCGGGGGAAGTTATCCAGCGGCCA GCTAATGCTATCAAAGAGATGATTGAGAACTGGTACGGAGGG AGTCGAGCCGGGCTCACTTAAGGGCTACGACTTAACGG | 2988 |
| | CCGTTAAGTCGTAGCCCTTAAGTGAGCCCGGCTCGACTCCCT CCGTACCAGTTCTCAATCATCTCTTTGATAGCATTAGCTGGCC GCTGGATAACTTCCCCCGCCGCGATGCGGTTCACCA | 2989 |
| | CAAAGAGATGATTGAGA | 2990 |
| | TCTCAATCATCTCTTTG | 2991 |
| Non-polyposis colorectal cancer Ser44Phe TCC-TTC | TAGAGTAGTTGCAGACTGATAAATTATTTTCTGTTTGATTTGCC AGTTTAGATGCAAAATCCACAAGTATTCAAGTGATTGTTAAAG AGGGAGGCCTGAAGTTGATTCAGATCCAAGACAA | 2992 |
| | TTGTCTTGGATCTGAATCAACTTCAGGCCTCCCTCTTTAACAA TCACTTGAATACTTGTGGATTTTGCATCTAAACTGGCAAATCA AACAGAAAATAATTTATCAGTCTGCAACTACTCTA | 2993 |
| | TGCAAAATCCACAAGTA | 2994 |
| | TACTTGTGGATTTTGCA | 2995 |
| Non-polyposis colorectal cancer Gln62Lys CAA-AAA | GCAAAATCCACAAGTATTCAAGTGATTGTTAAAGAGGGAGGC CTGAAGTTGATTCAGATCCAAGACAATGGCACCGGGATCAGG GTAAGTAAAACCTCAAAGTAGCAGGATGTTTGTGCGC | 2996 |
| | GCGCACAAACATCCTGCTACTTTGAGGTTTTACTTACCCTGAT CCCGGTGCCATTGTCTTGGATCTGAATCAACTTCAGGCCTCC CTCTTTTAACAATCACTTGAATACTTGTGGATTTTGC | 2997 |
| | TTCAGATCCAAGACAAT | 2998 |
| | ATTGTCTTGGATCTGAA | 2999 |
| Non-polyposis colorectal cancer Gln62Term CAA-TAA | GCAAAATCCACAAGTATTCAAGTGATTGTTAAAGAGGGAGGC CTGAAGTTGATTCAGATCCAAGACAATGGCACCGGGATCAGG GTAAGTAAAACCTCAAAGTAGCAGGATGTTTGTGCGC | 3000 |
| | GCGCACAAACATCCTGCTACTTTGAGGTTTTACTTACCCTGAT CCCGGTGCCATTGTCTTGGATCTGAATCAACTTCAGGCCTCC CTCTTTAACAATCACTTGAATACTTGTGGATTTTGC | 3001 |
| | TTCAGATCCAAGACAAT | 3002 |
| | ATTGTCTTGGATCTGAA | 3003 |
| Non-polyposis colorectal cancer Asn64Ser AAT-AGT | CCACAAGTATTCAAGTGATTGTTAAAGAGGGAGGCCTGAAGT TGATTCAGATCCAAGACAATGGCACCGGGATCAGGGTAAGTA AAACCTCAAAGTAGCAGGATGTTTGTGCGCTTCATGG | 3004 |
| | CCATGAAGCGCACAAACATCCTGCTACTTTGAGGTTTTACTTA CCCTGATCCCGGTGCCATTGTCTTGGATCTGAATCAACTTCA GGCCTCCCTCTTTAACAATCACTTGTGG | 3005 |
| | CCAAGACAATGGCACCG | 3006 |
| | CGGTGCCATTGTCTTGG | 3007 |
| Non-polyposis colorectal cancer Gly67Arg GGG-AGG | ATTCAAGTGATTGTTAAAGAGGGAGGCCTGAAGTTGATTCAGA TCCAAGACAATGGCACCGGGATCAGGGTAAGTAAAACCTCAA AGTAGCAGGATGTTTGTGCGCTTCATGGAAGAGTCA | 3008 |
| | TGACTCTTCCATGAAGCGCACAAACATCCTGCTACTTTGAGGT TTTACTTACCCTGATCCCGGTGCCATTGTCTTGGATCTGAATC AACTTCAGGCCTCCCTCTTTAACAATCACTTGAAT | 3009 |
| | ATGGCACCGGGATCAGG | 3010 |
| | CCTGATCCCGGTGCCAT | 3011 |
| Non-polyposis colorectal cancer Gly67Arg GGG-CGG | ATTCAAGTGATTGTTAAAGAGGGAGGCCTGAAGTTGATTCAGA TCCAAGACAATGGCACCGGGATCAGGGTAAGTAAAACCTCAA AGTAGCAGGATGTTTGTGCGCTTCATGGAAGAGTCA | 3012 |
| | TGACTCTTCCATGAAGCGCACAAACATCCTGCTACTTTGAGGT TTTACTTACCCTGATCCCGGTGCCATTGTCTTGGATCTGAATC AACTTCAGGCCTCCCTCTTTAACAATCACTTGAAT | 3013 |
| | ATGGCACCGGGATCAGG | 3014 |
| | CCTGATCCCGGTGCCAT | 3015 |
| Non-polyposis colorectal cancer Gly67Trp GGG-TGG | ATTCAAGTGATTGTTAAAGAGGGAGGCCTGAAGTTGATTCAGA TCCAAGACAATGGCACCGGGATCAGGGTAAGTAAAACCTCAA AGTAGCAGGATGTTTGTGCGCTTCATGGAAGAGTCA | 3016 |
| | TGACTCTTCCATGAAGCGCACAAACATCCTGCTACTTTGAGGT TTTACTTACCCTGATCCCGGTGCCATTGTCTTGGATCTGAATC AACTTCAGGCCTCCCTCTTTAACAATCACTTGAAT | 3017 |
| | ATGGCACCGGGATCAGG | 3018 |
| | CCTGATCCCGGTGCCAT | 3019 |
| Non-polyposis colorectal cancer Cys77Arg TGT-CGT | GTAACATGATTATTTACTCATCTTTTTGGTATCTAACAGAAAGA AGATCTGGATATTGTATGTGAAAGGTTCACTACTAGTAAACTG CAGTCCTTTGAGGATTTAGCCAGTATTCTACCT | 3020 |
| | AGGTAGAATACTGGCTAAATCCTCAAAGGACTGCAGTTTACT AGTAGTGAACCTTTCACATACAATATCCAGATCTTCTTTCTGTT AGATACCAAAAAGATGAGTAAATAATCATGTTAC | 3021 |

TABLE 24-continued

MLH1 Mutations and Genome-Correcting Oligos

| Clinical Phenotype & Mutation | Correcting Oligos | SEQ ID NO: |
|---|---|---|
| | ATATTGTATGTGAAAGG | 3022 |
| | CCTTTCACATACAATAT | 3023 |
| Non-polyposis colorectal cancer Cys77Tyr TGT-TAT | TAACATGATTATTTACTCATCTTTTTGGTATCTAACAGAAAGAA GATCTGGATATTGTATGTGAAAGGTTCACTACTAGTAAACTGC AGTCCTTTGAGGATTTAGCCAGTATTTCTACCTA | 3024 |
| | TAGGTAGAAATACTGGCTAAATCCTCAAAGGACTGCAGTTTAC TAGTAGTGAACCTTTCACATACAATATCCAGATCTTCTTTCTGT TAGATACCAAAAAGATGAGTAAATAATCATGTTA | 3025 |
| | TATTGTATGTGAAAGGT | 3026 |
| | ACCTTTCACATACAATA | 3027 |
| Non-polyposis colorectal cancer Ser93Gly AGT-GGT | CTGGATATTGTATGTGAAAGGTTCACTACTAGTAAACTGCAGT CCTTTGAGGATTTAGCCAGTATTTCTACCTATGGCTTTCGAGG TGAGGTAAGCTAAAGATTCAAGAAATGTGTAAAAT | 3028 |
| | ATTTTACACATTTCTTGAATCTTTAGCTTACCTCACCTCGAAAG CCATAGGTAGAAATACTGGCTAAATCCTCAAAGGACTGCAGTT TACTAGTAGTGAACCTTTCACATACAATATCCAG | 3029 |
| | ATTTAGCCAGTATTTCT | 3030 |
| | AGAAATACTGGCTAAAT | 3031 |
| Non-polyposis colorectal cancer Arg100Term CGA-TGA | TTCACTACTAGTAAACTGCAGTCCTTTGAGGATTTAGCCAGTA TTTCTACCTATGGCTTTCGAGGTGAGGTAAGCTAAAGATTCAA GAAATGTGTAAAATATCCTCCTGTGATGACATTGT | 3032 |
| | ACAATGTCATCACAGGAGGATATTTTACACATTTCTTGAATCTT TAGCTTACCTCACCTCGAAAGCCATAGGTAGAAATACTGGCTA AATCCTCAAAGGACTGCAGTTTACTAGTAGTGAA | 3033 |
| | ATGGCTTTCGAGGTGAG | 3034 |
| | CTCACCTCGAAAGCCAT | 3035 |
| Non-polyposis colorectal cancer Ile107Arg ATA-AGA | ACCCAGCAGTGAGTTTTTCTTTCAGTCTATTTTCTTTTCTTCCT TAGGCTTTGGCCAGCATAAGCCATGTGGCTCATGTTACTATTA CAACGAAAACAGCTGATGGAAAGTGTGCATACAG | 3036 |
| | CTGTATGCACACTTTCCATCAGCTGTTTTCGTTGTAATAGTAA CATGAGCCACATGGCTTATGCTGGCCAAAGCCTAAGGAAGAA AAGAAAATAGACTGAAAGAAAAACTCACTGCTGGGT | 3037 |
| | GGCCAGCATAAGCCATG | 3038 |
| | CATGGCTTATGCTGGCC | 3039 |
| Non-polyposis colorectal cancer Thr117Arg ACG-AGG | TTTCTTTTCTTCCTTAGGCTTTGGCCAGCATAAGCCATGTGGC TCATGTTACTATTACAACGAAAACAGCTGATGGAAAGTGTGCA TACAGGTATAGTGCTGACTTCTTTTACTCATATAT | 3040 |
| | ATATATGAGTAAAAGAAGTCAGCACTATACCTGTATGCACACT TTCCATCAGCTGTTTTCGTTGTAATAGTAACATGAGCCACATG GCTTATGCTGGCCAAAGCCTAAGGAAGAAAAGAAA | 3041 |
| | TATTACAACGAAAACAG | 3042 |
| | CTGTTTTCGTTGTAATA | 3043 |
| Non-polyposis colorectal cancer Thr117Met ACG-ATG | TTTCTTTTCTTCCTTAGGCTTTGGCCAGCATAAGCCATGTGGC TCATGTTACTATTACAACGAAAACAGCTGATGGAAAGTGTGCA TACAGGTATAGTGCTGACTTCTTTTACTCATATAT | 3044 |
| | ATATATGAGTAAAAGAAGTCAGCACTATACCTGTATGCACACT TTCCATCAGCTGTTTTCGTTGTAATAGTAACATGAGCCACATG GCTTATGCTGGCCAAAGCCTAAGGAAGAAAAGAAA | 3045 |
| | TATTACAACGAAAACAG | 3046 |
| | CTGTTTTCGTTGTAATA | 3047 |
| Non-polyposis colorectal cancer Gly133Term GGA-TGA | TCTATCTCTCTACTGGATATTAATTTGTTATATTTTCTCATTAGA GCAAGTTACTCAGATGGAAAACTGAAAGCCCCTCCTAAACCA TGTGCTGGCAATCAAGGGACCCAGATCACGGTAA | 3048 |
| | TTACCGTGATCTGGGTCCCTTGATTGCCAGCACATGGTTTAG GAGGGGCTTTCAGTTTTCCATCTGAGTAACTTGCTCTAATGAG AAAATATAACAAATTAATATCCAGTAGAGAGATAGA | 3049 |
| | ACTCAGATGGAAAACTG | 3050 |
| | CAGTTTTCCATCTGAGT | 3051 |
| Non-polyposis colorectal cancer Val185Gly GTA-GGA | TAGTGTGTGTTTTTGGCAACTCTTTTCTTACTCTTTTGTTTTTC TTTTCCAGGTATTCAGTACACAATGCAGGCATTAGTTTCTCAG TTAAAAAAGTAAGTTCTTGGTTTATGGGGGATGG | 3052 |
| | CCATCCCCCATAAACCAAGAACTTACTTTTTTAACTGAGAAAC TAATGCCTGCATTGTGTACTGAATACCTGGAAAAGAAAAACAA AAGAGTAAGAAAAGAGTTGCCAAAAACACACACTA | 3053 |
| | GTATTCAGTACACAATG | 3054 |
| | CATTGTGTACTGAATAC | 3055 |
| Non-polyposis colorectal cancer Ser193Pro TCA-CCA | TTTCTTACTCTTTTGTTTTTCTTTTCCAGGTATTCAGTACACAAT GCAGGCATTAGTTTCTCAGTTAAAAAAGTAAGTTCTTGGTTTAT GGGGGATGGTTTTGTTTTATGAAAAGAAAAAA | 3056 |
| | TTTTTTCTTTTTCATAAAACAAAACCATCCCCCATAAACCAAGAA CTTACTTTTTTAACTGAGAAACTAATGCCTGCATTGTGTACTG AATACCTGGAAAAGAAAAACAAAAGAGTAAGAAA | 3057 |
| | TTAGTTTCTCAGTTAAA | 3058 |
| | TTTAACTGAGAAACTAA | 3059 |

TABLE 24-continued

MLH1 Mutations and Genome-Correcting Oligos

| Clinical Phenotype & Mutation | Correcting Oligos | SEQ ID NO: |
|---|---|---|
| Non-polyposis colorectal cancer Val213Met GTG-ATG | TTTGTTTATCAGCAAGGAGAGACAGTAGCTGATGTTAGGACA CTACCCAATGCCTCAACCGTGGACAATATTCGCTCCATCTTTG GAAATGCTGTTAGTCGGTATGTCGATAACCTATATA | 3060 |
| | TATATAGGTTATCGACATACCGACTAACAGCATTTCCAAAGAT GGAGCGAATATTGTCCACGGTTGAGGCATTGGGTAGTGTCCT AACATCAGCTACTGTCTCTCCTTGCTGATAAACAAA | 3061 |
| | CCTCAACCGTGGACAAT | 3062 |
| | ATTGTCCACGGTTGAGG | 3063 |
| Non-polyposis colorectal cancer Arg217Cys CGC-TGC | CAAGGAGAGACAGTAGCTGATGTTAGGACACTACCCAATGCC TCAACCGTGGACAATATTCGCTCCATCTTTGGAAATGCTGTTA GTCGGTATGTCGATAACCTATATAAAAAAATCTTTT | 3064 |
| | AAAAGATTTTTTTATATAGGTTATCGACATACCGACTAACAGCA TTTCCAAAGATGGAGCGAATATTGTCCACGGTTGAGGCATTG GGTAGTGTCCTAACATCAGCTACTGTCTCTCCTTG | 3065 |
| | ACAATATTCGCTCCATC | 3066 |
| | GATGGAGCGAATATTGT | 3067 |
| Non-polyposis colorectal cancer Ile219Val ATC-GTC | GAGACAGTAGCTGATGTTAGGACACTACCCAATGCCTCAACC GTGGACAATATTCGCTCCATCTTTGGAAATGCTGTTAGTCGGT ATGTCGATAACCTATATAAAAAAATCTTTTACATTT | 3068 |
| | AAATGTAAAAGATTTTTTTATATAGGTTATCGACATACCGACTA ACAGCATTTCCAAAGATGGAGCGAATATTGTCCACGGTTGAG GCATTGGGTAGTGTCCTAACATCAGCTACTGTCTC | 3069 |
| | TTCGCTCCATCTTTGGA | 3070 |
| | TCCAAAGATGGAGCGAA | 3071 |
| Non-polyposis colorectal cancer Gly244Asp GGT-GAT | CTAATAGAGAACTGATAGAAATTGGATGTGAGGATAAAACCCT AGCCTTCAAAATGAATGGTTACATATCCAATGCAAACTACTCA GTGAAGAAGTGCATCTTCTTACTCTTCATCAACCG | 3072 |
| | CGGTTGATGAAGAGTAAGAAGATGCACTTCTTCACTGAGTAG TTTGCATTGGATATGTAACCATTCATTTTGAAGGCTAGGGTTT TATCCTCACATCCAATTTCTATCAGTTCTCTATTAG | 3073 |
| | AATGAATGGTTACATAT | 3074 |
| | ATATGTAACCATTCATT | 3075 |
| Non-polyposis colorectal cancer Ser252Term TCA-TAA | GATGTGAGGATAAAACCCTAGCCTTCAAAATGAATGGTTACAT ATCCAATGCAAACTACTCAGTGAAGAAGTGCATCTTCTTACTC TTCATCAACCGTAAGTTAAAAAGAACCACATGGGA | 3076 |
| | TCCCATGTGGTTCTTTTTAACTTACGGTTGATGAAGAGTAAGA AGATGCACTTCTTCACTGAGTAGTTTGCATTGGATATGTAACC ATTCATTTTGAAGGCTAGGGTTTTATCCTCACATC | 3077 |
| | AAACTACTCAGTGAAGA | 3078 |
| | TCTTCACTGAGTAGTTT | 3079 |
| Non-polyposis colorectal cancer Glu268Gly GAA-GGA | CACCCCTCAGGACAGTTTTGAACTGGTTGCTTTCTTTTTATTG TTTAGATCGTCTGGTAGAATCAACTTCCTTGAGAAAAGCCATA GAAACAGTGTATGCAGCCTATTTGCCCAAAAACAC | 3080 |
| | GTGTTTTTGGGCAAATAGGCTGCATACACTGTTTCTATGGCTT TCTCAAGGAAGTTGATTCTACCAGACGATCTAAACAATAAAA TAGAAAGCAACCAGTTCAAAACTGTCCTGAGGGGTG | 3081 |
| | TCTGGTAGAATCAACTT | 3082 |
| | AAGTTGATTCTACCAGA | 3083 |
| Non-polyposis colorectal cancer Ser269Term TCA-TGA | CCCTCAGGACAGTTTTGAACTGGTTGCTTTCTTTTTATTGTTTA GATCGTCTGGTAGAATCAACTTCCTTGAGAAAAGCCATAGAAA CAGTGTATGCAGCCTATTTGCCCAAAAACACACA | 3084 |
| | TGTGTGTTTTTGGGCAAATAGGCTGCATACACTGTTTCTATGG CTTTTCTCAAGGAAGTTGATTCTACCAGACGATCTAAACAATA AAAGAAAGCAACCAGTTCAAAACTGTCCTGAGGG | 3085 |
| | GGTAGAATCAACTTCCT | 3086 |
| | AGGAAGTTGATTCTACC | 3087 |
| Non-polyposis colorectal cancer Glu297Term GAA-TAA | CTTTTTCTCCCCCTCCCACTATCTAAGGTAATTGTTCTCTCTTA TTTTCCTGACAGTTTAGAAATCAGTCCCCAGAATGTGGATGTT AATGTGCACCCCACAAAGCATGAAGTTCACTTCC | 3088 |
| | GGAAGTGAACTTCATGCTTTGTGGGGTGCACATTAACATCCA CATTCTGGGGACTGATTTCTAAACTGTCAGGAAAATAAGAGAG AACAATTACCTTAGATAGTGGGAGGGGGAGAAAAAG | 3089 |
| | ACAGTTTAGAAATCAGT | 3090 |
| | ACTGATTTCTAAACTGT | 3091 |
| Non-polyposis colorectal cancer Gln301Term CAG-TAG | CTCCCACTATCTAAGGTAATTGTTCTCTCTTATTTTCCTGACAG TTTAGAAATCAGTCCCCAGAATGTGGATGTTAATGTGCACCCC ACAAAGCATGAAGTTCACTTCCTGCACGAGGAGA | 3092 |
| | TCTCCTCGTGCAGGAAGTGAACTTCATGCTTTGTGGGGTGCA CATTAACATCCACATTCTGGGGACTGATTTCTAAACTGTCAGG AAAATAAGAGAGAACAATTACCTTAGATAGTGGGAG | 3093 |
| | TCAGTCCCCAGAATGTG | 3094 |
| | CACATTCTGGGGACTGA | 3095 |
| Non-polyposis colorectal cancer | ATGTGCACCCCACAAAGCATGAAGTTCACTTCCTGCACGAGG AGAGCATCCTGGAGCGGGTGCAGCAGCACATCGAGAGCAAG | 3096 |

TABLE 24-continued

MLH1 Mutations and Genome-Correcting Oligos

| Clinical Phenotype & Mutation | Correcting Oligos | SEQ ID NO: |
|---|---|---|
| Val326Ala GTG-GCG | CTCCTGGGCTCCAATTCCTCCAGGATGTACTTCACCCA TGGGTGAAGTACATCCTGGAGGAATTGGAGCCCAGGAGCTT GCTCTCGATGTGCTGCTGCACCCGCTCCAGGATGCTCTCCT CGTGCAGGAAGTGAACTTCATGCTTTGTGGGGTGCACAT GGAGCGGGTGCAGCAGC GCTGCTGCACCCGCTCC | 3097<br><br><br>3098<br>3099 |
| Non-polyposis colorectal cancer His329Pro CAC-CCC | CCACAAAGCATGAAGTTCACTTCCTGCACGAGGAGAGCATCC TGGAGCGGGTGCAGCAGCACATCGAGAGCAAGCTCCTGGGC TCCAATTCCTCCAGGATGTACTTCACCCAGGTCAGGGC GCCCTGACCTGGGTGAAGTACATCCTGGAGGAATTGGAGCC CAGGAGCTTGCTCTCGATGTGCTGCTGCACCCGCTCCAGGA TGCTCTCCTCGTGCAGGAAGTGAACTTCATGCTTTGTGG GCAGCAGCACATCGAGA TCTCGATGTGCTGCTGC | 3100<br><br>3101<br><br><br>3102<br>3103 |
| Non-polyposis colorectal cancer Val384Asp GTT-GAT | CAAGTCTGACCTCGTCTTCTACTTCTGGAAGTAGTGATAAGGT CTATGCCCACCAGATGGTTCGTACAGATTCCCGGGAACAGAA GCTTGATGCATTTCTGCAGCCTCTGAGCAAACCCCT AGGGGTTTGCTCAGAGGCTGCAGAAATGCATCAAGCTTCTGT TCCCGGGAATCTGTACGAACCATCTGGTGGGCATAGACCTTA TCACTACTTCCAGAAGTAGAAGACGAGGTCAGACTTG CCAGATGGTTCGTACAG CTGTACGAACCATCTGG | 3104<br><br>3105<br><br><br>3106<br>3107 |
| Non-polyposis colorectal cancer Ala441Thr GCT-ACT | AGTGGCAGGGCTAGGCAGCAAGATGAGGAGATGCTTGAACT CCCAGCCCCTGCTGAAGTGGCTGCCAAAAATCAGAGCTTGGA GGGGGATACAACAAAGGGGACTTCAGAAATGTCAGAGA TCTCTGACATTTCTGAAGTCCCCTTTGTTGTATCCCCCTCCAA GCTCTGATTTTTGGCAGCCACTTCAGCAGGGGCTGGGAGTTC AAGCATCTCCTCATCTTGCTGCCTAGCCCTGCCACT CTGAAGTGGCTGCCAAA TTTGGCAGCCACTTCAG | 3108<br><br>3109<br><br><br>3110<br>3111 |
| Non-polyposis colorectal cancer Arg487Term CGA-TGA | CTTCATTGCAGAAAGAGACATCGGGAAGATTCTGATGTGGAA ATGGTGGAAGATGATTCCCGAAAGGAAATGACTGCAGCTTGT ACCCCCCGGAGAAGGATCATTAACCTCACTAGTGTTT AAACACTAGTGAGGTTAATGATCCTTCTCCGGGGGTACAAG CTGCAGTCATTTCCTTTCGGGAATCATCTTCCACCATTTCCAC ATCAGAATCTTCCCGATGTCTCTTTCTGCAATGAAG ATGATTCCCGAAAGGAA TTCCTTTCGGGAATCAT | 3112<br><br>3113<br><br><br>3114<br>3115 |
| Non-polyposis colorectal cancer Ala492Thr GCA-ACA | AGACATCGGGAAGATTCTGATGTGGAAATGGTGGAAGATGAT TCCCGAAAGGAAATGACTGCAGCTTGTACCCCCCGGAGAAG GATCATTAACCTCACTAGTGTTTTGAGTCTCCAGGAAG CTTCCTGGAGACTCAAAACACTAGTGAGGTTAATGATCCTTCT CCGGGGGGTACAAGCTGCAGTCATTTCCTTTCGGGAATCATC TTCCACCATTTCCACATCAGAATCTTCCCGATGTCT AAATGACTGCAGCTTGT ACAAGCTGCAGTCATTT | 3116<br><br>3117<br><br><br>3118<br>3119 |
| Non-polyposis colorectal cancer Val506Ala GTT-GCT | CCCGAAAGGAAATGACTGCAGCTTGTACCCCCCGGAGAAGG ATCATTAACCTCACTAGTGTTTTGAGTCTCCAGGAAGAAATTA ATGAGCAGGGACATGAGGGTACGTAAACGCTGTGCC GGCCACAGCGTTTACGTACCCTCATGTCCCTGCTCATTAATTT CTTCCTGGAGACTCAAAACACTAGTGAGGTTAATGATCCTTCT CCGGGGGGTACAAGCTGCAGTCATTTCCTTTCGGG CACTAGTGTTTTGAGTC GACTCAAAACACTAGTG | 3120<br><br>3121<br><br><br>3122<br>3123 |
| Non-polyposis colorectal cancer Gln542Leu CAG-CTG | GGGAGATGTTGCATAACCACTCCTTCGTGGGCTGTGTGAATC CTCAGTGGGCCTTGGCACAGCATCAAACCAAGTTATACCTTC TCAACACCACCAAGCTTAGGTAAATCAGCTGAGTGTG CACACTCAGCTGATTTACCTAAGCTTGGTGGTGTTGAGAAGG TATAACTTGGTTTGATGCTGTGCCAAGGCCCACTGAGGATTC ACACAGCCCACGAAGGAGTGGTTATGCAACATCTCCC CTTGGCACAGCATCAAA TTTGATGCTGTGCCAAG | 3124<br><br>3125<br><br><br>3126<br>3127 |
| Non-polyposis colorectal cancer Leu549Pro CTT-CCT | CCTTCGTGGGCTGTGTGAATCCTCAGTGGGCCTTGGCACAG CATCAAACCAAGTTATACCTTCTCAACACCACCAAGCTTAGGT AAATCAGCTGAGTGTGTGAACAAGCAGAGCTACTACA TGTAGTAGCTCTGCTTGTTCACACACTCAGCTGATTTACCTAA GCTTGGTGGTGTTGAGAAGGTATAACTTGGTTTGATGCTGTG CCAAGGCCCACTGAGGATTCACACAGCCCACGAAGG GTTATACCTTCTCAACA TGTTGAGAAGGTATAAC | 3128<br><br>3129<br><br><br>3130<br>3131 |
| Non-polyposis colorectal cancer Asn551Thr AAC-ACC | TGGGCTGTGTGAATCCTCAGTGGGCCTTGGCACAGCATCAAA CCAAGTTATACCTTCTCAACACCACCAAGCTTAGGTAAATCAG CTGAGTGTGTGAACAAGCAGAGCTACTACAACAATG CATTGTTGTAGTAGCTCTGCTTGTTCACACACTCAGCTGATTT | 3132<br><br><br>3133 |

TABLE 24-continued

MLH1 Mutations and Genome-Correcting Oligos

| Clinical Phenotype & Mutation | Correcting Oligos | SEQ ID NO: |
|---|---|---|
| | ACCTAAGCTTGGTGGTGTTGAGAAGGTATAACTTGGTTTGATG CTGTGCCAAGGCCCACTGAGGATTCACACAGCCCA | |
| | CCTTCTCAACACCACCA | 3134 |
| | TGGTGGTGTTGAGAAGG | 3135 |
| Non-polyposis colorectal cancer Gln562Term CAG-TAG | ATGAATTCAGCTTTTCCTTAAAGTCACTTCATTTTTATTTTCAG TGAAGAACTGTTCTACCAGATACTCATTTATGATTTTGCCAATT TTGGTGTTCTCAGGTTATCGGTAAGTTTAGATC | 3136 |
| | GATCTAAACTTACCGATAACCTGAGAACACCAAAATTGGCAAA ATCATAAATGAGTATCTGGTAGAACAGTTCTTCACTGAAAATA AAAATGAAGTGACTTTAAGGAAAAGCTGAATTCAT | 3137 |
| | TGTTCTACCAGATACTC | 3138 |
| | GAGTATCTGGTAGAACA | 3139 |
| Non-polyposis colorectal cancer Ile565Phe ATT-TTT | GCTTTTCCTTAAAGTCACTTCATTTTTATTTTCAGTGAAGAACT GTTCTACCAGATACTCATTTATGATTTTGCCAATTTTGGTGTTC TCAGGTTATCGGTAAGTTTAGATCCTTTTCACT | 3140 |
| | AGTGAAAAGGATCTAAACTTACCGATAACCTGAGAACACCAAA ATTGGCAAAATCATAAATGAGTATCTGGTAGAACAGTTCTTCA CTGAAAATAAAAATGAAGTGACTTTAAGGAAAAGC | 3141 |
| | AGATACTCATTTATGAT | 3142 |
| | ATCATAAATGAGTATCT | 3143 |
| Non-polyposis colorectal cancer Leu574Pro CTC-CCC | TTTTCAGTGAAGAACTGTTCTACCAGATACTCATTTATGATTTT GCCAATTTTGGTGTTCTCAGGTTATCGGTAAGTTTAGATCCTT TTCACTTCTGAAATTTCAACTGATCGTTTCTGAA | 3144 |
| | TTCAGAAACGATCAGTTGAAATTTCAGAAGTGAAAAGGATCTA AACTTACCGATAACCTGAGAACACCAAAATTGGCAAAATCATA AATGAGTATCTGGTAGAACAGTTCTTCACTGAAAA | 3145 |
| | TGGTGTTCTCAGGTTAT | 3146 |
| | ATAACCTGAGAACACCA | 3147 |
| Non-polyposis colorectal cancer Leu582Val CTC-GTC | TGGATGCTCCGTTAAAGCTTGCTCCTTCATGTTCTTGCTTCTT CCTAGGAGCCAGCACCGCTCTTTGACCTTGCCATGCTTGCCT TAGATAGTCCAGAGAGTGGCTGGACAGAGGAAGATG | 3148 |
| | CATCTTCCTCTGTCCAGCCACTCTCTGGACTATCTAAGGCAA GCATGGCAAGGTCAAAGAGCGGTGCTGGCTCCTAGGAAGAA GCAAGAACATGAAGGAGCAAGCTTTAACGGAGCATCCA | 3149 |
| | CAGCACCGCTCTTTGAC | 3150 |
| | GTCAAAGAGCGGTGCTG | 3151 |
| Non-polyposis colorectal cancer Leu607His CTT-CAT | TGCTTGCCTTAGATAGTCCAGAGAGTGGCTGGACAGAGGAAG ATGGTCCCAAAGAAGGACTTGCTGAATACATTGTTGAGTTTCT GAAGAAGAAGGCTGAGATGCTTGCAGACTATTTCTC | 3152 |
| | GAGAAATAGTCTGCAAGCATCTCAGCCTTCTTCTTCAGAAACT CAACAATGTATTCAGCAAAGTCCTTCTTTGGGACCATCTTCCTC TGTCCAGCCACTCTCTGGACTATCTAAGGCAAGCA | 3153 |
| | AGAAGGACTTGCTGAAT | 3154 |
| | ATTCAGCAAGTCCTTCT | 3155 |
| Non-polyposis colorectal cancer Lys618Term AAG-TAG | ACAGAGGAAGATGGTCCCAAAGAAGGACTTGCTGAATACATT GTTGAGTTTCTGAAGAAGAAGGCTGAGATGCTTGCAGACTAT TTCTCTTTGGAAATTGATGAGGTGTGACAGCCATTCT | 3156 |
| | AGAATGGCTGTCACACCTCATCAATTTCCAAAGAGAAATAGTC TGCAAGCATCTCAGCCTTCTTCTTCAGAAACTCAACAATGTAT TCAGCAAGTCCTTCTTTGGGACCATCTTCCTCTGT | 3157 |
| | TGAAGAAGAAGGCTGAG | 3158 |
| | CTCAGCCTTCTTCTTCA | 3159 |
| Non-polyposis colorectal cancer Lys618Thr AAG-ACG | CAGAGGAAGATGGTCCCAAAGAAGGACTTGCTGAATACATTG TTGAGTTTCTGAAGAAGAAGGCTGAGATGCTTGCAGACTATTT CTCTTTGGAAATTGATGAGGTGTGACAGCCATTCTT | 3160 |
| | AAGAATGGCTGTCACACCTCATCAATTTCCAAAGAGAAATAGT CTGCAAGCATCTCAGCCTTCTTCTTCAGAAACTCAACAATGTA TTCAGCAAGTCCTTCTTTGGGACCATCTTCCTCTG | 3161 |
| | GAAGAAGAAGGCTGAGA | 3162 |
| | TCTCAGCCTTCTTCTTC | 3163 |
| Non-polyposis colorectal cancer Arg659Leu CGA-CTA | TACCCCTTCTGATTGACAACTATGTGCCCCTTTGGAGGGAC TGCCTATCTTCATTCTTCGACTAGCCACTGAGGTCAGTGATCA AGCAGATACTAAGCATTTCGGTACATGCATGTGTGC | 3164 |
| | GCACACATGCATGTACCGAAATGCTTAGTATCTGCTTGATCAC TGACCTCAGTGGCTAGTCGAAGAATGAAGATAGGCAGTCCCT CCAAAGGGGGCACATAGTTGTCAATCAGAAGGGGTA | 3165 |
| | CATTCTTCGACTAGCCA | 3166 |
| | TGGCTAGTCGAACAATG | 3167 |
| Non-polyposis colorectal cancer Arg659Pro CGA-CCA | TACCCCTTCTGATTGACAACTATGTGCCCCCTTTGGAGGGAC TGCCTATCTTCATTCTTCGACTAGCCACTGAGGTCAGTGATCA AGCAGATACTAAGCATTTCGGTACATGCATGTGTGC | 3168 |
| | GCACACATGCATGTACCGAAATGCTTAGTATCTGCTTGATCAC TGACCTCAGTGGCTAGTCGAAGAATGAAGATAGGCAGTCCCT CCAAAGGGGGCACATAGTTGTCAATCAGAAGGGGTA | 3169 |

TABLE 24-continued

MLH1 Mutations and Genome-Correcting Oligos

| Clinical Phenotype & Mutation | Correcting Oligos | SEQ ID NO: |
|---|---|---|
| | CATTCTTCGACTAGCCA | 3170 |
| | TGGCTAGTCGAAGAATG | 3171 |
| Non-polyposis colorectal cancer Arg659Term CGA-TGA | TTACCCCTTCTGATTGACAACTATGTGCCCCCTTTGGAGGGA CTGCCTATCTTCATTCTTCGACTAGCCACTGAGGTCAGTGATC AAGCAGATACTAAGCATTTCGGTACATGCATGTGTG | 3172 |
| | CACACATGCATGTACCGAAATGCTTAGTATCTGCTTGATCACT GACCTCAGTGGCTAGTCGAAGAATGAAGATAGGCAGTCCCTC CAAAGGGGGCACATAGTTGTCAATCAGAAGGGGTAA | 3173 |
| | TCATTCTTCGACTAGCC | 3174 |
| | GGCTAGTCGAAGAATGA | 3175 |
| Non-polyposis colorectal cancer Ala681Thr GCT-ACT | TTGGACCAGGTGAATTGGGACGAAGAAAAGGAATGTTTTGAA AGCCTCAGTAAAGAATGCGCTATGTTCTATTCCATCCGGAAG CAGTACATATCTGAGGAGTCGACCCTCTCAGGCCAGC | 3176 |
| | GCTGGCCTGAGAGGGTCGACTCCTCAGATATGTACTGCTTCC GGATGGAATAGAACATAGCGCATTCTTTACTGAGGCTTTCAAA ACATTCCTTTTCTTCGTCCCAATTCACCTGGTCCAA | 3177 |
| | AAGAATGCGCTATGTTC | 3178 |
| | GAACATAGCGCATTCTT | 3179 |
| Non-polyposis colorectal cancer Trp712Term TGG-TAG | AGGCTTATGACATCTAATGTGTTTTCCAGAGTGAAGTGCCTGG CTCCATTCCAAACTCCTGGAAGTGGACTGTGGAACACATTGT CTATAAAGCCTTGCGCTCACACATTCTGCCTCCTAA | 3180 |
| | TTAGGAGGCAGAATGTGTGAGCGCAAGGCTTTATAGACAATG TGTTCCACAGTCCACTTCCAGGAGTTTGGAATGGAGCCAGGC ACTTCACTCTGGAAAACACATTAGATGTCATAAGCCT | 3181 |
| | AAACTCCTGGAAGTGGA | 3182 |
| | TCCACTTCCAGGAGTTT | 3183 |
| Non-polyposis colorectal cancer Trp714Term TGG-TAG | ATGACATCTAATGTGTTTTCCAGAGTGAAGTGCCTGGCTCCAT TCCAAACTCCTGGAAGTGGACTGTGGAACACATTGTCTATAAA GCCTTGCGCTCACACATTCTGCCTCCTAAACATTT | 3184 |
| | AAATGTTTAGGAGGCAGAATGTGTGAGCGCAAGGCTTTATAG ACAATGTGTTCCACAGTCCACTTCCAGGAGTTTGGAATGGAG CCAGGCACTTCACTCTGGAAAACACATTAGATGTCAT | 3185 |
| | CTGGAAGTGGACTGTGG | 3186 |
| | CCACAGTCCACTTCCAG | 3187 |
| Non-polyposis colorectal cancer Trp714Term TGG-TGA | TGACATCTAATGTGTTTTCCAGAGTGAAGTGCCTGGCTCCATT CCAAACTCCTGGAAGTGGACTGTGGAACACATTGTCTATAAA GCCTTGCGCTCACACATTCTGCCTCCTAAACATTTC | 3188 |
| | GAAATGTTTAGGAGGCAGAATGTGTGAGCGCAAGGCTTTATA GACAATGTGTTCCACAGTCCACTTCCAGGAGTTTGGAATGGA GCCAGGCACTTCACTCTGGAAAACACATTAGATGTCA | 3189 |
| | TGGAAGTGGACTGTGGA | 3190 |
| | TCCACAGTCCACTTCCA | 3191 |
| Non-polyposis colorectal cancer Val716Met GTG-ATG | ATCTAATGTGTTTTCCAGAGTGAAGTGCCTGGCTCCATTCCAA ACTCCTGGAAGTGGACTGTGGAACACATTGTCTATAAAGCCTT GCGCTCACACATTCTGCCTCCTAAACATTTCACAG | 3192 |
| | CTGTGAAATGTTTAGGAGGCAGAATGTGTGAGCGCAAGGCTT TATAGACAATGTGTTCCACAGTCCACTTCCAGGAGTTTGGAAT GGAGCCAGGCACTTCACTCTGGAAAACACATTAGAT | 3193 |
| | AGTGGACTGTGGAACAC | 3194 |
| | GTGTTCCACAGTCCACT | 3195 |
| Non-polyposis colorectal cancer Tyr721Term TAT-TAA | GAGTGAAGTGCCTGGCTCCATTCCAAACTCCTGGAAGTGGAC TGTGGAACACATTGTCTATAAAGCCTTGCGCTCACACATTCTG CCTCCTAAACATTTCACAGAAGATGGAAATATCCTG | 3196 |
| | CAGGATATTTCCATCTTCTGTGAAATGTTTAGGAGGCAGAATG TGTGAGCGCAAGGCTTTATAGACAATGTGTTCCACAGTCCAC TTCCAGGAGTTTGGAATGGAGCCAGGCACTTCACTC | 3197 |
| | ATTGTCTATAAAGCCTT | 3198 |
| | AAGGCTTTATAGACAAT | 3199 |
| Non-polyposis colorectal cancer Lys751Arg AAA-AGA | CTAAACATTTCACAGAAGATGGAAATATCCTGCAGCTTGCTAA CCTGCCTGATCTATACAAAGTCTTTGAGAGGTGTTAAATATGG TTATTTATGCACTGTGGGATGTGTTCTTCTTTCTC | 3200 |
| | GAGAAAGAAGAACACATCCCACAGTGCATAAATAACCATATTT AACACCTCTCAAAGACTTTGTATAGATCAGGCAGGTTAGCAAG CTGCAGGATATTTCCATCTTCTGTGAAATGTTTAG | 3201 |
| | TCTATACAAAGTCTTTG | 3202 |
| | CAAAGACTTTTGTATAGA | 3203 |
| Non-polyposis colorectal cancer Arg755Trp AGG-TGG | ACAGAAGATGGAAATATCCTGCAGCTTGCTAACCTGCCTGAT CTATACAAAGTCTTTGAGAGGTGTTAAATATGGTTATTTATGCA CTGTGGGATGTGTTCTTCTTTCTCTGTATTCCGAT | 3204 |
| | ATCGGAATACAGAGAAAGAAGAACACATCCCACAGTGCATAA ATAACCATATTTAACACCTCTCAAAGACTTTGTATAGATCAGG | 3205 |

TABLE 24-continued

MLH1 Mutations and Genome-Correcting Oligos

| Clinical Phenotype & Mutation | Correcting Oligos | SEQ ID NO: |
|---|---|---|
| | CAGGTTAGCAAGCTGCAGGATATTTCCATCTTCTGT TCTTTGAGAGGTGTTAA | 3206 |
| | TTAACACCTCTCAAAGA | 3207 |

EXAMPLE 18

Human Mismatch Repair—MSH2

The human MSH2 gene is homologous to the bacterial mutS gene, which is involved in mismatch repair. Mutations in the MSH2 gene have been identified in a variety of cancers, including, for example, ovarian tumors, colorectal cancer, endometrial cancer, uterine cancer. The attached table discloses the correcting oligonucleotide base sequences for the MSH2 oligonucleotides of the invention.

TABLE 25

MSH2 Mutations and Genome-Correcting Oligos

| Clinical Phenotype & Mutation | Correcting Oligos | SEQ ID NO: |
|---|---|---|
| Non polyposis colorectal cancer Gln252Term CAG-TAG | TTTTCCACAAAAGACATTTATCAGGACCTCAACCGGTTGTTGA AAGGCAAAAAGGGAGAGCAGATGAATAGTGCTGTATTGCCAG AAATGGAGAATCAGGTACATGGATTATAAATGTGAA | 3208 |
| | TTCACATTTATAATCCATGTACCTGATTCTCCATTTCTGGCAAT ACAGCACTATTCATCTGCTCTCCCTTTTTGCCTTTCAACAACC GGTTGAGGTCCTGATAAATGTCTTTTGTGGAAAA | 3209 |
| | AGGGAGAGCAGATGAAT | 3210 |
| | ATTCATCTGCTCTCCCT | 3211 |
| Non polyposis colorectal cancer Gln288Term CAG-TAG | TCATCACTGTCTGCGGTAATCAAGTTTTTAGAACTCTTATCAG ATGATTCCAACTTTGGACAGTTTGAACTGACTACTTTTGACTT CAGCCAGTATATGAAATTGGATATTGCAGCAGTCA | 3212 |
| | TGACTGCTGCAATATCCAATTTCATATACTGGCTGAAGTCAAA AGTAGTCAGTTCAAACTGTCCAAAGTTGGAATCATCTGATAAG AGTTCTAAAAACTTGATTACCGCAGACAGTGATGA | 3213 |
| | ACTTTGGACAGTTTGAA | 3214 |
| | TTCAAACTGTCCAAAGT | 3215 |
| Non polyposis colorectal cancer Ala305Thr GCA-ACA | AACTTTGGACAGTTTGAACTGACTACTTTTGACTTCAGCCAGT ATATGAAATTGGATATTGCAGCAGTCAGAGCCCTTAACCTTTT TCAGGTAAAAAAAAAAAAAAAAAAAAAAAAAAAGG | 3216 |
| | CCTTTTTTTTTTTTTTTTTTTTTTTTTTACCTGAAAAAGGTTAAG GGCTCTGACTGCTGCAATATCCAATTTCATATACTGGCTGAAG TCAAAAGTAGTCAGTTCAAACTGTCCAAAGTT | 3217 |
| | TGGATATTGCAGCAGTC | 3218 |
| | GACTGCTGCAATATCCA | 3219 |
| Non polyposis colorectal cancer Gly322Asp GGC-GAC | AGCTTGCCATTCTTTCTATTTTATTTTTGTTTACTAGGGTTCT GTTGAAGATACCACTGGCTCTCAGTCTCTGGCTGCCTTGCTG AATAAGTGTAAAACCCCTCAAGGACAAAGACTTGT | 3220 |
| | ACAAGTCTTTGTCCTTGAGGGGTTTTACACTTATTCAGCAAGG CAGCCAGAGACTGAGAGCCAGTGGTATCTTCAACAGAACCCT AGTAAACAAAAAATAAAATAGAAAGAATGGCAAGCT | 3221 |
| | TACCACTGGCTCTCAGT | 3222 |
| | ACTGAGAGCCAGTGGTA | 3223 |
| Non polyposis colorectal cancer Ser323Cys TCT-TGT | TTGCCATTCTTTCTATTTTATTTTTGTTTACTAGGGTTCTGTTG AAGATACCACTGGCTCTCAGTCTCTGGCTGCCTTGCTGAATA AGTGTAAAACCCCTCAAGGACAAAGACTTGTTAA | 3224 |
| | TTAACAAGTCTTTGTCCTTGAGGGGTTTTACACTTATTCAGCA AGGCAGCCAGAGACTGAGAGCCAGTGGTATCTTCAACAGAAC CCTAGTAAACAAAAAATAAAATAGAAAGAATGGCAA | 3225 |
| | CACTGGCTCTCAGTCTC | 3226 |
| | GAGACTGAGAGCCAGTG | 3227 |
| Non polyposis colorectal cancer Arg383Term CGA-TGA | GTGGAAGCTTTTGTAGAAGATGCAGAATTGAGGCAGACTTTA CAAGAAGATTTACTTCGTCGATTCCCAGATCTTAACCGACTTG CCAAGAAGTTTCAAAGACAAGCAGCAAACTTACAAG | 3228 |
| | CTTGTAAGTTTGCTGCTTGTCTTTGAAACTTCTTGGCAAGTCG GTTAAGATCTGGGAATCGACGAAGTAAATCTTCTTGTAAAGTC TGCCTCAATTCTGCATCTTCTACAAAAGCTTCCAC | 3229 |
| | TACTTCGTCGATTCCCA | 3230 |
| | TGGGAATCGACGAAGTA | 3231 |
| Non polyposis colorectal cancer Gln397Term CAA-TAA | CAAGAAGATTTACTTCGTCGATTCCCAGATCTTAACCGACTTG CCAAGAAGTTTCAAAGACAAGCAGCAAACTTACAAGATTGTTA CCGACTCTATCAGGGTATAAATCAACTACCTAATG | 3232 |
| | CATTAGGTAGTTGATTTATACCCTGATAGAGTCGGTAACAATC | 3233 |

TABLE 25-continued

MSH2 Mutations and Genome-Correcting Oligos

| Clinical Phenotype & Mutation | Correcting Oligos | SEQ ID NO: |
|---|---|---|
| | TTGTAAGTTTGCTGCTTGTCTTTGAAACTTCTTGGCAAGTCGG TTAAGATCTGGGAATCGACGAAGTAAATCTTCTTG | |
| | TTCAAAGACAAGCAGCA | 3234 |
| | TGCTGCTTGTCTTTGAA | 3235 |
| Non polyposis colorectal cancer Arg406Term CGA-TGA | GATCTTAACCGACTTGCCAAGAAGTTTCAAAGACAAGCAGCA AACTTACAAGATTGTTACCGACTCTATCAGGGTATAAATCAAC TACCTAATGTTATACAGGCTCTGGAAAAACATGAAG | 3236 |
| | CTTCATGTTTTTCCAGAGCCTGTATAACATTAGGTAGTTGATTT ATACCCTGATAGAGTCGGTAACAATCTTGTAAGTTTGCTGCTT GTCTTTGAAACTTCTTGGCAAGTCGGTTAAGATC | 3237 |
| | ATTGTTACCGACTCTAT | 3238 |
| | ATAGAGTCGGTAACAAT | 3239 |
| Non polyposis colorectal cancer Gln419Term CAG-TAG | GCAAACTTACAAGATTGTTACCGACTCTATCAGGGTATAAATC AACTACCTAATGTTATACAGGCTCTGGAAAAACATGAAGGTAA CAAGTGATTTTGTTTTTTTGTTTTCCTTCAACTCA | 3240 |
| | TGAGTTGAAGGAAAACAAAAAAACAAAATCACTTGTTACCTTC ATGTTTTTCCAGAGCCTGTATAACATTAGGTAGTTGATTTATAC CCTGATAGAGTCGGTAACAATCTTGTAAGTTTGC | 3241 |
| | ATGTTATACAGGCTCTG | 3242 |
| | CAGAGCCTGTATAACAT | 3243 |
| Non polyposis colorectal cancer Gln429Term CAG-TAG | TATTCTGTAAAATGAGATCTTTTTATTTGTTTGTTTTACTACTTT CTTTTAGGAAAACACCAGAAATTATTGTTGGCAGTTTTTGTGA CTCCTCTTACTGATCTTCGTTCTGACTTCTCCA | 3244 |
| | TGGAGAAGTCAGAACGAAGATCAGTAAGAGGAGTCACAAAAA CTGCCAACAATAATTTCTGGTGTTTTCCTAAAAGAAAGTAGTA AAACAAACAAATAAAAAGATCTCATTTTACAGAATA | 3245 |
| | GAAAACACCAGAAATTA | 3246 |
| | TAATTTCTGGTGTTTTC | 3247 |
| Non polyposis colorectal cancer Leu458Term TTA-TGA | CTCCTCTTACTGATCTTCGTTCTGACTTCTCCAAGTTTCAGGA AATGATAGAAACAACTTTAGATATGGATCAGGTATGCAATATA CTTTTTAATTTAAGCAGTAGTTATTTTTAAAAAGC | 3248 |
| | GCTTTTTAAAAATAACTACTGCTTAAATTAAAAAGTATATTGCA TACCTGATCCATATCTAAAGTTGTTTCTATCATTTCCTGAAACT TGGAGAAGTCAGAACGAAGATCAGTAAGAGGAG | 3249 |
| | AACAACTTTAGATATGG | 3250 |
| | CCATATCTAAAGTTGTT | 3251 |
| Non polyposis colorectal cancer Gln518Term CAG-TAG | TTTCTTCTTGATTATCAAGGCTTGGACCCTGGCAAACAGATTA AACTGGATTCCAGTGCACAGTTTGGATATTACTTTCGTGTAAC CTGTAAGGAAGAAAAAGTCCTTCGTAACAATAAAA | 3252 |
| | TTTTATTGTTACGAAGGACTTTTTCTTCCTTACAGGTTACACGA AAGTAATATCCAAACTGTGCACTGGAATCCAGTTTAATCTGTT TGCCAGGGTCCAAGCCTTGATAATCAAGAAGAAA | 3253 |
| | CCAGTGCACAGTTTGGA | 3254 |
| | TCCAAACTGTGCACTGG | 3255 |
| Non polyposis colorectal cancer Arg524Pro CGT-CCT | GCTTGGACCCTGGCAAACAGATTAAACTGGATTCCAGTGCAC AGTTTGGATATTACTTTCGTGTAACCTGTAAGGAAGAAAAAGT CCTTCGTAACAATAAAAACTTTAGTACTGTAGATAT | 3256 |
| | ATATCTACAGTACTAAAGTTTTTATTGTTACGAAGGACTTTTTC TTCCTTACAGGTTACACGAAAGTAATATCCAAACTGTGCACTG GAATCCAGTTTAATCTGTTTGCCAGGGTCCAAGC | 3257 |
| | TTACTTTCGTGTAACCT | 3258 |
| | AGGTTACACGAAAGTAA | 3259 |
| Non polyposis colorectal cancer Glu562Val GAG-GTG | TTAATATTTTTAATAAAACTGTTATTTCGATTTGCAGCAAATTGA CTTCTTTAAATGAAGAGTATACCAAAAATAAAACAGAATATGAA GAAGCCCAGGATGCCATTGTTAAAGAAATTGT | 3260 |
| | ACAATTTCTTTAACAATGGCATCCTGGGCTTCTTCATATTCTGT TTTATTTTTGGTATACTCTTCATTTAAAGAAGTCAATTTGCTGC AAATCGAAATAACAGTTTTATTAAAAATATTAA | 3261 |
| | AAATGAAGAGTATACCA | 3262 |
| | TGGTATACTCTTCATTT | 3263 |
| Glioma Glu580Term GAA-TAA | AATGAAGAGTATACCAAAAATAAAACAGAATATGAAGAAGCCC AGGATGCCATTGTTAAAGAAATTGTCAATATTCTTCAGGTAAA CTTAATGAACTAATAATGTTCTGAATGTCACCT | 3264 |
| | AGGTGACATTCAGAACATTATTAGTTCTATTAAGTTTACCTGAA GAAATATTGACAATTTCTTTAACAATGGCATCCTGGGCTTCTT CATATTCTGTTTTATTTTTGGTATACTCTTCATT | 3265 |
| | TTGTTAAAGAAATTGTC | 3266 |
| | GACAATTTCTTTAACAA | 3267 |
| Non polyposis colorectal cancer Gln601Term GAG-TAG | TGTTTTTATTTTTATACAGGCTATGTAGAACCAATGCAGACACT CAATGATGTGTTAGCTCAGCTAGATGCTGTTGTCAGCTTTGCT CACGTGTCAAATGGAGCACCTGTTCCATATGTAC | 3268 |
| | GTACATATGGAACAGGTGCTCCATTTGACACGTGAGCAAAGC TGACAACAGCATCTAGCTGAGCTAACACATCATTGAGTGTCTG CATTGGTTCTACATAGCCTGTATAAAAATAAAACA | 3269 |

TABLE 25-continued

MSH2 Mutations and Genome-Correcting Oligos

| Clinical Phenotype & Mutation | Correcting Oligos | SEQ ID NO: |
|---|---|---|
| | TGTTAGCTCAGCTAGAT | 3270 |
| | ATCTAGCTGAGCTAACA | 3271 |
| Non polyposis colorectal cancer Tyr619Term TAT-TAG | AGCTCAGCTAGATGCTGTTGTCAGCTTTGCTCACGTGTCAAAT GGAGCACCTGTTCCATATGTACGACCAGCCATTTTGGAGAAA GGACAAGGAAGAATTATATTAAAAGCATCCAGGCAT | 3272 |
| | ATGCCTGGATGCTTTTAATATAATTCTTCCTTGTCCTTTCTCCA AAATGGCTGGTCGTACATATGGAACAGGTGCTCCATTTGACA CGTGAGCAAAGCTGACAACAGCATCTAGCTGAGCT | 3273 |
| | GTTCCATATGTACGACC | 3274 |
| | GGTCGTACATATGGAAC | 3275 |
| Non polyposis colorectal cancer Arg621Term CGA-TGA | CAGCTAGATGCTGTTGTCAGCTTTGCTCACGTGTCAAATGGA GCACCTGTTCCATATGTACGACCAGCCATTTTGGAGAAAGGA CAAGGAAGAATTATATTAAAAGCATCCAGGCATGCTT | 3276 |
| | AAGCATGCCTGGATGCTTTTAATATAATTCTTCCTTGTCCTTTC TCCAAAATGGCTGGTCGTACATATGGAACAGGTGCTCCATTT GACACGTGAGCAAAGCTGACAACAGCATCTAGCTG | 3277 |
| | CATATGTACGACCAGCC | 3278 |
| | GGCTGGTCGTACATATG | 3279 |
| Non polyposis colorectal cancer Pro622Leu CCA-CTA | TAGATGCTGTTGTCAGCTTTGCTCACGTGTCAAATGGAGCAC CTGTTCCATATGTACGACCAGCCATTTTGGAGAAAGGACAAG GAAGAATTATATTAAAAGCATCCAGGCATGCTGTGT | 3280 |
| | ACACAAGCATGCCTGGATGCTTTTAATATAATTCTTCCTTGTC CTTTCTCCAAAATGGCTGGTCGTACATATGGAACAGGTGCTC CATTTGACACGTGAGCAAAGCTGACAACAGCATCTA | 3281 |
| | TGTACGACCAGCCATTT | 3282 |
| | AAATGGCTGGTCGTACA | 3283 |
| Non polyposis colorectal cancer Ala636Pro GCA-CCA | CCTGTTCCATATGTACGACCAGCCATTTTGGAGAAAGGACAA GGAAGAATTATATTAAAAGCATCCAGGCATGCTTGTGTTGAAG TTCAAGATGAAATTGCATTTATTCCTAATGACGTAT | 3284 |
| | ATACGTCATTAGGAATAAATGCAATTTCATCTTGAACTTCAACA CAAGCATGCCTGGATGCTTTTAATATAATTCTTCCTTGTCCTTT CTCCAAAATGGCTGGTCGTACATATGGAACAGG | 3285 |
| | TATTAAAAGCATCCAGG | 3286 |
| | CCTGGATGCTTTTAATA | 3287 |
| Non polyposis colorectal cancer His639Arg CAT-CGT | ATGTACGACCAGCCATTTTGGAGAAAGGACAAGGAAGAATTA TATTAAAAGCATCCAGGCATGCTTGTGTTGAAGTTCAAGATGA AATTGCATTTATTCCTAATGACGTATACTTTGAAAA | 3288 |
| | TTTTCAAAGTATACGTCATTAGGAATAAATGCAATTTCATCTTG AACTTCAACACAAGCATGCCTGGATGCTTTTAATATAATTCTTC CTTGTCCTTTCTCCAAAATGGCTGGTCGTACAT | 3289 |
| | ATCCAGGCATGCTTGTG | 3290 |
| | CACAAGCATGCCTGGAT | 3291 |
| Non polyposis colorectal cancer His639Tyr CAT-TAT | TATGTACGACCAGCCATTTTGGAGAAAGGACAAGGAAGAATT ATATTAAAAGCATCCAGGCATGCTTGTGTTGAAGTTCAAGATG AAATTGCATTTATTCCTAATGACGTATACTTTGAAA | 3292 |
| | TTTCAAAGTATACGTCATTAGGAATAAATGCAATTTCATCTTGA ACTTCAACACAAGCATGCCTGGATGCTTTTAATATAATTCTTC CTTGTCCTTTCTCCAAAATGGCTGGTCGTACATA | 3293 |
| | CATCCAGGCATGCTTGT | 3294 |
| | ACAAGCATGCCTGGATG | 3295 |
| Non polyposis colorectal cancer Glu647Lys GAA-AAA | AAAGGACAAGGAAGAATTATATTAAAAGCATCCAGGCATGCTT GTGTTGAAGTTCAAGATGAAATTGCATTTATTCCTAATGACGT ATACTTTGAAAAAGATAAACAGATGTTCCACATCA | 3296 |
| | TGATGTGGAACATCTGTTTATCTTTTTCAAAGTATACGTCATTA GGAATAAATGCAATTTCATCTTGAACTTCAACACAAGCATGCC TGGATGCTTTTAATATAATTCTTCCTTGTCCTTT | 3297 |
| | TTCAAGATGAAATTGCA | 3298 |
| | TGCAATTTCATCTTGAA | 3299 |
| Non polyposis colorectal cancer Tyr656Term TAC-TAG | ATCCAGGCATGCTTGTGTTGAAGTTCAAGATGAAATTGCATTT ATTCCTAATGACGTATACTTTGAAAAAGATAAACAGATGTTCCA CATCATTACTGGTAAAAAACCTGGTTTTGGGCT | 3300 |
| | AGCCCAAAAACCAGGTTTTTTACCAGTAATGATGTGGAACATC TGTTTATCTTTTTCAAAGTATACGTCATTAGGAATAAATGCAAT TTCATCTTGAACTTCAACACAAGCATGCCTGGAT | 3301 |
| | GACGTATACTTTGAAAA | 3302 |
| | TTTTCAAAGTATACGTC | 3303 |
| Non polyposis colorectal cancer Gly674Asp GGT-GAT | GAAAGAAGTTTAAAATCTTGCTTTCTGATATAATTTGTTTTGTA GGCCCCAATATGGGAGGTAAATCAACATATATTCGACAAACT GGGGTGATAGTACTCATGGCCCAAATTGGGTGTTT | 3304 |
| | AAACACCCAATTTGGGCCATGAGTACTATCACCCCAGTTTGTC GAATATATGTTGATTTACCTCCCATATTGGGGCCTACAAAACA AATTATATCAGAAAGCAAGATTTTAAACTTCTTTC | 3305 |
| | TATGGGAGGTAAATCAA | 3306 |
| | TTGATTTACCTCCCATA | 3307 |

TABLE 25-continued

MSH2 Mutations and Genome-Correcting Oligos

| Clinical Phenotype & Mutation | Correcting Oligos | SEQ ID NO: |
|---|---|---|
| Non polyposis colorectal cancer Arg680Term CGA-TGA | TTGCTTTCTGATATAATTTGTTTTGTAGGCCCCAATATGGGAG | 3308 |
| | GTAAATCAACATATATTCGACAAACTGGGGTGATAGTACTCAT | |
| | GGCCCAAATTGGGTGTTTTGTGCCATGTGAGTCAG | |
| | CTGACTCACATGGCACAAAACACCCAATTTGGGCCATGAGTA | 3309 |
| | CTATCACCCCAGTTTGTCGAATATATGTTGATTTACCTCCCAT | |
| | ATTGGGGCCTACAAAACAAATTATATCAGAAAGCAA | |
| | CATATATTCGACAAACT | 3310 |
| | AGTTTGTCGAATATATG | 3311 |
| Non polyposis colorectal cancer Gly692Arg GGG-CGG | ATGGGAGGTAAATCAACATATATTCGACAAACTGGGGTGATA | 3312 |
| | GTACTCATGGCCCAAATTGGGTGTTTTGTGCCATGTGAGTCA | |
| | GCAGAAGTGTCCATTGTGGACTGCATCTTAGCCCGAG | |
| | CTCGGGCTAAGATGCAGTCCACAATGGACACTTCTGCTGACT | 3313 |
| | CACATGGCACAAAACACCCAATTTGGGCCATGAGTACTATCA | |
| | CCCCAGTTTGTCGAATATATGTTGATTTACCTCCCAT | |
| | CCCAAATTGGGTGTTTT | 3314 |
| | AAAACACCCAATTTGGG | 3315 |
| Non polyposis colorectal cancer Cys697Arg TGT-CGT | ACATATATTCGACAAACTGGGGTGATAGTACTCATGGCCCAAA | 3316 |
| | TTGGGTGTTTTGTGCCATGTGAGTCAGCAGAAGTGTCCATTG | |
| | TGGACTGCATCTTAGCCCGAGTAGGGGCTGGTGACA | |
| | TGTCACCAGCCCCTACTCGGGCTAAGATGCAGTCCACAATGG | 3317 |
| | ACACTTCTGCTGACTCACATGGCACAAAACACCCAATTTGGG | |
| | CCATGAGTACTATCACCCCAGTTTGTCGAATATATGT | |
| | TTGTGCCATGTGAGTCA | 3318 |
| | TGACTCACATGGCACAA | 3319 |
| Non polyposis colorectal cancer Cys697Phe TGT-TTT | CATATATTCGACAAACTGGGGTGATAGTACTCATGGCCCAAAT | 3320 |
| | TGGGTGTTTTGTGCCATGTGAGTCAGCAGAAGTGTCCATTGT | |
| | GGACTGCATCTTAGCCCGAGTAGGGGCTGGTGACAG | |
| | CTGTCACCAGCCCCTACTCGGGCTAAGATGCAGTCCACAATG | 3321 |
| | GACACTTCTGCTGACTCACATGGCACAAAACACCCAATTTGG | |
| | GCCATGAGTACTATCACCCCAGTTTGTCGAATATATG | |
| | TGTGCCATGTGAGTCAG | 3322 |
| | CTGACTCACATGGCACA | 3323 |
| Non polyposis colorectal cancer Gln718Term CAA-TAA | GAGTCAGCAGAAGTGTCCATTGTGGACTGCATCTTAGCCCGA | 3324 |
| | GTAGGGGCTGGTGACAGTCAATTGAAAGGAGTCTCCACGTTC | |
| | ATGGCTGAAATGTTGGAAACTGCTTCTATCCTCAGGT | |
| | ACCTGAGGATAGAAGCAGTTTCCAACATTTCAGCCATGAACG | 3325 |
| | TGGAGACTCCTTTCAATTGACTGTCACCAGCCCCTACTCGGG | |
| | CTAAGATGCAGTCCACAATGGACACTTCTGCTGACTC | |
| | GTGACAGTCAATTGAAA | 3326 |
| | TTTCAATTGACTGTCAC | 3327 |
| Non polyposis colorectal cancer Leu811Term TTA-TGA | CCAATCAGATACCAACTGTTAATAATCTACATGTCACAGCACT | 3328 |
| | CACCCACTGAAGAGACCTTAACTATGCTTTATCAGGTGAAGAAA | |
| | GGTATGTACTATTGGAGTACTCTAAATTCAGAACT | |
| | AGTTCTGAATTTAGAGTACTCCAATAGTACATACCTTTCTTCAC | 3329 |
| | CTGATAAAGCATAGTTAAGGTCTCTTCAGTGGTGAGTGCTGT | |
| | GACATGTAGATTATTAACAGTTGGTATCTGATTGG | |
| | AGAGACCTTAACTATGC | 3330 |
| | GCATAGTTAAGGTCTCT | 3331 |
| Non polyposis colorectal cancer Ala834Thr GCT-ACT | TTCCCCAAATTTCTTATAGGTGTCTGTGATCAAAGTTTTGGGA | 3332 |
| | TTCATGTTGCAGAGCTTGCTAATTTCCCTAAGCATGTAATAGA | |
| | GTGTGCTAAACAGAAAGCCCTGGAACTTGAGGAGT | |
| | ACTCCTCAAGTTCCAGGGCTTTCTGTTTAGCACACTCTATTAC | 3333 |
| | ATGCTTAGGGAAATTAGCAAGCTCTGCAACATGAATCCCAAAA | |
| | CTTTGATCACAGACACCTATAAGAAATTTGGGGAA | |
| | CAGAGCTTGCTAATTTC | 3334 |
| | GAAATTAGCAAGCTCTG | 3335 |
| Non polyposis colorectal cancer Gln861Term CAA-TAA | ATAGAGTGTGCTAAACAGAAAGCCCTGGAACTTGAGGAGTTT | 3336 |
| | CAGTATATTGGAGAATCGCAAGGATATGATATCATGGAACCAG | |
| | CAGCAAAGAAGTGCTATCTGGAAAGAGAGGTTTGTC | |
| | GACAAACCTCTCTTTCCAGATAGCACTTCTTTGCTGCTGGTTC | 3337 |
| | CATGATATCATATCCTTGCGATTCTCCAATATACTGAAACTCCT | |
| | CAAGTTCCAGGGCTTTCTGTTTAGCACACTCTAT | |
| | GAGAATCGCAAGGATAT | 3338 |
| | ATATCCTTGCGATTCTC | 3339 |
| Non polyposis colorectal cancer Thr905Arg ACA-AGA | AGGAGTTCCTGTCCAAGGTGAAACAAATGCCCTTTACTGAAAT | 3340 |
| | GTCAGAAGAAAACATCACAATAAAGTTAAAACAGCTAAAAGCT | |
| | GAAGTAATAGCAAAGAATAATAGCTTTGTAAATGA | |
| | TCATTTACAAAGCTATTATTCTTTGCTATTACTTCAGCTTTTAG | 3341 |
| | CTGTTTTAACTTTATTGTGATGTTTTCTTCTGACATTTCAGTAA | |
| | AGGGCATTTGTTTCACCTTGGACAGGAACTCCT | |
| | AAACATCACAATAAAGT | 3342 |
| | ACTTTATTGTGATGTTT | 3343 |

EXAMPLE 19

Human Mismatch Repair—MSH6

The human MSH6 gene is homologous to the bacterial mutS gene, which is involved in mismatch repair. Mutations in the MSH6 gene have been identified in a variety of cancers, including particularly hereditary nonpolyposis colorectal cancer. The attached table discloses the correcting oligonucleotide base sequences for the MSH6 oligonucleotides of the invention.

TABLE 26

MSH6 Mutations and Genome-Correcting Oligos

| Clinical Phenotype & Mutation | Correcting Oligos | SEQ ID NO: |
|---|---|---|
| Non-polyposis colorectal cancer Ser144Ile AGC-ATC | GGAAATCAGTCCGTGTTCATGTACAGTTTTTTGATGACAGCCC AACAAGGGCTGGGTTAGCAAAAGGCTTTTAAAGCCATATAC AGGTAAGAGTCACTACTGCCATGTGTGTGTGTTTGT | 3344 |
| | ACAAACACACACACATGGCAGTAGTGACTCTTACCTGTATATG GCTTTAAAAGCCTTTTGCTAACCCAGCCCCTTGTTGGGCTGT CATCAAAAAACTGTACATGAACACGGACTGATTTCC | 3345 |
| | CTGGGTTAGCAAAAGGC | 3346 |
| | GCCTTTTGCTAACCCAG | 3347 |
| Endometrial cancer Ser156Term TCA-TGA | CGTGAGCCTCTGCACCCGGCCCTTATTGTTTATAAATACATTT CTTTCTAGGTTCAAAATCAAAGGAAGCCCAGAAGGGAGGTCA TTTTTACAGTGCAAAGCCTGAAATACTGAGAGCAAT | 3348 |
| | ATTGCTCTCAGTATTTCAGGCTTTGCACTGTAAAAATGACCTC CCTTCTGGGCTTCCTTTGATTTTGAACCTAGAAAGAAATGTAT TTATAAACAATAAGGGCCGGGTGCAGAGGCTCACG | 3349 |
| | TTCAAAATCAAAGGAAG | 3350 |
| | CTTCCTTTGATTTTGAA | 3351 |
| Early onset colorectal cancer Tyr214Term TAC-TAG | TTCCAAATTTTGATTTGTTTTTAAATACTCTTTCCTTGCCTGGC AGGTAGGCACAACTTACGTAACAGATAAGAGTGAAGAAGATA ATGAAATTGAGAGTGAAGAGGAAGTACAGCCTAAG | 3352 |
| | CTTAGGCTGTACTTCCTCTTCACTCTCAATTTCATTATCTTCTT CACTCTTATCTGTTACGTAAGTTGTGCCTACCTGCCAGGCAA GGAAAGAGTATTTAAAAACAAATCAAAATTTGGAA | 3353 |
| | ACAACTTACGTAACAGA | 3354 |
| | TCTGTTACGTAAGTTGT | 3355 |
| Endometrial cancer Arg248Term CGA-TGA | GAAGAGGAAGTACAGCCTAAGACACAAGGATCTAGGCGAAGT AGCCGCCAAATAAAAAAACGAAGGGTCATATCAGATTCTGAG AGTGACATTGGTGGCTCTGATGTGGAATTTAAGCCAG | 3356 |
| | CTGGCTTAAATTCCACATCAGAGCCACCAATGTCACTCTCAGA ATCTGATATGACCCTTCGTTTTTTTATTTGGCGGCTACTTCGC CTAGATCCTTGTGTCTTAGGCTGTACTTCCTCTTC | 3357 |
| | TAAAAAAACGAAGGGTC | 3358 |
| | GACCCTTCGTTTTTTTA | 3359 |
| Colorectal cancer Ser285Ile AGT-ATT | TTAAGCCAGACACTAAGGAGGAAGGAAGCAGTGATGAAATAA GCAGTGGAGTGGGGGATAGTGAGAGTGAAGGCCTGAACAGC CCTGTCAAAGTTGCTCGAAAGCGGAAGAGAATGGTGAC | 3360 |
| | GTCACCATTCTCTTCCGCTTTCGAGCAACTTTGACAGGGCTG TTCAGGCCTTCACTCTCACTATCCCCCACTCCACTGCTTATTT CATCACTGCTTCCTTCCTCCTTAGTGTCTGGCTTAA | 3361 |
| | GGGGGATAGTGAGAGTG | 3362 |
| | CACTCTCACTATCCCCC | 3363 |
| Colorectal cancer Gly566Arg GGA-AGA | GAGGAAGATTCTTCTGGCCATACTCGTGCATATGGTGTGTGC TTTGTTGATACTTCACTGGGAAAGTTTTTCATAGGTCAGTTTTC AGATGATCGCCATTGTTCGAGATTTAGGACTCTAG | 3364 |
| | CTAGAGTCCTAAATCTCGAACAATGGCGATCATCTGAAAACTG ACCTATGAAAAACTTTCCCAGTGAAGTATCAACAAAGCACACA CCATATGCACGAGTATGGCCAGAAGAATCTTCCTC | 3365 |
| | CTTCACTGGGAAAGTTT | 3366 |
| | AAACTTTCCCAGTGAAG | 3367 |
| Non-polyposis colorectal cancer Gln698Glu CAG-GAG | GAATTGGCCCTCTCTGCTCTAGGTGGTTGTGTCTTCTACCTC AAAAAATGCCTTATTGATCAGGAGCTTTTATCAATGGCTAATTT TGAAGAATATATTCCCTTGGATTCTGACACAGTCA | 3368 |
| | TGACTGTGTCAGAATCCAAGGGAATATATTCTTCAAAATTAGC CATTGATAAAAGCTCCTGATCAATAAGGCATTTTTTGAGGTAG AAGACACAACCACCTAGAGCAGAGAGGGCCAATTC | 3369 |
| | TTATTGATCAGGAGCTT | 3370 |
| | AAGCTCCTGATCAATAA | 3371 |
| Endometrial cancer Gln731Term CAA-TAA | CCCTTGGATTCTGACACAGTCAGCACTACAAGATCTGGTGCT ATCTTCACCAAAGCCTATCAACGAATGGTGCTAGATGCAGTG ACATTAAACAACTTGGAGATTTTCTGAATGGAACAA | 3372 |
| | TTGTTCCATTCAGAAAAATCTCCAAGTTGTTTAATGTCACTGCA TCTAGCACCATTCGTTGATAGGCTTTGGTGAAGATAGCACCA GATCTTGTAGTGCTGACTGTGTCAGAATCCAAGGG | 3373 |
| | AAGCCTATCAACGAATG | 3374 |
| | CATTCGTTGATAGGCTT | 3375 |

TABLE 26-continued

MSH6 Mutations and Genome-Correcting Oligos

| Clinical Phenotype & Mutation | Correcting Oligos | SEQ ID NO: |
|---|---|---|
| Colorectal cancer Val800Leu GTT-CTT | GCCCCACTCTGTAACCATTATGCTATTAATGATCGTCTAGATG CCATAGAAGACCTCATGGTTGTGCCTGACAAAATCTCCGAAG TTGTAGAGCTTCTAAAGAAGCTTCCAGATCTTGAGA | 3376 |
| | TCTCAAGATCTGGAAGCTTCTTTAGAAGCTCTACAACTTCGGA GATTTTGTCAGGCACAACCATGAGGTCTTCTATGGCATCTAGA CGATCATTAATAGCATAATGGTTACAGAGTGGGGC | 3377 |
| | ACCTCATGGTTGTGCCT | 3378 |
| | AGGCACAACCATGAGGT | 3379 |
| Colorectal cancer Asp803Gly GAC-GGC | GTAACCATTATGCTATTAATGATCGTCTAGATGCCATAGAAGA CCTCATGGTTGTGCCTGACAAAATCTCCGAAGTTGTAGAGCT TCTAAAGAAGCTTCCAGATCTTGAGAGGCTACTCAG | 3380 |
| | CTGAGTAGCCTCTCAAGATCTGGAAGCTTCTTTAGAAGCTCTA CAACTTCGGAGATTTTGTCAGGCACAACCATGAGGTCTTCTAT GGCATCTAGACGATCATTAATAGCATAATGGTTAC | 3381 |
| | TGTGCCTGACAAAATCT | 3382 |
| | AGATTTTGTCAGGCACA | 3383 |
| Non-polyposis colorectal cancer Tyr850Cys TAC-TGC | CTCCCCTGAAGAGTGAGAACCACCCAGACAGCAGGGCTATAA TGTATGAAGAAACTACATACAGCAAGAAGAAGATTATTGATTT TCTTTCTGCTCTGGAAGGATTCAAAGTAATGTGTAA | 3384 |
| | TTACACATTACTTTGAATCCTTCCAGAGCAGAAAGAAAATCAA TAATCTTCTTCTTGCTGTATGTAGTTTCTTCATACATTATAGCC CTGCTGTCTGGGTGGTTCTGACTCTTCAGGGGAG | 3385 |
| | AACTACATACAGCAAGA | 3386 |
| | TCTTGCTGTATGTAGTT | 3387 |
| Colorectal cancer Pro1087Thr CCC-ACC | TATAGTCGAGGGGGTGATGGTCCTATGTGTCGCCCAGTAATT CTGTTGCCGGAAGATACCCCCCCCTTCTTAGAGCTTAAAGGA TCACGCCATCCTTGCATTACGAAGACTTTTTTTGGAG | 3388 |
| | CTCCAAAAAAAGTCTTCGTAATGCAAGGATGGCGTGATCCTTT AAGCTCTAAGAAGGGGGGGGTATCTTCCGGCAACAGAATTAC TGGGCGACACATAGGACCATCACCCCCTCGACTATA | 3389 |
| | AAGATACCCCCCCCTTC | 3390 |
| | GAAGGGGGGGGTATCTT | 3391 |
| Non-polyposis colorectal cancer Gln1258Term CAA-TAA | ACTATAAAATGTCGTACATTATTTTCAACTCACTACCATTCATT AGTAGAAGATTATTCTCAAATGTTGCTGTGCGCCTAGGACAT ATGGTATGTGCAAATTGTTTTTTTCCACAAATTC | 3392 |
| | GAATTTGTGGAAAAAAACAATTTGCACATACCATATGTCCTAG GCGCACAGCAACATTTTGAGAATAATCTTCTACTAATGAATGG TAGTGAGTTGAAAATAATGTACGACATTTTATAGT | 3393 |
| | ATTATTCTCAAATGTT | 3394 |
| | AACATTTTGAGAATAAT | 3395 |

EXAMPLE 20

Hyperlipidemia—APOE

Hyperlipidemia is the abnormal elevation of plasma cholesterol and/or triglyceride levels and it is one of the most common diseased. The human apolipoprotein E protein is involved in the transport of endogenous lipids and appears to be crucial for both the direct removal of cholesterol-rich LDL from plasma and conversion of IDL particles to LDL particles. Individuals who either lack apolipoprotein E or who are homozygous for particular alleies of apoE may have a condition known as dysbetaiipoproteinemia, which is characterized by elevated plasma cholesterol and triglyceride levels and an increased risk for atherosclerosis.

In a comprehensive review of apoE variants, de Knijff et al., *Hum. Mutat.* 4:178–194 (1994) found that 30 variants had been characterized, including the most common variant, apoE3. To that time, 14 apoE variants had been found to be associated with familial dysbetalipoproteinemia. The attached table discloses the correcting oligonucleotide base sequences for the APOE oligonucleotides of the invention.

TABLE 27

APOE Mutations and Genome-Correcting Oligos

| Clinical Phenotype & Mutation | Correcting Oligos | SEQ ID NO: |
|---|---|---|
| Apolipoprotein E Glu13Lys cGAG-AAG | TTGTTCCACACAGGATGCCAGGCCAAGGTGGAGCAAGCGGT GGAGACAGAGCCGGAGCCCGAGCTGCGCCAGCAGACCGAG TGGCAGAGCGGCCAGCGCTGGGAACTGGCACTGGGTCGCT | 3396 |
| | AGCGACCCAGTGCCAGTTCCCAGCGCTGGCCGCTCTGCCAC TCGGTCTGCTGGCGCAGCTCGGGCTCCGGCTCTGTCTCCAC CGCTTGCTCCACCTTGGCCTGGCATCCTGTGTGGAACAA | 3397 |

TABLE 27-continued

APOE Mutations and Genome-Correcting Oligos

| Clinical Phenotype & Mutation | Correcting Oligos | SEQ ID NO: |
|---|---|---|
| | CGGAGCCCGAGCTGCGC | 3398 |
| | GCGCAGCTCGGGCTCCG | 3399 |
| Apolipoprotein E Trp20Term TGGc-TGA | CAAGGTGGAGCAAGCGGTGGAGACAGAGCCGGAGCCCGAG CTGCGCCAGCAGACCGAGTGGCAGAGCGGCCAGCGCTGGG AACTGGCACTGGGTCGCTTTTGGGATTACCTGCGCTGGGTG | 3400 |
| | CACCCAGCGCAGGTAATCCCAAAAGCGACCCAGTGCCAGTT CCCAGCGCTGGCCGCTCTGCCACTCGGTCTGCTGGCGCAGC TCGGGCTCCGGCTCTGTCTCCACCGCTTGCTCCACCTTG | 3401 |
| | ACCGAGTGGCAGAGCGG | 3402 |
| | CCGCTCTGCCACTCGGT | 3403 |
| Apolipoprotein E Leu28Pro CTG-CCG | CAGAGCCGGAGCCCGAGCTGCGCCAGCAGACCGAGTGGCA GAGCGGCCAGCGCTGGGAACTGGCACTGGGTCGCTTTTGGG ATTACCTGCGCTGGGTGCAGACACTGTCTGAGCAGGTGCA | 3404 |
| | TGCACCTGCTCAGACAGTGTCTGCACCCAGCGCAGGTAATCC CAAAAGCGACCCAGTGCCAGTTCCCAGCGCTGGCCGCTCTG CCACTCGGTCTGCTGGCGCAGCTCGGGCTCCGGCTCTG | 3405 |
| | CTGGGAACTGGCACTGG | 3406 |
| | CCAGTGCCAGTTCCCAG | 3407 |
| Apolipoprotein E Cys112Arg gTGC-CGC | CGGCTGTCCAAGGAGCTGCAGGCGGCGCAGGCCCGGCTGG GCGCGGACATGGAGGACGTGTGCGGCCGCCTGGTGCAGTA CCGCGGCGAGGTGCAGGCCATGCTCGGCCAGAGCACCGAG G | 3408 |
| | CCTCGGTGCTCTGGCCGAGCATGGCCTGCACCTCGCCGCGG TACTGCACCAGGCGGCCGCACACGTCCTCCATGTCCGCGCC CAGCCGGGCCTGCGCCGCCTGCAGCTCCTTGGACAGCCG | 3409 |
| | AGGACGTGTGCGGCCGC | 3410 |
| | GCGGCCGCACACGTCCT | 3411 |
| Apolipoprotein E Gly127Asp GGC-GAC | ACATGGAGGACGTGTGCGGCCGCCTGGTGCAGTACCGCGG CGAGGTGCAGGCCATGCTCGGCAGAGCACCGAGGAGCTG CGGGTGCGCCTCGCCTCCCACCTGCGCAAGCTGCGTAAGCG | 3412 |
| | CGCTTACGCAGCTTGCGCAGGTGGGAGGCGAGGCGCACCC GCAGCTCCTCGGTGCTCTGGCCGAGCATGGCCTGCACCTCG CCGCGGTACTGCACCAGGCGGCCGCACACGTCCTCCATGT | 3413 |
| | CATGCTCGGCCAGAGCA | 3414 |
| | TGCTCTGGCCGAGCATG | 3415 |
| Apolipoprotein E Arg136Cys gCGC-TGC | GTGCAGTACCGCGGCGAGGTGCAGGCCATGCTCGGCCAGA GCACCGAGGAGCTGCGGGTGCGCCTCGCCTCCCACCTGCG CAAGCTGCGTAAGCGGCTCCTCCGCGATGCCGATGACCTGC | 3416 |
| | GCAGGTCATCGGCATCGCGGAGGAGCCGCTTACGCAGCTTG CGCAGGTGGGAGGCGAGGCGCACCCGCAGCTCCTCGGTGC TCTGGCCGAGCATGGCCTGCACCTCGCCGCGGTACTGCAC | 3417 |
| | TGCGGGTGCGCCTCGCC | 3418 |
| | GGCGAGGCGCACCCGCA | 3419 |
| Apolipoprotein E Arg136His CGC-CAC | TGCAGTACCGCGGCGAGGTGCAGGCCATGCTCGGCCAGAG CACCGAGGAGCTGCGGGTGCGCCTCGCCTCCCACCTGCGC AAGCTGCGTAAGCGGCTCCTCCGCGATGCCGATGACCTGCA | 3420 |
| | TGCAGGTCATCGGCATCGCGGAGGAGCCGCTTACGCAGCTT GCGCAGGTGGGAGGCGAGGCGCACCCGCAGCTCCTCGGTG CTCTGGCCGAGCATGGCCTGCACCTCGCCGCGGTACTGCA | 3421 |
| | GCGGGTGCGCCTCGCCT | 3422 |
| | AGGCGAGGCGCACCCGC | 3423 |
| Apolipoprotein E Arg136Ser gCGC-AGC | GTGCAGTACCGCGGCGAGGTGCAGGCCATGCTCGGCCAGA GCACCGAGGAGCTGCGGGTGCGCCTCGCCTCCCACCTGCG CAAGCTGCGTAAGCGGCTCCTCCGCGATGCCGATGACCTGC | 3424 |
| | GCAGGTCATCGGCATCGCGGAGGAGCCGCTTACGCAGCTTG CGCAGGTGGGAGGCGAGGCGCACCCGCAGCTCCTCGGTGC TCTGGCCGAGCATGGCCTGCACCTCGCCGCGGTACTGCAC | 3425 |
| | TGCGGGTGCGCCTCGCC | 3426 |
| | GGCGAGGCGCACCCGCA | 3427 |
| Apolipoprotein E Arg142Cys gCGC-TGC | GTGCAGGCCATGCTCGGCCAGAGCACCGAGGAGCTGCGGG TGCGCCTCGCCTCCCACCTGCGCAAGCTGCGTAAGCGGCTC CTCCGCGATGCCGATGACCTGCAGAAGCGCCTGGCAGTGT | 3428 |
| | ACACTGCCAGGCGCTTCTGCAGGTCATCGGCATCGCGGAGG AGCCGCTTACGCAGCTTGCGCAGGTGGGAGGCGAGGCGCA CCCGCAGCTCCTCGGTGCTCTGGCCGAGCATGGCCTGCAC | 3429 |
| | CCCACCTGCGCAAGCTG | 3430 |
| | CAGCTTGCGCAGGTGGG | 3431 |
| Apolipoprotein E Arg142Leu CGC-CTC | TGCAGGCCATGCTCGGCCAGAGCACCGAGGAGCTGCGGGT GCGCCTCGCCTCCCACCTGCGCAAGCTGCGTAAGCGGCTCC TCCGCGATGCCGATGACCTGCAGAAGCGCCTGGCAGTGTA | 3432 |
| | CACTGCCAGGCGCTTCTGCAGGTCATCGGCATCGCGGAG GAGCCGCTTACGCAGCTTGCCGCAGGTGGGAGGCGAGGCGC ACCCGCAGCTCCTCGGTGCTCTGGCCGAGCATGGCCTGCA | 3433 |

TABLE 27-continued

APOE Mutations and Genome-Correcting Oligos

| Clinical Phenotype & Mutation | Correcting Oligos | SEQ ID NO: |
|---|---|---|
| | CCACCTGCGCAAGCTGC | 3434 |
| | GCAGCTTGCGCAGGTGG | 3435 |
| Apolipoprotein E Arg145Cys gCGT-TGT | ATGCTCGGCCAGAGCACCGAGGAGCTGCGGGTGCGCCTCG CCTCCCACCTGCGCAAGCTGCGTAAGCGGCTCCTCCGCGAT GCCGATGACCTGCAGAAGCGCCTGGCAGTGTACCAGGCCG | 3436 |
| | CGGCCTGGTACACTGCCAGGCGCTTCTGCAGGTCATCGGCA TCGCGGAGGAGCCGCTTACGCAGCTTGCGCAGGTGGGAGG CGAGGCGCACCCGCAGCTCCTCGGTGCTCTGGCCGAGCAT | 3437 |
| | GCAAGCTGCGTAAGCGG | 3438 |
| | CCGCTTACGCAGCTTGC | 3439 |
| Apolipoprotein E Arg145Pro CGT-CCT | TGCTCGGCCAGAGCACCGAGGAGCTGCGGGTGCGCCTCGC CTCCCACCTGCGCAAGCTGCGTAAGCGGCTCCTCCGCGATG CCGATGACCTGCAGAAGCGCCTGGCAGTGTACCAGGCGG | 3440 |
| | CCGGCCTGGTACACTGCCAGGCGCTTCTGCAGGTCATCGGC ATCGCGGAGGAGCCGCTTACGCAGCTTGCGCAGGTGGGAG GCGAGGCGCACCCGCAGCTCCTCGGTGCTCTGGCCGAGCA | 3441 |
| | CAAGCTGCGTAAGCGGC | 3442 |
| | GCCGCTTACGCAGCTTG | 3443 |
| Apolipoprotein E Lys146Gln tAAG-CAG | CTCGGCCAGAGCACCGAGGAGCTGCGGGTGCGCCTCGCCT CCCACCTGCGCAAGCTGCGTAAGCGGCTCCTCCGCGATGCC GATGACCTGCAGAAGCGCCTGGCAGTGTACCAGGCCGGGG | 3444 |
| | CCCCGGCCTGGTACACTGCCAGGCGCTTCTGCAGGTCATCG GCATCGCGGAGGAGCCGCTTACGCAGCTTGCGCAGGTGGGA GGCGAGGCGCACCCGCAGCTCCTCGGTGCTCTGGCCGAG | 3445 |
| | AGCTGCGTAAGCGGCTC | 3446 |
| | GAGCCGCTTACGCAGCT | 3447 |
| Apolipoprotein E Lys146Glu tAAG-GAG | CTCGGCCAGAGCACCGAGGAGCTGCGGGTGCGCCTCGCCT CCCACCTGCGCAAGCTGCGTAAGCGGCTCCTCCGCGATGCC GATGACCTGCAGAAGCGCCTGGCAGTGTACCAGGCCGGGG | 3448 |
| | CCCCGGCCTGGTACACTGCCAGGCGCTTCTGCAGGTCATCG GCATCGCGGAGGAGCCGCTTACGCAGCTTGCGCAGGTGGGA GGCGAGGCGCACCCGCAGCTCCTCGGTGCTCTGGCCGAG | 3449 |
| | AGCTGCGTAAGCGGCTC | 3450 |
| | GAGCCGCTTACGCAGCT | 3451 |
| Apolipoprotein E Arg158Cys gCGC-TGC | GCCTCCCACCTGCGCAAGCTGCGTAAGCGGCTCCTCCGCGA TGCCGATGACCTGCAGAAAGCGCCTGGCAGTGTACCAGGCCG GGGCCCGCGAGGGCGCCGAGCGCGGCCTCAGCGCCATCC | 3452 |
| | GGATGGCGCTGAGGCCGCGCTCGGCGCCCTCGCGGGCCCC GGCCTGGTACACTGCCAGGCGCTTCTGCAGGTCATCGGCAT CGCGGAGGAGCCGCTTACGCAGCTTGCGCAGGTGGGAGGC | 3453 |
| | TGCAGAAGCGCCTGGCA | 3454 |
| | TGCCAGGCGCTTCTGCA | 3455 |
| Apolipoprotein E Gln187Glu aCAG-GAG | CGCGAGGGCGCCGAGCGCGGCCTCAGCGCCATCCGCGAGC GCCTGGGGCCCCTGGTGGAACAGGGCCGCGTGCGGGCCGC CACTGTGGGCTCCCTGGCCGGCCAGCCGCTACAGGAGCGG G | 3456 |
| | CCCGCTCCTGTAGCGGCTGGCCGGCCAGGGAGCCCACAGT GGCGGCCCGCACGCGGCCCTGTTCCACCAGGGGCCCCAGG CGCTCGCGGATGGCGCTGAGGCCGCGCTCGGCGCCCTCGC G | 3457 |
| | TGGTGGAACAGGGCCGC | 3458 |
| | GCGGCCCTGTTCCACCA | 3459 |
| Apolipoprotein E Trp210Term TGG-TAG | TGCGGGCCGCCACTGTGGGCTCCCTGGCCGGCCAGCCGCT ACAGGAGCGGGCCCAGGCCTGGGGCGAGCGGCTGCGCGC GCGGATGGAGGAGATGGGCAGCCGGACCCGCGACCGCCTG GA | 3460 |
| | TCCAGGCGGTCGCGGGTCCGGCTGCCCATCTCCTCCATCCG CGCGCGCAGCCGCTCGCCCCAGGCCTGGGCCCGCTCCTGT AGCGGCTGGCCGGCCAGGGAGCCCACAGTGGCGGCCCGCA | 3461 |
| | CCAGGCCTGGGGCGAGC | 3462 |
| | GCTCGCCCCAGGCCTGG | 3463 |
| Apolipoprotein E Arg228Cys cCGC-TGC | CAGGCCTGGGGCGAGCGGCTGCGCGCGCGGATGGAGGAGA TGGGCAGCCGGACCCGCGACCGCCTGGACGAGGTGAAGGA GCAGGTGGCGGAGGTGCGCGCCAAGCTGGAGGAGCAGGCC C | 3464 |
| | GGGCCTGCTCCTCCAGCTTGGCGCGCACCTCCGCCACCTGC TCCTTCACCTCGTCCAGGCGGTCGCGGGTCCGGCTGCCCAT CTCCTCCATCCGCGCGCGCAGCCGCTCGCCCCAGGCCTG | 3465 |
| | CCCGCGACCGCCTGGAC | 3466 |
| | GTCCAGGCGGTCGCGGG | 3467 |
| Apolipoprotein E Glu244Lys gGAG-AAG | CGGACCCGCGACCGCCTGGACGAGGTGAAGGAGCAGGTGG CGGAGGTGCGCGCCAAGCTGGAGGAGCAGGCCCAGCAGAT ACGCCTGCAGGCCGAGGCCTTCCAGGCCCGCCTCAAGAGCT | 3468 |
| | AGCTCTTGAGGCGGGCCTGGAAGGCCTCGGCCTGCAGGCGT | 3469 |

TABLE 27-continued

APOE Mutations and Genome-Correcting Oligos

| Clinical Phenotype & Mutation | Correcting Oligos | SEQ ID NO: |
|---|---|---|
| | ATCTGCTGGGCCTGCTCCTCCAGCTTGGCGCGCACCTCCGC | |
| | CACCTGCTCCTTCACCTCGTCCAGGCGGTCGCGGGTCCG | |
| | CCAAGCTGGAGGAGCAG | 3470 |
| | CTGCTCCTCCAGCTTGG | 3471 |

EXAMPLE 21

Familial Hypercholesterolemia—LDLR

Familial hypercholesterolemia is characterized by elevation of serum cholesterol bound to low density lipoprotein (LDL) and is, hence, one of the conditions producing a hyperlipoproteinemia phenotype. Familial hypercholesterolemia is an autosomal dominant disorder characterized by elevation of serum cholesterol bound to low density lipoprotein (LDL). Mutations in the LDL receptor (LDLR) gene cause this disorder. The attached table discloses the correcting oligonucleotide base sequences for the LDLR oligonucleotides of the invention.

TABLE 28

LDLR Mutations and Genome-Correcting Oligos

| Clinical Phenotype & Mutation | Correcting Oligos | SEQ ID NO: |
|---|---|---|
| Hypercholesterolaemia Glu10Term cGAG-TAG | GCGTTGAGAGACCCTTTCTCCTTTTCCTCTCTCTCAGTGGGC GACAGATGCGAAAGAAACGAGTTCCAGTGCCAAGACGGGAA ATGCATCTCCTACAAGTGGGTCTGCGATGGCAGCGCTG | 3472 |
| | CAGCGCTGCCATCGCAGACCCACTTGTAGGAGATGCATTTCC CGTCTTGGCACTGGAACTCGTTTCTTTCGCATCTGTCGCCCA CTGAGAGAGAGGAAAAGGAGAAAGGGTCTCTCAACGC | 3473 |
| | AAAGAAACGAGTTCCAG | 3474 |
| | CTGGAACTCGTTTCTTT | 3475 |
| Hypercholesterolaemia Gln12Term cCAG-TAG | AGAGACCCTTTCTCCTTTTCCTCTCTCTCAGTGGGCGACAGA TGCGAAAGAAACGAGTTCCAGTGCCAAGACGGGAAATGCATC TCCTACAAGTGGGTCTGCGATGGCAGCGCTGAGTGCC | 3476 |
| | GGCACTCAGCGCTGCCATCGCAGACCCACTTGTAGGAGATG CATTTCCCGTCTTGGCACTGGAACTCGTTTCTTTCGCATCTGT CGCCCACTGAGAGAGAGGAAAAGGAGAAAGGGTCTCT | 3477 |
| | ACGAGTTCCAGTGCCAA | 3478 |
| | TTGGCACTGGAACTCGT | 3479 |
| Hypercholesterolaemia Gln14Term cCAA-TAA | CCTTTCTCCTTTTCCTCTCTCTCAGTGGGCGACAGATGCGAA AGAAACGAGTTCCAGTGCCAAGACGGGAAATGCATCTCCTAC AAGTGGGTCTGCGATGGCAGCGCTGAGTGCCAGGATG | 3480 |
| | CATCCTGGCACTCAGCGCTGCCATCGCAGACCCACTTGTAG GAGATGCATTTCCCGTCTTGGCACTGGAACTCGTTTCTTTCG CATCTGTCGCCCACTGAGAGAGAGGAAAAGGAGAAAGG | 3481 |
| | TCCAGTGCCAAGACGGG | 3482 |
| | CCCGTCTTGGCACTGGA | 3483 |
| Hypercholesterolaemia Trp23Term TGG-TAG | GCGACAGATGCGAAAGAAACGAGTTCCAGTGCCAAGACGGG AAATGCATCTCCTACAAGTGGGTCTGCGATGGCAGCGCTGAG TGCCAGGATGGCTCTGATGAGTCCCAGGAGACGTGCTG | 3484 |
| | CAGCACGTCTCCTGGGACTCATCAGAGCCATCCTGGCACTCA GCGCTGCCATCGCAGACCCACTTGTAGGAGATGCATTTCCCG TCTTGGCACTGGAACTCGTTTCTTTCGCATCTGTCGC | 3485 |
| | CTACAAGTGGGTCTGCG | 3486 |
| | CGCAGACCCACTTGTAG | 3487 |
| Hypercholesterolaemia Ala29Ser cGCT-TCT | AACGAGTTCCAGTGCCAAGACGGGAAATGCATCTCCTACAAG TGGGTCTGCGATGGCAGCGCTGAGTGCCAGGATGGCTCTGA TGAGTCCCAGGAGACGTGCTGTGAGTCCCCTTTGGGCA | 3488 |
| | TGCCCAAAGGGGACTCACAGCACGTCTCCTGGGACTCATCA GAGCCATCCTGGCACTCAGCGCTGCCATCGCAGACCCACTT GTAGGAGATGCATTTCCCGTCTTGGCACTGGAACTCGTT | 3489 |
| | ATGGCAGCGCTGAGTGC | 3490 |
| | GCACTCAGCGCTGCCAT | 3491 |
| Hypercholesterolaemia Cys31Tyr TGC-TAC | TCCAGTGCCAAGACGGGAAATGCATCTCCTACAAGTGGGTCT GCGATGGCAGCGCTGAGTGCCAGGATGGCTCTGATGAGTCC CAGGAGACGTGCTGTGAGTCCCCTTTGGGCATGATATG | 3492 |
| | CATATCATGCCCAAAGGGGACTCACAGCACGTCTCCTGGGAC TCATCAGAGCCATCCTGGCACTCAGCGCTGCCATCGCAGAC CCACTTGTAGGAGATGCATTTCCCGTCTTGGCACTGGA | 3493 |
| | CGCTGAGTGCCAGGATG | 3494 |
| | CATCCTGGCACTCAGCG | 3495 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Arg57Cys cCGT-TGT | AATCCTGTCTCTTCTGTAGTGTCTGTCACCTGCAAATCCGGG GACTTCAGCTGTGGGGGCCGTGTCAACCGCTGCATTCCTCA GTTCTGGAGGTGCGATGGCCAAGTGGACTGCGACAACG | 3496 |
| | CGTTGTCGCAGTCCACTTGGCCATCGCACCTCCAGAACTGAG GAATGCAGCGGTTGACACGGCCCCCACAGCTGAAGTCCCCG GATTTGCAGGTGACAGACACTACAGAAGAGACAGGATT | 3497 |
| | GTGGGGGCCGTGTCAAC | 3498 |
| | GTTGACACGGCCCCCAC | 3499 |
| Hypercholesterolaemia Gln64Term tCAG-TAG | TCTGTCACCTGCAAATCCGGGGACTTCAGCTGTGGGGCCG TGTCAACCGCTGCATTCCTCAGTTCTGGAGGTGCGATGGCCA AGTGGACTGCGACAACGGCTCAGACGAGCAAGGCTGTC | 3500 |
| | GACAGCCTTGCTCGTCTGAGCCGTTGTCGCAGTCCACTTGGC CATCGCACCTCCAGAACTGAGGAATGCAGCGGTTGACACGG CCCCCACAGCTGAAGTCCCCGGATTTGCAGGTGACAGA | 3501 |
| | GCATTCCTCAGTTCTGG | 3502 |
| | CCAGAACTGAGGAATGC | 3503 |
| Hypercholesterolaemia Trp66Gly cTGG-GGG | ACCTGCAAATCCGGGGACTTCAGCTGTGGGGGCCGTGTCAA CCGCTGCATTCCTCAGTTCTGGAGGTGCGATGGCCAAGTGG ACTGCGACAACGGCTCAGACGAGCAAGGCTGTCGTAAGT | 3504 |
| | ACTTACGACAGCCTTGCTCGTCTGAGCCGTTGTCGCAGTCCA CTTGGCCATCGCACCTCCAGAACTGAGGAATGCAGCGGTTG ACACGGCCCCCACAGCTGAAGTCCCCGGATTTGCAGGT | 3505 |
| | CTCAGTTCTGGAGGTGC | 3506 |
| | GCACCTCCAGAACTGAG | 3507 |
| Hypercholesterolaemia Trp66Term TGG-TAG | CCTGCAAATCCGGGGACTTCAGCTGTGGGGGCCGTGTCAACC CGCTGCATTCCTCAGTTCTGGAGGTGCGATGGCCAAGTGGA CTGCGACAACGGCTCAGACGAGCAAGGCTGTCGTAAGTG | 3508 |
| | CACTTACGACAGCCTTGCTCGTCTGAGCCGTTGTCGCAGTCC ACTTGGCCATCGCACCTCCAGAACTGAGGAATGCAGCGGTTG ACACGGCCCCCACAGCTGAAGTCCCCGGATTTGCAGG | 3509 |
| | TCAGTTCTGGAGGTGCG | 3510 |
| | CGCACCTCCAGAACTGA | 3511 |
| Hypercholesterolaemia Cys68Arg gTGC-CGC | AAATCCGGGGACTTCAGCTGTGGGGCCGTGTCAACCGCTG CATTCCTCAGTTCTGGAGGTGCGATGGCCAAGTGGACTGCGA CAACGGCTCAGACGAGCAAGGCTGTCGTAAGTGTGGCC | 3512 |
| | GGCCACACTTACGACAGCCTTGCTCGTCTGAGCCGTTGTCGC AGTCCACTTGGCCATCGCACCTCCAGAACTGAGGAATGCAG CGGTTGACACGGCCCCCACAGCTGAAGTCCCCGGATTT | 3513 |
| | TCTGGAGGTGCGATGGC | 3514 |
| | GCCATCGCACCTCCAGA | 3515 |
| Hypercholesterolaemia Cys68Trp TGCg-TGG | ATCCGGGGACTTCAGCTGTGGGGCCGTGTCAACCGCTGCA TTCCTCAGTTCTGGAGGTGCGATGGCCAAGTGGACTGCGACA ACGGCTCAGACGAGCAAGGCTGTCGTAAGTGTGGCCCT | 3516 |
| | AGGGCCACACTTACGACAGCCTTGCTCGTCTGAGCCGTTGTC GCAGTCCACTTGGCCATCGCACCTCCAGAACTGAGGAATGCA GCGGTTGACACGGCCCCCACAGCTGAAGTCCCCGGAT | 3517 |
| | TGGAGGTGCGATGGCCA | 3518 |
| | TGGCCATCGCACCTCCA | 3519 |
| Hypercholesterolaemia Cys68Tyr TGC-TAC | AATCCGGGGACTTCAGCTGTGGGGCCGTGTCAACCGCTGC ATTCCTCAGTTCTGGAGGTGCGATGGCCAAGTGGACTGCGAC AACGGCTCAGACGAGCAAGGCTGTCGTAAGTGTGGCCC | 3520 |
| | GGGCCACACTTACGACAGCCTTGCTCGTCTGAGCCGTTGTC GCAGTCCACTTGGCCATCGCACCTCCAGAACTGAGGAATGCA GCGGTTGACACGGCCCCCACAGCTGAAGTCCCCGGATT | 3521 |
| | CTGGAGGTGCGATGGCC | 3522 |
| | GGCCATCGCACCTCCAG | 3523 |
| Hypercholesterolaemia Asp69Asn cGAT-AAT | TCCGGGGACTTCAGCTGTGGGGCCGTGTCAACCGCTGCAT TCCTCAGTTCTGGAGGTGCGATGGCCAAGTGGACTGCGACA ACGGCTCAGACGAGCAAGGCTGTCGTAAGTGTGGCCCTG | 3524 |
| | CAGGGCCACACTTACGACAGCCTTGCTCGTCTGAGCCGTTGT CGCAGTCCACTTGGCCATCGCACCTCCAGAACTGAGGAATG CAGCGGTTGACACGGCCCCCACAGCTGAAGTCCCCGGA | 3525 |
| | GGAGGTGCGATGGCCAA | 3526 |
| | TTGGCCATCGCACCTCC | 3527 |
| Hypercholesterolaemia Asp69Gly GAT-GGT | CCGGGGACTTCAGCTGTGGGGCCGTGTCAACCGCTGCATT CCTCAGTTCTGGAGGTGCGATGGCCAAGTGGACTGCGACAA CGGCTCAGACGAGCAAGGCTGTCGTAAGTGTGGCCCTGC | 3528 |
| | GCAGGGCCACACTTACGACAGCCTTGCTCGTCTGAGCCGTT GTCGCAGTCCACTTGGCCATCGCACCTCCAGAACTGAGGAAT GCAGCGGTTGACACGGCCCCCACAGCTGAAGTCCCCG | 3529 |
| | GAGGTGCGATGGCCAAG | 3530 |
| | CTTGGCCATCGCACCTC | 3531 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Asp69Tyr cGAT-TAT | TCCGGGGACTTCAGCTGTGGGGCCGTGTCAACCGCTGCAT TCCTCAGTTCTGGAGGTGCGATGGCCAAGTGGACTGCGACA ACGGCTCAGACGAGCAAGGCTGTCGTAAGTGTGGCCCTG | 3532 |
| | CAGGGCCACACTTACGACAGCCTTGCTCGTCTGAGCCGTTGT CGCAGTCCACTTGGCCATCGCACCTCCAGAACTGAGGAATG CAGCGGTTGACACGGCCCCCACAGCTGAAGTCCCCGGA | 3533 |
| | GGAGGTGCGATGGCCAA | 3534 |
| | TTGGCCATCGCACCTCC | 3535 |
| Hypercholesterolaemia Gln71Glu cCAA-GAA | GACTTCAGCTGTGGGGGCCGTGTCAACCGCTGCATTCCTCA GTTCTGGAGGTGCGATGGCCAAGTGGACTGCGACAACGGCT CAGACGAGCAAGGCTGTCGTAAGTGTGGCCCTGCCTTTG | 3536 |
| | CAAAGGCAGGGCCACACTTACGACAGCCTTGCTCGTCTGAG CCGTTGTCGCAGTCCACTTGGCCATCGCACCTCCAGAACTGA GGAATGCAGCGGTTGACACGGCCCCCACAGCTGAAGTC | 3537 |
| | GCGATGGCCAAGTGGAC | 3538 |
| | GTCCACTTGGCCATCGC | 3539 |
| Hypercholesterolaemia Cys74Gly cTGC-GGC | TGTGGGGCCGTGTCAACCGCTGCATTCCTCAGTTCTGGAG GTGCGATGGCCAAGTGGACTGCGACAACGGCTCAGACGAGC AAGGCTGTCGTAAGTGTGGCCCTGCCTTTGCTATTGAGC | 3540 |
| | GCTCAATAGCAAAGGCAGGGCCACACTTACGACAGCCTTGCT CGTCTGAGCCGTTGTCGCAGTCCACTTGGCCATCGCACCTC CAGAACTGAGGAATGCAGCGGTTGACACGGCCCCCACA | 3541 |
| | AAGTGGACTGCGACAAC | 3542 |
| | GTTGTCGCAGTCCACTT | 3543 |
| Hypercholesterolaemia Ser78Term TCA-TGA | TCAACCGCTGCATTCCTCAGTTCTGGAGGTGCGATGGCCAAG TGGACTGCGACAACGGCTCAGACGAGCAAGGCTGTCGTAAG TGTGGCCCTGCCTTTGCTATTGAGCCTATCTGAGTCCT | 3544 |
| | AGGACTCAGATAGGCTCAATAGCAAAGGCAGGGCCACACTTA CGACAGCCTTGCTCGTCTGAGCCGTTGTCGCAGTCCACTTGG CCATCGCACCTCCAGAACTGAGGAATGCAGCGGTTGA | 3545 |
| | CAACGGCTCAGACGAGC | 3546 |
| | GCTCGTCTGAGCCGTTG | 3547 |
| Hypercholesterolaemia Glu80Lys cGAG-AAG | CGCTGCATTCCTCAGTTCTGGAGGTGCGATGGCCAAGTGGA CTGCGACAACGGCTCAGACGAGCAAGGCTGTCGTAAGTGTG GCCCTGCCTTTGCTATTGAGCCTATCTGAGTCCTGGGGA | 3548 |
| | TCCCCAGGACTCAGATAGGCTCAATAGCAAAGGCAGGGCCA CACTTACGACAGCCTTGCTCGTCTGAGCCGTTGTCGCAGTCC ACTTGGCCATCGCACCTCCAGAACTGAGGAATGCAGCG | 3549 |
| | GCTCAGACGAGCAAGGC | 3550 |
| | GCCTTGCTCGTCTGAGC | 3551 |
| Hypercholesterolaemia Glu80Term cGAG-TAG | CGCTGCATTCCTCAGTTCTGGAGGTGCGATGGCCAAGTGGA CTGCGACAACGGCTCAGACGAGCAAGGCTGTCGTAAGTGTG GCCCTGCCTTTGCTATTGAGCCTATCTGAGTCCTGGGGA | 3552 |
| | TCCCCAGGACTCAGATAGGCTCAATAGCAAAGGCAGGGCCA CACTTACGACAGCCTTGCTCGTCTGAGCCGTTGTCGCAGTCC ACTTGGCCATCGCACCTCCAGAACTGAGGAATGCAGCG | 3553 |
| | GCTCAGACGAGCAAGGC | 3554 |
| | GCCTTGCTCGTCTGAGC | 3555 |
| Hypercholesterolaemia Gln81Term gCAA-TAA | TGCATTCCTCAGTTCTGGAGGTGCGATGGCCAAGTGGACTGC GACAACGGCTCAGACGAGCAAGGCTGTCGTAAGTGTGGCCC TGCCTTTGCTATTGAGCCTATCTGAGTCCTGGGGAGTG | 3556 |
| | CACTCCCCAGGACTCAGATAGGCTCAATAGCAAAGGCAGGG CCACACTTACGACAGCCTTGCTCGTCTGAGCCGTTGTCGCAG TCCACTTGGCCATCGCACCTCCAGAACTGAGGAATGCA | 3557 |
| | CAGACGAGCAAGGCTGT | 3558 |
| | ACAGCCTTGCTCGTCTG | 3559 |
| Hypercholesterolaemia Cys88Arg gTGC-CGC | TGGGAGACTTCACACGGTGATGGTGGTCTCGGCCCATCCAT CCCTGCAGCCCCAAGACGTGCTCCCAGGACGAGTTTCGCT GCCACGATGGGAAGTGCATCTCTCGGCAGTTCGTCTGTG | 3560 |
| | CACAGACGAACTGCCGAGAGATGCACTTCCCATCGTGGCAG CGAAACTCGTCCTGGGAGCACGTCTTGGGGGCTGCAGGGAT GGATGGGCCGAGACCACCATCACCGTGTGAAGTCTCCCA | 3561 |
| | CCAAGACGTGCTCCCAG | 3562 |
| | CTGGGAGCACGTCTTGG | 3563 |
| Hypercholesterolaemia Glu92Term cGAG-TAG | CACGGTGATGGTGGTCTCGGCCCATCCATCCCTGCAGCCCC CAAGACGTGCTCCCAGGACGAGTTTCGCTGCCACGATGGGA AGTGCATCTCTCGGCAGTTCGTCTGTGACTCAGACCGGG | 3564 |
| | CCCGGTCTGAGTCACAGACGAACTGCCGAGAGATGCACTTC CCATCGTGGCAGCGAAACTCGTCCTGGGAGCACGTCTTGGG GCTGCAGGGATGGATGGGCCGAGACCACCATCACCGTG | 3565 |
| | CCCAGGACGAGTTTCGC | 3566 |
| | GCGAAACTCGTCCTGGG | 3567 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Cys95Arg cTGC-CGC | GGTGGTCTCGGCCCATCCATCCCTGCAGCCCCCAAGACGTG CTCCCAGGACGAGTTTCGCTGCCACGATGGGAAGTGCATCT CTCGGCAGTTCGTCTGTGACTCAGACCGGGACTGCTTGG | 3568 |
| | CCAAGCAGTCCCGGTCTGAGTCACAGACGAACTGCCGAGAG ATGCACTTCCCATCGTGGCAGCGAAACTCGTCCTGGGAGCA CGTCTTGGGGGCTGCAGGGATGGATGGGCCGAGACCACC | 3569 |
| | AGTTTCGCTGCCACGAT | 3570 |
| | ATCGTGGCAGCGAAACT | 3571 |
| Hypercholesterolaemia Asp97Tyr cGAT-TAT | CTCGGCCCATCCATCCCTGCAGCCCCCAAGACGTGCTCCCA GGACGAGTTTCGCTGCCACGATGGGAAGTGCATCTCTCGGC AGTTCGTCTGTGACTCAGACCGGGACTGCTTGGACGGCT | 3572 |
| | AGCCGTCCAAGCAGTCCCGGTCTGAGTCACAGACGAACTGC CGAGAGATGCACTTCCCATCGTGGCAGCGAAACTCGTCCTG GGAGCACGTCTTGGGGGCTGCAGGGATGGATGGGCCGAG | 3573 |
| | GCTGCCACGATGGGAAG | 3574 |
| | CTTCCCATCGTGGCAGC | 3575 |
| Hypercholesterolaemia Trp(-12)Arg cTGG-AGG | GGGTCGGGACACTGCCTGGCAGAGGCTGCGAGCATGGGGC CCTGGGGCTGGAAATTGCGCTGGACCGTCGCCTTGCTCCTC GCCGCGGCGGGGACTGCAGGTAAGGCTTGCTCCAGGCGCC | 3576 |
| | GGCGCCTGGAGCAAGCCTTACCTGCAGTCCCCGCCGCGGC GAGGAGCAAGGCGACGGTCCAGCGCAATTTCCAGCCCCAGG GCCCCATGCTCGCAGCCTCTGCCAGGCAGTGTCCCGACCC | 3577 |
| | AATTGCGCTGGACCGTC | 3578 |
| | GACGGTCCAGCGCAATT | 3579 |
| Hypercholesterolaemia Trp(-18)Term TGGg-TGA | CAGCAGGTCGTGATCCGGGTCGGGACACTGCCTGGCAGAGG CTGCGAGCATGGGGCCCTGGGGCTGGAAATTGCGCTGGACC GTCGCCTTGCTCCTCGCCGCGGCGGGGACTGCAGGTAAG | 3580 |
| | CTTACCTGCAGTCCCCGCCGCGGCGAGGAGCAAGGCGACG GTCCAGCGCAATTTCCAGCCCCAGGGCCCCATGCTCGCAGC CTCTGCCAGGCAGTGTCCCGACCCGGATCACGACCTGCTG | 3581 |
| | GGGCCCTGGGGCTGGAA | 3582 |
| | TTCCAGCCCCAGGGCCC | 3583 |
| Hypercholesterolaemia Met(-21)Leu cATG-TTG | CAGCTAGGACACAGCAGGTCGTGATCCGGGTCGGGACACTG CCTGGCAGAGGCTGCGAGCATGGGGCCCTGGGGCTGGAAA TTGCGCTGGACCGTCGCCTTGCTCCTCGCCGCGGCGGGGA | 3584 |
| | TCCCCGCCGCGGCGAGGAGCAAGGCGACGGTCCAGCGCAA TTTCCAGCCCCAGGGCCCCATGCTCGCAGCCTCTGCCAGGC AGTGTCCCGACCCGGATCACGACCTGCTGTGTCCTAGCTG | 3585 |
| | CTGCGAGCATGGGGCCC | 3586 |
| | GGGCCCCATGCTCGCAG | 3587 |
| Hypercholesterolaemia Met(-21)Val cATG-GTG | CAGCTAGGACACAGCAGGTCGTGATCCGGGTCGGGACACTG CCTGGCAGAGGCTGCGAGCATGGGGCCCTGGGGCTGGAAA TTGCGCTGGACCGTCGCCTTGCTCCTCGCCGCGGCGGGGA | 3588 |
| | TCCCCGCCGCGGCGAGGAGCAAGGCGACGGTCCAGCGCAA TTTCCAGCCCCAGGGCCCCATGCTCGCAGCCTCTGCCAGGC AGTGTCCCGACCCGGATCACGACCTGCTGTGTCCTAGCTG | 3589 |
| | CTGCGAGCATGGGGCCC | 3590 |
| | GGGCCCCATGCTCGCAG | 3591 |
| Hypercholesterolaemia Ile101Phe cATC-TTC | ATCCCTGCAGCCCCCAAGACGTGCTCCCAGGACGAGTTTCG CTGCCACGATGGGAAGTGCATCTCTCGGCAGTTCGTCTGTGA CTCAGACCGGGACTGCTTGGACGGCTCAGACGAGGCCT | 3592 |
| | AGGCCTCGTCTGAGCCGTCCAAGCAGTCCCGGTCTGAGTCA CAGACGAACTGCCGAGAGATGCACTTCCCATCGTGGCAGCG AAACTCGTCCTGGGAGCACGTCTTGGGGGCTGCAGGGAT | 3593 |
| | GGAAGTGCATCTCTCGG | 3594 |
| | CCGAGAGATGCACTTCC | 3595 |
| Hypercholesterolaemia Gln104Term gCAG-TAG | GCCCCCAAGACGTGCTCCCAGGACGAGTTTCGCTGCCACGA TGGGAAGTGCATCTCTCGGCAGTTCGTCTGTGACTCAGACCG GGACTGCTTGGACGGCTCAGACGAGGCCTCCTGCCCGG | 3596 |
| | CCGGGCAGGAGGCCTCGTCTGAGCCGTCCAAGCAGTCCCG GTCTGAGTCACAGACGAACTGCCGAGAGATGCACTTCCCATC GTGGCAGCGAAACTCGTCCTGGGAGCACGTCTTGGGGGC | 3597 |
| | TCTCTCGGCAGTTCGTC | 3598 |
| | GACGAACTGCCGAGAGA | 3599 |
| Hypercholesterolaemia Cys113Arg cTGC-CGC | TTTCGCTGCCACGATGGGAAGTGCATCTCTCGGCAGTTCGTC TGTGACTCAGACCGGGACTGCTTGGACGGCTCAGACGAGGC CTCCTGCCCGGTGCTCACCTGTCCCGCCAGCTTCC | 3600 |
| | GGAAGCTGGCGGGACCACAGGTGAGCACCGGGCAGGAGGC CTCGTCTGAGCCGTCCAAGCAGTCCCGGTCTGAGTCACAGA CGAACTGCCGAGAGATGCACTTCCCATCGTGGCAGCGAAA | 3601 |
| | ACCGGGACTGCTTGGAC | 3602 |
| | GTCCAAGCAGTCCCGGT | 3603 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Glu119Lys cGAG-AAG | AAGTGCATCTCTCGGCAGTTCGTCTGTGACTCAGACCGGGAC TGCTTGGACGGCTCAGACAGGCCTCCTGCCCGGTGCTCAC CTGTGGTCCCGCCAGCTTCCAGTGCAACAGCTCCACCT | 3604 |
| | AGGTGGAGCTGTTGCACTGGAAGCTGGCGGGACCACAGGTG AGCACCGGGCAGGAGGCCTCGTCTGAGCCGTCCAAGCAGTC CCGGTCTGAGTCACAGACGAACTGCCGAGAGATGCACTT | 3605 |
| | GCTCAGACGAGGCCTCC | 3606 |
| | GGAGGCCTCGTCTGAGC | 3607 |
| Hypercholesterolaemia Glu119Term cGAG-TAG | AAGTGCATCTCTCGGCAGTTCGTCTGTGACTCAGACCGGGAC TGCTTGGACGGCTCAGACAGGCCTCCTGCCCGGTGCTCAC CTGTGGTCCCGCCAGCTTCCAGTGCAACAGCTCCACCT | 3608 |
| | AGGTGGAGCTGTTGCACTGGAAGCTGGCGGGACCACAGGTG AGCACCGGGCAGGAGGCCTCGTCTGAGCCGTCCAAGCAGTC CCGGTCTGAGTCACAGACGAACTGCCGAGAGATGCACTT | 3609 |
| | GCTCAGACGAGGCCTCC | 3610 |
| | GGAGGCCTCGTCTGAGC | 3611 |
| Hypercholesterolaemia Cys122Term TGCc-TGA | TCGGCAGTTCGTCTGTGACTCAGACCGGGACTGCTTGGACG GCTCAGACGAGGCCTCCTGCCCGGTGCTCACCTGTGGTCCC GCCAGCTTCCAGTGCAACAGCTCCACCTGCATCCCCCAG | 3612 |
| | CTGGGGGATGCAGGTGGAGCTGTTGCACTGGAAGCTGGCGG GACCACAGGTGAGCACCGGGCAGGAGGCCTCGTCTGAGCC GTCCAAGCAGTCCCGGTCTGAGTCACAGACGAACTGCCGA | 3613 |
| | GCCTCCTGCCCGGTGCT | 3614 |
| | AGCACCGGGCAGGAGGC | 3615 |
| Hypercholesterolaemia Cys127Trp TGTg-TGG | TGACTCAGACCGGGACTGCTTGGACGGCTCAGACGAGGCCT CCTGCCCGGTGCTCACCTGTGGTCCCGCCAGCTTCCAGTGC AACAGCTCCACCTGCATCCCCCAGCTGTGGGCCTGCGAC | 3616 |
| | GTCGCAGGCCCACAGCTGGGGGATGCAGGTGGAGCTGTTGC ACTGGAAGCTGGCGGGACCACAGGTGAGCACCGGGCAGGA GGCCTCGTCTGAGCCGTCCAAGCAGTCCCGGTCTGAGTCA | 3617 |
| | CTCACCTGTGGTCCCGC | 3618 |
| | GCGGGACCACAGGTGAG | 3619 |
| Hypercholesterolaemia Gln133Term cCAG-TAG | TGCTTGGACGGCTCAGACGAGGCCTCCTGCCCGGTGCTCAC CTGTGGTCCCGCCAGCTTCCAGTGCAACAGCTCCACCTGCAT CCCCCAGCTGTGGGCCTGCGACAACGACCCCGACTGCG | 3620 |
| | CGCCAGTCGGGGTCGTTGTCGCAGGCCCACAGCTGGGGGAT GCAGGTGGAGCTGTTGCACTGGAAGCTGGCGGGACCACAGG TGAGCACCGGGCAGGAGGCCTCGTCTGAGCCGTCCAAGCA | 3621 |
| | CCAGCTTCCAGTGCAAC | 3622 |
| | GTTGCACTGGAAGCTGG | 3623 |
| Hypercholesterolaemia Cys134Gly gTGC-GGC | TTGGACGGCTCAGACGAGGCCTCCTGCCCGGTGCTCACCTG TGGTCCCGCCAGCTTCCAGTGCAACAGCTCCACCTGCATCC CCCAGCTGTGGGCCTGCGACAACGACCCCGACTGCGAAG | 3624 |
| | CTTCGCAGTCGGGGTCGTTGTCGCAGGCCCACAGCTGGGGG ATGCAGGTGGAGCTGTTGCACTGGAAGCTGGCGGGACCACA GGTGAGCACCGGGCAGGAGGCCTCGTCTGAGCCGTCCAA | 3625 |
| | GCTTCCAGTGCAACAGC | 3626 |
| | GCTGTTGCACTGGAAGC | 3627 |
| Hypercholesterolaemia Cys139Gly cTGC-GGC | GAGGCCTCCTGCCCGGTGCTCACCTGTGGTCCCGCCAGCTT CCAGTGCAACAGCTCCACCTGCATCCCCCAGCTGTGGGCCT GCGACAACGACCCCGACTGCGAAGATGGCTCGGATGAGT | 3628 |
| | ACTCATCCGAGCCATCTTCGCAGTCGGGGTCGTTGTCGCAG GCCCACAGCTGGGGGATGCAGGTGGAGCTGTTGCACTGGAA GCTGGCGGGACCACAGGTGAGCACCGGGCAGGAGGCCTC | 3629 |
| | GCTCCACCTGCATCCCC | 3630 |
| | GGGGATGCAGGTGGAGC | 3631 |
| Hypercholesterolaemia Cys139Tyr TGC-TAC | AGGCCTCCTGCCCGGTGCTCACCTGTGGTCCCGCCAGCTTC CAGTGCAACAGCTCCACCTGCATCCCCCAGCTGTGGGCCTG CGACAACGACCCCGACTGCGAAGATGGCTCGGATGAGTG | 3632 |
| | CACTCATCCGAGCCATCTTCGCAGTCGGGGTCGTTGTCGCA GGCCCACAGCTGGGGGATGCAGGTGGAGCTGTTGCACTGGA AGCTGGCGGGACCACAGGTGAGCACCGGGCAGGAGGCCT | 3633 |
| | CTCCACCTGCATCCCCC | 3634 |
| | GGGGGATGCAGGTGGAG | 3635 |
| Hypercholesterolaemia Cys146Term TGCg-TGA | CTGTGGTCCCGCCAGCTTCCAGTGCAACAGCTCCACCTGCAT CCCCAGCTGTGGGCCTGCCGACAACGACCCCGACTGCGAAG ATGGCTCGGATGAGTGGCCGCAGCGCTAGGGGTCTT | 3636 |
| | AAGACCCCTACAGCGCTGCGGCCACTCATCCGAGCCATCTT GCAGTCGGGGTCGTTGTCGCAGGCCCACAGCTGGGGGATG CAGGTGGAGCTGTTGCACTGGAAGCTGGCGGGACCACAG | 3637 |
| | TGGGCCTGCGACAACGA | 3638 |
| | TCGTTGTCGCAGGCCCA | 3639 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Asp147Asn cGAC-AAC | TGTGGTCCCGCCAGCTTCCAGTGCAACAGCTCCACCTGCATC CCCCAGCTGTGGGCCTGCGACAACGACCCCGACTGCGAAGA TGGCTCGGATGAGTGGCCGCAGCGCTGTAGGGGTCTTT | 3640 |
| | AAAGACCCCTACAGCGCTGCGGCCACTCATCCGAGCCATCTT CGCAGTCGGGGTCGTTGTCGCAGGCCCACAGCTGGGGGAT GCAGGTGGAGCTGTTGCACTGGAAGCTGGCGGGACCACA | 3641 |
| | GGGCCTGCGACAACGAC | 3642 |
| | GTCGTTGTCGCAGGCCC | 3643 |
| Hypercholesterolaemia Asp147His cGAC-CAC | TGTGGTCCCGCCAGCTTCCAGTGCAACAGCTCCACCTGCATC CCCCAGCTGTGGGCCTGCGACAACGACCCCGACTGCGAAGA TGGCTCGGATGAGTGGCCGCAGCGCTGTAGGGGTCTTT | 3644 |
| | AAAGACCCCTACAGCGCTGCGGCCACTCATCCGAGCCATCTT CGCAGTCGGGGTCGTTGTCGCAGGCCCACAGCTGGGGGAT GCAGGTGGAGCTGTTGCACTGGAAGCTGGCGGGACCACA | 3645 |
| | GGGCCTGCGACAACGAC | 3646 |
| | GTCGTTGTCGCAGGCCC | 3647 |
| Hypercholesterolaemia Asp147Tyr cGAC-TAC | TGTGGTCCCGCCAGCTTCCAGTGCAACAGCTCCACCTGCATC CCCCAGCTGTGGGCCTGCGACAACGACCCCGACTGCGAAGA TGGCTCGGATGAGTGGCCGCAGCGCTGTAGGGGTCTTT | 3648 |
| | AAAGACCCCTACAGCGCTGCGGCCACTCATCCGAGCCATCTT CGCAGTCGGGGTCGTTGTCGCAGGCCCACAGCTGGGGGAT GCAGGTGGAGCTGTTGCACTGGAAGCTGGCGGGACCACA | 3649 |
| | GGGCCTGCGACAACGAC | 3650 |
| | GTCGTTGTCGCAGGCCC | 3651 |
| Hypercholesterolaemia Cys152Arg cTGC-CGC | TTCCAGTGCAACAGCTCCACCTGCATCCCCCAGCTGTGGGC CTGCGACAACGACCCCGACTGCGAAGATGGCTCGGATGAGT GGCCGCAGCGCTGTAGGGGTCTTTACGTGTTCCAAGGGG | 3652 |
| | CCCCTTGGAACACGTAAAGACCCCTACAGCGCTGCGGCCAC TCATCCGAGCCATCTTCGCAGTCGGGGTCGTTGTCGCAGGC CCACAGCTGGGGGATGCAGGTGGAGCTGTTGCACTGGAA | 3653 |
| | ACCCCGACTGCGAAGAT | 3654 |
| | ATCTTCGCAGTCGGGGT | 3655 |
| Hypercholesterolaemia Cys152Gly cTGC-GGC | TTCCAGTGCAACAGCTCCACCTGCATCCCCCAGCTGTGGGC CTGCGACAACGACCCCGACTGCGAAGATGGCTCGGATGAGT GGCCGCAGCGCTGTAGGGGTCTTTACGTGTTCCAAGGGG | 3656 |
| | CCCCTTGGAACACGTAAAGACCCCTACAGCGCTGCGGCCAC TCATCCGAGCCATCTTCGCAGTCGGGGTCGTTGTCGCAGGC CCACAGCTGGGGGATGCAGGTGGAGCTGTTGCACTGGAA | 3657 |
| | ACCCCGACTGCGAAGAT | 3658 |
| | ATCTTCGCAGTCGGGGT | 3659 |
| Hypercholesterolaemia Cys152Trp TGCg-TGG | CCAGTGCAACAGCTCCACCTGCATCCCCCAGCTGTGGGCCT GCGACAACGACCCCGACTGCCGAAGATGGCTCGGATGAGTGG CCGCAGCGCTGTAGGGGTCTTTACGTGTTCCAAGGGGAC | 3660 |
| | GTCCCCTTGGAACACGTAAAGACCCCTACAGCGCTGCGGCC ACTCATCCGAGCCATCTTCGCAGTCGGGGTCGTTGTCGCAG GCCCACAGCTGGGGGATGCAGGTGGAGCTGTTGCACTGG | 3661 |
| | CCCGACTGCCGAAGATGG | 3662 |
| | CCATCTTCGCAGTCGGG | 3663 |
| Hypercholesterolaemia Asp154Asn aGAT-AAT | TGCAACAGCTCCACCTGCATCCCCCAGCTGTGGGCCTGCGA CAACGACCCCGACTGCGAAGATGGCTCGGATGAGTGGCCGC AGCGCTGTAGGGGTCTTTACGTGTTCCAAGGGGACAGTA | 3664 |
| | TACTGTCCCCTTGGAACACGTAAAGACCCCTACAGCGCTGCG GCCACTCATCCGAGCCATCTTCGCAGTCGGGGTCGTTGTCG CAGGCCCACAGCTGGGGGATGCAGGTGGAGCTGTTGCA | 3665 |
| | ACTGCGAAGATGGCTCG | 3666 |
| | CGAGCCATCTTCGCAGT | 3667 |
| Hypercholesterolaemia Ser156Leu TCG-TTG | GCTCCACCTGCATCCCCCAGCTGTGGGCCTGCGACAACGAC CCCGACTGCGAAGATGGCTCGGATGAGTGGCCGCAGCGCTG TAGGGGTCTTTACGTGTTCCAAGGGGACAGTAGCCCCTG | 3668 |
| | CAGGGGCTACTGTCCCCTTGGAACACGTAAAGACCCCTACAG CGCTGCGGCCACTCATCCGAGCCATCTTCGCAGTCGGGGTC GTTGTCGCAGGCCCACAGCTGGGGGATGCAGGTGGAGC | 3669 |
| | AGATGGCTCGGATGAGT | 3670 |
| | ACTCATCCGAGCCATCT | 3671 |
| Hypercholesterolaemia Cys163Tyr TGT-TAT | TGTGGGCCTGCGACAACGACCCCGACTGCGAAGATGGCTCG GATGAGTGGCCGCAGCGCTGTAGGGGTCTTTACGTGTTCCAA GGGGACAGTAGCCCCTGCTCGGCCTTCGAGTTCCACTG | 3672 |
| | CAGTGGAACTCGAAGGCCGAGCAGGGGCTACTGTCCCCTTG GAACACGTAAAGACCCCTACAGCGCTGCGGCCACTCATCCG AGCCATCTTCGCAGTCGGGGTCGTTGTCGCAGGCCCACA | 3673 |
| | GCAGCGCTGTAGGGGTC | 3674 |
| | GACCCCTACAGCGCTGC | 3675 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Tyr167Term TACg-TAG | CAACGACCCCGACTGCGAAGATGGCTCGGATGAGTGGCCGC AGCGCTGTAGGGGTCTTTACGTGTTCCAAGGGGACAGTAGC CCCTGCTCGGCCTTCGAGTTCCACTGCCTAAGTGGCGAG | 3676 |
| | CTCGCCACTTAGGCAGTGGAACTCGAAGGCCGAGCAGGGGC TACTGTCCCCTTGGAACACGTAAAGACCCCTACAGCGCTGCG GCCACTCATCCGAGCCATCTTCGCAGTCGGGGTCGTTG | 3677 |
| | GGTCTTTACGTGTTCCA | 3678 |
| | TGGAACACGTAAAGACC | 3679 |
| Hypercholesterolaemia Gln170Term cCAA-TAA | CCCGACTGCGAAGATGGCTCGGATGAGTGGCCGCAGCGCTG TAGGGGTCTTTACGTGTTCCAAGGGGACAGTAGCCCCTGCTC GGCCTTCGAGTTCCACTGCCTAAGTGGCGAGTGCATCC | 3680 |
| | GGATGCACTCGCCACTTAGGCAGTGGAACTCGAAGGCCGAG CAGGGGCTACTGTCCCCTTGGAACACGTAAAGACCCCTACAG CGCTGCGGCCACTCATCCGAGCCATCTTCGCAGTCGGG | 3681 |
| | ACGTGTTCCAAGGGGAC | 3682 |
| | GTCCCCTTGGAACACGT | 3683 |
| Hypercholesterolaemia Cys176Phe TGC-TTC | CGGATGAGTGGCCGCAGCGCTGTAGGGGTCTTTACGTGTTC CAAGGGGACAGTAGCCCCTGCTCGGCCTTCGAGTTCCACTG CCTAAGTGGCGAGTGCATCCACTCCAGCTGGCGCTGTGA | 3684 |
| | TCACAGCGCCAGCTGGAGTGGATGCACTCGCCACTTAGGCA GTGGAACTCGAAGGCCGAGCAGGGGCTACTGTCCCCTTGGA ACACGTAAAGACCCCTACAGCGCTGCGGCCACTCATCCG | 3685 |
| | TAGCCCCTGCTCGGCCT | 3686 |
| | AGGCCGAGCAGGGGCTA | 3687 |
| Hypercholesterolaemia Cys176Tyr TGC-TAC | CGGATGAGTGGCCGCAGCGCTGTAGGGGTCTTTACGTGTTC CAAGGGGACAGTAGCCCCTGCTCGGCCTTCGAGTTCCACTG CCTAAGTGGCGAGTGCATCCACTCCAGCTGGCGCTGTGA | 3688 |
| | TCACAGCGCCAGCTGGAGTGGATGCACTCGCCACTTAGGCA GTGGAACTCGAAGGCCGAGCAGGGGCTACTGTCCCCTTGGA ACACGTAAAGACCCCTACAGCGCTGCGGCCACTCATCCG | 3689 |
| | TAGCCCCTGCTCGGCCT | 3690 |
| | AGGCCGAGCAGGGGCTA | 3691 |
| Hypercholesterolaemia Ser177Leu TCG-TTG | ATGAGTGGCCGCAGCGCTGTAGGGGTCTTTACGTGTTCCAAG GGGACAGTAGCCCCTGCTCGGCCTTCGAGTTCCACTGCCTA AGTGGCGAGTGCATCCACTCCAGCTGGCGCTGTGATGG | 3692 |
| | CCATCACAGCGCCAGCTGGAGTGGATGCACTCGCCACTTAG GCAGTGGAACTCGAAGGCCGAGCAGGGGCTACTGTCCCCTT GGAACACGTAAAGACCCCTACAGCGCTGCGGCCACTCAT | 3693 |
| | CCCCTGCTCGGCCTTCG | 3694 |
| | CGAAGGCCGAGCAGGGG | 3695 |
| Hypercholesterolaemia Glu187Lys cGAG-AAG | TACGTGTTCCAAGGGGACAGTAGCCCCTGCTCGGCCTTCGA GTTCCACTGCCTAAGTGGCGAGTGCATCCACTCCAGCTGGC GCTGTGATGGTGCCCCGACTGCAAGGACAAATCTGACG | 3696 |
| | CGTCAGATTTGTCCTTGCAGTCGGGGCCACCATCACAGCGC CAGCTGGAGTGGATGCACTCGCCACTTAGGCAGTGGAACTC GAAGGCCGAGCAGGGGCTACTGTCCCCTTGGAACACGTA | 3697 |
| | TAAGTGGCGAGTGCATC | 3698 |
| | GATGCACTCGCCACTTA | 3699 |
| Hypercholesterolaemia His190Tyr cCAC-TAC | CAAGGGGACAGTAGCCCCTGCTCGGCCTTCGAGTTCCACTG CCTAAGTGGCGAGTGCATCCACTCCAGCTGGCGCTGTGATG GTGGCCCCGACTGCAAGGACAAATCTGACGAGGAAAACT | 3700 |
| | AGTTTTCCTCGTCAGATTTGTCCTTGCAGTCGGGGCCACCAT CACAGCGCCAGCTGGAGTGGATGCACTCGCCACTTAGGCAG TGGAACTCGAAGGCCGAGCAGGGGCTACTGTCCCCTTG | 3701 |
| | AGTGCATCCACTCCAGC | 3702 |
| | GCTGGAGTGGATGCACT | 3703 |
| Hypercholesterolaemia Gly198Asp GGC-GAC | CCTTCGAGTTCCACTGCCTAAGTGGCGAGTGCATCCACTCCA GCTGGCGCTGTGATGGTGGCCCCGACTGCAAGGACAAATCT GACGAGGAAAACTGCGGTATGGGCGGGGCCAGGGTGGG | 3704 |
| | CCCACCCTGGCCCCGCCCATACCGCAGTTTTCCTCGTCAGAT TTGTCCTTGCAGTCGGGGCCACCATCACAGCGCCAGCTGGA GTGGATGCACTCGCCACTTAGGCAGTGGAACTCGAAGG | 3705 |
| | TGATGGTGGCCCCGACT | 3706 |
| | AGTCGGGGCCACCATCA | 3707 |
| Hypercholesterolaemia Asp200Asn cGAC-AAC | GAGTTCCACTGCCTAAGTGGCGAGTGCATCCACTCCAGCTG GCGCTGTGATGGTGGCCCCGACTGCAAGGACAAATCTGACG AGGAAAACTGCGGTATGGGCGGGGCCAGGGTGGGGCGG | 3708 |
| | CCGCCCCACCCTGGCCCCGCCCATACCGCAGTTTTCCTCG TCAGATTTGTCCTTGCAGTCGGGGCCACCATCACAGCGCCAG CTGGAGTGGATGCACTCGCCACTTAGGCAGTGGAACTC | 3709 |
| | GTGGCCCCGACTGCAAG | 3710 |
| | CTTGCAGTCGGGGCCAC | 3711 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Asp200Gly GAC-GGC | AGTTCCACTGCCTAAGTGGCGAGTGCATCCACTCCAGCTGGC GCTGTGATGGTGGCCCCGACTGCAAGGACAAATCTGACGAG GAAAACTGCGGTATGGGCGGGGCCAGGGTGGGGCGGG | 3712 |
| | CCCGCCCCCACCCTGGCCCCGCCCATACCGCAGTTTTCCTC GTCAGATTTGTCCTTGCAGTCGGGGCCACCATCACAGCGCCA GCTGGAGTGGATGCACTCGCCACTTAGGCAGTGGAACT | 3713 |
| | TGGCCCCGACTGCAAGG | 3714 |
| | CCTTGCAGTCGGGGCCA | 3715 |
| Hypercholesterolaemia Asp200Tyr cGAC-TAC | GAGTTCCACTGCCTAAGTGGCGAGTGCATCCACTCCAGCTG GCGCTGTGATGGTGGCCCCGACTGCAAGGACAAATCTGACG AGGAAAACTGCGGTATGGGCGGGGCCAGGGTGGGGCGG | 3716 |
| | CCGCCCCCACCCTGGCCCCGCCCATACCGCAGTTTTCCTCG TCAGATTTGTCCTTGCAGTCGGGGCCACCATCACAGCGCCAG CTGGAGTGGATGCACTCGCCACTTAGGCAGTGGAACTC | 3717 |
| | GTGGCCCCGACTGCAAG | 3718 |
| | CTTGCAGTCGGGGCCAC | 3719 |
| Hypercholesterolaemia Cys201Term TGCa-TGA | CCACTGCCTAAGTGGCGAGTGCATCCACTCCAGCTGGCGCT GTGATGGTGGCCCCGACTGCAAGGACAAATCTGACGAGGAA AACTGCGGTATGGGCGGGGCCAGGGTGGGGCGGGGCGT | 3720 |
| | ACGCCCCGCCCCCACCCTGGCCCCGCCCATACCGCAGTTTT CCTCGTCAGATTTGTCCTTGCAGTCGGGGCCACCATCACAGC GCCAGCTGGAGTGGATGCACTCGCCACTTAGGCAGTGG | 3721 |
| | CCCGACTGCAAGGACAA | 3722 |
| | TTGTCCTTGCAGTCGGG | 3723 |
| Hypercholesterolaemia Cys201Tyr TGC-TAC | TCCACTGCCTAAGTGGCGAGTGCATCCACTCCAGCTGGCGC TGTGATGGTGGCCCCGACTGCAAGGACAAATCTGACGAGGA AAACTGCGGTATGGGCGGGGCCAGGGTGGGGCGGGGCG | 3724 |
| | CGCCCCGCCCCCACCCTGGCCCCGCCCATACCGCAGTTTTC CTCGTCAGATTTGTCCTTGCAGTCGGGGCCACCATCACAGCG CCAGCTGGAGTGGATGCACTCGCCACTTAGGCAGTGGA | 3725 |
| | CCCCGACTGCAAGGACA | 3726 |
| | TGTCCTTGCAGTCGGGG | 3727 |
| Hypercholesterolaemia Asp203Asn gGAC-AAC | TGCCTAAGTGGCGAGTGCATCCACTCCAGCTGGCGCTGTGA TGGTGGCCCCGACTGCAAGGACAAATCTGACGAGGAAAACT GCGGTATGGGCGGGGCCAGGGTGGGGCGGGGCGTCCTA | 3728 |
| | TAGGACGCCCCGCCCCCACCCTGGCCCCGCCCATACCGCA GTTTTCCTCGTCAGATTTGTCCTTGCAGTCGGGGCCACCATC ACAGCGCCAGCTGGAGTGGATGCACTCGCCACTTAGGCA | 3729 |
| | ACTGCAAGGACAAATCT | 3730 |
| | AGATTTGTCCTTGCAGT | 3731 |
| Hypercholesterolaemia Asp203Gly GAC-GGC | GCCTAAGTGGCGAGTGCATCCACTCCAGCTGGCGCTGTGAT GGTGGCCCCGACTGCAAGGACAAATCTGACGAGGAAAACTG CGGTATGGGCGGGGCCAGGGTGGGGCGGGGCGTCCTAT | 3732 |
| | ATAGGACGCCCCGCCCCCACCCTGGCCCCGCCCATACCGCA GTTTTCCTCGTCAGATTTGTCCTTGCAGTCGGGGCCACCATC ACAGCGCCAGCTGGAGTGGATGCACTCGCCACTTAGGC | 3733 |
| | CTGCAAGGACAAATCTG | 3734 |
| | CAGATTTGTCCTTGCAG | 3735 |
| Hypercholesterolaemia Asp203Val GAC-GTC | GCCTAAGTGGCGAGTGCATCCACTCCAGCTGGCGCTGTGAT GGTGGCCCCGACTGCAAGGACAAATCTGACGAGGAAAACTG CGGTATGGGCGGGGCCAGGGTGGGGCGGGGCGTCCTAT | 3736 |
| | ATAGGACGCCCCGCCCCCACCCTGGCCCCGCCCATACCGCA GTTTTCCTCGTCAGATTTGTCCTTGCAGTCGGGGCCACCATC ACAGCGCCAGCTGGAGTGGATGCACTCGCCACTTAGGC | 3737 |
| | CTGCAAGGACAAATCTG | 3738 |
| | CAGATTTGTCCTTGCAG | 3739 |
| Hypercholesterolaemia Ser205Pro aTCT-CCT | AGTGGCGAGTGCATCCACTCCAGCTGGCGCTGTGATGGTGG CCCCGACTGCAAGGACAAATCTGACGAGGAAAACTGCGGTAT GGGCGGGGCCAGGGTGGGGCGGGGCGTCCTATCACCT | 3740 |
| | AGGTGATAGGACGCCCCGCCCCCACCCTGGCCCCGCCCATA CCGCAGTTTTCCTCGTCAGATTTGTCCTTGCAGTCGGGGCCA CCATCACAGCGCCAGCTGGAGTGGATGCACTCGCCACT | 3741 |
| | AGGACAAATCTGACGAG | 3742 |
| | CTCGTCAGATTTGTCCT | 3743 |
| Hypercholesterolaemia Asp206Glu GACg-GAG | CGAGTGCATCCACTCCAGCTGGCGCTGTGATGGTGGCCCCG ACTGCAAGGACAAATCTGACGAGGAAAACTGCGGTATGGGC GGGGCCAGGGTGGGGCGGGGCGTCCTATCACCTGTCCC | 3744 |
| | GGGACAGGTGATAGGACGCCCCGCCCCCACCCTGGCCCCG CCCATACCGCAGTTTTCCTCGTCAGATTTGTCCTTGCAGTCG GGGCCACCATCACAGCGCCAGCTGGAGTGGATGCACTCG | 3745 |
| | AAATCTGACGAGGAAAA | 3746 |
| | TTTTCCTCGTCAGATTT | 3747 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Glu207Gln cGAG-CAG | GAGTGCATCCACTCCAGCTGGCGCTGTGATGGTGGCCCCGA CTGCAAGGACAAATCTGACGAGGAAAACTGCGGTATGGGCG GGGCCAGGGTGGGGCGGGGCGTCCTATCACCTGTCCCT | 3748 |
| | AGGGACAGGTGATAGGACGCCCCGCCCCCACCCTGGCCCC GCCCATACCGCAGTTTTCCTCGTCAGATTTGTCCTTGCAGTC GGGGCCACCATCACAGCGCCAGCTGGAGTGGATGCACTC | 3749 |
| | AATCTGACGAGGAAAAC | 3750 |
| | GTTTTCCTCGTCAGATT | 3751 |
| Hypercholesterolaemia Glu207Lys cGAG-AAG | GAGTGCATCCACTCCAGCTGGCGCTGTGATGGTGGCCCCGA CTGCAAGGACAAATCTGACGAGGAAAACTGCGGTATGGGCG GGGCCAGGGTGGGGCGGGGCGTCCTATCACCTGTCCCT | 3752 |
| | AGGGACAGGTGATAGGACGCCCCGCCCCCACCCTGGCCCC GCCCATACCGCAGTTTTCCTCGTCAGATTTGTCCTTGCAGTC GGGGCCACCATCACAGCGCCAGCTGGAGTGGATGCACTC | 3753 |
| | AATCTGACGAGGAAAAC | 3754 |
| | GTTTTCCTCGTCAGATT | 3755 |
| Hypercholesterolaemia Glu207Term cGAG-TAG | GAGTGCATCCACTCCAGCTGGCGCTGTGATGGTGGCCCCGA CTGCAAGGACAAATCTGACGAGGAAAACTGCGGTATGGGCG GGGCCAGGGTGGGGCGGGGCGTCCTATCACCTGTCCCT | 3756 |
| | AGGGACAGGTGATAGGACGCCCCGCCCCCACCCTGGCCCC GCCCATACCGCAGTTTTCCTCGTCAGATTTGTCCTTGCAGTC GGGGCCACCATCACAGCGCCAGCTGGAGTGGATGCACTC | 3757 |
| | AATCTGACGAGGAAAAC | 3758 |
| | GTTTTCCTCGTCAGATT | 3759 |
| Hypercholesterolaemia Glu219Lys cGAA-AAA | TCTTGAGAAAATCAACACACTCTGTCCTGTTTTCCAGCTGTGG CCACCTGTCGCCCTGACGAATTCCAGTGCTCTGATGGAAACT GCATCCATGGCAGCCGGCAGTGTGACCGGGAATATG | 3760 |
| | CATATTCCCGGTCACACTGCCGGCTGCCATGGATGCAGTTTC CATCAGAGCACTGGAATTCGTCAGGGCGACAGGTGGCCACA GCTGGAAAACAGGACAGAGTGTGTTGATTTTCTCAAGA | 3761 |
| | GCCCTGACGAATTCCAG | 3762 |
| | CTGGAATTCGTCAGGGC | 3763 |
| Hypercholesterolaemia Gln221Term cCAG-TAG | GAAAATCAACACACTCTGTCCTGTTTTCCAGCTGTGGCCACCT GTCGCCCTGACGAATTCCAGTGCTCTGATGGAAACTGCATCC ATGGCAGCCGGCAGTGTGACCGGGAATATGACTGCA | 3764 |
| | TGCAGTCATATTCCCGGTCACACTGCCGGCTGCCATGGATGC AGTTTCCATCAGAGCACTGGAATTCGTCAGGGCGACAGGTGG CCACAGCTGGAAAACAGGACAGAGTGTGTTGATTTTC | 3765 |
| | ACGAATTCCAGTGCTCT | 3766 |
| | AGAGCACTGGAATTCGT | 3767 |
| Hypercholesterolaemia Cys227Phe TGC-TTC | CCTGTTTTCCAGCTGTGGCCACCTGTCGCCCTGACGAATTCC AGTGCTCTGATGGAAACTGCATCCATGGCAGCCGGCAGTGT GACCGGGAATATGACTGCAAGGACATGAGCGATGAAGT | 3768 |
| | ACTTCATCGCTCATGTCCTTGCAGTCATATTCCCGGTCACACT GCCGGCTGCCATGGATGCAGTTTCCATCAGAGCACTGGAATT CGTCAGGGCGACAGGTGGCCACAGCTGGAAAACAGG | 3769 |
| | TGGAAACTGCATCCATG | 3770 |
| | CATGGATGCAGTTTCCA | 3771 |
| Hypercholesterolaemia Asp235Glu GACc-GAA | TCGCCCTGACGAATTCCAGTGCTCTGATGGAAACTGCATCCA TGGCAGCCGGCAGTGTGACCGGGAATATGACTGCAAGGACA TGAGCGATGAAGTTGGCTGCGTTAATGGTGAGCGCTGG | 3772 |
| | CCAGCGCTCACCATTAACGCAGCCAACTTCATCGCTCATGTC CTTGCAGTCATATTCCCGGTCACACTGCCGGCTGCCATGGAT GCAGTTTCCATCAGAGCACTGGAATTCGTCAGGGCGA | 3773 |
| | CAGTGTGACCGGGAATA | 3774 |
| | TATTCCCGGTCACACTG | 3775 |
| Hypercholesterolaemia Asp235Gly GAC-GGC | GTCGCCCTGACGAATTCCAGTGCTCTGATGGAAACTGCATCC ATGGCAGCCGGCAGTGTGACCGGGAATATGACTGCAAGGAC ATGAGCGATGAAGTTGGCTGCGTTAATGGTGAGCGCTG | 3776 |
| | CAGCGCTCACCATTAACGCAGCCAACTTCATCGCTCATGTCC TTGCAGTCATATTCCCGGTCACACTGCCGGCTGCCATGGATG CAGTTTCCATCAGAGCACTGGAATTCGTCAGGGCGAC | 3777 |
| | GCAGTGTGACCGGGAAT | 3778 |
| | ATTCCCGGTCACACTGC | 3779 |
| Hypercholesterolaemia Glu237Lys gGAA-AAA | CCTGACGAATTCCAGTGCTCTGATGGAAACTGCATCCATGGC AGCCGGCAGTGTGACCGGGAATATGACTGCAAGGACATGAG CGATGAAGTTGGCTGCGTTAATGGTGAGCGCTGGCCAT | 3780 |
| | ATGGCCAGCGCTCACCATTAACGCAGCCAACTTCATCGCTCA TGTCCTTGCAGTCATATTCCCGGTCACACTGCCGGCTGCCAT GGATGCAGTTTCCATCAGAGCACTGGAATTCGTCAGG | 3781 |
| | GTGACCGGGAATATGAC | 3782 |
| | GTCATATTCCCGGTCAC | 3783 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Cys240Phe TGC-TTC | TCCAGTGCTCTGATGGAAACTGCATCCATGGCAGCCGGCAGT GTGACCGGGAATATGACTGCAAGGACATGAGCGATGAAGTTG GCTGCGTTAATGGTGAGCGCTGGCCATCTGGTTTTCC | 3784 |
| | GGAAAACCAGATGGCCAGCGCTCACCATTAACGCAGCCAACT TCATCGCTCATGTCCTTGCAGTCATATTCCCGGTCACACTGC CGGCTGCCATGGATGCAGTTTCCATCAGAGCACTGGA | 3785 |
| | ATATGACTGCAAGGACA | 3786 |
| | TGTCCTTGCAGTCATAT | 3787 |
| Hypercholesterolaemia Asp245Glu GATg-GAA | AAACTGCATCCATGGCAGCCGGCAGTGTGACCGGGAATATG ACTGCAAGGACATGAGCGATGAAGTTGGCTGCGTTAATGGTG AGCGCTGGCCATCTGGTTTTCCATCCCCCATTCTCTGT | 3788 |
| | ACAGAGAATGGGGGATGGAAAACCAGATGGCCAGCGCTCAC CATTAACGCAGCCAACTTCATCGCTCATGTCCTTGCAGTCATA TTCCCGGTCACACTGCCGGCTGCCATGGATGCAGTTT | 3789 |
| | ATGAGCGATGAAGTTGG | 3790 |
| | CCAACTTCATCGCTCAT | 3791 |
| Hypercholesterolaemia Cys249Tyr TGC-TAC | ATGGCAGCCGGCAGTGTGACCGGGAATATGACTGCAAGGAC ATGAGCGATGAAGTTGGCTGCGTTAATGGTGAGCGCTGGCC ATCTGGTTTTCCATCCCCCATTCTCTGTGCCTTGCTGCT | 3792 |
| | AGCAGCAAGGCACAGAGAATGGGGGATGGAAAACCAGATGG CCAGCGCTCACCATTAACCCAGCCAACTTCATCGCTCATGTC CTTGCAGTCATATTCCCGGTCACACTGCCGGCTGCCAT | 3793 |
| | AGTTGGCTGCGTTAATG | 3794 |
| | CATTAACGCAGCCAACT | 3795 |
| Hypercholesterolaemia Glu256Lys cGAG-AAG | AGGCTCAGACACACCTGACCTTCCTCCTTCCTCTCTCTGGCT CTCACAGTGACACTCTGCGAGGGACCCAACAAGTTCAAGTGT CACAGCGGCGAATGCATCACCCTGGACAAAGTCTGCA | 3796 |
| | TGCAGACTTTGTCCAGGGTGATGCATTCGCCGCTGTGACACT TGAACTTGTTGGGTCCCTCGCAGAGTGTCACTGTGAGAGCCA GAGAGAGGAAGGAGGAAGGTCAGGTGTGTCTGAGCCT | 3797 |
| | CACTCTGCGAGGGACCC | 3798 |
| | GGGTCCCTCGCAGAGTG | 3799 |
| Hypercholesterolaemia Ser265Arg AGCg-AGA | CCTCTCTCTGGCTCTCACAGTGACACTCTGCGAGGGACCCAA CAAGTTCAAGTGTCACAGCGGCGAATGCATCACCCTGGACAA AGTCTGCAACATGGCTAGAGACTGCCGGGACTGGTCA | 3800 |
| | TGACCAGTCCCGGCAGTCTCTAGCCATGTTGCAGACTTTGTC CAGGGTGATGCATTCGCCGCTGTGACACTTGAACTTGTTGGG TCCCTCGCAGAGTGTCACTGTGAGAGCCAGAGAGAGG | 3801 |
| | TGTCACAGCGGCGAATG | 3802 |
| | CATTCGCCGCTGTGACA | 3803 |
| Hypercholesterolaemia Glu267Lys cGAA-AAA | TCTCTGGCTCTCACAGTGACACTCTGCGAGGGACCCAACAAG TTCAAGTGTCACAGCGGCGAATGCATCACCCTGGACAAAGTC TGCAACATGGCTAGAGACTGCCGGGACTGGTCAGATG | 3804 |
| | CATCTGACCAGTCCCGGCAGTCTCTAGCCATGTTGCAGACTT TGTCCAGGGTGATGCATTCGCCGCTGTGACACTTGAACTTGT TGGGTCCCTCGCAGAGTGTCACTGTGAGAGCCAGAGA | 3805 |
| | ACAGCGGCGAATGCATC | 3806 |
| | GATGCATTCGCCGCTGT | 3807 |
| Hypercholesterolaemia Glu267Term cGAA-TAA | TCTCTGGCTCTCACAGTGACACTCTGCGAGGGACCCAACAAG TTCAAGTGTCACAGCGGCGAATGCATCACCCTGGACAAAGTC TGCAACATGGCTAGAGACTGCCGGGACTGGTCAGATG | 3808 |
| | CATCTGACCAGTCCCGGCAGTCTCTAGCCATGTTGCAGACTT TGTCCAGGGTGATGCATTCGCCGCTGTGACACTTGAACTTGT TGGGTCCCTCGCAGAGTGTCACTGTGAGAGCCAGAGA | 3809 |
| | ACAGCGGCGAATGCATC | 3810 |
| | GATGCATTCGCCGCTGT | 3811 |
| Hypercholesterolaemia Lys273Glu cAAA-GAA | ACACTCTGCGAGGGACCCAACAAGTTCAAGTGTCACAGCGG CGAATGCATCACCCTGGACAAAGTCTGCAACATGGCTAGAGA CTGCCGGGACTGGTCAGATGAACCCATCAAAGAGTGCG | 3812 |
| | CGCACTCTTTGATGGGTTCATCTGACCAGTCCCGGCAGTCTC TAGCCATGTTGCAGACTTTGTCCAGGGTGATGCATTCGCCGC TGTGACACTTGAACTTGTTGGGTCCCTCGCAGAGTGT | 3813 |
| | CCCTGGACAAAGTCTGC | 3814 |
| | GCAGACTTTGTCCAGGG | 3815 |
| Hypercholesterolaemia Cys275Term TGCa-TGA | CGAGGGACCCAACAAGTTCAAGTGTCACAGCGGCGAATGCA TCACCCTGGACAAAGTCTGCAACATGGCTAGAGACTGCCGG GACTGGTCAGATGAACCCATCAAAGAGTGCGGTGAGTCT | 3816 |
| | AGACTCACCGCACTCTTTGATGGGTTCATCTGACCAGTCCCG GCAGTCTCTAGCCATGTTGCAGACTTTGTCCAGGGTGATGCA TTCGCCGCTGTGACACTTGAACTTGTTGGGTCCCTCG | 3817 |
| | AAAGTCTGCAACATGGC | 3818 |
| | GCCATGTTGCAGACTTT | 3819 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Asp280Gly GAC-GGC | AGTTCAAGTGTCACAGCGGCGAATGCATCACCCTGGACAAAG TCTGCAACATGGCTAGAGACTGCCGGGACTGGTCAGATGAA CCCATCAAAGAGTGCGGTGAGTCTCGGTGCAGGCGGCT | 3820 |
| | AGCCGCCTGCACCGAGACTCACCGCACTCTTTGATGGGTTCA TCTGACCAGTCCCGGCAGTCTCTAGCCATGTTGCAGACTTTG TCCAGGGTGATGCATTCGCCGCTGTGACACTTGAACT | 3821 |
| | GGCTAGAGACTGCCGGG | 3822 |
| | CCCGGCAGTCTCTAGCC | 3823 |
| Hypercholesterolaemia Cys281Tyr TGC-TAC | TCAAGTGTCACAGCGGCGAATGCATCACCCTGGACAAAGTCT GCAACATGGCTAGAGACTGCCGGGACTGGTCAGATGAACCC ATCAAAGAGTGCGGTGAGTCTCGGTGCAGGCGGCTTGC | 3824 |
| | GCAAGCCGCCTGCACCGAGACTCACCGCACTCTTTGATGGG TTCATCTGACCAGTCCCGGCAGTCTCTAGCCATGTTGCAGAC TTTGTCCAGGGTGATGCATTCGCCGCTGTGACACTTGA | 3825 |
| | TAGAGACTGCCGGGACT | 3826 |
| | AGTCCCGGCAGTCTCTA | 3827 |
| Hypercholesterolaemia Asp283Asn gGAC-AAC | TGTCACAGCGGCGAATGCATCACCCTGGACAAAGTCTGCAAC ATGGCTAGAGACTGCCGGGACTGGTCAGATGAACCCATCAAA GAGTGCGGTGAGTCTCGGTGCAGGCGGCTTGCAGAGT | 3828 |
| | ACTCTGCAAGCCGCCTGCACCGAGACTCACCGCACTCTTTGA TGGGTTCATCTGACCAGTCCCGGCAGTCTCTAGCCATGTTGC AGACTTTGTCCAGGGTGATGCATTCGCCGCTGTGACA | 3829 |
| | ACTGCCGGGACTGGTCA | 3830 |
| | TGACCAGTCCCGGCAGT | 3831 |
| Hypercholesterolaemia Asp283Glu GACt-GAG | TCACAGCGGCGAATGCATCACCCTGGACAAAGTCTGCAACAT GGCTAGAGACTGCCGGGACTGGTCAGATGAACCCATCAAAG AGTGCGGTGAGTCTCGGTGCAGGCGGCTTGCAGAGTTT | 3832 |
| | AAACTCTGCAAGCCGCCTGCACCGAGACTCACCGCACTCTTT GATGGGTTCATCTGACCAGTCCCGGCAGTCTCTAGCCATGTT GCAGACTTTGTCCAGGGTGATGCATTCGCCGCTGTGA | 3833 |
| | TGCCGGGACTGGTCAGA | 3834 |
| | TCTGACCAGTCCCGGCA | 3835 |
| Hypercholesterolaemia Asp283Tyr gGAC-TAC | TGTCACAGCGGCGAATGCATCACCCTGGACAAAGTCTGCAAC ATGGCTAGAGACTGCCGGGACTGGTCAGATGAACCCATCAAA GAGTGCGGTGAGTCTCGGTGCAGGCGGCTTGCAGAGT | 3836 |
| | ACTCTGCAAGCCGCCTGCACCGAGACTCACCGCACTCTTTGA TGGGTTCATCTGACCAGTCCCGGCAGTCTCTAGCCATGTTGC AGACTTTGTCCAGGGTGATGCATTCGCCGCTGTGACA | 3837 |
| | ACTGCCGGGACTGGTCA | 3838 |
| | TGACCAGTCCCGGCAGT | 3839 |
| Hypercholesterolaemia Trp284Term TGGt-TGA | CAGCGGCGAATGCATCACCCTGGACAAAGTCTGCAACATGG CTAGAGACTGCCGGGACTGGTCAGATGAACCCATCAAAGAGT GCGGTGAGTCTCGGTGCAGGCGCTTGCAGAGTTTGTG | 3840 |
| | CACAAACTCTGCAAGCCGCCTGCACCGAGACTCACCGCACT CTTTGATGGGTTCATCTGACCAGTCCCGGCAGTCTCTAGCCA TGTTGCAGACTTTGTCCAGGGTGATGCATTCGCCGCT | 3841 |
| | CGGGACTGGTCAGATGA | 3842 |
| | TCATCTGACCAGTCCCG | 3843 |
| Hypercholesterolaemia Ser285Leu TCA-TTA | GCGGCGAATGCATCACCCTGGACAAAGTCTGCAACATGGCTA GAGACTGCCGGGACTGGTCAGATGAACCCATCAAAGAGTGC GGTGAGTCTCGGTGCAGGCGGCTTGCAGAGTTTGTGGG | 3844 |
| | CCCACAAACTCTGCAAGCCGCCTGCACCGAGACTCACCGCA CTCTTTGATGGGTTCATCTGACCAGTCCCGGCAGTCTCTAGC CATGTTGCAGACTTTGTCCAGGGTGATGCATTCGCCGC | 3845 |
| | GGACTGGTCAGATGAAC | 3846 |
| | GTTCATCTGACCAGTCC | 3847 |
| Hypercholesterolaemia Lys290Arg AAA-AGA | CCCTGGACAAAGTCTGCAACATGGCTAGAGACTGCCGGGAC TGGTCAGATGAACCCATCAAAGAGTGCGGTGAGTCTCGGTG CAGGCGGCTTGCAGAGTTTGTGGGGAGCCAGGAAAGGGA | 3848 |
| | TCCCTTTCCTGGCTCCCCACAAACTCTGCAAGCCGCCTGCAC CGAGACTCACCGCACTCTTTGATGGGTTCATCTGACCAGTCC CGGCAGTCTCTAGCCATGTTGCAGACTTTGTCCAGGG | 3849 |
| | ACCCATCAAAGAGTGCG | 3850 |
| | CGCACTCTTTGATGGGT | 3851 |
| Hypercholesterolaemia Cys297Phe TGC-TTC | GGGTAGGGGCCCGAGAGTGACCAGTCTGCATCCCCTGGCCC TGCGCAGGGACCAACGAATGCTTGGACAACAACGGCGGCTG TTCCCACGTCTGCAATGACCTTAAGATCGGCTACGAGTG | 3852 |
| | CACTCGTAGCCGATCTTAAGGTCATTGCAGACGTGGGAACAG CCGCCGTTGTTGTCCAAGCATTCGTTGGTCCCTGCGCAGGG CCAGGGGATGCAGACTGGTCACTCTCGGGCCCCTACCC | 3853 |
| | CAACGAATGCTTGGACA | 3854 |
| | TGTCCAAGCATTCGTTG | 3855 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Cys297Tyr TGC-TAC | GGGTAGGGGCCCGAGAGTGACCAGTCTGCATCCCCTGGCCC TGCGCAGGGACCAACGAATGCTTGGACAACAACGGCGGCTG TTCCCACGTCTGCAATGACCTTAAGATCGGCTACGAGTG | 3856 |
| | CACTCGTAGCCGATCTTAAGGTCATTGCAGACGTGGGAACAG CCGCCGTTGTTGTCCAAGCATTCGTTGGTCCCTGCGCAGGG CCAGGGGATGCAGACTGGTCACTCTCGGGCCCCTACCC | 3857 |
| | CAACGAATGCTTGGACA | 3858 |
| | TGTCCAAGCATTCGTTG | 3859 |
| Hypercholesterolaemia His306Tyr cCAC-TAC | TGCATCCCCTGGCCCTGCGCAGGGACCAACGAATGCTTGGA CAACAACGGCGGCTGTTCCCACGTCTGCAATGACCTTAAGAT CGGCTACGAGTGCCTGTGCCCCGACGGCTTCCAGCTGG | 3860 |
| | CCAGCTGGAAGCCGTCGGGGCACAGGCACTCGTAGCCGATC TTAAGGTCATTGCAGACGTGGGAACAGCCGCCGTTGTTGTCC AAGCATTCGTTGGTCCCTGCGCAGGGCCAGGGGATGCA | 3861 |
| | GCTGTTCCCACGTCTGC | 3862 |
| | GCAGACGTGGGAACAGC | 3863 |
| Hypercholesterolaemia Cys308Gly cTGC-GGC | CCCTGGCCCTGCGCAGGGACCAACGAATGCTTGGACAACAA CGGCGGCTGTTCCCACGTCTGCAATGACCTTAAGATCGGCTA CGAGTGCCTGTGCCCCGACGGCTTCCAGCTGGTGGCCC | 3864 |
| | GGGCCACCAGCTGGAAGCCGTCGGGGCACAGGCACTCGTA GCCGATCTTAAGGTCATTGCAGACGTGGGAACAGCCGCCGT TGTTGTCCAAGCATTCGTTGGTCCCTGCGCAGGGCCAGGG | 3865 |
| | CCCACGTCTGCAATGAC | 3866 |
| | GTCATTGCAGACGTGGG | 3867 |
| Hypercholesterolaemia Cys308Tyr TGC-TAC | CCTGGCCCTGCGCAGGGACCAACGAATGCTTGGACAACAAC GGCGGCTGTTCCCACGTCTGCAATGACCTTAAGATCGGCTAC GAGTGCCTGTGCCCCGACGGCTTCCAGCTGGTGGCCCA | 3868 |
| | TGGGCCACCAGCTGGAAGCCGTCGGGGCACAGGCACTCGTA GCCGATCTTAAGGTCATTGCAGACGTGGGAACAGCCGCCGTT GTTGTCCAAGCATTCGTTGGTCCCTGCGCAGGGCCAGG | 3869 |
| | CCACGTCTGCAATGACC | 3870 |
| | GGTCATTGCAGACGTGG | 3871 |
| Hypercholesterolaemia Gly314Ser cGGC-AGC | ACCAACGAATGCTTGGACAACAACGGCGGCTGTTCCCACGTC TGCAATGACCTTAAGATCGGCTACGAGTGCCTGTGCCCCGAC GGCTTCCAGCTGGTGGCCCAGCGAAGATGCGAAGGTG | 3872 |
| | CACCTTCGCATCTTCGCTGGGCCACCAGCTGGAAGCCGTCG GGGCACAGGCACTCGTAGCCGATCTTAAGGTCATTGCAGAC GTGGGAACAGCCGCCGTTGTTGTCCAAGCATTCGTTGGT | 3873 |
| | TTAAGATCGGCTACGAG | 3874 |
| | CTCGTAGCCGATCTTAA | 3875 |
| Hypercholesterolaemia Gly314Val GGC-GTC | CCAACGAATGCTTGGACAACAACGGCGGCTGTTCCCACGTCT GCAATGACCTTAAGATCGGCTACGAGTGCCTGTGCCCCGAC GGCTTCCAGCTGGTGGCCCAGCGAAGATGCGAAGGTGA | 3876 |
| | TCACCTTCGCATCTTCGCTGGGCCACCAGCTGGAAGCCGTC GGGGCACAGGCACTCGTAGCCGATCTTAAGGTCATTGCAGA CGTGGGAACAGCCGCCGTTGTTGTCCAAGCATTCGTTGG | 3877 |
| | TAAGATCGGCTACGAGT | 3878 |
| | ACTCGTAGCCGATCTTA | 3879 |
| Hypercholesterolaemia Tyr315Term TACg-TAA | CGAATGCTTGGACAACAACGGCGGCTGTTCCCACGTCTGCAA TGACCTTAAGATCGGCTACGAGTGCCTGTGCCCCGACGGCTT CCAGCTGGTGGCCCAGCGAAGATGCGAAGGTGATTTC | 3880 |
| | GAAATCACCTTCGCATCTTCGCTGGGCCACCAGCTGGAAGCC GTCGGGGCACAGGCACTCGTAGCCGATCTTAAGGTCATTGCA GACGTGGGAACAGCCGCCGTTGTTGTCCAAGCATTCG | 3881 |
| | ATCGGCTACGAGTGCCT | 3882 |
| | AGGCACTCGTAGCCGAT | 3883 |
| Hypercholesterolaemia Cys317Gly gTGC-GGC | TGCTTGGACAACAACGGCGGCTGTTCCCACGTCTGCAATGAC CTTAAGATCGGCTACGAGTGCCTGTGCCCCGACGGCTTCCA GCTGGTGGCCCAGCGAAGATGCGAAGGTGATTTCCGGG | 3884 |
| | CCCGGAAATCACCTTCGCATCTTCGCTGGGCCACCAGCTGG AAGCCGTCGGGGCACAGGCACTCGTAGCCGATCTTAAGGTC ATTGCAGACGTGGGAACAGCCGCCGTTGTTGTCCAAGCA | 3885 |
| | GCTACGAGTGCCTGTGC | 3886 |
| | GCACAGGCACTCGTAGC | 3887 |
| Hypercholesterolaemia Cys317Ser gTGC-AGC | TGCTTGGACAACAACGGCGGCTGTTCCCACGTCTGCAATGAC CTTAAGATCGGCTACGAGTGCCTGTGCCCCGACGGCTTCCA GCTGGTGGCCCAGCGAAGATGCGAAGGTGATTTCCGGG | 3888 |
| | CCCGGAAATCACCTTCGCATCTTCGCTGGGCCACCAGCTGG AAGCCGTCGGGGCACAGGCACTCGTAGCCGATCTTAAGGTC ATTGCAGACGTGGGAACAGCCGCCGTTGTTGTCCAAGCA | 3889 |
| | GCTACGAGTGCCTGTGC | 3890 |
| | GCACAGGCACTCGTAGC | 3891 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Pro320Arg CCC-CGC | ACAACGGCGGCTGTTCCCACGTCTGCAATGACCTTAAGATCG GCTACGAGTGCCTGTGCCCCGACGGCTTCCAGCTGGTGGCC CAGCGAAGATGCGAAGGTGATTTCCGGGTGGGACTGAG | 3892 |
| | CTCAGTCCCACCCGGAAATCACCTTCGCATCTTCGCTGGGCC ACCAGCTGGAAGCCGTCGGGGCACAGGCACTCGTAGCCGAT CTTAAGGTCATTGCAGACGTGGGAACAGCCGCCGTTGT | 3893 |
| | CCTGTGCCCCGACGGCT | 3894 |
| | AGCCGTCGGGGCACAGG | 3895 |
| Hypercholesterolaemia Asp321Asn cGAC-AAC | AACGGCGGCTGTTCCCACGTCTGCAATGACCTTAAGATCGGC TACGAGTGCCTGTGCCCCGACGGCTTCCAGCTGGTGGCCCA GCGAAGATGCGAAGGTGATTTCCGGGTGGGACTGAGCC | 3896 |
| | GGCTCAGTCCCACCCGGAAATCACCTTCGCATCTTCGCTGGG CCACCAGCTGGAAGCCGTCGGGGCACAGGCACTCGTAGCCG ATCTTAAGGTCATTGCAGACGTGGGAACAGCCGCCGTT | 3897 |
| | TGTGCCCCGACGGCTTC | 3898 |
| | GAAGCCGTCGGGGCACA | 3899 |
| Hypercholesterolaemia Asp321Glu GACg-GAG | CGGCGGCTGTTCCCACGTCTGCAATGACCTTAAGATCGGCTA CGAGTGCCTGTGCCCCGACGGCTTCCAGCTGGTGGCCCAGC GAAGATGCGAAGGTGATTTCCGGGTGGGACTGAGCCCT | 3900 |
| | AGGGCTCAGTCCCACCCGGAAATCACCTTCGCATCTTCGCTG GGCCACCAGCTGGAAGCCGTCGGGGCACAGGCACTCGTAG CCGATCTTAAGGTCATTGCAGACGTGGGAACAGCCGCCG | 3901 |
| | TGCCCCGACGGCTTCCA | 3902 |
| | TGGAAGCCGTCGGGGCA | 3903 |
| Hypercholesterolaemia Gly322Ser cGGC-AGC | GGCGGCTGTTCCCACGTGTGCAATGACCTTAAGATCGGCTAC GAGTGCCTGTGCCCCGACGGCTTCCAGCTGGTGGCCCAGCG AAGATGCGAAGGTGATTTCCGGGTGGGACTGAGCCCTG | 3904 |
| | CAGGGCTCAGTCCCACCCGGAAATCACCTTCGCATCTTCGCT GGGCCACCAGCTGGAAGCCGTCGGGGCACAGGCACTCGTA GCCGATCTTAAGGTCATTGCAGACGTGGGAACAGCCGCC | 3905 |
| | GCCCCGACGGCTTCCAG | 3906 |
| | CTGGAAGCCGTCGGGGC | 3907 |
| Hypercholesterolaemia Gln324Term cCAG-TAG | TGTTCCCACGTCTGCAATGACCTTAAGATCGGCTACGAGTGC CTGTGCCCCGACGGCTTCCAGCTGGTGGCCCAGCGAAGATG CGAAGGTGATTTCCGGGTGGGACTGAGCCCTGGGCCCC | 3908 |
| | GGGGCCCAGGGCTCAGTCCCACCCGGAAATCACCTTCGCAT CTTCGCTGGGCCACCAGCTGGAAGCCGTCGGGGCACAGGCA CTCGTAGCCGATCTTAAGGTCATTGCAGACGTGGGAACA | 3909 |
| | ACGGCTTCCAGCTGGTG | 3910 |
| | CACCAGCTGGAAGCCGT | 3911 |
| Hypercholesterolaemia Arg329Pro CGA-CCA | ATGACCTTAAGATCGGCTACGAGTGCCTGTGCCCCGACGGC TTCCAGCTGGTGGCCCAGCGAAGATGCGAAGGTGATTTCCG GGTGGGACTGAGCCCTGGGCCCCCTCTGCGCTTCCTGAC | 3912 |
| | GTCAGGAAGCGCAGAGGGGGCCCAGGGCTCAGTCCCACCC GGAAATCACCTTCGCATCTTCGCTGGGCCACCAGCTGGAAG CCGTCGGGGCACAGGCACTCGTAGCCGATCTTAAGGTCAT | 3913 |
| | GGCCCAGCGAAGATGCG | 3914 |
| | CGCATCTTCGCTGGGCC | 3915 |
| Hypercholesterolaemia Arg329Term gCGA-TGA | AATGACCTTAAGATCGGCTACGAGTGCCTGTGCCCCGACGG CTTCCAGCTGGTGGCCCAGCGAAGATGCGAAGGTGATTTCC GGGTGGGACTGAGCCCTGGGCCCCCTCTGCGCTTCCTGA | 3916 |
| | TCAGGAAGCGCAGAGGGGGCCCAGGGCTCAGTCCCACCCG GAAATCACCTTCGCATCTTCGCTGGGCCACCAGCTGGAAGCC GTCGGGGCACAGGCACTCGTAGCCGATCTTAAGGTCATT | 3917 |
| | TGGCCCAGCGAAGATGC | 3918 |
| | GCATCTTCGCTGGGCCA | 3919 |
| Hypercholesterolaemia Glu336Lys tGAG-AAG | TCTAGCCATTGGGGAAGAGCCTCCCCACCAAGCCTCTTTCTC TCTCTTCCAGATATCGATGAGTGTCAGGATCCCGACACCTGC AGCCAGCTCTGCGTGAACCTGGAGGGTGGCTACAAGT | 3920 |
| | ACTTGTAGCCACCCTCCAGGTTCACGCAGAGCTGGCTGCAG GTGTCGGGATCCTGACACTCATCGATATCTGGAAGAGAGA AAGAGGCTTGGTGGGAGGCTCTTCCCCAATGGCTAGA | 3921 |
| | ATATCGATGAGTGTCAG | 3922 |
| | CTGACACTCATCGATAT | 3923 |
| Hypercholesterolaemia Gln338Term tCAG-TAG | CATTGGGGAAGAGCCTCCCCACCAAGCCTCTTTCTCTCTCTT CCAGATATCGATAGTGTCAGGATCCCGACACCTGCAGCCAG CTCTGCGTGAACCTGGAGGGTGGCTACAAGTGCCAGT | 3924 |
| | ACTGGCACTTGTAGCCACCCTCCAGGTTCACGCAGAGCTGG CTGCAGGTGTCGGGATCCTGACACTCATCGATATCTGGAAGA GAGAGAAAGAGGCTTGGTGGGAGGCTCTTCCCCAATG | 3925 |
| | ATGAGTGTCAGGATCCC | 3926 |
| | GGGATCCTGACACTCAT | 3927 |

TABLE 28-continued

LDLR Mutations and Genome-Correcting Oligos

| Clinical Phenotype & Mutation | Correcting Oligos | SEQ ID NO: |
|---|---|---|
| Hypercholesterolaemia Cys343Arg cTGC-CGC | TCCCCACCAAGCCTCTTTCTCTCTCTTCCAGATATCGATGAGT GTCAGGATCCCGACACCTGCAGCCAGCTCTGCGTGAACCTG GAGGGTGGCTACAAGTGCCAGTGTGAGGAAGGCTTCC | 3928 |
| | GGAAGCCTTCCTCACACTGGCACTTGTAGCCACCCTCCAGGT TCACGCAGAGCTGGCTGCAGGTGTCGGGATCCTGACACTCA TCGATATCTGGAAGAGAGAGAAAGAGGCTTGGTGGGGA | 3929 |
| | CCGACACCTGCAGCCAG | 3930 |
| | CTGGCTGCAGGTGTCGG | 3931 |
| Hypercholesterolaemia Gln345Arg CAG-CGG | CAAGCCTCTTTCTCTCTCTTCCAGATATCGATGAGTGTCAGGA TCCCGACACCTGCAGCCAGCTCTGCGTGAACCTGGAGGGTG GCTACAAGTGCCAGTGTGAGGAAGGCTTCCAGCTGGA | 3932 |
| | TCCAGCTGGAAGCCTTCCTCACACTGGCACTTGTAGCCACCC TCCAGGTTCACGCAGAGCTGGCTGCAGGTGTCGGGATCCTG ACACTCATCGATATCTGGAAGAGAGAGAAAGAGGCTTG | 3933 |
| | CTGCAGCCAGCTCTGCG | 3934 |
| | CGCAGAGCTGGCTGCAG | 3935 |
| Hypercholesterolaemia Cys347Tyr TGC-TAC | TCTTTCTCTCTCTTCCAGATATCGATGAGTGTCAGGATCCCGA CACCTGCAGCCAGCTCTGCGTGAACCTGGAGGGTGGCTACA AGTGCCAGTGTGAGGAAGGCTTCCAGCTGGACCCCCA | 3936 |
| | TGGGGGTCCAGCTGGAAGCCTTCCTCACACTGGCACTTGTA GCCACCCTCCAGGTTCACGCAGAGCTGGCTGCAGGTGTCGG GATCCTGACACTCATCGATATCTGGAAGAGAGAGAAAGA | 3937 |
| | CCAGCTCTGCGTGAACC | 3938 |
| | GGTTCACGCAGAGCTGG | 3939 |
| Hypercholesterolaemia Cys347Arg cTGC-CGC | CTCTTTCTCTCTCTTCCAGATATCGATGAGTGTCAGGATCCCG ACACCTGCAGCCAGCTCTGCGTGAACCTGGAGGGTGGCTAC AAGTGCCAGTGTGAGGAAGGCTTCCAGCTGGACCCCC | 3940 |
| | GGGGGTCCAGCTGGAAGCCTTCCTCACACTGGCACTTGTAG CCACCCTCCAGGTTCACGCAGAGCTGGCTGCAGGTGTCGGG ATCCTGACACTCATCGATATCTGGAAGAGAGAGAAAGAG | 3941 |
| | GCCAGCTCTGCGTGAAC | 3942 |
| | GTTCACGCAGAGCTGGC | 3943 |
| Hypercholesterolaemia Gly352Asp GGT-GAT | CAGATATCGATGAGTGTCAGGATCCCGACACCTGCAGCCAGC TCTGCGTGAACCTGGAGGGTGGCTACAAGTGCCAGTGTGAG GAAGGCTTCCAGCTGGACCCCCACACGAAGGCCTGCAA | 3944 |
| | TTGCAGGCCTTCGTGTGGGGGTCCAGCTGGAAGCCTTCCTC ACACTGGCACTTGTAGCCACCCTCCAGGTTCACGCAGAGCTG GCTGCAGGTGTCGGGATCCTGACACTCATCGATATCTG | 3945 |
| | CCTGGAGGGTGGCTACA | 3946 |
| | TGTAGCCACCCTCCAGG | 3947 |
| Hypercholesterolaemia Tyr354Cys TAC-TGC | TCGATGAGTGTCAGGATCCCGACACCTGCAGCCAGCTCTGC GTGAACCTGGAGGGTGGCTACAAGTGCCAGTGTGAGGAAGG CTTCCAGCTGGACCCCCACACGAAGGCCTGCAAGGCTGT | 3948 |
| | ACAGCCTTGCAGGCCTTCGTGTGGGGGTCCAGCTGGAAGCC TTCCTCACACTGGCACTTGTAGCCACCCTCCAGGTTCACGCA GAGCTGGCTGCAGGTGTCGGGATCCTGACACTCATCGA | 3949 |
| | GGGTGGCTACAAGTGCC | 3950 |
| | GGCACTTGTAGCCACCC | 3951 |
| Hypercholesterolaemia Cys358Arg gTGT-CGT | CAGGATCCCGACACCTGCAGCCAGCTCTGCGTGAACCTGGA GGGTGGCTACAAGTGCCAGTGTGAGGAAGGCTTCCAGCTGG ACCCCCACACGAAGGCCTGCAAGGCTGTGGGTGAGCACG | 3952 |
| | CGTGCTCACCCACAGCCTTGCAGGCCTTCGTGTGGGGGTCC AGCTGGAAGCCTTCCTCACACTGGCACTTGTAGCCACCCTCC AGGTTCACGCAGAGCTGGCTGCAGGTGTCGGGATCCTG | 3953 |
| | AGTGCCAGTGTGAGGAA | 3954 |
| | TTCCTCACACTGGCACT | 3955 |
| Hypercholesterolaemia Gln363Term cCAG-TAG | TGCAGCCAGCTCTGCGTGAACCTGGAGGGTGGCTACAAGTG CCAGTGTGAGGAAGGCTTCCAGCTGGACCCCCACACGAAGG CCTGCAAGGCTGTGGGTGAGCACGGGAAGGCGGCGGGTG | 3956 |
| | CACCCGCCGCCTTCCCGTGCTCACCCACAGCCTTGCAGGCC TTCGTGTGGGGGTCCAGCTGGAAGCCTTCCTCACACTGGCA CTTGTAGCCACCCTCCAGGTTCACGCAGAGCTGGCTGCA | 3957 |
| | AAGGCTTCCAGCTGGAC | 3958 |
| | GTCCAGCTGGAAGCCTT | 3959 |

EXAMPLE 22

UDP-glucuronosyltransferase—UGT1

Mutations in the human UGT1 gene result in a range of disease syndromes, ranging from relatively common diseases such as Gilbert's syndrome, which effects up to 7% of the population, to rare disorders such as Crigler-Najjar syndrome. Symptoms of these diseases are the result of diminished bilirubin conjugation and typically present with jaundice or, when mild, as an incidental finding during routing laboratory analysis. Severe cases of Crigler-Najjar syndrome are caused by an absence of UGT1 activity and the majority of these patients die in the neonatal period. The only known treatment is liver transplant. The attached table discloses the correcting oligonucleotide base sequences for the UGT1 oligonucleotides of the invention.

TABLE 29

UGT1 Mutations and Genome-Correcting Oligos

| Clinical Phenotype & Mutation | Correcting Oligos | SEQ ID NO: |
|---|---|---|
| Crigler-Najjar syndrome 2 Leu15Arg CTG-CGG | GCAGGAGCAAAGGCGCCATGGCTGTGGAGTCCCAGGGCGG ACGCCCACTTGTCCTGGGCCTGCTGCTGTGTGTGCTGGGCC CAGTGGTGTCCCATGCTGGGAAGATACTGTTGATCCCAGT | 3960 |
| | ACTGGGATCAACAGTATCTTCCCAGCATGGGACACCACTGGG CCCAGCACACACAGCAGCAGGCCCAGGACAAGTGGGCGTCC GCCCTGGGACTCCACAGCCATGGCGCCTTTGCTCCTGC | 3961 |
| | CCTGGGCCTGCTGCTGT | 3962 |
| | ACAGCAGCAGGCCCAGG | 3963 |
| Crigler-Najjar syndrome 1 Gln49Term CAG-TAG | GGGAAGATACTGTTGATCCCAGTGGATGGCAGCCACTGGCT GAGCATGCTTGGGGCCATCCAGCAGCTGCAGCAGAGGGGAC ATGAAATAGTTGTCCTAGCACCTGACGCCTCGTTGTACA | 3964 |
| | TGTACAACGAGGCGTCAGGTGCTAGGACAACTATTTCATGTC CCCTCTGCTGCAGCTGCTGGATGGCCCAAGCATGCTCAGC CAGTGGCTGCCATCCACTGGGATCAACAGTATCTTCCC | 3965 |
| | GGGCCATCCAGCAGCTG | 3966 |
| | CAGCTGCTGGATGGCCC | 3967 |
| Crigler-Najjar syndrome 1 Gly71Arg GGA-AGA | CAGCAGAGGGGACATGAAATAGTTGTCCTAGCACCTGACGCC TCGTTGTACATCAGAGACGGAGCATTTTACACCTTGAAGACGT ACCCTGTGCCATTCCAAAGGGAGGATGTGAAAGAGT | 3968 |
| | ACTCTTTCACATCCTCCCTTTGGAATGGCACAGGGTACGTCTT CAAGGTGTAAAATGCTCCGTCTCTGATGTACAACGAGGCGTC AGGTGCTAGGACAACTATTTCATGTCCCCTCTGCTG | 3969 |
| | TCAGAGACGGAGCATTT | 3970 |
| | AAATGCTCCGTCTCTGA | 3971 |
| Gilbert syndrome Pro229Gln CCG-CAG | GGGTGAAGAACATGCTCATTGCCTTTTCACAGAACTTTCTGTG CGACGTGGTTTATTCCCCGTATGCAACCCTTGCCTCAGAATT CCTTCAGAGAGAGGTGACTGTCCAGGACCTATTGAG | 3972 |
| | CTCAATAGGTCCTGGACAGTCACCTCTCTCTGAAGGAATTCT GAGGCAAGGGTTGCATACGGGGAATAAACCACGTCGCACAG AAAGTTCTGTGAAAAGGCAATGAGCATGTTCTTCACCC | 3973 |
| | TTATTCCCCGTATGCAA | 3974 |
| | TTGCATACGGGGAATAA | 3975 |
| Crigler-Najjar syndrome 1 Cys280Term TGC-TGA | TGTGAAGGATTACCCTAGGCCCATCATGCCCAATATGGTTTTT GTTGGTGGAATCAACTGCCTTCACCAAAATCCACTATCCCAG GTGTGTATTGGAGTGGGACTTTTACATGCGTATATT | 3976 |
| | AATTACGCATGTAAAAGTCCCACTCCAATACACACCTGGGAT AGTGGATTTTGGTGAAGGCAGTTGATTCCACCAACAAAAACC ATATTGGGCATGATGGGCCTAGGGTAATCCTTCACA | 3977 |
| | ATCAACTGCCTTCACCA | 3978 |
| | TGGTGAAGGCAGTTGAT | 3979 |
| Crigler-Najjar syndrome 1 Ala292Val GCC-GTC | ATCAAAGAATATGAGAAAAAATTAACTGAAAATTTTTCTTCTGG CTCTAGGAATTTGAAGCCTACATTAATGCTTCTGGAGAACATG GAATTGTGGTTTTCTCTTTGGGATCAATGGTCTC | 3980 |
| | GAGACCATTGATCCCAAAGAGAAAACCACAATTCCATGTTCTC CAGAAGCATTAATGTAGGCTTCAAATTCCTAGAGCCAGAAGAA AAATTTTCAGTTAATTTTTTCTCATATTCTTTGAT | 3981 |
| | ATTTGAAGCCTACATTA | 3982 |
| | TAATGTAGGCTTCAAAT | 3983 |
| Crigler-Najjar syndrome 1 Gly308Glu GGA-GAA | AGGAATTTGAAGCCTACATTAATGCTTCTGGAGAACATGGAAT TGTGGTTTTCTCTTTGGGATCAATGGTCTCAGAAATTCCAGAG AAGAAAGCTATGGCAATTGCTGATGCTTTGGGCAA | 3984 |
| | TTGCCCAAAGCATCAGCAATTGCCATAGCTTTCTTCTCTGGAA TTTCTGAGACCATTGATCCCAAAGAGAAAACCACAATTCCATG TTCTCCAGAAGCATTAATGTAGGCTTCAAATTCCT | 3985 |
| | CTCTTTGGGATCAATGG | 3986 |
| | CCATTGATCCCAAAGAG | 3987 |
| Crigler-Najjar syndrome 1 Gln331Term CAG-TAG | GTCTCAGAAATTCCAGAGAAGAAAGCTATGGCAATTGCTGAT GCTTTGGGCAAAATCCCTCAGACAGTAAGAAGATTCTATACCA TGGCCTCATATCTATTTTCACAGGAGCGCTAATCCC | 3988 |
| | GGGATTAGCGCTCCTGTGAAAATAGATATGAGGCCATGGTAT AGAATCTTCTTACTGTCTGAGGGATTTTGCCCAAAGCATCAGC AATTGCCATAGCTTTCTTCTCTGGAATTTCTGAGAC | 3989 |
| | AAATCCCTCAGACAGTA | 3990 |
| | TACTGTCTGAGGGATTT | 3991 |
| Crigler-Najjar syndrome 1 Trp335Term TGG-TGA | TCTAATCATATTATGTTCTTTCTTTACGTTCTGCTCTTTTTGCC CCTCCCAGGTCCTGTGGCGGTACACTGGAACCCGACCATCG AATCTTGCAACAACACGATACTTGTTAAGTGGCTA | 3992 |
| | TAGCCACTTAACAAGTATCGTGTTGTTCGCAAGATTCGATGGT CGGGTTCCAGTGTACCGCCACAGGACCTGGGAGGGGCAAAA AGAGCAGAACGTAAAGAAAGAACATAATATGATTAGA | 3993 |

TABLE 29-continued

UGT1 Mutations and Genome-Correcting Oligos

| Clinical Phenotype & Mutation | Correcting Oligos | SEQ ID NO: |
|---|---|---|
| | GTCCTGTGGCGGTACAC | 3994 |
| | GTGTACCGCCACAGGAC | 3995 |
| Crigler-Najjar syndrome 1 Gln357Arg CAA-CGA | ACACTGGAACCCGACCATCGAATCTTGCGAACAACACGATAC TTGTTAAGTGGCTACCCCAAAACGATCTGCTTGGTATGTTGG GCGGATTGGATGTATAGGTCAAACCAGGGTCAAATTA | 3996 |
| | TAATTTGACCCTGGTTTGACCTATACATCCAATCCGCCCAACA TACCAAGCAGATCGTTTTGGGGTAGCCACTTAACAAGTATCGT GTTGTTCGCAAGATTCGATGGTCGGGTTCCAGTGT | 3997 |
| | GCTACCCCAAAACGATC | 3998 |
| | GATCGTTTTGGGGTAGC | 3999 |
| Crigler-Najjar syndrome 1 Gln357Term CAA-TAA | TACACTGGAACCCGACCATCGAATCTTGCGAACAACACGATA CTTGTTAAGTGGCTACCCCAAAACGATCTGCTTGGTATGTTG GGCGGATTGGATGTATAGGTCAAACCAGGGTCAAATT | 4000 |
| | AATTTGACCCTGGTTTGACCTATACATCCAATCCGCCCAACAT ACCAAGCAGATCGTTTTGGGGTAGCCACTTAACAAGTATCGT GTTGTTCGCAAGATTCGATGGTCGGGTTCCAGTGTA | 4001 |
| | GGCTACCCCAAAACGAT | 4002 |
| | ATCGTTTTGGGGTAGCC | 4003 |
| Gilbert syndrome Arg367Gly CGT-GGT | AACTCAGAGATGTAACTGCTGACATCCTCCCTATTTTGCATCT CAGGTCACCCGATGACCCGTGCCTTTATCACCCATGCTGGTT CCCATGGTGTTTATGAAAGCATATGCAATGGCGTTC | 4004 |
| | GAACGCCATTGCATATGCTTTCATAAACACCATGGGAACCAG CATGGGTGATAAAGGCACGGGTCATCGGGTGACCTGAGATG CAAAATAGGGAGGATGTCAGCAGTTACATCTCTGAGTT | 4005 |
| | CGATGACCCGTGCCTTT | 4006 |
| | AAAGGCACGGGTCATCG | 4007 |
| Crigler-Najjar syndrome 1 Ala368Thr GCC-ACC | TCAGAGATGTAACTGCTGACATCCTCCCTATTTTGCATCTCAG GTCACCCGATGACCCGTGCCTTTATCACCCATGCTGGTTCCC ATGGTGTTTATGAAAGCATATGCAATGGCGTTCCCA | 4008 |
| | TGGGAACGCCATTGCATATGCTTTCATAAACACCATGGGAAC CAGCATGGGTGATAAAGGCACGGGTCATCGGGTGACCTGAG ATGCAAAATAGGGAGGATGTCAGCAGTTACATCTCTGA | 4009 |
| | TGACCCGTGCCTTTATC | 4010 |
| | GATAAAGGCACGGGTCA | 4011 |
| Crigler-Najjar syndrome 1 Ser375Phe TCC-TTC | CCTCCCTATTTTGCATCTCAGGTCACCCGATGACCCGTGCCT TTATCACCCATGCTGGTTCCCATGGTGTTTATGAAAGCATATG CAATGGCGTTCCCATGGTGATGATGCCCTTGTTTGG | 4012 |
| | CCAAACAAGGGCATCATCACCATGGGAACGCCATTGCATATG CTTTCATAAACACCATGGGAACCAGCATGGGTGATAAAGGCA CGGGTCATCGGGTGACCTGAGATGCAAAATAGGGAGG | 4013 |
| | TGCTGGTTCCCATGGTG | 4014 |
| | CACCATGGGAACCAGCA | 4015 |
| Crigler-Najjar syndrome 1 Ser381Arg AGC-AGG | AGGTCACCCGATGACCCGTGCCTTTATCACCCATGCTGGTTC CCATGGTGTTTATGAAAGCATATGCAATGGCGTTCCCATGGT GATGATGCCCTTGTTTGGTGATCAGATGGACAATGCA | 4016 |
| | TGCATTGTCCATCTGATCACCAAACAAGGGCATCATCACCAT GGGAACGCCATTGCATATGCTTTCATAAACACCATGGGAACC AGCATGGGTGATAAAGGCACGGGTCATCGGGTGACCT | 4017 |
| | TATGAAAGCATATGCAA | 4018 |
| | TTGCATATGCTTTCATA | 4019 |
| Crigler-Najjar syndrome 1 Ala401Pro GCA-CCA | AGCATATGCAATGGCGTTCCCATGGTGATGATGCCCTTGTTT GGTGATCAGATGGACAATGCAAAGCGCATGGAGACTAAGGG AGCTGGAGTGACCCTGAATGTTCTGGAAATGACTTCTG | 4020 |
| | CAGAAGTCATTTCCAGAACATTCAGGGTCACTCCAGCTCCCT TAGTCTCCATGCGCTTTGCATTGTCCATCTGATCACCAAACAA GGGCATCATCACCATGGGAACGCCATTGCATATGCT | 4021 |
| | TGGACAATGCAAAGCGC | 4022 |
| | GCGCTTTGCATTGTCCA | 4023 |
| Crigler-Najjar syndrome 1 Lys428Glu AAA-GAA | GGAGCTGGAGTGACCCTGAATGTTCTGGAAATGACTTCTGAA GATTTAGAAAATGCTCTAAAAGCAGTCATCAATGACAAAAGGT AAGAAAGAAGATACAGAAGAATACTTTGGTCATGGC | 4024 |
| | GCCATGACCAAAGTATTCTTCTGTATCTTCTTTCTTACCTTTTG TCATTGATGACTGCTTTTAGAGCATTTTCTAAATCTTCAGAAGT CATTTCCAGAACATTCAGGGTCACTCCAGCTCC | 4025 |
| | ATGCTCTAAAAGCAGTC | 4026 |
| | GACTGCTTTTAGAGCAT | 4027 |
| Crigler-Najjar syndrome 1 Tyr486Asp TAC-GAC | ATGAGGCACAAGGGCGCGCCACACCTGCGCCCCGCAGCCC ACGACCTCACCTGGTACCAGTACCATTCCTTGGACGTGATTG GTTTCCTCTTGGCCGTCGTGCTGACAGTGGCCTTCATCA | 4028 |
| | TGATGAAGGCCACTGTCAGCACGACGGCCAAGAGGAAACCA ATCACGTCCAAGGAATGGTACTGGTACCAGGTGAGGTCGTG GGCTGCGGGCGCAGGTGTGGCGCGCCCTTGTGCCTCAT | 4029 |
| | GGTACCAGTACCATTCC | 4030 |
| | GGAATGGTACTGGTACC | 4031 |

TABLE 29-continued

UGT1 Mutations and Genome-Correcting Oligos

| Clinical Phenotype & Mutation | Correcting Oligos | SEQ ID NO: |
|---|---|---|
| Crigler-Najjar syndrome 1<br>Ser488Phe<br>TCC-TTC | ACAAGGGCGCGCCACACCTGCGCCCCGCAGCCCACGACCT<br>CACCTGGTACCAGTACCATTCCTTGGACGTGATTGGTTTCCT<br>CTTGGCCGTCGTGCTGACAGTGGCCTTCATCACCTTTAA | 4032 |
| | TTAAAGGTGATGAAGGCCACTGTCAGCACGACGGCCAAGAG<br>GAAACCAATCACGTCCAAGGAATGGTACTGGTACCAGGTGAG<br>GTCGTGGGCTGCGGGGCGCAGGTGTGGCGCGCCCTTGT | 4033 |
| | GTACCATTCCTTGGACG | 4034 |
| | CGTCCAAGGAATGGTAC | 4035 |

EXAMPLE 23

Alzheimer's Disease—Amyloid Precursor Protein (APP)

Over the past few decades Alzheimer's disease (AD), once considered a rare disorder, has become recognized as a major public health problem. Although there is no agreement on the exact prevalence of Alzheimer's disease, in part due to difficulties of diagnosis, studies consistently point to an exponential rise in prevalence of this disease with age. After age 65, the percentage of affected people approximately doubles with every decade of life, regardless of definition. Among people age 85 or loder, studies suggest that 25 to 35 percent have dementia, including Alzheimer's disease; one study reports that 47.2 percent of people over age 85 have Alzheimer's disease, exclusive of other dementias.

Alzheimer's disease progressively destroys memory, reason, judgment, language, and, eventually, the ability to carry out even the simplest tasks. Anatomic changes associated with Alzheimer's disease begin in the entorhinal cortex, procees to the hippocampus, and then gradually spread to other regions, particularly the cerebral cortex. Chief among such anatomic changes are the presence of characteristic extracellular plaques and internal neureofibrillary tangles.

At least four genes have been identified to date that contribute to development of Alzheimer's disease: AD1 is caused by mutations in the amyloid precursor gene (APP); AD2 is associated with a particular allele of APOE (see Example 20); AD3 is caused by mutation in a gene encoding a 7-transmembrane domain protein, presenilin-1 (PSEN1), and AD4 is caused by mutation in a gene that encodes a similar 7-transmembrane domain protein, presenilin-2 (PSEN2). The attached table discloses the correcting oligonucleotide base sequences for the APP oligonucleotides of the invention.

TABLE 30

APP Mutations and Genome-Correcting Oligos

| Clinical Phenotype & Mutation | Correcting Oligos | SEQ ID NO: |
|---|---|---|
| Alzheimer disease<br>Glu665Asp<br>GAG-GAC | CTGCATACTTTAATTATGATGTAATACAGGTTCTGGGTTGACA<br>AATATCAAGACGGAGGAGATCTCTGAAGTGAAGATGGATGCA<br>GAATTCCGACATGACTCAGGATATGAAGTTCATCAT | 4036 |
| | ATGATGAACTTCATATCCTGAGTCATGTCGGAATTCTGCATCC<br>ATCTTCACTTCAGAGATCTCCTCCGTCTTGATATTTGTCAACC<br>CAGAACCTGTATTACATCATAATTAAAGTATGCAG | 4037 |
| | ACGGAGGAGATCTCTGA | 4038 |
| | TCAGAGATCTCCTCCGT | 4039 |
| Alzheimer disease<br>Ala692Gly<br>GCA-GGA | ATTATATTGCATTTAGAAATTAAAATTCTTTTTCTTAATTTGTTTT<br>CAAGGTGTTCTTTGCAGAAGATGTGGGTTCAAACAAAGGTGC<br>AATCATTGGACTCATGGTGGGCGGTGTTGTCAT | 4040 |
| | ATGACAACACCGCCCACCATGAGTCCAATGATTGCACCTTTG<br>TTTGAACCCACATCTTCTGCAAAGAACACCTTGAAAACAAATT<br>AAGAAAAAGAATTTTAATTTCTAAATGCAATATAAT | 4041 |
| | GTTCTTTGCAGAAGATG | 4042 |
| | CATCTTCTGCAAAGAAC | 4043 |
| Alzheimer disease<br>Glu693Gln<br>GAA-CAA | TATATTGCATTTAGAAATTAAAATTCTTTTTCTTAATTTGTTTTC<br>AAGGTGTTCTTTGCAGAAGATGTGGGTTCAAACAAAGGTGCA<br>ATCATTGGACTCATGGTGGGCGGTGTTGTCATAG | 4044 |
| | CTATGACAACACCGCCCACCATGAGTCCAATGATTGCACCTT<br>TGTTTGAACCCACATCTTCTGCAAAGAACACCTTGAAAACAAA<br>TTAAGAAAAGAATTTTAATTTCTAAATGCAATATA | 4045 |
| | TCTTTGCAGAAGATGTG | 4046 |
| | CACATCTTCTGCAAAGA | 4047 |
| Alzheimer disease<br>Glu693Gly<br>GAA-GGA | ATATTGCATTTAGAAATTAAAATTCTTTTTCTTAATTTGTTTTCA<br>AGGTGTTCTTTGCAGAAGATGTGGGTTCAAACAAAGGTGCAA<br>TCATTGGACTCATGGTGGGCGGTGTTGTCATAGC | 4048 |
| | GCTATGACAACACCGCCCACCATGAGTCCAATGATTGCACCT<br>TTGTTTGAACCCACATCTTCTGCAAAGAACACCTTGAAAACAA | 4049 |

TABLE 30-continued

APP Mutations and Genome-Correcting Oligos

| Clinical Phenotype & Mutation | Correcting Oligos | SEQ ID NO: |
|---|---|---|
| | ATTAAGAAAAAGAATTTTAATTTCTAAATGCAATAT CTTTGCAGAAGATGTGG | 4050 |
| | CCACATCTTCTGCAAAG | 4051 |
| Alzheimer disease Ala713Thr GCG-ACG | GAAGATGTGGGTTCAAACAAAGGTGCAATCATTGGACTCATG GTGGGCGGTGTTGTCATAGCGACAGTGATCGTCATCACCTTG GTGATGCTGAAGAAGAAACAGTACACATCCATTCATC | 4052 |
| | GATGAATGGATGTGTACTGTTTCTTCTTCAGCATCACCAAGGT GATGACGATCACTGTCGCTATGACAACACCGCCCACCATGAG TCCAATGATTGCACCTTTGTTTGAACCCACATCTTC | 4053 |
| | TTGTCATAGCGACAGTG | 4054 |
| | CACTGTCGCTATGACAA | 4055 |
| Schizophrenia Ala713Val GCG-GTG | AAGATGTGGGTTCAAACAAAGGTGCAATCATTGGACTCATGG TGGGCGGTGTTGTCATAGCGACAGTGATCGTCATCACCTTGG TGATGCTGAAGAAGAAACAGTACACATCCATTCATCA | 4056 |
| | TGATGAATGGATGTGTACTGTTTCTTCTTCAGCATCACCAAGG TGATGACGATCACTGTCGCTATGACAACACCGCCCACCATGA GTCCAATGATTGCACCTTTGTTTGAACCCACATCTT | 4057 |
| | TGTCATAGCGACAGTGA | 4058 |
| | TCACTGTCGCTATGACA | 4059 |
| Alzheimer disease Val715Met GTG-ATG | GTGGGTTCAAACAAAGGTGCAATCATTGGACTCATGGTGGGC GGTGTTGTCATAGCGACAGTGATCGTCATCACCTTGGTGATG CTGAAGAAGAAACAGTACACATCCATTCATCATGGTG | 4060 |
| | CACCATGATGAATGGATGTGTACTGTTTCTTCTTCAGCATCAC CAAGGTGATGACGATCACTGTCGCTATGACAACACCGCCCAC CATGAGTCCAATGATTGCACCTTTGTTTGAACCCAC | 4061 |
| | TAGCGACAGTGATCGTC | 4062 |
| | GACGATCACTGTCGCTA | 4063 |
| Alzheimer disease Ile716Val ATC-GTC | GGTTCAAACAAAGGTGCAATCATTGGACTCATGGTGGGCGGT GTTGTCATAGCGACAGTGATCGTCATCACCTTGGTGATGCTG AAGAAGAAACAGTACACATCCATTCATCATGGTGTGG | 4064 |
| | CCACACCATGATGAATGGATGTGTACTGTTTCTTCTTCAGCAT CACCAAGGTGATGACGATCACTGTCGCTATGACAACACCGCC CACCATGAGTCCAATGATTGCACCTTTGTTTGAACC | 4065 |
| | CGACAGTGATCGTCATC | 4066 |
| | GATGACGATCACTGTCG | 4067 |
| Alzheimer disease Val717Gly GTC-GGC | CAAACAAAGGTGCAATCATTGGACTCATGGTGGGCGGTGTTG TCATAGCGACAGTGATCGTCATCACCTTGGTGATGCTGAAGA AGAAACAGTACACATCCATTCATCATGGTGTGGTGGA | 4068 |
| | TCCACCACACCATGATGAATGGATGTGTACTGTTTCTTCTTCA GCATCACCAAGGTGATGACGATCACTGTCGCTATGACAACAC CGCCCACCATGAGTCCAATGATTGCACCTTTGTTTG | 4069 |
| | AGTGATCGTCATCACCT | 4070 |
| | AGGTGATGACGATCACT | 4071 |
| Alzheimer disease Val717Ile GTC-ATC | TCAAACAAAGGTGCAATCATTGGACTCATGGTGGGCGGTGTT GTCATAGCGACAGTGATCGTCATCACCTTGGTGATGCTGAAG AAGAAACAGTACACATCCATTCATCATGGTGTGGTGG | 4072 |
| | CCACCACACCATGATGAATGGATGTGTACTGTTTCTTCTTCAG CATCACCAAGGTGATGACGATCACTGTCGCTATGACAACACC GCCCACCATGAGTCCAATGATTGCACCTTTGTTTGA | 4073 |
| | CAGTGATCGTCATCACC | 4074 |
| | GGTGATGACGATCACTG | 4075 |
| Alzheimer disease Val717Phe GTC-TTC | TCAAACAAAGGTGCAATCATTGGACTCATGGTGGGCGGTGTT GTCATAGCGACAGTGATCGTCATCACCTTGGTGATGCTGAAG AAGAAACAGTACACATCCATTCATCATGGTGTGGTGG | 4076 |
| | CCACCACACCATGATGAATGGATGTGTACTGTTTCTTCTTCAG CATCACCAAGGTGATGACGATCACTGTCGCTATGACAACACC GCCCACCATGAGTCCAATGATTGCACCTTTGTTTGA | 4077 |
| | CAGTGATCGTCATCACC | 4078 |
| | GGTGATGACGATCACTG | 4079 |
| Alzheimer disease Leu723Pro CTG-CCG | TTGGACTCATGGTGGGCGGTGTTGTCATAGCGACAGTGATCG TCATCACCTTGGTGATGCTGAAGAAGAAACAGTACACATCCAT TCATCATGGTGTGGTGGAGGTAGGTAAACTTGACTG | 4080 |
| | CAGTCAAGTTTACCTACCTCCACCACACCATGATGAATGGAT GTGTACTGTTCTTCTTCAGCATCACCAAGGTGATGACGATCA CTGTCGCTATGACAACACCGCCCACCATGAGTCCAA | 4081 |
| | GGTGATGCTGAAGAAGA | 4082 |
| | TCTTCTTCAGCATCACC | 4083 |

EXAMPLE 24

Alzheimer's Disease—Presenilin-1 (PSEN1)

The attached table discloses the correcting oligonucleotide base sequences for the PSEN1 oligonucleotides of the invention.

TABLE 31

PSEN1 Mutations and Genome-Correcting Oligos

| Clinical Phenotype & Mutation | Correcting Oligos | SEQ ID NO: |
|---|---|---|
| Alzheimer disease Ala79Val GCC-GTC | CCCGGCAGGTGGTGGAGCAAGATGAGGAAGAAGATGAGGAG CTGACATTGAAATATGGCGCCAAGCATGTGATCATGCTCTTTG TCCCTGTGACTCTCTGCATGGTGGTGGTCGTGGCTAC | 4084 |
| | GTAGCCACGACCACCACCATGCAGAGAGTCACAGGGACAAA GAGCATGATCACATGCTTGGCGCCATATTTCAATGTCAGCTC CTCATCTTCTTCCTCATCTTGCTCCACCACCTGCCGGG | 4085 |
| | ATATGGCGCCAAGCATG | 4086 |
| | CATGCTTGGCGCCATAT | 4087 |
| Alzheimer disease Val82Leu tGTG-CTG | GTGGTGGAGCAAGATGAGGAAGAAGATGAGGAGCTGACATT GAAATATGGCGCCAAGCATGTGATCATGCTCTTTGTCCCTGT GACTCTCTGCATGGTGGTGGTCGTGGCTACCATTAAGT | 4088 |
| | ACTTAATGGTAGCCACGACCACCACCATGCAGAGAGTCACAG GGACAAAGAGCATGATCACATGCTTGGCGCCATATTTCAATG TCAGCTCCTCATCTTCCTCATCTTGCTCCACCAC | 4089 |
| | CCAAGCATGTGATCATG | 4090 |
| | CATGATCACATGCTTGG | 4091 |
| Alzheimer disease Val96Phe gGTC-TTC | AAATATGGCGCCAAGCATGTGATCATGCTCTTTGTCCCTGTG ACTCTCTGCATGGTGGTGGTCGTGGCTACCATTAAGTCAGTC AGCTTTTATACCCGGAAGGATGGGCAGCTGTACGTAT | 4092 |
| | ATACGTACAGCTGCCCATCCTTCCGGGTATAAAAGCTGACTG ACTTAATGGTAGCCACGACCACCACCATGCAGAGAGTCACAG GGACAAAGAGCATGATCACATGCTTGGCGCCATATTT | 4093 |
| | TGGTGGTGGTCGTGGCT | 4094 |
| | AGCCACGACCACCACCA | 4095 |
| Alzheimer disease Phe105Leu TTTt-TTG | CTTTGTCCCTGTGACTCTCTGCATGGTGGTGGTCGTGGCTAC CATTAAGTCAGTCAGCTTTTATACCCGGAAGGATGGGCAGCT GTACGTATGAGTTTTGTTTTATTATTCTCAAAGCCAG | 4096 |
| | CTGGCTTTGAGAATAATAAAACAAAACTCATACGTACAGCTGC CCATCCTTCCGGGTATAAAAGCTGACTGACTTAATGGTAGCC ACGACCACCACCATGCAGAGAGTCACAGGGACAAAG | 4097 |
| | GTCAGCTTTTATACCCG | 4098 |
| | CGGGTATAAAAGCTGAC | 4099 |
| Alzheimer disease Thr116Asn ACC-AAC | TGGTGATCTCCATTAACACTGACCTAGGGCTTTTGTGTTTGTT TTATTGTAGAATCTATACCCCATTCACAGAAGATACCGAGACT GTGGGCCAGAGAGCCCTGCACTCAATTCTGAATGC | 4100 |
| | GCATTCAGAATTGAGTGCAGGGCTCTCTGGCCCACAGTCTCG GTATCTTCTGTGAATGGGGTATAGAATTCTACAATAAAACAAAC ACAAAAGCCCTAGGTCAGTGTTAATGGAGATCACCA | 4101 |
| | AATCTATACCCCATTCA | 4102 |
| | TGAATGGGGTATAGATT | 4103 |
| Alzheimer disease Pro117Leu CCA-CTA | TGATCTCCATTAACACTGACCTAGGGCTTTTGTGTTTGTTTTAT TGTAGAATCTATACCCCATTCACAGAAGATACCGAGACTGTG GGCCAGAGAGCCCTGCACTCAATTCTGAATGCTGC | 4104 |
| | GCAGCATTCAGAATTGAGTGCAGGGCTCTCTGGCCCACAGTC TCGGTATCTTCTGTGAATGGGGTATAGATTCTACAATAAAACA AACACAAAAGCCCTAGGTCAGTGTTAATGGAGATCA | 4105 |
| | CTATACCCCATTCACAG | 4106 |
| | CTGTGAATGGGGTATAG | 4107 |
| Alzheimer disease Glu120Asp GAAg-GAT | TAACACTGACCTAGGGCTTTTGTGTTTGTTTTATTGTAGAATCT ATACCCCATTCACAGAAGATACCGAGACTGTGGGCCAGAGAG CCCTGCACTCAATTCTGAATGCTGCCATCATGATC | 4108 |
| | GATCATGATGGCAGCATTCAGAATTGAGTGCAGGGCTCTCTG GCCCACAGTCTCGGTATCTTCTGTGAATGGGGTATAGATTCT ACAATAAAACAAACACAAAAGCCCTAGGTCAGTGTTA | 4109 |
| | TTCACAGAAGATACCGA | 4110 |
| | TCGGTATCTTCTGTGAA | 4111 |
| Alzheimer disease Glu120Asp GAAg-GAC | TAACACTGACCTAGGGCTTTTGTGTTTGTTTTATTGTAGAATCT ATACCCCATTCACAGAAGATACCGAGACTGTGGGCCAGAGAG CCCTGCACTCAATTCTGAATGCTGCCATCATGATC | 4112 |
| | GATCATGATGGCAGCATTCAGAATTGAGTGCAGGGCTCTCTG GCCCACAGTCTCGGTATCTTCTGTGAATGGGGTATAGATTCT ACAATAAAACAAACACAAAAGCCCTAGGTCAGTGTTA | 4113 |
| | TTCACAGAAGATACCGA | 4114 |
| | TCGGTATCTTCTGTGAA | 4115 |

TABLE 31-continued

PSEN1 Mutations and Genome-Correcting Oligos

| Clinical Phenotype & Mutation | Correcting Oligos | SEQ ID NO: |
|---|---|---|
| Alzheimer disease Glu120Lys aGAA-AAA | ATTAACACTGACCTAGGGCTTTTGTGTTTGTTTTATTGTAGAAT CTATACCCCATTCACAGAAGATACCGAGACTGTGGGCCAGAG AGCCCTGCACTCAATTCTGAATGCTGCCATCATGA | 4116 |
| | TCATGATGGCAGCATTCAGAATTGAGTGCAGGGCTCTCTGGC CCACAGTCTCGGTATCTTCTGTGAATGGGGTATAGATTCTACA ATAAAACAAACACAAAAGCCCTAGGTCAGTGTTAAT | 4117 |
| | CATTCACAGAAGATACC | 4118 |
| | GGTATCTTCTGTGAATG | 4119 |
| Alzheimer disease Glu123Lys cGAG-AAG | GACCTAGGGCTTTTGTGTTTGTTTTATTGTAGAATCTATACCC CATTCACAGAAGATACCGAGACTGTGGGCCAGAGAGCCCTG CACTCAATTCTGAATGCTGCCATCATGATCAGTGTCA | 4120 |
| | TGACACTGATCATGATGGCAGCATTCAGAATTGAGTGCAGGG CTCTCTGGCCCACAGTCTCGGTATCTTCTGTGAATGGGGTAT AGATTCTACAATAAAACAAACACAAAAGCCCTAGGTC | 4121 |
| | AAGATACCGAGACTGTG | 4122 |
| | CACAGTCTCGGTATCTT | 4123 |
| Alzheimer disease Asn135Asp gAAT-GAT | TATACCCCATTCACAGAAGATACCGAGACTGTGGGCCAGAGA GCCCTGCACTCAATTCTGAATGCTGCCATCATGATCAGTGTC ATTGTTGTCATGACTATCCTCCTGGTGGTTCTGTATA | 4124 |
| | TATACAGAACCACCAGGAGGATAGTCATGACAACAATGACAC TGATCATGATGGCAGCATTCAGAATTGAGTGCAGGGCTCTCT GGCCCACAGTCTCGGTATCTTCTGTGAATGGGTATA | 4125 |
| | CAATTCTGAATGCTGCC | 4126 |
| | GGCAGCATTCAGAATTG | 4127 |
| Alzheimer disease Met139Ile ATGa-ATA | AGAAGATACCGAGACTGTGGGCCAGAGAGCCCTGCACTCAA TTCTGAATGCTGCCATCATGATCAGTGTCATTGTTGTCATGAC TATCCTCCTGGTGGTTCTGTATAAATACAGGTGCTAT | 4128 |
| | ATAGCACCTGTATTTATACAGAACCACCAGGAGGATAGTCATG ACAACAATGACACTGATCATGATGGCAGCATTCAGAATTGAGT GCAGGGCTCTCTGGCCCACAGTCTCGGTATCTTCT | 4129 |
| | GCCATCATGATCAGTGT | 4130 |
| | ACACTGATCATGATGGC | 4131 |
| Alzheimer disease Met139Lys ATG-AAG | CAGAAGATACCGAGACTGTGGGCCAGAGAGCCCTGCACTCA ATTCTGAATGCTGCCATCATGATCAGTGTCATTGTTGTCATGA CTATCCTCCTGGTGGTTCTGTATAAATACAGGTGCTA | 4132 |
| | TAGCACCTGTATTTATACAGAACCACCAGGAGGATAGTCATGA CAACAATGACACTGATCATGATGGCAGCATTCAGAATTGAGT GCAGGGCTCTCTGGCCCACAGTCTCGGTATCTTCTG | 4133 |
| | TGCCATCATGATCAGTG | 4134 |
| | CACTGATCATGATGGCA | 4135 |
| Alzheimer disease Met139Thr ATG-ACG | CAGAAGATACCGAGACTGTGGGCCAGAGAGCCCTGCACTCA ATTCTGAATGCTGCCATCATGATCAGTGTCATTGTTGTCATGA CTATCCTCCTGGTGGTTCTGTATAAATACAGGTGCTA | 4136 |
| | TAGCACCTGTATTTATACAGAACCACCAGGAGGATAGTCATGA CAACAATGACACTGATCATGATGGCAGCATTCAGAATTGAGT GCAGGGCTCTCTGGCCCACAGTCTCGGTATCTTCTG | 4137 |
| | TGCCATCATGATCAGTG | 4138 |
| | CACTGATCATGATGGCA | 4139 |
| Alzheimer disease Met139Val cATG-GTG | ACAGAAGATACCGAGACTGTGGGCCAGAGAGCCCTGCACTC AATTCTGAATGCTGCCATCATGATCAGTGTCATTGTTGTCATG ACTATCCTCCTGGTGGTTCTGTATAAATACAGGTGCT | 4140 |
| | AGCACCTGTATTTATACAGAACCACCAGGAGGATAGTCATGA CAACAATGACACTGATCATGATGGCAGCATTCAGAATTGAGT GCAGGGCTCTCTGGCCCACAGTCTCGGTATCTTCTGT | 4141 |
| | CTGCCATCATGATCAGT | 4142 |
| | ACTGATCATGATGGCAG | 4143 |
| Alzheimer disease Ile143Phe cATT-TTT | GAGACTGTGGGCCAGAGAGCCCTGCACTCAATTCTGAATGCT GCCATCATGATCAGTGTCATTGTTGTCATGACTATCCTCCTGG TGGTTCTGTATAAATACAGGTGCTATAAGGTGAGCA | 4144 |
| | TGCTCACCTTATAGCACCTGTATTTATACAGAACCACCAGGAG GATAGTCATGACAACAATGACACTGATCATGATGGCAGCATTC AGAATTGAGTGCAGGGCTCTCTGGCCCACAGTCTC | 4145 |
| | TCAGTGTCATTGTTGTC | 4146 |
| | GACAACAATGACACTGA | 4147 |
| Alzheimer disease Ile143Thr ATT-ACT | AGACTGTGGGCCAGAGAGCCCTGCACTCAATTCTGAATGCTG CCATCATGATCAGTGTCATTGTTGTCATGACTATCCTCCTGGT GGTTCTGTATAAATACAGGTGCTATAAGGTGAGCAT | 4148 |
| | ATGCTCACCTTATAGCACCTGTATTTATACAGAACCACCAGGA GGATAGTCATGACAACAATGACACTGATCATGATGGCAGCAT TCAGAATTGAGTGCAGGGCTCTCTGGCCCACAGTCT | 4149 |
| | CAGTGTCATTGTTGTCA | 4150 |
| | TGACAACAATGACACTG | 4151 |

TABLE 31-continued

PSEN1 Mutations and Genome-Correcting Oligos

| Clinical Phenotype & Mutation | Correcting Oligos | SEQ ID NO: |
|---|---|---|
| Alzheimer disease Met146Ile ATGa-ATA | CCAGAGAGCCCTGCACTCAATTCTGAATGCTGCCATCATGAT CAGTGTCATTGTTGTCATGACTATCCTCCTGGTGGTTCTGTAT AAATACAGGTGCTATAAGGTGAGCATGAGACACAGA | 4152 |
| | TCTGTGTCTCATGCTCACCTTATAGCACCTGTATTTATACAGA ACCACCAGGAGGATAGTCATGACAACAATGACACTGATCATG ATGGCAGCATTCAGAATTGAGTGCAGGGCTCTCTGG | 4153 |
| | GTTGTCATGACTATCCT | 4154 |
| | AGGATAGTCATGACAAC | 4155 |
| Alzheimer disease Met146Ile ATGa-ATC | CCAGAGAGCCCTGCACTCAATTCTGAATGCTGCCATCATGAT CAGTGTCATTGTTGTCATGACTATCCTCCTGGTGGTTCTGTAT AAATACAGGTGCTATAAGGTGAGCATGAGACACAGA | 4156 |
| | TCTGTGTCTCATGCTCACCTTATAGCACCTGTATTTATACAGA ACCACCAGGAGGATAGTCATGACAACAATGACACTGATCATG ATGGCAGCATTCAGAATTGAGTGCAGGGCTCTCTGG | 4157 |
| | GTTGTCATGACTATCCT | 4158 |
| | AGGATAGTCATGACAAC | 4159 |
| Alzheimer disease Met146Leu cATG-TTG | GGCCAGAGAGCCCTGCACTCAATTCTGAATGCTGCCATCATG ATCAGTGTCATTGTTGTCATGACTATCCTCCTGGTGGTTCTGT ATAAATACAGGTGCTATAAGGTGAGCATGAGACACA | 4160 |
| | TGTGTCTCATGCTCACCTTATAGCACCTGTATTTATACAGAAC CACCAGGAGGATAGTCATGACAACAATGACACTGATCATGAT GGCAGCATTCAGAATTGAGTGCAGGGCTCTCTGGCC | 4161 |
| | TTGTTGTCATGACTATC | 4162 |
| | GATAGTCATGACAACAA | 4163 |
| Alzheimer disease Met146Val cATG-GTG | GGCCAGAGAGCCCTGCACTCAATTCTGAATGCTGCCATCATG ATCAGTGTCATTGTTGTCATGACTATCCTCCTGGTGGTTCTGT ATAAATACAGGTGCTATAAGGTGAGCATGAGACACA | 4164 |
| | TGTGTCTCATGCTCACCTTATAGCACCTGTATTTATACAGAAC CACCAGGAGGATAGTCATGACAACAATGACACTGATCATGAT GGCAGCATTCAGAATTGAGTGCAGGGCTCTCTGGCC | 4165 |
| | TTGTTGTCATGACTATC | 4166 |
| | GATAGTCATGACAACAA | 4167 |
| Alzheimer disease Thr147Ile ACT-ATT | AGAGAGCCCTGCACTCAATTCTGAATGCTGCCATCATGATCA GTGTCATTGTTGTCATGACTATCCTCCTGGTGGTTCTGTATAA ATACAGGTGCTATAAGGTGAGCATGAGACACAGATC | 4168 |
| | GATCTGTGTCTCATGCTCACCTTATAGCACCTGTATTTATACA GAACCACCAGGAGGATAGTCATGACAACAATGACACTGATCA TGATGGCAGCATTCAGAATTGAGTGCAGGGCTCTCT | 4169 |
| | TGTCATGACTATCCTCC | 4170 |
| | GGAGGATAGTCATGACA | 4171 |
| Alzheimer disease His163Arg CAT-CGT | CTTTTTAAGGGTTGTGGGACCTGTTAATTATATTGAAATGCTTT CTTTTCTAGGTCATCCATGCCTGGCTTATTATATCATCTCTATT GTTGCTGTTCTTTTTTTCATTCATTTACTTGGG | 4172 |
| | CCCAAGTAAATGAATGAAAAAAAGAACAGCAACAATAGAGATG ATATAATAAGCCAGGCATGGATGACCTAGAAAAGAAAGCATTT CAATATAATTAACAGGTCCCACAACCCTTAAAAAG | 4173 |
| | GGTCATCCATGCCTGGC | 4174 |
| | GCCAGGCATGGATGACC | 4175 |
| Alzheimer disease His163Tyr cCAT-TAT | ACTTTTTAAGGGTTGTGGGACCTGTTAATTATATTGAAATGCTT TCTTTTCTAGGTCATCCCATGCCTGGCTTATTATATCATCTCTAT TGTTGCTGTTCTTTTTTTCATTCATTTACTTGG | 4176 |
| | CCAAGTAAATGAATGAAAAAAAGAACAGCAACAATAGAGATGA TATAATAAGCCAGGCATGGATGACCTAGAAAAGAAAGCATTTC AATATAATTAACAGGTCCCACAACCCTTAAAAAGT | 4177 |
| | AGGTCATCCCATGCCTGG | 4178 |
| | CCAGGCATGGATGACCT | 4179 |
| Alzheimer disease Trp165Cys TGGc-TGC | AGGGTTGTGGGACCTGTTAATTATATTGAAATGCTTTCTTTTCT AGGTCATCCATGCCTGGGCTTATTATATCATCTCTATTGTTGCT GTTCTTTTTTTCATTCATTTACTTGGGGTAAGTT | 4180 |
| | AACTTACCCCAAGTAAATGAATGAAAAAAGAACAGCAACAAT AGAGATGATATAATAAGCCAGGCATGGATGACCTAGAAAAGA AAGCATTTCAATATAATTAACAGGTCCCACAACCCT | 4181 |
| | CATGCCTGGCTTATTAT | 4182 |
| | ATAATAAGCCAGGCATG | 4183 |
| Alzheimer disease Ser169Leu TCA-TTA | ACCTGTTAATTATATTGAAATGCTTTCTTTTCTAGGTCATCCAT GCCTGGCTTATTATATCATCTCTATTGTTGCTGTTCTTTTTTTC ATTCATTTACTTGGGGTAAGTTGTGAAATTTTT | 4184 |
| | AAAAATTTCACAACTTACCCCAAGTAAATGAATGAAAAAAGAA CAGCAACAATAGAGATGATATAATAAGCCAGGCATGGATGAC CTAGAAAAGAAAGCATTTCAATATAATTAACAGGT | 4185 |
| | TATTATATCATCTCTAT | 4186 |
| | ATAGAGATGATATAATA | 4187 |

TABLE 31-continued

PSEN1 Mutations and Genome-Correcting Oligos

| Clinical Phenotype & Mutation | Correcting Oligos | SEQ ID NO: |
|---|---|---|
| Alzheimer disease Leu171Pro CTA-CCA | TAATTATATTGAAATGCTTTCTTTTCTAGGTCATCCATGCCTGG CTTATTATATCATCTCTATTGTTGCTGTTCTTTTTTTCATTCATT TACTTGGGGTAAGTTGTGAAATTTTTGGTCTG | 4188 |
| | CAGACCAAAAATTTCACAACTTACCCCAAGTAAATGAATGAAA AAAAGAACAGCAACAATAGAGATGATATAATAAGCCAGGCAT GGATGACCTAGAAAAGAAAGCATTTCAATATAATTA | 4189 |
| | ATCATCTCTATTGTTGC | 4190 |
| | GCAACAATAGAGATGAT | 4191 |
| Alzheimer disease Leu173Trp TTG-TGG | TATTGAAATGCTTTCTTTTCTAGGTCATCCATGCCTGGCTTATT ATATCATCTCTATTGTTGCTGTTCTTTTTTTCATTCATTTACTTG GGGTAAGTTGTGAAATTTTTGGTCTGTCTTTC | 4192 |
| | GAAAGACAGACCAAAAATTTCACAACTTACCCCAAGTAAATGA ATGAAAAAAAGAACAGCAACAATAGAGATGATATAATAAGCCA GGCATGGATGACCTAGAAAAGAAAGCATTTCAATA | 4193 |
| | TCTATTGTTGCTGTTCT | 4194 |
| | AGAACAGCAACAATAGA | 4195 |
| Alzheimer disease Gly209Arg gGGA-AGA | TATAACGTTGCTGTGGACTACATTACTGTTGCACTCCTGATCT GGAATTTTGGTGTGGTGGGAATGATTTCCATTCACTGGAAAG GTCCACTTCGACTCCAGCAGGCATATCTCATTATGA | 4196 |
| | TCATAATGAGATATGCCTGCTGGAGTCGAAGTGGACCTTTCC AGTGAATGGAAATCATTCCCACCACACCAAAATTCCAGATCAG GAGTGCAACAGTAATGTAGTCCACAGCAACGTTATA | 4197 |
| | GTGTGGTGGGAATGATT | 4198 |
| | AATCATTCCCACCACAC | 4199 |
| Alzheimer disease Gly209Val GGA-GTA | ATAACGTTGCTGTGGACTACATTACTGTTGCACTCCTGATCTG GAATTTTGGTGTGGTGGGAATGATTTCCATTCACTGGAAAGGT CCACTTCGACTCCAGCAGGCATATCTCATTATGAT | 4200 |
| | ATCATAATGAGATATGCCTGCTGGAGTCGAAGTGGACCTTTC CAGTGAATGGAAATCATTCCCACCACACCAAAATTCCAGATCA GGAGTGCAACAGTAATGTAGTCCACAGCAACGTTAT | 4201 |
| | TGTGGTGGGAATGATTT | 4202 |
| | AAATCATTCCCACCACA | 4203 |
| Alzheimer disease Ile213Thr ATT-ACT | TGGACTACATTACTGTTGCACTCCTGATCTGGAATTTTGGTGT GGTGGGAATGATTTCCATTCACTGGAAAGGTCCACTTCGACT CCAGCAGGCATATCTCATTATGATTAGTGCCCTCAT | 4204 |
| | ATGAGGGCACTAATCATAATGAGATATGCCTGCTGGAGTCGA AGTGGACCTTTCCAGTGAATGGAAATCATTCCCACCACACCA AAATTCCAGATCAGGAGTGCAACAGTAATGTAGTCCA | 4205 |
| | GATTTCCATTCACTGGA | 4206 |
| | TCCAGTGAATGGAAATC | 4207 |
| Alzheimer disease Leu219Pro CTT-CCT | CACTCCTGATCTGGAATTTTGGTGTGGTGGGAATGATTTCCAT TCACTGGAAAGGTCCACTTCGACTCCAGCAGGCATATCTCAT TATGATTAGTGCCCTCATGGCCCTGGTGTTTATCAA | 4208 |
| | TTGATAAACACCAGGGCCATGAGGGCACTAATCATAATGAGA TATGCCTGCTGGAGTCGAAGTGGACCTTTCCAGTGAATGGAA ATCATTCCCACCACACCAAAATTCCAGATCAGGAGTG | 4209 |
| | AGGTCCACTTCGACTCC | 4210 |
| | GGAGTCGAAGTGGACCT | 4211 |
| Alzheimer disease Ala231Thr tGCC-ACC | ATTTCCATTCACTGGAAAGGTCCACTTCGACTCCAGCAGGCA TATCTCATTATGATTAGTGCCCTCATGGCCCTGGTGTTTATCA AGTACCTCCCTGAATGGACTGCGTGGCTCATCTTGG | 4212 |
| | CCAAGATGAGCCACGCAGTCCATTCAGGGAGGTACTTGATAA ACACCAGGGCCATGAGGGCACTAATCATAATGAGATATGCCT GCTGGAGTCGAAGTGGACCTTTCCAGTGAATGGAAAT | 4213 |
| | TGATTAGTGCCCTCATG | 4214 |
| | CATGAGGGCACTAATCA | 4215 |
| Alzheimer disease Ala231Val GCC-GTC | TTTCCATTCACTGGAAAGGTCCACTTCGACTCCAGCAGGCAT ATCTCATTATGATTAGTGCCCTCATGGCCCTGGTGTTTATCAA GTACCTCCCTGAATGGACTGCGTGGCTCATCTTGGC | 4216 |
| | GCCAAGATGAGCCACGCAGTCCATTCAGGGAGGTACTTGATA AACACCAGGGCCATGAGGGCACTAATCATAATGAGATATGCC TGCTGGAGTCGAAGTGGACCTTTCCAGTGAATGGAAA | 4217 |
| | GATTAGTGCCCTCATGG | 4218 |
| | CCATGAGGGCACTAATC | 4219 |
| Alzheimer disease Met233Thr ATG-ACG | TTCACTGGAAAGGTCCACTTCGACTCCAGCAGGCATATCTCA TTATGATTAGTGCCCTCATGGCCCTGGTGTTTATCAAGTACCT CCCTGAATGGACTGCGTGGCTCATCTTGGCTGTGAT | 4220 |
| | ATCACAGCCAAGATGAGCCACGCAGTCCATTCAGGGAGGTAC TTGATAAACACCAGGGCCATGAGGGCACTAATCATAATGAGA TATGCCTGCTGGAGTCGAAGTGGACCTTTCCAGTGAA | 4221 |
| | TGCCCTCATGGCCCTGG | 4222 |
| | CCAGGGCCATGAGGGCA | 4223 |

TABLE 31-continued

PSEN1 Mutations and Genome-Correcting Oligos

| Clinical Phenotype & Mutation | Correcting Oligos | SEQ ID NO: |
|---|---|---|
| Alzheimer disease Leu235Pro CTG-CCG | GGAAAGGTCCACTTCGACTCCAGCAGGCATATCTCATTATGA TTAGTGCCCTCATGGCCCTGGTGTTTATCAAGTACCTCCCTG AATGGACTGCGTGGCTCATCTTGGCTGTGATTTCAGT | 4224 |
| | ACTGAAATCACAGCCAAGATGAGCCACGCAGTCCATTCAGGG AGGTACTTGATAAACACCAGGGCCATGAGGGCACTAATCATA ATGAGATATGCCTGCTGGAGTCGAAGTGGACCTTTCC | 4225 |
| | CATGGCCCTGGTGTTTA | 4226 |
| | TAAACACCAGGGCCATG | 4227 |
| Alzheimer disease Ala246Glu GCG-GAG | TCATTATGATTAGTGCCCTCATGGCCCTGGTGTTTATCAAGTA CCTCCCTGAATGGACTGCGTGGCTCATCTTGGCTGTGATTTC AGTATATGGTAAAACCCAAGACTGATAATTTGTTTG | 4228 |
| | CAAACAAATTATCAGTCTTGGGTTTTACCATATACTGAAATCAC AGCCAAGATGAGCCACGCAGTCCATTCAGGGAGGTACTTGAT AAACACCAGGGCCATGAGGGCACTAATCATAATGA | 4229 |
| | ATGGACTGCGTGGCTCA | 4230 |
| | TGAGCCACGCAGTCCAT | 4231 |
| Alzheimer disease Leu250Ser TTG-TCG | GTGCCCTCATGGCCCTGGTGTTTATCAAGTACCTCCCTGAAT GGACTGCGTGGCTCATCTTGGCTGTGATTTCAGTATATGGTA AAACCCAAGACTGATAATTTGTTTGTCACAGGAATGC | 4232 |
| | GCATTCCTGTGACAAACAAATTATCAGTCTTGGGTTTTACCAT ATACTGAAATCACAGCCAAGATGAGCCACGCAGTCCATTCAG GGAGGTACTTGATAAACACCAGGGCCATGAGGGCAC | 4233 |
| | GCTCATCTTGGCTGTGA | 4234 |
| | TCACAGCCAAGATGAGC | 4235 |
| Alzheimer disease Ala260Val GCT-GTT | AGTTTAGCCCATACATTTTATTAGATGTCTTTTATGTTTTCTTT TTCTAGATTTAGTGGCTGTTTTGTGTCCGAAAGGTCCACTTCG TATGCTGGTTGAAACAGCTCAGGAGAGAAATGA | 4236 |
| | TCATTTCTCTCCTGAGCTGTTTCAACCAGCATACGAAGTGGAC CTTTCGGACACAAAACAGCCACTAAATCTAGAAAAAGAAAAAC ATAAAAGACATCTAATAAAATGTATGGGCTAAACT | 4237 |
| | TTTAGTGGCTGTTTTGT | 4238 |
| | ACAAAACAGCCACTAAA | 4239 |
| Alzheimer disease Leu262Phe TTGt-TTC | CCCATACATTTTATTAGATGTCTTTTATGTTTTCTTTTTCTAGA TTTAGTGGCTGTTTTGTGTCCGAAAGGTCCACTTCGTATGCTG GTTGAAACAGCTCAGGAGAGAAATGAAACGCTT | 4240 |
| | AAGCGTTTCATTTCTCTCCTGAGCTGTTTCAACCAGCATACGA AGTGGACCTTTCGGACACAAAACAGCCACTAAATCTAGAAAAA GAAAAACATAAAAGACATCTAATAAAATGTATGGG | 4241 |
| | GCTGTTTTGTGTCCGAA | 4242 |
| | TTCGGACACAAAACAGC | 4243 |
| Alzheimer disease Cys263Arg gTGT-CGT | CCATACATTTTATTAGATGTCTTTTATGTTTTCTTTTTCTAGAT TTAGTGGCTGTTTTGTGTCCGAAAGGTCCACTTCGTATGCTG GTTGAAACAGCTCAGGAGAGAAATGAAACGCTTT | 4244 |
| | AAAGCGTTTCATTTCTCTCCTGAGCTGTTTCAACCAGCATACG AAGTGGACCTTTCGGACACAAAACAGCCACTAAATCTAGAAA AAGAAAAACATAAAAGACATCTAATAAAATGTATGG | 4245 |
| | CTGTTTTGTGTCCGAAA | 4246 |
| | TTTCGGACACAAAACAG | 4247 |
| Alzheimer disease Pro264Leu CCG-CTG | ACATTTTATTAGATGTCTTTTATGTTTTCTTTTTCTAGATTTAG TGGCTGTTTTGTGTCCGAAAGGTCCACTTCGTATGCTGGTTG AAACAGCTCAGGAGAGAAATGAAACGCTTTTTCC | 4248 |
| | GGAAAAAGCGTTTCATTTCTCTCCTGAGCTGTTTCAACCAGCA TACGAAGTGGACCTTTCGGACACAAAACAGCCACTAAATCTA GAAAAAGAAAAACATAAAAGACATCTAATAAAATGT | 4249 |
| | TTTGTGTCCGAAAGGTC | 4250 |
| | GACCTTTCGGACACAAA | 4251 |
| Alzheimer disease Arg269Gly tCGT-GGT | GTCTTTTATGTTTTCTTTTTCTAGATTTAGTGGCTGTTTTGTG TCCGAAAGGTCCACTTCGTATGCTGGTTGAAACAGCTCAGGA GAGAAATGAAACGCTTTTTCCAGCTCTCATTTACT | 4252 |
| | AGTAAATGAGAGCTGGAAAAAGCGTTTCATTTCTCTCCTGAGC TGTTTCAACCAGCATACGAAGTGGACCTTTCGGACACAAAAC AGCCACTAAATCTAGAAAAGAAAAACATAAAAGAC | 4253 |
| | GTCCACTTCGTATGCTG | 4254 |
| | CAGCATACGAAGTGGAC | 4255 |
| Alzheimer disease Arg269His CGT-CAT | TCTTTTATGTTTTCTTTTTCTAGATTTAGTGGCTGTTTTGTGTC CGAAAGGTCCACTTCGTATGCTGGTTGAAACAGCTCAGGAGA GAAATGAAACGCTTTTTCCAGCTCTCATTTACTC | 4256 |
| | GAGTAAATGAGAGCTGGAAAAAGCGTTTCATTTCTCTCCTGAG CTGTTTCAACCAGCATACGAAGTGGACCTTTCGGACACAAAA CAGCCACTAAATCTAGAAAAGAAAAACATAAAAGA | 4257 |
| | TCCACTTCGTATGCTGG | 4258 |
| | CCAGCATACGAAGTGGA | 4259 |

TABLE 31-continued

PSEN1 Mutations and Genome-Correcting Oligos

| Clinical Phenotype & Mutation | Correcting Oligos | SEQ ID NO: |
|---|---|---|
| Alzheimer disease Arg278Thr AGA-ACA | TAGTGGCTGTTTTGTGTCCGAAAGGTCCACTTCGTATGCTGG TTGAAACAGCTCAGGAGAGAAATGAAACGCTTTTTCCAGCTCT CATTTACTCCTGTAAGTATTTGAGAATGATATTGAA | 4260 |
| | TTCAATATCATTCTCAAATACTTACAGGAGTAAATGAGAGCTG GAAAAAGCGTTTCATTTCTCTCCTGAGCTGTTTCAACCAGCAT ACGAAGTGGACCTTTCGGACACAAAACAGCCACTA | 4261 |
| | TCAGGAGAGAAATGAAA | 4262 |
| | TTTCATTTCTCTCCTGA | 4263 |
| Alzheimer disease Glu280Ala GAA-GCA | CTGTTTTGTGTCCGAAAGGTCCACTTCGTATGCTGGTTGAAAC AGCTCAGGAGAGAAATGAAACGCTTTTTCCAGCTCTCATTTAC TCCTGTAAGTATTTGAGAATGATATTGAATTAGTA | 4264 |
| | TACTAATTCAATATCATTCTCAAATACTTACAGGAGTAAATGAG AGCTGGAAAAAGCGTTTCATTTCTCTCCTGAGCTGTTTCAACC AGCATACGAAGTGGACCTTTCGGACACAAAACAG | 4265 |
| | GAGAAATGAAACGCTTT | 4266 |
| | AAAGCGTTTTCATTTCTC | 4267 |
| Alzheimer disease Glu280Gly GAA-GGA | CTGTTTTGTGTCCGAAAGGTCCACTTCGTATGCTGGTTGAAAC AGCTCAGGAGAGAAATGAAACGCTTTTTCCAGCTCTCATTTAC TCCTGTAAGTATTTGAGAATGATATTGAATTAGTA | 4268 |
| | TACTAATTCAATATCATTCTCAAATACTTACAGGAGTAAATGAG AGCTGGAAAAAGCGTTTCATTTCTCTCCTGAGCTGTTTCAACC AGCATACGAAGTGGACCTTTCGGACACAAAACAG | 4269 |
| | GAGAAATGAAACGCTTT | 4270 |
| | AAAGCGTTTTCATTTCTC | 4271 |
| Alzheimer disease Leu282Arg CTT-CGT | TGTGTCCGAAAGGTCCACTTCGTATGCTGGTTGAAACAGCTC AGGAGAGAAATGAAACGCTTTTTCCAGCTCTCATTTACTCCTG TAAGTATTTGAGAATGATATTGAATTAGTAATCAGT | 4272 |
| | ACTGATTACTAATTCAATATCATTCTCAAATACTTACAGGAGTA AATGAGAGCTGGAAAAAGCGTTTCATTTCTCTCCTGAGCTGTT TCAACCAGCATACGAAGTGGACCTTTCGGACACA | 4273 |
| | TGAAACGCTTTTTCCAG | 4274 |
| | CTGGAAAAAGCGTTTCA | 4275 |
| Alzheimer disease Ala285Val GCT-GTT | AAGGTCCACTTCGTATGCTGGTTGAAACAGCTCAGGAGAGAA ATGAAACGCTTTTTCCAGCTCTCATTTACTCCTGTAAGTATTTG AGAATGATATTGAATTAGTAATCAGTGTAGAATTT | 4276 |
| | AAATTCTACACTGATTACTAATTCAATATCATTCTCAAATACTTA CAGGAGTAAATGAGAGCTGGAAAAAGCGTTTCATTTCTCTCCT GAGCTGTTTCAACCAGCATACGAAGTGGACCTT | 4277 |
| | TTTTCCAGCTCTCATTT | 4278 |
| | AAATGAGAGCTGGAAAA | 4279 |
| Alzheimer disease Leu286Val tCTC-GTC | GGTCCACTTCGTATGCTGGTTGAAACAGCTCAGGAGAGAAAT GAAACGCTTTTTCCAGCTCTCATTTACTCCTGTAAGTATTTGA GAATGATATTGAATTAGTAATCAGTGTAGAATTTAT | 4280 |
| | ATAAATTCTACACTGATTACTAATTCAATATCATTCTCAAATACT TACAGGAGTAAATGAGAGCTGGAAAAGCGTTTCATTTCTCTC CTGAGCTGTTTCAACCAGCATACGAAGTGGACC | 4281 |
| | TTCCAGCTCTCATTTAC | 4282 |
| | GTAAATGAGAGCTGGAA | 4283 |
| Alzheimer disease Gly384Ala GGA-GCA | GTGACCAACTTTTTAATATTTGTAACCTTTCCTTTTTAGGGGGA GTAAAACTTGGATTGGGAGATTTCATTTTCTACAGTGTTCTGG TTGGTAAAGCCTCAGCAACAGCCAGTGGAGACTG | 4284 |
| | CAGTCTCCACTGGCTGTTGCTGAGGCTTTACCAACCAGAACA CTGTAGAAAATGAAATCTCCCAATCCAAGTTTTACTCCCCCTA AAAAGGAAAGGTTACAAATATTAAAAAGTTGGTCAC | 4285 |
| | TGGATTGGGAGATTTCA | 4286 |
| | TGAAATCTCCCAATCCA | 4287 |
| Alzheimer disease Ser390Ile AGT-ATT | TTTGTAACCTTTCCTTTTTAGGGGGAGTAAAACTTGGATTGGG AGATTTCATTTTCTACAGTGTTCTGGTTGGTAAAGCCTCAGCA ACAGCCAGTGGAGACTGGAACACAACCATAGCCTG | 4288 |
| | CAGGCTATGGTTGTGTTCCAGTCTCCACTGGCTGTTGCTGAG GCTTTACCAACCAGAACACTGTAGAAAATGAAATCTCCCAATC CAAGTTTTACTCCCCCTAAAAAGGAAAGGTTACAAA | 4289 |
| | TTTCTACAGTGTTCTGG | 4290 |
| | CCAGAACACTGTAGAAA | 4291 |
| Alzheimer disease Leu392Val tCTG-GTG | AACCTTTCCTTTTTAGGGGGAGTAAAACTTGGATTGGGAGATT TCATTTTCTACAGTGTTCTGGTTGGTAAAGCCTCAGCAACAGC CAGTGGAGACTGGAACACAACCATAGCCTGTTTCG | 4292 |
| | CGAAACAGGCTATGGTTGTGTTCCAGTCTCCACTGGCTGTTG CTGAGGCTTTACCAACCAGAACACTGTAGAAAATGAAATCTCC CAATCCAAGTTTTACTCCCCCTAAAAAGGAAAGGTT | 4293 |
| | ACAGTGTTCTGGTTGGT | 4294 |
| | ACCAACCAGAACACTGT | 4295 |

TABLE 31-continued

PSEN1 Mutations and Genome-Correcting Oligos

| Clinical Phenotype & Mutation | Correcting Oligos | SEQ ID NO: |
|---|---|---|
| Alzheimer disease Asn405Ser AAC-AGC | ATTTCATTTTCTACAGTGTTCTGGTTGGTAAAGCCTCAGCAAC AGCCAGTGGAGACTGGAACACAACCATAGCCTGTTTCGTAGC CATATTAATTGTAAGTATACACTAATAAGAATGTGT | 4296 |
| | ACACATTCTTATTAGTGTATACTTACAATTAATATGGCTACGAA ACAGGCTATGGTTGTGTTCCAGTCTCCACTGGCTGTTGCTGA GGCTTTACCAACCAGAACACTGTAGAAAATGAAAT | 4297 |
| | AGACTGGAACACAACCA | 4298 |
| | TGGTTGTGTTCCAGTCT | 4299 |
| Alzheimer disease Ala409Thr aGCC-ACC | TACAGTGTTCTGGTTGGTAAAGCCTCAGCAACAGCCAGTGGA GACTGGAACACAACCATAGCCTGTTTCGTAGCCATATTAATTG TAAGTATACACTAATAAGAATGTGTCAGAGCTCTTA | 4300 |
| | TAAGAGCTCTGACACATTCTTATTAGTGTATACTTACAATTAAT ATGGCTACGAAACAGGCTATGGTTGTGTTCCAGTCTCCACTG GCTGTTGCTGAGGCTTTACCAACCAGAACACTGTA | 4301 |
| | CAACCATAGCCTGTTTC | 4302 |
| | GAAACAGGCTATGGTTG | 4303 |
| Alzheimer disease Cys410Tyr TGT-TAT | GTGTTCTGGTTGGTAAAGCCTCAGCAACAGCCAGTGGAGACT GGAACACAACCATAGCCTGTTTCGTAGCCATATTAATTGTAAG TATACACTAATAAGAATGTGTCAGAGCTCTTAATGT | 4304 |
| | ACATTAAGAGCTCTGACACATTCTTATTAGTGTATACTTACAAT TAATATGGCTACGAAACAGGCTATGGTTGTGTTCCAGTCTCCA CTGGCTGTTGCTGAGGCTTTACCAACCAGAACAC | 4305 |
| | CATAGCCTGTTTCGTAG | 4306 |
| | CTACGAAACAGGCTATG | 4307 |
| Alzheimer disease Ala426Pro tGCC-CCC | TGTGAATGTGTGTCTTTCCCATCTTCTCCACAGGGTTTGTGCC TTACATTATTACTCCTTGCCATTTTCAAGAAAGCATTGCCAGCT CTTCCAATCTCCATCACCTTTGGGCTTGTTTTCT | 4308 |
| | AGAAAACAAGCCCAAAGGTGATGGAGATTGGAAGAGCTGGCA ATGCTTTCTTGAAAATGGCAAGGAGTAATAATGTAAGGCACAA ACCCTGTGGAGAAGATGGGAAAGACACACATTCACA | 4309 |
| | TACTCCTTGCCATTTTC | 4310 |
| | GAAAATGGCAAGGAGTA | 4311 |
| Alzheimer disease Pro436Gln CCA-CAA | AGGGTTTGTGCCTTACATTATTACTCCTTGCCATTTTCAAGAA AGCATTGCCAGCTCTTCCAATCTCCATCACCTTTGGGCTTGTT TTCTACTTTGCCACAGATTATCTTGTACAGCCTTT | 4312 |
| | AAAGGCTGTACAAGATAATCTGTGGCAAAGTAGAAAACAAGC CCAAAGGTGATGGAGATTGGAAGAGCTGGCAATGCTTTCTTG AAAATGGCAAGGAGTAATAATGTAAGGCACAAACCCT | 4313 |
| | AGCTCTTCCAATCTCCA | 4314 |
| | TGGAGATTGGAAGAGCT | 4315 |
| Alzheimer disease Pro436Ser tCCA-TCA | CAGGGTTTGTGCCTTACATTATTACTCCTTGCCATTTTCAAGA AAGCATTGCCAGCTCTTCCAATCTCCATCACCTTTGGGCTTGT TTTCTACTTTGCCACAGATTATCTTGTACAGCCTT | 4316 |
| | AAGGCTGTACAAGATAATCTGTGGCAAAGTAGAAAACAAGCC CAAAGGTGATGGAGATTGGAAGAGCTGGCAATGCTTTCTTGA AAATGGCAAGGAGTAATAATGTAAGGCACAAACCCTG | 4317 |
| | CAGCTCTTCCAATCTCC | 4318 |
| | GGAGATTGGAAGAGCTG | 4319 |

EXAMPLE 25

Alzheimer's Disease—Presenilin-2 (PSEN2)

The attached table discloses the correcting oligonucleotide base sequences for the PSEN2 oligonucleotides of the invention.

TABLE 32

PSEN2 Mutations and Genome-Correcting Oligos

| Clinical Phenotype & Mutation | Correcting Oligos | SEQ ID NO: |
|---|---|---|
| Alzheimer disease Arg62His CGC-CAC | GATGTGGTTTCCCACAGAGAAGCCAGGAGAACGAGGAGGAC GGTGAGGAGGACCCTGACCGCTATGTCTGTAGTGGGGTTCC CGGGCGGCCGCCAGGCCTGGAGGAAGAGCTGACCCTCAA | 4320 |
| | TTGAGGGTCAGCTCTTCCTCCAGGCCTGGCGGCCGCCCGGG AACCCCACTACAGACATAGCGGTCAGGGTCCTCCTCACCGTC | 4321 |

TABLE 32-continued

PSEN2 Mutations and Genome-Correcting Oligos

| Clinical Phenotype & Mutation | Correcting Oligos | SEQ ID NO: |
|---|---|---|
| | CTCCTCGTTCTCCTGGCTTCTCTGTGGGAAACCACATC CCCTGACCGCTATGTCT | 4322 |
| | AGACATAGCGGTCAGGG | 4323 |
| Alzheimer disease Thr122Pro cACG-CCG | GCCTCGAGGAGCAGTCAGGGCCGGGAGCATCAGCCCTTTGC CTTCTCCCTCAGCATCTACACGACATTCACTGAGGACACACC CTCGGTGGGCCAGCGCCTCCTCAACTCCGTGCTGAACA | 4324 |
| | TGTTCAGCACGGAGTTGAGGAGGCGCTGGCCCACCGAGGGT GTGTCCTCAGTGAATGTCGTGTAGATGCTGAGGGAGAAGGCA AAGGGCTGATGCTCCCGGCCCTGACTGCTCCTCGAGGC | 4325 |
| | GCATCTACACGACATTC | 4326 |
| | GAATGTCGTGTAGATGC | 4327 |
| Alzheimer disease Asn141Ile AAC-ATC | ACACGCCATTCACTGAGGACACACCCTCGGTGGGCCAGCGC CTCCTCAACTCCGTGCTGAACACCCTCATCATGATCAGCGTC ATCGTGGTTATGACCATCTTCTTGGTGGTGCTCTACAA | 4328 |
| | TTGTAGAGCACCACCAAGAAGATGGTCATAACCACGATGACG CTGATCATGATGAGGGTGTTCAGCACGGAGTTGAGGAGGCG CTGGCCCACCGAGGGTGTGTCCTCAGTGAATGGCGTGT | 4329 |
| | CGTGCTGAACACCCTCA | 4330 |
| | TGAGGGTGTTCAGCACG | 4331 |
| Alzheimer disease Met239Ile ATGg-ATA | CCACTGGAAGGGCCCTCTGGTGCTGCAGCAGGCCTACCTCA TCATGATCAGTGCGCTCATGGCCCTAGTGTTCATCAAGTACCT CCCAGAGTGGTCCGCGTGGGTCATCCTGGGCGCCATC | 4332 |
| | GATGGCGCCCAGGATGACCCACGCGGACCACTCTGGGAGGT ACTTGATGAACACTAGGGCCATGAGCGCACTGATCATGATGA GGTAGGCCTGCTGCAGCACCAGAGGGCCCTTCCAGTGG | 4333 |
| | GCGCTCATGGCCCTAGT | 4334 |
| | ACTAGGGCCATGAGCGC | 4335 |
| Alzheimer disease Met239Val cATG-GTG | ATCCACTGGAAGGGCCCTCTGGTGCTGCAGCAGGCCTACCT CATCATGATCAGTGCGCTCATGGCCCTAGTGTTCATCAAGTA CCTCCCAGAGTGGTCCGCGTGGGTCATCCTGGGCGCCA | 4336 |
| | TGGCGCCCAGGATGACCCACGCGGACCACTCTGGGAGGTAC TTGATGAACACTAGGGCCATGAGCGCACTGATCATGATGAGG TAGGCCTGCTGCAGCACCAGAGGGCCCTTCCAGTGGAT | 4337 |
| | GTGCGCTCATGGCCCTA | 4338 |
| | TAGGGCCATGAGCGCAC | 4339 |

EXAMPLE 26

Plant Cells

The oligonucleotides of the invention can also be used to repair or direct a mulagenic event in plants and animal cells. Although little information is available on plant mutations amongst natural cultivars, the oligonucleotides of the invention can be used to produce "knock out" mutations by modification of specific amino acid codons to produce stop codons (e.g., a CAA codon specifying Gln can be modified at a specific site to TAA; a AAG codon specifying Lys can be modified to UAG at a specific site; and a CGA codon for Arg can be modified to a UGA codon at a specific site). Such base pair changes will terminate the reading frame and produce a defective truncated protein, shortened at the site of the stop codon. Alternatively, frameshift additions or deletions can be directed into the genome at a specific sequence to interrupt the reading frame and produce a garbled downstream protein. Such stop or frameshift mutations can be introduced to determine the effect of knocking out the protein in either plant or animal cells.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of oridinary skill in the art in light of the teachings of this invention that certain changes and modifications may by made thereto without departing from the spirit or scope of the appended claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6936467B2). An electronic copy of the "Sequence Listing" will also be available from the USPTO upon request and payment of the fee set forth in 37 CFR 1.19(b)(3).

What is claimed is:

1. A method of targeted alteration of a chromosomal sequence present within a cell in vitro, the method comprising:
   introducing a sequence-altering oligonucleotide into a cell in vitro,
   wherein said sequence-altering oligonucleotide:
      is a single-stranded nonhairpin oligonucleotide 17–121 nucleotides in length;
      has an unmodified DNA domain of at least 8 contiguous deoxyribonucleotides;
      is fully complementary in sequence to a first strand of the cell's chromosomal DNA at a chromosomal target sequence, except for one or two mismatches positioned (i) within said oligonucleotide's unmodified DNA domain and (ii) at least 8 nucleotides from said oligonucleotide's 5' and 3' termini; and
      has chemical modifications consisting essentially of at least one terminal locked nucleic acid (LNA), or at least one terminal 2'-O-Me base analog, or at least three terminal phosphorothioate linkages, or combinations thereof, and
   wherein said cell is not a human embryonic stem cell,
   whereby said introduced oligonucleotide directs sequence alteration at said chromosomal target sequence by the cellular repair enzyme machinery.

2. The method of claim 1, wherein said sequence alteration is a substitution of at least one base.

3. The method of claim 1, wherein said sequence alteration is a deletion of at least one base.

4. The method of claim 1, wherein said alteration is an insertion of at least one base.

5. The method of claim 1, wherein said chromosome is an artificial chromosome.

6. The method of claim 1, wherein said cellular repair proteins are purified.

7. The method of claim 1, wherein said cellular repair proteins are present in a cell-free protein extract.

8. The method of claim 1, wherein said cellular repair proteins are present within an intact cell.

9. The method of claim 8, wherein said cell is cultured ex vivo.

10. The method of claim 1, wherein said cellular repair proteins are of a cell selected from the group consisting of: prokaryotic cells and eukaryotic cells.

11. The method of claim 10, wherein said cell is a prokaryotic cell.

12. The method of claim 11, wherein said prokaryotic cell is a bacterial cell.

13. The method of claim 12, wherein said bacterial cell is an *E. coli* cell.

14. The method of claim 10, wherein said cell is a eukaryotic cell.

15. The method of claim 14, wherein said eukaryotic cell is a yeast cell, plant cell, human cell, or a mammalian cell.

16. The method of claim 15, wherein said eukaryotic cell is a yeast cell.

17. The method of claim 16, wherein said yeast cell is a *Saccharomyces cerevisiae, Ustilago maydis*, or *Candida albicans* cell.

18. The method of claim 15, wherein said eukaryotic cell is a plant cell.

19. The method of claim 15, wherein said eukaryotic cell is a human cell.

20. The method of claim 19, wherein said human cell is selected from the group consisting of liver cell, lung cell, colon cell, cervical cell, kidney cell, epithelial cell, cancer cell, and stem cell.

21. The method of claim 15, wherein said eukaryotic cell is from a mammal.

22. The method of claim 21, wherein said mammal is selected from the group consisting of: rodent, mouse, hamster, rat, and monkey.

23. The method of claim 1, wherein said oligonucleotide is at least 25 nucleotides in length.

24. The method of claim 1, wherein said oligonucleotide is no more than 74 nucleotides in length.

25. The method of claim 1, wherein said first strand is the nontranscribed strand of the target nucleic acid.

26. The method of claim 1, wherein the sequences of said unmodified DNA domain and of the target nucleic acid first strand are mismatched at a single nucleotide.

27. The method of claim 1, wherein the sequences of said unmodified DNA domain and of its complement on the target nucleic acid first strand are mismatched at two or more nucleotides.

28. The method of claim 1, wherein said at least one terminal modification is at least one 3' terminal LNA analogue.

29. The method of claim 28, wherein said oligonucleotide has no more than 3 LNA analogues at its 3' terminus.

30. The method of claim 28, wherein said oligonucleotide has at least one LNA at its 3' terminus and at least one LNA at its 5' terminus.

31. The method of claim 30, wherein said oligonucleotide has no more than 3 contiguous LNA at each of its 3' or 5' termini.

32. The method of claim 1, wherein said at least one terminal modification is at least one 2'-O-methyl ribonucleotide analog at its 3' terminus.

33. The method of claim 32, wherein said oligonucleotide has no more than 4 contiguous 2'-O-methyl ribonucleotide analogs.

34. The method of claim 32, wherein said oligonucleotide has at least one 2'-O-methyl ribonucleotide analog at its 3' terminus and at least one 2'-O-methyl ribonucleotide analog at its 5' terminus.

35. The method of claim 34, wherein said oligonucleotide has no more than 4 contiguous 2'-O-methyl ribonucleotide analogs.

36. The method of claim 1, wherein said at least one terminal modification comprises at least three terminal phosphorothioate linkages.

37. The method of claim 36, wherein said phosphorothioate linkages at said oligonucleotide's 3' terminus.

38. The method of claim 36, wherein said oligonucleotide comprises no more than 6 contiguous phosphorothioate linkages.

39. A method of targeted sequence alteration of a nucleic acid present within selectively enriched cells in vitro, cells in culture, or cell-free extracts, comprising:
   contacting the targeted nucleic acid in the presence of cellular repair proteins with a single-stranded nonhairpin oligonucleotide 17–121 nucleotides in length, said oligonucleotide having a domain of at least B contiguous deoxyribonucleotides,
   wherein said oligonucleotide is fully complementary in sequence to the sequence of a first strand of the targeted nucleic acid, but for one or more mismatches as between the sequences of said deoxyribonucleotide domain and its complement on the target nucleic acid first strand, each of said mismatches positioned at least B nucleotides from said oligonucleotide's 5' and 3' termini;
   wherein said oligonucleotide has at least one terminal modification selected from the group consisting of: at least one terminal locked nucleic acid (LNA), at least one terminal 2'-O-Me base analog, and at least three terminal phosphorothioate linkages;

wherein said cultured or selectively enriched cells are not human embryonic stem cells, and wherein said targeted nucleic acid is selected from the group of human genes consisting of: ADA, p53, beta-globin, RB, BRCA1, BRCA2, CFTR, CDKN2A, APC, Factor V, Factor VIII, Factor IX, hemoglobin alpha 1, hemoglobin alpha 2, MLH1, MSH2, MSH6, ApoE, LDL receptor, UGT1, APP, PSEN1, and PSEN2.

40. The method of claim 39, wherein said targeted nucleic acid is the human beta-globin gene.

41. The method of claim 40, wherein said human beta-globin gene is targeted in a human hematopoietic stem cell.

42. A method of targeted sequence alteration of a nucleic acid present within selectively enriched cells in vitro, cells in culture, or cell-free extracts, comprising:

contacting the targeted nucleic acid in the presence of cellular repair proteins with a single-stranded nonhairpin oligonucleotide 17–121 nucleotides in length, said oligonucleotide having a domain of at least 8 contiguous deoxyribonucleotides, wherein said oligonucleotide is fully complementary in sequence to the sequence of a first strand of the targeted nucleic acid, but for one or more mismatches as between the sequences of said deoxyribonucleotide domain and its complement on the target nucleic acid first strand, each of said mismatches positioned at least 8 nucleotides from said oligonucleotide's 5' and 3' termini;

wherein said oligonucleotide has at least one terminal modification selected from the group consisting of: at least one terminal locked nucleic acid (LNA), at least one terminal 2'-O-Me base analog, and at least three terminal phosphorothioate linkages;

wherein said cultured or selectively enriched cells are not human embryonic stem cells, and wherein said oligonucleotide includes the sequence of any one of SEQ ID NOs: 1–4340.

43. The method of claim 42, wherein said oligonucleotide has sequence identical to any one of SEQ ID NOs: 1–4340.

44. A method of targeted sequence alteration of a nucleic acid present within selectively enriched cells in vitro, cells in culture, or cell-free extracts, comprising:

contacting the targeted nucleic acid in the presence of cellular repair proteins with a single-stranded nonhairpin oligonucleotide 17–121 nucleotides in length, said oligonucleotide having a domain of at least 8 contiguous deoxyribonucleotides, wherein said oligonucleotide is fully complementary in sequence to the sequence of a first strand of the targeted nucleic acid, but for one or more mismatches as between the sequences of said deoxyribonucleotide domain and its complement on the target nucleic acid first strand, each of said mismatches positioned at least 8 nucleotides from said oligonucleotide's 5' and 3' termini;

wherein said oligonucleotide has at least one terminal modification, said oligonucleotide includes the sequence of any one of SEQ ID NOs: 1–4340, and said cultured or selectively enriched cells are not human embryonic stem cells.

45. The method of claim 44, wherein said at least one terminal modification is selected from the group consisting of: at least one terminal locked nucleic acid (LNA), at least one terminal 2'-O-Me base analog, and at least three terminal phosphorothioate linkages.

46. The method of claim 44, wherein said target is chromosomal genomic DNA.

47. A method of targeted sequence alteration of a nucleic acid present within selectively enriched hematopoietic stem cells in vitro or hematopoietic stem cells in culture, comprising:

contacting the targeted nucleic acid in the presence of cellular repair proteins with a single-stranded nonhairpin oligonucleotide 17–121 nucleotides in length, said oligonucleotide having a domain of at least 8 contiguous deoxyribonucleotides, wherein said oligonucleotide is fully complementary in sequence to the sequence of a first strand of the targeted nucleic acid, but for one or more mismatches as between the sequences of said deoxyribonucleotide domain and its complement on the target nucleic acid first strand, each of said mismatches positioned at least 8 nucleotides from said oligonucleotide's 5' and 3' termini; and wherein said oligonucleotide has at least one terminal modification selected from the group consisting of: at least one terminal locked nucleic acid (LNA), at least one terminal 2'-O-Me base analog, and at least three terminal phosphorothioate linkages.

48. The method of claim 39, wherein said targeted nucleic acid is the human ADA gene.

49. The method of claim 48, wherein said ADA gene is targeted in a human hematopoietic stem cell.

50. The method of claim 39, wherein said targeted nucleic acid is the human p53 gene.

51. The method of claim 39, wherein said targeted nucleic acid is the human RB gene.

52. The method of claim 39, wherein said targeted nucleic acid is the human BRCA1 gene.

53. The method of claim 39, wherein said targeted nucleic acid is the human BRCA2 gene.

54. The method of claim 39, wherein said targeted nucleic acid is the human CFTR gene.

55. The method of claim 39, wherein said targeted nucleic acid is the human CDKN2A gene.

56. The method of claim 39, wherein said targeted nucleic acid is the human APC gene.

57. The method of claim 39, wherein said targeted nucleic acid is the human Factor V gene.

58. The method of claim 39, wherein said targeted nucleic acid is the human Factor VIII gene.

59. The method of claim 39, wherein said targeted nucleic acid is the human Factor IX gene.

60. The method of claim 39, wherein said targeted nucleic acid is the human hemoglobin alpha 1 gene.

61. The method of claim 60, wherein said hemoglobin gene is targeted in a human hematopoietic stem cell.

62. The method of claim 39, wherein said targeted nucleic acid is the human hemoglobin alpha 2 gene.

63. The method of claim 62, wherein said hemoglobin gene is targeted in a human hematopoietic stem cell.

64. The method of claim 39, wherein said targeted nucleic acid is the human MLH1 gene.

65. The method of claim 39, wherein said targeted nucleic acid is the human MSH2 gene.

66. The method of claim 39, wherein said targeted nucleic acid is the human MSH6 gene.

67. The method of claim 39, wherein said targeted nucleic acid is the human ApoE gene.

68. The method of claim 39, wherein said targeted nucleic acid is the human LDL receptor.

69. The method of claim 39, wherein said targeted nucleic acid is the human UGT1 gene.

70. The method of claim 39, wherein said targeted nucleic acid is the human APP gene.

71. The method of claim 39, wherein said targeted nucleic acid is the human PSEN1 gene.

72. The method of claim 39, wherein said targeted nucleic acid is the human PSEN2 gene.

73. The method of claim 42, wherein said oligonucleotide includes the sequence of any one of SEQ ID NOs: 1–160.

74. The method of claim 42, wherein said oligonucleotide includes the sequence of any one of SEQ ID NOs: 161–356.

75. The method of claim 42, wherein said oligonucleotide includes the sequence of any one of SEQ ID NOs: 357–500.

76. The method of claim 42, wherein said oligonucleotide includes the sequence of any one of SEQ ID NOs: 501–652.

77. The method of claim 42, wherein said oligonucleotide includes the sequence of any one of SEQ ID NOs: 653–1028.

78. The method of claim 42, wherein said oligonucleotide includes the sequence of any one of SEQ ID NOs: 1029–1128.

79. The method of claim 42, wherein said oligonucleotide includes the sequence of any one of SEQ ID NOs: 1129–1320.

80. The method of claim 42, wherein said oligonucleotide includes the sequence of any one of SEQ ID NOs: 1321–1432.

81. The method of claim 42, wherein said oligonucleotide includes the sequence of any one of SEQ ID NOs: 1433–1768.

82. The method of claim 42, wherein said oligonucleotide includes the sequence of any one of SEQ ID NOs: 4340, 1769–1799.

83. The method of claim 42, wherein said oligonucleotide includes the sequence of any one of SEQ ID NOs: 1800–2271.

84. The method of claim 42, wherein said oligonucleotide includes the sequence of any one of SEQ ID NOs: 2272–2775.

85. The method of claim 42, wherein said oligonucleotide includes the sequence of any one of SEQ ID NOs: 2776–2855.

86. The method of claim 42, wherein said oligonucleotide includes the sequence of any one of SEQ ID NOs: 2856–2979.

87. The method of claim 42, wherein said oligonucleotide includes the sequence of any one of SEQ ID NOs: 2980–3207.

88. The method of claim 42, wherein said oligonucleotide includes the sequence of any one of SEQ ID NOs: 3208–3343.

89. The method of claim 42, wherein said oligonucleotide includes the sequence of any one of SEQ ID NOs: 3344–3395.

90. The method of claim 42, wherein said oligonucleotide includes the sequence of any one of SEQ ID NOs: 3396–3471.

91. The method of claim 42, wherein said oligonucleotide includes the sequence of any one of SEQ ID NOs: 3472–3959.

92. The method of claim 42, wherein said oligonucleotide includes the sequence of any one of SEQ ID NOs: 3960–4035.

93. The method of claim 42, wherein said oligonucleotide includes the sequence of any one of SEQ ID NOs: 4036–4083.

94. The method of claim 42, wherein said oligonucleotide includes the sequence of any one of SEQ ID NOs: 4084–4319.

95. The method of claim 42, wherein said oligonucleotide includes the sequence of any one of SEQ ID NOs: 4320–4339.

96. The method of claim 42, wherein said oligonucleotide has sequence identical to any one of SEQ ID NOs: 1–4340.

97. The method of claim 44, wherein said oligonucleotide includes the sequence of any one of SEQ ID NOs: 1–160.

98. The method of claim 44, wherein said oligonucleotide includes the sequence of any one of SEQ ID NOs: 161–356.

99. The method of claim 44, wherein said oligonucleotide includes the sequence of any one of SEQ ID NOs: 357–500.

100. The method of claim 44, wherein said oligonucleotide includes the sequence of any one of SEQ ID NOs: 501–652.

101. The method of claim 44, wherein said oligonucleotide includes the sequence of any one of SEQ ID NOs: 653–1028.

102. The method of claim 44, wherein said oligonucleotide includes the sequence of any one of SEQ ID NOs: 1029–1128.

103. The method of claim 44, wherein said oligonucleotide includes the sequence of any one of SEQ ID NOs: 1129–1320.

104. The method of claim 44, wherein said oligonucleotide includes the sequence of any one of SEQ ID NOs: 1321–1432.

105. The method of claim 44, wherein said oligonucleotide includes the sequence of any one of SEQ ID NOs: 1433–1768.

106. The method of claim 44, wherein said oligonucleotide includes the sequence of any one of SEQ ID NOs: 4340, 1769–1799.

107. The method of claim 44, wherein said oligonucleotide includes the sequence of any one of SEQ ID NOs: 1800–2271.

108. The method of claim 44, wherein said oligonucleotide includes the sequence of any one of SEQ ID NOs: 2272–2775.

109. The method of claim 44, wherein said oligonucleotide includes the sequence of any one of SEQ ID NOs: 2776–2855.

110. The method of claim 44, wherein said oligonucleotide includes the sequence of any one of SEQ ID NOs: 2856–2979.

111. The method of claim 44, wherein said oligonucleotide includes the sequence of any one of SEQ ID NOs: 2980–3207.

112. The method of claim 44, wherein said oligonucleotide includes the sequence of any one of SEQ ID NOs: 3208–3343.

113. The method of claim 44, wherein said oligonucleotide includes the sequence of any one of SEQ ID NOs: 3344–3395.

114. The method of claim 44, wherein said oligonucleotide includes the sequence of any one of SEQ ID NOs: 3396–3471.

115. The method of claim 44, wherein said oligonucleotide includes the sequence of any one of SEQ ID NOs: 3472–3959.

116. The method of claim 44, wherein said oligonucleotide includes the sequence of any one of SEQ ID Nos: 3960–4035.

117. The method of claim 44, wherein said oligonucleotide includes the sequence of any one of SEQ ID NOs: 4036–4083.

118. The method of claim 44, wherein said oligonucleotide includes the sequence of any one of SEQ ID NOs: 4084–4319.

119. The method of claim 44, wherein said oligonucleotide includes the sequence of any one of SEQ ID NOs: 4320–4339.

120. The method of claim 44, wherein said oligonucleotide has sequence identical to any one of SEQ ID NOs: 1–4340.

121. The method of claim 47, wherein said oligonucleotide has at least three terminal phosphorothioate linkages.

122. The method of claim 121, wherein said targeted nucleic acid is the human ADA gene.

123. The method of claim 122, wherein said oligonucleotide includes the sequence of any one of SEQ ID NOs: 1–160.

124. The method of claim 121, wherein said targeted nucleic acid is the human beta globin gene.

125. The method of claim 124, wherein said oligonucleotide includes the sequence of any one of SEQ ID NOs: 357–500.

126. The method of claim 121, wherein said targeted nucleic acid is the human hemoglobin alpha 1 gene.

127. The method of claim 126, wherein said oligonucleotide includes the sequence of any one of SEQ ID NOs: 2776–2855.

128. The method of claim 121, wherein said targeted nucleic acid is the human hemoglobin alpha 2 gene.

129. The method of claim 128, wherein said oligonucleotide includes the sequence of any one of SEQ ID NOs: 2856–2979.

* * * * *